United States Patent
Gruver et al.

(10) Patent No.: US 11,203,619 B2
(45) Date of Patent: Dec. 21, 2021

(54) INSECTICIDAL PROTEINS AND METHODS FOR THEIR USE

(71) Applicant: PIONEER HI-BRED INTERNATIONAL, INC., Johnston, IA (US)

(72) Inventors: Steven D Gruver, Pacifica, CA (US); Heather Kozy, Walnut Creek, CA (US); Jessica O'Rear, Redwood City, CA (US); Barbara Rosen, Mountain View, CA (US); Ute Schellenberger, Palo Alto, CA (US); Jun-Zhi Wei, Hayward, CA (US); Weiping Xie, East Palo Alto, CA (US); Xiaohong Zhong, San Leandro, CA (US); Genhai Zhu, San Jose, CA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/034,019

(22) Filed: Sep. 28, 2020

(65) Prior Publication Data

US 2021/0007361 A1 Jan. 14, 2021

Related U.S. Application Data

(63) Continuation of application No. 16/567,200, filed on Sep. 11, 2019, now Pat. No. 10,820,596, which is a continuation of application No. 16/259,720, filed on Jan. 28, 2019, now Pat. No. 10,448,648, which is a continuation of application No. 15/543,689, filed as application No. PCT/US2016/012473 on Jan. 7, 2016, now Pat. No. 10,231,460.

(60) Provisional application No. 62/103,787, filed on Jan. 15, 2015.

(51) Int. Cl.
| | |
|---|---|
| *C07K 14/00* | (2006.01) |
| *C07K 14/21* | (2006.01) |
| *C12N 15/82* | (2006.01) |
| *A01N 37/46* | (2006.01) |
| *A01N 63/50* | (2020.01) |

(52) U.S. Cl.
CPC ............. *C07K 14/21* (2013.01); *A01N 37/46* (2013.01); *A01N 63/50* (2020.01); *C12N 15/8286* (2013.01); *Y02A 40/146* (2018.01)

(58) Field of Classification Search
None
See application file for complete search history.

(56) References Cited

U.S. PATENT DOCUMENTS

| | | |
|---|---|---|
| 8,404,933 B2 | 3/2013 | Chen et al. |
| 2014/0007292 A1 | 1/2014 | Cerf et al. |
| 2014/0366227 A1 | 12/2014 | Gatehouse et al. |

FOREIGN PATENT DOCUMENTS

WO WO-2007147068 A2 * 12/2007 ......... C12N 15/8271

OTHER PUBLICATIONS

Baida, N., et al.: "*Pseudomonas brenneri* sp. nov., a new species isolated from natural mineral waters", Research Microbiology, Jul. 2001 (Jul. 2001), vol. 152, No. 5, pp. 493-502.
Li, Xiang-Qian, et al.: "Resistance to root-knot nematode in tomato roots expressing a nematicidal Bacillus thuringiensis crystal protein", Plant BiotechnologyJoumal, Apr. 19, 2007 (Apr. 19, 2007), vol. 5, pp. 455-464.
Wei, Jun-Zhi, et al.: "Bacillus thuringiensis crystal proteins that target nematodes", Proceedings of the National Academy of Sciences of the United States of America (PNAS), Mar. 4, 2003 (Mar. 4, 2003), vol. 100, No. 5, pp. 2760-2765.
International Search Report and Written Opinion of the International Application PCT/US2016/012473, dated Jun. 2, 2016.
NCBI Reference Sequence Accession: WP_007969132.1, Dated May 29, 2013 (May 29, 2013).
NCBI Reference Sequence Accession: WP_007925627.1, Dated Apr. 5, 2017 (Apr. 5, 2017).
NCBI Reference Sequence Accession: WP_023965133.1, Dated Jan. 21, 2018 (Jan. 21, 2018).
Park, Ju Yeon; et al.: "Antiviral Peptide from Pseudomonas chlororaphis O6 against Tobacco Mosaic Virus (TMV)", The Korean Society for Applied Biological Chemistry, Feb. 29, 2012 (Feb. 29, 2012), vol. 55, pp. 89-94.
NCBI Accession No. ZP_10476580 (Jul. 18, 2012).
NCBI Accession No. ZP_10476581 (Jul. 18, 2012).
NCBI Accession No. ZP_10430003 (Jul. 16, 2012).
NCBI Accession No. ZP_10430004 (Jul. 16, 2012).
NCBI Accession No. ZP_15599911 (Nov. 18, 2012).
NCBI Accession No. ZP_15599912 (Nov. 18, 2012).
NCBI Accession No. WP_017475319 (Jun. 28, 2013).
NCBI Accession No. WP_017475320 (Jun. 28, 2013).
NCBI Accession No. YP_004702107 (Dec. 17, 2014).
NCBI Accession No. YP_004702108 (Dec. 17, 2014).

(Continued)

*Primary Examiner* — Jeanette M Lieb

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

9 Claims, 35 Drawing Sheets
Specification includes a Sequence Listing.

(56) References Cited

OTHER PUBLICATIONS

NCBI Accession No. AGA73481 (Feb. 11, 2015).
NCBI Accession No. AGA73480 (Feb. 11, 2015).
NCBI Accession No. WP_023380724 (Mar. 3, 2018).
Database EMBL [Online] Jul. 13, 2012 (Jul. 13, 2012), Alvarez C., et al.: "*Pseudomonas* sp. Ag1 hypothetical protein", XP002781662, retrieved from EBI Database accession No. EJF70241.
"*Pseudomonas* sp. PAMC 26793 ctg7180000039284, whole genome shotgun sequence, NCBI Reference Sequence: NZ_AMXG01000009. 1", Nucleotide 1-3.

* cited by examiner

Fig. 1a

```
                    1                                                    50
PIP-45Aa-1    (1)   MSTPFKQGTSPAGQAPKDYNKLGLEN-QLPQFETDWNNDLTGWTQSAIIG
PIP-45Ab-1    (1)   MSTPFKQGTSPAGQAPKDYNKLGLEN-QLPQFETDWNNDLTGWTQSAIIG
PIP-45Ac-1    (1)   MSTPFNQGTSPAGQAPKDYNKLGLEN-QLPQFETDWNNDLTGWTQSAIIG
PIP-45Ad-1    (1)   MSTPFKQGTSPAGQAPKDYNKLGLEN-QLPQFETDWNNDLTGWTQSAIIG
PIP-45Ae-1    (1)   MSTPFKQGTSPAGQAPKDYNKLGLEN-QLPQFETDWNNDLTGWTQSAIIG
PIP-45Af-1    (1)   MSTPFKQGTSPAGQAPKDYNKLGLEN-QLPQFETDWNNDLTGWTQSAIIG
PIP-45Ba-1    (1)   MSTPFKQGTSPAGQAPKDYNKLGLED-QLPQFETDWNNNLTGWTESSIIG
PIP-45Bb-1    (1)   MSTPFKQGTSPAGQAPKDYNKLGLED-QLPQFETDWNNNLTGWTESSIIG
PIP-45Bc-1    (1)   MSTPFKQGTSPAGQAPKDYNKLGLED-QLPQFETDWNNNLTGWTESSIIG
PIP-45Bd-1    (1)   MSTPFKQGTSPAGQAPKDYNKLGLED-QLPQFETDWNNNLTGWTQSSIIG
PIP-45Be-1    (1)   MSTPFKQGTSPAGQAPKDYNKLGLED-QLPQFETDWNNDITGWTEAAIIG
PIP-45Bf-1    (1)   MSTPFKQGTSPAGQAPKDYNKLGLED-QLPQFETDWNNDVTGWTEAAIIG
PIP-45Bg-1    (1)   MSAPFKQGTSPAGQAPKDYNKLGLED-QLPQFETDWNNNLTGWTESSIIG
PIP-45Bh-1    (1)   MSTPFKQGTSPAGQAPKDYNKLGLED-QLPQFETDWNNNLTGWTESSIIG
PIP-45Bi-1    (1)   MSTPFKQGTSPAGQAPKDYNKLGLED-QLPQFETDWNNNLTGWTESSIIG
PIP-45Bj-1    (1)   MSTPFKQGTSPAGQAPKDYNKLGLED-QLPQFETDWNNNLTGWTESSIIG
PIP-45Bk-1    (1)   MSTPFNQGTSPAEQAPKDYNKLGLEN-QLPQFESDWNNYLTGWTESSIIG
PIP-45Bl-1    (1)   MSTSFTQGTSPAGQAPKDYNKLGLED-QLPQFETDWNNNLTGWTQSSIIG
PIP-46Bm-1    (1)   MSTPFKQGTSPAGQAPKDYNKLGLED-QLQQFETDWNNDLTGWTESSIIG
PIP-45Ca-1    (1)   MSTPFTQGTSPAEQAPKDYNKLGLED-QLPAFETDWNNNVTGWTQMSIIG
PIP-45Cb-1    (1)   MSTPFTQGTSPAEQAPKDYNKLGLEN-QLPTFETNWNNNVTGWTQMSVIG
PIP-45Cc-1    (1)   MSTPFTQGTSPAEQAPKDYNKLGLED-QLSTFETNWNNNVTGWTQMSVIG
PIP-45Cd-1    (1)   MSTPFTQGTSPAEQAPKDYNKLGLEN-QLPTFETDWNNNVTGWTQMSVIG
PIP-45Ce-1    (1)   MSTPFTQGTSPAEQAPKDYNKLGLEN-QLPTFETDWNNNVTGWTQMSVIG
PIP-45Cf-1    (1)   MSTPFTQGTSPAEQAPKDYNKLGLED-QLPTFETDWNNNVTGWTQMSIIG
PIP-45Da-1    (1)   MSIPFTRGSPPANQAQKDYQKLGLEQ-QQAQFDTDWSNNLAGWTEAAIIG
PIP-45Db-1    (1)   MSTPFARGTSPAHQAPKDYKKLGMEN-ELSAFETDWNNNVAGWTEMAIIG
PIP-45Ea-1    (1)   -MTIFTEGSTPAQQGPKDYQLLGLPAADLAAFEADWSANIAGWTQMSIIG
PIP-45Ga-1    (1)   ----MSAGTFSTPALIQDFSDNPSLQ--Q-QLNQNWDLAIDAYTQAALVS
```

Fig. 1b

```
                     51                                                   100
PIP-45Aa-1    (50)  NPWSGLNDAPRSGYYNP-LVEGYGPTTPPAITWAPFPNRLWTFFYNNGTA
PIP-45Ab-1    (50)  NPWSGLNDAPRSGYYNP-LVEGYGPTTPPAITWAPFPNRLWTFFYNNGTA
PIP-45Ac-1    (50)  NPWSGLNDAPRSGYYNP-LVEGYGPTTPPAITWAPFPNRLWTFFYNNGTA
PIP-45Ad-1    (50)  NPWSGLNDAPRSGYYNP-LVEGYGPTTPPAITWAPFPNRLWTFFYNNGTA
PIP-45Ae-1    (50)  NPWSGLNDAPRSGYYNP-LVEGYGPTTPPAITWAPFPNRLWTFFYNNGTA
PIP-45Af-1    (50)  NPWSGLNDAPRSGYYNP-LVEGYGPSTPPAITWAPFPNRLWTFFYNNGTA
PIP-45Ba-1    (50)  NPWSGLNDAPRSGYYNP-LVEGFGDVTAPAITWAPFPNRLWTFFYNNGAA
PIP-45Bb-1    (50)  NPWSGLNDAPRSGYYNP-LVEGFGDVTAPAITWAPFPNRLWTFFYNNGAA
PIP-45Bc-1    (50)  NPWSGLNDAPRSGYYNP-LVEGFGDVTAPAITWAPFPNRLWTFFYNNGAA
PIP-45Bd-1    (50)  NPWSGLNDAPRSGYYNP-LVEGFGDVTPPAITWAPFPNRLWTFFYNNGAA
PIP-45Be-1    (50)  NPWSGLYDAPRSAYYNP-LVEGYGDTTLPAITWQPFPNRLWTFFYNNGTA
PIP-45Bf-1    (50)  NPWSGLYDAPRSGYYNP-LVEGYGDTTPPAITWQPFPNRLWTFFYSNGTA
PIP-45Bg-1    (50)  NPWSGLNDAPRSGYYNP-LVEGFGDVTAPAITWAPFPNRLWTFFYNNGAA
PIP-45Bh-1    (50)  NPWSGLNDAPRSGYYNP-LVEGFGDVTAPAITWAPFPNRLWTFFYNNGAA
PIP-45Bi-1    (50)  NPWSGLNDAPRSGYYNP-LVEGFGDVTAPAITWAPFPNRLWTFFYNNGAA
PIP-45Bj-1    (50)  NPWSGLNDAPRSGYYNP-LVEGFGDVTPPAITWAPFPNRLWTFFYNNGTA
PIP-45Bk-1    (50)  NPWSSLYDAPRSGYYNP-LVEGFGDVVPAITWAPFPNRLWTFFYNNGAA
PIP-45Bl-1    (50)  NPWSNLNDAPRSGYYNP-LVEGFGDVTVPAITWAPFPNRLWTFFYNNGAA
PIP-46Bm-1    (50)  NPWSGQNDAPRSGYYNP-LVEGFGEVTPPAITWAPFPNRLWTFFYNNGAA
PIP-45Ca-1    (50)  NPWSNLNDAPRSGYYNP-LESGYGTLTPKTITWQPFPNRLWTFFYNEGAA
PIP-45Cb-1    (50)  NPWSNLNDAPRSGYYNP-LESGYGTQTPVTITWQPFPNRLWTFFYNNGAA
PIP-45Cc-1    (50)  NPWSNLNDAPRSGYYNP-LESGYGTQTPLTITWQPFPNRLWTFFYNNGAA
PIP-45Cd-1    (50)  NPWSNLNDAPRSGYYNP-LDSGYGTQTPVTITWQPFPNRLWTFFYNDGAA
PIP-45Ce-1    (50)  NPWSNLNDAPRSGYYNP-IESGYGTQTPVTITWQPFPNRLWTFFYNNGAA
PIP-45Cf-1    (50)  NPWSNLNDAPRSGYYNP-LESGYGTLTPKTITWQPFPNRLWTFFYNNGAA
PIP-45Da-1    (50)  NPWTGLNDAPRTGYFNP-LISGFGDAPPAVIDWTPFPNRLITYLTQADSA
PIP-45Db-1    (50)  DPWSNLNDAPRADYYNP-LTEGFGEAGDAVISWTPFPNRLIAFLTPPEAS
PIP-45Ea-1    (50)  NPWSNLNDTPRDNYYDP-LVEGMGEATAAVISWPPFPNRLIQFLTNPGIV
PIP-45Ga-1    (44)  NPWTVDYQAPCDWYVNPKQADITAANPVEPIFWTAFPNRLKIYFSAAEKS
```

Fig. 1c

```
                     101                                                    150
PIP-45Aa-1    (99) VIPQLGGKAMSLQQVMELTDNGQITINNTLYMLYDPNKQGTLLQLPVTRC
PIP-45Ab-1    (99) VIPQLGGKAMSMQQVMELTDNGQITINNTLYMLYDPNKQGTLLQLPVTRC
PIP-45Ac-1    (99) VIPQLGGKAMTLQQVMELTDNGQITLNNTLYTLYDPNKQGTLLQLPVTRC
PIP-45Ad-1    (99) VIPQLGGKAMTLQQVMELTDNGQITLNNTLYTLYDPNKQGTLLQLPVTRC
PIP-45Ae-1    (99) VIPQLGGKAMSMQQVMELTDNGQITINNTLYMLYDPKKQGTLLQLPVTRC
PIP-45Af-1    (99) VIPQLGGKAMSMQQVMELTDNGQITINNTLYMLYDPNKQGTLLQLPVTRC
PIP-45Ba-1    (99) VIPQLGGKAMTLDQVMELTDHGQITLDNTLYMLYDPNKQGTVLQLPAKRC
PIP-45Bb-1    (99) VIPQLGGKAMTLDQVMALTDHGQITLDNTLYMLYDPNKQGTVLQLPAKRC
PIP-45Bc-1    (99) VIPQLGGKAMTLDQVMELTDHGQITLDNTLYMLYDPNKQGTVLQLPAKRC
PIP-45Bd-1    (99) VIPQLGGKAMTLDQVMELADHGQITLDNTLYTLYDPNKKGTVLQLPVKRC
PIP-45Be-1    (99) VIPQLGNKAMTLQQVMELTDNGQITINGTLYTLYDPDKKGTLLQLPVTRC
PIP-45Bf-1    (99) VIPQLGGKAMTLQQVMELTDNGQITINDTLYTLYDPDKKGTLLQLPVTRC
PIP-45Bg-1    (99) VIPQLGGKAMTLDQVMALTDHGQITLDNTLYMLYDPNKQGTVLQLPAKRC
PIP-45Bh-1    (99) VIPQLGGKAMTLDQVMELTDHGQITLDNTLYMLYDPNKRGTVLQLPAKRC
PIP-45Bi-1    (99) VIPQLGGKAMTLDQVMALTDHGQITLDNTLYMLYDPNKQGTVLQLPAKRC
PIP-45Bj-1    (99) VIPQLGGKAMTLDQVMELADHGQISLDNTVYRLYDPNKQGNLLQLPAKRC
PIP-45Bk-1    (99) VIPQLGGKAMTLQQVMELADYGQITLNDTLYTLYDPDNKGTLLQLPAKRC
PIP-45Bl-1    (99) IVPQLGGNAMTLEQVMELADHGQITLNNTLYKLYDPDNQGTLLQLPAKRC
PIP-46Bm-1    (99) VVPQLG-RAMTLNQVMELADRGQITLDNTLYTLYDPDKQGTLLQLPAKRC
PIP-45Ca-1    (99) VVPQLGGKAMTLDQVMQLTDHGQITLNDTLYSLYP-DPKATQLQIPSVLC
PIP-45Cb-1    (99) VVPQLGGKAMTLDQVMQLTDHGQITLNNTLYSLYP-DPKATQLQIPSVLC
PIP-45Cc-1    (99) VVPQLGGTAMTLDQVMQLTDHGQITLNNTLYSLYP-DPAATQLQIPKVLC
PIP-45Cd-1    (99) VVPQLGGKAMTLDQVMQLTDHGQITLNNTLYSLYP-DPKATQLQIPSVLC
PIP-45Ce-1    (99) VVPQLGGKAMTLDQVMQLTDHGQITLNNTLYSLYP-DPKATQLQIPSVLC
PIP-45Cf-1    (99) VVPQLGGKAMTLDQVMQLTDHGQITLNNTLYSLYP-DPQATQLQIPSVLC
PIP-45Da-1    (99) KNPQLGGKPLTMDQVMQLADTGEIDINGTPLKLYDPLG-SNTLQLPSIRC
PIP-45Db-1    (99) NNPQLH-RPLTMDEVMSLADSGEITVDGTLYKLYDPSGSAPILKIPAKRC
PIP-45Ea-1    (99) KGGQLT-APLSQDAVQELADSGRITQGGTSFVLFDPEPGQVLLKIPADRC
PIP-45Ga-1    (94) P------YQMANAQVFALADFGNVPQS--K----A-FPTGLPFIIPSKRC
```

Fig. 1d

```
                  151                                                    200
PIP-45Aa-1  (149) PTIDWQG---KYKDFSPSGPRGWLDEYCEWSIVRD-ADGNMRKITFTCEN
PIP-45Ab-1  (149) PSIDWQG---KYKDFSPSGPRGWLDEYCEWSIVRD-ADGNMRKITFTCEN
PIP-45Ac-1  (149) PSIDWQG---KYKDFSPSGPRGWLDEYCEWSIVRDPGTQNMRKITFTCEN
PIP-45Ad-1  (149) PSIDWQG---KYKDFSPSGPRGWLDEYCEWSIVRDPGTQNMRKITFTCEN
PIP-45Ae-1  (149) PSIDWQG---KYKDFSPSGPRGWLDEYCEWSIVRD-ADGNMRKITFTCEN
PIP-45Af-1  (149) PTIDWQG---KYKDFSPSGPRGWLDEYCEWSIVRD-ANGNMRKITFTCEN
PIP-45Ba-1  (149) PSIDWNG---KYTAFSPSGPRGWLDEYCEWSIVRD-ANGNMRKITFTCEN
PIP-45Bb-1  (149) PSIDWNG---KYTAFSPSGPRGWLDEYCEWSIVRD-ANGNMRKITFTCEN
PIP-45Bc-1  (149) PSIDWNG---KYTAFSPSGPRGWLDEYCEWSIVRD-ANGNMRKITFTCEN
PIP-45Bd-1  (149) PSIAWNG---TYKDFTPSGPRGWLDEYCEWSIVRD-ANGNMRKITFTCEN
PIP-45Be-1  (149) PTIDWNG---KYKDFSPSGPRGWLDEYCEWSIVRD-TNGNMRKITFTSEN
PIP-45Bf-1  (149) PSIDWNG---KYKDFSPSGPRGWLDEYCEWSIVRD-ANGDMRKITFTSEN
PIP-45Bg-1  (149) PSIDWNG---KYTAFSPSGPRGWLDEYCEWSIVRD-ANGNMRKITFTCEN
PIP-45Bh-1  (149) PSIDWNG---KYTAFSPSGPRGWLDEYCEWSIVRD-ANGNMRKITFTCEN
PIP-45Bi-1  (149) PSIDWNG---KYTAFSPSGPRGWLDEYCEWSIVRD-ANGNMRKITFTCEN
PIP-45Bj-1  (149) PSIAWNG---PYKDFSPSGPRGWLDEYCEWSIVRD-GNGKMRKITFTCEN
PIP-45Bk-1  (149) PSIDWNG---KYTAFSPSGPRGWLDEYCEWSIVRD-ANGNMRKITFTCEN
PIP-45Bl-1  (149) PSIDWKG---QYTAFSPSGPRGWLDEYCEWSIVRD-TDGNMRKITFTCEN
PIP-46Bm-1  (148) PSIDWNG---RYTAFSPSGPRGWLDEYCEWSIVRD-ANGNMRKITFTCEN
PIP-45Ca-1  (148) KSINWNG---PYADFSPSGPRGWLDEYCEWSITRD-PDGNMRSIMFTSEN
PIP-45Cb-1  (148) KSINWNG---PYADFSPSGPRGWLDEYCEWSITRD-PDGNMRSIMFTSEN
PIP-45Cc-1  (148) KSINWHG---PYADFSPSGPRGWLDEYCEWSITRD-PDGNMRSIMFTSEN
PIP-45Cd-1  (148) KSINWNG---PYADFSPSGPRGWLDEYCEWSITRD-PDGNMRSIMFTSEN
PIP-45Ce-1  (148) KSINWNG---PYADFSPSGPRGWLDEYCEWSITRD-PDGNMRSIMFTSEN
PIP-45Cf-1  (148) KSINWNG---PYADFSPSGPRGWLDEYCEWSITRD-PDGNMRSIMFTSEN
PIP-45Da-1  (148) PQIDWTG---PYAAFTPSGPRGWLDEYCEWSITLDANG-NMRSVMFTCEN
PIP-45Db-1  (148) PEIDWTG---EYVDFSPSGPRGWLDEYCEWSITYDASGSKMQSVMFTCEN
PIP-45Ea-1  (148) PAIDWDG---KYVDFSPSGPRGWQDEYCEWSILRNAQG-KMQSIAFTCEN
PIP-45Ga-1  (131) PNLNWQQSIAEWVQYDPKGPRGWLDEYCEWSVTRN-ADGKITKIAFTCEN
```

Fig. 1e

```
                      201                                              250
PIP-45Aa-1  (195)  PAYFLAMWRIDPNAVIGLYRDYIDPQVQLEDLYLRYTADCPTGKAGDPVI
PIP-45Ab-1  (195)  PAYFLAMWRIDPTAVIGLYRDYIDPQVQLEDLYLRYTADCPTGKAGDPVI
PIP-45Ac-1  (196)  PAYFLAMWRIDPNAVIGLYRDYIDPQVQLEDLYLRYTADCPTGNKGDPVM
PIP-45Ad-1  (196)  PAYFLAMWRIDPNAVIGLYRDYIDPQVQLEDLYLRYTADCPTGNKGDPVM
PIP-45Ae-1  (195)  PAYFLAMWRIDPTAVIGLYRDYIDPQVQLEDLYLRYTADCPTGKAGDPVI
PIP-45Af-1  (195)  PAYFLAMWRIDPNAVIGLYRDYIDPQVQLEDLYLRYTADCPTGKAGDPVI
PIP-45Ba-1  (195)  PAYFLTMWRIDPNAVIGLYRDYIDPNVQLEDLYLRYTVDCPTGKAGDPVI
PIP-45Bb-1  (195)  PAYFLTMWRIDPNAVIGLYRDYIDPNVQLEDLYLRYTVDCPTGKAGDPVI
PIP-45Bc-1  (195)  PAYFLTMWRIDPNAVIGLYRDYIDPNVQLEDLYLRYTVDCPTGKAGDPVI
PIP-45Bd-1  (195)  PAYFLAMWRIDPNAVIGLYREYIDPSVQLEDLYLRYAEDCPTGKAGDPVM
PIP-45Be-1  (195)  PAYFLAMWRIDPNAVIGLYRDYIDPNVQLQDLYLRYTADCKTGKAGDPVI
PIP-45Bf-1  (195)  PAYFLAMWRIDPNAVIGLYRDYIDPNVQLEDLYLRYATDCPTGNAGDPVI
PIP-45Bg-1  (195)  PAYFLTMWRIDPNAVIGLYRDYIDPNVQLEDLYLRYTVDCPTGKAGDPVI
PIP-45Bh-1  (195)  PAYFLTMWRIDPNAVIGLYRDYIDPNVQLEDLYLRYTADGPTGKAGDPVI
PIP-45Bi-1  (195)  PAYFLTMWRIDPNAVIGLYRDYIDPNVQLEDLYLRYTVDCPTGKAGDPVI
PIP-45Bj-1  (195)  PAYFLTMWRIDPNAVIGLYREYIDPNVQLEDLYLRYTEDGPTGKAGEPVI
PIP-45Bk-1  (195)  PAYYLAMWRIDPNAVIGLYREYIDPNVQLEDLYLRYTVDCPTGKAGDPVI
PIP-45Bl-1  (195)  PAYFLAMWRIDPNAVIGLYRDYIDPNVQLEDLYLRYAVDCPTGKAGDPVI
PIP-46Bm-1  (194)  PAYFLAMWRIDPQAVIGLYRDYIDPSVQLEDLYLRYTVDCPTGKAGDPVI
PIP-45Ca-1  (194)  PAYFLTMWNIDPGAVIGLYQAYVDPQVKLEDLYLRYTADGPTGKAGEPVL
PIP-45Cb-1  (194)  PAYFLTMWNIDPQAVIGLYKAYVDPQVKIEDLYLRYTANGPTGQAGEPVL
PIP-45Cc-1  (194)  PAYFLTMWNIDPNAVIGLYQAYVDPQVKLEDLYLRYTANGPTGNAGDPVI
PIP-45Cd-1  (194)  PAYFLTMWNIDPQAVIGLYKAYVDPQVKIEDLYLRYTANGPTGKAGEPVL
PIP-45Ce-1  (194)  PAYFLTMWNIDPQAVIGLYKAYVDPQVKIEDLYLRYTANGPTGKAGDPVL
PIP-45Cf-1  (194)  PAYFLTMWNIDPGAVIGLYQAYVDPQVKLEDLYLRYTADGPTGKAGEPVL
PIP-45Da-1  (194)  PAYYLTMWRIDPKAVIGLYRMYIDSAVQLEDLYLRYPVDQPTGKQGEPVI
PIP-45Db-1  (195)  PAYYLTMWRINPEAVIGLYQMYVDPAVKLEDLYLRYTVDQPTGKKGDPVM
PIP-45Ea-1  (194)  PAYYLTMWRONPKAVIGIYQRYIDPAVQLEDLFLRYEYDQPTGKKGDPVL
PIP-45Ga-1  (180)  PEYWFTLWQVSPEKVLALYQQLVSPNVVLEDLQL------PSADGKGFVI
```

Fig. 1f

```
                       251                                                  300
PIP-45Aa-1   (245)  DPTTGQPAYDTVNKWNAGTACVPGQYGGAMHLTSGPNTLSAEVYLAAAAT
PIP-45Ab-1   (245)  DPTTGQPAYDTVNKWNAGTACVPGQYGGAMHLTSGPNTLSAEVYLAAAAT
PIP-45Ac-1   (246)  DPTTGQPAYDTVNKWNAGTACVPGQYGGAMHLTSGPNTLSAEVYLAAAAT
PIP-45Ad-1   (246)  DPTTGQPAYDTVNKWNAGTACVPGQYGGAMHLTSGPNTLSAEVYLAAAAT
PIP-45Ae-1   (245)  DPTTGQPAYDTVNKWNAGTACVPGQYGGAMHLTSGPNTLSAEVYLAAAAT
PIP-45Af-1   (245)  DPTTGQPAYDTVNKWNAGTACVPGQYGGAMHLTSGPNTLSAEVYLAAAAT
PIP-45Ba-1   (245)  DPTTGKPAYDTVNKWNAGTACVPGQYGGAMHLTSGPNTLSAEVYLAAAAT
PIP-45Bb-1   (245)  DPTTGKPAYDTVNKWNAGTACVPGQYGGAMHLTSGPNTLSAEVYLAAAAT
PIP-45Bc-1   (245)  DPTTGKPAYDTVNKWNAGTACVPGQYGGAMHLTSGPNTLSAEVYLAAAAT
PIP-45Bd-1   (245)  DPTTGKPAYDTVNKWNAGTACVPGQYGGAMHLTSGPNTLSAEVYLAAAAT
PIP-45Be-1   (245)  DPTTGIPAYDTVNKWNSGTACTPGQFGGAMHLTSGPNTLSAEVYLAAAAT
PIP-45Bf-1   (245)  DPTTGIPAYDTVNKWNAGTACTPGQFGGAMHLTSGPNTLSAEVYLAAAAT
PIP-45Bg-1   (245)  DPTTGKPAYDTVNKWNAGTACVPGQYGGAMHLTSGPNTLSAEVYLAAAAT
PIP-45Bh-1   (245)  DPTTGKPAYDTVNKWNAGTACVPGQFGGAMHLTSGPNTLSAEVYLAAAAT
PIP-45Bi-1   (245)  DPTTGKPAYDTVNKWNAGTACVPGQYGGAMHLTSGPNTLSAEVYLAAAAT
PIP-45Bj-1   (245)  DPTTGKPAYDTVNKWNAGTVSVPGQYGGAMHLTSGPNTLSAEVYLAAAAT
PIP-45Bk-1   (245)  DPTTGIPAYDTVNKWNAGTACVPGQFGGAMHLTSGPNTLSAEVYLAAAAT
PIP-45Bl-1   (245)  DPTTGQPAYDTVNKWNAGTACVPGQYGGAMHLTSGPNTLSAEVYLAAAAT
PIP-46Bm-1   (244)  DPTTGQPAYDTVNKWNAGTACVPGQYGGAMHLTSGPNTLSAEVYLAAAAT
PIP-45Ca-1   (244)  DPTTGQPAYDTVNKWNSGTVRIPGVSGGAMHLTSGPNTLSAEIYLAAAAT
PIP-45Cb-1   (244)  DPTTGQPAYDTVNKWNSGTVRIPGVSGGAMHLTSGPNTLSAEIYLAAAAT
PIP-45Cc-1   (244)  DETTGRPAYDTVNKWNAGTVRIPGVSGGAMHLTSGPNTLSAEIYLAAAAT
PIP-45Cd-1   (244)  DPTTGQPAYDTVNKWNSGTVRIPGVSGGAMHLTSGPNTLSAEIYLAAAAT
PIP-45Ce-1   (244)  DPTTGQPAYDTVNKWNSGTVRIPGVSGGAMHLTSGPNTLSAEIYLAAAAT
PIP-45Cf-1   (244)  DPTTGQPAYDTVNKWNSGTVRIPGVSGGAMHLTSGPNTLSAEIYLAAAAT
PIP-45Da-1   (244)  DPTTGIPAYDVNKWNSGTARKPGLFGGALHLTSAPNTLSAEIYLAGAST
PIP-45Db-1   (245)  DPTTGRPAYDVTNKWNRGTVRVPGQSGGALHLTSGPNTLSAEIYLAAAAT
PIP-45Ea-1   (244)  DPTTGNPAYDPTNKWNRGPARVPGSFGGAMHLTSPPNTLSAEIYLAAAAT
PIP-45Ga-1   (224)  DPTTGRPAYNPINKWNSGTVAT-ETYGGAVHLTSPPNTIGAEIMLAAQAT
```

Fig. 1g

```
                    301                                                350
PIP-45Aa-1  (295)   ILRPLASSQ-NSQALICCAQYGQNYRNSDPHIGFSAN----SVAVNNRLS
PIP-45Ab-1  (295)   ILRPLSSSQ-NSQALICCAQYGQNYRNSDPHIGFSAN----SVAVNNRLS
PIP-45Ac-1  (296)   ILRPLASSQ-NSQALICCAQYGQNYRNSDPHIGFSAN----SVAVNNRLS
PIP-45Ad-1  (296)   ILRPLSSSQ-NSQALICCAQYGQNYRNSDPHIGFSAN----SVAVNNRLS
PIP-45Ae-1  (295)   ILRPLSSSQ-NSQALICCAQYGQNYRNSDPHIGFSAN----SVAVNNRLS
PIP-45Af-1  (295)   ILRPLASSQ-NSQALICCAQYGQNYRNSDPHIGFSAN----SVAVNNRLS
PIP-45Ba-1  (295)   ILRPVSSSQ-NAQSLICCAQYGQNYRNSDPHIGFMAN----TTAVNNRLS
PIP-45Bb-1  (295)   ILRPVSSSQ-NAQSLICCAQYGQNYRNSDPHIGFMAN----TTAVNNRLS
PIP-45Bc-1  (295)   ILRPVSSSQ-NAQSLICCAQYGQNYRNSDPHIGFMAN----TTAVNNRLS
PIP-45Bd-1  (295)   ILRPVSSSQ-NAQSLICCAQYGQNYRNSDPHIGFMAN----TTAVNNRLS
PIP-45Be-1  (295)   IMRPLKSSQ-SAQALICCAQYGQNYRNSDPHIGFAANGATNDGATPSRIS
PIP-45Bf-1  (295)   IMRPLKSSQ-NPQSLICCAQYGQNYRNSDPHIGFAAN----EAAISNRIS
PIP-45Bg-1  (295)   ILGPVSSSQ-NAQSLICCAQYGQNYRNSDPHIGFMAN----TTAVNNRLS
PIP-45Bh-1  (295)   ILRPVSSSQ-NAQSLICCAQYGQNYRNSDPHIGFMAN----TTAVNNRLS
PIP-45Bi-1  (295)   ILRPVSSSQ-NAQSLICCAQYGQNYRNSDPHIGFMAN----TTAVNNRLS
PIP-45Bj-1  (295)   ILRPVSSSQ-NAQSLICCAQYGQNYRNSDPHIGFMAN----STAVNNRLS
PIP-45Bk-1  (295)   ILRPVTSSQ-NAQSLICCAQYGQNYRNSDPHIGFMAN----SKAVNNRLS
PIP-45Bl-1  (295)   LLRPVSSSQ-NAQSLICCAQYGQNYRNSDPHIGFMAN----TKAVNNRLS
PIP-46Bm-1  (294)   ILRPVSSSQ-NAQSLICCAQYGQNYRNSDPHIGFMAN----STAVKNRLS
PIP-45Ca-1  (294)   ILRPLTSSQ-NQSLICCAQYGQNYRNSDPHIGFSAN----QAAVNNLIS
PIP-45Cb-1  (294)   ILRPLNSSR-NQQSLICCAQYGQNYRNSDPHIGFSAN----QAAVNNLIS
PIP-45Cc-1  (294)   ILRPIQSSG-NQQNLICCAQYGQNYRNSDPHIGFSAN----QAAVKNLIS
PIP-45Cd-1  (294)   ILRPIKSSA-NQQSLICCAQYGQNYRNSDPHIGFSAN----QEAVKALIS
PIP-45Ce-1  (294)   ILRPLNSSR-NQQSLICCAQYGQNYRNSDPHIGYSAN----QEAVKALIS
PIP-45Cf-1  (294)   ILRPLSSSQ-NQQSLICCAQYGQNYRNSDPHIGFSAN----QAAVNNLIS
PIP-45Da-1  (294)   IQRSDKSSE-TPQTLICCAKYGRNYRNSDPHIGYVAN----GIAYGNRIS
PIP-45Db-1  (295)   IQRPDLSSR-DPQSLICCAQYGQNYRNSDPHIGFIAN----RAAARYRIS
PIP-45Ea-1  (294)   IQRPSSVNG-NPQSLICCAQYGQNFRNSDPNIGYGAN----VAARTARLT
PIP-45Ga-1  (273)   LLRDLPPDQYNMQRMVCAGAYGRAYRNSDPHIGLQAN--QLVKNLGVKIT
```

Fig. 1h

```
                    351                                                400
PIP-45Aa-1  (340)   LTNPIGLYLQQPTDFSAWKGPQGQDVSQYWKITRG-TAKSAANGSDQILQ
PIP-45Ab-1  (340)   LTNPIGLYLQQPTDFSAWKGPQGQDVSQYWKITRG-TAKSAANGSDQILQ
PIP-45Ac-1  (341)   LTNPIGLYLQQPTDFSAWKGPQGQDVSQYWKITRG-TAKSAANGSDQILQ
PIP-45Ad-1  (341)   LTNPIGLYLQQPTDFSAWKGPQGQDVSQYWKITRG-AAKSAANGSDQILQ
PIP-45Ae-1  (340)   LTNPIGLYLQQPTDFSAWKGPQGQDVSQYWKITRG-TAKSAANGSDQILQ
PIP-45Af-1  (340)   LTNPIGLYLQQPTDFSAWKGPQGQDVSQYWKITRG-TAKSAANGSDQILQ
PIP-45Ba-1  (340)   LTNPIGLYLQQPTDFSAWKGPQGQDVSQYWRITRG-TAKSAANGSDQILQ
PIP-45Bb-1  (340)   LTNPIGLYLQQPTDFSAWKGPQGQDVSQYWRITRG-TAKSAANGSDQILQ
PIP-45Bc-1  (340)   LTNPIGLYLQQPTDFSAWKGPQGQDVSQYWRITRG-TAKSAANGSDQILQ
PIP-45Bd-1  (340)   LTNPIGLYLQQPTDFSAWKGPQGQDVSQYWRITRG-TAKSAANGSDQILQ
PIP-45Be-1  (344)   LTNPIALYLQQPTNFNAWKGPQGQDVSQYWRITRG-TAKSAINGSDQILQ
PIP-45Bf-1  (340)   LTNPIALYLQQPTNFSAWKGPQGQDVSQYWRITRG-TAKSAINGSDQILQ
PIP-45Bg-1  (340)   LTNPIGLYLQQPTDFSAWKGPQGQDVSQYWRITRG-TAKSAANGSDQILQ
PIP-45Bh-1  (340)   LTNPIGLYLQQPTDFSAWKGPQGQDVSQYWRITRG-TAKSAANGSDQILQ
PIP-45Bi-1  (340)   LTNPIGLYLQQPTDFSAWKGPQGQDVSQYWRITRG-TAKSAANGSDQILQ
PIP-45Bj-1  (340)   LTNPIGLYLQQPTDFSTWKGPQGQDVSQYWHITRG-AAKSAANGSDQILQ
PIP-45Bk-1  (340)   LTNPIGLYLQQPTDFSTWKGPQGQDVSQYWRVTRG-TAKSAANGSDQILQ
PIP-45Bl-1  (340)   LTNPIGLYLQQPTDFSAWKGPQGQDVSQYWRITRG-TAKSAANGSDQILQ
PIP-46Bm-1  (339)   LTNPIGLYLQQPTDFSGWKGPQGQDVSQYWRITRG-TAKSAANGSDQILQ
PIP-45Ca-1  (339)   LTNPIGLYLQQPKSFSTWKGPQGQDVSSYWRVTRG-TAGTGPNNSDQILQ
PIP-45Cb-1  (339)   LTNPIGLYLQQPKSFSTWKGPQGQDVSSYWRVTRG-TAGTGPNNSDQILQ
PIP-45Cc-1  (339)   LTNPIGLYLQQPKSFSTWKGPQGQDVSSYWRVTRG-TAGTGPNNSDQILQ
PIP-45Cd-1  (339)   LTNPIGLYLQQPKSFSTWKGPQGQDVSSYWHVTRG-TAGTGPNKSDQILQ
PIP-45Ce-1  (339)   LTNPIGLYLQQPKSFSTWKGPQGQDVSSYWRITRG-TAGTGPNNSDQILQ
PIP-45Cf-1  (339)   LTNPIGLYLQQPKSFSTWKGPQGEDVSSYWRVTRG-TAGTGPNNSDQILQ
PIP-45Da-1  (339)   LTDPVGLYLQQPKNFSKWKDPQGNSVSQYWQITRG-TAGTGPLGSDQILH
PIP-45Db-1  (340)   LTDPVGLYIQQPQNLSNWKGPNGEDISQYWKITRG-TAGTGPNNSDQILH
PIP-45Ea-1  (339)   LTDPVGLYIQQPQNFQGWSGPNGEDVSGYWQILRG-TAGTGPNGSDQILH
PIP-45Ga-1  (321)   LTNPVGLYLQRP-DFSSYKTPDGKDAGQFYKVIRGRTAQQAGTTYDQILH
```

Fig. 1i

```
                     401                                              450
PIP-45Aa-1  (389)  AVEEVPVSAGFSINDITISGQP---------IDYVWVIAQQLLVGISVTT
PIP-45Ab-1  (389)  AVEEVPVSAGFSINEITISGQP---------IDYVWVIAQQLLVGISVTT
PIP-45Ac-1  (390)  AVEEVPVSAGFSINDITISGQS---------IDYVWVIAQQLLVGISVTT
PIP-45Ad-1  (390)  AVEEVPVSAGFSINDITISGQS---------IDYVWVIAQQLLVGISVTT
PIP-45Ae-1  (389)  AVEEVPVSAGFSINDITISGQP---------IDYVWVIAQQLLVGISVTT
PIP-45Af-1  (389)  AVEEVPVSAGFSINDITISGQP---------INYVWVIAQQLLVGISVTT
PIP-45Ba-1  (389)  AVEEVPESAGFSINDITINNQK---------VNYVWVIAQQLLVGISVTV
PIP-45Bb-1  (389)  AVEEVPESAGFSINDITINNQK---------VNYVWVIAQQLLVGISVTV
PIP-45Bc-1  (389)  AVEEVPESAGFSINDITINNQK---------VNYVWVIAQQLLVGISVTA
PIP-45Bd-1  (389)  AVEEVPESAGFSINDITINNQK---------VNYVWVIAQQLLVGISVTV
PIP-45Be-1  (393)  AVEEVPESAGFSINDITINGQA---------VDYVWVIAQQLLVGISVTT
PIP-45Bf-1  (389)  AVEEVPQSAGFSINDITINGQA---------VDYVWVIAQQLLVGISVTV
PIP-45Bg-1  (389)  AVEEVPESAGFSINDITINNQK---------VNYVWVIAQQLLVGISVTV
PIP-45Bh-1  (389)  AVEEVPESAGFSINDITINNQK---------VNYVWVIAQQLLVGISVTV
PIP-45Bi-1  (389)  AVEEVPESAGFSINDITINNQK---------VNYVWVIAQQLLVGISVTV
PIP-45Bj-1  (389)  AVEEIPESAGFSINEVTINKQP---------VNHVWVIAQQLLVGISVTV
PIP-45Bk-1  (389)  AVEEVPESAGFSINEITINKQP---------VDYVWVIAQQLLVGISVSA
PIP-45Bl-1  (389)  AVEEVPQSAGFSINDITINGQR---------VDYVWVIAQQLLVGISVTA
PIP-46Bm-1  (388)  AVEEVPESAGFSINDITINNQP---------VNYVWVIAQQLLVGISVTV
PIP-45Ca-1  (388)  AVEEVPASAGFSINEITINGTP---------IDYVWVIANELNVAISVTP
PIP-45Cb-1  (388)  AVEEVPQSAGFSINDITINGTP---------IDYVWVIANELNVAISVTP
PIP-45Cc-1  (388)  AVEEVPQSAGFSINDITINGTP---------IDYVWVIANELNVAISVTP
PIP-45Cd-1  (388)  AVEEVPQSAGFSINEITINGTP---------IDYVWVIANELSVAISVTP
PIP-45Ce-1  (388)  AVEEVPASAGFSINDITINGTP---------IDYVWVIANELNVAISVTP
PIP-45Cf-1  (388)  AVEEVPASAGFSINDITISGTP---------IDYVWVIANELNVAISVTP
PIP-45Da-1  (388)  AVEEVPEQAGFSINDITIDGQK---------ITHVGVIANQMKVAISASP
PIP-45Db-1  (389)  AVEDIPPSAGFTINDCTINGQK---------IAHIGDIANQMKIAISATQ
PIP-45Ea-1  (388)  AVEAIPESAGYSIEDCTIYGLP---------ISHVGVILDQMKVAIAVTP
PIP-45Ga-1  (370)  AEESVPEELGYTVSDILIGNAVPGSSQVPVPILYAGQIAETFHVCIAGTA
```

Fig. 1j

```
                        451                                                      500
PIP-45Aa-1    (430)    TP-ISPTP--DSCPCVKDRVNG-------VQPWPVQLLPLDLFYGQSPTD
PIP-45Ab-1    (430)    TP-ISPTP--DSCPCVTDRVNG-------VQPWPVQLLPLDLFYGQSPTD
PIP-45Ac-1    (431)    TP-ISPTP--ESCPCVTDRVTG-------VQPWPVQLLPLDLFYGQSPTD
PIP-45Ad-1    (431)    TP-ISPTP--DSCPCVTDRVNG-------VQPWPVQLLPLDLFYGQSPTD
PIP-45Ae-1    (430)    TP-ISPTP--DSCPCVTDRVNG-------VQPWPVQLLPLDLFYGQSPTD
PIP-45Af-1    (430)    TP-ISPTP--DSCPCVTDRVNG-------VQPWPVQLLPLDLFYGQSPTD
PIP-45Ba-1    (430)    KP-LSATL--QAFPCVQDRVAG-------LQPWPVQLLPLDLFYGQSPTD
PIP-45Bb-1    (430)    KP-LSTTP--QAFPCVQDRVAG-------RQPWPVQLLPLDLFYGQSPTD
PIP-45Bc-1    (430)    KP-LSATP--QAFPCVQDRVAG-------LQPWPVQLLPLDLFYGQSPTD
PIP-45Bd-1    (430)    KP-LSVTP--QSFPCVQDRVAG-------LQPWPVQLLPLDLFYGNSPTD
PIP-45Be-1    (434)    MP-STAQ---QQSPCVQDRVNG-------LQPWPVQLLPLDLFYGQSPTD
PIP-45Bf-1    (430)    MP-STTA---APSPCVQDRVNG-------LQPWPVQLLPLDLFYGQSPTD
PIP-45Bg-1    (430)    KP-LSTAP--QAFPCVQDRVAG-------LQPWPVQLLPLDLFYGQSPTD
PIP-45Bh-1    (430)    KP-LSTTP--QAFPCVQDRVAG-------LQPWPVQLLPLDLFYGQSPTD
PIP-45Bi-1    (430)    KP-LSTAP--QAFPCVQDRVAG-------LQPWPVQLLPLDLFYGQSPTD
PIP-45Bj-1    (430)    KP-LAATP--ASYPCVQDRVAG-------LQPWPVQLLPLDLFYGNSPTD
PIP-45Bk-1    (430)    LP-PATTP--PSFPCVQDRVTG-------LQPWPVQLLPLDLFYGQSPTD
PIP-45Bl-1    (430)    KP-ITVTP--PSFPCVQARVEG-------LQPWPVQLLPVDLFYGQSPTD
PIP-46Bm-1    (429)    KP-LATTP--PSFPCVQDRQTG-------RQPWPVQLLPLDLFYGQSPTD
PIP-45Ca-1    (429)    AP-LTAQP--KECACVAANTTD-------AQPWPVQLLPIDLFYGQSPSD
PIP-45Cb-1    (429)    AP-LPAPP--KECDCVAANNTD-------AQPWPVQLLPIDLFYGQSPSD
PIP-45Cc-1    (429)    AP-LTATP--KECDCVAANNTD-------AQPWPVQLLPLDLFYGQSPSD
PIP-45Cd-1    (429)    AP-LTATP--EECDCVAANTTD-------AQPWPVQLLPIDLFYGQSPSD
PIP-45Ce-1    (429)    AP-LSGTP--KECDCVAANNTD-------AQPWPVQLLPIDLFYGQSPSD
PIP-45Cf-1    (429)    AP-LTAQP--KECACVAANTTD-------AQPWPVQLLPIDLFYGQSPSD
PIP-45Da-1    (429)    LD--AIKP--VIQPCVTDRSTG-------LQPCPVQLLPLSLFYGLSPSD
PIP-45Db-1    (430)    MTPNQPLQ--SPMKCVSSRSSGS------MQPWPVQFVPIDLFYGESPTD
PIP-45Ea-1    (429)    NN-AAPDT--TAFACVTDRTDG-------TQPWPVQMVPESLFYGESPSD
PIP-45Ga-1    (420)    IAPATGEPSQAFLPPVTDKTGNTNGQVSMLLANPVLLAMQAVNPFPPFVQ
```

Fig. 1k

```
              501                                                    550
PIP-45Aa-1  (470) LPAWLAPGTSGQ-FAIVVQGADLKTTAETARVQFS----NPGVTAQVTQF
PIP-45Ab-1  (470) LPAWLAPGTSGQ-FAIVVQGADLKTTAETARVQFS----NPGVTAQVTKF
PIP-45Ac-1  (471) LPAWLAPGTSGQ-FAIVVQGADLKTTAETARVQFS----NPGVTAVVTKF
PIP-45Ad-1  (471) LPAWLAPGTSGQ-FAIVVQGADLKTTAETARVQFS----NPGVTAVVTKF
PIP-45Ae-1  (470) LPAWLAPGTSGQ-FAIVVQGADLKTTAETARVQFS----NPGVTAQVTKF
PIP-45Af-1  (470) LPAWLAPGTSGQ-FAIVVQGADLKTTAETARVQFS----NPSVTAQVTQF
PIP-45Ba-1  (470) LPAWLAPGSSNQ-FVIVVQGADPTTAQNARVQFS----NPGVTAQVTQY
PIP-45Bb-1  (470) LPAWLAPGSSNQ-FVIVVQGADPTTAQNARVQFS----NPGVTAQVTQY
PIP-45Bc-1  (470) LPAWLAPGSSNQ-FVIVVQGADPTTAQNARVQFS----NPGVTAQVTQY
PIP-45Bd-1  (470) LPAWLAPGSSNQ-FVIVVQGADKTTAQNARVQFS----NPGVTAQVTQY
PIP-45Be-1  (473) LPAWLAPGTSGQ-FAIVVQGADLKTTAATARIQFN----NPGVTAQVTEF
PIP-45Bf-1  (469) LPAWLAPGSSGQ-FVIVVQGADLQTTAATARIQFS----NPGVTAQVTKF
PIP-45Bg-1  (470) LPAWLAPGSSNQ-FVIVVQGADPTTAQNARVQFS----NPGVTAQVTQY
PIP-45Bh-1  (470) LPAWLAPGSSNQ-FVIVVQGADPTTAQNARVQFS----NPGVTAQVTQY
PIP-45Bi-1  (470) LPAWLAPGSSNQ-FVIVVQGADPTTAQNARVQFS----NPGVTAQVTQY
PIP-45Bj-1  (470) LPAWLAPGSSNQ-FVIVVQGADENTTAENARVQFS----NPGVTAQVTQY
PIP-45Bk-1  (470) LPACLAPGSSNQ-FVIVVQGADPNTTAQSARVQFS----NPGISAQVTQF
PIP-45Bl-1  (470) LPAWLAPGSSNS-FVIVVQGADPSTTQNARVQFS----NPGITAQVTHY
PIP-46Bm-1  (469) LPAWLAPGSSNS-FVIVVQGADANTTAQNARVQFS----NPGVTAQVTQY
PIP-45Ca-1  (469) LPASFAPGSSGQ-FVIVVQGADPNTTAADARVQFS----NPGITAQVTQF
PIP-45Cb-1  (469) LPASFAPGSSGQ-FVIVVQGADPNTTAADARVQFS----NPGITAQVTQF
PIP-45Cc-1  (469) LPASFAPGSSAQ-FVIVVQGADPNTTVADARVQFS----NPGISAQVTQF
PIP-45Cd-1  (469) LPASFAPGSSGQ-FVIVVQGADPNTTAADARVQFS----NPGITAQVTEF
PIP-45Ce-1  (469) LPASFAPGSSGQ-FVIVVQGADPNTTAADARVQFS----NPGITAQVTQF
PIP-45Cf-1  (469) LPASFAPGSSSQ-FVIVVQGADPNTTAADARVQFS----NPGITAQVTQF
PIP-45Da-1  (468) LPAWLAPSSSNQ-FILLVQGSDAATTAANARIQFS----NPGVKAQVIEF
PIP-45Db-1  (472) LPAIMVPGTVNS-FVIIVQGADKNTTIDNARIEFS----NPGIKAKVTKF
PIP-45Ea-1  (469) LPALLRPGSKFR-FVLIVQGADENTTPATARVEFS----DPNITVTVEQF
PIP-45Ga-1  (470) LPVQIAQGQTLTNMALQVSYANDNFQEAQIAFWDAQGNSEPGISVTVTAI
```

Fig. 1I

```
                         551                                            600
PIP-45Aa-1      (515)    LPDASAIPGQTNSG-GTQGYLLTITVSPTAAPGLVTVRALNEGEADNPSA
PIP-45Ab-1      (515)    LPDASAIPGQTNSG-GTQGYLLTITVSPTAAPGLVTVRALNEGEADNPSA
PIP-45Ac-1      (516)    LPDASAIPGQTNSG-GTQGYLLTITVSPTAAPGLVTVRALNEGEADNPSA
PIP-45Ad-1      (516)    LPDASAIPGQTNSG-GTQGYLLTITVSPTAAPGLVTVRALNEGEADNPSA
PIP-45Ae-1      (515)    LPDASAIPGQTNSG-GTQGYLLTITVSPTAAPGLVTVRALNEGEADNPSA
PIP-45Af-1      (515)    LPDASAIPGQTNSG-GTQGYLLTITVSPTAAPGLVTVRALNEGEADNPSA
PIP-45Ba-1      (515)    LPDASAIPGQTNSG-GTQAYILTITVSPSAAPGLVTVRALNEGEDVNVSA
PIP-45Bb-1      (515)    LPDASAIPGQTNSG-GTQAYILTITVSPSAAPGLVAVRALNEGEDVNVSA
PIP-45Bc-1      (515)    LPDASAIPGQTNSG-GTQAYILTITVSPSAAPGLVALRALNEGEDVNVSA
PIP-45Bd-1      (515)    LPDASAIPGQTNAG-GTQAYILTITVSPTAAPGLVTVRALNEDEDVNVSA
PIP-45Be-1      (518)    LPDASAIPGQTNAG-GTQGYIMTITVAKDAAPGLVTVRALNEGEADNVSA
PIP-45Bf-1      (514)    MPDASAIPGQTNAG-GTQGYIMTISVAANAAPGLVTVRALNEGEADNVSA
PIP-45Bg-1      (515)    LPDASAIPSQTNSG-GTQAYILTITVSPSAAPGLVAVRALNEGEDVNVSA
PIP-45Bh-1      (515)    LPDASAIPGQTNSG-GTQAYILTITVSPSAAPGLVTVRALNEGEDVNVSA
PIP-45Bi-1      (515)    LPDASAIPGQTNSG-GTQAYILTITVSPSAAPGLVAVRALNEGEDVNVSA
PIP-45Bj-1      (515)    LPDATAIPGQTNTG-GTQAYILTITVSPTAAPGLVTVRALNEDEDANVSA
PIP-45Bk-1      (515)    LPDASAIPGQTNAG-GTQAYILTITVSPSAAPGLVTVRALNEGEDGNVSA
PIP-45Bl-1      (515)    LPDASAIPGQTNSG-GTQAYILTITVSPTAAPGLVMVRALNEGEDANVSA
PIP-46Bm-1      (514)    LPDASAIPGQTNSG-GTQAYMLTITVSPNAAPGLVTVRALNEGEDVNVSA
PIP-45Ca-1      (514)    LPDASAIPGQTDGG-GTQGYIMTITVSSNAAPGLVSVRALNESEAANPSA
PIP-45Cb-1      (514)    LPDASAIPGQTDSG-GTQGYIMTVTVSSNAAPGLVSVRALNESEGANPSA
PIP-45Cc-1      (514)    LPDASAIPGQTDSG-GTQGYVMTVNVSGNAAPGLVSVRALNESEAANPSA
PIP-45Cd-1      (514)    LPDASAIPGQTDSG-GTQGYIMTVTVSSNAVPGLVSVRALNESEAANPSA
PIP-45Ce-1      (514)    LPDASAIPGQTDSG-GTQGYIMTVTVSSNAAPGLVSVRALNESEAANPSA
PIP-45Cf-1      (514)    LPDASAIPGQTDGG-GTQGYIMTITVSSNAAPGLVSVRALNENEAANPSA
PIP-45Da-1      (513)    QTNATPIAGTTDNS-GTQGYIITITVAANAAPGLVQLRVLNPDEPVNPSD
PIP-45Db-1      (517)    LPDASAIPGQTDGG-GTQGFIMDVAVSSSAKPGSVSLRVLNPNEPANPSD
PIP-45Ea-1      (514)    LKNASAVPGQTNGG-GTQGYVMDIAVGANAQPGPVSVRALNESEGPAPTP
PIP-45Ga-1      (520)    ETADGTPAGKSAGGDGLFNYIISISVAPGVSPGFKGVTVRNP-----ACD
```

Fig. 1m

```
                    601          616
PIP-45Aa-1  (564)  TEHPWESGIALVPGA-
PIP-45Ab-1  (564)  AEHPWESGIALVPGA-
PIP-45Ac-1  (565)  AQHPWESGIALVPGA-
PIP-45Ad-1  (565)  AEHPWESGIALVPGA-
PIP-45Ae-1  (564)  AEHPWESGIALVPGA-
PIP-45Af-1  (564)  TEHPWESGIALVPGA-
PIP-45Ba-1  (564)  TDHPWESGIALVPGA-
PIP-45Bb-1  (564)  TDHPWESGIALVPGA-
PIP-45Bc-1  (564)  TDHPWESGIALVPGA-
PIP-45Bd-1  (564)  ADHPWESGIALVPGA-
PIP-45Be-1  (567)  ADHPWESGIALVPST-
PIP-45Bf-1  (563)  ADHPWESGIALVPST-
PIP-45Bg-1  (564)  TDHPWESGIALVPGA-
PIP-45Bh-1  (564)  TDHPWESGIALVPGA-
PIP-45Bi-1  (564)  TDHPWESGIALVPGA-
PIP-45Bj-1  (564)  ADHPWESGIALVPGA-
PIP-45Bk-1  (564)  ADHPWESGIALVPGA-
PIP-45Bl-1  (564)  ADHPWEAGIALVPGA-
PIP-46Bm-1  (563)  ADHPWESGIALVPGA-
PIP-45Ca-1  (563)  SEHPWESGIALVPSA-
PIP-45Cb-1  (563)  TQHPWESGIALVPDA-
PIP-45Cc-1  (563)  AQHPWESGIALVPGA-
PIP-45Cd-1  (563)  TQHPWESGIALVPGV-
PIP-45Ce-1  (563)  TQHPWESGIALVPVA-
PIP-45Cf-1  (563)  TEHPWESGIALVPSA-
PIP-45Da-1  (562)  TDHPWASSIAIVPAL-
PIP-45Db-1  (566)  ADHPWESGIAVIPSH-
PIP-45Ea-1  (563)  EQHPWEAGIAVISSR-
PIP-45Ga-1  (565)  MPLPLPGVIFVTAKGN
```

Fig. 2a

```
                   1                                                    50
PIP-45Aa-2   (1)   ------MSRLRLSVLSLLTSVVLSLFAMQAAYASPTSD-----------A
PIP-45Ab-2   (1)   ------MSRLRLSVLSLLTSVVLSLFAMQAAYASPTSD-----------A
PIP-45Ac-2   (1)   ------MSRLRLSVLSLLTSVVLSLFAVQSAYATPQSD-----------A
PIP-45Ad-2   (1)   ------MSRLRLSVLSLLASVVLSLFALQSAYATPQSD-----------A
PIP-45Ae-2   (1)   ------MSRLRLSVLSLLTSVVLSLFAMQAAYASPTSD-----------A
PIP-45Af-2   (1)   ------MSRLRLSVLSLLTSVVLSLFAMQAAYASPTSD-----------A
PIP-45Ba-2   (1)   -----MMSRSRLSPLSLLCGILLCLSTLQPATAATLSD-----------A
PIP-45Bb-2   (1)   ------MSRSRLSLLSLLCGILLCLSTPQPATAATLSD-----------A
PIP-45Bc-2   (1)   -----MMSRSRLSLLSLLCGILLCLSTPQPATAATLSD-----------A
PIP-45Bd-2   (1)   ------MSRSRLSLLSLLCGILLCLSTPQPAMAATLSD-----------A
PIP-45Be-2   (1)   ------MYRFRLRGLLLVG---TLLS-LFLLPTAQASD-----------A
PIP-45Bf-2   (1)   ------MSRFRLSRLLLVS---TLLS-LFILPLAHASD-----------A
PIP-45Bg-2   (1)   ------MSRSRLSLLSLLCGILLCLSTPQPATAATLSD-----------A
PIP-45Bh-2   (1)   ------MSRSRLSLLSLLCGILLCLSTLQPATAATLSD-----------A
PIP-45Bi-2   (1)   ------MSRSRLSLLSLLCGILLCLSTPQPATAATLSD-----------A
PIP-45Bj-2   (1)   ------MSSLRLSLLSLLSGILLCLSAQQTATAATQSD-----------A
PIP-45Bk-2   (1)   ------MSRLRLSLLSLLSGMLLCLSTLPAATAAPMTE-----------A
PIP-45Bl-2   (1)   ------MSRSRLSLISLLSGMLLYLSALPPAAAATMSD-----------A
PIP-45Bm-2   (1)   ------MSSLRLSLLSLLSGILLCLQTLQPAAAATLSD-----------A
PIP-45Ca-2   (1)   --MNGWLRPLRRARLRIACAITCTLLPLLAATPANAAS-----------D
PIP-45Cb-2   (1)   --MNGWLRPLRRARLRVFCWITCALLPLLAPSPANAAT-----------D
PIP-45Cc-2   (1)   --MYGWPRPLCRARLNVFSLLAGALLSLVAPPPASAS------------D
PIP-45Cd-2   (1)   --MNKWLRPLRRARLSVLCWIPCALLP-LAPAPAIAAS-----------D
PIP-45Ce-2   (1)   --MNGWLRPLRRARLNVLCWITCALLP-FAPAPVSAAS-----------D
PIP-45Cf-2   (1)   --MNGWLRPLRRARLRIVCTITCALLPWLAPAPASAAS-----------D
PIP-45Da-2   (1)   MFSLDCSRGNGRFCLPPLLLIIWLLGSLVARNAYALSDP---------ET
PIP-45Db-2   (1)   --MNRLHLGAGCVIAGFCILAIAGLLWVIDVPAGRADEINISRVTEIAQS
PIP-45Ea-2   (1)   ---------------MRTGQILIALVAGVMLAFAASGGK-----------A
PIP-45Ga-2   (1)   ------MKHTLLIGVTTGLLVAACQQPVQESSAAVDAPAVSTVS-----S
```

Fig. 2b

```
                    51                                                    100
PIP-45Aa-2   (34)   DACVQQQLVFNPKSGGFLPINNFNATGQSFMNCFGWQLFIALNWPVNPGW
PIP-45Ab-2   (34)   DACVQQQLVFNPKSGGFLPINNFNATGQSFMNCFGWQLFIALNWPVNPGW
PIP-45Ac-2   (34)   DACVQQQLVFNPASGGFLPVNNFNATGQSFMNCFGWQLFIALNWPVNPGW
PIP-45Ad-2   (34)   DACVQQQLVFNPKSGGFLPVNNFNATGQSFMNCFGWQLFIALNWPVNPGW
PIP-45Ae-2   (34)   DACVQQQLVFNPKSGGFLPINNFNATGQSFMNCFGWQLFIALNWPVNPGW
PIP-45Af-2   (34)   DACVQQQLVFNPKSGGFLPINNFNATGQSFMNCFGWQLFIALNWPVNPGW
PIP-45Ba-2   (35)   DTCVQQQLVFNPASGGFLPVNNFNATSQAFMNCFGWQLFIALNWPVNPGW
PIP-45Bb-2   (34)   DTCVQQQLVFNPASGGFLPVNNFNATSQAFMNCFGWQLFIALNWPVNPGW
PIP-45Bc-2   (35)   DTCVQQQLVFNPASGGFLPVNNFNATSQAFMNCFGWQLFIALNWPVNPGW
PIP-45Bd-2   (34)   DACVQQQLVFNPASGGFLPVNNFNATSQAFMNCFGWQLFIALNWPVNPGW
PIP-45Be-2   (30)   DTCVQQQLVFDPNSGGFLPVNNFNTTGQSFMNCFGWQLFIALNWPVDPGW
PIP-45Bf-2   (30)   DNCVQQQLVFNPKSGGFMPVNNFNTTGQSFMNCFGWQLFIALNWPVDPGW
PIP-45Bg-2   (34)   DTCVQKQLVFNPASGGFLPVNNFNATSQAFMNCFGWQLFIALNWPVNPGW
PIP-45Bh-2   (34)   DTCVQQQLVFNPASGGFLPVNNFNATSQAFMNCFGWQLFIALNWPVNPGW
PIP-45Bi-2   (34)   DTCVQKQLVFNPASGGFLPVNNFNATSQAFMNCFGWQLFIALNWPVNPGW
PIP-45Bj-2   (34)   DSCVQQQLVFNPASGGFLPVNNFNATSQAFMNCFAWQLFIALNWPVNLGW
PIP-45Bk-2   (34)   DACVQQQLVFNPASGGFLPVNNFNASNQAFMNCFAWQLFIALNWPVNPGW
PIP-45Bl-2   (34)   DSCVQQQLVFNPASGGFLPVNNFNATNQAFMNCFAWQLFIALNWPVNPGW
PIP-45Bm-2   (34)   DACVQQQLVFNPASGGFLPVNNFNATSQAFMNCFGWQLFIALNWPVNPGW
PIP-45Ca-2   (38)   AQSCVSQLVFDPTSGGFLPVNNFG-TEQAFLNCFGWQLFIAMNWPVNPGW
PIP-45Cb-2   (38)   AQSCVSQLVFDPTSGGFLPVNNFG-TEQDFLNCFGWQLFIAMNWPVNPGW
PIP-45Cc-2   (37)   AQTCVQQLVFDPASGGFLPVNNFG-TEQDFLNCFGWQLFIAMNWPVNPGW
PIP-45Cd-2   (37)   AQSCVSQLVFDPTSGGFLPVNNFG-TEQDFLNCFGWQLFIAMNWPVNPGW
PIP-45Ce-2   (37)   AQSCVSQLVFDPTSGGFLPVNNFG-TEQDFLNCFGWQLFIAMNWPVNPGW
PIP-45Cf-2   (38)   AQSCVSQLVFDPTSGGFLPVNNFG-TEQAFLNCFGWQLFIAMNWPVNPGW
PIP-45Da-2   (42)   PAQCVQQLVFDPTNGSFLTSDTPFVAQQATFNCYAWQMFIAMNWPVNPGW
PIP-45Db-2   (49)   AQQCPDQLVFDPTSGSFMTSDNLFLPTQQGNNCYAWQMFIAMNWPVSSSW
PIP-45Ea-2   (26)   QTACSAMLITDPTSADFLTGDTPFGHTQDGMNCYGWQMFLSLNWPADPGW
PIP-45Ga-2   (40)   SSAPISFPCLNKPAVNYNTPGDTPITSQDGVNCFAWQTFIGLNWPVDASH
```

Fig. 2c

```
                 101                                                150
PIP-45Aa-2  (84) PATPALAGEPDMNSTLAQFGVPTASGQPMSVAPVWASYKDANDIELPGAP
PIP-45Ab-2  (84) PATPALAGEPDMNSTLAQFGVPTASGQPMSVAPVWASYKDANDIELPGAP
PIP-45Ac-2  (84) PATPALAGEPDMHSSLAQFGVPPASGQPMTVAPVWASYKDANDIELPGAP
PIP-45Ad-2  (84) PTTAALAGEPDMNSSLAQFGVPTTAGQPMTVAPVWASYKDANDIELPGAP
PIP-45Ae-2  (84) PATPALAGEPDMNSTLAQFGVPTASGQPMSVAPVWASYKDANDIELPGAP
PIP-45Af-2  (84) PATPALAGEPDMNSTLAQFGVPPASGQPMSVAPVWASYKDANDIELPGAP
PIP-45Ba-2  (85) PATASLAGEPDMQSTLAQFGVPSAPGQPMSVAPVWASYKDANDIELPGAP
PIP-45Bb-2  (84) PATASLAGEPDMQSTLAQFGVPSAPGQPMSVAPVWASYKDANDIELPGAP
PIP-45Bc-2  (85) PATASLAGEPDMQSTLAQFGVPSTPGQPMSVAPVWASYKDANDIELPGAP
PIP-45Bd-2  (84) PATASLAGEPDMNSTLAQFGVPSAPGQPMSVAPVWASYKDANDIELPGAP
PIP-45Be-2  (80) PANAALAGEPNRKISMAQFGVPQVAGQPMTTAPVWASEKDANDIELPGAP
PIP-45Bf-2  (80) PANASLAGEPDRTITVAQFGVPTTAGQPMSVAPVWASYKDANEIELPGAP
PIP-45Bg-2  (84) PATASLAGEPDMQSTLAQFGVPSAPGQPMSVAPVWASYKDANDIELPGAP
PIP-45Bh-2  (84) PATASLAGEPDMQSTLAQFGVPSAPGQPMSVAPVWASYKDANDIELPGAP
PIP-45Bi-2  (84) PATASLAGEPDMQSTLAQFGVPSTPGQPMSVAPVWASYKDANDIELPGAP
PIP-45Bj-2  (84) EGTASLAGEPDLNSSLAQFGVPATPGQPMSVAPVWASYKDANDIELPGAP
PIP-45Bk-2  (84) PATASLAGEPDMNSTLAQFGVPSDPGQPMSVAPVWASYKDANDIELPGAP
PIP-45Bl-2  (84) PATASLAGEPDMNSTLAQFGVPSSPGQPMSVAPVWASYKDANDIELPGAP
PIP-45Bm-2  (84) PATPSLAGEPDRQSTLAQFGVPTTAGEPMSVAPVWASYKDANDIELPGAP
PIP-45Ca-2  (87) PANPSLAGEPDTQSSAAQFGVPPTPGQPMSNAPVWASYKDASEIELPGAA
PIP-45Cb-2  (87) PANASLAGEPDTQSSVAQFGVPATPGQPMSNAPVWASYKDASEIELPGAP
PIP-45Cc-2  (86) PADPTLAGEPDTQSSAAQFGVPQTPGKPMSNAPVWASYKDANDIELPGAP
PIP-45Cd-2  (86) PADPSLAGEPDTQSTAAQFGVPPTSGQPMGNAPVWASYKDASEIELPGAP
PIP-45Ce-2  (86) PANPSLAGEPDTQSTAAQFGVPPTPGQPMSNAPVWASYKDASEIELPGAP
PIP-45Cf-2  (87) PANPSLAGEPDTQSSAAQFGVPPTPGQPMSNAPVWASYKDASEIELPGAA
PIP-45Da-2  (92) PTHPELAGEPDTKSPAAQFGVPTIADQPMSVAPVWASYKDANDIELHGAA
PIP-45Db-2  (99) PGTPSAAGEPDQNVSVENWGVPENPTSPLTSVPVWGSFKDAQAIELPDAA
PIP-45Ea-2  (76) PQTPAMAGEPDRSATIADFCLPGPAGQPMQRPTVWQSFMPAPEIEKPFAA
PIP-45Ga-2  (90) P------GEPDKTASASVFGEPG-----LHQTSVWETYANSKSVERANAQ
```

Fig. 2d

```
                   151                                                200
PIP-45Aa-2 (134)  APTGWGVQTLVPSNCSTQGSLRAISVGARKFMTATSESAINARHGDHLSS
PIP-45Ab-2 (134)  APTGWGVQTLVPSNCSTQGSLRAMSVGARKFMTATSESAINARHGDHLSS
PIP-45Ac-2 (134)  VPTGWGVQTLVPSNCSTQGSLKAMAVGARKFMTATSESAINARHGDHLSS
PIP-45Ad-2 (134)  VPSGWGVQTLVPSNCSTQGSLKAMSVGARKFMTATSESAINARHGDHLSS
PIP-45Ae-2 (134)  VPTGWGVQTLVPSNCSTQGSLRAMSVGARKFMTATSESAINARHGDHLSS
PIP-45Af-2 (134)  APTGWGVQTLVPSNCSTQGSLRAMSVGARKFMTATSESAINARHGDHLSS
PIP-45Ba-2 (135)  TPTGWGVQTLVPSGCSTQGSLKALKVGARKFMNATSEGAINALHGDHLST
PIP-45Bb-2 (134)  TPTGWGVQTLVPSGCSTQGNLKALKVGARKFMNATSEGAINALHGDHLST
PIP-45Bc-2 (135)  TPTGWGVQTLVPSDCSTQGSLKTLKVGARKFMNATSEGAINALHGDHLST
PIP-45Bd-2 (134)  TPTGWGVQTLVPSGCSTQGSLKSLKVGARKFMNATSEGAINALHRDHLST
PIP-45Be-2 (130)  PPTGWGVQTLVPSNCSSEGSLKALSVGARKFMNATSESATNAKHRDHLSS
PIP-45Bf-2 (130)  KPSGWGVQTLVPPNCSSQDSLQALSVGARKFMNATSESATNAKHRDHLSS
PIP-45Bg-2 (134)  TPTGWGVETLVPSGCSTQGSLKALKVGARKFMNATSEGAINALHGDHLST
PIP-45Bh-2 (134)  TPTGWGVQTLVPSGCSTQGSLKALKVGARKFMNATSEGAINALHGDHLST
PIP-45Bi-2 (134)  TPTGWGVQTLVPSDCSTQGSLKTLKVGARKFMNATSEGAINALHGDHLST
PIP-45Bj-2 (134)  TPSGWGVQTLVPANCSTQGSLKALKVGARKFMNATSKSAINVLHGDHLSS
PIP-45Bk-2 (134)  KPSGWGVQTLVPSGCGTQGSLKALKVGARKFMNATSESAINAVHGDHLSS
PIP-45Bl-2 (134)  TPTGWGVQTMVPSGCSTQGSLKALKVGARKFMNATSEGAINALHGDHLST
PIP-45Bm-2 (134)  APTGWGVQTLVPSSCNSQGSLKALKVGARKFMNATSEGAINALHGDHLST
PIP-45Ca-2 (137)  KPSGWGVETLVPSNCTATGNLKAFATGARKFITATSESAINRKHRDHLSS
PIP-45Cb-2 (137)  KPSGWGLETLVPSNCTASGNLKAYATGARKFITATSESAINRKHRDHLSS
PIP-45Cc-2 (136)  KPTGWGVETLVPSNCTATGNLKALSTGARKFITATSESAINRKHRDHLSS
PIP-45Cd-2 (136)  KPSGWGVETLVPSNCTATGNLKAFATGARKFMAATSESAINRKHRDHLSS
PIP-45Ce-2 (136)  KPSGWGVETRVPSNCTATGNLKAFSTGARKFITATSESAINRKHRDHLSS
PIP-45Cf-2 (137)  KPSGWGVETLVPSNCTATGNLKAFATGARKFITATSESAINRKHRDHLSS
PIP-45Da-2 (142)  IPTAWGMQPPEPVGCQTKPSLLSLRVGARKFMTATSESAVNAKHRDHLSS
PIP-45Db-2 (149)  KPTDWGVPQAVPSGCKSDKMLLGYPAGSAKILTTLSKNAVNTAHRDHLSS
PIP-45Ea-2 (126)  MPTGWGETSPPPASCGSAS--LAASAGSIRMLNAVSKSAVSPRHGDNLDT
PIP-45Ga-2 (129)  PPLPWGHTPDVPSSCQKISQTLGLRVMQASRMPGSFNMSKEASQADPGNN
```

Fig. 2e

```
                201                                                  250
PIP-45Aa-2 (184) GTLASIPDPIMEASGGWLTDQSQNLVFFERKVGKAEFDYIVSKGLYDAAN
PIP-45Ab-2 (184) GTLASIPDPIMEASGGWLTDQSQNLVFFERKVGKAEFDYIVSKGLYDAAN
PIP-45Ac-2 (184) GTLASIPDPIMEASGGWLTDQSKNLVFFERKVGKAEFDYIVSKGLYDAAN
PIP-45Ad-2 (184) GTLATIPDPIMEASGGWLTDQAGQLVFFERKVGKAEFDYIVSKGLYDAAN
PIP-45Ae-2 (184) GTLASIPDPIMEASGGWLTDQSQNLVFFERKVGKAEFDYIVSKGLYDAAN
PIP-45Af-2 (184) GTLASIPDPIMEASGGWLTDQSQNLVFFERKVGKAEFDYIVSKGLYDAAN
PIP-45Ba-2 (185) GTLASIPDPVMEASGGWLTDQAGKLVFFERKVGKAEFDYIVDKGLYDAAN
PIP-45Bb-2 (184) GTLASIPDPVMEASGGWLTDQAGKLVFFERKVGKAEFDYIVDKGLYDAAN
PIP-45Bc-2 (185) GTLASIPDPVMEASGGWLTDQAGKLVFFERKVGKAEFDYIVDKGLYDAAN
PIP-45Bd-2 (184) GTLASIPDPVMEASGGWLTDQSGNLVFFERKVGKAEFDYIVDKGLYDAAN
PIP-45Be-2 (180) GTLASIPDPIMEAAGGWLTDQTGNLVYFERKVGKAEFDYIVKYGLYDAAN
PIP-45Bf-2 (180) GTLASIPDPIMEAAGGWLTDQTGNLVYFERKVGKAEFDYIVDNGLYDAAN
PIP-45Bg-2 (184) GTLASIPDPVMEASGGWLTDQAGKLVFFERKVGKAEFDYIVDKGLYDAAN
PIP-45Bh-2 (184) GTLASIPDPVMEASGGWLTDQAGKLVFFERKVGKAEFDYIVDKGLYDAAN
PIP-45Bi-2 (184) GTLASIPDPVMEASGGWLTDQAGKLVFFERKVGKAEFDYIVDKGLYDAAN
PIP-45Bj-2 (184) GTLASSPDPFMEASGGWLTDQSGNLVFFERKVGKAEFDYIVDNGLYDAAN
PIP-45Bk-2 (184) GTLASLPDSIMEASGGWLTDQAGNLVFFERKVGKAEFDYIVGKGLYDAAN
PIP-45Bl-2 (184) GTVASIPDPVMEASGGWLTDQSGNLVFFERKVGKAEFDYIVEKGLYDAAN
PIP-45Bm-2 (184) GTLASIPDPVMEASGGWLTDQSGNLVFFERKVGKAEFDYIVEHGLYDAAN
PIP-45Ca-2 (187) GTQVTLPDSIMEASGGWLTDQSGNLVFFERKVGKAEFDYIVDNGLYDAAN
PIP-45Cb-2 (187) GTQVTLPDSIMEASGGWLTDQSGNLVFFERKVGKAEFDYIVDNGLYDAAN
PIP-45Cc-2 (186) GTQVTLPDSIMEAAGGWLTDQSGNLVFFERKVGKAEFDYIVNNGLYDAAN
PIP-45Cd-2 (186) GTQVTLPDSIMEASGGWLTDQSGNLVFFERKVGKAEFDYIVDNGLYDAAN
PIP-45Ce-2 (186) GTQVTLPDSIMEASGGWLTDQSGNLVFFERKVGKAEFDYIVDNGLYDAAN
PIP-45Cf-2 (187) GTQVTLPDSIMEASGGWLTDQSGNLVFFERKVGKAEFDYIVDNGLYDAAN
PIP-45Da-2 (192) STLVTASDPTLEATGGWLTDQAGKLVYFERKVGKAEFDYIVSNELYDAAN
PIP-45Db-2 (199) GTRDTQSDEIMEATGGWLTDQNGNLVFFERKVGKAEFDYIMNNALYDAAY
PIP-45Ea-2 (174) GTMSSISDEIEEATGGWLTDQKGKLVFFERMIGKAEYDYIVAKGLYDAAN
PIP-45Ga-2 (179) ----------PN----WLADKSGNLVYYEILIGKDEYDYINNNGLYNANT
```

Fig. 2f

```
                      251                                                  300
PIP-45Aa-2  (234)  QLTVAQNLDNQNPGGLSLPIGEPMRSLPPNPVPQEQLGALEVKAAWRILT
PIP-45Ab-2  (234)  QLKVAQNLDNQNPGGLSLPIGEPMRSLPPNPVPQEQLGALEVKAAWRILT
PIP-45Ac-2  (234)  QLTVAQNLDNQNPGGLSLPIGEPMRSLPPDPVPQEQLGALEVKAAWRILT
PIP-45Ad-2  (234)  QLKVAQNLDNQNPGGLSLPIGEPMRSLPPTPVPQEQLGALEIKAAWRILT
PIP-45Ae-2  (234)  QLKVAQNLDNQNPGGLSLPIGEPMRSLPPNPVPQEQLGALEVKAAWRILT
PIP-45Af-2  (234)  QLKVAQNIDNQNPGGLSLPIGEPMRSLPPNPVPQEQLGALEVKAAWRILT
PIP-45Ba-2  (235)  QLKVAQNLDGQTPEGLSLPIGEPMRSLPTSPVPQEQLGAIEIKAAWRVLT
PIP-45Bb-2  (234)  QLKVAQNLDGQTPEGLSLPIGEPMRSLPTSPVPQEQLGAIEIKAAWRVLT
PIP-45Bc-2  (235)  QLKVARNLDGQTPEGLSLPIGEPMRSLPTSPVPQEQLGAIEIKAAWRVLT
PIP-45Bd-2  (234)  QLKVAQNQDGKTPEGLSLPIGEPMRSLPPSPVPQEQLGAIEIKAAWRVLT
PIP-45Be-2  (230)  QMVVAQNSDGNHPAGLSLPAGELMRSMPAQPLPQEQLGALEIKAAWRILT
PIP-45Bf-2  (230)  QLIVAQNSDGKHPAGLSLPAGELMRSMPTTPLPQEQLGALEIKAAWRILT
PIP-45Bg-2  (234)  QLKVAQNLDGQTPEGLSLPIGEPMRSLPTSPVPQEQLGAIEIKAAWRVLT
PIP-45Bh-2  (234)  QLKVAQNLDGQTPEGLSLPIGEPMRSLPTSPVPQEQLGAIEIKAAWRVLT
PIP-45Bi-2  (234)  QLKVARNLDGQTPEGLSLPIGEPMRSLPTSPVPQEQLGAIEIKAAWRVLT
PIP-45Bj-2  (234)  QLKVAQNQDGKSPAGLSLPAGEPMRSLPAAPVPQEQLGAIEVKAAWRVLT
PIP-45Bk-2  (234)  QLKVAQNADGTTPEGLSLPIGEPMRSLPPSPVPQEQLGAIEIKAAWRILT
PIP-45Bl-2  (234)  QLKVAQNLDGNTPEGLSLPLGEPMRSLPPTPVPQEQLGALEIKAAWRVLT
PIP-45Bm-2  (234)  QLKLAQ------TEGLSLPIGEAMRELPPSPVPQEQLGAIEIKAAWRVLT
PIP-45Ca-2  (237)  QLIVAQNSDNRHPAGLSLPAGKPVRELPAKALPQEELGALEIKAAWRVLT
PIP-45Cb-2  (237)  QLIVAQNSDNRHPAGLSLPAGKLVRELPAQALPQEELGALEIKAAWRVLT
PIP-45Cc-2  (236)  QLIVAQNSDNRHPAGLSLPAGKLVRELPAKALPQEELGALEIKAAWRVLT
PIP-45Cd-2  (236)  QLIVAQNSDNRHPAGLSLPAGKLVRELPAKALPQEELGALEIKAAWRVLT
PIP-45Ce-2  (236)  QLIVAQNSDNRHPAGLSLPAGKLVRELPAQALPQEELGALEIKAAWRVLT
PIP-45Cf-2  (237)  QLIVAQNSDNRHPAGLSLPAGKLVRELPAKALPQEELGALEIKAAWRVLT
PIP-45Da-2  (242)  QLQVAKN------QGLSLPAGAHFRSPPTSPIAQEKLGAFEIKAAWRILT
PIP-45Db-2  (249)  QMRVATNADGRHPAGLSLPSGKFLRVPPTEPQGDALGAFEIKAAWRVLT
PIP-45Ea-2  (224)  QLKVATNADGATPEGLSLPKGTPPGS---AVQNQDELGAFEIKAAWRNLT
PIP-45Ga-2  (215)  QAAHIQQ--N---KNIAMPLG----------HDKVLGGLEIKAAWLSVS
```

Fig. 2g

```
                       301                                                350
PIP-45Aa-2    (284)    G-KPELYGRYLTTVAWLKNPATLQCTQQVVGLVGLHIINKTQASPNFIWT
PIP-45Ab-2    (284)    G-KPELYGRYLTTVAWLKNPATLQCTQQVVGLVGLHIINKTQASPNFIWT
PIP-45Ac-2    (284)    G-KPELYGRYLTTVAWLKNPATLQCTQQVVGLVGLHIINKTQASPNFIWT
PIP-45Ad-2    (284)    G-KPELYGRYLTTVAWLKNPATLQCTQQVVGLVGLHIINKTQASPNFIWT
PIP-45Ae-2    (284)    G-KPELYGRYLTTVAWLKNPATLQCTQQVVGLVGLHIINKTQASPNFIWT
PIP-45Af-2    (284)    G-KPELYGRYLTTVAWLKNPATLQCTQQVVGLVGLHIINKTQASPNFIWT
PIP-45Ba-2    (285)    G-KPELFGRYLTTVAWLKRPDTLECTQEVVGLVGLHIINKTQASPNFIWT
PIP-45Bb-2    (284)    G-KPELFGRYLTTVAWLKRPDTLECTQEVVGLVGLHIINKTQASPNFIWT
PIP-45Bc-2    (285)    G-KPELFGRYLTTVAWLKRPDTLECTQEVVGLVGLHIINKTQASPNFIWT
PIP-45Bd-2    (284)    G-KPELFGRYLTTVAWLKRPDTLNCTQEVVGLVGLHIINKTQASPNFIWT
PIP-45Be-2    (280)    G-KPQLYGRYLTTVAWLKNPATLQCTQQVVGLVGLHIINKTQSSPNFIWT
PIP-45Bf-2    (280)    G-QPQLYGRYLTTVAWLKNPATLQCTQQVVGLVGLHIINKTQSSPNFIWT
PIP-45Bg-2    (284)    G-KPELFGRYLTTVAWLKRPDTLECTQEVVGLVGLHIINKTQASPNFIWT
PIP-45Bh-2    (284)    D-KPELFGRYLTTVAWLKRPDTLECTQEVVGLVGLHIINKTQASPNFIWT
PIP-45Bi-2    (284)    G-KPELFGRYLTTVAWLKRPDTLECTQEVVGLVGLHIINKTQASPNFIWT
PIP-45Bj-2    (284)    G-KPELFGRYLTTVAWLKRPDTLACTQEVVGLVGLHIINKTQASPNFIWT
PIP-45Bk-2    (284)    G-KPELFGRYLTTVAWLKRPDTLTCTQEVVGLVGLHIINKTQASPNFIWT
PIP-45Bl-2    (284)    G-KPELFGRYLTTVAWLKRPDTLECTQEVVGLVGLHIINKTQASPNFIWT
PIP-45Bm-2    (278)    G-KPELFGRYLTTVAWLKRPDTLACTQEVVGLVGLHIINKTQASPNFIWT
PIP-45Ca-2    (287)    N-KPDLYGRYLTTVAWLQRPDTLQCTQEVIGLVGLHIINKTQTQPNFIWT
PIP-45Cb-2    (287)    N-KPELYGRYLTTVAWLQRPDTLQCTQEVVGLVGLHIINKTQTQPNFIWT
PIP-45Cc-2    (286)    H-KPELYARYLTTVAWLQRPDTLQCTQEVVGLVGLHIINKTQTQPNFIWT
PIP-45Cd-2    (286)    N-KPQLYGRYLTTVAWLQRPDTLQCTQEVVGLVGLHIINKTQTQPNFIWT
PIP-45Ce-2    (286)    N-KPELYGRYLTTVAWLQRPDTLQCTQEVVGLVGLHIINKTQTQPNFIWT
PIP-45Cf-2    (287)    N-KPALYGRYLTTVAWLQRPDTLQCTQEVIGLVGLHIINKTQTQPNFIWT
PIP-45Da-2    (286)    D-KPQLYDRYLTTVTWLKHPETGQCTQEVVGLVGLHIIHKTASQPDFIWT
PIP-45Db-2    (299)    G-QSDIYDRYLTSVAWLKRPDTGECSQEVVGLVGLHIIHKTDTPPDLIWA
PIP-45Ea-2    (271)    G-LDDLYGRYLTSTVYLLYPD-GSCEKAVVGLVGLHIIHKTASMPDFVWS
PIP-45Ga-2    (249)    DPQNPKWKNYKLSTSVIYDPVSKDCHASTIALVGMHIIRKTASQPQWIWA
```

Fig. 2h

```
                351                                                    400
PIP-45Aa-2 (333) TFEQVDNVPEPNQVPPQQTPPDSFAGNNPNCGTGP---------ECTPNV
PIP-45Ab-2 (333) TFEQVDNVPEPDQVPPQQTPPDSFAGNNPNCGTGP---------ECTPNV
PIP-45Ac-2 (333) TFEQVDNVPEPDQVPPQQTPPDSFAGNNPNCGTGP---------ECTPNV
PIP-45Ad-2 (333) TFEQVDNVPEPNQLPPQQTPPDSFAGNNPNCGTGP---------ECTPNV
PIP-45Ae-2 (333) TFEQVDNVPEPNQVPPQQTPPDSFAGNNPNCGTGP---------ECTPNV
PIP-45Af-2 (333) TFEQVDNVPEPNQVPPQQTPPDSFAGNNPNCGTGP---------ECTPNV
PIP-45Ba-2 (334) TFEQVDNVPEPAQVPPQQTPPNGFAGNNPDCGDGP---------ECTPNQ
PIP-45Bb-2 (333) TFEQVDNVPEPAQVPPQQTPPNGFAGNNPDCGDGP---------ECTPNQ
PIP-45Bc-2 (334) TFEQVDNVPEPAQVPPQQTPPNGFAGNNPDCGNGP---------ECTPNQ
PIP-45Bd-2 (333) TFEQVDNVPEPAQAPPQQTPPNGFAGNNPDCGSGP---------ECTPNQ
PIP-45Be-2 (329) TFEQVDNVQEPGQVPAQQTPPDGFTGYNPNCTGGPD--------VCTPNV
PIP-45Bf-2 (329) TFEHVDNVPEPGQVPAQQLPPDGYTGNNPNCTGGPD--------VCTPNV
PIP-45Bg-2 (333) TFEQVDNVPEPAQVPPQQTPPNGFAGNNPDCGDGP---------ECTPNQ
PIP-45Bh-2 (333) TFEQVDNVPEPAQVPPQQTPPNGFAGNNPDCGNGP---------ECTPNQ
PIP-45Bi-2 (333) TFEQVDNVPEPAQVPPQQTPPNGFAGNNPDCGNGP---------ECTPNQ
PIP-45Bj-2 (333) TFEQVDNVPEPAQAPPQQTPPNGFAGNNPDCGSGP---------ECTPNQ
PIP-45Bk-2 (333) TFEQVDNVPEPGQVPPQQTPPNGFAGNNPDCGSGP---------ECPNQ
PIP-45Bl-2 (333) TFEQVDNVPEPDQAPPQGTPPNGFSGNNPDCGSGP---------ACEPNV
PIP-45Bm-2 (327) TFEQVDNVPEPAQVPPQQTPPGGFAGNNPECGTGP---------ECKPNV
PIP-45Ca-2 (336) TFEQIDNVPDGAAPPQ-----GYSGNNPECTGDA----------CAPNV
PIP-45Cb-2 (336) TFEQVDNVPDAGPTPPQ-----GYSGNNPACSGTA----------CTPNV
PIP-45Cc-2 (335) TFEQVDNVPDGATPPQ-----GYSGNNPACTGDA----------CTPNV
PIP-45Cd-2 (335) TFEQVDNVPDNGTAAPE-----GYSGNNPTCTGDA----------CTPNV
PIP-45Ce-2 (335) TFEQVDNVPDGATPPG-----GYSGNNPACTGDT----------CTPNV
PIP-45Cf-2 (336) TFEQVDNVPDGAAPPE-----GYSGNNPACTGDA----------CTPNV
PIP-45Da-2 (335) TFEHVDNVPDGGSTPTA-----GYTGNNPKCTGPD----------CTPNQ
PIP-45Db-2 (348) TFEQVDNVPDGQATLPP----GGYSGNNPNCTGPD----------CKPNQ
PIP-45Ea-2 (319) TFEQIDNVPGASAPEVD------FSGNNPASNAKP--------------
PIP-45Ga-2 (299) TFEHKDNAPDTASIKSDGTVDGDYTGYSNSCTVKPVPAGCKAKVENGTSV
```

Fig. 2i

```
                        401                                                    450
PIP-45Aa-2  (374)  ARIQCKQHHPDRDCTEPF--PRDQPVQTTREHPLPT----ELQALNGAVQ
PIP-45Ab-2  (374)  ARIQCKQQHPDRDCTEPF--PRDQPVQTTREHPLPT----ELQALNGAVQ
PIP-45Ac-2  (374)  ARIQCKQHHPDRDCTEPY--PRDQPVQTTREHPLPT----ELQALNGAVQ
PIP-45Ad-2  (374)  ARIQCQQHHPDRDCTEPY--PRDQPVQTTREHPLPT----ELQALNGAVQ
PIP-45Ae-2  (374)  ARIQCKQQHPDRDCTEPF--PRDQPVQTTREHPLPT----ELQALNGAVQ
PIP-45Af-2  (374)  ARIQCKQHHPDRDCTEPF--PRDQPVQTTREHPLPT----ELQALNGAVQ
PIP-45Ba-2  (375)  ARIQCKQTHPDKDCTDLF--PRDQPVQTTREHPVPG----DLQALNSAVQ
PIP-45Bb-2  (374)  ARIQCKQTHPDKDCTDLF--PRDQPVQTTREHPVPG----DLQALNSAVQ
PIP-45Bc-2  (375)  ARIQCKQTHPDKDCTDLF--PRDQPVQTTREHPVPG----DLQALNSAVQ
PIP-45Bd-2  (374)  ARIQCKQHHPDKQCTDLF--PRDQPVQTTREHPIPS----DLQALNSAVQ
PIP-45Be-2  (371)  ARIQCQQHHPDRECTEPY--PRNQPVQTTREHPLPS----DMQALNGAVQ
PIP-45Bf-2  (371)  ARIQCKQHHPDRECTEPY--PRDQPVQTTREHPLSS----DMQALNGAVQ
PIP-45Bg-2  (374)  ARIQCKQTHPDKDCTDLF--PRDQPVQTTRVHPVPG----DLQALNSAVQ
PIP-45Bh-2  (374)  ARIQCKQTHPDKDCTDLF--PRDQPVQTTREHPVPG----DLQALNSAVQ
PIP-45Bi-2  (374)  ARIQCKQTHPDKDCTDLF--PRDQPVQTTREHPVPG----DLQALNSAVQ
PIP-45Bj-2  (374)  ARIQCKQHHPDKDCTDRF--PRDQPVQTTREHPVPG----DLQALNSAVQ
PIP-45Bk-2  (374)  PRIQCKQHHPDRDCTDLF--PRDQPVQTTREHPVPS----DLQALNGAVQ
PIP-45Bl-2  (374)  ARIQCKQYHPDKDCTDLF--PRDQPVQTTREHPVPS----DLQALNSAVQ
PIP-45Bm-2  (368)  ARIQCKQHHPDRDCSDLF--PRDQPVQTTREYPVPS----ALQALNSAVQ
PIP-45Ca-2  (371)  ARVQCDATHTPPDCT-----PLDQPVQATRLNATPQ----DMQALNTAVQ
PIP-45Cb-2  (371)  ARVQCDATHAPPNCT-----PLDQPVQATRVNATPQ----DLQALNTAVQ
PIP-45Cc-2  (370)  ARVQCDATHTPPNCT-----PFNQPVQATRANATPE----DMQALNTAVQ
PIP-45Cd-2  (370)  ARVQCDATHTPPDCT-----PLDQPVQATRVNATPQ----DLQMLNTAVQ
PIP-45Ce-2  (370)  ARVQCDATHTPPNCT-----PLDQPVQATRVNATPQ----DMQALNTAVQ
PIP-45Cf-2  (371)  PRVQCDATHTPPNCT-----PLDQPVQATRANATPQ----DMQALNTAVQ
PIP-45Da-2  (370)  RRITCTALGCKDNYP------RNEPVQVTREDSVPS----TINDLNTVVQ
PIP-45Db-2  (384)  PRIDCNDQNQCKDLY------PRDQPVQVTREQALTS----EMDTLNAGVA
PIP-45Ea-2  (348)  -------NQMPHCVNGVC--DYSLPIQVTREVAIPA----GVAQTNRDVQ
PIP-45Ga-2  (349)  TQTSCHVNVSPAYYLDTSGNCPAYPIQVSRDFAIKDSTDNHVASLNRAVQ
```

Fig. 2j

```
              451                                                500
PIP-45Aa-2  (418) ANFAQQSQGKSVFQYYKLINVLWTLTPNPPTQPEPGVSAQVPLSYGPFIS
PIP-45Ab-2  (418) ANFAQQSQGKSVFQYYKLINVLWTLTPNPPTQPEPGVSAQVPLSYGPFIS
PIP-45Ac-2  (418) ANFAQQSQGKSVFQYYKLINVLWTLTPNPPTQPEPGVSAQVPLSYGPFIS
PIP-45Ad-2  (418) ANFAQQSQGKSVFQYYKLINVLWTLTPNPPVQPEPGVSAAVPLSYGPFIS
PIP-45Ae-2  (418) ANFAQQSQGKSVFQYYKLINVLWTLTPNPPTQPEPGVSAQVPLSYGPFIS
PIP-45Af-2  (418) ANFAQQSQGKSVFQYYKLINVLWTLTPNPPTQPEPGVSAQVPLSYGPFIS
PIP-45Ba-2  (419) ANFAQHSQGKSVFQYYKLINVLWTLAPNPPS-PEPGANAQVPLSYGPFIS
PIP-45Bb-2  (418) ANFAQHSQGKSVFQYYKLINVLWTLAPNPPS-PEPGANAQVPLSYGPFIS
PIP-45Bc-2  (419) ANFAQHSQGKSVFQYYKLVNVLWTLAPNPPS-PEPGANAQVPLSYGPFIS
PIP-45Bd-2  (418) ANFAQHSQGQSVFQYYKLINVLWTLAPNPPS-PEPGANAQVPLSYGPFIS
PIP-45Be-2  (415) ANFAQQTNGQSVFQYYKLVNVLWITAPTAPD-PEPGAGAKVPLSYGAFIS
PIP-45Bf-2  (415) ASFAQQTNGQSVFQYYKLINVLWITAPTPPD-PEPGPNAKVPLSYGAFIS
PIP-45Bg-2  (418) ANFAQHSQGKSVFQYYKLINVLWTLAPNPPS-PEPGANAQVPLSYGPFIS
PIP-45Bh-2  (418) ANFAQHSQGKSVFQYYKLINVLWTLAPNPPS-PEPGANAQVPLSYGPFIS
PIP-45Bi-2  (418) ANFAQHSQGKSVFQYYKLVNVLWTLAPNPPS-PEPGANAQVPLSYGPFIS
PIP-45Bj-2  (418) ANFAQHSQGQSVFQYYKLINVLWTLAPNPPS-PEPGANAQVPLSYGPFIS
PIP-45Bk-2  (418) ATFAQHSQGKSVFQYYKLINVLWTLAPNPPS-PEPGANAPVPLSYGAYIS
PIP-45Bl-2  (418) SNFAQQTHGQSVFQYYKLINVLWTLAPNPPS-PEPGANAQVPLSYGPFIS
PIP-45Bm-2  (412) ANFAQQSQGQSVFQYYKLINVLWTLAPNPPS-PEPGANAQVPLSYGPFIS
PIP-45Ca-2  (412) QTFAQQTQGQSVFQYYKLVNVLWSKTPNAPNDPGPGPNVKVPLSYGPFVS
PIP-45Cb-2  (412) QTFAQKTQGQSVFQYYKLVNVLWSKTPNAPNDPGPGPNVKTPLSYGPFVS
PIP-45Cc-2  (411) QTFAQQTQGQSVFQYYKLVNVLWSKTPNAPNDPGPGPNVKTPLSYGPFVS
PIP-45Cd-2  (411) QTFAQKTQGQSVFQYYKLVNVLWSKTPNAPNDPGPGPNVKVPLSYGPFVS
PIP-45Ce-2  (411) QTFAQKTQGQSVFQYYKLVNVLWSKTPNAPNDPGPGPNVKVPLSYGPFVS
PIP-45Cf-2  (412) QTFAQQTQGQSVFQYYKLVNVLWSKTPNAPNDPGPGPNVQVPLSYGPFVS
PIP-45Da-2  (410) QAISTKTAGKSVFQYYKLVNVLWDASPHIPD-PEPGANATVPLVYGSFSS
PIP-45Db-2  (425) QKIASQTGGKSVFQYYKLVNVLWDGSPSPP-VMEPGANASIPLRYGTFES
PIP-45Ea-2  (385) QLLADRTGGKSVFQYYQLVNVLWDGAPTPPS-PEPGANAQVPLVYGTFQT
PIP-45Ga-2  (399) QLIAS-SNADSVYTHYQLVNVLWSSAAVNDN-APPGNPPLTPLSISGETP
```

Fig. 2I

```
                       551                              583
PIP-45Aa-2   (504)  SDFSFLENSADSASKNSLVKRVKAFQTLKDQP-
PIP-45Ab-2   (504)  SDFSFLENSADSASKKSLVKRVKAFQTLKDGSP
PIP-45Ac-2   (504)  SDFSFLENSADSASKKSLVKRVKAFETLKDQP-
PIP-45Ad-2   (504)  SDFSFLENSADSASKKSLVKRVKAFETLKDQP-
PIP-45Ae-2   (504)  SDFSFLENSADSASKKSLVKRVKAFQTLKDGSP
PIP-45Af-2   (504)  SDFSFLENSADSASKKSLVKRVKAFQTLKDQP-
PIP-45Ba-2   (504)  SDFSFLENSAGSASNKSLIKSVKAFETLKDRP-
PIP-45Bb-2   (503)  SDFSFLENSAGSASNKSLIKSVKAFETLKDRP-
PIP-45Bc-2   (504)  SDFSFLENSAGSASNKSLIKSVKAFETLKDRP-
PIP-45Bd-2   (503)  SDFSFLENSAGSASTKSLIKSVKAFQTLKDQP-
PIP-45Be-2   (500)  SDFSFLENNADSAKQKSLIKRVNAFETLKDGPP
PIP-45Bf-2   (500)  SDFSFLENNADSAKHTSLIKRVHAFETLKDGQP
PIP-45Bg-2   (503)  SDFSFLENSAGSASNKSLIKSVKAFETLKDRP-
PIP-45Bh-2   (503)  SDFSFLENSAGSASNKSLIKSVKAFETLKDRP-
PIP-45Bi-2   (503)  SDFSFLENSAGSASNKSLIKSVKAFETLKDRP-
PIP-45Bj-2   (503)  SDFSFLENSADSASNKSLIKSVKAFETLKDLP-
PIP-45Bk-2   (503)  SDFSFLENSAGSASKHSLIKRVQAFETLKDRR-
PIP-45Bl-2   (503)  SDFSFLENSASSAGHKSLIKRVKAFETLKDRP-
PIP-45Bm-2   (497)  SDFSFLENTASSASQKSLIKRVKAFETLKDRP-
PIP-45Ca-2   (498)  SDFSFLGGNADSAKNTRLIKRIESFKTLKDNP-
PIP-45Cb-2   (498)  SDFSFLGGNADSAKNTRLIKRIEGFKTLKDDQ-
PIP-45Cc-2   (497)  SDFSFLGGSADSAKNTRLIKRIEAFKTLKDDH-
PIP-45Cd-2   (497)  SDFSFLGGNADSAKNARLIKRIEAFKTLKDSP-
PIP-45Ce-2   (497)  SDFSFLGGNADSAKNTRLIKRIEAFKTLKDNP-
PIP-45Cf-2   (498)  SDFSFLGSNADSAKNTRLIKRIESFKTLKDNP-
PIP-45Da-2   (496)  SDFSFLEESADSSKIPTLIKKMP---------
PIP-45Db-2   (510)  SDFSFIERDAGSAKNPSLVEEVKQFMEQAQ---
PIP-45Ea-2   (476)  SDFSFLESTASSATKLPGLFISRDFVP------
PIP-45Ga-2   (491)  TDYSFIESFATSPAAK-----------------
```

Fig. 3a

```
                  1                                                50
PIP-64Aa-1   (1)  ----------MGSITDHNQLLAWVASLDIPEASGVKTRSRN----VVARA
PIP-64Ba-1   (1)  ----------MGSITDHDQLIAWVQSLDIPEPTKSIARSRN----AVVRA
PIP-64Ca-1   (1)  ----------MGSITDHGKLLAWVESLDVPKSTGNANLKRASAVLRSAAQ
PIP-64Ea-1   (1)  ----------MSTITDHKQVLAWINALDIPDAPAGGNRVAAR-----ATS
PIP-64Eb-1   (1)  ----------MSTITDHKQVLAWINALDIPDAPAGGNRVAAR-----ASS
PIP-64Ec-1   (1)  ----------MSTITDHKQVLAWINALDIPDAPAGGNRVTAR-----ATS
PIP-64Ga-1   (1)  MNTNALDFVLKTPIETTADLAPLLERLKGVPDHGQSKRK--------TML
PIP-64Ha-1   (1)  ----------MSFEVCDSSVAACVARLESYDIYPDISPR-----SLYSGD
PIP-64Hb-1   (1)  ----------MSFEMCDSAVAACVARLESYDIYPDVSPR-----SLYVDD
PIP-64Hc-1   (1)  ---------MSVNMIDSATVAACVRRLESYEIDEVPVVRSRA-FAASGIV
PIP-64Hd-1   (1)  ---------MNVHDVEDCTVAECIHRLESYELDGAEVMRPRS-FSVP--V 51                                               100
PIP-64Aa-1  (37)  NAEDEGAAVVRGSITSEVTGFSQCARDDVQNSTFLMQIAADKKFNPEKQR
PIP-64Ba-1  (37)  SSEEEGAAVVRGSVTSEVTGFKQCARDDVQNSTFLMQIAADKKYNPDTQR
PIP-64Ca-1  (41)  NSDEDGAAVVRGSITSEVTGFTPCARDDVQNSTFLMQIAADKKYNPDTQR
PIP-64Ea-1  (36)  SADEDGAVVAKASIPCEVSGFTECSRADVQNSTFLMQIAADKKYPNENDR
PIP-64Eb-1  (36)  SADEDGAVVAKASIPCEVSGFTECSRADVQNSTFLMQIAADKKYPDENDR
PIP-64Ec-1  (36)  SADEDGAVVAKASIPCEVSGFTECSRADVQNSTFLMQIAADKKYPNENDR
PIP-64Ga-1  (43)  TDNKVSAQVNAGSLISETERFDGCNKQDVQNSTFFAQIAADKHCNRYTAP
PIP-64Ha-1  (36)  IEPPAKGSVVGEGILAEAGGFSSCHQEDAQHAPFFASIVANRQYPLESQG
PIP-64Hb-1  (36)  VEPPAKGSVVGEGILAEAGGFSPCHQEDAQHAPFFASIVANRQYPLESQG
PIP-64Hc-1  (41)  VEEPSKGAVVGEGILSEVGNFSECNQVDAMHAPFFASIVANKQFPYEYQG
PIP-64Hd-1  (39)  VNEPGKGSIVGEGILSETGNFSECNREDVQHAPFFASIVANKKYPYEYQG 101                                              150
PIP-64Aa-1  (87)  EEWFKFYTDGLANLGWGRVSSYYQSYQPRNTNVTMDQVVLEVIAAVVG--
PIP-64Ba-1  (87)  EEWFKFYTDGLANLGWGRVSSIYQKYNPRNTNVTMDEVVLEVIAAVVG--
PIP-64Ca-1  (91)  EEWFKFYTDGLANLGWGRVSSAYQRYKPTNTNATMDQVVLEIISSVVS--
PIP-64Ea-1  (86)  EKWFKFYSDGLTNLGWGSSSSFFERFQPKNTDVTMDQVVLEVILTVVNN-
PIP-64Eb-1  (86)  EKWFKFYSDGLTNLGWGSSSSFFERFQPKNTDVTMDQVVLEVILTVVNN-
PIP-64Ec-1  (86)  EKWFKFYSDGLTNLGWGSSSSFFERFQPKNTDVTMDQVVLEVILTVVNN-
PIP-64Ga-1  (93)  MDYRFYVNVLGQIGWNQPAFAFDTYTSGASTVKLDEAVLGIIAQIATVG-
PIP-64Ha-1  (86)  REWYYKFVEVMTNAGWVATQRFYDDLSIAGNTVRMDKLVLDILASVVSGI
PIP-64Hb-1  (86)  REWYYKFVEVMTNAGWVATQRFYDDLSVGGNTVRMDKLVLDILASVVSGI
PIP-64Hc-1  (91)  KEYYKFVEVMTSAGWLTSQKYYNDIEISGNTVRMDQLVLEILGSVVAGL
PIP-64Hd-1  (89)  KEWYYQFLEVMTHAGWLPTSKYYNDMNISGNTVRMDQLVLEILGSVVAGL
```

Fig. 3b

```
              151                                                 200
PIP-64Aa-1 (135) -----ADSAVYKVTEKTFSSLQDNPKNQAPLKLFDSSSTRDSVGTFQILP
PIP-64Ba-1 (135) -----ADSAVYKVTEKTFAAIESNPKNQGALKLFDSTTTRDDIGTFQILP
PIP-64Ca-1 (139) -----PESALYKVTEKTFLAIKNNPNNKDALKLFDVSSTRNDLGTFQILP
PIP-64Ea-1 (135) -----VNNPLYKIAQETFGAIN-KPANQKPMKLFDHSSTKEDRGKFQILP
PIP-64Eb-1 (135) -----VNNPLYKIAQETFGAIN-KPANQKPMKLFDHSSTKEDRGKFQILP
PIP-64Ec-1 (135) -----VNNPLYKIAQETFGAIN-KPANQKPMKLFDHSSTKEDRGKFQILP
PIP-64Ga-1 (143) ------EVALVAAAMKALSSLS---DTSKQMLIWDAKSNSENTGNFQIFP
PIP-64Ha-1 (136) ALGSATSALLLRVADSAITALQ---KKEKTLTLFERNLLEHGVGGMAAG-
PIP-64Hb-1 (136) ALGSATSALLLRVVDSAITALQ---KKEETLTLFERNLLEHGVGGMAAG-
PIP-64Hc-1 (141) AIPGTASALMLKVAGDAITALK---KKETALTLYERNLLEHGVGGMAAG-
PIP-64Hd-1 (139) AVPGSASVLMLKVAGDAITALK---KRETALTLYERNMLEHGVGGMAAG- 201                                                 250
PIP-64Aa-1 (180) VMQDRDGNVVMVLTTVNASTTVQRGSFLFWSWSKTTAWMYRAAQQTVLNE
PIP-64Ba-1 (180) VMQDRDGNVVMVLTTVNASTTVQKGSFLFWSWSKTTAWMYRAAQQTVLNE
PIP-64Ca-1 (184) VMQDKDGNVVTVLTCINAHTEVQKGSFLFWHWSSTSAEMYRAAQQVVLNQ
PIP-64Ea-1 (179) AGQDQHGTVSMVLTAINARTDIQSGSFLFWKWSKSTAWLYRAANLIVLNE
PIP-64Eb-1 (179) AGQDQHGTVSMVLTAINARTDIQSGSFLFWKWSKSTAWLYRAANLIVLNE
PIP-64Ec-1 (179) AGQDQHGTVSMVLTAINARTDIQSGSFLFWKWSKSTAWLYRAANLIVLNE
PIP-64Ga-1 (184) ADLLPNGDVVMMLDGMQFDAKRNEGRFLWVTWQSTSIKIQRAANKFVLNE
PIP-64Ha-1 (182) TCVEIDGEVSMLLGTVRFIRRNSATQVLFADWNSREVKLYKGESVFRKVP
PIP-64Hb-1 (182) TCVEIDGEVSMMLGTVRFIRRNSATQVLFADWNSREVKLYKGESVFRKVP
PIP-64Hc-1 (187) TCTEVNGEVTLALGTVRFIRKNTATQVLFMDWDSRDVQLYKGESVFRKVP
PIP-64Hd-1 (185) TCTEVNGEVTMALGTVRFIRKNTAKQVLFMDWDSREVKLYRGDSVFRKVP 251                      277
PIP-64Aa-1 (230) SVYATVRQSVIKKLGKNAEEFIDDLEI
PIP-64Ba-1 (230) SVYSRVRESVIQKLGKNAEDFIDGLDI
PIP-64Ca-1 (234) NVYATVRQSVLKKLGKNAEDFIDGLDI
PIP-64Ea-1 (229) SVYSKVRQAVIDKLGDNAVNFVLDLDI
PIP-64Eb-1 (229) SVYSKVRQAVIDKLGDNAVNFVLDLDI
PIP-64Ec-1 (229) SVYSKVRQAVIDKLGDNAVNFVLDLDI
PIP-64Ga-1 (234) GVYKGVRQAVIDKLGDRAIDMIANIEI
PIP-64Ha-1 (232) SIVERTRGIIIGRLGNHAVSKIEEYEI
PIP-64Hb-1 (232) SVVERTRDIIIGRLGNHAVSKIEEYEI
PIP-64Hc-1 (237) YIADQTRDLIRTKLGTNAVSKIEGYEI
PIP-64Hd-1 (235) YIVEQTRDTIRAKLGLNAKPKIEDYDI
```

Fig. 4a

```
                  1                                                50
PIP-64Aa-2    (1) MKLSADEVYVISGNLLSATPSLTDPTVLEDIANSNLLCQLAADKNQGTRF
PIP-64Ab-2    (1) MKLSTDEVYVISGNLLSATPSLTDPAVLEDIANSNLLCQLAADKNQGTRF
PIP-64Ba-2    (1) MALSADEVYVVSGNLLSAMPKLVDPVMFEDFANSNLLCQLAADKNQGTRF
PIP-64Ca-2    (1) MSFTAPEVHVVSGNLISAMPSVNSPQVLEDILESNLLCQMAADKSLGSRF
PIP-64Ea-2    (1) MAFSTEQTYVVSGNLISATTEDTNTLSYEDFIHSNLLAQMGADKKLGSRF
PIP-64Eb-2    (1) MAFSTEQTYVVSGNLISATTKDTNTLSYEDFIHSNLLAQMGADKKLGSRF
PIP-64Ec-2    (1) MAFSTEQTYVVSGNLISATTEDTNTLSYEDFIHSNLLAQMGADKKLGSRF
PIP-64Ha-2    (1) --MDKAYSIFVNAAAIVLVSSTVRGTGVEDLMNSVLLAQLVANKN--LQR
PIP-64Hb-2    (1) --MDKEYSVFVNAAAIVLAPCALRRTEVDDLMNSVLLAQLVADKS--LLR
PIP-64Hd-2    (1) --MSYEYSVLIVGACVVIIPAADGAAQYTDLVNSVLLAQLIANKK--IEK 51                                               100
PIP-64Aa-2   (51) IDPAAWLDFYRSSLGRLFWRISNSGTVSYAIPQLVHKITVKEVLEKTFYK
PIP-64Ab-2   (51) IDPAAWLDFYRNSLGKLFWRISNSGTVSYAIPQLVHKITVKEVLEKTFYK
PIP-64Ba-2   (51) VDPPAWLDFYRNALGKVFWRISNSGTVSFNIPPLVRSITIKEVLEKTFYK
PIP-64Ca-2   (51) NNPAAWLDFYRNSLGKLFWKITNFNTVSYPVPSPTRSVSVMGILEHTFFK
PIP-64Ea-2   (51) VDPAGWLSFFKNTVGNLFWNLSEQGTSTLKISAGTASITVQQILEQSFFK
PIP-64Eb-2   (51) VDPAGWLSFFKNTVGNLFWNLSEQGTSTLKISAGTASITVLQILEQSFFK
PIP-64Ec-2   (51) VDPAGWLSFFKNTVGNLFWNLSEQGTSTLKISAGTASITVLQILEQSFFK
PIP-64Ha-2   (47) IPSADWYASYMDVLSVAWVAGAKR-RKDLLPKQDAASSPVEWVTAIPLDD
PIP-64Hb-2   (47) APAVDWYATYLEVLSVAWISAAKR-RKDLQPQKEDTHSPLEWVAAIPLDD
PIP-64Hd-2   (47) APEIDWYNAYVEFLDDYWLRRTRA-RQDWSIAQDRVESVSDWVIAAISQD 101                                              150
PIP-64Aa-2  (101) TLDRPQRIRVEESIELLGEQSADSPSATLYSLKTQVNFNETTSSPGLLPH
PIP-64Ab-2  (101) NLDRPQRIRVEDSIELLGEQSVDSPSATLYSLKTQVNFNETTSSPGLLPH
PIP-64Ba-2  (101) TLDHEVSLQLDSSIERLEEQPEESAAARLYRAKTQVTYKSAVSDLAVRPH
PIP-64Ca-2  (101) VLAQPLRHQIEADIELLMELPLTSPASQLYTSKTHVEMSTRARS-SFDGR
PIP-64Ea-2  (101) RLNQAQIDSATASVDLFSQLSEDDPAFILYNAKSHAQISTATKVIKPPQK
PIP-64Eb-2  (101) RLNQAQIDSATASIDLFDQLPEDDPAFILYNVKSHAQISAAAKAIKPPQK
PIP-64Ec-2  (101) RLNQAQIDSATASVDLFSQLSEDDPAFILYNAKSHAQISAATKVIKPPQK
PIP-64Ha-2   (96) RPDQQQ--QIMAVLDRVAALPGSLPALSILRKHMQKPNEPEPTQ---SPS
PIP-64Hb-2   (96) QVDQQQ--RIMAVMERIAALPGSLPAMGIVRKHVQKQYEPDAAQ---SPS
PIP-64Hd-2   (96) AVDKGS--ATAATLQRLARLSGNEPAMGLLRGHMQKISTDESGD---VLA
```

Fig. 4b

```
                    151                                                       200
PIP-64Aa-2  (151)   SISSVNLQLSVVHSETCISVCSVYFKTSTRIGDDVFNQKFPVKELLGNVS
PIP-64Ab-2  (151)   SVSSVNLQLSVVHSETCISVCSVYFKTSTRIGDDVFNQKFPVKELLGNVS
PIP-64Ba-2  (151)   PISTINLQISAVQSGGKISVCSVYFTTSADIESDVFNQKFLVSQLGNVS
PIP-64Ca-2  (150)   SESVISLQISVVHSGSLISVCSVYFKTAEPVAADVFSQKFKVRDLLGNIS
PIP-64Ea-2  (151)   ETYSVNLQISIAHTGSEIALCNIFFQTSQAVSDELFTQKFAIKDLIGNIN
PIP-64Eb-2  (151)   ATYSVNLQISIAHTGSEIALCNVFFQTSQAVSDELFTQKFAIKDLIGNIN
PIP-64Ec-2  (151)   ETYSVNLQISIAHTGSEIALCNIFFQTSQAVSDELFTQKFAIKNLIGNIN
PIP-64Ha-2  (141)   ASSPVRLLVIVAHSPVSMTGICLQFNTGKAINANPWGQCFDGKDIDGCVS
PIP-64Hb-2  (141)   SSSPVRLLVIVAQSPVSMAGVYLQFNTAKVIEANPWRQCFDGKDIDGCVT
PIP-64Hd-2  (141)   PAKAVRLLVVIAQTPTSVASVYIELKTRQIISANPLAQRHLAEDVQCSVC 201                                                       250
PIP-64Aa-2  (201)   VSTFEAKLLESSYAGIRQSIIDKLGEDNIRENILLVPAVSPSLSNTRHAG
PIP-64Ab-2  (201)   VSTFEAKLLESSYASIRQSIIDKLGEDNIRENILLVPAVSPSLSNSRHAG
PIP-64Ba-2  (201)   VSTFDAKLLESSYAGIRQSVIEKLGPENIRENIIQVSAEVFSLAGPRHAG
PIP-64Ca-2  (200)   VNSFEADLLEGSYEGVRQQIKTKLGEANIRENILLIADNPIPVDELPHAN
PIP-64Ea-2  (201)   VFYLKALLSETNYGHIRQQVIEKLG-ENINTNIVLVADNSDKPSPPFSHR
PIP-64Eb-2  (201)   IFYLKAQLSETNYGQIRQQVIEKLG-ENINTNILLVADNSETPSPSPAE
PIP-64Ec-2  (201)   VFYLKALLSETNYGHIRQQVIEKLG-ENINTNIVLVADNSDKPSPSPTE
PIP-64Ha-2  (191)   ARYLRMQLSETLFAPAREVIARKVG-TVVGDNVVDITGAIEDSVVRPAEE
PIP-64Hb-2  (191)   ARYFRTQLSETLFAPAREVIARKVA-AAVGDNIVDITKAIDDSGVLPAEE
PIP-64Hd-2  (191)   MRYAAANLSETLYSPVRDAIALKVR-DKYQDNVAMLTLSDDASAMEICAV 251       269
PIP-64Aa-2  (251)   ALQFVQELDI----------
PIP-64Ab-2  (251)   ARQFVQELDI----------
PIP-64Ba-2  (251)   AKQFIQELEI----------
PIP-64Ca-2  (250)   AHQFLKGLDI----------
PIP-64Ea-2  (250)   GAQFHTQPENLIQQRTGPP
PIP-64Eb-2  (250)   ARSFIRSLKI----------
PIP-64Ec-2  (250)   ARSFIRSLKI----------
PIP-64Ha-2  (240)   VGR-----------------
PIP-64Hb-2  (240)   VCR-----------------
PIP-64Hd-2  (240)   D-------------------
```

Fig. 5a

```
                    1                                                 50
PIP-74Aa-1    (1)   MAKLTQFSTPADIQDFSDSPAQQERMNAAWSGNINRWVNAALVGDVWDLI
PIP-74Ab-1    (1)   MAKLTQFSTPADIQDFSDSPAQQERMNAAWSGNINRWVNAALVGDVWDLI
PIP-74Ca-1    (1)   MAKLAQFSPPARIQDFSNDPAQQECLNAAWSGNINRWVNAALLGDVWDRI 51                                                100
PIP-74Aa-1    (51)  NYGPRPAFYNPLDTDTPSTSVNAPITWNAFPGRIPALFPNQSANWLQWAD
PIP-74Ab-1    (51)  NYGPRPAFYNPLDTDTPSTSVNAPITWNAFPGRIPALFPNQSANWLQWAD
PIP-74Ca-1    (51)  NYGPRPAFYNPLVTDTPDTAGNVPITWNAFPGRLQALFPNQGASWQQWAD 101                                               150
PIP-74Aa-1    (101) QGVPANVTTNLCTQQSVPPAPYSPTGPRGWQDEYCEWSVTRNAAGQITSV
PIP-74Ab-1    (101) QGVPANVTTNLCTQQSIPAAPYSPTGPRGWQDEYCEWSVTRNAAGQITSV
PIP-74Ca-1    (101) QGVPDKVTTDLCSGKPIDPAPYSPTGPRGWQDEYCEWSVTRNGAGQITSV 151                                               200
PIP-74Aa-1    (151) MFTCENPEYWMTLWQVDPGKVLQRYQQLINPAVQLADLSLKDAQGQTVID
PIP-74Ab-1    (151) MFTCENPEYWMTLWQVDPGKVLQRYQQLINPAVQLADLSLKDAQGQTVID
PIP-74Ca-1    (151) MFTCENPEYWMTLWQVDPGKVLQIYQQVINPAVQLSDLCLKDSHGQTVND 201                                               250
PIP-74Aa-1    (201) PVTGAPCYNPLNKWNSGTQTLPGSGGAMHLTSSPNTLGAEYDLAAAATMP
PIP-74Ab-1    (201) PVTGAPCYNPLNKWNSGTQTLPGSGGAMHLTSSPNTLGAEYDLAAAATMP
PIP-74Ca-1    (201) PLTGQPCYNPLNKWNSGTRTLANSGGAMHLTSSPNTLGAEYDLAAAATMP 251                                               300
PIP-74Aa-1    (251) RELNNEPVTSASQLVCYARYGRIGRHSDPTIGQNVNQYVNYTSGLTEVRA
PIP-74Ab-1    (251) RELNNEPVTSASQLVCYARYGRIGRHSDPTIGQNVNQYVNYTSGLTEVRA
PIP-74Ca-1    (251) REKDHDPVTSAAALVCFARYGRIGRHSDPTIGQNVNQYANYTPTLPHPQA 301                                               350
PIP-74Aa-1    (301) TLTNPPGLYIQTPDFSGYTTPDGSPAAACWTINRGHLAQ--TSDDIDRIL
PIP-74Ab-1    (301) TLTNPPGLYIQTPDFSGYTTPDGSPAAACWTINRGHLAQ--TSDDIDRIL
PIP-74Ca-1    (301) TLADPPGLYMQTPQFSDYVTPDNTPAQTFWTVVRGSLKDPNTSEDIDRIL 351                                               400
PIP-74Aa-1    (349) HATFSVPAGKNFTVSDISINGAKIQYASQIAGTITMGLMATVFGNSGVTQ
PIP-74Ab-1    (349) HATFSVPAGKNFTVSDISINGAKIQYASQIAGTITMGLMATVFGNSGVTQ
PIP-74Ca-1    (351) HATFSVPPELGYTVSDIKIGNQPIRYGSQIAATITMALLATAFPNSGVVQ
```

Fig. 5b

```
                    401                                              450
PIP-74Aa-1  (399)   QPVAGTLDSDNPSPSVSALQPLSVFNAYRAQELASNEQALSIPILALAIR
PIP-74Ab-1  (399)   QPVAGTLDSDNPSPSVSALQPLSVFNAYRAQELASNEQALSIPILALAIR
PIP-74Ca-1  (401)   TPVGATLDNSNPSPSVSALQALAVFTAYRAQELASNEQPLSIPVLALAVS 451                                              500
PIP-74Aa-1  (449)   PGQQVDNIALLLNTSQTPNGASFSVVEGGVSISITGTQDLPGLDMSLYLV
PIP-74Ab-1  (449)   PGQQVDNIALLLNTSQTPNGASFSVVEGGVSISITGTQDLPGLDMSLYLV
PIP-74Ca-1  (451)   PGQQVSNIALLLNTSDTPDGAVFTVPEGGVSIRIDGTQALPNAELSLYQV 501                                              550
PIP-74Aa-1  (499)   SISADANAAPGDRTVLASVPGMASTQQAAIGLLTVGGPTLVTSQTGPSKP
PIP-74Ab-1  (499)   SISADANAAPGDRTVLASVPGMASTQQAAIGLLTVGGPTLVTSQTGPSKP
PIP-74Ca-1  (501)   TLCVDANAAIGDRSILASVPSMPATQQAAIGLLTVVAPPQVRLAGGPRKP

551
PIP-74Aa-1  (549)   NFRRGRG
PIP-74Ab-1  (549)   NFRRGRG
PIP-74Ca-1  (551)   HARHSR-
```

Fig. 6

```
                      1                                                  50
PIP-74Aa-2     (1)    MRRRPTVLLGLALLLGLPATQAMGAPLCGSPFVPSPTLQPTLAPPNFSAS
PIP-74Ab-2     (1)    MRRRPTVLLGLALLLGLPATQAMGAPLCGSPFVPSPTLQPTLANPNFSAS
PIP-74Ca-2     (1)    MRAILALLLYAGLSLAPVAARAAGNP-CGSPFSPEPVIQPVLANPQISNL 51                                                100
PIP-74Aa-2     (51)   DSAVDCFMWQTMVYLNWPATPGQRGVPNAAASLGSPGPSVWQTYKDYNEL
PIP-74Ab-2     (51)   DSAVDCFMWQTMVYLNWPATPGQRGVPNAAASLGSPGPSVWQTYKDYNEL
PIP-74Ca-2     (50)   DPSVDCFMWQTMVYLNWPAQAGQRGLPNTDAHLGDPGPTVWQTFKDFNEL 101                                               150
PIP-74Aa-2     (101)  YLPNGQQPPAWNDNFLSVQRLQTRGVARALPSIRLLNSTSKVFRAANANE
PIP-74Ab-2     (101)  YLPNGQQPPAWNDNFLSVQRLQTRGVARALPSIRLLNSTSKVFRAANANE
PIP-74Ca-2     (100)  YLPGGQRPAPWNDNFLTMQRLELRGVERPRPSIRLLNSTSKVFRNADASE 151                                               200
PIP-74Aa-2     (151)  SPALREIEQVGGGVLYDQAGSPVYYEMLVNEVNFDFIYNNQLYNPAQQNL
PIP-74Ab-2     (151)  SPALREIEQVGGGVLYDQAGSPVYYEMLVNEVNFDFIYNNQLYNPAQQNL
PIP-74Ca-2     (150)  QKALDEFKQVGGGVLYDQNGQPVYYEMLINQINFDYIYSNQLYNAAQQNL 201                                               250
PIP-74Aa-2     (201)  YAKQKGIVLPNNSIEIKAAWKVLS--DPDNPQRFLTAQALLPGSSTPVTV
PIP-74Ab-2     (201)  YAKQKGIVLPNNSIEIKAAWKVLS--APDNPQRFLTAQALLPGSSTPVTV
PIP-74Ca-2     (200)  HAAKQGIVLPSNSIELKAAWKVLSPQEAAPPLRFLTAQALLPGSQVPVTV 251                                               300
PIP-74Aa-2     (249)  GLVGLHVFQMPSSAFNQGFWATFQQLDNAPTVAGATPGAHYSFNNPQCAP
PIP-74Ab-2     (249)  GLVGLHVFQMPSSAFNQGFWATFQQLDNAPTVAGASPGAHYSFNNPQCAP
PIP-74Ca-2     (250)  GLVGLHVFQMPSKDFAQGFWATFSQVDNAPTLN-TPGQAHYSFNNPQCS- 301                                               350
PIP-74Aa-2     (299)  AQCPPNDKTSNPTQVVQNFPPTPEAQNINHYMQNLIAQQAPGSALQYYQL
PIP-74Ab-2     (299)  AQCPPNDKTSNPTQVVQNFPPTPEAQNINQYMQNLIAQQAPGSALQYYQL
PIP-74Ca-2     (298)  -QCPVNDLGSKPTQVVQVQANAVYAQAVNQYMQALIQQQAPNSALQYYQL 351                                               400
PIP-74Aa-2     (349)  VDVQWPTSPQAIGQPGATAPAPSGTPNHDTLINPVLETFLQANHKSCLGC
PIP-74Ab-2     (349)  VDVQWPTSPQAIGQPGATAPAPSGTPNHDTLINPVLETFLQTNHTSCLGC
PIP-74Ca-2     (347)  INVQWPNSSVPIGQPGQPTPAPTGSPSTDTLVNPVLETFMQVSNMSCLGC 401                                               450
PIP-74Aa-2     (399)  HVYASVAADGSNPPTHYQASFSFLLGHAKSPALGSNLKSLAQQIEDASLS
PIP-74Ab-2     (399)  HVYASVAADGSKPATDYQASFSFLLGHAKSPALGSNLKSLAQQIEDASLS
PIP-74Ca-2     (397)  HKSASVADNGTQPPSGYQASYSFLLGHAQNPPPQGSLKSLARQVEEASTA

451
PIP-74Aa-2     (449)  LQH
PIP-74Ab-2     (449)  LQH
PIP-74Ca-2     (447)  RQ-
```

Fig. 7

```
              1                                                  50
PIP-75Aa  (1) MKLSNVLLLSIVFAWQGMAFADTQK----SNAETLLSNDKPPLTQAAQEK
PIP-75Ba  (1) MKMSSVLLMSIAFVCQGMVFADTQK----SNTETLFSNDKPPLIQTAQEQ
PIP-75Da  (1) -MKTLVIAILTAVLCQGMAMADTQK----PATGALPANEKPPLVQPADEH
PIP-75Ea  (1) -MKTLVIAILTAVLCQGMAMAETQQ----PASGALPANEKPPLVLTADEK
PIP-75Ga  (1) MKKLLLIASLLVSISGANVFAQAPSSGDAPAAVAGKQDGASHKDTEQAAN
PIP-75Gd  (1) ----------------------MKLKYE----RIRIYVMKSLSIVITLASCLL
PIP-75Gb  (1) ---MQCNGAILKLLCAQRKDQFMNL----RIRTHAMKNLSILVVLSSCLL
PIP-75Gc  (1) ----MREEAILKLLCAQRKDQFMNS----RIRTHAMKNLSILVVLSSCLL
PIP-75Ge  (1) ----------------------MNS----RIRTYAMKNLSILVVLSSCLL 51                                                 100
PIP-75Aa  (47) EQENVEADRNECWSAKNCSGKILNNKDAHNCKLSG-GKSWRSKTTG----
PIP-75Ba  (47) EQKEVEVDRNQCWSAKNCSGKILNNKDAHNCKLSG-GKSWRSKTTG----
PIP-75Da  (46) KTSEANANRNECWSAKNCTGKILNNKDAHNCKNSG-GKSWRSKTTG----
PIP-75Ea  (46) KASEANADRNECWSARNCSGKILNNKDAHNCKNSG-GKSWRGKNSS----
PIP-75Ga  (51) VECDVNATVQQCSAAKCQGKVLSNRDAHNCKDKSGKGKSWHAAAQGGQPA
PIP-75Gd  (28) LPLTASAAAGTCYSAKNCSGKVLSHRDAHNCKVKDKGKSWRSDITG----
PIP-75Gb  (44) LPLTASAAAGTCYSAKNCSGKVLSHRDAHNCKVKDKGKSWRSDITN----
PIP-75Gc  (43) LPLTASAASGKCYSAKNCSGKVLSKRDAHNCKVKDRGKSWLSDVTG----
PIP-75Ge  (25) LPLTASAAAGTCYSAKNCSGKVLSHRDAHNCKVKDKGKSWRSDITG----

101
PIP-75Aa  (92)  QCTNL
PIP-75Ba  (92)  QCTNL
PIP-75Da  (91)  QCTNL
PIP-75Ea  (91)  QCTNL
PIP-75Ga  (101) ACQRM
PIP-75Gd  (74)  QCTNL
PIP-75Gb  (90)  QCTNL
PIP-75Gc  (89)  KCTNL
PIP-75Ge  (71)  KCTNL
```

Fig. 8a

```
                    1                                                  50
PIP-77Aa    (1)  MSAQEN--FVGGWTPYHKLTPKDQEVEKEALAGFVGVQYTPELVSTQVVN
PIP-77Ab    (1)  MSAQEN--FVGGWTPYHKLTPKDQEVEKEALAGFVGVHYTPEQVSTQVVN
PIP-77Ac    (1)  MSAQEN--FVGGWTPYHELTPKDREVEKEALAGFVGVQYTPEKVSTQVVN
PIP-77Ad    (1)  MSAQEN--FVGGWTPYHELTPKDREVEKEALAGFVGVHYTPEKVSTQVVN
PIP-77Ae    (1)  MSAQEH--FVGGWTPYHELTPKDKEVEKEALAGFVGVHYTPEKVSTQVVN
PIP-77Af    (1)  MSAQEN--FVGGWTPYHELTPKDREVEKEALAGFVGVNYTPEKVSTQVVN
PIP-77Ba    (1)  MSAQEN--LVGGWTPYHELTPKDQEVEDEALAGLVGVHYTAELVSTQVVN
PIP-77Bb    (1)  MSAQEN--LVGGWTPYHELTPKDQEVEDEALAGLVGVHYTAELVSTQVVN
PIP-77Bc    (1)  MSAQEN--LVGGWTPYHELTPKDQEVEDEALAGLVGVHYTAELVSTQVVN
PIP-77Bd    (1)  MSAQEN--LVGGWTPYHELTPKDQEVEDEALAGLVGVHYTAELVSTQVVN
PIP-77Be    (1)  MSAQEN--LVGGWTGYHELTPKDKEVEKEALEGLVGVHYTPELVSSQIVN
PIP-77Bf    (1)  MSAQEN--LVGGWTPYHELTPKDQEVEDVALAGLVGVHYTAELVSTQVVN
PIP-77Bg    (1)  MTAQEH--LVGGWTPYHKLTPKDQEVEKEALAGFVGVSYTPEBVSSQVVN
PIP-77Bh    (1)  MSAQEN--LVGGWTPYHELTPKDQEVEDEALAGLVGVHYTAELVSTQVVN
PIP-77Bi    (1)  MSAQEN--LVGGWTPYHVLTPKDQEVEDEALAGLVGVHYTAELVSTQVVN
PIP-77Ca    (1)  MSAQENHVGVGGWTAYHELTPKDHAVEKEALEGFVGVQYTPETVSTQVVA
PIP-77Ea    (1)  MSEQQT-LLPGGWTAYHPLTAQDRKVEEEALNGHLGVDYEPQKVKTQVVA
PIP-77Eb    (1)  MSNNET--IVGGWTAYNAITSAEREIENKAMEGFVGVSYMPETVSTQVVA
PIP-77Ec    (1)  --MSDQAVLVGGWTAYHRLTAEDQAVEQEALKGFVGVEYKPFEVSTQVVA
PIP-77Ed    (1)  --MSEQAVLVGGWTAYHKLTAEDQAVEDQALKGFVGVQYVPFEVCTQVVA
PIP-77Ee    (1)  --MSEQAVLVGGWTAYHKLTAEDQAVEDQALKGFVGVQYVPFEVSTQVVA
PIP-77Ef    (1)  --MSEQAVLLGGWTAYHKLSAKDQAVENQALEGFVGVQYTPFEVSTQVVA
PIP-77Eg    (1)  --MSEQAVLLGGWTAYHKLSAKDQAVENQALEGFVGVQYTPFEVSTQVVA
PIP-77Eh    (1)  --MSEQAVLLGGWTAYHKLSAKDQAVENQALEGFVGVQYTPFEVSTQVVA
PIP-77Ei    (1)  --MSEQAVLVGGWTAYHKLTAEDQAVENQAMKGFVGVQYVPFEVSTQVVA
PIP-77Ej    (1)  --MSEQAVLLGGWTAYHKLSAKDQAVEDLALKGFVGVQYQPFEVSTQVVA
```

Fig. 8b

```
                  51                                           94
PIP-77Aa  (49)  GTNYRYQSKATLP-GSSESWQAVVEIYAPIKGK--PHITQIHRI
PIP-77Ab  (49)  GTNYRYLSKATVP-GSSDSWQAVVEIYAPIKGK--PHITQIHRI
PIP-77Ac  (49)  GTNYRYLSKATVP-GSSDSWQAVVEIYAPIKGK--PHITQIHRI
PIP-77Ad  (49)  GTNYRYLSKATVP-GSSDSWQAVVEIYAPIKGK--PHITQIHRI
PIP-77Ae  (49)  GTNYRYLSKATLP-GSSDSWQAVVEIYAPIKGK--PHITQIHRI
PIP-77Af  (49)  GTNYRYLSKATVP-GSSDSWQAVVEIYAPIKGK--PHITQIHRI
PIP-77Ba  (49)  GTNYRYQTKATQP-GSSNSWQAVVEIYAPINGK--PHITQIIRI
PIP-77Bb  (49)  GTNYRYQAKATQP-GSPNSWQAVVEIYAPINGK--PHITQIIRI
PIP-77Bc  (49)  GTNYRYQAQATQP-GSPNSWQAVVEIYAPINGK--PHITQIIRI
PIP-77Bd  (49)  GTNYRYQAKATQP-GSPNSWQAVVEIYAPINGK--PYVTQIIRI
PIP-77Be  (49)  GTNYRYQTKATQP-GSSTSWQAIVEIYAPIKGK--PHITQIIRI
PIP-77Bf  (49)  GTNYRYQAKATQP-GSPNSWQAVVEIYAPINGK--PYVTQIIRI
PIP-77Bg  (49)  GTNYRYKSKATLP-GSPNGWQAIVEIYAPTNGK--PHITQIHRI
PIP-77Bh  (49)  GTNYRYQTKATQP-GSSNSWQAIVEIYAPINGK--PHITQIIRI
PIP-77Bi  (49)  GTNYRYQAKATQP-GSPNSWQAVVEIYAPINGK--PYVTQIIRI
PIP-77Ca  (51)  GTNYRYHSKAQQP-GSPAIWAAIVEIYAPLKGK--PHITQIIRI
PIP-77Ea  (50)  GTNYRFLCEASVP-PSTAVWEAIVEIYAPLPGQGAPHITQIIRI
PIP-77Eb  (49)  GMNYRFKCEASMP-PSEVLWEAIVEIYQPLKGI--PHITNITKI
PIP-77Ec  (49)  GMNYRYKCKTTVPLPTPIHGEAVVQIFQSLDGS--AHITSITPI
PIP-77Ed  (49)  GTNYRFKCKSTVPLAKPIHGEAVVQIFQSLDGS--AHITSITPI
PIP-77Ee  (49)  GTNYRFKCKSTVPLAKPIHGEAVVQIFKSLDGD--AHITSITPI
PIP-77Ef  (49)  GTNYRFKCKSTVPLPNPIHGEAVVQIFQALFPK--SMQLEWN--
PIP-77Eg  (49)  GTNYRFKCKTTVPLPNPIHGEAVVQIFQSLDGS--AHITSITPI
PIP-77Eh  (49)  GTNYRFKCKSTVPLPNPIHGEAVVQIFQSLDGS--AHITSITPI
PIP-77Ei  (49)  GTNYRFKCKSTVPLAKPIHGEAVVQIFKSLDGD--AHITSITPI
PIP-77Ej  (49)  GTNYRFKCKTTVPLPNPIHGEAVVQIFQSLDGS--AHITSITPI
```

INSECTICIDAL PROTEINS AND METHODS FOR THEIR USE

CROSS REFERENCE

This application is a Continuation of U.S. Ser. No. 16/567,200 filed Sep. 11, 2019, which is a Continuation of U.S. Ser. No. 16/259,270 filed Jan. 28, 2019, now U.S. Pat. No. 10,448,648, which is a Continuation of U.S. Ser. No. 15/543,689 filed Jul. 14, 2017, now U.S. Pat. No. 10,231,460, which is a 371 (National Stage) of PCT/US16/12473 filed Jan. 7, 2016, which claims the benefit of U.S. Provisional Application No. 62/103,787 filed Jan. 15, 2015, which are incorporated herein by reference in their entireties.

GOVERNMENT SUPPORT

The government has certain rights in the invention pursuant to Agreement No. LB09005376.

REFERENCE TO SEQUENCE LISTING SUBMITTED ELECTRONICALLY

A sequence listing having the file name "5914-PCT_seq_list.txt" created on Nov. 19, 2015, and having a size of 542 kilobytes is filed in computer readable form concurrently with the specification. The sequence listing is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues and seeds.

In particular, isolated or recombinant nucleic acid molecules are provided encoding *Pseudomonas* Insecticidal Protein-45-1 (PIP-45-1) polypeptides including amino acid substitutions, deletions, insertions, and fragments thereof, and combinations thereof. Additionally, amino acid sequences corresponding to the PIP-45-1 polypeptides are encompassed. Provided are isolated or recombinant nucleic acid molecules capable of encoding a PIP-45-1 polypeptide of SEQ ID NO: 1 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-45-1 polypeptides of SEQ ID NO: 1 as well as amino acid substitutions, deletions, insertions, fragments thereof and combinations thereof.

In particular, isolated or recombinant nucleic acid molecules are provided encoding *Pseudomonas* Insecticidal Protein-45-2 (PIP-45-2) polypeptides including amino acid substitutions, deletions, insertions, and fragments thereof, and combinations thereof. Additionally, amino acid sequences corresponding to the PIP-45-2 polypeptides are encompassed. Provided are isolated or recombinant nucleic acid molecules capable of encoding a PIP-45-2 polypeptide of SEQ ID NO: 2 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-45-2 polypeptides of SEQ ID NO: 2 as well as amino acid substitutions, deletions, insertions, fragments thereof and combinations thereof.

In particular, isolated or recombinant nucleic acid molecules are provided encoding *Pseudomonas* Insecticidal Protein-64-1 (PIP-64-1) polypeptides including amino acid substitutions, deletions, insertions, and fragments thereof, and combinations thereof. Additionally, amino acid sequences corresponding to the PIP-64-1 polypeptides are encompassed. Provided are isolated or recombinant nucleic acid molecules capable of encoding a PIP-64-1 polypeptide of SEQ ID NO: 53 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-64-1 polypeptides of SEQ ID NO: 53 as well as amino acid substitutions, deletions, insertions, fragments thereof and combinations thereof.

In particular, isolated or recombinant nucleic acid molecules are provided encoding *Pseudomonas* Insecticidal Protein-64-2 (PIP-64-2) polypeptides including amino acid substitutions, deletions, insertions, and fragments thereof, and combinations thereof. Additionally, amino acid sequences corresponding to the PIP-64-2 polypeptides are encompassed. Provided are isolated or recombinant nucleic acid molecules capable of encoding a PIP-64-2 polypeptide of SEQ ID NO: 54 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-64-2 polypeptides of SEQ ID NO: 54 as well as amino acid substitutions, deletions, insertions, fragments thereof and combinations thereof.

In particular, isolated or recombinant nucleic acid molecules are provided encoding *Pseudomonas* Insecticidal Protein-74-1 (PIP-74-1) polypeptides including amino acid substitutions, deletions, insertions, and fragments thereof, and combinations thereof. Additionally, amino acid sequences corresponding to the PIP-74-1 polypeptides are encompassed. Provided are isolated or recombinant nucleic acid molecules capable of encoding a PIP-74-1 polypeptide of SEQ ID NO: 73 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-74-1 polypeptides of SEQ ID NO: 73 as well as amino acid substitutions, deletions, insertions, fragments thereof and combinations thereof.

In particular, isolated or recombinant nucleic acid molecules are provided encoding *Pseudomonas* Insecticidal Protein-74-2 (PIP-74-2) polypeptides including amino acid substitutions, deletions, insertions, and fragments thereof, and combinations thereof. Additionally, amino acid sequences corresponding to the PIP-74-2 polypeptides are encompassed. Provided are isolated or recombinant nucleic acid molecules capable of encoding a PIP-74-2 polypeptide of SEQ ID NO: 74 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-74-2 polypeptides of SEQ ID NO: 74 as well as amino acid substitutions, deletions, insertions, fragments thereof and combinations thereof.

In particular, isolated or recombinant nucleic acid molecules are provided encoding *Pseudomonas* Insecticidal Protein-75 (PIP-75) polypeptides including amino acid substitutions, deletions, insertions, and fragments thereof, and combinations thereof. Additionally, amino acid sequences corresponding to the PIP-75 polypeptides are encompassed. Provided are isolated or recombinant nucleic acid molecules capable of encoding a PIP-75 polypeptide of SEQ ID NO: 79 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-75 polypeptides of SEQ ID NO: 79 as well as amino acid substitutions, deletions, insertions, fragments thereof and combinations thereof.

In particular, isolated or recombinant nucleic acid molecules are provided encoding *Pseudomonas* Insecticidal Protein-77 (PIP-77) polypeptides including amino acid substitutions, deletions, insertions, and fragments thereof, and combinations thereof. Additionally, amino acid sequences corresponding to the PIP-77 polypeptides are encompassed. Provided are isolated or recombinant nucleic acid molecules capable of encoding a PIP-77 polypeptide of SEQ ID NO: 88 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant PIP-77 polypeptides of SEQ ID NO: 88 as well as amino acid substitutions, deletions, insertions, fragments thereof and combinations thereof.

Methods are provided for producing the insecticidal polypeptides and for using these polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

Methods for detecting the nucleic acids and polypeptides of the embodiments in a sample are also included. A kit for detecting the presence of an insecticidal polypeptide of the disclosure or detecting the presence of a nucleotide sequence encoding an insecticidal polypeptide of the disclosure in a sample is provided. The kit may be provided along with all reagents and control samples necessary for carrying out a method for detecting the intended agent, as well as instructions for use.

The compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of the insecticidal polypeptides of the disclosure or nucleic acids encoding same in products or organisms.

BRIEF DESCRIPTION OF THE FIGURES

FIG. 1a-1m shows the amino acid sequence alignment of PIP-45Aa1 (SEQ ID NO: 1), PIP-45Ab1 (SEQ ID NO: 3), PIP-45Ac1 (SEQ ID NO: 5), PIP-45Ad1 (SEQ ID NO: 7), PIP-45Ae1 (SEQ ID NO: 9), PIP-45Af1 (SEQ ID NO: 11), PIP-45Ba1 (SEQ ID NO: 13), PIP-45Bb1 (SEQ ID NO: 15), PIP-45Bc1 (SEQ ID NO: 17), PIP-45Bd1 (SEQ ID NO: 19), PIP-45Be1 (SEQ ID NO: 21), PIP-45Bf1 (SEQ ID NO: 23), PIP-45Bg1 (SEQ ID NO: 25), PIP-45Bh1 (SEQ ID NO: 27), PIP-45Bi1 (SEQ ID NO: 29), PIP-45Bj1 (SEQ ID NO: 31), PIP-45Bk1 (SEQ ID NO: 33), PIP-45Bl1 (SEQ ID NO: 232), PIP-45Bm1 (SEQ ID NO: 234), PIP-45Ca1 (SEQ ID NO: 35), PIP-45Cb1 (SEQ ID NO: 37), PIP-45Cc1 (SEQ ID NO: 39), PIP-45Cd1 (SEQ ID NO: 41), PIP-45Ce1 (SEQ ID NO: 43), PIP-45Cf1 (SEQ ID NO: 236), PIP-45 Da1 (SEQ ID NO: 45), PIP-45Db1 (SEQ ID NO: 47), PIP-45Ea1 (SEQ ID NO: 49), and PIP-45Ga1 (SEQ ID NO: 51). The amino acid diversity between the PIP-45-1 polypeptide homologs is indicated with shading.

FIG. 2a-2l shows an alignment of the amino acid sequences of PIP-45Aa2 (SEQ ID NO: 2), PIP-45Ab2 (SEQ ID NO: 4), PIP-45Ac2 (SEQ ID NO: 6), PIP-45Ad2 (SEQ ID NO: 8), PIP-45Ae2 (SEQ ID NO: 10), PIP-45Af2 (SEQ ID NO: 12), PIP-45Ba2 (SEQ ID NO: 14), PIP-45Bb2 (SEQ ID NO: 16), PIP-45Bc2 (SEQ ID NO: 18), PIP-45Bd2 (SEQ ID NO: 20), PIP-45Be2 (SEQ ID NO: 22), PIP-45Bf2 (SEQ ID NO: 24), PIP-45Bg2 (SEQ ID NO: 26), PIP-45Bh2 (SEQ ID NO: 28), PIP-45Bi2 (SEQ ID NO: 30), PIP-45Bj2 (SEQ ID NO: 32), PIP-45Bk2 (SEQ ID NO: 34), PIP-45Bl2 (SEQ ID NO: 233), PIP-45Bm2 (SEQ ID NO: 235), PIP-45Ca2 (SEQ ID NO: 36), PIP-45Cb2 (SEQ ID NO: 38), PIP-45Cc2 (SEQ ID NO: 40), PIP-45Cd2 (SEQ ID NO: 42), PIP-45Ce2 (SEQ ID NO: 44), PIP-45Cf2 (SEQ ID NO: 237), PIP-45 Da2 (SEQ ID NO: 46), PIP-45Db2 (SEQ ID NO: 48), PIP-45Ea2 (SEQ ID NO: 50), and PIP-45Ga2 (SEQ ID NO: 52). The amino acid diversity between the PIP-45-2 polypeptide homologs is indicated with shading.

FIG. 3a-3b shows the amino acid sequence alignment of PIP-64Aa1 (SEQ ID NO: 53), PIP-64Ba1 (SEQ ID NO: 238), PIP-64Ca1 (SEQ ID NO: 56), PIP-64Ea1 (SEQ ID NO: 58), PIP-64Eb1 (SEQ ID NO: 60), PIP-64Ec1 (SEQ ID NO: 62), PIP-64Ga1 (SEQ ID NO: 64), PIP-64Ha1 (SEQ ID NO: 65), PIP-64Hb1 (SEQ ID NO: 67), PIP-64Hc1 (SEQ ID NO: 69), and PIP-64Hd1 (SEQ ID NO: 71). The amino acid diversity between the PIP-64-1 polypeptide homologs is indicated with shading.

FIG. 4a-4b shows the amino acid sequence alignment of PIP-64Aa2 (SEQ ID NO: 54), PIP-64Ab2 (SEQ ID NO: 55), PIP-64Ba2 (SEQ ID NO: 239), PIP-64Ca2 (SEQ ID NO: 57), PIP-64Ea2 (SEQ ID NO: 59), PIP-64Eb2 (SEQ ID NO: 61), PIP-64Ec2 (SEQ ID NO: 63), PIP-64Ha2 (SEQ ID NO: 66), PIP-64Hb2 (SEQ ID NO: 68), PIP-64Hc2 (SEQ ID NO: 70), and PIP-64Hd2 (SEQ ID NO: 72). The amino acid diversity between the PIP-64-2 polypeptide homologs is indicated with shading.

FIG. 5a-5b shows an alignment of the amino acid sequences of PIP-74Aa1 (SEQ ID NO: 73), PIP-74Ab1 (SEQ ID NO: 75), and PIP-74Ca1 (SEQ ID NO: 77). The amino acid diversity between the PIP-74-1 polypeptide homologs is indicated with shading.

FIG. 6 shows an alignment of the amino acid sequences of PIP-74Aa2 (SEQ ID NO: 74), PIP-74Ab2 (SEQ ID NO: 76), and PIP-74Ca2 (SEQ ID NO: 78). The amino acid diversity between PIP-74-2 polypeptide homologs is indicated with shading.

FIG. 7 shows an alignment of the amino acid sequences of PIP-75Aa (SEQ ID NO: 79), PIP-75Ba (SEQ ID NO: 80), PIP-75 Da (SEQ ID NO: 81), PIP-75Ea (SEQ ID NO: 82), PIP-75Ga (SEQ ID NO: 83), PIP-75Gb (SEQ ID NO: 84), PIP-75Gc (SEQ ID NO: 85), PIP-75Gd (SEQ ID NO: 86), PIP-75Ge (SEQ ID NO: 87). The amino acid diversity between the PIP-75 polypeptide homologs is indicated with shading.

FIG. 8a-8b shows an alignment of the amino acid sequences of PIP-77Aa (SEQ ID NO: 88, PIP-77Ab (SEQ ID NO: 89), PIP-77Ac (SEQ ID NO: 90), PIP-77Ad (SEQ ID NO: 91), PIP-77Ae (SEQ ID NO: 92), PIP-77Af (SEQ ID NO: 240), PIP-77Ba (SEQ ID NO: 93), PIP-77Bb (SEQ ID NO: 94), PIP-77Bc (SEQ ID NO: 95), PIP-77Bd (SEQ ID NO: 96), PIP-77Be (SEQ ID NO: 97), PIP-77Bf (SEQ ID NO: 98), PIP-77Bg (SEQ ID NO: 99), PIP-77Bh (SEQ ID NO: 241), PIP-77Bi (SEQ ID NO: 242), PIP-77Ca (SEQ ID NO: 100), PIP-77Ea (SEQ ID NO: 101), PIP-77Eb (SEQ ID NO: 102), PIP-77Ec (SEQ ID NO: 103), PIP-77Ed (SEQ ID NO: 104), PIP-77Ee (SEQ ID NO: 105), PIP-77Ef (SEQ ID NO: 106), PIP-77Eg (SEQ ID NO: 107), PIP-77Eh (SEQ ID NO: 243), PIP-77Ei (SEQ ID NO: 244), and PIP-77Ej (SEQ ID NO: 245). The amino acid diversity between the PIP-77 polypeptide homologs is indicated with shading.

DETAILED DESCRIPTION

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise. The present disclosure is drawn to compositions and methods for controlling pests.

The methods involve transforming organisms with nucleic acid sequences encoding an insecticidal polypeptide of the disclosure. In particular, the nucleic acid sequences of the embodiments are useful for preparing plants and microorganisms that possess pesticidal activity. Thus, transformed bacteria, plants, plant cells, plant tissues and seeds are provided. The compositions are pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered insecticidal polypeptides by methods known in the art, such as site-directed mutagenesis, domain swapping or DNA shuffling. The insecticidal polypeptides of the disclosure find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) *PLoS Pathogens* 7:1-13); from *Pseudomonas protegens* strain CHAO and Pf-5 (previously *fluorescens*) (Pechy-Tarr, (2008) *Environmental Microbiology* 10:2368-2386; GenBank Accession No. EU400157); from *Pseudomonas Taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication Number US2014-0007292A1; an AfIP-1A and/or AfIP-1B polypeptide(s) of US Patent Publication Number US2014-0033361; a PHI-4 polypeptides of U.S. Ser. No. 13/839,702; PIP-47 polypeptides of PCT Serial Number PCT/US14/51063; a PHI-4 polypeptide of US patent Publication US20140274885 or PCT Patent Publication WO2014/150914; a PIP-72 polypeptide of PCT Serial Number PCT/US14/55128; the insecticidal proteins of U.S. Ser. No. 61/863,761 and 61/863,763; and δ-endotoxins including but not limited to: the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51, Cry52, Cry 53, Cry 54, Cry55, Cry56, Cry57, Cry58, Cry59. Cry60, Cry61, Cry62, Cry63, Cry64, Cry65, Cry66, Cry67, Cry68, Cry69, Cry70, Cry71 and Cry72 classes of δ-endotoxin genes and the *B. thuringiensis* cytolytic cyt1 and cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #I26149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #I12419); Cry1Ab12 (Accession #AAC64003); Cry1Ab13 (Accession #AAN76494); Cry1Ab14 (Accession #AAG16877); Cry1Ab15 (Accession #AAO13302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AAO39719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5

(Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #176415); Cry1Da3 (Accession #HQ439784); Cry1Db1 (Accession #CAA80234); Cry1Db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1 Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1 Ga1 (Accession #CAA80233); Cry1 Ga2 (Accession #CAA70506); Cry1Gb1 (Accession #AAD10291); Cry1 Gb2 (Accession #AAO13756); Cry1Gc1 (Accession #AAQ52381); Cry1 Ha1 (Accession #CAA80236); Cry1Hb1 (Accession #AAA79694); Cry1Hb2 (Accession #HQ439786); Cry1H-like (Accession #AAF01213); Cry1 a1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AAO13750); Cry2Aa10 (Accession #AAQ04263); Cry2Aa11 (Accession #AAQ52384); Cry2Aa12 (Accession #AB183671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658; Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession

AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #I15475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #I34543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8Db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9Db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #I32932); Cry21Aa2 (Accession #I66477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #I34547); Cry22Aa2 (Accession #CAD43579); Cry22Aa3 (Accession #ACD93211); Cry22Ab1 (Accession #AAK50456); Cry22Ab2 (Accession

CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30Db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EAO57254); Cry60Aa3 (Accession #EEM99278); Cry60Ba1 (Accession #GU810818); Cry60Ba2 (Accession #EAO57253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #ADO51070); Cry70Bb1 (Accession #EEL67276); Cry71Aa1 (Accession #JX025568); Cry72Aa1 (Accession #JX025569); Cyt1Aa (GenBank Accession Number X03182); Cyt1Ab (GenBank Accession Number X98793); Cyt1B (GenBank Accession Number U37196); Cyt2A (GenBank Accession Number Z14147); and Cyt2B (GenBank Accession Number U52043).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology*, 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; TIC853 toxins of U.S. Pat. No. 8,513,494, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), LSI Research Foundation, Washington D.C. at cera-gmc.org/index.php?action=gm_crop_database, which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

In some embodiments the insecticidal polypeptides of the disclosure include amino acid sequences deduced from the full-length nucleic acid sequences disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of insecticidal polypeptides of the disclosure. The protein resulting from translation of these insecticidal polypeptide genes allows cells to control or kill pests that ingest it.

Nucleic Acid Molecules, and Variants and Fragments Thereof

One aspect of the disclosure pertains to isolated or recombinant nucleic acid molecules comprising nucleic acid sequences encoding insecticidal polypeptides of the disclosure or biologically active portions thereof, as well as nucleic acid molecules sufficient for use as hybridization probes to identify nucleic acid molecules encoding proteins with regions of sequence homology. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecule encoding an insecticidal polypeptide can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding an insecticidal polypeptide of the disclosure has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an insecticidal polypeptide is a non-genomic sequence.

Polynucleotides encoding PIP-45-1 polypeptides are encompassed by the disclosure. A variety of polynucleotides encoding PIP-45-1 polypeptides are contemplated. One source of a polynucleotide encoding a PIP-45-1 polypeptide or related proteins is a bacterial strain that contains the polynucleotide of SEQ ID NO: 108, SEQ ID NO: 124, SEQ ID NO: 126, SEQ ID NO: 128, SEQ ID NO: 130, SEQ ID NO: 134, SEQ ID NO: 136, SEQ ID NO: 138, SEQ ID NO: 140, SEQ ID NO: 142, SEQ ID NO: 146, SEQ ID NO: 150, SEQ ID NO: 152, SEQ ID NO: 220 or SEQ ID NO: 222 that encode the PIP-45-1 polypeptide of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 and SEQ ID NO: 236, respectively. One source of a polynucleotide encoding a PIP-45-1 polypeptide or related proteins is from a *Pseudomonas*, *Thalassuspira*, *Paracoccus* or *Cellvibrio* strain. One source of a polynucleotide encoding a PIP-45-1 polypeptide or related proteins is from a *Pseudomonas* strain selected from but not limited to *Pseudomonas brenneri*, *Pseudomonas monteilii*, *Pseudomonas gessardii*, *Pseudomonas plecoglossicida*, *Pseudomonas putida*, *Pseudomonas poae*, *Pseudomonas trivialis*, *Pseudomonas libanensis*, *Pseudomonas fluorescens* and *Pseudomonas asplenii*.

In some embodiments the nucleic acid molecule encoding the PIP-45-1 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

In some embodiments the polynucleotide encodes a PIP-45-1 polypeptide sufficiently homologous to the amino acid sequence of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. As used herein the term "about" when used with sequence identity means±0.5%. In some embodiments the sequence homology is against the full length sequence of a PIP-45-1 polypeptide.

In some embodiments the polynucleotide encodes a PIP-45-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236.

In some embodiments the polynucleotide encodes a PIP-45-1 polypeptide having at least 99.1% or greater sequence identity compared to SEQ ID NO: 1. In some embodiments the polynucleotide encodes a PIP-45-1 polypeptide having at least 99.4% or greater sequence identity compared to SEQ ID NO: 17. In some embodiments the polynucleotide encodes a PIP-45-1 polypeptide having at least 99.6% or greater sequence identity compared to SEQ ID NO: 19. In some embodiments the polynucleotide encodes a PIP-45-1 polypeptide having at least 87% or greater sequence identity compared to SEQ ID NO: 21. In some embodiments the polynucleotide encodes a PIP-45-1 polypeptide having at least 88% or greater sequence identity compared to SEQ ID NO: 23. In some embodiments the polynucleotide encodes a PIP-45-1 polypeptide having at least 99.1% or greater sequence identity compared to SEQ ID NO: 27. In some embodiments the polynucleotide encodes a PIP-45-1 polypeptide having at least 99.8% or greater sequence identity compared to SEQ ID NO: 29. In some embodiments the polynucleotide encodes a PIP-45-1 polypeptide having at least 92.3% or greater sequence identity compared to SEQ ID NO: 31. In some embodiments the polynucleotide encodes a PIP-45-1 polypeptide having at least 91.1% or greater sequence identity compared to SEQ ID NO: 33. In some embodiments the polynucleotide encodes a PIP-45-1 polypeptide having at least 95.4% or greater sequence identity compared to SEQ ID NO: 35. In some embodiments the polynucleotide encodes a PIP-45-1 polypeptide having at least 93% or greater sequence identity compared to SEQ ID NO: 39. In some embodiments the polynucleotide encodes a PIP-45-1 polypeptide having at least 97.5% or greater sequence identity compared to SEQ ID NO: 43. In some embodiments the polynucleotide encodes a PIP-45-1 polypeptide having at least 70% or greater sequence identity compared to SEQ ID NO: 45. In some embodiments the polynucleotide encodes a PIP-45-1 polypeptide having at least 94% or greater sequence identity compared to SEQ ID NO: 234. In some embodiments the polynucleotide encodes a PIP-45-1 polypeptide having at least 96% or greater sequence identity compared to SEQ ID NO: 236.

Polynucleotides encoding PIP-45-2 polypeptides are encompassed by the disclosure. A variety of polynucleotides encoding PIP-45-2 polypeptides are contemplated. One source of a polynucleotides encoding a PIP-45-2 polypeptide or related protein is a bacterial strain that contains the polynucleotide of SEQ ID NO: 109, SEQ ID NO: 125, SEQ ID NO: 127, SEQ ID NO: 129, SEQ ID NO: 131, SEQ ID NO: 135, SEQ ID NO: 137, SEQ ID NO: 139, SEQ ID NO: 141, SEQ ID NO: 143, SEQ ID NO: 147, SEQ ID NO: 151, SEQ ID NO: 153, SEQ ID NO: 221 or SEQ ID NO: 223 that encode the PIP-45-2 polypeptide of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 and SEQ ID NO: 237, respectively. One source of a polynucleotide encoding PIP-45-2 polypeptide or related protein is from a *Pseudomonas*, *Thalassuspira*, *Paracoccus* or *Cellvibrio* strain. One source of a polynucleotide encoding a PIP-45-2 polypeptide or related proteins is from a *Pseudomonas* strain selected from but not limited to *Pseudomonas brenneri*, *Pseudomonas monteilii*, *Pseudomonas gessardii*, *Pseudomonas plecoglossicida*, *Pseudomonas putida*, *Pseudomonas poae*, *Pseudomonas trivialis*, *Pseudomonas libanensis*, *Pseudomonas fluorescens* and *Pseudomonas asplenii*.

In some embodiments the nucleic acid molecule encoding the PIP-45-2 polypeptide is a non-genomic nucleic acid sequence. In some embodiments the non-genomic nucleic acid molecule is a cDNA. In some embodiments the non-genomic nucleic acid molecule is a synthetic nucleic acid sequence.

In some embodiments the polynucleotide encodes a PIP-45-2 polypeptide sufficiently homologous to the amino acid sequence of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-45-2 polypeptide. In some embodiments the polynucleotide encodes a PIP-45-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237.

In some embodiments the polynucleotide encodes a PIP-45-2 polypeptide having at least 99.2% or greater sequence identity compared to SEQ ID NO: 2. In some embodiments the polynucleotide encodes a PIP-45-2 polypeptide having at least 98.5% or greater sequence identity compared to SEQ ID NO: 18. In some embodiments the polynucleotide encodes a PIP-45-2 polypeptide having at least 96% or greater sequence identity compared to SEQ ID NO: 20. In some embodiments the polynucleotide encodes a PIP-45-2 polypeptide having at least 80% or greater sequence identity compared to SEQ ID NO: 22. In some embodiments the polynucleotide encodes a PIP-45-2 polypeptide having at least 81% or greater sequence identity compared to SEQ ID NO: 24. In some embodiments the polynucleotide encodes a PIP-45-2 polypeptide having at least 99.5% or greater sequence identity compared to SEQ ID NO: 28. In some embodiments the polynucleotide encodes a PIP-45-2 polypeptide having at least 98.5% or greater sequence identity compared to SEQ ID NO: 30. In some embodiments the polynucleotide encodes a PIP-45-2 polypeptide having at least 92% or greater sequence identity compared to SEQ ID NO: 32. In some embodiments the polynucleotide encodes a PIP-45-2 polypeptide having at least 91.5% or greater sequence identity compared to SEQ ID NO: 34. In some embodiments the polynucleotide encodes a PIP-45-2 polypeptide having at least 70% or greater sequence identity compared to SEQ ID NO: 36. In some embodiments the polynucleotide encodes a PIP-45-2 polypeptide having at least 90% or greater sequence identity compared to SEQ ID NO: 40. In some embodiments the polynucleotide encodes a PIP-45-2 polypeptide having at least 94% or greater sequence identity compared to SEQ ID NO: 44. In some embodiments the polynucleotide encodes a PIP-45-2 polypeptide having at least 70% or greater sequence identity compared to SEQ ID NO: 46. In some embodiments the polynucleotide encodes a PIP-45-2 polypeptide having at least 91% or greater sequence identity compared to SEQ ID NO: 235. In some embodiments the polynucleotide encodes a PIP-45-2 polypeptide having at least 93.5% or greater sequence identity compared to SEQ ID NO: 237.

Polynucleotides encoding PIP-64-1 polypeptides are encompassed by the disclosure. A variety of polynucleotides encoding PIP-64-1 polypeptides are contemplated. One source of a polynucleotide encoding a PIP-64-1 polypeptide or related protein is a bacterial strain that contains the polynucleotide of SEQ ID NO: 160, SEQ ID NO: 165 or SEQ ID NO: 224 that encode the PIP-64-1 polypeptide of SEQ ID NO: 53, SEQ ID NO: 58 and SEQ ID NO: 238. One source of a polynucleotide encoding a PIP-64-1 polypeptide or related protein is from a *Pseudomonas, Enterobacter* or *Alcaligenes* strain. One source of a polynucleotide encoding a PIP-64-1 polypeptide or related proteins is from a *Pseudomonas* or *Alcaligenes* strain selected from but not limited to *Pseudomonas brenneri, Pseudomonas gessardii, Pseudomonas fluorescens, Pseudomonas brassicacearum, Pseudomonas entomophila* and *Alcaligenes faecalis*.

In some embodiments the nucleic acid molecule encoding the PIP-64-1 polypeptide is a non-genomic nucleic acid sequence. In some embodiments the non-genomic nucleic acid molecule is a cDNA. In some embodiments the non-genomic nucleic acid molecule is a synthetic nucleic acid sequence In some embodiments the polynucleotide encodes a PIP-64-1 polypeptide sufficiently homologous to the amino acid sequence of SEQ ID NO: 53, SEQ ID NO: 58 or SEQ ID NO: 238 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-1 polypeptide. In some embodiments the polynucleotide encodes a PIP-64-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 58 or SEQ ID NO: 238.

In some embodiments the polynucleotide encodes a PIP-64-1 polypeptide having at least 75% or greater sequence identity compared to SEQ ID NO: 53. In some embodiments the polynucleotide encodes a PIP-64-1 polypeptide having at least 99.7% or greater sequence identity compared to SEQ ID NO: 58. In some embodiments the polynucleotide encodes a PIP-64-1 polypeptide having at least 75% or greater sequence identity compared to SEQ ID NO: 238.

Polynucleotides encoding PIP-64-2 polypeptides are encompassed by the disclosure. A variety of polynucleotides encodes a PIP-64-2 polypeptide are contemplated. One source of a polynucleotide encoding a PIP-64-2 polypeptide or related protein is a bacterial strain that contains the polynucleotide of SEQ ID NO: 161, SEQ ID NO: 162, SEQ ID NO: 166 or SEQ ID NO: 225 that encode the PIP-64-2 polypeptide of SEQ ID NO: 54, SEQ ID NO: 55, SEQ ID NO: 59 and SEQ ID NO: 239, respectively. One source of a polynucleotide encoding a PIP-64-2 polypeptide or related protein is from a *Pseudomonas, Enterobacter* or *Alcaligenes* strain. One source of a polynucleotide encoding a PIP-64-2 polypeptide or related protein is from a *Pseudomonas* or *Alcaligenes* strain selected from but not limited to *Pseudomonas brenneri, Pseudomonas gessardii, Pseudomonas fluorescens, Pseudomonas brassicacearum, Pseudomonas entomophila* and *Alcaligenes faecalis*.

In some embodiments the nucleic acid molecule encoding the PIP-64-2 polypeptide is a non-genomic nucleic acid sequence. In some embodiments the non-genomic nucleic acid molecule is a cDNA. In some embodiments the non-genomic nucleic acid molecule is a synthetic nucleic acid sequence In some embodiments the polynucleotide encodes a PIP-64-2 polypeptide sufficiently homologous to the amino acid sequence of SEQ ID NO: 54, SEQ ID NO: 55, SEQ ID NO: 59 or SEQ ID NO: 239 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-2 polypeptide. In some embodiments the PIP-64-2 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 59 or SEQ ID NO: 239.

In some embodiments the polynucleotide encodes a PIP-64-2 polypeptide having at least 70% or greater sequence identity compared to SEQ ID NO: 54. In some embodiments the polynucleotide encodes a PIP-64-2 polypeptide having at least 70% or greater sequence identity compared to SEQ ID NO: 55. In some embodiments the polynucleotide encodes a PIP-64-2 polypeptide having at least 91% or greater sequence identity compared to SEQ ID NO: 59. In some embodiments the polynucleotide encodes a PIP-64-2 polypeptide having at least 70% or greater sequence identity compared to SEQ ID NO: 239.

Polynucleotides encoding PIP-74-1 polypeptides are encompassed by the disclosure. A variety of polynucleotides encoding PIP-74-1 polypeptides are contemplated. One source of a polynucleotide encoding a PIP-74-1 polypeptide or related protein is a bacterial strain that contains the polynucleotide of SEQ ID NO: 180, SEQ ID NO: 182 or SEQ ID NO: 184 that encode the PIP-74-1 polypeptide of SEQ ID NO: 73, SEQ ID NO: 75 and SEQ ID NO: 77, respectively. One source of the polynucleotide encoding a PIP-74-1 polypeptide or related protein is from a *Pseudomonas* strain. One source of the polynucleotide encoding a PIP-74-1 polypeptide or related proteins is from a *Pseudomonas* strain selected from but not limited to *Pseudomonas rhodesiae* and *Pseudomonas orientalis*.

In some embodiments the nucleic acid molecule encoding the PIP-74-1 polypeptide is a non-genomic nucleic acid sequence. In some embodiments the non-genomic nucleic acid molecule is a cDNA. In some embodiments the non-genomic nucleic acid molecule is a synthetic nucleic acid sequence In some embodiments the polynucleotide encodes a PIP-74-1 polypeptide sufficiently homologous to the amino acid sequence of SEQ ID NO: 73, SEQ ID NO: 75 or SEQ ID NO: 77 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-1 polypeptide. In some embodiments the polynucleotide encodes a PIP-74-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 73, SEQ ID NO: 75 or SEQ ID NO: 77.

In some embodiments the polynucleotide encodes a PIP-74-1 polypeptide having at least 75% or greater sequence identity compared to SEQ ID NO: 73. In some embodiments the polynucleotide encodes a PIP-74-1 polypeptide having at least 75% or greater sequence identity compared to SEQ ID NO: 75. In some embodiments the polynucleotide encodes a PIP-74-1 polypeptide having at least 75% or greater sequence identity compared to SEQ ID NO: 77.

Polynucleotides encoding PIP-74-2 polypeptides are encompassed by the disclosure. A variety of polynucleotides encoding PIP-74-2 polypeptides are contemplated. One source of the polynucleotide encoding a PIP-74-2 polypeptide or related protein is a bacterial strain that contains the polynucleotide of SEQ ID NO: 181, SEQ ID NO: 183, SEQ ID NO: 185 that encode the PIP-74-2 polypeptide of SEQ ID NO: 74, SEQ ID NO: 76 and SEQ ID NO: 78, respectively. One source of the polynucleotide encoding a PIP-74-2 polypeptide or related proteins is from a *Pseudomonas* strain. One source of a PIP-74-2 polypeptide or related proteins is from a *Pseudomonas* strain selected from but not limited to *Pseudomonas rhodesiae* and *Pseudomonas orientalis*.

In some embodiments the nucleic acid molecule encoding the PIP-74-2 polypeptide is a non-genomic nucleic acid sequence. In some embodiments the non-genomic nucleic acid molecule is a cDNA. In some embodiments the non-genomic nucleic acid molecule is a synthetic nucleic acid sequence In some embodiments the polynucleotide encodes a PIP-74-2 polypeptide sufficiently homologous to the amino acid sequence of SEQ ID NO: 74, SEQ ID NO: 76 or SEQ ID NO: 78 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-2 polypeptide. In some embodiments the polynucleotide encodes a PIP-74-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 74, SEQ ID NO: 76 or SEQ ID NO: 78.

In some embodiments the polynucleotide encodes a PIP-74-2 polypeptide having at least 75% or greater sequence identity compared to SEQ ID NO: 74. In some embodiments the polynucleotide encodes a PIP-74-2 polypeptide having at least 75% or greater sequence identity compared to SEQ ID NO: 76. In some embodiments the polynucleotide encodes a PIP-74-2 polypeptide having at least 75% or greater sequence identity compared to SEQ ID NO: 78.

Polynucleotides encoding PIP-75 polypeptides are encompassed by the disclosure. A variety of polynucleotides encoding a PIP-75 polypeptide are contemplated. One source of a polynucleotide encoding a PIP-75 polypeptide or related protein is a bacterial strain that contains the polynucleotide of SEQ ID NO: 186, SEQ ID NO: 187, SEQ ID NO: 188, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 84, SEQ ID NO: 85, SEQ ID NO: 86 and SEQ ID NO: 87. One source of a polynucleotide encoding a PIP-75 polypeptide or related protein is from a *Pseudomonas, Enterobacter* or *Serratia* strain. One source of a PIP-75 polypeptide or related proteins is from a *Pseudomonas, Enterobacter* or *Serratia* strain selected from but not limited to *Pseudomonas Antarctica, Pseudomonas orientalis, Enterobacter asburiae, Serratia plymuthica,* and *Serratia liquefaciens*.

In some embodiments the nucleic acid molecule encoding the PIP-75 polypeptide is a non-genomic nucleic acid sequence. In some embodiments the non-genomic nucleic acid molecule is a cDNA. In some embodiments the non-genomic nucleic acid molecule is a synthetic nucleic acid sequence In some embodiments the polynucleotide encodes a PIP-75 polypeptide sufficiently homologous to the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-75 polypeptide. In some embodiments the polynucleotide encodes a PIP-75 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 84, SEQ ID NO: 85, SEQ ID NO: 86 or SEQ ID NO: 87.

In some embodiments the polynucleotide encodes a PIP-75 polypeptide having at least 75% or greater sequence identity compared to SEQ ID NO: 79. In some embodiments the polynucleotide encodes a PIP-75 polypeptide having at least 75% or greater sequence identity compared to SEQ ID NO: 80. In some embodiments the polynucleotide encodes a PIP-75 polypeptide having at least 86% or greater sequence identity compared to SEQ ID NO: 81. In some embodiments the polynucleotide encodes a PIP-75 polypeptide having at least 75% or greater sequence identity compared to SEQ ID NO: 84. In some embodiments the polynucleotide encodes a PIP-75 polypeptide having at least 75% or greater sequence identity compared to SEQ ID NO: 85. In some embodiments the polynucleotide encodes a PIP-75 polypeptide having at least 75% or greater sequence identity compared to SEQ ID NO: 86. In some embodiments the polynucleotide encodes a PIP-75 polypeptide having at least 75% or greater sequence identity compared to SEQ ID NO: 87.

Polynucleotides encoding PIP-77 polypeptides are encompassed by the disclosure. A variety of polynucleotides encoding a PIP-77 polypeptide are contemplated. One source of a polynucleotide encoding a PIP-77 polypeptide or related proteins is a bacterial strain that contains the polynucleotide of SEQ ID NO: 195, SEQ ID NO:196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 227, SEQ ID NO: 228 or SEQ ID NO: 231 that encode the PIP-77 polypeptide of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 and SEQ ID NO: 245, respectively. One source of a polynucleotide encoding a PIP-77 polypeptide or related proteins is from a *Pseudomonas, Enterobacter, Shewanella, Haemophilus* or *Aeromonas* strain. One source of a PIP-77 polypeptide or related proteins is from a *Pseudomonas* strain selected from but not limited to *Pseudomonas chlororaphis, Pseudomonas brassicacearum, Pseudomonas fluorescens* and *Pseudomonas rhodesiae*.

In some embodiments the nucleic acid molecule encoding the PIP-77 polypeptide is a non-genomic nucleic acid sequence. In some embodiments the non-genomic nucleic acid molecule is a cDNA. In some embodiments the non-genomic nucleic acid molecule is a synthetic nucleic acid sequence.

In some embodiments the polynucleotide encodes a PIP-77 polypeptide sufficiently homologous to the amino acid sequence of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-77 polypeptide. In some embodiments the polynucleotide encodes a PIP-77 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245.

In some embodiments the polynucleotide encodes a PIP-77 polypeptide having at least 93% or greater sequence identity compared to SEQ ID NO: 88. In some embodiments the polynucleotide encodes a PIP-77 polypeptide having at least 97% or greater sequence identity compared to SEQ ID NO: 89. In some embodiments the polynucleotide encodes a PIP-77 polypeptide having at least 99% or greater sequence identity compared to SEQ ID NO: 90. In some embodiments the polynucleotide encodes a PIP-77 polypeptide having at least 97% or greater sequence identity compared to SEQ ID NO: 92. In some embodiments the polynucleotide encodes a PIP-77 polypeptide having at least 87% or greater sequence identity compared to SEQ ID NO: 93. In some embodiments the polynucleotide encodes a PIP-77 polypeptide having at least 86% or greater sequence identity compared to SEQ ID NO: 94. In some embodiments the polynucleotide encodes a PIP-77 polypeptide having at least 85% or greater sequence identity compared to SEQ ID NO: 95. In some embodiments the polynucleotide encodes a PIP-77 polypeptide having at least 84% or greater sequence identity compared to SEQ ID NO: 96. In some embodiments the polynucleotide encodes a PIP-77 polypeptide having at least 85% or greater sequence identity compared to SEQ ID NO: 97. In some embodiments the polynucleotide encodes a PIP-77 polypeptide having at least 83% or greater sequence identity compared to SEQ ID NO: 98. In some embodiments the polynucleotide encodes a PIP-77 polypeptide having at least 79% or greater sequence identity compared to SEQ ID NO: 100.

These polynucleotide sequences were isolated from a *Pseudomonas* or other bacterial host and are thus suitable for expression of the encoded insecticidal polypeptides in other bacterial hosts that include but are not limited to *Agrobac-* terium, *Bacillus*, *Escherichia*, *Salmonella*, *Pseudomonas* and *Rhizobium* bacterial host cells. The polynucleotides are also useful as probes for isolating homologous or substantially homologous polynucleotides that encode the insecticidal polypeptides of the disclosure or related proteins. Such probes can be used to identify homologous or substantially homologous polynucleotides derived from *Pseudomonas* or other related bacteria.

Polynucleotides that encode an insecticidal polypeptide can also be synthesized de novo from a polypeptide sequence. The sequence of the polynucleotide gene can be deduced from a polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Furthermore, synthetic polynucleotide sequences of the disclosure can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052.

"Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments a nucleic acid molecule encoding the insecticidal polypeptide of the disclosure is a non-genomic nucleic acid sequence. As used herein a "non-genomic nucleic acid sequence" or "non-genomic nucleic acid molecule" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA.

Also provided are nucleic acid molecules that encode transcription and/or translation products that are subsequently spliced to ultimately produce functional insecticidal polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate a insecticidal polypeptide encoding sequence of the disclosure. An example of trans splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length insecticidal polypeptide of the disclosure, but rather encode a fragment or fragments of an insecticidal polypeptide of the disclosure. These polynucleotides can be used to express a functional Insecticidal polypeptide of the disclosure through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding insecticidal polypeptides are also encompassed by the embodiments. "Fragment" as used herein refers to a portion of the nucleic acid sequence encoding an insecticidal polypeptide of the disclosure. A fragment of a nucleic acid sequence may encode a biologically active portion of an insecticidal polypeptide of the disclosure or it may be a fragment that can be used as a hybridization probe or PCR primer using methods disclosed below. Nucleic acid molecules that are fragments of a nucleic acid sequence encoding an insecticidal polypeptide of the disclosure comprise at least about 130, 140, 150, 160, 170, 180, 190, 200, 210, 220, 230, 240, 250 or 260, contiguous nucleotides or up to the number of nucleotides present in a full-length nucleic acid sequence encoding an insecticidal polypeptide of the disclosure disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the insecticidal polypeptide of the disclosure and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length native polypeptide. In one embodiment, the insecticidal activity is Lepidoptera activity. In one embodiment, the insecticidal activity is against a Coleopteran species. In one embodiment, the insecticidal activity is against a *Diabrotica* species. In one embodiment, the insecticidal activity is against one or more insect pests of the corn rootworm complex: Western corn rootworm, *Diabrotica virgifera virgifera*; northern corn rootworm, *D. barberi*: Southern corn rootworm or spotted cucumber beetle; *Dia-* brotica undecimpunctata howardi, and the Mexican corn rootworm, *D. virgifera zeae*. In one embodiment, the insecticidal activity is against Western corn rootworm, *Diabrotica virgifera virgifera*.

In some embodiments a fragment of a nucleic acid sequence encoding an insecticidal polypeptide of the disclosure encoding a biologically active portion of a protein will encode at least about 15, 20, 30, 40, 50, 60, 70, 75, 76, 77, 78, 79, 80, 81, 82, 83, 84 or 85, contiguous amino acids or up to the total number of amino acids present in a full-length insecticidal polypeptide of the embodiments. In some embodiments, the fragment is an N-terminal and/or a C-terminal truncation of at least about 1, 2, 3, 4, 5, 6, 7, 8, 9, 10, 11, 12, 13, 14 or more amino acids from the N-terminus and/or C-terminus by proteolysis, insertion of a start codon, deletion of the codons encoding the deleted amino acids with the concomitant insertion of a stop codon or by insertion of a stop codon in the coding sequence.

The present disclosure provides isolated or recombinant polynucleotides that encode any of the insecticidal polypeptides disclosed herein. Those having ordinary skill in the art will readily appreciate that due to the degeneracy of the genetic code, a multitude of nucleotide sequences encoding insecticidal polypeptides of the present disclosure exist. Table 1 is a codon table that provides the synonymous codons for each amino acid. For example, the codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

TABLE 1

| | | |
|---|---|---|
| Alanine | Ala | GCA GCC GCG GCU |
| Cysteine | Cys | UGC UGU |
| Aspartic acid | Asp | GAC GAU |
| Glutamic acid | Glu | GAA GAG |
| Phenylalanine | Phe | UUC UUU |
| Glycine | Gly | GGA GGC GGG GGU |
| Histidine | His | CAC CAU |
| Isoleucine | Ile | AUA AUC AUU |
| Lysine | Lys | AAA AAG |
| Leucine | Leu | UUA UUG CUA CUC CUG CUU |
| Methionine | Met | AUG |
| Asparagine | Asn | AAC AAU |
| Proline | Pro | CCA CCC CCG CCU |
| Glutamine | Gln | CAA CAG |
| Arginine | Arg | AGA AGG CGA CGC CGG CGU |
| Serine | Ser | AGC AGU UCA UCC UCG UCU |
| Threonine | Thr | ACA ACC ACG ACU |
| Valine | Val | GUA GUC GUG UU |
| Tryptophan | Trp | UGG |
| Tyrosine | Tyr | UAC UAU |

The skilled artisan will further appreciate that changes can be introduced by mutation of the nucleic acid sequences thereby leading to changes in the amino acid sequence of the encoded insecticidal polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produces by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Tar-* geting 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from other organisms, particularly other bacteria, particularly a *Pseudomonas* species and more particularly a *Pseudomonas putida*, a *Pseudomonas fulva* or a *Pseudomonas chlororaphis* strain. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential insecticidal polypeptides from bacterial collections, the bacterial cell lysates can be screened with antibodies generated against an insecticidal polypeptide of the disclosure using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of the insecticidal polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands) with sequence information of the insecticidal polypeptides of the disclosure. Any match in peptide sequences indicates the potential of having the homologs in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the insecticidal polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an insecticidal polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding an insecticidal polypeptide of the disclosure, disclosed herein or one or more portions thereof may be used as a probe capable of specifically hybridizing to corresponding nucleic acid sequences encoding insecticidal polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl, (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology-Hybridization with Nucleic Acid Probes, Part I, Chapter 2 (Elsevier, N.Y.); and Ausubel, et al., eds. (1995) Current Protocols in Molecular Biology, Chapter 2 (Greene Publishing and Wiley-Interscience, New York). See, Sambrook, et al., (1989) Molecular Cloning: A Laboratory Manual (2d ed., Cold Spring Harbor Laboratory Press, Cold Spring Harbor, N.Y.).

Proteins and Variants and Fragments Thereof

One aspect of the disclosure is isolated insecticidal polypeptides.

PIP-45-1 polypeptides are encompassed by the disclosure. "*Pseudomonas* Insecticidal Protein-45-1", "PIP-45-1 polypeptide" or "PIP-45-1 protein" as used herein interchangeably refers to a polypeptide having insecticidal activity against one or more insect pests of the Lepidoptera and/or Coleoptera orders, and is sufficiently homologous to the protein of SEQ ID NO: 1. A variety of PIP-45-1 polypeptides are contemplated. One source of a PIP-45-1 polypeptide or related proteins is a bacterial strain that contains the polynucleotide of SEQ ID NO: 108, SEQ ID NO: 124, SEQ ID NO: 126, SEQ ID NO: 128, SEQ ID NO: 130, SEQ ID NO: 134, SEQ ID NO: 136, SEQ ID NO: 138, SEQ ID NO: 140, SEQ ID NO: 142, SEQ ID NO: 146, SEQ ID NO: 150, SEQ ID NO: 152, SEQ ID NO: 220 or SEQ ID NO: 222 that encode the PIP-45-1 polypeptide of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 and SEQ ID NO: 236, respectively. One source of a PIP-45-1 polypeptide or related proteins is from a *Pseudomonas, Thalassuspira, Paracoccus* or *Cellvibrio* strain. One source of a PIP-45-1 polypeptide or related proteins is from a *Pseudomonas* strain selected from but not limited to *Pseudomonas brenneri, Pseudomonas monteilii, Pseudomonas gessardii, Pseudomonas plecoglossicida, Pseudomonas putida, Pseudomonas poae, Pseudomonas trivialis, Pseudomonas libanensis, Pseudomonas fluorescens* and *Pseudomonas asplenii*.

In some embodiments a PIP-45-1 polypeptide is sufficiently homologous to the amino acid sequence of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-45-1 polypeptide.

In some embodiments the PIP-45-1 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236.

In some embodiments the PIP-45-1 polypeptide has at least 99.1% or greater sequence identity compared to SEQ ID NO: 1. In some embodiments the PIP-45-1 polypeptide has at least 99.4% or greater sequence identity compared to SEQ ID NO: 17. In some embodiments the PIP-45-1 polypeptide has at least 99.6% or greater sequence identity compared to SEQ ID NO: 19. In some embodiments the PIP-45-1 polypeptide has at least 87% or greater sequence identity compared to SEQ ID NO: 21. In some embodiments the PIP-45-1 polypeptide has at least 88% or greater sequence identity compared to SEQ ID NO: 23. In some embodiments the PIP-45-1 polypeptide has at least 99.1% or greater sequence identity compared to SEQ ID NO: 27. In some embodiments the PIP-45-1 polypeptide has at least 99.8% or greater sequence identity compared to SEQ ID NO: 29. In some embodiments the PIP-45-1 polypeptide has at least 92.3% or greater sequence identity compared to SEQ ID NO: 31. In some embodiments the PIP-45-1 polypeptide has at least 91.1% or greater sequence identity compared to SEQ ID NO: 33. In some embodiments the PIP-45-1 polypeptide has at least 95.4% or greater sequence identity compared to SEQ ID NO: 35. In some embodiments the PIP-45-1 polypeptide has at least 93% or greater sequence identity compared to SEQ ID NO: 39. In some embodiments the PIP-45-1 polypeptide has at least 97.5% or greater sequence identity compared to SEQ ID NO: 43. In some embodiments the PIP-45-1 polypeptide has at least 70% or greater sequence identity compared to SEQ ID NO: 45.

PIP-45-2 polypeptides are encompassed by the disclosure. "*Pseudomonas* Insecticidal Protein-45-2", "PIP-45-2 polypeptide" or "PIP-45-2 protein" as used herein interchangeably refers to a polypeptide having insecticidal activity against one or more insect pests of the Lepidoptera and/or Coleoptera orders, and is sufficiently homologous to the protein of SEQ ID NO: 2. A variety of PIP-45-2 polypeptides are contemplated. One source of a PIP-45-2 polypeptide or related proteins is a bacterial strain that contains the polynucleotide of SEQ ID NO: 109, SEQ ID NO: 125, SEQ ID NO: 127, SEQ ID NO: 129, SEQ ID NO: 131, SEQ ID NO: 135, SEQ ID NO: 137, SEQ ID NO: 139, SEQ ID NO: 141, SEQ ID NO: 143, SEQ ID NO: 147, SEQ ID NO: 151, SEQ ID NO: 153, SEQ ID NO: 221 or SEQ ID NO: 223 that encode the PIP-45-2 polypeptide of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 and SEQ ID NO: 237, respectively. One source of a PIP-45-2 polypeptide or related proteins is from a *Pseudomonas, Thalassuspira, Paracoccus* or *Cellvibrio* strain. One source of a PIP-45-2 polypeptide or related proteins is from a *Pseudomonas* strain selected from but not limited to *Pseudomonas brenneri, Pseudomonas monteilii, Pseudomonas gessardii, Pseudomonas plecoglossicida, Pseudomonas putida, Pseudomonas poae, Pseudomonas trivialis, Pseudomonas libanensis, Pseudomonas fluorescens* and *Pseudomonas asplenii*.

In some embodiments a PIP-45-2 polypeptide is sufficiently homologous to the amino acid sequence of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-45-2 polypeptide. In some embodiments the PIP-45-2 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237.

In some embodiments the PIP-45-2 polypeptide has at least 99.2% or greater sequence identity compared to SEQ ID NO: 2. In some embodiments the PIP-45-2 polypeptide has at least 98.5% or greater sequence identity compared to SEQ ID NO: 18. In some embodiments the PIP-45-2 polypeptide has at least 96% or greater sequence identity compared to SEQ ID NO: 20. In some embodiments the PIP-45-2 polypeptide has at least 80% or greater sequence identity compared to SEQ ID NO: 22. In some embodiments the PIP-45-2 polypeptide has at least 81% or greater sequence identity compared to SEQ ID NO: 24. In some embodiments the PIP-45-2 polypeptide has at least 99.5% or greater sequence identity compared to SEQ ID NO: 28. In some embodiments the PIP-45-2 polypeptide has at least 98.5% or greater sequence identity compared to SEQ ID NO: 30. In some embodiments the PIP-45-2 polypeptide has at least 92% or greater sequence identity compared to SEQ ID NO: 32. In some embodiments the PIP-45-2 polypeptide has at least 91.5% or greater sequence identity compared to SEQ ID NO: 34. In some embodiments the PIP-45-2 polypeptide has at least 70% or greater sequence identity compared to SEQ ID NO: 36. In some embodiments the PIP-45-2 polypeptide has at least 90% or greater sequence identity compared to SEQ ID NO: 40. In some embodiments the PIP-45-2 polypeptide has at least 94% or greater sequence identity compared to SEQ ID NO: 44. In some embodiments the PIP-45-2 polypeptide has at least 70% or greater sequence identity compared to SEQ ID NO: 46.

PIP-64-1 polypeptides are encompassed by the disclosure. "*Pseudomonas* Insecticidal Protein-64-1", "PIP-64-1 polypeptide" or "PIP-64-1 protein" as used herein interchangeably refers to a polypeptide having insecticidal activity against one or more insect pests of the Lepidoptera and/or Coleoptera orders, and is sufficiently homologous to the protein of SEQ ID NO: 53. A variety of PIP-64-1 polypeptides are contemplated. One source of a PIP-64-1 polypeptide or related proteins is a bacterial strain that contains the polynucleotide of SEQ ID NO: 160, SEQ ID NO: 165 or SEQ ID NO: 224 that encode the PIP-64-1 polypeptide of SEQ ID NO: 53, SEQ ID NO: 58 and SEQ ID NO: 238. One source of a PIP-64-1 polypeptide or related proteins is from a *Pseudomonas*, *Enterobacter* or *Alcaligenes* strain. One source of a PIP-64-1 polypeptide or related proteins is from a *Pseudomonas* or *Alcaligenes* strain selected from but not limited to *Pseudomonas brenneri*, *Pseudomonas gessardii*, *Pseudomonas fluorescens*, *Pseudomonas brassicacearum*, *Pseudomonas entomophila* and *Alcaligenes faecalis*.

In some embodiments a PIP-64-1 polypeptide is sufficiently homologous to the amino acid sequence of SEQ ID NO: 53, SEQ ID NO: 58 or SEQ ID NO: 238 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-1 polypeptide. In some embodiments the PIP-64-1 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 58 or SEQ ID NO: 238.

In some embodiments the PIP-64-1 polypeptide has at least 75% or greater sequence identity compared to SEQ ID NO: 53. In some embodiments the PIP-64-1 polypeptide has at least 99.7% or greater sequence identity compared to SEQ ID NO: 58. In some embodiments the PIP-64-1 polypeptide has at least 75% or greater sequence identity compared to SEQ ID NO: 238.

PIP-64-2 polypeptides are encompassed by the disclosure. "*Pseudomonas* Insecticidal Protein-64-2", "PIP-64-2 polypeptide" or "PIP-64-2 protein" as used herein interchangeably refers to a polypeptide having insecticidal activity against one or more insect pests of the Lepidoptera and/or Coleoptera orders, and is sufficiently homologous to the protein of SEQ ID NO:54. A variety of PIP-64-2 polypeptides are contemplated. One source of a PIP-64-2 polypeptide or related proteins is a bacterial strain that contains the polynucleotide of SEQ ID NO: 161, SEQ ID NO: 162, SEQ ID NO: 166 or SEQ ID NO: 225 that encode the PIP-64-2 polypeptide of SEQ ID NO: 54, SEQ ID NO: 55, SEQ ID NO: 59 and SEQ ID NO: 239, respectively. One source of a PIP-64-2 polypeptide or related proteins is from a *Pseudomonas*, *Enterobacter* or *Alcaligenes* strain. One source of a PIP-64-2 polypeptide or related proteins is from a *Pseudomonas* or *Alcaligenes* strain selected from but not limited to *Pseudomonas brenneri*, *Pseudomonas gessardii*, *Pseudomonas fluorescens*, *Pseudomonas brassicacearum*, *Pseudomonas entomophila* and *Alcaligenes faecalis*.

In some embodiments a PIP-64-2 polypeptide is sufficiently homologous to the amino acid sequence of SEQ ID NO: 54, SEQ ID NO: 55, SEQ ID NO: 59 or SEQ ID NO: 239 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-2 polypeptide. In some embodiments the PIP-64-2 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 59 or SEQ ID NO: 239.

In some embodiments the PIP-64-2 polypeptide has at least 70% or greater sequence identity compared to SEQ ID NO: 54. In some embodiments the PIP-64-2 polypeptide has at least 70% or greater sequence identity compared to SEQ ID NO: 55. In some embodiments the PIP-64-2 polypeptide has at least 91% or greater sequence identity compared to SEQ ID NO: 59. In some embodiments the PIP-64-2 polypeptide has at least 70% or greater sequence identity compared to SEQ ID NO: 239.

PIP-74-1 polypeptides are encompassed by the disclosure. "*Pseudomonas* Insecticidal Protein-74-1", "PIP-74-1 polypeptide" or "PIP-74-1 protein" as used herein interchangeably refers to a polypeptide having insecticidal activity against one or more insect pests of the Lepidoptera and/or Coleoptera orders, and is sufficiently homologous to the protein of SEQ ID NO: 73. A variety of PIP-74-1 polypeptides are contemplated. One source of a PIP-74-1 polypeptide or related proteins is a bacterial strain that contains the polynucleotide of SEQ ID NO: 180, SEQ ID NO: 182 or SEQ ID NO: 184 that encode the PIP-74-1 polypeptide of SEQ ID NO: 73, SEQ ID NO: 75 and SEQ ID NO: 77, respectively. One source of a PIP-74-1 polypeptide or related proteins is from a *Pseudomonas* strain. One source of a PIP-74-1 polypeptide or related proteins is from a *Pseudomonas* strain selected from but not limited to *Pseudomonas rhodesiae* and *Pseudomonas orientalis*.

In some embodiments a PIP-74-1 polypeptide is sufficiently homologous to the amino acid sequence of SEQ ID NO: 73, SEQ ID NO: 75 or SEQ ID NO: 77 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-1 polypeptide. In some embodiments the PIP-74-1 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 73, SEQ ID NO: 75 or SEQ ID NO: 77.

In some embodiments the PIP-74-1 polypeptide has at least 75% or greater sequence identity compared to SEQ ID NO: 73. In some embodiments the PIP-74-1 polypeptide has at least 75% or greater sequence identity compared to SEQ ID NO: 75. In some embodiments the PIP-74-1 polypeptide has at least 75% or greater sequence identity compared to SEQ ID NO: 77.

PIP-74-2 polypeptides are encompassed by the disclosure. "*Pseudomonas* Insecticidal Protein-74-2", "PIP-74-2 polypeptide" or "PIP-74-2 protein" as used herein interchangeably refers to a polypeptide having insecticidal activity against one or more insect pests of the Lepidoptera and/or Coleoptera orders, and is sufficiently homologous to the protein of SEQ ID NO: 74. A variety of PIP-74-2 polypeptides are contemplated. One source of a PIP-74-2 polypeptide or related proteins is a bacterial strain that contains the polynucleotide of SEQ ID NO: 181, SEQ ID NO: 183, SEQ ID NO: 185 that encode the PIP-74-2 polypeptide of SEQ ID NO: 74, SEQ ID NO: 76 and SEQ ID NO: 78, respectively. One source of a PIP-74-2 polypeptide or related proteins is from a *Pseudomonas* strain. One source of a PIP-74-2 polypeptide or related proteins is from a *Pseudomonas* strain selected from but not limited to *Pseudomonas rhodesiae* and *Pseudomonas orientalis*.

In some embodiments a PIP-74-2 polypeptide is sufficiently homologous to the amino acid sequence of SEQ ID NO: 74, SEQ ID NO: 76 or SEQ ID NO: 78 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-2 polypeptide. In some embodiments the PIP-74-2 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 74, SEQ ID NO: 76 or SEQ ID NO: 78.

In some embodiments the PIP-74-2 polypeptide has at least 75% or greater sequence identity compared to SEQ ID NO: 74. In some embodiments the PIP-74-2 polypeptide has at least 75% or greater sequence identity compared to SEQ ID NO: 76. In some embodiments the PIP-74-2 polypeptide has at least 75% or greater sequence identity compared to SEQ ID NO: 78.

PIP-75 polypeptides are encompassed by the disclosure. "*Pseudomonas* Insecticidal Protein-75", "PIP-75 polypeptide" or "PIP-75 protein" as used herein interchangeably refers to a polypeptide having insecticidal activity against one or more insect pests of the Lepidoptera and/or Coleoptera orders, and is sufficiently homologous to the protein of SEQ ID NO: 79. A variety of PIP-75 polypeptides are contemplated. One source of a PIP-75 polypeptide or related proteins is a bacterial strain that contains the polynucleotide of SEQ ID NO: 186, SEQ ID NO: 187, SEQ ID NO: 188, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 84, SEQ ID NO: 85, SEQ ID NO: 86 and SEQ ID NO: 87, respectively. One source of a PIP-75 polypeptide or related proteins is from a *Pseudomonas*, *Enterobacter* or *Serratia* strain. One source of a PIP-75 polypeptide or related proteins is from a *Pseudomonas*, *Enterobacter* or *Serratia* strain selected from but not limited to *Pseudomonas Antarctica*, *Pseudomonas orientalis*, *Enterobacter asburiae*, *Serratia plymuthica*, and *Serratia liquefaciens*.

In some embodiments a PIP-75 polypeptide is sufficiently homologous to the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-75 polypeptide. In some embodiments the PIP-75 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 84, SEQ ID NO: 85, SEQ ID NO: 86 or SEQ ID NO: 87.

In some embodiments the PIP-75 polypeptide has at least 75% or greater sequence identity compared to SEQ ID NO: 79. In some embodiments the PIP-75 polypeptide has at least 75% or greater sequence identity compared to SEQ ID NO: 80. In some embodiments the PIP-75 polypeptide has at least 86% or greater sequence identity compared to SEQ ID NO: 81. In some embodiments the PIP-75 polypeptide has at least 75% or greater sequence identity compared to SEQ ID NO: 84. In some embodiments the PIP-75 polypeptide has at least 75% or greater sequence identity compared to SEQ ID NO: 85. In some embodiments the PIP-75 polypeptide has at least 75% or greater sequence identity compared to SEQ ID NO: 86. In some embodiments the PIP-75 polypeptide has at least 75% or greater sequence identity compared to SEQ ID NO: 87.

PIP-77 polypeptides are encompassed by the disclosure. "*Pseudomonas* Insecticidal Protein-77", "PIP-77 polypeptide" or "PIP-77 protein" as used herein interchangeably refers to a polypeptide having insecticidal activity against one or more insect pests of the Lepidoptera and/or Coleoptera orders, and is sufficiently homologous to the protein of SEQ ID NO: 88. A variety of PIP-77 polypeptides are contemplated. One source of a PIP-77 polypeptide or related proteins is a bacterial strain that contains the polynucleotide of SEQ ID NO: 195, SEQ ID NO:196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 227, SEQ ID NO: 228 or SEQ ID NO: 231 that encode the PIP-77 polypeptide of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 and SEQ ID NO: 245, respectively. One source of a PIP-77 polypeptide or related proteins is from a *Pseudomonas, Enterobacter, Shewanella, Haemophilus* or *Aeromonas* strain. One source of a PIP-77 polypeptide or related proteins is from a *Pseudomonas* strain selected from but not limited to *Pseudomonas chlororaphis, Pseudomonas brassicacearum, Pseudomonas fluorescens* and *Pseudomonas rhodesiae*.

In some embodiments a PIP-77 polypeptide is sufficiently homologous to the amino acid sequence of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-77 polypeptide. In some embodiments the PIP-77 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245.

In some embodiments the PIP-77 polypeptide has at least 93% or greater sequence identity compared to SEQ ID NO: 88. In some embodiments the PIP-77 polypeptide has at least 97% or greater sequence identity compared to SEQ ID NO: 89. In some embodiments the PIP-77 polypeptide has at least 99% or greater sequence identity compared to SEQ ID NO: 90. In some embodiments the PIP-77 polypeptide has at least 97% or greater sequence identity compared to SEQ ID NO: 92. In some embodiments the PIP-77 polypeptide has at least 87% or greater sequence identity compared to SEQ ID NO: 93. In some embodiments the PIP-77 polypeptide has at least 86% or greater sequence identity compared to SEQ ID NO: 94. In some embodiments the PIP-77 polypeptide has at least 85% or greater sequence identity compared to SEQ ID NO: 95. In some embodiments the PIP-77 polypeptide has at least 84% or greater sequence identity compared to SEQ ID NO: 96. In some embodiments the PIP-77 polypeptide has at least 85% or greater sequence identity compared to SEQ ID NO: 97. In some embodiments the PIP-77 polypeptide has at least 83% or greater sequence identity compared to SEQ ID NO: 98. In some embodiments the PIP-77 polypeptide has at least 80% or greater sequence identity compared to SEQ ID NO: 100. In some embodiments the PIP-77 polypeptide has at least 85% or greater sequence identity compared to SEQ ID NO: 241. In some embodiments the PIP-77 polypeptide has at least 83% or greater sequence identity compared to SEQ ID NO: 242. In some embodiments the PIP-77 polypeptide has at least 96% or greater sequence identity compared to SEQ ID NO: 245.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

In some embodiments a PIP-45-1 polypeptide has a calculated molecular weight of between about 40 kDa and about 80 kDa, between about 50 kDa and about 70 kDa, between about 60 kDa and about 65 kDa, between about 61 kDa and about 64 kDa, between about 62 kDa and about 63 kDa, and between about 62.25 kDa, about 62.75 kDa. As used herein, the term "about" used in the context of molecular weight of an insecticidal polypeptide means±0.25 kilodaltons.

In some embodiments a PIP-45-2 polypeptide has a calculated molecular weight of between about 40 kDa and about 80 kDa, between about 50 kDa and about 64 kDa, between about 55 kDa and about 60 kDa, between about 56.5 kDa and about 59 kDa, and between about 57.25 kDa and about 58 kDa.

In some embodiments a PIP-64-1 polypeptide has a calculated molecular weight of between about 20 kDa and about 40 kDa, between about 25 kDa and about 32 kDa, between about 26 kDa and about 31 kDa, between about 27 kDa and about 30 kDa, between about 28 kDa and about 29 kDa, and between about 28.1 kDa and about 28.7 kDa.

In some embodiments a PIP-64-2 polypeptide has a calculated molecular weight of between about 20 kDa and about 40 kDa, between about 25 kDa and about 32 kDa, between about 26 kDa and about 31 kDa, between about 27 kDa and about 30 kDa, and between about 28.25 kDa and about 29 kDa.

In some embodiments a PIP-74-1 polypeptide has a calculated molecular weight of between about 40 kDa and about 80 kDa, between about 50 kDa and about 70 kDa, between about 55 kDa and about 73 kDa, between about 57 kDa and about 61 kDa, between about 58 kDa and about 60 kDa and between about 58.75 kDa, about 59.25 kDa. As used herein, the term "about" used in the context of molecular weight of an insecticidal polypeptide means±0.25 kilodaltons.

In some embodiments a PIP-74-2 polypeptide has a calculated molecular weight of between about 35 kDa and about 65 kDa, between about 45 kDa and about 51.5 kDa, between about 47.5 kDa and about 49.5 kDa, and between about 48.25 kDa and about 48.75 kDa.

In some embodiments a PIP-75 polypeptide has a calculated molecular weight of between about 6 kDa and about 14 kDa, between about 8 kDa and about 13.5 kDa, between about 9 kDa and about 12 kDa, between about 9.5 kDa and about 11.5 kDa, and between about 10.4 kDa and about 10.8 kDa.

In some embodiments a PIP-77 polypeptide has a calculated molecular weight of between about 7 kDa and about 13 kDa, between about 8 kDa and about 12 kDa, between about 9 kDa and about 11 kDa, between about 9.5 kDa and about 10.3 kDa, and between about 9.75 kDa and about 10.25 kDa.

In some embodiments the insecticidal polypeptides of the disclosure have a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the insecticidal polypeptides of the disclosure have increased digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In another aspect the insecticidal polypeptide of the disclosure may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271: 22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterification reaction between the two termini to form a branched ester or thioester intermediate and peptide bond cleavage coupled to cyclization of the intein C-terminal asparagine to free the intein (Evans, et al., (2000) *J. Biol. Chem.*, 275: 9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273: 10567-10577; Cotton, et al., (1999) *J. Am. Chem. Soc.* 121:1100-1101; Evans, et al., (1999) *J. Biol. Chem.* 274: 18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.,* 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another aspect the insecticidal polypeptide of the disclosure may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the insecticidal polypeptide of the disclosure and the 3' intein coding sequence is linked to the 5' end of the second fragment coding for the C-terminal part of the insecticidal polypeptide of the disclosure.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387:422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In another aspect the insecticidal polypeptide of the disclosure is a circular permuted variant. The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Funct. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted insecticidal polypeptides of the disclosure with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted insecticidal polypeptides of the disclosure with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another aspect fusion proteins are provided that include within its amino acid sequence an amino acid sequence comprising an insecticidal polypeptide of the disclosure. Methods for design and construction of fusion proteins (and polynucleotides encoding same) are known to those of skill in the art. Polynucleotides encoding an insecticidal polypeptide of the disclosure may be fused to signal sequences which will direct the localization of the insecticidal polypeptide of the disclosure to insecicidal polypeptide of the embodiments from a prokaryotic or eukaryotic cell. For example, in *E. coli*, one may wish to direct the expression of the protein to the periplasmic space. Examples of signal sequences or proteins (or fragments thereof) to which the insecticidal polypeptide of the disclosure may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs® (240 County Road, Ipswich, Mass. 01938-2723). In a specific embodiment, the insecticidal polypeptide of the disclosure may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat. No. 7,193,133). Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the insecticidal polypeptide of the disclosure to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9.

In some embodiments fusion proteins are provide comprising an insecticidal polypeptide of the disclosure, and an insecticidal polypeptide joined by an amino acid linker.

In some embodiments fusion proteins are provided represented by a formula selected from the group consisting of:

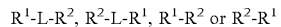

$R^1$-L-$R^2$, $R^2$-L-$R^1$, $R^1$-$R^2$ or $R^2$-$R^1$ wherein $R^1$ is an insecticidal polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO: 215) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

In another aspect chimeric insecticidal polypeptides are provided that are created through joining two or more portions of insecticidal polypeptides genes of disclosure, which originally encoded separate insecticidal proteins to create a chimeric gene. The translation of the chimeric gene results in a single chimeric insecicidal polypeptide with regions, motifs or domains derived from each of the original polypeptides.

It is recognized that DNA sequences may be altered by various methods, and that these alterations may result in DNA sequences encoding proteins with amino acid sequences different than that encoded by the wild-type (or native) pesticidal protein. In some embodiments an insecticidal polypeptide of the disclosure may be altered in various ways including amino acid substitutions, deletions, truncations and insertions of one or more amino acids, including up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more amino acid substitutions, deletions and/or insertions or combinations thereof compared to any one of SEQ ID NO: 1-SEQ ID NO: 107, and SEQ ID NO: 232-SEQ ID NO: 245. In some embodiments an insecticidal polypeptide of the disclosure comprises the deletion of 1, 2, 3, 4, 5, 6, 7, 8, 9, 10, 11, 12, 13, 14, 15 or more amino acids from the N-terminus and/or C-terminus of the insecicidal polypeptide of the disclosure.

Methods for such manipulations are generally known in the art. For example, amino acid sequence variants of an insecticidal polypeptide of the disclosure can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of an insecticidal polypeptide of the disclosure to confer pesticidal activity may be improved by the use of such techniques upon the compositions of this disclosure.

For example, conservative amino acid substitutions may be made at one or more, predicted, nonessential amino acid residues. A "nonessential" amino acid residue is a residue that can be altered from the wild-type sequence of an insecticidal polypeptide of the disclosure without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cysteine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologs). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment of the homologs). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol*. 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+ 0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different insecticidal polypeptide of the disclosure coding regions can be used to create a new insecticidal polypeptide of the disclosure possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered insecticidal polypeptides of the disclosure. Domains may be swapped between insecticidal polypeptides of the disclosure, resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Alignment of homologs of the insecticidal polypeptide (FIGS. 1, 2, 3, 4, 5, 6, 7 & 8) allows for identification of residues that are highly conserved among homologs in these families.

Compositions

Compositions comprising the insecticidal polypeptides of the present disclosure are also envisioned. Compositions comprising a PIP-45-1 polypeptide of the disclosure and a PIP-45-2 polypeptide of the disclosure are contemplated. In some embodiments the compositions comprise an insecticidally effective concentration of a PIP-45-1 polypeptide of the disclosure and a PIP-45-2 polypeptide of the disclosure. Compositions comprising a PIP-64-1 polypeptide of the disclosure and a PIP-64-2 polypeptide of the disclosure are contemplated. In some embodiments the compositions comprise an insecticidally effective concentration of a PIP-64-1 polypeptide of the disclosure and a PIP-64-2 polypeptide of the disclosure. Compositions comprising a PIP-74-1 polypeptide of the disclosure and a PIP-74-2 polypeptide of the disclosure are contemplated. In some embodiments the compositions comprise an insecticidally effective concentration of a PIP-74-1 polypeptide of the disclosure and a PIP-74-2 polypeptide of the disclosure. Compositions comprising a PIP-75 polypeptide of the disclosure are contemplated. In some embodiments the compositions comprise an insecticidally effective concentration of a PIP-75 polypeptide of the disclosure. Compositions comprising a PIP-77 polypeptide of the disclosure are contemplated. In some embodiments the compositions comprise an insecticidally effective concentration of a PIP-77 polypeptide of the disclosure. In some embodiments the composition further comprises an agriculturally acceptable carrier.

Antibodies

Antibodies to an insecticidal polypeptide of the disclosure of the embodiments or to variants or fragments thereof are also encompassed. The antibodies of the disclosure include polyclonal and monoclonal antibodies as well as fragments thereof which retain their ability to bind to insecticidal proteins found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y.

(1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies to the insecticidal polypeptides of the disclosure or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an insecticidal polypeptide of the disclosure as antigens.

A kit for detecting the presence of an insecticidal polypeptide of the disclosure or detecting the presence of a nucleotide sequence encoding an insecticidal polypeptide of the disclosure, in a sample is provided. In one embodiment, the kit provides antibody-based reagents for detecting the presence of an insecticidal polypeptide of the disclosure in a tissue sample. In another embodiment, the kit provides labeled nucleic acid probes useful for detecting the presence of one or more polynucleotides encoding an insecticidal polypeptide(s) of the disclosure. The kit is provided along with appropriate reagents and controls for carrying out a detection method, as well as instructions for use of the kit.

Receptor Identification and Isolation

Receptors to the insecicidal polypeptide of the embodiments or to variants or fragments thereof, are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the insecticidal polypeptides of the disclosure using the brush-border membrane vesicles from susceptible insects. In addition to the radioactive labeling method listed in the cited literature, insecicidal polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled insecticidal polypeptides of the disclosure can be incubated with blotted membrane of BBMV and labeled the insecticidal polypeptides of the disclosure can be identified with the labeled reporters. Identification of protein band(s) that interact with the insecticidal polypeptides of the disclosure can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the insecticidal polypeptides of the disclosure. Receptor function for insecticidal activity by the insecticidal polypeptides of the disclosure can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the insecticidal polypeptide gene sequence to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464; Christensen and Quail (1996) *Transgenic Res.* 5:213-218; Christensen et al. (1992) *Plant Molecular Biology* 18:675-689)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96), the maize AdhI intron (Kyozuka et al. (1991) *Mol. Gen. Genet.* 228:40-48; Kyozuka et al. (1990) *Maydica* 35:353-357) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A *Zea* maize codon usage table can be also found at kazusa.or.jp/codon/cgi-bin/showcodon.cgi?species=4577, which can be accessed using the www prefix. Table 2 shows a maize optimal codon analysis (adapted from Liu H et al. *Mol Bio Rep* 37:677-684, 2010).

TABLE 2

| Amino Acid | Codon | High Count | RSCU | Low Count | RSCU |
|---|---|---|---|---|---|
| Phe | UUU | 115 | 0.04 | 2,301 | 1.22 |
|  | UUC* | 5,269 | 1.96 | 1,485 | 0.78 |
| Ser | UCU | 176 | 0.13 | 2,498 | 1.48 |
|  | UCC* | 3,489 | 2.48 | 1,074 | 0.63 |
|  | UCA | 104 | 0.07 | 2,610 | 1.54 |
|  | UCG* | 1,975 | 1.4 | 670 | 0.4 |
|  | AGU | 77 | 0.05 | 1,788 | 1.06 |
|  | AGC* | 2,617 | 1.86 | 1,514 | 0.89 |
| Leu | UUA | 10 | 0.01 | 1,326 | 0.79 |
|  | UUG | 174 | 0.09 | 2,306 | 1.37 |
|  | CUU | 223 | 0.11 | 2,396 | 1.43 |
|  | CUC* | 5,979 | 3.08 | 1,109 | 0.66 |
|  | CUA | 106 | 0.05 | 1,280 | 0.76 |
|  | CUG* | 5,161 | 2.66 | 1,646 | 0.98 |
| Pro | CCU | 427 | 0.22 | 1,900 | 1.47 |
|  | CCC* | 3,035 | 1.59 | 601 | 0.47 |
|  | CCA | 311 | 0.16 | 2,140 | 1.66 |
|  | CCG* | 3,846 | 2.02 | 513 | 0.4 |
| Ile | AUU | 138 | 0.09 | 2,388 | 1.3 |
|  | AUC* | 4,380 | 2.85 | 1,353 | 0.74 |
|  | AUA | 88 | 0.06 | 1,756 | 0.96 |
| Thr | ACU | 136 | 0.09 | 1,990 | 1.43 |
|  | ACC* | 3,398 | 2.25 | 991 | 0.71 |
|  | ACA | 133 | 0.09 | 2,075 | 1.5 |
|  | ACG* | 2,378 | 1.57 | 495 | 0.36 |
| Val | GUU | 182 | 0.07 | 2,595 | 1.51 |
|  | GUC* | 4,584 | 1.82 | 1,096 | 0.64 |
|  | GUA | 74 | 0.03 | 1,325 | 0.77 |
|  | GUG* | 5,257 | 2.08 | 1,842 | 1.07 |
| Ala | GCU | 629 | 0.17 | 3,063 | 1.59 |
|  | GCC* | 8,057 | 2.16 | 1,136 | 0.59 |
|  | GCA | 369 | 0.1 | 2,872 | 1.49 |
|  | GCG* | 5,835 | 1.57 | 630 | 0.33 |
| Tyr | UAU | 71 | 0.04 | 1,632 | 1.22 |
|  | UAC* | 3,841 | 1.96 | 1,041 | 0.78 |
| His | CAU | 131 | 0.09 | 1,902 | 1.36 |
|  | CAC* | 2,800 | 1.91 | 897 | 0.64 |
| Cys | UGU | 52 | 0.04 | 1,233 | 1.12 |
|  | UGC* | 2,291 | 1.96 | 963 | 0.88 |
| Gln | CAA | 99 | 0.05 | 2,312 | 1.04 |
|  | CAG* | 3,557 | 1.95 | 2,130 | 0.96 |
| Arg | CGU | 153 | 0.12 | 751 | 0.74 |
|  | CGC* | 4,278 | 3.25 | 466 | 0.46 |
|  | CGA | 92 | 0.07 | 659 | 0.65 |
|  | CGG* | 1,793 | 1.36 | 631 | 0.62 |
|  | AGA | 83 | 0.06 | 1,948 | 1.91 |
|  | AGG* | 1,493 | 1.14 | 1,652 | 1.62 |
| Asn | AAU | 131 | 0.07 | 3,074 | 1.26 |
|  | AAC* | 3,814 | 1.93 | 1,807 | 0.74 |
| Lys | AAA | 130 | 0.05 | 3,215 | 0.98 |
|  | AAG* | 5,047 | 1.95 | 3,340 | 1.02 |
| Asp | GAU | 312 | 0.09 | 4,217 | 1.38 |
|  | GAC* | 6,729 | 1.91 | 1,891 | 0.62 |
| Gly | GGU | 363 | 0.13 | 2,301 | 1.35 |
|  | GGC* | 7,842 | 2.91 | 1,282 | 0.75 |
|  | GGA | 397 | 0.15 | 2,044 | 1.19 |
|  | GGG* | 2,186 | 0.81 | 1,215 | 0.71 |
| Glu | GAA | 193 | 0.06 | 4,080 | 1.1 |
|  | GAG* | 6,010 | 1.94 | 3,307 | 0.9 |

Codon usage was compared using Chi squared contingency test to identify optimal codons. Codons that occur significantly more often (P\0.01) are indicated with an asterisk.

A *Glycine max* codon usage table is shown in Table 3 and can also be found at kazusa.or.jp/codon/cgi-bin/showcodon.cgi?species=3847&aa=1&style=N, which can be accessed using the www prefix.

TABLE 3

| Codon | AA | Freq | Count |
|---|---|---|---|
| TTT | F | 21.2 | (10493) |
| TTC | F | 21.2 | (10487) |
| TTA | L | 9.2 | (4545) |
| TTG | L | 22.9 | (11340) |
| CTT | L | 23.9 | (11829) |
| CTC | L | 17.1 | (8479) |
| CTA | L | 8.5 | (4216) |
| CTG | L | 12.7 | (6304) |
| ATT | I | 25.1 | (12411) |
| ATC | I | 16.3 | (8071) |
| ATA | I | 12.9 | (6386) |
| ATG | M | 22.7 | (11218) |
| GTT | V | 26.1 | (12911) |
| GTC | V | 11.9 | (5894) |
| GTA | V | 7.7 | (3803) |
| GTG | V | 21.4 | (10610) |
| TAT | Y | 15.7 | (7779) |
| TAC | Y | 14.9 | (7367) |
| TAA | * | 0.9 | (463) |
| TAG | * | 0.5 | (263) |
| CAT | H | 14.0 | (6930) |
| CAC | H | 11.6 | (5759) |
| CAA | Q | 20.5 | (10162) |
| CAG | Q | 16.2 | (8038) |
| AAT | N | 22.4 | (11088) |
| AAC | N | 22.8 | (11284) |
| AAA | K | 26.9 | (13334) |
| AAG | K | 35.9 | (17797) |
| GAT | D | 32.4 | (16040) |
| GAC | D | 20.4 | (10097) |
| GAA | E | 33.2 | (16438) |
| GAG | E | 33.2 | (16426) |
| TCT | S | 18.4 | (9107) |
| TCC | S | 12.9 | (6409) |
| TCA | S | 15.6 | (7712) |
| TCG | S | 4.8 | (2397) |
| CCT | P | 18.9 | (9358) |
| CCC | P | 10.1 | (5010) |
| CCA | P | 19.1 | (9461) |
| CCG | P | 4.7 | (2312) |
| ACT | T | 17.1 | (8490) |
| ACC | T | 14.3 | (7100) |
| ACA | T | 14.9 | (7391) |
| ACG | T | 4.3 | (2147) |
| GCT | A | 26.7 | (13201) |
| GCC | A | 16.2 | (8026) |
| GCA | A | 21.4 | (10577) |
| GCG | A | 6.3 | (3123) |
| TGT | C | 8.1 | (3995) |
| TGC | C | 8.0 | (3980) |
| TGA | * | 1.0 | (480) |
| TGG | W | 13.0 | (6412) |
| CGT | R | 6.6 | (3291) |
| CGC | R | 6.2 | (3093) |
| CGA | R | 4.1 | (2018) |
| CGG | R | 3.1 | (1510) |
| AGT | S | 12.6 | (6237) |
| AGC | S | 11.3 | (5594) |
| AGA | R | 14.8 | (7337) |
| AGG | R | 13.3 | (6574) |
| GGT | G | 20.9 | (10353) |
| GGC | G | 13.4 | (6650) |
| GGA | G | 22.3 | (11022) |
| GGG | G | 13.0 | (6431) |

In some embodiments the recombinant nucleic acid molecule encoding an insecticidal polypeptide of the disclosure has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, Science 296:92-100, 2002) is a suitable source for lumen targeting signal peptide which may be used in accordance with the present disclosure.

Suitable chloroplast transit peptides (CTP) are well known to one skilled in the art also include chimeric CTPs comprising but not limited to, an N-terminal domain, a central domain or a C-terminal domain from a CTP from Oryza sativa 1-deoxy-D xyulose-5-Phosphate Synthase Oryza sativa-Superoxide dismutase Oryza sativa-soluble starch synthase Oryza sativa-NADP-dependent Malic acid enzyme Oryza sativa-Phospho-2-dehydro-3-deoxyhepto-nate Aldolase 2 Oryza sativa-L-Ascorbate peroxidase 5 Oryza sativa-Phosphoglucan water dikinase, Zea Mays ssRUBISCO, Zea Mays-beta-glucosidase, Zea Mays-Malate dehydrogenase, Zea Mays Thioredoxin M-type (US Patent Application Publication 2012/0304336). Chloroplast transit peptides of US Patent Publications US20130205440A1, US20130205441A1 and US20130210114A1.

The insecticidal polypeptide gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) Nature 313:810-812); rice actin (McElroy, et al., (1990) Plant Cell 2:163-171); ubiquitin (Christensen, et al., (1989) Plant Mol. Biol. 12:619-632 and Christensen, et al., (1992) Plant Mol. Biol. 18:675-689); pEMU (Last, et al., (1991) Theor. Appl. Genet. 81:581-588); MAS (Velten, et al., (1984) EMBO J. 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611. Suitable constitutive promoters also include promoters that have strong expression in nearly all tissues but have low expression in pollen, including but not limited to: Banana Streak Virus (Acuminata Yunnan) promoters (BSV(AY)) disclosed in U.S. Pat. No. 8,338,662; Banana Streak Virus (Acuminata Vietnam) promoters (BSV(AV)) disclosed in U.S. Pat. No. 8,350,121; and Banana Streak Virus (Mysore) promoters (BSV(MYS)) disclosed in U.S. Pat. No. 8,395,022.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) Ann. Rev. Phytopath. 28:425-449; Duan, et al., (1996) Nature Biotechnology 14:494-498); wun1 and wun2, U.S. Pat. No. 5,428,148; win1 and win2 (Stanford, et al., (1989) Mol. Gen. Genet. 215:200-208); systemin (McGurl, et al., (1992) Science 225:1570-1573); WIP1 (Rohmeier, et al., (1993) Plant Mol. Biol. 22:783-792; Eckelkamp, et al., (1993) FEBS Letters 323:73-76); MPI gene (Corderok, et al., (1994) Plant J. 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) Neth. J. Plant Pathol. 89:245-254; Uknes, et al., (1992) Plant Cell 4: 645-656 and Van Loon, (1985) Plant Mol. Virol. 4:111-116. See also, WO 1999/43819, herein incorporated by reference.

Of interest are promoters that are expressed locally at or near the site of pathogen infection. See, for example, Marineau, et al., (1987) Plant Mol. Biol. 9:335-342; Matton, et al., (1989) Molecular Plant-Microbe Interactions 2:325-331; Somsisch, et al., (1986) Proc. Natl. Acad. Sci. USA 83:2427-2430; Somsisch, et al., (1988) Mol. Gen. Genet. 2:93-98 and Yang, (1996) Proc. Natl. Acad. Sci. USA 93:14972-14977. See also, Chen, et al., (1996) Plant J. 10:955-966; Zhang, et al., (1994) Proc. Natl. Acad. Sci. USA 91:2507-2511; Warner, et al., (1993) Plant J. 3:191-201; Siebertz, et al., (1989) Plant Cell 1:961-968; U.S. Pat. No. 5,750,386 (nematode-inducible) and the references cited therein. Of particular interest is the inducible promoter for the maize PRms gene, whose expression is induced by the pathogen Fusarium moniliforme (see, for example, Cordero, et al., (1992) Physiol. Mol. Plant Path. 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) Proc. Natl. Acad. Sci. USA 88:10421-10425 and McNellis, et al., (1998) Plant J. 14(2):247-257) and tetracycline-inducible and tetracycline-repressible promoters (see, for example, Gatz, et al., (1991) Mol. Gen. Genet. 227:229-237 and U.S. Pat. Nos. 5,814,618 and 5,789,156), herein incorporated by reference.

Tissue-preferred promoters can be utilized to target enhanced insecticidal polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3): 337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5): 773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20): 9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US Patent Application US20130117883. Root-preferred sorghum (*Sorghum bicolor*) RCc3 promoters are disclosed in US Patent Application US20120210463.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about $\frac{1}{1000}$ transcripts to about $\frac{1}{100,000}$ transcripts to about $\frac{1}{500,000}$ transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608, 144; 5,604,121; 5,569,597; 5,466,785; 5,399,680; 5,268, 463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wssman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

DNA Constructs

DNA constructs comprising a polynucleotide encoding an insecticidal polypeptide of the disclosure are encompassed. In some embodiments the DNA construct comprises a polynucleotide encoding a PIP-45-1 polypeptide operably linked to a heterologous regulatory element. In some embodiments the DNA construct comprises the polynucleotide of SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 218, SEQ ID NO: 220 or SEQ ID NO: 222 that encodes the PIP-45-1 polypeptide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 and SEQ ID NO: 236, respectively. In some embodiments the DNA construct comprises the polynucleotide of SEQ ID NO: 108, SEQ ID NO: 124, SEQ ID NO: 126, SEQ ID NO: 128, SEQ ID NO: 130, SEQ ID NO: 134, SEQ ID NO: 136, SEQ ID NO: 138, SEQ ID NO: 140, SEQ ID NO: 142, SEQ ID NO: 146, SEQ ID NO: 150, SEQ ID NO: 152, SEQ ID NO: 220 or SEQ ID NO: 222, that encodes the PIP-45-1 polypeptide of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 and SEQ ID NO: 236, respectively. In some embodiments the DNA construct comprises a non-genomic nucleic acid molecule encoding the PIP-45-1 polypeptide. In some embodiments the DNA construct comprises a polynucleotide encoding a PIP-45-1 polypeptide sufficiently homologous to the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 or SEQ ID NO: 236 and which has insecticidal activity. In some embodiments the DNA construct comprises a polynucleotide encoding a PIP-45-1 polypeptide sufficiently homologous to the amino acid sequence of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of the PIP-45-1 polypeptide.

In some embodiments the DNA construct comprises a polynucleotide encoding a PIP-45-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 or SEQ ID NO: 236 and which has insecticidal activity. In some embodiments the DNA construct comprises a polynucleotide encoding a PIP-45-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO:

43, SEQ ID NO: 45, SEQ ID NO: 234 or SEQ ID NO: 236 and which has insecticidal activity.

In some embodiments the DNA construct comprises a polynucleotide encoding a PIP-45-1 polypeptide having at least 99.1% or greater sequence identity compared to SEQ ID NO: 1. In some embodiments the DNA construct comprises a polynucleotide encoding a PIP-45-1 polypeptide having at least 99.4% or greater sequence identity compared to SEQ ID NO: 17. In some embodiments the DNA construct comprises a polynucleotide encoding a PIP-45-1 polypeptide having at least 99.6% or greater sequence identity compared to SEQ ID NO: 19. In some embodiments the DNA construct comprises a polynucleotide encoding a PIP-45-1 polypeptide having at least 87% or greater sequence identity compared to SEQ ID NO: 21. In some embodiments the DNA construct comprises a polynucleotide encoding a PIP-45-1 polypeptide having at least 88% or greater sequence identity compared to SEQ ID NO: 23. In some embodiments the DNA construct comprises a polynucleotide encoding a PIP-45-1 polypeptide having at least 99.1% or greater sequence identity compared to SEQ ID NO: 27. In some embodiments the DNA construct comprises a polynucleotide encoding a PIP-45-1 polypeptide having at least 99.8% or greater sequence identity compared to SEQ ID NO: 29. In some embodiments the DNA construct comprises a polynucleotide encoding a PIP-45-1 polypeptide having at least 92.3% or greater sequence identity compared to SEQ ID NO: 31. In some embodiments the DNA construct comprises a polynucleotide encoding a PIP-45-1 polypeptide having at least 91.1% or greater sequence identity compared to SEQ ID NO: 33. In some embodiments the DNA construct comprises a polynucleotide encoding a PIP-45-1 polypeptide having at least 95.4% or greater sequence identity compared to SEQ ID NO: 35. In some embodiments the DNA construct comprises a polynucleotide encoding a PIP-45-1 polypeptide having at least 93% or greater sequence identity compared to SEQ ID NO: 39. In some embodiments the DNA construct comprises a polynucleotide encoding a PIP-45-1 polypeptide having at least 97.5% or greater sequence identity compared to SEQ ID NO: 43. In some embodiments the DNA construct comprises a polynucleotide encoding a PIP-45-1 polypeptide having at least 70% or greater sequence identity compared to SEQ ID NO: 45.

Transgenic plants or plant cells comprising a polynucleotide encoding a PIP-45-2 polypeptide are also encompassed by the disclosure. In some embodiments the DNA construct comprises the polynucleotide of SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 219, SEQ ID NO: 221 or SEQ ID NO: 223, that encode the PIP-45-2 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 and SEQ ID NO: 237, respectively. In some embodiments the DNA construct comprises the polynucleotide of SEQ ID NO: 109, SEQ ID NO: 125, SEQ ID NO: 127, SEQ ID NO: 129, SEQ ID NO: 131, SEQ ID NO: 135, SEQ ID NO: 137, SEQ ID NO: 139, SEQ ID NO: 141, SEQ ID NO: 143, SEQ ID NO: 147, SEQ ID NO: 151, SEQ ID NO: 153, SEQ ID NO: 221 or SEQ ID NO: 223 that encode the PIP-45-2 polypeptide of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 and SEQ ID NO: 237, respectively. In some embodiments the DNA construct comprises a non-genomic nucleic acid molecule encoding the PIP-45-2 polypeptide. In some embodiments the DNA construct comprises a polynucleotide encoding a PIP-45-2 polypeptide sufficiently homologous to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 and SEQ ID NO: 237 and which has insecticidal activity. In some embodiments the DNA construct comprises a polynucleotide encoding a PIP-45-2 polypeptide sufficiently homologous to the amino acid sequence of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-45-2 polypeptide.

In some embodiments the DNA construct comprises a polynucleotide encoding a PIP-45-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 or SEQ ID NO: 237 and which has insecticidal activity. In some embodiments the DNA construct comprises a polynucleotide encoding a PIP-45-2 polypeptide having at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and which has insecticidal activity.

In some embodiments the DNA construct comprises a polynucleotide encoding a PIP-45-2 polypeptide having at least 99.2% or greater sequence identity compared to SEQ ID NO: 2. In some embodiments the DNA construct comprises a polynucleotide encoding a PIP-45-2 polypeptide having at least 98.5% or greater sequence identity compared to SEQ ID NO: 18. In some embodiments the DNA construct comprises a polynucleotide encoding a PIP-45-2 polypeptide having at least 96% or greater sequence identity compared to SEQ ID NO: 20. In some embodiments the DNA construct comprises a polynucleotide encoding a PIP-45-2 polypeptide having at least 80% or greater sequence identity compared to SEQ ID NO: 22. In some embodiments the DNA construct comprises a polynucleotide encoding a PIP-45-2 polypeptide having at least 81% or greater sequence identity compared to SEQ ID NO: 24. In some embodiments the DNA construct comprises a polynucleotide encoding a PIP-45-2 polypeptide having at least 99.5% or greater sequence identity compared to SEQ ID NO: 28. In some embodiments the DNA construct comprises a polynucleotide encoding a PIP-45-2 polypeptide having at least 98.5% or greater sequence identity compared to SEQ ID NO: 30. In some embodiments the DNA construct comprises a polynucleotide encoding a PIP-45-2 polypeptide having at least 92% or greater sequence identity compared to SEQ ID NO: 32. In some embodiments the DNA construct comprises a polynucleotide encoding a PIP-45-2 polypeptide having at least 91.5% or greater sequence identity compared to SEQ ID NO: 34. In some embodiments the DNA construct comprises a polynucleotide encoding a PIP-45-2 polypeptide having at least 70% or greater sequence identity compared to SEQ ID NO: 36. In some embodiments the DNA construct comprises a polynucleotide encoding a PIP-45-2 polypeptide having at least 90% or greater sequence identity compared to SEQ ID NO: 40. In some embodiments the DNA construct comprises a polynucleotide encoding a PIP-45-2 polypeptide having at least 94% or greater sequence identity compared to SEQ ID NO: 44. In some embodiments the DNA construct comprises a polynucleotide encoding a PIP-45-2 polypeptide having at least 70% or greater sequence identity compared to SEQ ID NO: 46.

Transgenic plants or plant cells comprising a polynucleotide encoding a PIP-64-1 polypeptide are also encompassed by the disclosure. In some embodiments the DNA construct comprises the polynucleotide of SEQ ID NO: 160, SEQ ID NO: 163, SEQ ID NO: 165, SEQ ID NO: 167, SEQ ID NO: 169, SEQ ID NO: 171, SEQ ID NO: 172, SEQ ID NO: 174, SEQ ID NO: 176, SEQ ID NO: 178 or SEQ ID NO: 224 that encodes the PIP-64-1 polypeptide of SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 and SEQ ID NO: 238, respectively. In some embodiments the DNA construct comprises the polynucleotide of SEQ ID NO: 160, SEQ ID NO: 165 or SEQ ID NO: 224 that encode the PIP-64-1 polypeptide of SEQ ID NO: 53, SEQ ID NO: 58 and SEQ ID NO: 238. In some embodiments the DNA construct comprises a non-genomic nucleic acid molecule encoding the PIP-64-1 polypeptide. In some embodiments the DNA construct comprises a polynucleotide encoding a PIP-64-1 polypeptide sufficiently homologous to the amino acid sequence of SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 or SEQ ID NO: 238 and which has insecticidal activity. In some embodiments the DNA construct comprises a polynucleotide encoding a PIP-64-1 polypeptide sufficiently homologous to the amino acid sequence of SEQ ID NO: 53, SEQ ID NO: 58 or SEQ ID NO: 238 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-1 polypeptide. In some embodiments the DNA construct comprises a polynucleotide encoding a PIP-64-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 or SEQ ID NO: 238. In some embodiments the DNA construct comprises a polynucleotide encoding a PIP-64-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 58 or SEQ ID NO: 238.

In some embodiments the DNA construct comprises a polynucleotide encoding a PIP-64-1 polypeptide having at least 75% or greater sequence identity compared to SEQ ID NO: 53. In some embodiments the DNA construct comprises a polynucleotide encoding a PIP-64-1 polypeptide having at least 99.7% or greater sequence identity compared to SEQ ID NO: 58. In some embodiments the DNA construct comprises a polynucleotide encoding a PIP-64-1 polypeptide having at least 75% or greater sequence identity compared to SEQ ID NO: 238.

Transgenic plants or plant cells comprising a polynucleotide encoding a PIP-64-2 polypeptide are also encompassed by the disclosure. In some embodiments the DNA construct comprises the polynucleotide of SEQ ID NO: 161, SEQ ID NO: 162, SEQ ID NO: 164, SEQ ID NO: 166, SEQ ID NO: 168, SEQ ID NO: 170, SEQ ID NO: 173, SEQ ID NO: 175, SEQ ID NO: 177, SEQ ID NO: 179 or SEQ ID NO: 225 that encode the PIP-64-2 polypeptide of SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 and SEQ ID NO: 239, respectively. In some embodiments the DNA construct comprises the polynucleotide of SEQ ID NO: 161, SEQ ID NO: 162, SEQ ID NO: 166 or SEQ ID NO: 225 that encode the PIP-64-2 polypeptide of SEQ ID NO: 54, SEQ ID NO: 55, SEQ ID NO: 59 and SEQ ID NO: 239, respectively. In some embodiments the DNA construct comprises a non-genomic nucleic acid molecule encoding the PIP-64-2 polypeptide. In some embodiments the DNA construct comprises a polynucleotide encoding a PIP-64-2 polypeptide sufficiently homologous to the amino acid sequence of SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 or SEQ ID NO: 239 and which has insecticidal activity. In some embodiments the DNA construct comprises a polynucleotide encoding a PIP-64-2 polypeptide sufficiently homologous to the amino acid sequence of SEQ ID NO: 54, SEQ ID NO: 55, SEQ ID NO: 59 or SEQ ID NO: 239 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-2 polypeptide. In some embodiments the DNA construct comprises a polynucleotide encoding a PIP-64-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 or SEQ ID NO: 239 and which has insecticidal activity. In some embodiments the DNA construct comprises a polynucleotide encoding a PIP-64-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 59 or SEQ ID NO: 239 and which has insecticidal activity.

In some embodiments the DNA construct comprises a polynucleotide encoding a PIP-64-2 polypeptide having at least 70% or greater sequence identity compared to SEQ ID NO: 54. In some embodiments the DNA construct comprises a polynucleotide encoding a PIP-64-2 polypeptide having at least 70% or greater sequence identity compared to SEQ ID NO: 55. In some embodiments the DNA construct comprises a polynucleotide encoding a PIP-64-2 polypeptide having at least 91% or greater sequence identity compared to SEQ ID NO: 59. In some embodiments the DNA construct comprises a polynucleotide encoding a PIP-64-2 polypeptide having at least 70% or greater sequence identity compared to SEQ ID NO: 239.

Transgenic plants or plant cells comprising a polynucleotide encoding a PIP-74-1 polypeptide are also encompassed by the disclosure. In some embodiments the DNA construct comprises the polynucleotide of SEQ ID NO: 180, SEQ ID NO: 182 or SEQ ID NO: 184 that encode the PIP-74-1 polypeptide of SEQ ID NO: 73, SEQ ID NO: 75 and SEQ ID NO: 77, respectively. In some embodiments the DNA construct comprises a non-genomic nucleic acid molecule encoding the PIP-74-1 polypeptide. In some embodiments the polynucleotide encodes a PIP-74-1 polypeptide sufficiently homologous to the amino acid sequence of SEQ ID NO: 73, SEQ ID NO: 75 or SEQ ID NO: 77 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-1 polypeptide. In some embodiments the polynucleotide encodes a PIP-74-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 73, SEQ ID NO: 75 or SEQ ID NO: 77.

In some embodiments the DNA construct comprises a polynucleotide encoding a PIP-74-1 polypeptide having at least 75% or greater sequence identity compared to SEQ ID NO: 73. In some embodiments the DNA construct comprises a polynucleotide encoding a PIP-74-1 polypeptide having at least 75% or greater sequence identity compared to SEQ ID NO: 75. In some embodiments the DNA construct comprises a polynucleotide encoding a PIP-74-1 polypeptide having at least 75% or greater sequence identity compared to SEQ ID NO: 77.

Transgenic plants or plant cells comprising a polynucleotide encoding a PIP-74-2 polypeptide are also encompassed by the disclosure. In some embodiments the DNA construct comprises the polynucleotide of SEQ ID NO: 181, SEQ ID NO: 183, SEQ ID NO: 185 that encode the PIP-74-2 polypeptide of SEQ ID NO: 74, SEQ ID NO: 76 and SEQ ID NO: 78, respectively. In some embodiments the DNA construct comprises a non-genomic nucleic acid molecule encoding the PIP-74-2 polypeptide. In some embodiments the polynucleotide encodes a PIP-74-2 polypeptide sufficiently homologous to the amino acid sequence of SEQ ID NO: 74, SEQ ID NO: 76 or SEQ ID NO: 78 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-2 polypeptide. In some embodiments the polynucleotide encodes a PIP-74-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 74, SEQ ID NO: 76 or SEQ ID NO: 78.

In some embodiments the DNA construct comprises a polynucleotide encoding a PIP-74-2 polypeptide having at least 75% or greater sequence identity compared to SEQ ID NO: 74. In some embodiments the DNA construct comprises a polynucleotide encoding a PIP-74-2 polypeptide having at least 75% or greater sequence identity compared to SEQ ID NO: 76. In some embodiments the DNA construct comprises a polynucleotide encoding a PIP-74-2 polypeptide having at least 75% or greater sequence identity compared to SEQ ID NO: 78.

Transgenic plants or plant cells comprising a polynucleotide encoding a PIP-75 polypeptide are also encompassed by the disclosure. In some embodiments the DNA construct comprises the polynucleotide of SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 and SEQ ID NO: 87, respectively. In some embodiments the DNA construct comprises the polynucleotide of SEQ ID NO: 186, SEQ ID NO: 187, SEQ ID NO: 188, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 84, SEQ ID NO: 85, SEQ ID NO: 86 and SEQ ID NO: 87, respectively. In some embodiments the DNA construct comprises a non-genomic nucleic acid molecule encoding the PIP-75 polypeptide. In some embodiments the DNA construct comprises a polynucleotide encoding a PIP-75 polypeptide sufficiently homologous to the amino acid sequence of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 or SEQ ID NO: 87. In some embodiments the DNA construct comprises a polynucleotide encoding a PIP-75 polypeptide sufficiently homologous to the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-75 polypeptide. In some embodiments the polynucleotide encodes a PIP-75 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 or SEQ ID NO: 87 and which has insecticidal activity. In some embodiments the polynucleotide encodes a PIP-75 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 84, SEQ ID NO: 85, SEQ ID NO: 86 or SEQ ID NO: 87 and which has insecticidal activity.

In some embodiments the DNA construct comprises a polynucleotide encoding a PIP-75 polypeptide having at least 75% or greater sequence identity compared to SEQ ID NO: 79. In some embodiments the DNA construct comprises a polynucleotide encoding a PIP-75 polypeptide having at least 75% or greater sequence identity compared to SEQ ID NO: 80. In some embodiments the DNA construct comprises a polynucleotide encoding a PIP-75 polypeptide having at least 86% or greater sequence identity compared to SEQ ID NO: 81. In some embodiments the DNA construct comprises a polynucleotide encoding a PIP-75 polypeptide having at least 75% or greater sequence identity compared to SEQ ID NO: 84. In some embodiments the DNA construct comprises a polynucleotide encoding a PIP-75 polypeptide having at least 75% or greater sequence identity compared to SEQ ID NO: 85. In some embodiments the DNA construct comprises a polynucleotide encoding a PIP-75 polypeptide having at least 75% or greater sequence identity compared to SEQ ID NO: 86. In some embodiments the DNA construct comprises a polynucleotide encoding a PIP-75 polypeptide having at least 75% or greater sequence identity compared to SEQ ID NO: 87.

DNA constructs comprising a polynucleotide encoding a PIP-77 polypeptide are also encompassed by the disclosure. In some embodiments the DNA construct comprises the polynucleotide of SEQ ID NO: 195, SEQ ID NO: 196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 226, SEQ ID NO: 227, SEQ ID NO: 228, SEQ ID NO: 229, SEQ ID NO: 230 or SEQ ID NO: 231 that encodes the PIP-77 polypeptide of SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 240, SEQ ID NO: 241, SEQ ID NO: 242, SEQ ID NO: 243, SEQ ID NO: 244 and SEQ ID NO: 245, respectively. In some embodiments the DNA construct comprises the polynucleotide of SEQ ID NO: 195, SEQ ID NO:196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 227, SEQ ID NO: 228 or SEQ ID NO: 231 that encode the PIP-77 polypeptide of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 and SEQ ID NO: 245, respectively. In some embodiments the DNA construct comprises a polynucleotide encoding a PIP-77 polypeptide sufficiently homologous to the amino acid sequence of SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 or SEQ ID NO: 245 and which has insecticidal activity. In some embodiments the DNA construct comprises a polynucleotide encoding a PIP-77 polypeptide sufficiently homologous to the amino acid sequence of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO:

241, SEQ ID NO: 242 or SEQ ID NO: 245 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-77 polypeptide.

In some embodiments the DNA construct comprises a polynucleotide encoding a PIP-77 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 or SEQ ID NO: 245 and which has insecticidal activity. In some embodiments the DNA construct comprises a polynucleotide encoding a PIP-77 polypeptide having at least 80% or greater sequence identity compared to SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 or SEQ ID NO: 245 and which has insecticidal activity. In some embodiments the DNA construct comprises a polynucleotide encoding a PIP-77 polypeptide having at least 90% or greater sequence identity compared to SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 or SEQ ID NO: 245 and which has insecticidal activity. In some embodiments the DNA construct comprises a polynucleotide encoding a PIP-77 polypeptide having at least 95% or greater sequence identity compared to SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 or SEQ ID NO: 245 and which has insecticidal activity.

In some embodiments the DNA construct comprises a polynucleotide encoding a PIP-77 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity. In some embodiments the DNA construct comprises a polynucleotide encoding a PIP-77 polypeptide having at least 80% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity. In some embodiments the DNA construct comprises a polynucleotide encoding a PIP-77 polypeptide having at least 95% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity.

In some embodiments the DNA construct comprises a polynucleotide encoding a PIP-77 polypeptide having at least 93% or greater sequence identity compared to SEQ ID NO: 88. In some embodiments the DNA construct comprises a polynucleotide encoding a PIP-77 polypeptide having at least 97% or greater sequence identity compared to SEQ ID NO: 89. In some embodiments the DNA construct comprises a polynucleotide encoding a PIP-77 polypeptide having at least 99% or greater sequence identity compared to SEQ ID NO: 90. In some embodiments the DNA construct comprises a polynucleotide encoding a PIP-77 polypeptide having at least 97% or greater sequence identity compared to SEQ ID NO: 92. In some embodiments the DNA construct comprises a polynucleotide encoding a PIP-77 polypeptide having at least 87% or greater sequence identity compared to SEQ ID NO: 93. In some embodiments the DNA construct comprises a polynucleotide encoding a PIP-77 polypeptide having at least 86% or greater sequence identity compared to SEQ ID NO: 94. In some embodiments the DNA construct comprises a polynucleotide encoding a PIP-77 polypeptide having at least 85% or greater sequence identity compared to SEQ ID NO: 95. In some embodiments the DNA construct comprises a polynucleotide encoding a PIP-77 polypeptide having at least 84% or greater sequence identity compared to SEQ ID NO: 96. In some embodiments the DNA construct comprises a polynucleotide encoding a PIP-77 polypeptide having at least 85% or greater sequence identity compared to SEQ ID NO: 97. In some embodiments the DNA construct comprises a polynucleotide encoding a PIP-77 polypeptide having at least 83% or greater sequence identity compared to SEQ ID NO: 98. In some embodiments the DNA construct comprises a polynucleotide encoding a PIP-77 polypeptide having at least 80% or greater sequence identity compared to SEQ ID NO: 100. In some embodiments the DNA construct comprises a polynucleotide encoding a PIP-77 polypeptide having at least 85% or greater sequence identity compared to SEQ ID NO: 241. In some embodiments the DNA construct comprises a polynucleotide encoding a PIP-77 polypeptide having at least 83% or greater sequence identity compared to SEQ ID NO: 242. In some embodiments the DNA construct comprises a polynucleotide encoding a PIP-77 polypeptide having at least 96% or greater sequence identity compared to SEQ ID NO: 245.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio/technology* 6:923-926) and LecI transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (*Longman*, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the insecticidal polypeptide of the disclosure or variants and fragments thereof directly into the plant or the introduction of the insecticidal polypeptide of the disclosure transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the insecticidal polypeptide of the disclosure polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired insecticidal polypeptide. It is also recognized that such a viral polyprotein, comprising at least a portion of the amino acid sequence of an insecticidal polypeptide of the disclosure of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vul-*

*garis*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annus*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mungbean, lima bean, fava bean, lentils, chickpea, etc.

Transgenic Plants

Transgenic plants or plant cells comprising a polynucleotide encoding an insecticidal polypeptide are also encompassed by the disclosure. Transgenic plants or plant cells comprising a polynucleotide encoding a PIP-45-1 polypeptide are encompassed by the disclosure. In some embodiments the transgenic plant or plant cell comprises the polynucleotide of SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 218, SEQ ID NO: 220 or SEQ ID NO: 222 that encodes the PIP-45-1 polypeptide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 and SEQ ID NO: 236, respectively. In some embodiments the transgenic plant or plant cell comprises the polynucleotide of SEQ ID NO: 108, SEQ ID NO: 124, SEQ ID NO: 126, SEQ ID NO: 128, SEQ ID NO: 130, SEQ ID NO: 134, SEQ ID NO: 136, SEQ ID NO: 138, SEQ ID NO: 140, SEQ ID NO: 142, SEQ ID NO: 146, SEQ ID NO: 150, SEQ ID NO: 152, SEQ ID NO: 220 or SEQ ID NO: 222, that encodes the PIP-45-1 polypeptide of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 and SEQ ID NO: 236, respectively. In some embodiments the transgenic plant or plant cell comprises a non-genomic nucleic acid molecule encoding the PIP-45-1 polypeptide. In some embodiments the transgenic plant or plant cell comprises a polynucleotide encoding a PIP-45-1 polypeptide sufficiently homologous to the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 or SEQ ID NO: 236 and which has insecticidal activity. In some embodiments the transgenic plant or plant cell comprises a polynucleotide encoding a PIP-45-1 polypeptide sufficiently homologous to the amino acid sequence of SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of the PIP-45-1 polypeptide.

In some embodiments the transgenic plant or plant cell comprises a polynucleotide encoding a PIP-45-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 232, SEQ ID NO: 234 or SEQ ID NO: 236 and which has insecticidal activity. In some embodiments the transgenic plant or plant cell comprises a polynucleotide encoding a PIP-45-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 39, SEQ ID NO: 43, SEQ ID NO: 45, SEQ ID NO: 234 or SEQ ID NO: 236 and which has insecticidal activity.

In some embodiments the transgenic plant or plant cell comprises a polynucleotide encoding a PIP-45-1 polypeptide having at least 99.1% or greater sequence identity compared to SEQ ID NO: 1. In some embodiments the transgenic plant or plant cell comprises a polynucleotide encoding a PIP-45-1 polypeptide having at least 99.4% or greater sequence identity compared to SEQ ID NO: 17. In some embodiments the transgenic plant or plant cell comprises a polynucleotide encoding a PIP-45-1 polypeptide having at least 99.6% or greater sequence identity compared to SEQ ID NO: 19. In some embodiments the transgenic plant or plant cell comprises a polynucleotide encoding a PIP-45-1 polypeptide having at least 87% or greater sequence identity compared to SEQ ID NO: 21. In some embodiments the transgenic plant or plant cell comprises a polynucleotide encoding a PIP-45-1 polypeptide having at least 88% or greater sequence identity compared to SEQ ID NO: 23. In some embodiments the transgenic plant or plant cell comprises a polynucleotide encoding a PIP-45-1 polypeptide having at least 99.1% or greater sequence identity compared to SEQ ID NO: 27. In some embodiments the transgenic plant or plant cell comprises a polynucleotide encoding a PIP-45-1 polypeptide having at least 99.8% or greater sequence identity compared to SEQ ID NO: 29. In some embodiments the transgenic plant or plant cell comprises a polynucleotide encoding a PIP-45-1 polypeptide having at least 92.3% or greater sequence identity compared to SEQ ID NO: 31. In some embodiments the transgenic plant or plant cell comprises a polynucleotide encoding a PIP-45-1 polypeptide having at least 91.1% or greater sequence identity compared to SEQ ID NO: 33. In some embodiments the transgenic plant or plant cell comprises a polynucleotide encoding a PIP-45-1 polypeptide having at least 95.4% or greater sequence identity compared to SEQ ID NO: 35. In some embodiments the transgenic plant or plant cell comprises a polynucleotide encoding a PIP-45-1 polypeptide having at least 95% or greater sequence identity compared to SEQ ID NO: 39. In some embodiments the transgenic plant or plant cell comprises a polynucleotide encoding a PIP-45-1 polypeptide having at least 97.5% or greater sequence identity compared to SEQ ID NO: 43. In some embodiments the transgenic plant or plant cell comprises a polynucleotide encoding a PIP-45-1 polypeptide having at least 70% or greater sequence identity compared to SEQ ID NO: 45. In some embodiments the transgenic plant or plant cell comprises a polynucleotide encoding a PIP-45-1 polypeptide having at least 94% or greater sequence identity compared to SEQ ID NO: 234. In some embodiments the transgenic plant or plant cell comprises a polynucleotide encoding a PIP-45-1 polypeptide having at least 96% or greater sequence identity compared to SEQ ID NO: 236.

Transgenic plants or plant cells comprising a polynucleotide encoding a PIP-45-2 polypeptide are also encompassed by the disclosure. In some embodiments the transgenic plant or plant cell comprises the polynucleotide of SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 219, SEQ ID NO: 221 or SEQ ID NO: 223 that encodes the PIP-45-2 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 and SEQ ID NO: 237, respectively. In some embodiments the transgenic plant or plant cell comprises the polynucleotide of SEQ ID NO: 109, SEQ ID NO: 125, SEQ ID NO: 127, SEQ ID NO: 129, SEQ ID NO: 131, SEQ ID NO: 135, SEQ ID NO: 137, SEQ ID NO: 139, SEQ ID NO: 141, SEQ ID NO: 143, SEQ ID NO: 147, SEQ ID NO: 151, SEQ ID NO: 153, SEQ ID NO: 221 or SEQ ID NO: 223 that encode the PIP-45-2 polypeptide of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 and SEQ ID NO: 237, respectively. In some embodiments the transgenic plant or plant cell comprises a non-genomic nucleic acid molecule encoding the PIP-45-2 polypeptide. In some embodiments the transgenic plant or plant cell comprises a polynucleotide encoding a PIP-45-2 polypeptide sufficiently homologous to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 and SEQ ID NO: 237 and which has insecticidal activity. In some embodiments the transgenic plant or plant cell comprises a polynucleotide encoding a PIP-45-2 polypeptide sufficiently homologous to the amino acid sequence of SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-45-2 polypeptide.

In some embodiments the transgenic plant or plant cell comprises a polynucleotide encoding a PIP-45-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 233, SEQ ID NO: 235 or SEQ ID NO: 237 and which has insecticidal activity. In some embodiments the transgenic plant or plant cell comprises a polynucleotide encoding a PIP-45-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 40, SEQ ID NO: 44, SEQ ID NO: 46, SEQ ID NO: 235 or SEQ ID NO: 237 and which has insecticidal activity.

In some embodiments the transgenic plant or plant cell comprises a polynucleotide encoding a PIP-45-2 polypeptide having at least 99.2% or greater sequence identity compared to SEQ ID NO: 2. In some embodiments the transgenic plant or plant cell comprises a polynucleotide encoding a PIP-45-2 polypeptide having at least 98.5% or greater sequence identity compared to SEQ ID NO: 18. In some embodiments the transgenic plant or plant cell comprises a polynucleotide encoding a PIP-45-2 polypeptide having at least 96% or greater sequence identity compared to SEQ ID NO: 20. In some embodiments the transgenic plant or plant cell comprises a polynucleotide encoding a PIP-45-2 polypeptide having at least 80% or greater sequence identity compared to SEQ ID NO: 22. In some embodiments the transgenic plant or plant cell comprises a polynucleotide encoding a PIP-45-2 polypeptide having at least 81% or greater sequence identity compared to SEQ ID NO: 24. In some embodiments the transgenic plant or plant cell comprises a polynucleotide encoding a PIP-45-2 polypeptide having at least 99.5% or greater sequence identity compared to SEQ ID NO: 28. In some embodiments the transgenic plant or plant cell comprises a polynucleotide encoding a PIP-45-2 polypeptide having at least 98.5% or greater sequence identity compared to SEQ ID NO: 30. In some embodiments the transgenic plant or plant cell comprises a polynucleotide encoding a PIP-45-2 polypeptide having at least 92% or greater sequence identity compared to SEQ ID NO: 32. In some embodiments the transgenic plant or plant cell comprises a polynucleotide encoding a PIP-45-2 polypeptide having at least 91.5% or greater sequence identity compared to SEQ ID NO: 34. In some embodiments the transgenic plant or plant cell comprises a polynucleotide encoding a PIP-45-2 polypeptide having at least 70% or greater sequence identity compared to SEQ ID NO: 36. In some embodiments the transgenic plant or plant cell comprises a polynucleotide encoding a PIP-45-2 polypeptide having at least 90% or greater sequence identity compared to SEQ ID NO: 40. In some embodiments the transgenic plant or plant cell comprises a polynucleotide encoding a PIP-45-2 polypeptide having at least 94% or greater sequence identity compared to SEQ ID NO: 44. In some embodiments the transgenic plant or plant cell comprises a polynucleotide encoding a PIP-45-2 polypeptide having at least 70% or greater sequence identity compared to SEQ ID NO: 46.

Transgenic plants or plant cells comprising a polynucleotide encoding a PIP-64-1 polypeptide are also encompassed by the disclosure. In some embodiments the transgenic plant or plant cell comprises the polynucleotide of SEQ ID NO: 160, SEQ ID NO: 163, SEQ ID NO: 165, SEQ ID NO: 167, SEQ ID NO: 169, SEQ ID NO: 171, SEQ ID NO: 172, SEQ ID NO: 174, SEQ ID NO: 176, SEQ ID NO: 178 or SEQ ID NO: 224 that encodes the PIP-64-1 polypeptide of SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 and SEQ ID NO: 238, respectively. In some embodiments the transgenic plant or plant cell comprises the polynucleotide of SEQ ID NO: 160, SEQ ID NO: 165 or SEQ ID NO: 224 that encode the PIP-64-1 polypeptide of SEQ ID NO: 53, SEQ ID NO: 58 and SEQ ID NO: 238. In some embodiments the transgenic plant or plant cell comprises a non-genomic nucleic acid molecule encoding the PIP-64-1 polypeptide. In some embodiments the transgenic plant or plant cell comprises a polynucleotide encoding a PIP-64-1 polypeptide sufficiently homologous to the amino acid sequence of SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 or SEQ ID NO: 238 and which has insecticidal activity. In some embodiments the transgenic plant or plant cell comprises a polynucleotide encoding a PIP-64-1 polypeptide sufficiently homologous to the amino acid sequence of SEQ ID NO: 53, SEQ ID NO: 58 or SEQ ID NO: 238 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-1 polypeptide. In some embodiments the transgenic plant or plant cell comprises a polynucleotide encoding a PIP-64-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 56, SEQ ID NO: 58, SEQ ID NO: 60, SEQ ID NO: 62, SEQ ID NO: 64, SEQ ID NO: 65, SEQ ID NO: 67, SEQ ID NO: 69, SEQ ID NO: 71 or SEQ ID NO: 238. In some embodiments the transgenic plant or plant cell comprises a polynucleotide encoding a PIP-64-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 53, SEQ ID NO: 58 or SEQ ID NO: 238.

In some embodiments the transgenic plant or plant cell comprises a polynucleotide encoding a PIP-64-1 polypeptide having at least 75% or greater sequence identity compared to SEQ ID NO: 53. In some embodiments the transgenic plant or plant cell comprises a polynucleotide encoding a PIP-64-1 polypeptide having at least 99.7% or greater sequence identity compared to SEQ ID NO: 58. In some embodiments the transgenic plant or plant cell comprises a polynucleotide encoding a PIP-64-1 polypeptide having at least 75% or greater sequence identity compared to SEQ ID NO: 238.

Transgenic plants or plant cells comprising a polynucleotide encoding a PIP-64-2 polypeptide are also encompassed by the disclosure. In some embodiments the transgenic plant or plant cell comprises the polynucleotide of SEQ ID NO: 161, SEQ ID NO: 162, SEQ ID NO: 164, SEQ ID NO: 166, SEQ ID NO: 168, SEQ ID NO: 170, SEQ ID NO: 173, SEQ ID NO: 175, SEQ ID NO: 177, SEQ ID NO: 179 or SEQ ID NO: 225 that encode the PIP-64-2 polypeptide of SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 and SEQ ID NO: 239, respectively. In some embodiments the transgenic plant or plant cell comprises the polynucleotide of SEQ ID NO: 161, SEQ ID NO: 162, SEQ ID NO: 166 or SEQ ID NO: 225 that encode the PIP-64-2 polypeptide of SEQ ID NO: 54, SEQ ID NO: 55, SEQ ID NO: 59 and SEQ ID NO: 239, respectively. In some embodiments the transgenic plant or plant cell comprises a non-genomic nucleic acid molecule encoding the PIP-64-2 polypeptide. In some embodiments the transgenic plant or plant cell comprises a polynucleotide encoding a PIP-64-2 polypeptide sufficiently homologous to the amino acid sequence SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 or SEQ ID NO: 239 and which has insecticidal activity. In some embodiments the transgenic plant or plant cell comprises a polynucleotide encoding a PIP-64-2 polypeptide sufficiently homologous to the amino acid sequence of SEQ ID NO: 54, SEQ ID NO: 55, SEQ ID NO: 59 or SEQ ID NO: 239 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-64-2 polypeptide. In some embodiments the transgenic plant or plant cell comprises a polynucleotide encoding a PIP-64-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 57, SEQ ID NO: 59, SEQ ID NO: 61, SEQ ID NO: 63, SEQ ID NO: 66, SEQ ID NO: 68, SEQ ID NO: 70, SEQ ID NO: 72 or SEQ ID NO: 239 and which has insecticidal activity. In some embodiments the transgenic plant or plant cell comprises a polynucleotide encoding a PIP-64-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 54, SEQ ID NO: 55, SEQ ID NO: 59 or SEQ ID NO: 239 and which has insecticidal activity.

In some embodiments the transgenic plant or plant cell comprises a polynucleotide encoding a PIP-64-2 polypeptide having at least 70% or greater sequence identity compared to SEQ ID NO: 54. In some embodiments the transgenic plant or plant cell comprises a polynucleotide encoding a PIP-64-2 polypeptide having at least 70% or greater sequence identity compared to SEQ ID NO: 55. In some embodiments the transgenic plant or plant cell comprises a polynucleotide encoding a PIP-64-2 polypeptide having at least 91% or greater sequence identity compared to SEQ ID NO: 59. In some embodiments the transgenic plant or plant cell comprises a polynucleotide encoding a PIP-64-2 polypeptide having at least 70% or greater sequence identity compared to SEQ ID NO: 239.

Transgenic plants or plant cells comprising a polynucleotide encoding a PIP-74-1 polypeptide are also encompassed by the disclosure. In some embodiments the transgenic plant or plant cell comprises the polynucleotide of SEQ ID NO: 180, SEQ ID NO: 182 or SEQ ID NO: 184 that encode the PIP-74-1 polypeptide of SEQ ID NO: 73, SEQ ID NO: 75 and SEQ ID NO: 77, respectively. In some embodiments the transgenic plant or plant cell comprises a non-genomic nucleic acid molecule encoding the PIP-74-1 polypeptide. In some embodiments the transgenic plant or plant cell comprises a polynucleotide encoding a PIP-74-1 polypeptide sufficiently homologous to the amino acid sequence of SEQ ID NO: 73, SEQ ID NO: 75 or SEQ ID NO: 77 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-1 polypeptide. In some embodiments the polynucleotide encodes a PIP-74-1 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 73, SEQ ID NO: 75 or SEQ ID NO: 77.

In some embodiments the transgenic plant or plant cell comprises a polynucleotide encoding a PIP-74-1 polypeptide having at least 75% or greater sequence identity compared to SEQ ID NO: 73. In some embodiments the transgenic plant or plant cell comprises a polynucleotide encoding a PIP-74-1 polypeptide having at least 75% or greater sequence identity compared to SEQ ID NO: 75. In some embodiments the transgenic plant or plant cell comprises a polynucleotide encoding a PIP-74-1 polypeptide having at least 75% or greater sequence identity compared to SEQ ID NO: 77.

Transgenic plants or plant cells comprising a polynucleotide encoding a PIP-74-2 polypeptide are also encompassed by the disclosure. In some embodiments the transgenic plant or plant cell comprises the polynucleotide of SEQ ID NO: 181, SEQ ID NO: 183, SEQ ID NO: 185 that encode the PIP-74-2 polypeptide of SEQ ID NO: 74, SEQ ID NO: 76 and SEQ ID NO: 78, respectively. In some embodiments the transgenic plant or plant cell comprises a non-genomic nucleic acid molecule encoding the PIP-74-2 polypeptide. In some embodiments the polynucleotide encodes a PIP-74-2 polypeptide sufficiently homologous to the amino acid sequence of SEQ ID NO: 74, SEQ ID NO: 76 or SEQ ID NO: 78 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-74-2 polypeptide. In some embodiments the polynucleotide encodes a PIP-74-2 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 74, SEQ ID NO: 76 or SEQ ID NO: 78.

In some embodiments the transgenic plant or plant cell comprises a polynucleotide encoding a PIP-74-2 polypeptide having at least 75% or greater sequence identity compared to SEQ ID NO: 74. In some embodiments the transgenic plant or plant cell comprises a polynucleotide encoding a PIP-74-2 polypeptide having at least 75% or greater sequence identity compared to SEQ ID NO: 76. In some embodiments the transgenic plant or plant cell comprises a polynucleotide encoding a PIP-74-2 polypeptide having at least 75% or greater sequence identity compared to SEQ ID NO: 78.

Transgenic plants or plant cells comprising a polynucleotide encoding a PIP-75 polypeptide are also encompassed by the disclosure. In some embodiments the transgenic plant or plant cell comprises the polynucleotide of SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 and SEQ ID NO: 87, respectively. In some embodiments the transgenic plant or plant cell comprises the polynucleotide of SEQ ID NO: 186, SEQ ID NO: 187, SEQ ID NO: 188, SEQ ID NO: 191, SEQ ID NO: 192, SEQ ID NO: 193 or SEQ ID NO: 194 that encode the PIP-75 polypeptide of SEQ ID NO: 79, SEQ ID NO: 80, SEQ ID NO: 81, SEQ ID NO: 84, SEQ ID NO: 85, SEQ ID NO: 86 and SEQ ID NO: 87, respectively. In some embodiments the transgenic plant or plant cell comprises a non-genomic nucleic acid molecule encoding the PIP-75 polypeptide. In some embodiments the transgenic plant or plant cell comprises a polynucleotide encoding a PIP-75 polypeptide sufficiently homologous to the amino acid sequence of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 or SEQ ID NO: 87. In some embodiments the transgenic plant or plant cell comprises a polynucleotide encoding a PIP-75 polypeptide sufficiently homologous to the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-75 polypeptide. In some embodiments the polynucleotide encodes a PIP-75 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86 or SEQ ID NO: 87 and which has insecticidal activity. In some embodiments the polynucleotide encodes a PIP-75 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 79, SEQ ID NO: 80, SEQ ID NO: 81, SEQ ID NO: 84, SEQ ID NO: 85, SEQ ID NO: 86 or SEQ ID NO: 87 and which has insecticidal activity.

In some embodiments the transgenic plant or plant cell comprises a polynucleotide encoding a PIP-75 polypeptide having at least 75% or greater sequence identity compared to SEQ ID NO: 79. In some embodiments the transgenic plant or plant cell comprises a polynucleotide encoding a PIP-75 polypeptide having at least 75% or greater sequence identity compared to SEQ ID NO: 80. In some embodiments the transgenic plant or plant cell comprises a polynucleotide encoding a PIP-75 polypeptide having at least 86% or greater sequence identity compared to SEQ ID NO: 81. In some embodiments the transgenic plant or plant cell comprises a polynucleotide encoding a PIP-75 polypeptide having at least 75% or greater sequence identity compared to SEQ ID NO: 84. In some embodiments the transgenic plant or plant cell comprises a polynucleotide encoding a PIP-75 polypeptide having at least 75% or greater sequence identity compared to SEQ ID NO: 85. In some embodiments the transgenic plant or plant cell comprises a polynucleotide encoding a PIP-75 polypeptide having at least 75% or greater sequence identity compared to SEQ ID NO: 86. In some embodiments the transgenic plant or plant cell comprises a polynucleotide encoding a PIP-75 polypeptide having at least 75% or greater sequence identity compared to SEQ ID NO: 87.

Transgenic plants or plant cells comprising a polynucleotide encoding a PIP-77 polypeptide are also encompassed by the disclosure. In some embodiments the transgenic plant or plant cell comprises the polynucleotide of SEQ ID NO: 195, SEQ ID NO: 196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 226, SEQ ID NO: 227, SEQ ID NO: 228, SEQ ID NO: 229, SEQ ID NO: 230 or SEQ ID NO: 231 that encodes the PIP-77 polypeptide of SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 241, SEQ ID NO: 242, SEQ ID NO: 243, SEQ ID NO: 244 and SEQ ID NO: 245, respectively. In some embodiments the transgenic plant or plant cell comprises the polynucleotide of SEQ ID NO: 195, SEQ ID NO:196, SEQ ID NO:197, SEQ ID NO:198, SEQ ID NO:199, SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 227, SEQ ID NO: 228 or SEQ ID NO: 231 that encode the PIP-77 polypeptide of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 and SEQ ID NO: 245, respectively. In some embodiments the transgenic plant or plant cell comprises a polynucleotide encoding a PIP-77 polypeptide sufficiently homologous to the amino acid sequence of SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 240, SEQ ID NO: 241, SEQ ID NO: 242, SEQ ID NO: 243, SEQ ID NO: 244 or SEQ ID NO: 245 and which has insecticidal activity. In some embodiments the transgenic plant or plant cell comprises a polynucleotide encoding a PIP-77 polypeptide sufficiently homologous to the amino acid sequence of SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. In some embodiments the sequence homology is against the full length sequence of a PIP-77 polypeptide.

In some embodiments the transgenic plant or plant cell comprises a polynucleotide encoding a PIP-77 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 240, SEQ ID NO: 241, SEQ ID NO: 242, SEQ ID NO: 243, SEQ ID NO: 244 or SEQ ID NO: 245 and which has insecticidal activity. In some embodiments the transgenic plant or plant cell comprises a polynucleotide encoding a PIP-77 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 88, SEQ ID NO: 89, SEQ ID NO: 90, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 100, SEQ ID NO: 241, SEQ ID NO: 242 or SEQ ID NO: 245 and which has insecticidal activity.

In some embodiments the transgenic plant or plant cell comprises a polynucleotide encoding a PIP-77 polypeptide having at least 86% or greater sequence identity compared to SEQ ID NO: 88. In some embodiments the transgenic plant or plant cell comprises a polynucleotide encoding a PIP-77 polypeptide having at least 85% or greater sequence identity compared to SEQ ID NO: 89. In some embodiments the transgenic plant or plant cell comprises a polynucleotide encoding a PIP-77 polypeptide having at least 85% or greater sequence identity compared to SEQ ID NO: 90. In some embodiments the transgenic plant or plant cell comprises a polynucleotide encoding a PIP-77 polypeptide having at least 85% or greater sequence identity compared to SEQ ID NO: 91. In some embodiments the transgenic plant or plant cell comprises a polynucleotide encoding a PIP-77 polypeptide having at least 85% or greater sequence identity compared to SEQ ID NO: 92. In some embodiments the transgenic plant or plant cell comprises a polynucleotide encoding a PIP-77 polypeptide having at least 85% or greater sequence identity compared to SEQ ID NO: 93. In some embodiments the transgenic plant or plant cell comprises a polynucleotide encoding a PIP-77 polypeptide having at least 85% or greater sequence identity compared to SEQ ID NO: 94. In some embodiments the transgenic plant or plant cell comprises a polynucleotide encoding a PIP-77 polypeptide having at least 85% or greater sequence identity compared to SEQ ID NO: 95. In some embodiments the transgenic plant or plant cell comprises a polynucleotide encoding a PIP-77 polypeptide having at least 80% or greater sequence identity compared to SEQ ID NO: 96. In some embodiments the transgenic plant or plant cell comprises a polynucleotide encoding a PIP-77 polypeptide having at least 80% or greater sequence identity compared to SEQ ID NO: 97. In some embodiments the transgenic plant or plant cell comprises a polynucleotide encoding a PIP-77 polypeptide having at least 80% or greater sequence identity compared to SEQ ID NO: 98. In some embodiments the transgenic plant or plant cell comprises a polynucleotide encoding a PIP-77 polypeptide having at least 80% or greater sequence identity compared to SEQ ID NO: 100.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the insecticidal polypeptide of the disclosure.

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the insecticidal polypeptides disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/ 31248; WO 2001/12731; WO 1999/24581 and WO 1997/ 40162.

Genes encoding pesticidal proteins may also be stacked including but are not limited to: insecticidal proteins from *Pseudomonas* sp. such as PSEEN3174 (Monalysin, (2011)

*PLoS Pathogens,* 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas* pseudoalcligenes (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of US Patent Publication Number US2014-0007297-A1; an AflP-1A and/or AflP-1B polypeptides of US Patent Publication Number US2014-0033361; a PHI-4 polypeptides of U.S. Ser. No. 13/839,702; PIP-47 polypeptides of PCT Serial Number PCT/US14/51063; a PHI-4 polypeptide of US patent Publication US20140274885 or PCT Patent Publication WO2014/150914; a PIP-72 polypeptide of PCT Serial Number PCT/US14/55128; the insecticidal proteins of U.S. Ser. No. 61/863,761 and 61/863,763; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51, Cry52, Cry 53, Cry 54, Cry55, Cry56, Cry57, Cry58, Cry59. Cry60, Cry61, Cry62, Cry63, Cry64, Cry65, Cry66, Cry67, Cry68, Cry69, Cry70, Cry71 and Cry72 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #I26149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #I12419); Cry1Ab12 (Accession #AAC64003); Cry1Ab13 (Accession #AAN76494); Cry1Ab14 (Accession #AAG16877); Cry1Ab15 (Accession #AAO13302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AAO39719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #ABO20894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #I76415); Cry1Da3 (Accession

HQ439784); Cry1Db1 (Accession #CAA80234); Cry1Db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AAO13756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AAO13750); Cry2Aa10 (Accession #AAQ04263); Cry2Aa11 (Accession #AAQ52384); Cry2Aa12 (Accession #ABI83671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #ABO30519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #I15475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession

CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #I34543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8Db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9Db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #I32932); Cry21Aa2 (Accession #I66477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #I34547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781);

Cry30Da1 (Accession #EF095955); Cry30Db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EAO57254); Cry60Aa3 (Accession #EEM99278); Cry60Ba1 (Accession #GU810818); Cry60Ba2 (Accession #EAO57253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC807 of US2040194351, TIC853 toxins of U.S. Pat. No. 8,513,494, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; AXMI221 of US20140196175; AXMI345 of US 20140373195; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/intro.html which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex-.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity, including but not limited to 7-epizingiberene synthase (US Patent Publication 20140157456).

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373;

5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 5,094,945, 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-52 and Acc1-53 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) Plant Physiol 106:17), genes for glutathione reductase and superoxide dismutase (Aono, et al., (1995) Plant Cell Physiol 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Deiftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtI) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that confers male fertility to be transcribed.

(A) Introduction of a deacetylase gene under the control of a tapetum-specific promoter and with the application of the chemical N-Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859, 341; 6,297,426; 5,478,369; 5,824,524; 5,850,014 and 6,265, 640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417, 428, 6,664,446, 6,706,866, 6,717,034, 6,801,104, WO 2000/ 060089, WO 2001/026459, WO 2001/035725, WO 2001/ 034726, WO 2001/035727, WO 2001/036444, WO 2001/ 036597, WO 2001/036598, WO 2002/015675, WO 2002/ 017430, WO 2002/077185, WO 2002/079403, WO 2003/ 013227, WO 2003/013228, WO 2003/014327, WO 2004/ 031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/ 0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177, 275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/ 14414 (CON), WO 1996/38560, WO 2001/21822 (VRN1), WO 2000/44918 (VRN2), WO 1999/49064 (GI), WO 2000/ 46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/ 0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events in Table 4A-4F.

TABLE 4A

*Helianthus annuus* Sunflower

| Event | Company | Description |
|---|---|---|
| X81359 | BASF Inc. | Tolerance to imidazolinone herbicides by selection of a naturally occurring mutant. |

TABLE 4B

*Oryza sativa* Rice

| Event | Company | Description |
|---|---|---|
| CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). |
| IMINTA-1, IMINTA-4 | BASF Inc. | Tolerance to imidazolinone herbicides induced by chemical mutagenesis of the acetolactate synthase (ALS) enzyme using sodium azide. |
| LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). |
| LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). |
| PWC16 | BASF Inc. | Tolerance to the imidazolinone herbicide, imazethapyr, induced by chemical mutagenesis of the acetolactate synthase (ALS) enzyme using ethyl methanesulfonate (EMS). |

TABLE 4C

*Glycine max* L. Soybean

| Event | Company | Description |
|---|---|---|
| A2704-12, A2704-21, A5547-35 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| A5547-127 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| BPS-CV127-9 | BASF Inc. | The introduced csr1-2 gene from *Arabidopsis thaliana* encodes an acetohydroxyacid synthase protein that confers tolerance to imidazolinone herbicides due to a point mutation that results in a single amino acid substitution in which the serine residue at position 653 is replaced by asparagine (S653N). |
| DP-305423 | Pioneer Hi-Bred International Inc. | High oleic acid soybean produced by inserting additional copies of a portion of the omega-6 desaturase encoding gene, gm-fad2-1 resulting in silencing of the endogenous omega-6 desaturase gene (FAD2-1). |
| DP356043 | Pioneer Hi-Bred International Inc. | Soybean event with two herbicide tolerance genes: glyphosate N-acetyltransferase, which detoxifies glyphosate, and a modified acetolactate synthase (ALS) gene which is tolerant to ALS-inhibiting herbicides. |

TABLE 4C-continued

| Glycine max L. Soybean | | |
|---|---|---|
| Event | Company | Description |
| G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. |
| GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. |
| GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| MON87701 | Monsanto Company | Resistance to Lepidopteran pests of soybean including velvetbean caterpillar (*Anticarsia gemmatalis*) and soybean looper (*Pseudoplusia includens*). |
| MON87701 × MON89788 | Monsanto Company | Glyphosate herbicide tolerance through expression of the EPSPS encoding gene from *A. tumefaciens* strain CP4, and resistance to Lepidopteran pests of soybean including velvetbean caterpillar (*Anticarsia gemmatalis*) and soybean looper (*Pseudoplusia includens*) via expression of the Cry1Ac encoding gene from *B. thuringiensis*. |
| MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4. |
| OT96-15 | Agriculture & Agri-Food Canada | Low linolenic acid soybean produced through traditional cross-breeding to incorporate the novel trait from a naturally occurring fan1 gene mutant that was selected for low linolenic acid. |
| W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. |

TABLE 4D

| Triticum aestivum Wheat | | |
|---|---|---|
| Event | Company | Description |
| AP205CL | BASF Inc. | Selection for a mutagenized version of the enzyme acetohydroxyacid synthase (AHAS), also known as acetolactate synthase (ALS) or acetolactate pyruvate-lyase. |
| AP602CL | BASF Inc. | Selection for a mutagenized version of the enzyme acetohydroxyacid synthase (AHAS), also known as acetolactate synthase (ALS) or acetolactate pyruvate-lyase. |
| BW255-2, BW238-3 | BASF Inc. | Selection for a mutagenized version of the enzyme acetohydroxyacid synthase (AHAS), also known as acetolactate synthase (ALS) or acetolactate pyruvate-lyase. |
| BW7 | BASF Inc. | Tolerance to imidazolinone herbicides induced by chemical mutagenesis of the acetohydroxyacid synthase (AHAS) gene using sodium azide. |
| MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. |
| SWP965001 | Cyanamid Crop Protection | Selection for a mutagenized version of the enzyme acetohydroxyacid synthase (AHAS), also known as acetolactate synthase (ALS) or acetolactate pyruvate-lyase. |
| Teal 11A | BASF Inc. | Selection for a mutagenized version of the enzyme acetohydroxyacid synthase (AHAS), also known as acetolactate synthase (ALS) or acetolactate pyruvate-lyase. |

TABLE 4E

Medicago sativa Alfalfa

| Event | Company | Description |
|---|---|---|
| J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. |

TABLE 4F

Zea mays L. Maize

| Event | Company | Description |
|---|---|---|
| 176 | Syngenta Seeds, Inc. | Insect-resistant maize produced by inserting the Cry1Ab gene from *Bacillus thuringiensis* subsp. *kurstaki*. The genetic modification affords resistance to attack by the European corn borer (ECB). |
| 3751IR | Pioneer Hi-Bred International Inc. | Selection of somaclonal variants by culture of embryos on imidazolinone containing media. |
| 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. |
| B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. |
| BT11 (X4334CBR, X4734CBR) | Syngenta Seeds, Inc. | Insect-resistant and herbicide tolerant maize produced by inserting the Cry1Ab gene from *Bacillus thuringiensis* subsp. *kurstaki*, and the phosphinothricin N-acetyltransferase (PAT) encoding gene from *S. viridochromogenes*. |
| BT11 × GA21 | Syngenta Seeds, Inc. | Stacked insect resistant and herbicide tolerant maize produced by conventional cross breeding of parental lines BT11 (OECD unique identifier: SYN-BTO11-1) and GA21 (OECD unique identifier: MON-OOO21-9). |
| BT11 × MIR162 × MIR604 × GA21 | Syngenta Seeds, Inc. | Resistance to Coleopteran pests, particularly corn rootworm pests (*Diabrotica* spp.) and several Lepidopteran pests of corn, including European corn borer (ECB, *Ostrinia nubilalis*), corn earworm (CEW, *Helicoverpa zea*), fall army worm (FAW, *Spodoptera frugiperda*), and black cutworm (BCW, *Agrotis ipsilon*); tolerance to glyphosate and glufosinate-ammonium containing herbicides. |
| BT11 × MIR162 | Syngenta Seeds, Inc. | Stacked insect resistant and herbicide tolerant maize produced by conventional cross breeding of parental lines BT11 (OECD unique identifier: SYN-BTO11-1) and MIR162 (OECD unique identifier: SYN-IR162-4). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Resistance to other Lepidopteran pests, including *H. zea, S. frugiperda, A. ipsilon*, and *S. albicosta*, is derived from MIR162, which contains the vip3Aa gene from *Bacillus thuringiensis* strain AB88. |
| BT11 × MIR162 × MIR604 | Syngenta Seeds, Inc. | *Bacillus thuringiensis* Cry1Ab delta-endotoxin protein and the genetic material necessary for its production (via elements of vector pZO1502) in Event Bt11 corn (OECD Unique Identifier: SYN-BTO11-1) × *Bacillus thuringiensis* Vip3Aa20 insecticidal protein and the genetic material necessary for its production (via elements of vector pNOV1300) in Event MIR162 maize (OECD |

TABLE 4F-continued

Zea mays L. Maize

| Event | Company | Description |
|---|---|---|
| | | Unique Identifier: SYN-IR162-4) × modified Cry3A protein and the genetic material necessary for its production (via elements of vector pZM26) in Event MIR604 corn (OECD Unique Identifier: SYN-IR6O4-5). |
| CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. |
| DAS-06275-8 | DOW AgroSciences LLC | Lepidopteran insect resistant and glufosinate ammonium herbicide-tolerant maize variety produced by inserting the Cry1F gene from *Bacillus thuringiensis* var *aizawai* and the phosphinothricin acetyltransferase (PAT) from *Streptomyces hygroscopicus*. |
| BT11 × MIR604 | Syngenta Seeds, Inc. | Stacked insect resistant and herbicide tolerant maize produced by conventional cross breeding of parental lines BT11 (OECD unique identifier: SYN-BTO11-1) and MIR604 (OECD unique identifier: SYN-IR6O5-5). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. |
| BT11 × MIR604 × GA21 | Syngenta Seeds, Inc. | Stacked insect resistant and herbicide tolerant maize produced by conventional cross breeding of parental lines BT11 (OECD unique identifier: SYN-BTO11-1), MIR604 (OECD unique identifier: SYN-IR6O5-5) and GA21 (OECD unique identifier: MON-OOO21-9). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. Tolerance to glyphosate herbicide is derived from GA21 which contains a a modified EPSPS gene from maize. |
| DAS-59122-7 | DOW AgroSciences LLC and Pioneer Hi-Bred International Inc. | Corn rootworm-resistant maize produced by inserting the Cry34Ab1 and Cry35Ab1 genes from *Bacillus thuringiensis* strain PS149B1. The PAT encoding gene from *Streptomyces viridochromogenes* was introduced as a selectable marker. |
| DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-O15O7-1) with NK603 (OECD unique identifier: MON-OO6O3-6). Corn rootworm-resistance is derived from DAS-59122-7 which contains the Cry34Ab1 and Cry35Ab1 genes from *Bacillus thuringiensis* strain PS149B1. Lepidopteran resistance and tolerance to glufosinate ammonium herbicide is derived from TC1507. Tolerance to glyphosate herbicide is derived from NK603. |
| DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* |
| MIR604 × GA21 | Syngenta Seeds, Inc. | Stacked insect resistant and herbicide tolerant maize produced by conventional cross breeding of parental lines MIR604 (OECD unique identifier: |

TABLE 4F-continued

Zea mays L. Maize

| Event | Company | Description |
|---|---|---|
| | | SYN-IR6O5-5) and GA21 (OECD unique identifier: MON-OOO21-9). Corn rootworm-resistance is derived from MIR604 which contains the mCry3A gene from *Bacillus thuringiensis*. Tolerance to glyphosate herbicide is derived from GA21. |
| MON80100 | Monsanto Company | Insect-resistant maize produced by inserting the Cry1Ab gene from *Bacillus thuringiensis* subsp. *kurstaki*. The genetic modification affords resistance to attack by the European corn borer (ECB). |
| MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. |
| MON809 | Pioneer Hi-Bred International Inc. | Resistance to European corn borer (*Ostrinia nubilalis*) by introduction of a synthetic Cry1Ab gene. Glyphosate resistance via introduction of the bacterial version of a plant enzyme, 5-enolpyruvyl shikimate-3-phosphate synthase (EPSPS). |
| MON810 | Monsanto Company | Insect-resistant maize produced by inserting a truncated form of the Cry1Ab gene from *Bacillus thuringiensis* subsp. *kurstaki* HD-1. The genetic modification affords resistance to attack by the European corn borer (ECB). |
| MON810 × LY038 | Monsanto Company | Stacked insect resistant and enhanced lysine content maize derived from conventional cross-breeding of the parental lines MON810 (OECD identifier: MON-OO81O-6) and LY038 (OECD identifier: REN-OOO38-3). |
| MON810 × MON88017 | Monsanto Company | Stacked insect resistant and glyphosate tolerant maize derived from conventional cross-breeding of the parental lines MON810 (OECD identifier: MON-OO81O-6) and MON88017 (OECD identifier: MON-88O17-3). European corn borer (ECB) resistance is derived from a truncated form of the Cry1Ab gene from *Bacillus thuringiensis* subsp. *kurstaki* HD-1 present in MON810. Corn rootworm resistance is derived from the Cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. |
| MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. |
| MON863 | Monsanto Company | Corn rootworm resistant maize produced by inserting the Cry3Bb1 gene from *Bacillus thuringiensis* subsp. *kumamotoensis*. |
| MON863 × MON810 | Monsanto Company | Stacked insect resistant corn hybrid derived from conventional cross-breeding of the parental lines MON863 (OECD identifier: MON-OO863-5) and MON810 (OECD identifier: MON-OO81O-6) |
| MON863 × M0N810 × NK603 | Monsanto Company | Stacked insect resistant and herbicide tolerant corn hybrid derived from conventional cross-breeding of the stacked hybrid MON-OO863-5 × MON-OO81O-6 and NK603 (OECD identifier: MON-OO6O3-6). |
| MON863 × NK603 | Monsanto Company | Stacked insect resistant and herbicide tolerant corn hybrid derived from conventional cross-breeding of the parental lines MON863 (OECD identifier: MON-OO863-5) and NK603 (OECD identifier: MON-OO6O3-6). |
| MON87460 | Monsanto Company | MON 87460 was developed to provide reduced yield loss under water-limited conditions compared to conventional maize. Efficacy in MON 87460 is derived by expression of the inserted *Bacillus subtilis* cold shock protein B (CspB). |
| MON88017 | Monsanto Company | Corn rootworm-resistant maize produced by inserting the Cry3Bb1 gene from *Bacillus thuringiensis* subspecies *kumamotoensis* strain |

TABLE 4F-continued

| Zea mays L. Maize | | |
|---|---|---|
| Event | Company | Description |
| | | EG4691. Glyphosate tolerance derived by inserting a 5-enolpyruvylshikimate-3-phosphate synthase (EPSPS) encoding gene from *Agrobacterium tumefaciens* strain CP4. |
| MON89034 | Monsanto Company | Maize event expressing two different insecticidal proteins from *Bacillus thuringiensis* providing resistance to number of Lepidopteran pests. |
| MON89034 × MON88017 | Monsanto Company | Stacked insect resistant and glyphosate tolerant maize derived from conventional cross-breeding of the parental lines MON89034 (OECD identifier: MON-89O34-3) and MON88017 (OECD identifier: MON-88O17-3). Resistance to Lepidopteran insects is derived from two Cry genes present in MON89043. Corn rootworm resistance is derived from a single Cry genes and glyphosate tolerance is derived from the 5-enolpyruvylshikimate-3-phosphate synthase (EPSPS) encoding gene from *Agrobacterium tumefaciens* present in MON88017. |
| MON89034 × NK603 | Monsanto Company | Stacked insect resistant and herbicide tolerant maize produced by conventional cross breeding of parental lines MON89034 (OECD identifier: MON-89O34-3) with NK603 (OECD unique identifier: MON-OO6O3-6). Resistance to Lepidopteran insects is derived from two Cry genes present in MON89043. Tolerance to glyphosate herbicide is derived from NK603. |
| NK603 × MON810 | Monsanto Company | Stacked insect resistant and herbicide tolerant corn hybrid derived from conventional cross-breeding of the parental lines NK603 (OECD identifier: MON-OO6O3-6) and MON810 (OECD identifier: MON-OO81O-6). |
| MON89034 × TC1507 × MON88017 × DAS-59122-7 | Monsanto Company and Mycogen Seeds c/o Dow AgroSciences LLC | Stacked insect resistant and herbicide tolerant maize produced by conventional cross breeding of parental lines: MON89034, TC1507, MON88017, and DAS-59122. Resistance to the above-ground and below-ground insect pests and tolerance to glyphosate and glufosinate-ammonium containing herbicides. |
| MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). |
| MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). |
| NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. |
| NK603 × T25 | Monsanto Company | Stacked glufosinate ammonium and glyphosate herbicide tolerant maize hybrid derived from conventional cross-breeding of the parental lines NK603 (OECD identifier: MON-OO6O3-6) and T25 (OECD identifier: ACS-ZM003-2). |
| T25 × MON810 | Bayer CropScience (Aventis CropScience(AgrEvo)) | Stacked insect resistant and herbicide tolerant corn hybrid derived from conventional cross-breeding of the parental lines T25 (OECD identifier: ACS-ZMOO3-2) and MON810 (OECD identifier: MON-OO81O-6). |
| TC1507 | Mycogen (c/o Dow AgroSciences); Pioneer (c/o DuPont) | Insect-resistant and glufosinate ammonium herbicide tolerant maize produced by inserting the Cry1F gene from *Bacillus thuringiensis* var. *aizawai* and the phosphinothricin N-acetyltransferase encoding gene from *Streptomyces viridochromogenes*. |
| TC1507 × NK603 | DOW AgroSciences LLC | Stacked insect resistant and herbicide tolerant corn hybrid derived from conventional cross-breeding of the parental lines 1507 (OECD identifier: DAS-O15O7-1) and NK603 (OECD identifier: MON-OO6O3-6). |

TABLE 4F-continued

Zea mays L. Maize

| Event | Company | Description |
| --- | --- | --- |
| TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-O15O7-1) with DAS-59122-7 (OECD unique identifier: DAS-59122-7). Resistance to Lepidopteran insects is derived from TC1507 due the presence of the Cry1F gene from *Bacillus thuringiensis* var. *aizawai*. Corn rootworm-resistance is derived from DAS-59122-7 which contains the Cry34Ab1 and Cry35Ab1 genes from *Bacillus thuringiensis* strain PS149B1. Tolerance to glufosinate ammonium herbicide is derived from TC1507 from the phosphinothricin N-acetyltransferase encoding gene from *Streptomyces viridochromogenes*. |

Other events with regulatory approval are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more polynucleotide encoding the polypeptides of the insecticidal polypeptides of the disclosure or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant.

"Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) Nature 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) Trends Genet. 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) Nature 409:363). Short interfering RNAs derived from dicer activity are typically about 21 to about 23 nucleotides in length and comprise about 19 base pair duplexes (Elbashir, et al., (2001) Genes Dev. 15:188). Dicer has also been implicated in the excision of 21- and 22-nucleotide small temporal RNAs (stRNAs) from precursor RNA of conserved structure that are implicated in translational control (Hutvagner, et al., (2001) Science 293: 834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) Genes Dev. 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) Science 297:1818-1819; Volpe, et al., (2002) Science 297: 1833-1837; Jenuwein, (2002) Science 297:2215-2218 and Hall, et al., (2002) Science 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence.

Use in Pesticidal Control

General methods for employing strains comprising a nucleic acid sequence of the embodiments or a variant thereof, in pesticide control or in engineering other organisms as pesticidal agents are known in the art. See, for example U.S. Pat. No. 5,039,523 and EP 0480762A2.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the insecticidal polypeptide of the disclosure, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes,* fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Pseudomonas chlororaphis, Serratia marc-* escens, *Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporoboomyces roseus, S. odorus, Kluyveromyces veronae,* and *Aureobasidium pollulans*. Of particular interest are the pigmented microorganisms. Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. fluorescens, P. chlororaphis*), *Erwinia* spp., and *Flavobacterium* spp., and other such organisms, including *Agrobacterium tumefaciens, E. coli, Bacillus subtilis, Bacillus cereus* and the like.

Genes encoding the insecticidal polypeptides of the embodiments can be introduced into microorganisms that multiply on plants (epiphytes) to deliver insecicidal polypeptides to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the insecticidal polypeptides of the embodiments can be introduced into a root-colonizing *Bacillus cereus* by standard methods known in the art.

Genes encoding insecticidal polypeptides of the disclosure can be introduced, for example, into the root-colonizing *Bacillus* by means of electro transformation. Specifically, genes encoding the insecticidal polypeptides of the disclosure can be cloned into a shuttle vector, for example, pHT3101 (Lerecius, et al., (1989) *FEMS Microbiol. Letts.* 60:211-218. The shuttle vector pHT3101 containing the coding sequence for the particular insecticidal polypeptide gene of the disclosure can, for example, be transformed into the root-colonizing *Bacillus* by means of electroporation (Lerecius, et al., (1989) *FEMS Microbiol. Letts.* 60:211-218).

Expression systems can be designed so that insecticidal polypeptides of the disclosure are secreted outside the cytoplasm of gram-negative bacteria, such as *E. coli*, for example. Advantages of having insecticidal polypeptides of the disclosure secreted are: (1) avoidance of potential cytotoxic effects of the insecticidal polypeptide of the disclosure expressed; and (2) improvement in the efficiency of purification of the insecticidal polypeptide of the disclosure, including, but not limited to, increased efficiency in the recovery and purification of the protein per volume cell broth and decreased time and/or costs of recovery and purification per unit protein.

Insecticidal polypeptides of the disclosure can be made to be secreted in *E. coli*, for example, by fusing an appropriate *E. coli* signal peptide to the amino-terminal end of the insecticidal polypeptide of the disclosure. Signal peptides recognized by *E. coli* can be found in proteins already known to be secreted in *E. coli*, for example the OmpA protein (Ghrayeb, et al., (1984) *EMBO J,* 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud, et al., (1987) *Meth. Enzymol.* 153:492).

Insecticidal polypeptides of the embodiments can be fermented in a bacterial host and the resulting bacteria processed and used as a microbial spray in the same manner that Bt strains have been used as insecticidal sprays. In the case of an insecticidal polypeptide of the disclosure(s) that is secreted from *Bacillus*, the secretion signal is removed or mutated using procedures known in the art. Such mutations and/or deletions prevent secretion of the insecticidal polypeptide(s) into the growth medium during the fermentation process. The insecticidal polypeptides of the disclosure are retained within the cell, and the cells are then processed to yield the encapsulated insecicidal polypeptides. Any suitable microorganism can be used for this purpose. *Pseudomonas* has been used to express Bt toxins as encapsulated proteins and the resulting cells processed and sprayed as an insecticide (Gaertner, et al., (1993), in: *Advanced Engineered Pesticides*, ed. Kim).

Alternatively, the insecticidal polypeptides of the disclosure are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated insecicidal polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agrochemical composition that contains at least one of the insecticidal polypeptides of the disclosure produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoximmethyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Ternbotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Athetis lepigone; Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms; *Sesamia inferens* (Asiatic pink stem borer), and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Conogethes punctiferalis* (Yellow Peach Moth); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonotycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicomis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii*

Cockerell (strawberry aphid); *Diuraphis noxia* Kurdjumov/ Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stυl (rice leafhopper); *Nilaparvata lugens* Stυl (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743, 477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *Bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest with an insecticidally-effective amount of an insecticidal polypeptide of the disclosure. In some embodiments methods are provided for killing an insect pest, comprising contacting the insect pest with an insecticidally-effective amount of a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments and/or a PIP-77 polypeptide of the embodiments.

In some embodiments methods are provided for controlling an insect pest population, comprising contacting the insect pest population with an insecticidally-effective amount of a recombinant insecticidal polypeptide of the embodiments. In some embodiments methods are provided for controlling an insect pest population, comprising contacting the insect pest population with an insecticidally-effective amount of a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments and/or a PIP-77 polypeptide of the embodiments. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population with an insecticidally-effective amount of a recombinant insecticidal polypeptide of the disclosure. In some embodiments methods are provided for controlling an insect pest population resistant to a pesticidal protein, comprising contacting the insect pest population with an insecticidally-effective amount of a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments and/or a PIP-77 polypeptide of the embodiments.

In some embodiments methods are provided for protecting a plant from an insect pest, comprising expressing in the plant or cell thereof a recombinant polynucleotide encoding an insecticidal polypeptide of the disclosure. In some embodiments methods are provided for protecting a plant from an insect pest, comprising expressing in the plant or cell thereof a recombinant polynucleotide encoding pesticidal protein of a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments and/or a PIP-77 polypeptide of the embodiments.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the insecticidal polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management the at least one of the insecticidal proteins comprise an insecticidal polypeptide of the disclosure insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an insecticidal polypeptide of the disclosure and a Cry protein insecticidal to insects in the order Lepidoptera and/or Coleoptera having different modes of action.

In some embodiments the methods of controlling Lepidoptera and/or Coleoptera insect infestation in a transgenic plant and promoting insect resistance management comprise in the transgenic plant a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments or a PIP-77 polypeptide of the embodiments and a Cry protein insecticidal to insects in the order Lepidoptera and/or Coleoptera having different modes of action.

Also provided are methods of reducing likelihood of emergence of Lepidoptera and/or Coleoptera insect resistance to transgenic plants expressing in the plants insecticidal proteins to control the insect species, comprising expression of an insecticidal polypeptide of the disclosure insecticidal to the insect species in combination with a second insecticidal protein to the insect species having different modes of action.

Also provided are methods of reducing likelihood of emergence of Lepidoptera and/or Coleoptera insect resistance to transgenic plants expressing in the plants insecticidal proteins to control the insect species, comprising expression of a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments or a PIP-77 polypeptide of the embodiments, insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an insecticidal polypeptide of the disclosure and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise a PIP-45-1 polypeptide of the embodiments and a PIP-45-2 polypeptide of the embodiments, a PIP-64-1 polypeptide of the embodiments and a PIP-64-2 polypeptide of the embodiments, a PIP-74-1 polypeptide of the embodiments and a PIP-74-2 polypeptide of the embodiments, a PIP-75 polypeptide of the embodiments or a PIP-77 polypeptide of the embodiments, and a Cry protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the insecticidal polypeptide of the disclosure does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the PIP-45-1 polypeptide of the embodiments & the PIP-45-2 polypeptide of the embodiments, the PIP-64-1 polypeptide of the embodiments & the PIP-64-2 polypeptide of the embodiments, the PIP-74-1 polypeptide of the embodiments & the PIP-74-2 polypeptide of the embodiments, the PIP-75 polypeptide of the embodiments or the PIP-77 polypeptide of the embodiments does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an insecticidal polypeptide of the disclosure disclosed herein. Expression of the insecticidal polypeptide of the disclosure results in a reduced ability of a pest to infest or feed on the plant, thus improving plant yield.

Methods of Processing

Further provided are methods of processing a plant, plant part or seed to obtain a food or feed product from a plant, plant part or seed comprising an insecticidal polypeptide of the disclosure. The plants, plant parts or seeds provided herein, can be processed to yield oil, protein products and/or by-products that are derivatives obtained by processing that have commercial value. Non-limiting examples include transgenic seeds comprising a nucleic acid molecule encoding an insecticidal polypeptide of the disclosure which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXPERIMENTALS

Example 1. Insect Feeding Assays

Insecticidal activity bioassay screens were conducted on the cleared lysate to evaluate the effects of the insecticidal proteins on a variety of Lepidoptera species (European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*)), a Coleoptera specie (Western corn rootworm (*Diabrotica virgifera*), and two Hemiptera species, *Lygus hesperus* and *Nezara viridula* (Southern Green Stinkbug).

Lepidoptera Assays

Lepidoptera feeding assays were conducted on an artificial diet containing the cleared lysates of bacterial strains in a 96 well plate set up. The cleared lysate was incorporated with the Lepidopteran-specific artificial diet in a ratio of 20 ul cleared lysate and 40 ul of diet mixture. Two to five neonate larvas were placed in each well to feed for 5 days. Results were expressed as positive for larvae reactions such as stunting and/or mortality. Results were expressed as negative if the larvae were similar to the negative control that is feeding diet to which the above buffer only has been applied. Each cleared lysate was assayed on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). A series of concentrations of the purified protein sample was assayed against those insects and concentrations for 50% mortality (LC50) or inhibition of 50% of the individuals (1050) were calculated.

Coleoptera Assays

Coleoptera feeding assays were conducted on an artificial diet containing the cleared lysates of bacterial strains in a 96 well plate set up. The cleared lysate was incorporated with the coleopteran-specific artificial diet in a ratio of 10 ul cleared lysate and 50 ul of diet mixture. Two to five Western corn rootworm (*Diabrotica virgifera*) neonate larva were placed in each well to feed for 5 days. Results were expressed as positive for larvae reactions such as stunting and/or mortality. Results were expressed as negative if the larvae were similar to the negative control that is feeding diet to which the above buffer only has been applied. A series of concentrations of the purified protein sample was assayed against those insects and concentrations for 50% mortality (LC50) or inhibition of 50% of the individuals (1050) were calculated.

*Lygus* (*Lygus hesperus*) Bioassay 20 ul of the cleared lysate samples were mixed with 75 ul *Lygus* diet (Bio-Sery F9644B) in each well of a 96 well bioassay plate (BD Falcon 353910) and covered with a sheet of Parafilm. A variable numbers of *Lygus hesperus* second instar nymphs (2 to 7) were placed into each well of a 96 well filter plate. The sample plate was then flipped on to the filter plate and held together with rubber bands. The assay was run four days at 25° C. and then was scored for insect mortality and/or stunting of insect growth. A series of concentrations of the purified protein sample was assayed against those insects and concentrations for 50% mortality (LC50) or inhibition of 50% of the individuals (1050) were calculated.

Southern Green Stinkbug (*Nezara viridula*) and Brown Marmorated Stinkbug (*Halyomorpha haly*) Bioassay 40 ul of the cleared lysate samples were mixed with 360 ul of *Lygus* diet (Bio-Sery F9644B) in Parafilm® packets. 10 to 15 newly molted instar nymphs were placed in polystyrene Petri dishes (100 mm×20 mm) lined with moist Whatman® filter paper (100 mm diameter). Included in the dish was a water source. The bioassay was incubated at 25° C. in the dark for four days. The bioassay was scored for mortality and stunting. To generate ILC50 or LC50 data, a series of concentrations of purified proteins were assayed against insects and the concentration at which 50% of the insects experienced severe damage was the ILC50 and the concentration at which 50% of insects were dead was the LC50.

Colorado Potato Beetle (*Leptinotarsa decemlineata*) Bioassay 20 ul of cleared lysate samples were mixed with 75 ul of modified Coleopteran diet (Bio-Sery F9800B) in each well of a 96 well bioassay plate (BD Falcon 353910) and allowed to solidify. A single neonate larva was placed in each well and the plate sealed with a Mylar® covering. Holes were punched in the Mylar® sheet and the plate incubated at 25° C. with no light for four days. The bioassay was scored for mortality and/or stunting.

Example 2. Identification of Insecticidal Active Strains

Insecticidal activities against SBL, CEW, BCW, VBC, ECB, Lygus, SGSB, and WCRW were observed from a clear cell lysate of bacterial strains grown in either LB medium (10 g/L tryptone, 5 g/L yeast extract, and 10 g/L NaCl) or TSB (Tryptic Soy Broth) medium (17 g/L tryptone, 3 g/L soytone, 2.5 g/L dextrose, 2.5 g/L $K_2HPO_4$ and 5 g/L NaCl) and cultured overnight at 26° C. with shaking at 250 rpm. This insecticidal activity exhibited heat and proteinase sensitivity indicating proteinaceous nature. Active strains and their insecticidal activities were listed in Table 5.

TABLE 5

| Strain | Species | Target insects | Gene | Seq. No. |
|---|---|---|---|---|
| LBV5480 | *Pseudomonas brenneri* | WCRW | PIP-45Aa-1/2 | SEQ ID NO: 1/ SEQ ID NO: 2 |
| LBV9691 | *Pseudomonas brenneri* | WCRW | PIP-64Aa-1 alone | SEQ ID NO: 53 |
| LBV9691 | *Pseudomonas brenneri* | SBL, CEW, BCW, VBC, ECB, Lygus, SGSB | PIP-64Aa-1/2 | SEQ ID NO: 53/ SEQ ID NO: 54 |
| SS135B4b | *Pseudomonas rhodesiae* | WCRW | PIP-74Aa-1/2 | SEQ ID NO: 73/ SEQ ID NO: 74 |
| LBV6019 | *Pseudomonas antarctica* | WCRW | PIP-75Aa | SEQ ID NO: 79 |
| SSP344E5a | *Pseudomonas chlororaphis* | WCRW | PIP-77Aa | SEQ ID NO: 88 |

Example 3. Species Identification and Genome Sequencing of Active Strains

Genomic DNA from active strains was extracted with a Sigma® Bacterial Genomic DNA Extraction Kit (Cat #NA2110-KT, Sigma-Aldrich, PO Box 14508, St. Louis, Mo. 63178) according to the manufactures' instructions. The DNA concentration was determined using a NanoDrop™ Spectrophotometer (Thermo Scientific, 3411 Silverside Road, Bancroft Building, Suite 100, Wilmington, Del. 19810) and the genomic DNA was diluted to 40 ng/ul with sterile water. A 25 ul PCR reaction was set up by combining 80 ng genomic DNA, 2 ul (5 uM) 16S ribosomal DNA primers TACCTTGTTACGACTT (SEQ ID NO: 216) and AGAGTTTGATCMTGGCTCAG (SEQ ID NO: 217), 1 ul 10 cmM dNTP, 1× Phusion® HF buffer, and 1 unit of Phusion® High-Fidelity DNA Polymerase (New England Biolabs, Cat #M0530L, 240 County Road, Ipswich, Mass. 01938-2723). The PCR reaction was run in MJ Research PTC-200 Thermo Cycler (Bio-Rad Laboratories, Inc., 1000 Alfred Nobel Drive, Hercules, Calif., 94547, USA) with the following program: 96° C. 1 min; 30 cycles of 96° C. 15 seconds, 52° C. 2 minutes and 72° C. 2 minutes; 72° C. 10 minutes; and hold on 4° C. The PCR products were purified with Qiaquick® DNA purification Kit (Cat #28104, QIAGEN Inc., 27220 Turnberry Lane, Valencia, Calif. 91355). The purified PCR sample was DNA sequenced and the resulting 16S ribosomal DNA sequence was BLAST searched against the NCBI database. The top hits indicated the species of the strain (see Table 5).

Genomic DNA of active strains was also prepared according to a library construction protocol developed by Illumina and sequenced using the Illumina MiSeq™. The nucleic acid contig sequences were assembled and open reading frames were generated.

Example 4. Identification of Insecticidal Proteins by LC-MS/MS

All insecticidal proteins were fractionated and enriched as described. For identification candidate protein bands were excised, digested with trypsin and analyzed by nano-liquid chromatography/electrospray tandem mass spectrometry (nano-LC/ESI-MS/MS) on a Thermo Q Exactive™ Orbitrap™ mass spectrometer (Thermo Fisher Scientific) interfaced with an Eksigent® NanoLC-1D™ Plus nanoLC™ system (AB Sciex). Ten product ion spectra were collected in an information dependent acquisition mode after a MS1 survey scan.

Protein identification was done by database searches using Mascot (Matrix Science). The searches were done against the in-house database Bacteria-Plus, which combines all bacterial protein sequences and keratin sequences derived from the NCBI non-redundant database (nr) as well as in-house protein sequences.

Example 5. Isolation and Identification of Insecticidal Proteins

Isolation and Identification of PIP-45-Aa-1 and PIP-45-Aa-2

Insecticidal activity against WCRW (*Diabrotica virgifera*) was observed from a clear cell lysate of from *Pseudomonas brenneri* strain LBV 5480 grown in Nutrient Broth (Peptone—5 g/L, Meat extract—1 g/L, Yeast extract—2 g/L, Sodium chloride—5 g/L) and cultured overnight at 26° C. with shaking at 250 rpm. This insecticidal activity exhibited heat and protease sensitivity indicating proteinaceous nature.

Cell pellets of LBV 5480 were homogenized at ~20,000 psi after re-suspension in Tris buffer, pH 8. The crude lysate was cleared by centrifugation and loaded onto a HiTrap® Q-FF column (GE Healthcare). Bound protein was eluted with a linear sodium chloride gradient and fractionated. Fractions containing protein of interest were pooled and adjusted to 1 M ammonium sulfate concentration in 50 mM Tris (buffer A). This material was loaded onto a Phenyl Sepharose HP HiTrap® column (GE Healthcare) equilibrated in buffer A. Active protein was eluted with a linear gradient from 1 M to 0 M ammonium sulfate and further purified by size exclusion chromatography. For this the Phenyl-pool was concentrated and loaded onto a Superdex® 200 column (GE Healthcare), equilibrated in 20 mM Tris, 150 mM NaCl, pH 8. SDS-PAGE analysis of fractions with WCRW activity showed 2 predominant bands after staining with Coomassie® Blue dye. LC-MS/MS was used to identify two novel genes encoded by strain LBV 5480. These genes form an operon and both gene products are required for insecticidal activity as confirmed with recombinant protein. These proteins were designated as PIP-45-Aa-1 (SEQ ID NO: 1) and PIP-45-Aa-2 (SEQ ID NO: 2).

Isolation and Identification of PIP-64-Aa-1 and PIP-64-Aa-2

Insecticidal activity against WCRW (*Diabrotica virgifera*) and soybean looper (SBL *Chrysodeixis includes*) was observed from a clear cell lysate of *Pseudomonas brenneri* strain LBV 9691 grown in 2×YT medium (16 g/L Tryptone, 10 g/L Yeast Extract, 5 g/L NaCl) and cultured for 3 days at 26° C. with shaking at 250 rpm. This insecticidal activity exhibited heat and protease sensitivity indicating proteinaceous nature.

Growth conditions and insect activity varied greatly. Higher activity also correlated with higher expression levels of a protein band of ~28 kDa, detectable by SDS-PAGE. To further confirm this candidate band, cell pellets of LVB 9691 were homogenized at 30,000 psi after re-suspension in 20 mM Tris buffer, pH 8. The crude lysate was cleared by centrifugation and loaded onto a Superdex® 75 column (GE Healthcare). WCRW and SBL activities were strongly associated with the 28 kDa band in the elution fractions. The protein band was identified LC-MS/MS. Database search identified two novel proteins of similar size encoded in an operon by strain LBV 9691, designated PIP-64-Aa-1 (SEQ ID NO: 53) and PIP-64-Aa-2 (SEQ ID NO: 54). Recombinant expression showed that at the concentrations tested both proteins are required for activity against Lepidopteran and Hemipteran species. Activity was found to be optimal at a molar ratio of 5:1 of PIP-64Aa1 (SEQ ID NO: 53) and PIP-64Aa2 (SEQ ID NO: 54), respectively. PIP-64-Aa-1 (SEQ ID NO: 53) alone was sufficient for WCRW activity.

Isolation and Identification of PIP-74-Aa-1 and PIP-74-Aa-2

Insecticidal activity against WCRW (*Diabrotica virgifera*) was observed from a clear cell lysate of *Pseudomonas brenneri* strain SS135B4 grown in 2×YT medium and cultured for 2 days at 26° C. with shaking at 250 rpm. This insecticidal activity exhibited heat and protease sensitivity indicating proteinaceous nature.

Cell pellets of SS135B4 were homogenized at 30,000 psi after re-suspension in 25 mM Tris buffer, pH 9. The crude lysate was cleared by centrifugation, adjusted to 0.5 M ammonium sulfate and loaded onto a Phenyl Sepharose FF column (GE Healthcare). WCRW active protein was eluted with a linear gradient to 0 M ammonium sulfate, pooled and dialyzed into 50 mM sodium acetate buffer, pH 5. The adjusted pool was then loaded onto an S-Sepharose FF column (GE Healthcare) which was equilibrated with the same buffer. The unbound protein fraction, containing WCRW active protein, was buffer exchanged to 50 mM CAPS, pH 10, loaded onto a MonoQ® column (GE Healthcare) and eluted with a linear sodium chloride gradient in 50 mM CAPS, pH10. SDS-PAGE analysis of these fractions showed several bands after staining with Coomassie® Blue dye. The protein bands were excised and identified by LC-MS/MS. Database search identified two novel proteins encoded in an operon by strain SS135B4, designated PIP-74-Aa-1 (SEQ ID NO: 73) and PIP-74-Aa-2 (SEQ ID NO: 74), respectively. Recombinant expression showed that at the concentrations tested both proteins are required for activity against WCRW.

Isolation and Identification of PIP-75-Aa

Insecticidal activity against WCRW (*Diabrotica virgifera*) was observed from a clear cell lysate of *Pseudomonas antarctica* LBV 6019 grown in 2×YT medium for 1 day at 26° C. with shaking at 250 rpm. This insecticidal activity exhibited heat and protease sensitivity indicating proteinaceous nature.

Cell pellets of LBV 6019 were homogenized at ~30,000 psi after re-suspension in 25 mM Tris buffer, pH 8.5. The crude lysate was cleared by centrifugation and loaded onto a POROS® Q column (Life Technologies). The unbound protein fraction, containing WCRW active protein, was buffer exchanged by dialysis against 10 mM MES, pH 6 and then loaded onto a HiTrap® S-HP column (GE Healthcare) and eluted with a linear sodium chloride gradient. Fractions containing active protein were pooled, buffer adjusted and subjected to a repeated anion exchange step at pH 8.5. The unbound fraction was buffer exchanged again before a final fractionation step on a Mono S® column (GE Healthcare), equilibrated with 20 mM MES, pH 6. Several active fractions were obtained after elution with a linear gradient to 0.3 M NaCl. SDS-PAGE analysis of fractions with WCRW activity showed several predominant bands after staining with Coomassie® Blue dye. The protein bands were excised and identified through LC-MS/MS.

Database search revealed 3 novel gene candidates encoded by strain LBV 6019. Cloning and recombinant expression confirmed the insecticidal activity of one of the candidates. This protein was designated as PIP-75-Aa (SEQ ID NO: 79).

Isolation and Identification of PIP-77-Aa

Insecticidal activity against WCRW (*Diabrotica virgifera*) was observed from a clear cell lysate of *Pseudomonas chlororaphis* strain SS344E5 grown in Tryptic Soy broth (TSB, peptone from casein 15 g/L; peptone from soymeal 5 g/L; sodium chloride 5.0 g/L) for 1 day at 26° C. with shaking at 250 rpm. This insecticidal activity exhibited heat and protease sensitivity indicating proteinaceous nature.

Cell pellets of SS344E5 were homogenized at 30,000 psi after re-suspension in 25 mM Tris buffer, pH 8.5. The crude lysate was cleared by centrifugation and loaded onto a POROS® Q column (Life Technologies). The unbound protein fraction, containing WCRW active protein, was dialyzed against 10 mM MES, pH 6, loaded onto a HiTrap® S-HP column (GE Healthcare), and eluted with a linear sodium chloride gradient to 0.5 M. Fractions containing WCRW active protein were pooled and further separated by size exclusion chromatography using a Superdex® 75 column (GE Healthcare). SDS-PAGE analysis of fractions with WCRW activity showed a predominant band of 7 kDa after staining with Coomassie® Blue dye. LC-MS/MS was used to identify two novel genes encoded by strain SS344E5. Cloning and recombinant expression confirmed the insecticidal activity of this gene product, which was designated as PIP-77-Aa (SEQ ID NO: 88).

Example 6. Identification of Homologs

Genomic DNA was extracted from various internal strains, the species was identified and the genome was sequences as described in Example 3. Gene identities may be determined by conducting BLAST (Basic Local Alignment 20 Search Tool; Altschul, et al., (1993) *J. Mol. Biol.* 215:403-410; see also ncbi.nlm.nih.gov/BLAST/, which can be accessed using the www prefix) searches under default parameters for similarity to sequences contained in the internal genomes and in the publically available BLAST "nr" database (comprising all non-redundant GenBank CDS translations, sequences derived from the 3-dimensional structure Brookhaven Protein Data Bank, the last major release of the 25 SWISS-PROT protein sequence database, EMBL, and DDBJ databases). The polypeptide sequences of SEQ ID NO: 1, SEQ ID NO: 2, SEQ ID NO: 53, SEQ ID NO: 54, SEQ ID NO: 73, SEQ ID NO: 74, SEQ ID NO: 79 and SEQ ID NO: 88 were analyzed.

Table 6 shows the PIP-45-1 polypeptide and PIP-45-2 polypeptide homologs identified, sequence identification numbers for each and the bacterial strains they were identified from. Table 7 shows the percent sequence identity between the PIP-45-1 polypeptide homologs. FIG. 1a-1m shows an amino acid sequence alignment of the PIP-45-1 polypeptide homologs.

TABLE 6

| Gene | Sequence # | Source | Species | Activity |
| --- | --- | --- | --- | --- |
| PIP-45Aa-1 | SEQ ID NO: 1 | LBV5480 | *Pseudomonas brenneri* | yes |
| PIP-45Aa-2 | SEQ ID NO: 2 | | | |
| PIP-45Ab-1 | SEQ ID NO: 3 | LBV2335-5 (1-2aa difference); | *Pseudomonas* sp. Ag1 | n.d. † |
| PIP-45Ab-2 | SEQ ID NO: 4 | LBV8526-5; NCBI hypothetical protein ZP_10476580) and ZP_10476581 | | |
| PIP-45Ac-1 | SEQ ID NO: 5 | NCBI hypothetical protein ZP_10430003 and ZP_10430004 | *Pseudomonas* sp. PAMC 25886 | n.d. |
| PIP-45Ac-2 | SEQ ID NO: 6 | | | |
| PIP-45Ad-1 | SEQ ID NO: 7 | NCBI hypothetical protein ZP_10430003, JGI_XylAfBL_518010 | *Pseudomonas* sp. PAMC 25886 | yes |
| PIP-45Ad-2 | SEQ ID NO: 8 | | | |
| PIP-45Ae-1 | SEQ ID NO: 9 | internal strain SSP143E2; LBV9925-5; EMBL K1AVN2_PSEFL; NCBI ZP_1559991; | *Pseudomonas fluorescens* | n.d. |
| PIP-45Ae-2 | SEQ ID NO: 10 | internal strain SSP143E2; EMBL K1B453_PSEFL; NCBI ZP_15599912; | | |
| PIP-45Af-1 | SEQ ID NO: 11 | NCBI hypothetical protein WP_017475319 | *Pseudomonas* sp. PAMC 26793 | n.d. |
| PIP-45Af-2 | SEQ ID NO: 12 | NCBI hypothetical protein WP_017475320 | | |
| PIP-45Ba-1 | SEQ ID NO: 13 | NCBI hypothetical protein PPs_2675 (YP_004702108.1) and PPS_2674 (YP_004702107.1) | *Pseudomonas putida* | yes |
| PIP-45Ba-2 | SEQ ID NO: 14 | | | |
| PIP-45Bb-1 | SEQ ID NO: 15 | JGI - AECFG_342250 hypothetical protein | Fungus garden combined | n.d. |
| PIP-45Bb-2 | SEQ ID NO: 16 | JGI - AECFG_342240 hypothetical protein | | |
| PIP-45Bc-1 | SEQ ID NO: 17 | internal collectionSSP145B2; SSP469C8a | *Pseudomonas monteilii* | n.d. |
| PIP-45Bc-2 | SEQ ID NO: 18 | | | |
| PIP-45Bd-1 | SEQ ID NO: 19 | internal collection - SS160F12; SSP165H7; SS153D5a; SS165D11-2; JH23144-1; | *Pseudomonas monteilii* | yes |
| PIP-45Bd-2 | SEQ ID NO: 20 | | | |
| PIP-45Be-1 | SEQ ID NO: 21 | LBV9691 | *Pseudomonas brenneri* | yes |
| PIP-45Be-2 | SEQ ID NO: 22 | | | |
| PIP-45Bf-1 | SEQ ID NO: 23 | LBV11272; LBV11224: LBV10925 | *Pseudomonas gessardii* | n.d. |
| PIP-45Bf-2 | SEQ ID NO: 24 | | | |
| PIP-45Bg-1 | SEQ ID NO: 25 | NCBI B479_12925 | *Pseudomonas putida* | n.d. |
| PIP-45Bg-2 | SEQ ID NO: 26 | NCBI B479_12920 | | |
| PIP-45Bh-1 | SEQ ID NO: 27 | internal collection - SSP339E12-1 | *Pseudomonas plecoglossicida* | n.d. |
| PIP-45Bh-2 | SEQ ID NO: 28 | | | |
| PIP-45Bi-1 | SEQ ID NO: 29 | internal collection - SSP340D9a | *Pseudomonas putida* | n.d. |
| PIP-45Bi-2 | SEQ ID NO: 30 | | | |
| PIP-45Bj-1 | SEQ ID NO: 31 | internal collection - JH27606-2, SSP4C8 | *Pseudomonas putida* | n.d. |
| PIP-45Bj-2 | SEQ ID NO: 32 | | | |
| PIP-45Bk-1 | SEQ ID NO: 33 | internal collection - SSP4E8 | *Pseudomonas monteilii* | n.d. |
| PIP-45Bk-2 | SEQ ID NO: 34 | | | |
| PIP-45Bl-1 | SEQ ID NO: 232 | internal collection - JH59565-1; NCBI YP_008763564 and WP_023380724 hypothetical proteins | *Pseudomonas* sp. VLB120 | n.d. |
| PIP-45Bl-2 | SEQ ID NO: 233 | | | |
| PIP-45Bm-1 | SEQ ID NO: 234 | internal collection - JH58750-1 | *Pseudomonas putida* | n.d. |
| PIP-45Bm-2 | SEQ ID NO: 235 | | | |
| PIP-45Ca-1 | SEQ ID NO: 35 | internal collection - SSi43B5; SSi44A10; SSP259D11-1; SSP429D11a; SSP429D6a; SS143D2; LBV8661 (2aa difference for 45-2) | *Pseudomonas poae* | yes |
| PIP-45Ca-2 | SEQ ID NO: 36 | | | |
| PIP-45Cb-1 | SEQ ID NO: 37 | JGI - hypothetical protein DPOB_377060 and DPOB_377050 | Mountain Pine Beetle microbial communities | yes |
| PIP-45Cb-2 | SEQ ID NO: 38 | | | |

TABLE 6-continued

| Gene | Sequence # | Source | Species | Activity |
|---|---|---|---|---|
| PIP-45Cc-1 | SEQ ID NO: 39 | internal collection - SS137B2 | *Pseudomonas trivialis* | n.d. |
| PIP-45Cc-2 | SEQ ID NO: 40 | | | |
| PIP-45Cd-1 | SEQ ID NO: 41 | NCBI-ZP_11188561 | *Pseudomonas* sp. R81 | n.d. |
| PIP-45Cd-2 | SEQ ID NO: 42 | NCBI-ZP_11188562 | | |
| PIP-45Ce-1 | SEQ ID NO: 43 | internal collection - SSP493B7b | *Pseudomonas libanensis* | n.d. |
| PIP-45Ce-2 | SEQ ID NO: 44 | | | |
| PIP-45Cf-1 | SEQ ID NO: 236 | internal collection - SSP557A12-2 | *Pseudomonas poae* | n.d. |
| PIP-45Cf-2 | SEQ ID NO: 237 | | *Pseudomonas poae* | n.d. |
| PIP-45Da-1 | SEQ ID NO: 45 | internal active strain - SSP347B8a | *Pseudomonas asplenii* | n.d. |
| PIP-45Da-2 | SEQ ID NO: 46 | | | |
| PIP-45Db-1 | SEQ ID NO: 47 | NCBI-ZP_11115718 | *Thalassospira xiamenensis* | n.d. |
| PIP-45Db-2 | SEQ ID NO: 48 | NCBI-ZP_11115719 | | |
| PIP-45Ea-1 | SEQ ID NO: 49 | NCBI hypothetical protein Pden_4642 (YP_918399.1) and Pden_4641 (YP_918398.1) | *Paracoccus denitrificans* PD1222 | yes |
| PIP-45Ea-2 | SEQ ID NO: 50 | | | |
| PIP-45Ga-1 | SEQ ID NO: 51 | NCBI hypothetical protein YP_001984231.1 and YP_001984230.1 | *Cellvibrio japonicus* Ueda107 | no |
| PIP-45Ga-2 | SEQ ID NO: 52 | | | |

† n.d. = not determined

TABLE 7

| | PIP-45 Ab-1 SEQ ID NO: 3 | PIP-45 Ac-1 SEQ ID NO: 5 | PIP-45 Ad-1 SEQ ID NO: 7 | PIP-45 Ae-1 SEQ ID NO: 9 | PIP-45 Af-1 SEQ ID NO: 11 | PIP-45 Ba-1 SEQ ID NO: 13 | PIP-45 Bb-1 SEQ ID NO: 15 | PIP-45 Bc-1 SEQ ID NO: 17 | PIP-45 Bd-1 SEQ ID NO: 19 | PIP-45 Be-1 SEQ ID NO: 21 | PIP-45 Bf-1 SEQ ID NO: 23 |
|---|---|---|---|---|---|---|---|---|---|---|---|
| PIP-45 Aa-1 | 98.6 | 96.5 | 96.9 | 98.6 | 99.0 | 88.6 | 88.4 | 88.4 | 87.9 | 87.1 | 87.5 |
| PIP-45 Ab-1 | — | 96.5 | 97.2 | 99.7 | 98.3 | 88.1 | 87.9 | 87.9 | 87.7 | 86.6 | 87.5 |
| PIP-45 Ac-1 | — | — | 99.0 | 96.5 | 96.0 | 87.2 | 87.0 | 87.0 | 87.6 | 85.9 | 87.0 |
| PIP-45 Ad-1 | — | — | — | 97.2 | 96.4 | 87.4 | 87.2 | 87.2 | 87.7 | 86.1 | 87.2 |
| PIP-45 Ae-1 | — | — | — | — | 98.3 | 88.1 | 87.9 | 87.9 | 87.7 | 86.8 | 87.7 |
| PIP-45 Af-1 | — | — | — | — | — | 88.6 | 88.4 | 88.4 | 87.9 | 86.6 | 87.0 |
| PIP-45 Ba-1 | — | — | — | — | — | — | 99.1 | 99.3 | 95.5 | 84.7 | 86.3 |
| PIP-45 Bb-1 | — | — | — | — | — | — | — | 99.1 | 95.2 | 84.4 | 86.0 |
| PIP-45 Bc-1 | — | — | — | — | — | — | — | — | 95.2 | 84.4 | 85.8 |
| PIP-45 Bd-1 | — | — | — | — | — | — | — | — | — | 84.2 | 86.3 |
| PIP-45 Be-1 | — | — | — | — | — | — | — | — | — | — | 92.6 |
| PIP-45 Bf-1 | — | — | — | — | — | — | — | — | — | — | — |
| PIP-45 Bg-1 | — | — | — | — | — | — | — | — | — | — | — |
| PIP-45 Bh-1 | — | — | — | — | — | — | — | — | — | — | — |
| PIP-45 Bi-1 | — | — | — | — | — | — | — | — | — | — | — |
| PIP-45 Bj-1 | — | — | — | — | — | — | — | — | — | — | — |
| PIP-45 Bk-1 | — | — | — | — | — | — | — | — | — | — | — |
| PIP-45 Bl-1 | — | — | — | — | — | — | — | — | — | — | — |
| PIP-45 Bm-1 | — | — | — | — | — | — | — | — | — | — | — |
| PIP-45 Ca-1 | — | — | — | — | — | — | — | — | — | — | — |
| PIP-45 Cb-1 | — | — | — | — | — | — | — | — | — | — | — |
| PIP-45 Cc-1 | — | — | — | — | — | — | — | — | — | — | — |
| PIP-45 Cd-1 | — | — | — | — | — | — | — | — | — | — | — |
| PIP-45 Ce-1 | — | — | — | — | — | — | — | — | — | — | — |

TABLE 7-continued

| | PIP-45<br>Bg-1<br>SEQ ID<br>NO: 25 | PIP-45<br>Bh-1<br>SEQ ID<br>NO: 27 | PIP-45<br>Bi-1<br>SEQ ID<br>NO: 29 | PIP-45<br>Bj-1<br>SEQ ID<br>NO: 31 | PIP-45<br>Bk-1<br>SEQ ID<br>NO: 33 | PIP-45<br>Bl-1<br>SEQ ID<br>NO: 232 | PIP-45<br>Bm-1<br>SEQ ID<br>NO: 234 | PIP-45<br>Ca-1<br>SEQ ID<br>NO: 35 | PIP-45<br>Cb-1<br>SEQ ID<br>NO: 37 |
|---|---|---|---|---|---|---|---|---|---|
| PIP-45 Cf-1 | — | — | — | — | — | — | — | — | — |
| PIP-45 Da-1 | — | — | — | — | — | — | — | — | — |
| PIP-45 Db-1 | — | — | — | — | — | — | — | — | — |
| PIP-45 Ea-1 | | | | | | | | | |
| PIP-45 Aa-1 | 87.7 | 88.4 | 88.2 | 86.0 | 86.2 | 86.5 | 87.4 | 77.9 | 77.3 |
| PIP-45 Ab-1 | 87.2 | 87.9 | 87.7 | 86.2 | 86.2 | 86.5 | 87.4 | 77.9 | 76.8 |
| PIP-45 Ac-1 | 86.4 | 87.0 | 86.9 | 85.3 | 85.8 | 86.0 | 86.7 | 77.2 | 77.0 |
| PIP-45 Ad-1 | 86.5 | 87.2 | 87.0 | 85.8 | 85.3 | 86.0 | 86.7 | 77.0 | 76.5 |
| PIP-45 Ae-1 | 87.2 | 87.9 | 87.7 | 85.8 | 86.0 | 86.7 | 87.5 | 77.9 | 77.2 |
| PIP-45 Af-1 | 87.7 | 88.4 | 88.2 | 86.0 | 85.8 | 85.8 | 87.4 | 77.2 | 76.6 |
| PIP-45 Ba-1 | 98.6 | 99.0 | 99.1 | 82.2 | 91.0 | 91.7 | 93.6 | 77.3 | 76.8 |
| PIP-45 Bb-1 | 99.1 | 98.8 | 99.7 | 91.7 | 90.8 | 91.5 | 93.8 | 77.3 | 76.8 |
| PIP-45 Bc-1 | 98.6 | 98.6 | 99.1 | 91.9 | 91.0 | 91.9 | 93.3 | 77.3 | 76.8 |
| PIP-45 Bd-1 | 94.6 | 95.3 | 95.2 | 92.9 | 90.0 | 90.8 | 92.6 | 77.0 | 76.1 |
| PIP-45 Be-1 | 84.2 | 85.1 | 84.7 | 81.6 | 83.8 | 82.3 | 83.0 | 75.6 | 73.9 |
| PIP-45 Bf-1 | 85.5 | 86.5 | 86.0 | 83.6 | 86.0 | 84.3 | 85.3 | 77.4 | 76.0 |
| PIP-45 Bg-1 | — | 98.3 | 99.5 | 91.2 | 90.3 | 91.0 | 92.9 | 76.8 | 76.3 |
| PIP-45 Bh-1 | — | — | 98.8 | 92.0 | 91.2 | 91.2 | 93.3 | 77.7 | 77.2 |
| PIP-45 Bi-1 | — | — | — | 91.7 | 90.8 | 91.5 | 93.4 | 77.3 | 76.8 |
| PIP-45 Bj-1 | — | — | — | — | 88.6 | 87.9 | 90.3 | 77.0 | 75.8 |
| PIP-45 Bk-1 | — | — | — | — | — | 90.1 | 90.8 | 77.7 | 76.3 |
| PIP-45 Bl-1 | — | — | — | — | — | — | 91.0 | 77.3 | 76.6 |
| PIP-45 Bm-1 | — | — | — | — | — | — | — | 76.5 | 76.0 |
| PIP-45 Ca-1 | — | — | — | — | — | — | — | — | 95.3 |
| PIP-45 Cb-1 | — | — | — | — | — | — | — | — | — |
| PIP-45 Cc-1 | — | — | — | — | — | — | — | — | — |
| PIP-45 Cd-1 | — | — | — | — | — | — | — | — | — |
| PIP-45 Ce-1 | — | — | — | — | — | — | — | — | — |
| PIP-45 Cf-1 | — | — | — | — | — | — | — | — | — |
| PIP-45 Da-1 | — | — | — | — | — | — | — | — | — |
| PIP-45 Db-1 | — | — | — | — | — | — | — | — | — |
| PIP-45 Ea-1 | | | | | | | | | |

| | PIP-45<br>Cc-1<br>SEQ ID<br>NO: 39 | PIP-45<br>Cd-1<br>SEQ ID<br>NO: 41 | PIP-45<br>Ce-1<br>SEQ ID<br>NO: 43 | PIP-45<br>Cf-1<br>SEQ ID<br>NO: 236 | PIP-45<br>Da-1<br>SEQ ID<br>NO: 45 | PIP-45<br>Db-1<br>SEQ ID<br>NO: 47 | PIP-45<br>Ea-1<br>SEQ ID<br>NO: 49 | PIP-45<br>Ga-1<br>SEQ ID<br>NO: 51 |
|---|---|---|---|---|---|---|---|---|
| PIP-45 Aa-1 | 76.8 | 76.8 | 77.9 | 78.5 | 65.1 | 63.5 | 59.8 | 38.8 |
| PIP-45 Ab-1 | 76.5 | 76.8 | 77.3 | 78.2 | 65.1 | 63.9 | 59.8 | 38.8 |

TABLE 7-continued

| | | | | | | | | |
|---|---|---|---|---|---|---|---|---|
| PIP-45 Ac-1 | 76.9 | 76.7 | 77.4 | 77.7 | 64.3 | 63.9 | 59.1 | 38.0 |
| PIP-45 Ad-1 | 76.3 | 76.0 | 76.9 | 77.7 | 64.0 | 63.7 | 59.0 | 37.9 |
| PIP-45 Ae-1 | 76.6 | 76.9 | 77.7 | 78.4 | 65.3 | 64.0 | 59.9 | 39.0 |
| PIP-45 Af-1 | 76.1 | 76.1 | 77.2 | 77.9 | 65.5 | 63.5 | 59.9 | 38.6 |
| PIP-45 Ba-1 | 76.5 | 76.1 | 77.0 | 78.0 | 67.0 | 65.1 | 59.9 | 38.4 |
| PIP-45 Bb-1 | 76.5 | 76.1 | 77.2 | 78.0 | 66.8 | 64.9 | 59.8 | 38.4 |
| PIP-45 Bc-1 | 76.5 | 76.1 | 77.0 | 78.0 | 67.5 | 65.1 | 60.1 | 38.2 |
| PIP-45 Bd-1 | 75.8 | 75.4 | 76.5 | 77.2 | 66.5 | 64.4 | 59.4 | 38.3 |
| PIP-45 Be-1 | 73.4 | 73.9 | 74.2 | 75.3 | 65.4 | 63.1 | 57.9 | 38.8 |
| PIP-45 Bf-1 | 76.0 | 75.5 | 76.0 | 76.9 | 66.7 | 64.2 | 59.6 | 37.9 |
| PIP-45 Bg-1 | 75.8 | 75.4 | 76.5 | 77.5 | 66.7 | 64.4 | 59.7 | 38.3 |
| PIP-45 Bh-1 | 76.8 | 76.5 | 77.5 | 78.2 | 67.0 | 64.7 | 60.1 | 38.5 |
| PIP-45 Bi-1 | 76.3 | 76.0 | 77.0 | 78.0 | 67.0 | 64.9 | 60.1 | 38.3 |
| PIP-45 Bj-1 | 75.4 | 75.8 | 75.4 | 77.2 | 66.1 | 64.4 | 59.6 | 37.7 |
| PIP-45 Bk-1 | 76.1 | 76.0 | 76.1 | 76.8 | 66.1 | 64.4 | 59.4 | 39.4 |
| PIP-45 Bl-1 | 77.0 | 76.3 | 76.6 | 77.9 | 64.6 | 64.4 | 59.6 | 39.1 |
| PIP-45 Bm-1 | 76.3 | 75.6 | 76.5 | 77.0 | 66.0 | 64.8 | 60.2 | 38.7 |
| PIP-45 Ca-1 | 92.7 | 94.3 | 94.6 | 98.1 | 64.9 | 66.8 | 60.8 | 38.7 |
| PIP-45 Cb-1 | 94.3 | 96.0 | 97.4 | 95.3 | 64.2 | 66.1 | 59.5 | 37.7 |
| PIP-45 Cc-1 | — | 92.9 | 93.6 | 92.9 | 63.1 | 65.6 | 59.5 | 38.1 |
| PIP-45 Cd-1 | — | — | 96.2 | 93.8 | 64.4 | 65.4 | 59.4 | 37.9 |
| PIP-45 Ce-1 | — | — | — | 94.6 | 64.4 | 65.9 | 59.8 | 37.6 |
| PIP-45 Cf-1 | — | — | — | — | 65.2 | 67.0 | 61.0 | 38.8 |
| PIP-45 Da-1 | — | — | — | — | — | 66.6 | 59.9 | 37.6 |
| PIP-45 Db-1 | — | — | — | — | — | — | 66.2 | 37.0 |
| PIP-45 Ea-1 | | | | | | | | 35.7 |

Table 8 shows the percent sequence identity between the PIP-45-2 polypeptide homologs. FIG. 2a-2l shows an amino acid sequence alignment of the PIP-45-2 polypeptide homologs.

TABLE 8

| | PIP-45 Ab-2 SEQ ID NO: 4 | PIP-45 Ac-2 SEQ ID NO: 6 | PIP-45 Ad-2 SEQ ID NO: 8 | PIP-45 Ae-2 SEQ ID NO: 10 | PIP-45 Af-2 SEQ ID NO: 12 | PIP-45 Ba-2 SEQ ID NO: 14 | PIP-45 Bb-2 SEQ ID NO: 16 | PIP-45 Bc-2 SEQ ID NO: 18 | PIP-45 Bd-2 SEQ ID NO: 20 | PIP-45 Be-2 SEQ ID NO: 22 | PIP-45 Bf-2 SEQ ID NO: 24 |
|---|---|---|---|---|---|---|---|---|---|---|---|
| PIP-45 Aa-2 | 98.7 | 96.3 | 94.4 | 98.7 | 99.1 | 84.0 | 83.9 | 83.4 | 84.3 | 78.0 | 80.1 |
| PIP-45 Ab-2 | — | 96.1 | 94.2 | 99.6 | 98.9 | 84.2 | 84.1 | 83.6 | 84.1 | 78.2 | 79.9 |
| PIP-45 Ac-2 | — | — | 95.7 | 96.1 | 96.4 | 84.3 | 84.3 | 83.8 | 84.1 | 79.1 | 79.7 |
| PIP-45 Ad-2 | — | — | — | 94.6 | 94.6 | 84.0 | 83.7 | 83.6 | 83.4 | 79.5 | 80.8 |
| PIP-45 Ae-2 | — | — | — | — | 98.9 | 84.2 | 84.1 | 83.6 | 84.1 | 78.2 | 79.9 |
| PIP-45 Af-2 | — | — | — | — | — | 84.1 | 84.1 | 83.6 | 84.7 | 78.2 | 79.9 |

TABLE 8-continued

| | | | | | | | | | | |
|---|---|---|---|---|---|---|---|---|---|---|
| PIP-45 Ba-2 | — | — | — | — | — | — | 99.3 | 98.3 | 95.5 | 76.2 | 76.7 |
| PIP-45 Bb-2 | — | — | — | — | — | — | — | 98.3 | 95.9 | 75.9 | 76.5 |
| PIP-45 Bc-2 | — | — | — | — | — | — | — | — | 95.0 | 75.6 | 76.4 |
| PIP-45 Bd-2 | — | — | — | — | — | — | — | — | — | 76.3 | 76.7 |
| PIP-45 Be-2 | — | — | — | — | — | — | — | — | — | — | 88.7 |
| PIP-45 Bf-2 | — | — | — | — | — | — | — | — | — | — | — |
| PIP-45 Bg-2 | — | — | — | — | — | — | — | — | — | — | — |
| PIP-45 Bh-2 | — | — | — | — | — | — | — | — | — | — | — |
| PIP-45 Bi-2 | — | — | — | — | — | — | — | — | — | — | — |
| PIP-45 Bj-2 | — | — | — | — | — | — | — | — | — | — | — |
| PIP-45 Bk-2 | — | — | — | — | — | — | — | — | — | — | — |
| PIP-45 Bl-2 | — | — | — | — | — | — | — | — | — | — | — |
| PIP-45 Bm-2 | — | — | — | — | — | — | — | — | — | — | — |
| PIP-45 Ca-2 | — | — | — | — | — | — | — | — | — | — | — |
| PIP-45 Cb-2 | — | — | — | — | — | — | — | — | — | — | — |
| PIP-45 Cc-2 | — | — | — | — | — | — | — | — | — | — | — |
| PIP-45 Cd-2 | — | — | — | — | — | — | — | — | — | — | — |
| PIP-45 Ce-2 | — | — | — | — | — | — | — | — | — | — | — |
| PIP-45 Cf-2 | — | — | — | — | — | — | — | — | — | — | — |
| PIP-45 Da-2 | — | — | — | — | — | — | — | — | — | — | — |
| PIP-45 Db-2 | — | — | — | — | — | — | — | — | — | — | — |
| PIP-45 Ea-2 | — | — | — | — | — | — | — | — | — | — | — |

| | PIP-45 Bg-2 SEQ ID NO: 26 | PIP-45 Bh-2 SEQ ID NO: 28 | PIP-45 Bi-2 SEQ ID NO: 30 | PIP-45 Bj-2 SEQ ID NO: 32 | PIP-45 Bk-2 SEQ ID NO: 34 | PIP-45 Bl-2 SEQ ID NO: 233 | PIP-45 Bm-2 SEQ ID NO: 235 | PIP-45 Ca-2 SEQ ID NO: 36 | PIP-45 Cb-2 SEQ ID NO: 38 |
|---|---|---|---|---|---|---|---|---|---|
| PIP-45 Aa-2 | 83.6 | 83.9 | 83.4 | 83.0 | 83.7 | 82.4 | 82.6 | 67.0 | 66.8 |
| PIP-45 Ab-2 | 83.8 | 84.1 | 83.6 | 83.0 | 83.6 | 82.8 | 82.6 | 66.9 | 66.9 |
| PIP-45 Ac-2 | 83.9 | 84.3 | 83.7 | 83.7 | 83.6 | 82.8 | 82.6 | 67.7 | 67.5 |
| PIP-45 Ad-2 | 83.4 | 83.9 | 83.6 | 83.6 | 83.9 | 82.4 | 82.1 | 67.3 | 67.5 |
| PIP-45 Ae-2 | 83.8 | 84.1 | 83.6 | 83.0 | 83.6 | 82.6 | 82.5 | 66.9 | 66.7 |
| PIP-45 Af-2 | 83.7 | 84.1 | 83.6 | 83.4 | 83.9 | 82.6 | 82.8 | 67.2 | 66.8 |
| PIP-45 Ba-2 | 98.9 | 99.3 | 97.9 | 91.2 | 90.1 | 91.6 | 90.1 | 67.2 | 67.4 |
| PIP-45 Bb-2 | 99.3 | 99.3 | 98.3 | 91.4 | 90.1 | 91.6 | 90.1 | 67.3 | 67.9 |
| PIP-45 Bc-2 | 97.9 | 98.3 | 99.6 | 90.8 | 89.2 | 90.7 | 89.9 | 67.3 | 67.9 |
| PIP-45 Bd-2 | 95.5 | 95.7 | 94.9 | 91.8 | 89.7 | 91.8 | 90.1 | 67.2 | 68.1 |
| PIP-45 Be-2 | 75.6 | 76.1 | 75.6 | 75.9 | 75.9 | 76.5 | 75.7 | 67.9 | 67.7 |
| PIP-45 Bf-2 | 76.1 | 76.7 | 76.3 | 77.2 | 77.4 | 77.1 | 76.3 | 68.7 | 69.1 |
| PIP-45 Bg-2 | — | 98.9 | 98.3 | 91.0 | 89.7 | 91.2 | 89.7 | 67.3 | 68.1 |
| PIP-45 Bh-2 | — | — | 98.3 | 91.4 | 90.3 | 91.8 | 90.3 | 67.2 | 67.4 |
| PIP-45 Bi-2 | — | — | — | 90.8 | 89.1 | 90.6 | 89.9 | 67.3 | 67.9 |

TABLE 8-continued

| | | | | | | | | | |
|---|---|---|---|---|---|---|---|---|---|
| PIP-45 Bj-2 | — | — | — | — | 88.2 | 88.8 | 87.5 | 68.3 | 69.0 |
| PIP-45 Bk-2 | — | — | — | — | — | 89.0 | 86.5 | 66.6 | 67.3 |
| PIP-45 Bl-2 | — | — | — | — | — | — | 88.2 | 68.3 | 68.5 |
| PIP-45 Bm-2 | — | — | — | — | — | — | — | 66.8 | 66.2 |
| PIP-45 Ca-2 | — | — | — | — | — | — | — | — | 93.0 |
| PIP-45 Cb-2 | — | — | — | — | — | — | — | — | — |
| PIP-45 Cc-2 | — | — | — | — | — | — | — | — | — |
| PIP-45 Cd-2 | — | — | — | — | — | — | — | — | — |
| PIP-45 Ce-2 | — | — | — | — | — | — | — | — | — |
| PIP-45 Cf-2 | — | — | — | — | — | — | — | — | — |
| PIP-45 Da-2 | — | — | — | — | — | — | — | — | — |
| PIP-45 Db-2 | — | — | — | — | — | — | — | — | — |
| PIP-45 Ea-2 | — | — | — | — | — | — | — | — | — |

| | PIP-45 Cc-2 SEQ ID NO: 40 | PIP-45 Cd-2 SEQ ID NO: 42 | PIP-45 Ce-2 SEQ ID NO: 44 | PIP-45 Cf-2 SEQ ID NO: 237 | PIP-45 Da-2 SEQ ID NO: 46 | PIP-45 Db-2 SEQ ID NO: 48 | PIP-45 Ea-2 SEQ ID NO: 50 | PIP-45 Ga-2 SEQ ID NO: 52 |
|---|---|---|---|---|---|---|---|---|
| PIP-45 Aa-2 | 68.6 | 67.7 | 68.3 | 66.8 | 56.6 | 51.3 | 47.4 | 30.6 |
| PIP-45 Ab-2 | 68.5 | 67.6 | 68.1 | 66.7 | 56.5 | 51.4 | 47.7 | 30.1 |
| PIP-45 Ac-2 | 68.8 | 68.1 | 68.1 | 67.3 | 56.4 | 51.8 | 47.7 | 30.8 |
| PIP-45 Ad-2 | 68.8 | 67.9 | 68.1 | 67.0 | 57.3 | 52.6 | 48.4 | 29.8 |
| PIP-45 Ae-2 | 68.5 | 67.8 | 68.1 | 66.7 | 65.5 | 51.4 | 47.7 | 30.1 |
| PIP-45 Af-2 | 68.6 | 67.9 | 68.5 | 67.0 | 56.4 | 51.3 | 47.8 | 30.6 |
| PIP-45 Ba-2 | 67.9 | 67.3 | 67.9 | 67.1 | 58.1 | 52.6 | 49.3 | 30.5 |
| PIP-45 Bb-2 | 68.3 | 67.5 | 68.0 | 67.2 | 57.8 | 52.4 | 49.5 | 30.2 |
| PIP-45 Bc-2 | 68.3 | 67.5 | 68.0 | 67.2 | 58.0 | 52.3 | 49.8 | 30.8 |
| PIP-45 Bd-2 | 67.9 | 67.3 | 67.7 | 67.2 | 57.6 | 52.6 | 50.2 | 31.1 |
| PIP-45 Be-2 | 70.2 | 67.7 | 68.9 | 67.7 | 58.8 | 51.9 | 48.3 | 30.8 |
| PIP-45 Bf-2 | 69.9 | 69.7 | 70.2 | 68.8 | 58.6 | 53.4 | 47.9 | 32.1 |
| PIP-45 Bg-2 | 68.3 | 67.7 | 68.1 | 67.2 | 57.6 | 52.5 | 49.5 | 30.4 |
| PIP-45 Bh-2 | 67.9 | 67.2 | 67.7 | 66.7 | 58.3 | 52.5 | 79.7 | 30.5 |
| PIP-45 Bi-2 | 68.3 | 67.5 | 68.0 | 67.2 | 58.0 | 52.6 | 49.9 | 30.9 |
| PIP-45 Bj-2 | 68.5 | 68.3 | 68.5 | 67.9 | 56.7 | 52.0 | 48.0 | 31.8 |
| PIP-45 Bk-2 | 67.5 | 66.8 | 67.0 | 66.3 | 57.8 | 53.5 | 49.4 | 31.2 |
| PIP-45 Bl-2 | 68.6 | 67.3 | 67.9 | 67.5 | 56.7 | 53.4 | 49.4 | 31.5 |
| PIP-45 Bm-2 | 67.3 | 67.0 | 67.5 | 66.7 | 57.0 | 51.8 | 48.7 | 31.9 |
| PIP-45 Ca-2 | 89.0 | 92.1 | 93.6 | 96.6 | 56.8 | 53.6 | 46.4 | 30.1 |
| PIP-45 Cb-2 | 89.4 | 91.7 | 93.8 | 93.2 | 56.6 | 53.0 | 46.5 | 31.5 |
| PIP-45 Cc-2 | — | 88.3 | 90.3 | 89.8 | 58.3 | 53.1 | 46.2 | 31.8 |
| PIP-45 Cd-2 | — | — | 93.6 | 92.6 | 56.5 | 51.9 | 46.1 | 31.6 |
| PIP-45 Ce-2 | — | — | — | 94.7 | 56.9 | 53.6 | 46.7 | 32.5 |

TABLE 8-continued

| | | | | | | | | |
|---|---|---|---|---|---|---|---|---|
| PIP-45 Cf-2 | — | — | — | — | 57.2 | 53.7 | 47.0 | 32.1 |
| PIP-45 Da-2 | — | — | — | — | — | 55.6 | 48.6 | 32.0 |
| PIP-45 Db-2 | — | — | — | — | — | — | 49.1 | 30.4 |
| PIP-45 Ea-2 | — | — | — | — | — | — | — | 32.5 |

Table 9 shows the PIP-64-1 polypeptide and PIP-64-2 polypeptide homologs identified, sequence identification numbers for each and the bacterial strains they were identified from. Table 10 shows the percent sequence identity between the PIP-64-1 polypeptide homologs. FIG. 3a-3b shows an amino acid sequence alignment of the PIP-64-1 polypeptide homologs. Table 11 shows the percent sequence identity between the PIP-64-2 polypeptide homologs. FIG. 4a-4b shows an amino acid sequence alignment of the PIP-64-2 polypeptide homologs.

TABLE 9

| Gene | | Source | Species |
|---|---|---|---|
| PIP-64Aa-1 | SEQ ID NO: 53 | LBV9691 | *Pseudomonas brenneri* |
| PIP-64Aa-2 | SEQ ID NO: 54 | | |
| PIP-64Aa-1 | SEQ ID NO: 53 | LBV10925; LBV10914 | *Pseudomonas gessardii* |
| PIP-64Ab-2 | SEQ ID NO: 55 | | |
| PIP-64Ba-1 | SEQ ID NO: 238 | internal collection - SSP560F2b | *Pseudomonas entomophila* |
| PIP-64Ba-2 | SEQ ID NO: 239 | | |
| PIP-64Ca-1 | SEQ ID NO: 56 | NCBI hypothetical protein WP_016977798 | *Pseudomonas fluorescens* |
| PIP-64Ca-2 | SEQ ID NO: 57 | NCBI hypothetical protein WP_016977799 | |
| PIP-64Ea-1 | SEQ ID NO: 58 | internal DuPont collection P4G7 | *Alcaligenes faecalis* |
| PIP-64Ea-2 | SEQ ID NO: 59 | | |
| PIP-64Eb-1 | SEQ ID NO: 60 | ATCC33950-internal genome sequence | *Alcaligenes faecalis* |
| PIP-64Eb-2 | SEQ ID NO: 61 | | |
| PIP-64Ec-1 | SEQ ID NO: 62 | EMBL-Uncharacterized protein M5J334_9BURK and M5IW68_9BURK | *Alcaligenes* sp. HPC1271 |
| PIP-64Ec-2 | SEQ ID NO: 63 | | |
| PIP-64Ga-1 | SEQ ID NO: 64 | EMBL R9VGC3_9ENTR | *Enterobacter* |
| PIP-64Ha-1 | SEQ ID NO: 65 | NCBI hypothetical protein PSF113_0646 (YP_005206077.1) and PSF113_0647 (YP_005206078.1) | *Pseudomonas fluorescens* |
| PIP-64Ha-2 | SEQ ID NO: 66 | | |
| PIP-64Hb-1 | SEQ ID NO: 67 | NCBI-hypothetical protein PSEBR_a622 (YP_004351774.1) and PSEBR_a623 (YP_004351775.1) | *Pseudomonas brassicacearum* |
| PIP-64Hb-2 | SEQ ID NO: 68 | | |
| PIP-64Hc-1 | SEQ ID NO: 69 | JGI- SwiRh_808460 hypothetical protein | Switchgrass rhizosphere microbial community from Michigan |
| PIP-64Hc-2 | SEQ ID NO: 70 | JGI- SwBS_00338360 hypothetical protein | |
| PIP-64Hd-1 | SEQ ID NO: 71 | JGI- SwiRh_668170 hypothetical protein | *Miscanthus* rhizosphere microbial communities from Kellogg |
| PIP-64Hd-2 | SEQ ID NO: 72 | JGI - MRS2a_00580520 hypothetical protein | |

TABLE 10

| | PIP-64 Ba-1 SEQ ID NO: 238 | PIP-64 Ca-1 SEQ ID NO: 56 | PIP-64 Ea-1 SEQ ID NO: 58 | PIP-64 Eb-1 SEQ ID NO: 60 | PIP-64 Ec-1 SEQ ID NO: 62 | PIP-64 Ga-1 SEQ ID NO: 64 | PIP-64 Ha-1 SEQ ID NO: 65 | PIP-64 Hb-1 SEQ ID NO: 67 | PIP-64 Hc-1 SEQ ID NO: 69 | PIP-64 Hd-1 SEQ ID NO: 71 |
|---|---|---|---|---|---|---|---|---|---|---|
| PIP-64Aa-1 | 84.0 | 72.3 | 59.1 | 59.1 | 59.1 | 33.2 | 27.8 | 27.4 | 28.6 | 27.9 |
| PIP-64Ba-1 | — | 74.2 | 56.4 | 56.8 | 56.4 | 31.4 | 25.7 | 26.9 | 26.0 | 27.2 |
| PIP-64Ca-1 | — | — | 55.6 | 55.6 | 55.6 | 32.1 | 23.7 | 23.4 | 25.2 | 26.4 |
| PIP-64Ea-1 | — | — | — | 99.2 | 99.6 | 31.6 | 25.4 | 24.6 | 25.3 | 26.0 |
| PIP-64Eb-1 | — | — | — | — | 98.8 | 31.6 | 25.0 | 24.6 | 25.3 | 26.0 |
| PIP-64Ec-1 | — | — | — | — | — | 31.6 | 25.4 | 24.6 | 25.3 | 26.0 |
| PIP-64Ga-1 | — | — | — | — | — | — | 22.1 | 23.1 | 22.4 | 22.6 |
| PIP-64Ha-1 | — | — | — | — | — | — | — | 94.6 | 66.2 | 62.1 |
| PIP-64Hb-1 | — | — | — | — | — | — | — | — | 66.2 | 62.1 |
| PIP-64Hc-1 | — | — | — | — | — | — | — | — | — | 76.8 |

TABLE 11

| | PIP-64 Ab-2 SEQ ID NO: 55 | PIP-64 Ba-2 SEQ ID NO: 239 | PIP-64 Ca-2 SEQ ID NO: 57 | PIP-64 Ea-2 SEQ ID NO: 59 | PIP-64 Eb-2 SEQ ID NO: 61 | PIP-64 Ec-2 SEQ ID NO: 63 | PIP-64 Ha-2 SEQ ID NO: 66 | PIP-64 Hb-2 SEQ ID NO: 68 | PIP-64 Hc-2 SEQ ID NO: 70 | PIP-64 Hd-2 SEQ ID NO: 72 |
|---|---|---|---|---|---|---|---|---|---|---|
| PIP-64Aa-2 | 95.8 | 66.9 | 54.8 | 38.9 | 40.0 | 39.6 | 24.0 | 24.8 | 24.0 | 23.0 |
| PIP-64Ab-2 | — | 66.2 | 54.8 | 39.6 | 41.2 | 40.8 | 25.9 | 23.1 | 22.3 | 22.3 |
| PIP-64Ba-2 | — | — | 49.8 | 38.5 | 41.1 | 39.6 | 21.3 | 24.4 | 24.0 | 19.0 |
| PIP-64Ca-2 | — | — | — | 39.0 | 42.5 | 40.6 | 22.5 | 24.5 | 23.8 | 22.5 |
| PIP-64Ea-2 | — | — | — | — | 85.4 | 90.7 | 22.3 | 18.2 | 22.0 | 21.9 |
| PIP-64Eb-2 | — | — | — | — | — | 93.4 | 25.5 | 21.6 | 22.7 | 21.9 |
| PIP-64Ec-2 | — | — | — | — | — | — | 23.3 | 19.0 | 23.0 | 21.7 |
| PIP-64Ha-2 | — | — | — | — | — | — | — | 72.3 | 49.2 | 35.7 |
| PIP-64Hb-2 | — | — | — | — | — | — | — | — | 52.5 | 38.5 |
| PIP-64Hc-2 | — | — | — | — | — | — | — | — | — | 41.2 |

Table 12 shows the PIP-74-1 polypeptide and PIP-74-2 polypeptide homologs identified, sequence identification numbers for each and the bacterial strains they were identified from. Table 13 shows the percent sequence identity between the PIP-74-1 polypeptide family members. FIG. 5a-5b shows an amino acid sequence alignment of the PIP-74-1 polypeptide homologs. Table 14 shows the percent sequence identity between the PIP-74-2 polypeptide family members. FIG. 6 shows an amino acid sequence alignment of the PIP-74-2 polypeptide homologs.

TABLE 14

| | PIP-74Ab-2 | PIP-74Ca-2 |
|---|---|---|
| PIP-74Aa-2 | 98.0 | 66.3 |
| PIP-74Ab-2 | — | 66.3 |

Table 15 shows the PIP-75 polypeptide homologs identified, sequence identification numbers for each and the bacterial strains they were identified from. Table 16 shows the percent sequence identity between the PIP-75 polypeptide family members. FIG. 7 shows an amino acid sequence alignment of the PIP-75 polypeptide homologs.

TABLE 15

| Gene | | Source | Species |
|---|---|---|---|
| PIP-75Aa | SEQ ID NO: 79 | LBV6019 | *Pseudomonas antarctica* |
| PIP-75Ba | SEQ ID NO: 80 | LBV2669 | *Pseudomonas orientalis* |
| PIP-75Da | SEQ ID NO: 81 | internal - JH34920-1 | *Enterobacter asburiae* |
| PIP-75Ea | SEQ ID NO: 82 | NCBI A936_14984 | *Enterobacter* sp. |
| PIP-75Ga | SEQ ID NO: 83 | NCBI-YP_004234966 | *Acidovorax avenae* subsp. *avenae* ATCC 19860 |
| PIP-75Gb | SEQ ID NO: 84 | internal collection - SSP443E10-1 | *Serratia plymuthica* |
| PIP-75Gc | SEQ ID NO: 85 | internal collection - JH20785-4 | *Serratia liquefaciens* |
| PIP-75Gd | SEQ ID NO: 86 | internal collection - SSP291H3-2 | *Serratia* sp. |
| PIP-75Ge | SEQ ID NO: 87 | internal collection - JH20487-2 | *Serratia* sp. |

TABLE 12

| Gene | | Source | Species |
|---|---|---|---|
| PIP-74Aa-1 | SEQ ID NO: 73 | internal collection - SS135B4b | *Pseudomonas rhodesiae* |
| PIP-74Aa-2 | SEQ ID NO: 74 | | |
| PIP-74Ab-1 | SEQ ID NO: 75 | internal collection - SSP427D6-1 | *Pseudomonas orientalis* |
| PIP-74Ab-2 | SEQ ID NO: 76 | | |
| PIP-74Ca-1 | SEQ ID NO: 77 | internal collection - JH21146-1 | *Pseudomonas* sp. PKRS11 |
| PIP-74Ca-2 | SEQ ID NO: 78 | | |

TABLE 13

| | PIP-74Ab-1 | PIP-74Ca-1 |
|---|---|---|
| PIP-74Aa-1 | 99.6 | 74.5 |
| PIP-74Ab-1 | — | 74.5 |

TABLE 16

| | PIP-75Ba | PIP-75Da | PIP-75Ea | PIP-75Ga | PIP-75Gb | PIP-75Gc | PIP-75Gd | PIP-75Ge |
|---|---|---|---|---|---|---|---|---|
| PIP-75Aa | 83.3 | 65.6 | 60.4 | 33.6 | 36.7 | 33.7 | 33.7 | 32.7 |
| PIP-75Ba | — | 65.6 | 59.4 | 33.6 | 34.0 | 32.0 | 38.1 | 31.6 |
| PIP-75Da | — | — | 85.3 | 35.2 | 39.6 | 38.5 | 32.3 | 34.4 |
| PIP-75Ea | — | — | — | 35.8 | 37.5 | 35.4 | 30.2 | 31.2 |
| PIP-75Ga | — | — | — | — | 24.8 | 25.2 | 24.6 | 23.8 |
| PIP-75Gb | — | — | — | — | — | 86.2 | 67.0 | 75.5 |
| PIP-75Gc | — | — | — | — | — | — | 61.3 | 73.1 |
| PIP-75Gd | — | — | — | — | — | — | — | 82.1 |

Table 17 shows the PIP-77 polypeptide homologs identified, sequence identification numbers for each and the bacterial strains they were identified from. Table 18 shows the percent sequence identity between the PIP-77 polypeptide family members. FIG. 8a-8b shows an amino acid sequence alignment of the PIP-77 polypeptide homologs.

TABLE 17

| Gene | Source | | Species |
|---|---|---|---|
| PIP-77Aa | SEQ ID NO: 88 | SSP344E5 and other 29 internal strains | *Pseudomonas chlororaphis* |
| PIP-77Ab | SEQ ID NO: 89 | SSP346A11a | *Pseudomonas chlororaphis* |
| PIP-77Ac | SEQ ID NO: 90 | JH19897-4; JH19820-2; JH19887-2; JH20257-4; JH19881-4; JH19896-4; JH20401-2; | *Pseudomonas brassicacearum* |
| PIP-77Ad | SEQ ID NO: 91 | SSP423G5-1; SSP344E7a; SSP283E1-2; SSP283E2-1; SSP283E6-1; SSP259H3-2; JH20450-1; SSP459A9-4; SSP459B9-3; JH21227-2; JH22700-1; NCBI-WP_007925627; | *Pseudomonas chlororaphis* |
| PIP-77Ae | SEQ ID NO: 92 | SSP346D1a | *Pseudomonas chlororaphis* |
| PIP-77Af | SEQ ID NO: 240 | NCBI hypothetical protein WP_023965133.1; internal collection- SSP555A5b | *Pseudomonas chlororaphis* |
| PIP-77Ba | SEQ ID NO: 93 | JH17731-2; JH17330-1; JH17729-3; JH17728-1; JH17574-1; JH17564-4 | *Pseudomonas fluorescens* |
| PIP-77Bb | SEQ ID NO: 94 | JH20704-3; JH20495-2 | *Pseudomonas fluorescens* |
| PIP-77Bc | SEQ ID NO: 95 | JH18994-3; JH18447-2 | *Pseudomonas fluorescens* |
| PIP-77Bd | SEQ ID NO: 96 | JH17494-4; JH17581-1; JH19353-3; JH17541-1; JH17554-4; JH16392-2; JH17546-4; JH17696-1; JH17549-1; JH17110-1; SSP454G12-1; JH17430-2 | *Pseudomonas fluorescens* |
| PIP-77Be | SEQ ID NO: 97 | SSP347B8a | *Pseudomonas fluorescens* |
| PIP-77Bf | SEQ ID NO: 98 | JH18110-4; JH18354-4; JH18107-3; SSP450C9-1 | *Pseudomonas rhodesiae* |
| PIP-77Bg | SEQ ID NO: 99 | NCBI-WP_007969132 | *Pseudomonas-sp* |
| PIP-77Bh | SEQ ID NO: 241 | internal collection - SSP535F3b | *Pseudomonas rhodesiae* |
| PIP-77Bi | SEQ ID NO: 242 | internal collection - SSP557G7-4 | *Pseudomonas rhodesiae* |
| PIP-77Ca | SEQ ID NO: 100 | SS154F1; SSP154F5a | *Pseudomonas fluorescens* |
| PIP-77Ea | SEQ ID NO: 101 | NCBI-WP_008458969 | *Enterobacter-sp* |
| PIP-77Eb | SEQ ID NO: 102 | NCBI-YP_564720 | *Shewanella denitrificans* |
| PIP-77Ec | SEQ ID NO: 103 | NCBI-WP_005351930 | *Aeromonas diversa* |
| PIP-77Ed | SEQ ID NO: 104 | NCBI-YP_001141694 | *Aeromonas salmonicida* |
| PIP-77Ee | SEQ ID NO: 105 | NCBI-YP_004392889 | *Aeromonas veronii* |
| PIP-77Ef | SEQ ID NO: 106 | NCBI-WP_005909090 | *Aeromonas molluscorum* |
| PIP-77Eq | SEQ ID NO: 107 | NCBI-WP_010633780 | *Aeromonas aquariorum* |
| PIP-77Eh | SEQ ID NO: 243 | NCBI hypothetical protein AH4AK4_1885 AHE49340 | *Aeromonas hydrophila* |
| PIP-77Ei | SEQ ID NO: 244 | EMBL-U1H356_9GAMM | *Aeromonas veronii* |
| PIP-77Ej | SEQ ID NO: 245 | internal collection - JH58766-1 | *Haemophilus piscium* |

TABLE 18

| | PIP-77Ab SEQ ID NO: 89 | PIP-77Ac SEQ ID NO: 90 | PIP-77Ad SEQ ID NO: 91 | PIP-77Ae SEQ ID NO: 92 | PIP-77Af SEQ ID NO: 240 | PIP-77Ba SEQ ID NO: 93 | PIP-77Bb SEQ ID NO: 94 | PIP-77Bc SEQ ID NO: 95 | PIP-77Bd SEQ ID NO: 96 | PIP-77Be SEQ ID NO: 97 |
|---|---|---|---|---|---|---|---|---|---|---|
| PIP-77Aa | 94.4 | 93.3 | 92.1 | 92.1 | 92.1 | 87.6 | 86.5 | 85.4 | 84.3 | 84.3 |
| PIP-77Ab | — | 95.5 | 96.6 | 94.4 | 95.5 | 86.5 | 85.4 | 84.3 | 83.1 | 83.1 |
| PIP-77Ac | — | — | 98.9 | 95.5 | 98.9 | 85.4 | 84.3 | 83.1 | 82.0 | 83.1 |
| PIP-77Ad | — | — | — | 96.6 | 98.9 | 86.5 | 85.4 | 84.3 | 83.1 | 84.3 |
| PIP-77Ae | — | — | — | — | 95.5 | 85.4 | 84.3 | 83.1 | 82.0 | 84.3 |
| PIP-77Af | — | — | — | — | — | 85.4 | 84.3 | 83.1 | 82.0 | 83.1 |
| PIP-77Ba | — | — | — | — | — | — | 97.8 | 96.6 | 95.5 | 88.8 |
| PIP-77Bb | — | — | — | — | — | — | — | 98.9 | 97.8 | 86.5 |
| PIP-77Bc | — | — | — | — | — | — | — | — | 96.6 | 85.4 |
| PIP-77Bd | — | — | — | — | — | — | — | — | — | 84.3 |
| PIP-77Be | — | — | — | — | — | — | — | — | — | — |
| PIP-77Bf | — | — | — | — | — | — | — | — | — | — |
| PIP-77Bg | — | — | — | — | — | — | — | — | — | — |
| PIP-77Bh | — | — | — | — | — | — | — | — | — | — |
| PIP-77Bi | — | — | — | — | — | — | — | — | — | — |
| PIP-77Ca | — | — | — | — | — | — | — | — | — | — |
| PIP-77Ea | — | — | — | — | — | — | — | — | — | — |
| PIP-77Eb | — | — | — | — | — | — | — | — | — | — |
| PIP-77Ec | — | — | — | — | — | — | — | — | — | — |
| PIP-77Ed | — | — | — | — | — | — | — | — | — | — |
| PIP-77Ee | — | — | — | — | — | — | — | — | — | — |
| PIP-77Ef | — | — | — | — | — | — | — | — | — | — |

TABLE 18-continued

| | | | | | | | | | |
|---|---|---|---|---|---|---|---|---|---|
| PIP-77Eg | — | — | — | — | — | — | — | — | — |
| PIP-77Eh | — | — | — | — | — | — | — | — | — |
| PIP-77Ei | — | — | — | — | — | — | — | — | — |

| | PIP-77Bf SEQ ID NO: 98 | PIP-77Bg SEQ ID NO: 99 | PIP-77Bh SEQ ID NO: 241 | PIP-77Bi SEQ ID NO: 242 | PIP-77Ca SEQ ID NO: 100 | PIP-77Ea SEQ ID NO: 101 | PIP-77Eb SEQ ID NO: 102 | PIP-77Ec SEQ ID NO: 103 | PIP-77Ed SEQ ID NO: 104 |
|---|---|---|---|---|---|---|---|---|---|
| PIP-77Aa | 83.1 | 85.4 | 86.5 | 84.3 | 78.0 | 56.5 | 55.1 | 55.6 | 55.6 |
| PIP-77Ab | 82.0 | 84.3 | 85.4 | 83.1 | 76.9 | 58.7 | 55.1 | 56.7 | 55.6 |
| PIP-77Ac | 80.9 | 82.0 | 84.3 | 80.9 | 79.1 | 60.9 | 56.2 | 55.6 | 54.4 |
| PIP-77Ad | 82.0 | 82.0 | 85.4 | 82.0 | 78.0 | 60.9 | 56.2 | 55.6 | 533 |
| PIP-77Ae | 80.9 | 84.3 | 84.3 | 80.9 | 78.0 | 58.7 | 55.1 | 54.4 | 52.2 |
| PIP-77Af | 80.9 | 82.0 | 84.3 | 80.9 | 78.0 | 60.9 | 56.2 | 55.6 | 53.3 |
| PIP-77Ba | 94.4 | 80.9 | 98.9 | 94.4 | 74.7 | 57.6 | 51.7 | 54.4 | 53.3 |
| PIP-77Bb | 96.6 | 82.0 | 96.6 | 96.6 | 75.8 | 57.6 | 51.7 | 55.6 | 54.4 |
| PIP-77Bc | 95.5 | 80.9 | 95.5 | 95.5 | 74.7 | 57.6 | 51.7 | 54.4 | 53.3 |
| PIP-77Bd | 98.9 | 79.8 | 94.4 | 98.9 | 73.6 | 55.4 | 49.4 | 53.3 | 52.2 |
| PIP-77Be | 83.1 | 78.7 | 89.9 | 83.1 | 78.0 | 57.6 | 53.9 | 51.1 | 48.9 |
| PIP-77Bf | — | 78.7 | 93.3 | 97.8 | 72.5 | 54.3 | 49.4 | 52.2 | 52.2 |
| PIP-77Bg | — | — | 82.0 | 79.8 | 75.8 | 56.5 | 55.1 | 56.7 | 55.6 |
| PIP-77Bh | — | — | — | 93.3 | 75.8 | 58.7 | 52.8 | 53.3 | 52.2 |
| PIP-77Bi | — | — | — | | 72.5 | 55.4 | 49.4 | 53.3 | 52.2 |
| PIP-77Ca | — | — | — | — | — | 62.4 | 57.1 | 57.6 | 54.3 |
| PIP-77Ea | — | — | — | — | — | — | 57.6 | 53.8 | 54.8 |
| PIP-77Eb | — | — | — | — | — | — | — | 53.3 | 51.1 |
| PIP-77Ec | — | — | — | — | — | — | — | — | 86.7 |
| PIP-77Ed | — | — | — | — | — | — | — | — | — |
| PIP-77Ee | — | — | — | — | — | — | — | — | — |
| PIP-77Ef | — | — | — | — | — | — | — | — | — |
| PIP-77Eg | — | — | — | — | — | — | — | — | — |
| PIP-77Eh | — | — | — | — | — | — | — | — | — |
| PIP-77Ei | — | — | — | — | — | — | — | — | — |

| | PIP-77Ee SEQ ID NO: 105 | PIP-77Ef SEQ ID NO: 106 | PIP-77Eg SEQ ID NO: 107 | PIP-77Eh SEQ ID NO: 243 | PIP-77Ei SEQ ID NO: 244 | PIP-77Ej SEQ ID NO: 245 |
|---|---|---|---|---|---|---|
| PIP-77Aa | 56.7 | 51.1 | 56.7 | 56.7 | 55.6 | 55.6 |
| PIP-77Ab | 56.7 | 51.1 | 56.7 | 56.7 | 55.6 | 55.6 |
| PIP-77Ac | 55.6 | 50.0 | 55.6 | 55.6 | 54.4 | 54.4 |
| PIP-77Ad | 54.4 | 48.9 | 54.4 | 54.4 | 53.3 | 53.3 |
| PIP-77Ae | 53.3 | 47.8 | 53.3 | 53.3 | 52.2 | 52.2 |
| PIP-77Af | 54.4 | 48.9 | 54.4 | 54.4 | 53.3 | 53.3 |
| PIP-77Ba | 54.4 | 47.8 | 53.3 | 53.3 | 52.2 | 53.3 |
| PIP-77Bb | 55.6 | 48.9 | 54.4 | 54.4 | 53.3 | 54.4 |
| PIP-77Bc | 54.4 | 47.8 | 53.3 | 53.3 | 52.2 | 53.3 |
| PIP-77Bd | 53.3 | 48.9 | 52.2 | 52.2 | 51.1 | 52.2 |
| PIP-77Be | 50.0 | 45.6 | 51.1 | 51.1 | 48.9 | 48.9 |
| PIP-77Bf | 53.3 | 48.9 | 52.2 | 52.2 | 51.1 | 52.2 |
| PIP-77Bg | 56.7 | 51.1 | 56.7 | 56.7 | 55.6 | 55.6 |
| PIP-77Bh | 3.3 | 46.7 | 52.2 | 52.2 | 51.1 | 52.2 |
| PIP-77Bi | 53.3 | 48.9 | 52.2 | 52.2 | 51.1 | 52.2 |
| PIP-77Ca | 55.4 | 51.1 | 56.5 | 56.5 | 54.3 | 54.3 |
| PIP-77Ea | 54.8 | 50.0 | 55.9 | 55.9 | 53.8 | 55.9 |
| PIP-77Eb | 51.1 | 46.7 | 53.3 | 53.3 | 53.3 | 51.1 |
| PIP-77Ec | 85.6 | 70.3 | 85.6 | 84.4 | 84.4 | 86.7 |
| PIP-77Ed | 96.7 | 75.8 | 88.9 | 90.0 | 94.4 | 90.0 |
| PIP-77Ee | — | 75.6 | 87.8 | 88.9 | 97.8 | 88.9 |
| PIP-77Ef | — | — | 84.6 | 85.7 | 75.6 | 80.2 |
| PIP-77Eg | — | — | — | 98.9 | 87.8 | 95.6 |
| PIP-77Eh | — | — | — | — | 88.9 | 94.4 |
| PIP-77Ei | — | — | — | — | — | 86.7 |

Example 7. Functional Test of PIP-45-1 and PIP-45-2 Components from Different Origins In order to test the functionality of the PIP-45-1 and PIP-45-2 components from different PIP-45 homologs, five selected active homolog pairs were expressed individually (listed in Table 19). Each PIP-45-1 component was mixed with every one of the five PIP-45-2 components. All of the pairs were tested for WCRW insecticidal activity in diet based assays as described above. The results are shown in Table 19, indicating that when paired together PIP-45-1 and PIP-45-2 components from different sources can provide insecticidal activity.

TABLE 19

| Activity | PIP045Aa-2<br>SEQ ID NO: 2 | PIP045Ad-2<br>SEQ ID NO: 8 | PIP045Ba-2<br>SEQ ID NO: 14 | PIP045Ca-2<br>SEQ ID NO: 36 | PIP045Cb-2<br>SEQ ID NO: 38 |
|---|---|---|---|---|---|
| PIP045Aa-1<br>SEQ ID NO: 1 | Active | Active | Active | Active | Active |
| PIP045Ad-1<br>SEQ ID NO: 7 | Active | Active | Active | Active | Active |
| PIP045Ba-1<br>SEQ ID NO: 13 | Active | Inactive | Active | Inactive | Inactive |
| PIP045Ca-1<br>SEQ ID NO: 35 | Inactive | Inactive | Inactive | Active | Active |
| PIP045Cb-1<br>SEQ ID NO: 37 | Inactive | Inactive | Inactive | Active | Active |

Active in bold = from the original pair;
Active = insecticidal activity detected with components from different origins

Example 8. Gene Subcloning and *E. coli* Expression

The target genes encoding the insecticidal proteins were first amplified by PCR using their genomic DNA as templates. The PCR primers were designed based on the 5' end an3' end sequences with appropriate restriction sites incorporated. After restriction enzyme digestion, the PCR products were cloned into various *E. coli* expression vectors, i.e. pCOLD™ 1 with N-His tag, pMAL™ vector with and without MBP fusion or pCOLD™ vectors with and without His tag. The proteins were expressed in BL21(DE3) or C41 *E. coli* hosts cells with 1 mM IPTG overnight induction at 16° C.

The recombinant protein was extracted from *E. coli* culture after induction, purified and assayed on insect targets as described in Example 1.

Example 9. Transient Expression and Insect Bioassay on Transient Leaf Tissues Polynucleotides encoding both PIP-64Aa1 (SEQ ID NO: 160) and PIP-64Aa2 (SEQ ID NO: 161) were cloned into a transient expression vector under control of a viral promoter pDMMV respectively (Day, et. al., (1999) *Plant Mol. Biol.* 40:771-782). The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, young plantlets of bush bean (common bean, *Phaseolus vulgaris*) and soybean (*Glycine max*), were agro-infiltrated with normalized bacterial cell cultures of test and control strains. 10 leaf discs were generated for each plantlets and infested with 3 neonates of both Soy Bean Looper (SBL) (*Pseudoplusia includes*) and Velvet bean caterpillar (VBC) (Velvet *Anticarsia gemmatalis*) alone with two controls of leaf discs generated with *Agrobacterium* only and DsRed2 fluorescence marker (Clontech, Mountain View, Calif.) expression vector in *Agrobacterium*. The consumption of green leaf tissues was scored two days after infestation. Transient protein expressions of both PIP-64-1 (SEQ ID NO: 53) and PIP-64-2 (SEQ ID NO: 54) were confirmed by Mass spectrometry based protein identification method using extracted protein lysates from co-infiltrated leaf tissues (Patterson, (1998) 10(22):1-24, Current Protocol in Molecular Biology published by John Wiley & Son Inc). The transiently co-expressed PIP-64-1 (SEQ ID NO: 53) and PIP-64-2 (SEQ ID NO: 54) protected leaf discs from consumption by the infested insects while total green tissue consumption was observed for the two negative controls.

Example 10—*Agrobacterium*-Mediated Stable Transformation of Maize

For *Agrobacterium*-mediated maize transformation of insecticidal polypeptides, the method of Zhao is employed (U.S. Pat. No. 5,981,840 and International Patent Publication Number WO 1998/32326, the contents of which are hereby incorporated by reference). Briefly, immature embryos are isolated from maize and the embryos contacted with an *Agrobacterium* suspension, where the bacteria were capable of transferring a polynucleotide encoding an insecticidal polypeptide of the disclosure to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium with antibiotic, but without a selecting agent, for *Agrobacterium* elimination and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

For detection of the insecticidal polypeptide in leaf tissue 4 lyophilized leaf punches/sample are pulverized and resuspended in 100 µL PBS containing 0.1% TWEEN™ 20 (PBST), 1% beta-mercaptoethanol containing 1 tablet/7 mL complete Mini proteinase inhibitor (Roche 1183615301). The suspension is sonicated for 2 min and then centrifuged at 4° C., 20,000 g for 15 min. To a supernatant aliquot ⅓ volume of 3× NuPAGE® LDS Sample Buffer (Invitrogen™ (CA, USA), 1% B-ME containing 1 tablet/7 mL complete Mini proteinase inhibitor was added. The reaction is heated at 80° C. for 10 min and then centrifuged. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified rabbit anti-insecticidal polypeptide in PBST overnight. The membrane is rinsed three times with PBST and then incubated in PBST for 15 min and then two times 5 min before incubating for 2 hours in PBST with goat anti-rabbit-HRP for 3 hours. The detected proteins are visualized using ECL Western Blotting Reagents (GE Healthcare cat #RPN2106) and Kodak® Biomax® MR film. For detection of the insecticidal protein in roots the roots are lyophilized and 2 mg powder per sample is resuspended in LDS, 1% beta-mercaptoethanol containing 1 tablet/7 mL Complete Mini proteinase inhibitor is added. The reaction is heated at 80° C. for 10 min and then centrifuged at 4° C., 20,000 g for 15 min. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified polyclonal rabbit anti-insecticidal antibody in PBST overnight. The membrane is rinsed three times with PBST and then incubated in PBST for 15 min and then two times 5 min before incubating for 2 hours in PBST with goat anti-rabbit-HRP for 3 hrs. The antibody bound insecticidal proteins are detected using ECL™ Western Blotting Reagents (GE Healthcare cat #RPN2106) and Kodak® Biomax® MR film.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054 and International Publication Number WO 2003/018810.

Example 11—Expression Vector Constructs for Expression of Insecticidal Polypeptides in Plants The plant expression vectors, can be constructed to include a transgene cassette containing the coding sequence pf the insecticidal polypeptide, under control of the Mirabilis Mosaic Virus (MMV) promoter [Dey N and Maiti I B, 1999, Plant Mol. Biol. 40(5):771-82] in combination with an enhancer element. These constructs can be used to generate transgenic maize events to test for efficacy against corn rootworm provided by expression of the insecticidal polypeptide of the disclosure.

T0 greenhouse efficacy of the events can be measured by root protection from Western corn rootworm. Root protection is measured according to the number of nodes of roots injured (CRWNIS=corn rootworm node injury score) using the method developed by Oleson, et al. (2005) [J. Econ Entomol. 98(1):1-8]. The root injury score is measured from "0" to "3" with "0" indicating no visible root injury, "1" indicating 1 node of root damage, "2" indicating 2 nodes or root damage, and "3" indicating a maximum score of 3 nodes of root damage. Intermediate scores (e.g. 1.5) indicate additional fractions of nodes of damage (e.g. one and a half nodes injured).

That which is claimed:

1. An insecticidal polypeptide selected from:
   a) PIP-75 polypeptide comprising an amino acid sequence having greater than 80% sequence identity compared to the amino acid sequence of SEQ ID NO: 79; and
   b) a PIP-75 polypeptide comprising the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87, wherein the insecticidal polypeptide is operably linked to a heterologous signal peptide or transit peptide and the insecticidal polypeptide has insecticidal activity against Western corn rootworm.

2. An insecticidal composition comprising the PIP-75 polypeptide of claim 1.

3. A recombinant polynucleotide encoding the insecticidal polypeptide selected from:
   a) a PIP-75 polypeptide comprising an amino acid sequence having greater than 80% sequence identity compared to the amino acid sequence of SEQ ID NO: 79; and
   b) a PIP-75 polypeptide comprising the amino acid sequence of SEQ ID NO: 79, SEQ ID NO: 80, SEQ ID NO: 81, SEQ ID NO: 84, SEQ ID NO: 85, SEQ ID NO: 86 or SEQ ID NO: 87, wherein the polynucleotide is operably linked to a heterologous regulatory element.

4. The recombinant polynucleotide of claim 3, wherein the recombinant polynucleotide is selected from the polynucleotide SEQ ID NO: 186, SEQ ID NO: 187, SEQ ID NO: 188, SEQ ID NO: 191, SEQ ID NO: 192, SEQ ID NO: 193 and SEQ ID NO: 194.

5. A DNA construct comprising, the recombinant polynucleotide of claim 3 or 4 and a heterologous regulatory sequence operably linked to the recombinant polynucleotide.

6. A transgenic plant or plant cell comprising the DNA construct of claim 5.

7. A method of inhibiting growth or killing an insect pest, comprising contacting the insect pest with an insecticidally-effective amount of the PIP-75 polypeptide of claim 1.

8. A method of controlling Lepidoptera and/or Coleoptera insect infestation in a transgenic plant and providing insect resistance management, comprising expressing in the plant the polynucleotide of claim 3 or 4.

9. The method of claim 7 or 8, wherein the insect pest or insect pest population is resistant to a Bt toxin.

* * * * *

SEQUENCE LISTING

```
<160> NUMBER OF SEQ ID NOS: 245

<210> SEQ ID NO 1
<211> LENGTH: 578
<212> TYPE: PRT
<213> ORGANISM: Pseudomonas brenneri

<400> SEQUENCE: 1

Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
            20                  25                  30

Thr Asp Trp Asn Asn Asp Leu Thr Gly Trp Thr Gln Ser Ala Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Tyr Gly Pro Thr Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Ser Leu Gln Gln
            100                 105                 110

Val Met Glu Leu Thr Asp Asn Gly Gln Ile Thr Ile Asn Asn Thr Leu
        115                 120                 125

Tyr Met Leu Tyr Asp Pro Asn Lys Gln Gly Thr Leu Leu Gln Leu Pro
    130                 135                 140

Val Thr Arg Cys Pro Thr Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175
```

```
Ile Val Arg Asp Ala Asp Gly Asn Met Arg Lys Ile Thr Phe Thr Cys
            180                 185                 190

Glu Asn Pro Ala Tyr Phe Leu Ala Met Trp Arg Ile Asp Pro Asn Ala
        195                 200                 205

Val Leu Gly Leu Tyr Arg Asp Tyr Ile Asp Pro Gln Val Gln Leu Glu
    210                 215                 220

Asp Leu Tyr Leu Arg Tyr Thr Ala Asp Cys Pro Thr Gly Lys Ala Gly
225                 230                 235                 240

Asp Pro Val Ile Asp Pro Thr Thr Gly Gln Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Arg Pro Leu Ala Ser Ser Gln Asn
    290                 295                 300

Ser Gln Ala Leu Ile Cys Cys Ala Gln Tyr Gly Gln Asn Tyr Arg Asn
305                 310                 315                 320

Ser Asp Pro His Ile Gly Phe Ser Ala Asn Ser Val Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
        355                 360                 365

Trp Lys Ile Thr Arg Gly Thr Ala Lys Ser Ala Ala Asn Gly Ser Asp
    370                 375                 380

Gln Ile Leu Gln Ala Val Phe Glu Val Pro Val Ser Ala Gly Phe Ser
385                 390                 395                 400

Ile Asn Asp Ile Thr Ile Ser Gly Gln Pro Ile Asp Tyr Val Trp Val
                405                 410                 415

Ile Ala Gln Gln Leu Leu Val Gly Leu Ser Val Thr Thr Thr Pro Ile
            420                 425                 430

Ser Pro Thr Pro Asp Ser Cys Pro Cys Val Lys Asp Arg Val Asn Gly
        435                 440                 445

Val Gln Pro Trp Pro Val Gln Leu Leu Pro Leu Asp Leu Phe Tyr Gly
    450                 455                 460

Gln Ser Pro Thr Asp Leu Pro Ala Trp Leu Ala Pro Gly Thr Ser Gly
465                 470                 475                 480

Gln Phe Ala Leu Val Val Gln Gly Ala Asp Leu Lys Thr Thr Ala Glu
                485                 490                 495

Thr Ala Arg Val Gln Phe Ser Asn Pro Gly Val Thr Ala Gln Val Thr
            500                 505                 510

Gln Phe Leu Pro Asp Ala Ser Ala Ile Pro Gly Gln Thr Asn Ser Gly
        515                 520                 525

Gly Thr Gln Gly Tyr Leu Leu Thr Ile Thr Val Ser Pro Thr Ala Ala
    530                 535                 540

Pro Gly Leu Val Thr Val Arg Ala Leu Asn Pro Gly Glu Ala Asp Asn
545                 550                 555                 560

Pro Ser Ala Thr Glu His Pro Trp Glu Ser Gly Leu Ala Leu Val Pro
                565                 570                 575

Gly Ala

<210> SEQ ID NO 2
```

-continued

```
<211> LENGTH: 535
<212> TYPE: PRT
<213> ORGANISM: Pseudomonas brenneri

<400> SEQUENCE: 2

Met Ser Arg Leu Arg Leu Ser Val Leu Ser Leu Leu Thr Ser Val Val
1               5                   10                  15

Leu Ser Leu Phe Ala Met Gln Ala Ala Tyr Ala Ser Pro Thr Ser Asp
                20                  25                  30

Ala Asp Ala Cys Val Gln Gln Leu Val Phe Asn Pro Lys Ser Gly
            35                  40                  45

Gly Phe Leu Pro Ile Asn Asn Phe Asn Ala Thr Gly Gln Ser Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Pro Ala Leu Ala Gly Glu Pro Asp Met Asn
                85                  90                  95

Ser Thr Leu Ala Gln Phe Gly Val Pro Thr Ala Ser Gly Gln Pro Met
                100                 105                 110

Ser Val Ala Pro Val Trp Ala Ser Tyr Lys Asp Ala Asn Asp Ile Phe
            115                 120                 125

Leu Pro Gly Ala Pro Ala Pro Thr Gly Trp Gly Val Gln Thr Leu Val
    130                 135                 140

Pro Ser Asn Cys Ser Thr Gln Gly Ser Leu Arg Ala Ile Ser Val Gly
145                 150                 155                 160

Ala Arg Lys Phe Met Thr Ala Thr Ser Glu Ser Ala Ile Asn Ala Arg
                165                 170                 175

His Gly Phe His Leu Ser Ser Gly Thr Leu Ala Ser Ile Pro Asp Pro
                180                 185                 190

Ile Met Glu Ala Ser Gly Gly Trp Leu Thr Asp Gln Ser Gln Asn Leu
            195                 200                 205

Val Phe Phe Glu Arg Lys Val Gly Lys Ala Glu Phe Asp Tyr Ile Val
    210                 215                 220

Ser Lys Gly Leu Tyr Asp Ala Ala Asn Gln Leu Thr Val Ala Gln Asn
225                 230                 235                 240

Leu Asp Asn Gln Asn Pro Gly Gly Leu Ser Leu Pro Ile Gly Glu Pro
                245                 250                 255

Met Arg Ser Leu Pro Pro Asn Pro Val Pro Gln Glu Gln Leu Gly Ala
                260                 265                 270

Leu Glu Val Lys Ala Ala Trp Arg Ile Leu Thr Gly Lys Pro Glu Leu
            275                 280                 285

Tyr Gly Arg Tyr Leu Thr Thr Val Ala Trp Leu Lys Asn Pro Ala Thr
    290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asn Gln Val Pro Pro Gln Gln Thr Pro
                340                 345                 350

Pro Asp Ser Phe Ala Phe Asn Asn Pro Asn Cys Gly Thr Gly Pro Glu
            355                 360                 365

Cys Thr Pro Asn Val Ala Arg Ile Gln Cys Lys Gln His His Pro Asp
    370                 375                 380

Arg Asp Cys Thr Glu Pro Phe Pro Arg Asp Gln Pro Val Gln Thr Thr
```

```
                385                 390                 395                 400
Arg Glu His Pro Leu Pro Thr Glu Leu Gln Ala Leu Asn Gly Ala Val
                    405                 410                 415

Gln Ala Asn Phe Ala Gln Gln Ser Gln Gly Lys Ser Val Phe Gln Tyr
                420                 425                 430

Tyr Lys Leu Ile Asn Val Leu Trp Thr Leu Thr Pro Asn Pro Pro Thr
            435                 440                 445

Gln Pro Glu Pro Gly Val Ser Ala Gln Val Pro Leu Ser Tyr Gly Pro
450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile
                485                 490                 495

Ala Gly Ser Ser Thr Leu Ala Ser Asp Phe Ser Phe Leu Phe Asn Ser
                500                 505                 510

Ala Asp Ser Ala Ser Lys Asn Ser Leu Val Lys Arg Val Lys Ala Phe
            515                 520                 525

Gln Thr Leu Lys Asp Gln Pro
530                 535

<210> SEQ ID NO 3
<211> LENGTH: 578
<212> TYPE: PRT
<213> ORGANISM: Pseudomonas sp. Ag1

<400> SEQUENCE: 3

Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
                20                  25                  30

Thr Asp Trp Asn Asn Asp Leu Thr Gly Trp Thr Gln Ser Ala Ile Ile
            35                  40                  45

Gly Asn Pro Trp Ser Gly Leu Asn Asp Ala Pro Arg Ser Gly Tyr Tyr
50                  55                  60

Asn Pro Leu Val Glu Gly Tyr Gly Pro Thr Thr Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Ser Met Gln Gln
                100                 105                 110

Val Met Glu Leu Thr Asp Asn Gly Gln Ile Thr Ile Asn Asn Thr Leu
            115                 120                 125

Tyr Met Leu Tyr Asp Pro Asn Lys Gln Gly Thr Leu Leu Gln Leu Pro
130                 135                 140

Val Thr Arg Cys Pro Ser Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asp Gly Asn Met Arg Lys Ile Thr Phe Thr Cys
                180                 185                 190

Glu Asn Pro Ala Tyr Phe Leu Ala Met Trp Arg Ile Asp Pro Thr Ala
            195                 200                 205

Val Leu Gly Leu Tyr Arg Asp Tyr Ile Asp Pro Gln Val Gln Leu Glu
210                 215                 220
```

```
Asp Leu Tyr Leu Arg Tyr Thr Ala Asp Cys Pro Thr Gly Lys Ala Gly
225                 230                 235                 240

Asp Pro Val Ile Asp Pro Thr Thr Gly Gln Pro Ala Tyr Asp Thr Val
            245                 250                 255

Asn Lys Trp Asn Ala Gly Thr Ala Cys Val Pro Gly Gln Tyr Gly Gly
        260                 265                 270

Ala Met His Leu Thr Ser Gly Pro Asn Thr Leu Ser Ala Glu Val Tyr
    275                 280                 285

Leu Ala Ala Ala Thr Ile Leu Arg Pro Leu Ser Ser Gln Asn
290                 295                 300

Ser Gln Ala Leu Ile Cys Cys Ala Gln Tyr Gly Gln Asn Tyr Arg Asn
305                 310                 315                 320

Ser Asp Pro His Ile Gly Phe Ser Ala Asn Ser Val Ala Val Asn Asn
            325                 330                 335

Arg Leu Ser Leu Thr Asn Pro Ile Gly Leu Tyr Leu Gln Gln Pro Thr
        340                 345                 350

Asp Phe Ser Ala Trp Lys Gly Pro Gln Gly Gln Asp Val Ser Gln Tyr
    355                 360                 365

Trp Lys Ile Thr Arg Gly Thr Ala Lys Ser Ala Asn Gly Ser Asp
370                 375                 380

Gln Ile Leu Gln Ala Val Phe Glu Val Pro Val Ser Ala Gly Phe Ser
385                 390                 395                 400

Ile Asn Glu Ile Thr Ile Ser Gly Gln Pro Ile Asp Tyr Val Trp Val
            405                 410                 415

Ile Ala Gln Gln Leu Leu Val Gly Leu Ser Val Thr Thr Thr Pro Ile
        420                 425                 430

Ser Pro Thr Pro Asp Ser Cys Pro Cys Val Thr Asp Arg Val Asn Gly
    435                 440                 445

Val Gln Pro Trp Pro Val Gln Leu Leu Pro Leu Asp Leu Phe Tyr Gly
450                 455                 460

Gln Ser Pro Thr Asp Leu Pro Ala Trp Leu Ala Pro Gly Thr Ser Gly
465                 470                 475                 480

Gln Phe Ala Leu Val Val Gln Gly Ala Asp Leu Lys Thr Thr Ala Glu
            485                 490                 495

Thr Ala Arg Val Gln Phe Ser Asn Pro Gly Val Thr Ala Gln Val Thr
        500                 505                 510

Lys Phe Leu Pro Asp Ala Ser Ala Ile Pro Gly Gln Thr Asn Ser Gly
    515                 520                 525

Gly Thr Gln Gly Tyr Leu Leu Thr Ile Thr Val Ser Pro Thr Ala Ala
530                 535                 540

Pro Gly Leu Val Thr Val Arg Ala Leu Asn Pro Gly Glu Ala Asp Asn
545                 550                 555                 560

Pro Ser Ala Ala Glu His Pro Trp Glu Ser Gly Leu Ala Leu Val Pro
            565                 570                 575

Gly Ala

<210> SEQ ID NO 4
<211> LENGTH: 536
<212> TYPE: PRT
<213> ORGANISM: Pseudomonas sp. Ag1

<400> SEQUENCE: 4

Met Ser Arg Leu Arg Leu Ser Val Leu Ser Leu Leu Thr Ser Val Val
1               5                   10                  15
```

-continued

Leu Ser Leu Phe Ala Met Gln Ala Ala Tyr Ala Ser Pro Thr Ser Asp
            20                  25                  30

Ala Asp Ala Cys Val Gln Gln Leu Val Phe Asn Pro Lys Ser Gly
        35                  40                  45

Gly Phe Leu Pro Ile Asn Asn Phe Asn Ala Thr Gly Gln Ser Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Pro Ala Leu Ala Gly Glu Pro Asp Met Asn
                85                  90                  95

Ser Thr Leu Ala Gln Phe Gly Val Pro Thr Ala Ser Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Ala Pro Thr Gly Trp Gly Val Gln Thr Leu Val
    130                 135                 140

Pro Ser Asn Cys Ser Thr Gln Gly Ser Leu Arg Ala Met Ser Val Gly
145                 150                 155                 160

Ala Arg Lys Phe Met Thr Ala Thr Ser Glu Ser Ala Ile Asn Ala Arg
                165                 170                 175

His Gly Phe His Leu Ser Ser Gly Thr Leu Ala Ser Ile Pro Asp Pro
            180                 185                 190

Ile Met Glu Ala Ser Gly Gly Trp Leu Thr Asp Gln Ser Gln Asn Leu
        195                 200                 205

Val Phe Phe Glu Arg Lys Val Gly Lys Ala Glu Phe Asp Tyr Ile Val
    210                 215                 220

Ser Lys Gly Leu Tyr Asp Ala Ala Asn Gln Leu Lys Val Ala Gln Asn
225                 230                 235                 240

Leu Asp Asn Gln Asn Pro Gly Gly Leu Ser Leu Pro Ile Gly Glu Pro
                245                 250                 255

Met Arg Ser Leu Pro Pro Asn Pro Val Pro Gln Glu Gln Leu Gly Ala
            260                 265                 270

Leu Glu Val Lys Ala Ala Trp Arg Ile Leu Thr Gly Lys Pro Glu Leu
        275                 280                 285

Tyr Gly Arg Tyr Leu Thr Thr Val Ala Trp Leu Lys Asn Pro Ala Thr
    290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asp Gln Val Pro Pro Gln Gln Thr Pro
            340                 345                 350

Pro Asp Ser Phe Ala Phe Asn Asn Pro Asn Cys Gly Thr Gly Pro Glu
        355                 360                 365

Cys Thr Pro Asn Val Ala Arg Ile Gln Cys Lys Gln Gln His Pro Asp
    370                 375                 380

Arg Asp Cys Thr Glu Pro Phe Pro Arg Asp Gln Pro Val Gln Thr Thr
385                 390                 395                 400

Arg Glu His Pro Leu Pro Thr Glu Leu Gln Ala Leu Asn Gly Ala Val
                405                 410                 415

Gln Ala Asn Phe Ala Gln Gln Ser Gln Gly Lys Ser Val Phe Gln Tyr
            420                 425                 430

Tyr Lys Leu Ile Asn Val Leu Trp Thr Leu Thr Pro Asn Pro Pro Thr

```
            435                 440                 445
Gln Pro Glu Pro Gly Val Ser Ala Gln Val Pro Leu Ser Tyr Gly Pro
    450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile
                485                 490                 495

Ala Gly Ser Ser Thr Leu Ala Ser Asp Phe Ser Phe Leu Phe Asn Ser
                500                 505                 510

Ala Asp Ser Ala Ser Lys Lys Ser Leu Val Lys Arg Val Lys Ala Phe
            515                 520                 525

Gln Thr Leu Lys Asp Gly Ser Pro
    530                 535

<210> SEQ ID NO 5
<211> LENGTH: 579
<212> TYPE: PRT
<213> ORGANISM: Pseudomonas sp. PAMC 25886

<400> SEQUENCE: 5

Met Ser Thr Pro Phe Asn Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
            20                  25                  30

Thr Asp Trp Asn Asn Asp Leu Thr Gly Trp Thr Gln Ser Ala Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Tyr Gly Pro Thr Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Thr Leu Gln Gln
            100                 105                 110

Val Met Glu Leu Thr Asp Asn Gly Gln Ile Thr Leu Asn Asn Thr Leu
        115                 120                 125

Tyr Thr Leu Tyr Asp Pro Asn Lys Gln Gly Thr Leu Leu Gln Leu Pro
    130                 135                 140

Val Thr Arg Cys Pro Ser Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Pro Gly Thr Gln Asn Met Arg Lys Ile Thr Phe Thr
            180                 185                 190

Cys Glu Asn Pro Ala Tyr Phe Leu Ala Met Trp Arg Ile Asp Pro Asn
        195                 200                 205

Ala Val Leu Gly Leu Tyr Arg Asp Tyr Ile Asp Pro Gln Val Gln Leu
    210                 215                 220

Glu Asp Leu Tyr Leu Arg Tyr Thr Ala Asp Cys Pro Thr Gly Asn Lys
225                 230                 235                 240

Gly Asp Pro Val Met Asp Pro Thr Thr Gly Gln Pro Ala Tyr Asp Thr
                245                 250                 255

Val Asn Lys Trp Asn Ala Gly Thr Ala Cys Val Pro Gly Gln Tyr Gly
            260                 265                 270
```

Gly Ala Met His Leu Thr Ser Gly Pro Asn Thr Leu Ser Ala Glu Val
            275                 280                 285

Tyr Leu Ala Ala Ala Thr Ile Leu Arg Pro Leu Ala Ser Ser Gln
290                 295                 300

Asn Ser Gln Ala Leu Ile Cys Cys Ala Gln Tyr Gly Gln Asn Tyr Arg
305                 310                 315                 320

Asn Ser Asp Pro His Ile Gly Phe Ser Ala Asn Ser Val Ala Val Asn
                325                 330                 335

Asn Arg Leu Ser Leu Thr Asn Pro Ile Gly Leu Tyr Leu Gln Gln Pro
                340                 345                 350

Thr Asp Phe Ser Ala Trp Lys Gly Pro Gln Gly Gln Asp Val Ser Gln
            355                 360                 365

Tyr Trp Lys Ile Thr Arg Gly Thr Ala Lys Ser Ala Ala Asn Gly Ser
370                 375                 380

Asp Gln Ile Leu Gln Ala Val Phe Glu Val Pro Val Ser Ala Gly Phe
385                 390                 395                 400

Ser Ile Asn Asp Ile Thr Ile Ser Gly Gln Ser Ile Asp Tyr Val Trp
                405                 410                 415

Val Ile Ala Gln Gln Leu Leu Val Gly Leu Ser Val Thr Thr Thr Pro
            420                 425                 430

Ile Ser Pro Thr Pro Glu Ser Cys Pro Cys Val Thr Asp Arg Val Thr
            435                 440                 445

Gly Val Gln Pro Trp Pro Val Gln Leu Leu Pro Leu Asp Leu Phe Tyr
450                 455                 460

Gly Gln Ser Pro Thr Asp Leu Pro Ala Trp Leu Ala Pro Gly Thr Ser
465                 470                 475                 480

Gly Gln Phe Ala Leu Val Val Gln Gly Ala Asp Leu Lys Thr Thr Ala
                485                 490                 495

Glu Thr Ala Arg Val Gln Phe Ser Asn Pro Gly Val Thr Ala Val Val
            500                 505                 510

Thr Lys Phe Leu Pro Asp Ala Ser Ala Ile Pro Gly Gln Thr Asn Ser
            515                 520                 525

Gly Gly Thr Gln Gly Tyr Leu Leu Thr Ile Thr Val Ser Pro Thr Ala
530                 535                 540

Ala Pro Gly Leu Val Thr Val Arg Ala Leu Asn Pro Gly Glu Ala Asp
545                 550                 555                 560

Asn Pro Ser Ala Ala Gln His Pro Trp Glu Ser Gly Leu Ala Leu Val
                565                 570                 575

Pro Gly Ala

<210> SEQ ID NO 6
<211> LENGTH: 535
<212> TYPE: PRT
<213> ORGANISM: Pseudomonas sp. PAMC 25886

<400> SEQUENCE: 6

Met Ser Arg Leu Arg Leu Ser Val Leu Ser Leu Leu Thr Ser Val Val
1               5                   10                  15

Leu Ser Leu Phe Ala Val Gln Ser Ala Tyr Ala Thr Pro Gln Ser Asp
            20                  25                  30

Ala Asp Ala Cys Val Gln Gln Gln Leu Val Phe Asn Pro Ala Ser Gly
        35                  40                  45

Gly Phe Leu Pro Val Asn Phe Asn Ala Thr Gly Gln Ser Phe Met
    50                  55                  60

-continued

Asn Cys Phe Gly Trp Gln Leu Phe Ile Ala Leu Asn Trp Pro Val Asn
 65                  70                  75                  80

Pro Gly Trp Pro Ala Thr Pro Ala Leu Ala Gly Glu Pro Asp Met His
                 85                  90                  95

Ser Ser Leu Ala Gln Phe Gly Val Pro Pro Ala Ser Gly Gln Pro Met
                100                 105                 110

Thr Val Ala Pro Val Trp Ala Ser Tyr Lys Asp Ala Asn Asp Ile Phe
                115                 120                 125

Leu Pro Gly Ala Pro Val Pro Thr Gly Trp Gly Val Gln Thr Leu Val
        130                 135                 140

Pro Ser Asn Cys Ser Thr Gln Gly Ser Leu Lys Ala Met Ala Val Gly
145                 150                 155                 160

Ala Arg Lys Phe Met Thr Ala Thr Ser Glu Ser Ala Ile Asn Ala Arg
                165                 170                 175

His Gly Phe His Leu Ser Ser Gly Thr Leu Ala Ser Ile Pro Asp Pro
                180                 185                 190

Ile Met Glu Ala Ser Gly Gly Trp Leu Thr Asp Gln Ser Lys Asn Leu
                195                 200                 205

Val Phe Phe Glu Arg Lys Val Gly Lys Ala Glu Phe Asp Tyr Ile Val
        210                 215                 220

Ser Lys Gly Leu Tyr Asp Ala Ala Asn Gln Leu Thr Val Ala Gln Asn
225                 230                 235                 240

Leu Asp Asn Gln Asn Pro Gly Gly Leu Ser Leu Pro Ile Gly Glu Pro
                245                 250                 255

Met Arg Ser Leu Pro Pro Asp Pro Val Pro Gln Glu Gln Leu Gly Ala
                260                 265                 270

Leu Glu Val Lys Ala Ala Trp Arg Ile Leu Thr Gly Lys Pro Glu Leu
        275                 280                 285

Tyr Gly Arg Tyr Leu Thr Thr Val Ala Trp Leu Lys Asn Pro Ala Thr
        290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asp Gln Val Pro Pro Gln Gln Thr Pro
                340                 345                 350

Pro Asp Ser Phe Ala Phe Asn Asn Pro Asn Cys Gly Thr Gly Pro Glu
                355                 360                 365

Cys Thr Pro Asn Val Ala Arg Ile Gln Cys Lys Gln His His Pro Asp
        370                 375                 380

Arg Asp Cys Thr Glu Pro Tyr Pro Arg Asp Gln Pro Val Gln Thr Thr
385                 390                 395                 400

Arg Glu His Pro Leu Pro Thr Glu Leu Gln Ala Leu Asn Gly Ala Val
                405                 410                 415

Gln Ala Asn Phe Ala Gln Gln Ser Gln Gly Lys Ser Val Phe Gln Tyr
                420                 425                 430

Tyr Lys Leu Ile Asn Val Leu Trp Thr Leu Thr Pro Asn Pro Pro Thr
        435                 440                 445

Gln Pro Glu Pro Gly Val Ser Ala Gln Val Pro Leu Ser Tyr Gly Pro
        450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile

-continued

```
                    485                 490                 495
Ala Gly Ser Ser Thr Leu Ala Ser Asp Phe Ser Phe Leu Phe Asn Ser
                500                 505                 510

Ala Asp Ser Ala Ser Lys Lys Ser Leu Val Lys Arg Val Lys Ala Phe
                515                 520                 525

Glu Thr Leu Lys Asp Gln Pro
            530                 535

<210> SEQ ID NO 7
<211> LENGTH: 579
<212> TYPE: PRT
<213> ORGANISM: Pseudomonas sp. PAMC 25886

<400> SEQUENCE: 7

Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
                20                  25                  30

Thr Asp Trp Asn Asn Asp Leu Thr Gly Trp Thr Gln Ser Ala Ile Ile
            35                  40                  45

Gly Asn Pro Trp Ser Gly Leu Asn Asp Ala Pro Arg Ser Gly Tyr Tyr
        50                  55                  60

Asn Pro Leu Val Glu Gly Tyr Gly Pro Thr Thr Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Thr Leu Gln Gln
                100                 105                 110

Val Met Glu Leu Thr Asp Asn Gly Gln Ile Thr Leu Asn Asn Thr Leu
            115                 120                 125

Tyr Thr Leu Tyr Asp Pro Asn Lys Gln Gly Thr Leu Leu Gln Leu Pro
        130                 135                 140

Val Thr Arg Cys Pro Ser Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Pro Gly Thr Gln Asn Met Arg Lys Ile Thr Phe Thr
                180                 185                 190

Cys Glu Asn Pro Ala Tyr Phe Leu Ala Met Trp Arg Ile Asp Pro Asn
            195                 200                 205

Ala Val Leu Gly Leu Tyr Arg Asp Tyr Ile Asp Pro Gln Val Gln Leu
        210                 215                 220

Glu Asp Leu Tyr Leu Arg Tyr Thr Ala Asp Cys Pro Thr Gly Asn Lys
225                 230                 235                 240

Gly Asp Pro Val Met Asp Pro Thr Thr Gly Gln Pro Ala Tyr Asp Thr
                245                 250                 255

Val Asn Lys Trp Asn Ala Gly Thr Ala Cys Val Pro Gly Gln Tyr Gly
                260                 265                 270

Gly Ala Met His Leu Thr Ser Gly Pro Asn Thr Leu Ser Ala Glu Val
            275                 280                 285

Tyr Leu Ala Ala Ala Ala Thr Ile Leu Arg Pro Leu Ser Ser Ser Gln
        290                 295                 300

Asn Ser Gln Ala Leu Ile Cys Cys Ala Gln Tyr Gly Gln Asn Tyr Arg
305                 310                 315                 320
```

Asn Ser Asp Pro His Ile Gly Phe Ser Ala Asn Ser Val Ala Val Asn
            325                 330                 335

Asn Arg Leu Ser Leu Thr Asn Pro Ile Gly Leu Tyr Leu Gln Gln Pro
        340                 345                 350

Thr Asp Phe Ser Ala Trp Lys Gly Pro Gln Gly Gln Asp Val Ser Gln
            355                 360                 365

Tyr Trp Lys Ile Thr Arg Gly Ala Ala Lys Ser Ala Ala Asn Gly Ser
    370                 375                 380

Asp Gln Ile Leu Gln Ala Val Phe Glu Val Pro Val Ser Ala Gly Phe
385                 390                 395                 400

Ser Ile Asn Asp Ile Thr Ile Ser Gly Gln Ser Ile Asp Tyr Val Trp
                405                 410                 415

Val Ile Ala Gln Gln Leu Leu Val Gly Leu Ser Val Thr Thr Thr Pro
            420                 425                 430

Ile Ser Pro Thr Pro Asp Ser Cys Pro Cys Val Thr Asp Arg Val Asn
        435                 440                 445

Gly Val Gln Pro Trp Pro Val Gln Leu Leu Pro Leu Asp Leu Phe Tyr
    450                 455                 460

Gly Gln Ser Pro Thr Asp Leu Pro Ala Trp Leu Ala Pro Gly Thr Ser
465                 470                 475                 480

Gly Gln Phe Ala Leu Val Val Gln Gly Ala Asp Leu Lys Thr Thr Ala
                485                 490                 495

Glu Thr Ala Arg Val Gln Phe Ser Asn Pro Gly Val Thr Ala Val Val
            500                 505                 510

Thr Lys Phe Leu Pro Asp Ala Ser Ala Ile Pro Gly Gln Thr Asn Ser
        515                 520                 525

Gly Gly Thr Gln Gly Tyr Leu Leu Thr Ile Thr Val Ser Pro Thr Ala
    530                 535                 540

Ala Pro Gly Leu Val Thr Val Arg Ala Leu Asn Pro Gly Glu Ala Asp
545                 550                 555                 560

Asn Pro Ser Ala Ala Glu His Pro Trp Glu Ser Gly Leu Ala Leu Val
                565                 570                 575

Pro Gly Ala

<210> SEQ ID NO 8
<211> LENGTH: 535
<212> TYPE: PRT
<213> ORGANISM: Pseudomonas sp. PAMC 25886

<400> SEQUENCE: 8

Met Ser Arg Leu Arg Leu Ser Val Leu Ser Leu Leu Ala Ser Val Val
1               5                   10                  15

Leu Ser Leu Phe Ala Leu Gln Ser Ala Tyr Ala Thr Pro Gln Ser Asp
            20                  25                  30

Ala Asp Ala Cys Val Gln Gln Leu Val Phe Asn Pro Lys Ser Gly
        35                  40                  45

Gly Phe Leu Pro Val Asn Asn Phe Asn Ala Thr Gly Gln Ser Phe Met
    50                  55                  60

Asn Cys Phe Gly Trp Gln Leu Phe Ile Ala Leu Asn Trp Pro Val Asn
65                  70                  75                  80

Pro Gly Trp Pro Thr Thr Ala Ala Leu Ala Gly Glu Pro Asp Met Asn
                85                  90                  95

Ser Ser Leu Ala Gln Phe Gly Val Pro Thr Thr Ala Gly Gln Pro Met
            100                 105                 110

```
Thr Val Ala Pro Val Trp Ala Ser Tyr Lys Asp Ala Asn Asp Ile Phe
            115                 120                 125
Leu Pro Gly Ala Pro Val Pro Ser Gly Trp Gly Val Gln Thr Leu Val
        130                 135                 140
Pro Ser Asn Cys Ser Thr Gln Gly Ser Leu Lys Ala Met Ser Val Gly
145                 150                 155                 160
Ala Arg Lys Phe Met Thr Ala Thr Ser Glu Ser Ala Ile Asn Ala Arg
                165                 170                 175
His Gly Phe His Leu Ser Ser Gly Thr Leu Ala Thr Ile Pro Asp Pro
            180                 185                 190
Ile Met Glu Ala Ser Gly Gly Trp Leu Thr Asp Gln Ala Gly Gln Leu
        195                 200                 205
Val Phe Phe Glu Arg Lys Val Gly Lys Ala Glu Phe Asp Tyr Ile Val
        210                 215                 220
Ser Lys Gly Leu Tyr Asp Ala Ala Asn Gln Leu Lys Val Ala Gln Asn
225                 230                 235                 240
Leu Asp Asn Gln Asn Pro Gly Gly Leu Ser Leu Pro Ile Gly Glu Pro
                245                 250                 255
Met Arg Ser Leu Pro Pro Thr Pro Val Pro Gln Glu Gln Leu Gly Ala
            260                 265                 270
Leu Glu Leu Lys Ala Ala Trp Arg Ile Leu Thr Gly Lys Pro Glu Leu
        275                 280                 285
Tyr Gly Arg Tyr Leu Thr Thr Val Ala Trp Leu Lys Asn Pro Ala Thr
        290                 295                 300
Leu Gln Cys Thr Gln Gln Val Val Gly Leu Val Gly Leu His Ile Ile
305                 310                 315                 320
Asn Lys Thr Gln Ala Ser Pro Asn Phe Ile Trp Thr Thr Phe Glu Gln
                325                 330                 335
Val Asp Asn Val Pro Glu Pro Asn Gln Leu Pro Pro Gln Gln Thr Pro
            340                 345                 350
Pro Asp Ser Phe Ala Phe Asn Asn Pro Asn Cys Gly Thr Gly Pro Glu
        355                 360                 365
Cys Thr Pro Asn Val Ala Arg Ile Gln Cys Gln Gln His His Pro Asp
        370                 375                 380
Arg Asp Cys Thr Glu Pro Tyr Pro Arg Asp Gln Pro Val Gln Thr Thr
385                 390                 395                 400
Arg Glu His Pro Leu Pro Thr Glu Leu Gln Ala Leu Asn Gly Ala Val
                405                 410                 415
Gln Ala Asn Phe Ala Gln Gln Ser Gln Gly Lys Ser Val Phe Gln Tyr
            420                 425                 430
Tyr Lys Leu Ile Asn Val Leu Trp Thr Leu Thr Pro Asn Pro Pro Val
        435                 440                 445
Gln Pro Glu Pro Gly Val Ser Ala Val Pro Leu Ser Tyr Gly Pro
        450                 455                 460
Phe Ile Ser Gln Gly Asn Val Pro Val Ala Asn Thr Thr Leu Glu Thr
465                 470                 475                 480
Tyr Val Gln Gly Asp Asn Cys Asn Ala Cys His Gln Tyr Ala Thr Ile
                485                 490                 495
Ala Gly Ser Ser Thr Leu Ala Ser Asp Phe Ser Phe Leu Phe Asn Ser
            500                 505                 510
Ala Asp Ser Ala Ser Lys Lys Ser Leu Val Lys Arg Val Lys Ala Phe
        515                 520                 525
Glu Thr Leu Lys Asp Gln Pro
```

```
       530                 535

<210> SEQ ID NO 9
<211> LENGTH: 578
<212> TYPE: PRT
<213> ORGANISM: Pseudomonas fluorescens

<400> SEQUENCE: 9

Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
            20                  25                  30

Thr Asp Trp Asn Asn Asp Leu Thr Gly Trp Thr Gln Ser Ala Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Tyr Gly Pro Thr Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Ser Met Gln Gln
            100                 105                 110

Val Met Glu Leu Thr Asp Asn Gly Gln Ile Thr Ile Asn Asn Thr Leu
        115                 120                 125

Tyr Met Leu Tyr Asp Pro Lys Lys Gln Gly Thr Leu Leu Gln Leu Pro
    130                 135                 140

Val Thr Arg Cys Pro Ser Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asp Gly Asn Met Arg Lys Ile Thr Phe Thr Cys
            180                 185                 190

Glu Asn Pro Ala Tyr Phe Leu Ala Met Trp Arg Ile Asp Pro Thr Ala
        195                 200                 205

Val Leu Gly Leu Tyr Arg Asp Tyr Ile Asp Pro Gln Val Gln Leu Glu
    210                 215                 220

Asp Leu Tyr Leu Arg Tyr Thr Ala Asp Cys Pro Thr Gly Lys Ala Gly
225                 230                 235                 240

Asp Pro Val Ile Asp Pro Thr Gly Gln Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Ala Thr Ile Leu Arg Pro Leu Ser Ser Ser Gln Asn
    290                 295                 300

Ser Gln Ala Leu Ile Cys Cys Ala Gln Tyr Gly Asn Tyr Arg Asn
305                 310                 315                 320

Ser Asp Pro His Ile Gly Phe Ser Ala Asn Ser Val Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
        355                 360                 365
```

```
Trp Lys Ile Thr Arg Gly Thr Ala Lys Ser Ala Ala Asn Gly Ser Asp
    370                 375                 380

Gln Ile Leu Gln Ala Val Phe Glu Val Pro Val Ser Ala Gly Phe Ser
385                 390                 395                 400

Ile Asn Asp Ile Thr Ile Ser Gly Gln Pro Ile Asp Tyr Val Trp Val
                405                 410                 415

Ile Ala Gln Gln Leu Leu Val Gly Leu Ser Val Thr Thr Thr Pro Ile
            420                 425                 430

Ser Pro Thr Pro Asp Ser Cys Pro Cys Val Thr Asp Arg Val Asn Gly
        435                 440                 445

Val Gln Pro Trp Pro Val Gln Leu Leu Pro Leu Asp Leu Phe Tyr Gly
    450                 455                 460

Gln Ser Pro Thr Asp Leu Pro Ala Trp Leu Ala Pro Gly Thr Ser Gly
465                 470                 475                 480

Gln Phe Ala Leu Val Val Gln Gly Ala Asp Leu Lys Thr Thr Ala Glu
                485                 490                 495

Thr Ala Arg Val Gln Phe Ser Asn Pro Gly Val Thr Ala Gln Val Thr
            500                 505                 510

Lys Phe Leu Pro Asp Ala Ser Ala Ile Pro Gly Gln Thr Asn Ser Gly
        515                 520                 525

Gly Thr Gln Gly Tyr Leu Leu Thr Ile Thr Val Ser Pro Thr Ala Ala
    530                 535                 540

Pro Gly Leu Val Thr Val Arg Ala Leu Asn Pro Gly Glu Ala Asp Asn
545                 550                 555                 560

Pro Ser Ala Ala Glu His Pro Trp Glu Ser Gly Leu Ala Leu Val Pro
                565                 570                 575

Gly Ala

<210> SEQ ID NO 10
<211> LENGTH: 536
<212> TYPE: PRT
<213> ORGANISM: Pseudomonas fluorescens

<400> SEQUENCE: 10

Met Ser Arg Leu Arg Leu Ser Val Leu Ser Leu Leu Thr Ser Val Val
1               5                   10                  15

Leu Ser Leu Phe Ala Met Gln Ala Ala Tyr Ala Ser Pro Thr Ser Asp
            20                  25                  30

Ala Asp Ala Cys Val Gln Gln Gln Leu Val Phe Asn Pro Lys Ser Gly
        35                  40                  45

Gly Phe Leu Pro Ile Asn Asn Phe Asn Ala Thr Gly Gln Ser Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Pro Ala Leu Ala Gly Glu Pro Asp Met Asn
                85                  90                  95

Ser Thr Leu Ala Gln Phe Gly Val Pro Thr Ala Ser Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Val Pro Thr Gly Trp Gly Val Gln Thr Leu Val
    130                 135                 140

Pro Ser Asn Cys Ser Thr Gln Gly Ser Leu Arg Ala Met Ser Val Gly
145                 150                 155                 160
```

Ala Arg Lys Phe Met Thr Ala Thr Ser Glu Ser Ala Ile Asn Ala Arg
            165                 170                 175

His Gly Phe His Leu Ser Ser Gly Thr Leu Ala Ser Ile Pro Asp Pro
        180                 185                 190

Ile Met Glu Ala Ser Gly Gly Trp Leu Thr Asp Gln Ser Gln Asn Leu
        195                 200                 205

Val Phe Phe Glu Arg Lys Val Gly Lys Ala Glu Phe Asp Tyr Ile Val
        210                 215                 220

Ser Lys Gly Leu Tyr Asp Ala Ala Asn Gln Leu Lys Val Ala Gln Asn
225                 230                 235                 240

Leu Asp Asn Gln Asn Pro Gly Leu Ser Leu Pro Ile Gly Glu Pro
                245                 250                 255

Met Arg Ser Leu Pro Pro Asn Pro Val Pro Gln Glu Gln Leu Gly Ala
        260                 265                 270

Leu Glu Val Lys Ala Ala Trp Arg Ile Leu Thr Gly Lys Pro Glu Leu
        275                 280                 285

Tyr Gly Arg Tyr Leu Thr Thr Val Ala Trp Leu Lys Asn Pro Ala Thr
        290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asn Gln Val Pro Gln Gln Thr Pro
                340                 345                 350

Pro Asp Ser Phe Ala Phe Asn Asn Pro Asn Cys Gly Thr Gly Pro Glu
        355                 360                 365

Cys Thr Pro Asn Val Ala Arg Ile Gln Cys Lys Gln Gln His Pro Asp
        370                 375                 380

Arg Asp Cys Thr Glu Pro Phe Pro Arg Asp Gln Pro Val Gln Thr Thr
385                 390                 395                 400

Arg Glu His Pro Leu Pro Thr Glu Leu Gln Ala Leu Asn Gly Ala Val
                405                 410                 415

Gln Ala Asn Phe Ala Gln Gln Ser Gln Gly Lys Ser Val Phe Gln Tyr
        420                 425                 430

Tyr Lys Leu Ile Asn Val Leu Trp Thr Leu Thr Pro Asn Pro Pro Thr
        435                 440                 445

Gln Pro Glu Pro Gly Val Ser Ala Gln Val Pro Leu Ser Tyr Gly Pro
        450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile
                485                 490                 495

Ala Gly Ser Ser Thr Leu Ala Ser Asp Phe Ser Phe Leu Phe Asn Ser
        500                 505                 510

Ala Asp Ser Ala Ser Lys Lys Ser Leu Val Lys Arg Val Lys Ala Phe
        515                 520                 525

Gln Thr Leu Lys Asp Gly Ser Pro
        530                 535

<210> SEQ ID NO 11
<211> LENGTH: 578
<212> TYPE: PRT
<213> ORGANISM: Pseudomonas sp. PAMC 26793

<400> SEQUENCE: 11

```
Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
                20                  25                  30

Thr Asp Trp Asn Asp Leu Thr Gly Trp Thr Gln Ser Ala Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Tyr Gly Pro Ser Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Ser Met Gln Gln
                100                 105                 110

Val Met Glu Leu Thr Asp Asn Gly Gln Ile Thr Ile Asn Asn Thr Leu
            115                 120                 125

Tyr Met Leu Tyr Asp Pro Asn Lys Gln Gly Thr Leu Leu Gln Leu Pro
    130                 135                 140

Val Thr Arg Cys Pro Thr Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asn Met Arg Lys Ile Thr Phe Thr Cys
            180                 185                 190

Glu Asn Pro Ala Tyr Phe Leu Ala Met Trp Arg Ile Asp Pro Asn Ala
            195                 200                 205

Val Leu Gly Leu Tyr Arg Asp Tyr Ile Asp Pro Gln Val Gln Leu Glu
    210                 215                 220

Asp Leu Tyr Leu Arg Tyr Thr Ala Asp Cys Pro Thr Gly Lys Ala Gly
225                 230                 235                 240

Asp Pro Val Ile Asp Pro Thr Thr Gly Gln Pro Ala Tyr Asp Thr Val
                245                 250                 255

Asn Lys Trp Asn Ala Gly Thr Ala Cys Val Pro Gly Tyr Gly Gly
            260                 265                 270

Ala Met His Leu Thr Ser Gly Pro Asn Thr Leu Ser Ala Glu Val Tyr
        275                 280                 285

Leu Ala Ala Ala Ala Thr Ile Leu Arg Pro Leu Ala Ser Ser Gln Asn
    290                 295                 300

Ser Gln Ala Leu Ile Cys Cys Ala Gln Tyr Gly Gln Asn Tyr Arg Asn
305                 310                 315                 320

Ser Asp Pro His Ile Gly Phe Ser Ala Asn Ser Val Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
        355                 360                 365

Trp Lys Ile Thr Arg Gly Thr Ala Lys Ser Ala Ala Asn Gly Ser Asp
    370                 375                 380

Gln Ile Leu Gln Ala Val Phe Glu Val Pro Val Ser Ala Gly Phe Ser
385                 390                 395                 400

Ile Asn Asp Ile Thr Ile Ser Gly Gln Pro Ile Asn Tyr Val Trp Val
                405                 410                 415
```

```
Ile Ala Gln Gln Leu Leu Val Gly Leu Ser Val Thr Thr Thr Pro Ile
                420                 425                 430
Ser Pro Thr Pro Asp Ser Cys Pro Cys Val Thr Asp Arg Val Asn Gly
            435                 440                 445
Val Gln Pro Trp Pro Val Gln Leu Leu Pro Leu Asp Leu Phe Tyr Gly
450                 455                 460
Gln Ser Pro Thr Asp Leu Pro Ala Trp Leu Ala Pro Gly Thr Ser Gly
465                 470                 475                 480
Gln Phe Ala Leu Val Val Gln Gly Ala Asp Leu Lys Thr Thr Ala Glu
                485                 490                 495
Thr Ala Arg Val Gln Phe Ser Asn Pro Ser Val Thr Ala Gln Val Thr
            500                 505                 510
Gln Phe Leu Pro Asp Ala Ser Ala Ile Pro Gly Gln Thr Asn Ser Gly
        515                 520                 525
Gly Thr Gln Gly Tyr Leu Leu Thr Ile Thr Val Ser Pro Thr Ala Ala
530                 535                 540
Pro Gly Leu Val Thr Val Arg Ala Leu Asn Pro Gly Glu Ala Asp Asn
545                 550                 555                 560
Pro Ser Ala Thr Glu His Pro Trp Glu Ser Gly Leu Ala Leu Val Pro
                565                 570                 575
Gly Ala

<210> SEQ ID NO 12
<211> LENGTH: 535
<212> TYPE: PRT
<213> ORGANISM: Pseudomonas sp. PAMC 26793

<400> SEQUENCE: 12

Met Ser Arg Leu Arg Leu Ser Val Leu Ser Leu Leu Thr Ser Val Val
1               5                   10                  15
Leu Ser Leu Phe Ala Met Gln Ala Ala Tyr Ala Ser Pro Thr Ser Asp
                20                  25                  30
Ala Asp Ala Cys Val Gln Gln Gln Leu Val Phe Asn Pro Lys Ser Gly
            35                  40                  45
Gly Phe Leu Pro Ile Asn Asn Phe Asn Ala Thr Gly Gln Ser Phe Met
        50                  55                  60
Asn Cys Phe Gly Trp Gln Leu Phe Ile Ala Leu Asn Trp Pro Val Asn
65                  70                  75                  80
Pro Gly Trp Pro Ala Thr Pro Ala Leu Ala Gly Glu Pro Asp Met Asn
                85                  90                  95
Ser Thr Leu Ala Gln Phe Gly Val Pro Pro Ala Ser Gly Gln Pro Met
            100                 105                 110
Ser Val Ala Pro Val Trp Ala Ser Tyr Lys Asp Ala Asn Asp Ile Phe
        115                 120                 125
Leu Pro Gly Ala Pro Ala Pro Thr Gly Trp Gly Val Gln Thr Leu Val
130                 135                 140
Pro Ser Asn Cys Ser Thr Gln Gly Ser Leu Arg Ala Met Ser Val Gly
145                 150                 155                 160
Ala Arg Lys Phe Met Thr Ala Thr Ser Glu Ser Ala Ile Asn Ala Arg
                165                 170                 175
His Gly Phe His Leu Ser Ser Gly Thr Leu Ala Ser Ile Pro Asp Pro
            180                 185                 190
Ile Met Glu Ala Ser Gly Gly Trp Leu Thr Asp Gln Ser Gln Asn Leu
        195                 200                 205
```

Val Phe Phe Glu Arg Lys Val Gly Lys Ala Glu Phe Asp Tyr Ile Val
                210                 215                 220

Ser Lys Gly Leu Tyr Asp Ala Ala Asn Gln Leu Lys Val Ala Gln Asn
225                 230                 235                 240

Ile Asp Asn Gln Asn Pro Gly Gly Leu Ser Leu Pro Ile Gly Glu Pro
                    245                 250                 255

Met Arg Ser Leu Pro Pro Asn Pro Val Pro Gln Glu Gln Leu Gly Ala
                260                 265                 270

Leu Glu Val Lys Ala Ala Trp Arg Ile Leu Thr Gly Lys Pro Glu Leu
                275                 280                 285

Tyr Gly Arg Tyr Leu Thr Thr Val Ala Trp Leu Lys Asn Pro Ala Thr
            290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                    325                 330                 335

Val Asp Asn Val Pro Glu Pro Asn Gln Val Pro Pro Gln Thr Pro
                340                 345                 350

Pro Asp Ser Phe Ala Phe Asn Asn Pro Asn Cys Gly Thr Gly Pro Glu
                355                 360                 365

Cys Thr Pro Asn Val Ala Arg Ile Gln Cys Lys Gln His His Pro Asp
            370                 375                 380

Arg Asp Cys Thr Glu Pro Phe Pro Arg Asp Gln Pro Val Gln Thr Thr
385                 390                 395                 400

Arg Glu His Pro Leu Pro Thr Glu Leu Gln Ala Leu Asn Gly Ala Val
                    405                 410                 415

Gln Ala Asn Phe Ala Gln Gln Ser Gln Gly Lys Ser Val Phe Gln Tyr
                420                 425                 430

Tyr Lys Leu Ile Asn Val Leu Trp Thr Leu Thr Pro Asn Pro Pro Thr
            435                 440                 445

Gln Pro Glu Pro Gly Val Ser Ala Gln Val Pro Leu Ser Tyr Gly Pro
                450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile
                    485                 490                 495

Ala Gly Ser Ser Thr Leu Ala Ser Asp Phe Ser Phe Leu Phe Asn Ser
                500                 505                 510

Ala Asp Ser Ala Ser Lys Lys Ser Leu Val Lys Arg Val Lys Ala Phe
            515                 520                 525

Gln Thr Leu Lys Asp Gln Pro
                530                 535

<210> SEQ ID NO 13
<211> LENGTH: 578
<212> TYPE: PRT
<213> ORGANISM: Pseudomonas putida

<400> SEQUENCE: 13

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
                20                  25                  30

Thr Asp Trp Asn Asn Asn Leu Thr Gly Trp Thr Glu Ser Ser Ile Ile
            35                  40                  45

-continued

Gly Asn Pro Trp Ser Gly Leu Asn Asp Ala Pro Arg Ser Gly Tyr Tyr
 50                  55                  60

Asn Pro Leu Val Glu Gly Phe Gly Asp Val Thr Ala Pro Ala Ile Thr
 65                  70                  75                  80

Trp Ala Pro Phe Pro Asn Arg Leu Trp Thr Phe Phe Tyr Asn Asn Gly
                 85                  90                  95

Ala Ala Val Ile Pro Gln Leu Gly Gly Lys Ala Met Thr Leu Asp Gln
                100                 105                 110

Val Met Glu Leu Thr Asp His Gly Gln Ile Thr Leu Asp Asn Thr Leu
            115                 120                 125

Tyr Met Leu Tyr Asp Pro Asn Lys Gln Gly Thr Val Leu Gln Leu Pro
        130                 135                 140

Ala Lys Arg Cys Pro Ser Ile Asp Trp Asn Gly Lys Tyr Thr Ala Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asn Met Arg Lys Ile Thr Phe Thr Cys
            180                 185                 190

Glu Asn Pro Ala Tyr Phe Leu Thr Met Trp Arg Ile Asp Pro Asn Ala
        195                 200                 205

Val Leu Gly Leu Tyr Arg Asp Tyr Ile Asp Pro Asn Val Gln Leu Glu
    210                 215                 220

Asp Leu Tyr Leu Arg Tyr Thr Val Asp Cys Pro Thr Gly Lys Ala Gly
225                 230                 235                 240

Asp Pro Val Ile Asp Pro Thr Thr Gly Lys Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Arg Pro Val Ser Ser Gln Asn
    290                 295                 300

Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Thr Thr Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
        355                 360                 365

Trp Arg Ile Thr Arg Gly Thr Ala Lys Ser Ala Ala Asn Gly Ser Asp
    370                 375                 380

Gln Ile Leu Gln Ala Val Phe Glu Val Pro Glu Ser Ala Gly Phe Ser
385                 390                 395                 400

Ile Asn Asp Ile Thr Ile Asn Asn Gln Lys Val Asn Tyr Val Trp Val
                405                 410                 415

Ile Ala Gln Gln Leu Leu Val Gly Leu Ser Val Thr Val Lys Pro Leu
            420                 425                 430

Ser Ala Thr Leu Gln Ala Phe Pro Cys Val Gln Asp Arg Val Ala Gly
        435                 440                 445

Leu Gln Pro Trp Pro Val Gln Leu Leu Pro Leu Asp Leu Phe Tyr Gly
    450                 455                 460

```
Gln Ser Pro Thr Asp Leu Pro Ala Trp Leu Ala Pro Gly Ser Ser Asn
465                 470                 475                 480

Gln Phe Val Leu Val Gln Gly Ala Asp Pro Thr Thr Thr Ala Gln
            485                 490                 495

Asn Ala Arg Val Gln Phe Ser Asn Pro Gly Val Thr Ala Gln Val Thr
            500                 505                 510

Gln Tyr Leu Pro Asp Ala Ser Ala Ile Pro Gly Gln Thr Asn Ser Gly
            515                 520                 525

Gly Thr Gln Ala Tyr Ile Leu Thr Ile Thr Val Ser Pro Ser Ala Ala
            530                 535                 540

Pro Gly Leu Val Thr Val Arg Ala Leu Asn Pro Gly Glu Asp Val Asn
545                 550                 555                 560

Val Ser Ala Thr Asp His Pro Trp Glu Ser Gly Leu Ala Leu Val Pro
            565                 570                 575

Gly Ala

<210> SEQ ID NO 14
<211> LENGTH: 535
<212> TYPE: PRT
<213> ORGANISM: Pseudomonas putida

<400> SEQUENCE: 14

Met Met Ser Arg Ser Arg Leu Ser Pro Leu Ser Leu Leu Cys Gly Ile
1               5                   10                  15

Leu Leu Cys Leu Ser Thr Leu Gln Pro Ala Thr Ala Ala Thr Leu Ser
            20                  25                  30

Asp Ala Asp Thr Cys Val Gln Gln Leu Val Phe Asn Pro Ala Ser
            35                  40                  45

Gly Gly Phe Leu Pro Val Asn Asn Phe Asn Ala Thr Ser Gln Ala Phe
50                  55                  60

Met Asn Cys Phe Gly Trp Gln Leu Phe Ile Ala Leu Asn Trp Pro Val
65                  70                  75                  80

Asn Pro Gly Trp Pro Ala Thr Ala Ser Leu Ala Gly Glu Pro Asp Met
            85                  90                  95

Gln Ser Thr Leu Ala Gln Phe Gly Val Pro Ser Ala Pro Gly Gln Pro
            100                 105                 110

Met Ser Val Ala Pro Val Trp Ala Ser Tyr Lys Asp Ala Asn Asp Ile
            115                 120                 125

Phe Leu Pro Gly Ala Pro Thr Pro Thr Gly Trp Gly Val Gln Thr Leu
130                 135                 140

Val Pro Ser Gly Cys Ser Thr Gln Gly Ser Leu Lys Ala Leu Lys Val
145                 150                 155                 160

Gly Ala Arg Lys Phe Met Asn Ala Thr Ser Glu Gly Ala Ile Asn Ala
            165                 170                 175

Leu His Gly Phe His Leu Ser Thr Gly Thr Leu Ala Ser Ile Pro Asp
            180                 185                 190

Pro Val Met Glu Ala Ser Gly Gly Trp Leu Thr Asp Gln Ala Gly Lys
            195                 200                 205

Leu Val Phe Phe Glu Arg Lys Val Gly Lys Ala Glu Phe Asp Tyr Ile
            210                 215                 220

Val Asp Lys Gly Leu Tyr Asp Ala Ala Asn Gln Leu Lys Val Ala Gln
225                 230                 235                 240

Asn Leu Asp Gly Gln Thr Pro Glu Gly Leu Ser Leu Pro Ile Gly Glu
            245                 250                 255
```

```
Pro Met Arg Ser Leu Pro Thr Ser Pro Val Pro Gln Glu Gln Leu Gly
            260                 265                 270

Ala Ile Glu Leu Lys Ala Ala Trp Arg Val Leu Thr Gly Lys Pro Glu
        275                 280                 285

Leu Phe Gly Arg Tyr Leu Thr Thr Val Ala Trp Leu Lys Arg Pro Asp
    290                 295                 300

Thr Leu Glu Cys Thr Gln Glu Val Val Gly Leu Val Gly Leu His Ile
305                 310                 315                 320

Ile Asn Lys Thr Gln Ala Ser Pro Asn Phe Ile Trp Thr Thr Phe Glu
                325                 330                 335

Gln Val Asp Asn Val Pro Glu Pro Ala Gln Val Pro Pro Gln Gln Thr
            340                 345                 350

Pro Pro Asn Gly Phe Ala Phe Asn Asn Pro Asp Cys Gly Asp Gly Pro
        355                 360                 365

Glu Cys Thr Pro Asn Gln Ala Arg Ile Gln Cys Lys Gln Thr His Pro
    370                 375                 380

Asp Lys Asp Cys Thr Asp Leu Phe Pro Arg Asp Gln Pro Val Gln Thr
385                 390                 395                 400

Thr Arg Glu His Pro Val Pro Gly Asp Leu Gln Ala Leu Asn Ser Ala
                405                 410                 415

Val Gln Ala Asn Phe Ala Gln His Ser Gln Gly Lys Ser Val Phe Gln
            420                 425                 430

Tyr Tyr Lys Leu Ile Asn Val Leu Trp Thr Leu Ala Pro Asn Pro Pro
        435                 440                 445

Ser Pro Glu Pro Gly Ala Asn Ala Gln Val Pro Leu Ser Tyr Gly Pro
    450                 455                 460

Phe Ile Ser Gln Gly Asn Val Pro Val Ala Asn Thr Thr Met Glu Thr
465                 470                 475                 480

Tyr Val Gln Gly Asp Asp Cys Asn Gln Cys His Gln Tyr Ala Thr Ile
                485                 490                 495

Ala Gly Ser Pro Ser Leu Ala Ser Asp Phe Ser Phe Leu Phe Asn Ser
            500                 505                 510

Ala Gly Ser Ala Ser Asn Lys Ser Leu Ile Lys Ser Val Lys Ala Phe
        515                 520                 525

Glu Thr Leu Lys Asp Arg Pro
    530                 535

<210> SEQ ID NO 15
<211> LENGTH: 578
<212> TYPE: PRT
<213> ORGANISM: unknown
<220> FEATURE:
<223> OTHER INFORMATION: Fungus garden combined

<400> SEQUENCE: 15

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asn Leu Thr Gly Trp Thr Glu Ser Ser Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Phe Gly Asp Val Thr Ala Pro Ala Ile Thr
65                  70                  75                  80
```

```
Trp Ala Pro Phe Pro Asn Arg Leu Trp Thr Phe Phe Tyr Asn Asn Gly
                85                  90                  95
Ala Ala Val Ile Pro Gln Leu Gly Gly Lys Ala Met Thr Leu Asp Gln
            100                 105                 110
Val Met Ala Leu Thr Asp His Gly Gln Ile Thr Leu Asp Asn Thr Leu
            115                 120                 125
Tyr Met Leu Tyr Asp Pro Asn Lys Gln Gly Thr Val Leu Gln Leu Pro
            130                 135                 140
Ala Lys Arg Cys Pro Ser Ile Asp Trp Asn Gly Lys Tyr Thr Ala Phe
145                 150                 155                 160
Ser Pro Ser Gly Pro Arg Gly Trp Leu Asp Glu Tyr Cys Glu Trp Ser
                165                 170                 175
Ile Val Arg Asp Ala Asn Gly Asn Met Arg Lys Ile Thr Phe Thr Cys
            180                 185                 190
Glu Asn Pro Ala Tyr Phe Leu Thr Met Trp Arg Ile Asp Pro Asn Ala
            195                 200                 205
Val Leu Gly Leu Tyr Arg Asp Tyr Ile Asp Pro Asn Val Gln Leu Glu
    210                 215                 220
Asp Leu Tyr Leu Arg Tyr Thr Val Asp Cys Pro Thr Gly Lys Ala Gly
225                 230                 235                 240
Asp Pro Val Ile Asp Pro Thr Thr Gly Lys Pro Ala Tyr Asp Thr Val
                245                 250                 255
Asn Lys Trp Asn Ala Gly Thr Ala Cys Val Pro Gly Gln Tyr Gly Gly
                260                 265                 270
Ala Met His Leu Thr Ser Gly Pro Asn Thr Leu Ser Ala Glu Val Tyr
            275                 280                 285
Leu Ala Ala Ala Ala Thr Ile Leu Arg Pro Val Ser Ser Ser Gln Asn
    290                 295                 300
Ala Gln Ser Leu Ile Cys Cys Ala Gln Tyr Gly Gln Asn Tyr Arg Asn
305                 310                 315                 320
Ser Asp Pro His Ile Gly Phe Met Ala Asn Thr Thr Ala Val Asn Asn
                325                 330                 335
Arg Leu Ser Leu Thr Asn Pro Ile Gly Leu Tyr Leu Gln Gln Pro Thr
            340                 345                 350
Asp Phe Ser Ala Trp Lys Gly Pro Gln Gly Gln Asp Val Ser Gln Tyr
            355                 360                 365
Trp Arg Ile Thr Arg Gly Thr Ala Lys Ser Ala Ala Asn Gly Ser Asp
    370                 375                 380
Gln Ile Leu Gln Ala Val Phe Glu Val Pro Glu Ser Ala Gly Phe Ser
385                 390                 395                 400
Ile Asn Asp Ile Thr Ile Asn Asn Gln Lys Val Asn Tyr Val Trp Val
                405                 410                 415
Ile Ala Gln Gln Leu Leu Val Gly Leu Ser Val Thr Val Lys Pro Leu
            420                 425                 430
Ser Thr Thr Pro Gln Ala Phe Pro Cys Val Asp Arg Val Ala Gly
            435                 440                 445
Arg Gln Pro Trp Pro Val Gln Leu Leu Pro Leu Asp Leu Phe Tyr Gly
    450                 455                 460
Gln Ser Pro Thr Asp Leu Pro Ala Trp Leu Pro Gly Ser Ser Asn
465                 470                 475                 480
Gln Phe Val Leu Val Gln Gly Ala Asp Pro Thr Thr Ala Gln
            485                 490                 495
Asn Ala Arg Val Gln Phe Ser Asn Pro Gly Val Thr Ala Gln Val Thr
```

```
                500                 505                 510
Gln Tyr Leu Pro Asp Ala Ser Ala Ile Pro Gly Gln Thr Asn Ser Gly
            515                 520                 525

Gly Thr Gln Ala Tyr Ile Leu Thr Ile Thr Val Ser Pro Ser Ala Ala
        530                 535                 540

Pro Gly Leu Val Ala Val Arg Ala Leu Asn Pro Gly Glu Asp Val Asn
545                 550                 555                 560

Val Ser Ala Thr Asp His Pro Trp Glu Ser Gly Leu Ala Leu Val Pro
                565                 570                 575

Gly Ala

<210> SEQ ID NO 16
<211> LENGTH: 534
<212> TYPE: PRT
<213> ORGANISM: unknown
<220> FEATURE:
<223> OTHER INFORMATION: Fungus garden combined

<400> SEQUENCE: 16

Met Ser Arg Ser Arg Leu Ser Leu Leu Ser Leu Leu Cys Gly Ile Leu
1               5                   10                  15

Leu Cys Leu Ser Thr Pro Gln Pro Ala Thr Ala Ala Thr Leu Ser Asp
            20                  25                  30

Ala Asp Thr Cys Val Gln Gln Leu Val Phe Asn Pro Ala Ser Gly
        35                  40                  45

Gly Phe Leu Pro Val Asn Asn Phe Asn Ala Thr Ser Gln Ala Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Ala Ser Leu Ala Gly Glu Pro Asp Met Gln
                85                  90                  95

Ser Thr Leu Ala Gln Phe Gly Val Pro Ser Ala Pro Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Thr Pro Thr Gly Trp Gly Val Gln Thr Leu Val
    130                 135                 140

Pro Ser Gly Cys Ser Thr Gln Gly Asn Leu Lys Ala Leu Lys Val Gly
145                 150                 155                 160

Ala Arg Lys Phe Met Asn Ala Thr Ser Glu Gly Ala Ile Asn Ala Leu
                165                 170                 175

His Gly Phe His Leu Ser Thr Gly Thr Leu Ala Ser Ile Pro Asp Pro
            180                 185                 190

Val Met Glu Ala Ser Gly Gly Trp Leu Thr Asp Gln Ala Gly Lys Leu
        195                 200                 205

Val Phe Phe Glu Arg Lys Val Gly Lys Ala Glu Phe Asp Tyr Ile Val
    210                 215                 220

Asp Lys Gly Leu Tyr Asp Ala Ala Asn Gln Leu Lys Val Ala Gln Asn
225                 230                 235                 240

Leu Asp Gly Gln Thr Pro Glu Gly Leu Ser Leu Pro Ile Gly Glu Pro
                245                 250                 255

Met Arg Ser Leu Pro Thr Ser Pro Val Pro Gln Glu Gln Leu Gly Ala
            260                 265                 270

Ile Glu Leu Lys Ala Ala Trp Arg Val Leu Thr Gly Lys Pro Glu Leu
        275                 280                 285
```

```
Phe Gly Arg Tyr Leu Thr Thr Val Ala Trp Leu Lys Arg Pro Asp Thr
    290                 295                 300

Leu Glu Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Ala Gln Val Pro Pro Gln Gln Thr Pro
            340                 345                 350

Pro Asn Gly Phe Ala Phe Asn Asn Pro Asp Cys Gly Asp Gly Pro Glu
        355                 360                 365

Cys Thr Pro Asn Gln Ala Arg Ile Gln Cys Lys Gln Thr His Pro Asp
370                 375                 380

Lys Asp Cys Thr Asp Leu Phe Pro Arg Asp Gln Pro Val Gln Thr Thr
385                 390                 395                 400

Arg Glu His Pro Val Pro Gly Asp Leu Gln Ala Leu Asn Ser Ala Val
                405                 410                 415

Gln Ala Asn Phe Ala Gln His Ser Gln Gly Lys Ser Val Phe Gln Tyr
            420                 425                 430

Tyr Lys Leu Ile Asn Val Leu Trp Thr Leu Ala Pro Asn Pro Pro Ser
        435                 440                 445

Pro Glu Pro Gly Ala Asn Ala Gln Val Pro Leu Ser Tyr Gly Pro Phe
    450                 455                 460

Ile Ser Gln Gly Asn Val Pro Val Ala Asn Thr Thr Met Glu Thr Tyr
465                 470                 475                 480

Val Gln Gly Asp Asp Cys Asn Gln Cys His Gln Tyr Ala Thr Ile Ala
                485                 490                 495

Gly Ser Pro Ser Leu Ala Ser Asp Phe Ser Phe Leu Phe Asn Ser Ala
            500                 505                 510

Gly Ser Ala Ser Asn Lys Ser Leu Ile Lys Ser Val Lys Ala Phe Glu
        515                 520                 525

Thr Leu Lys Asp Arg Pro
    530

<210> SEQ ID NO 17
<211> LENGTH: 578
<212> TYPE: PRT
<213> ORGANISM: Pseudomonas monteilii

<400> SEQUENCE: 17

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asn Leu Thr Gly Trp Thr Glu Ser Ser Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Phe Gly Asp Val Thr Ala Pro Ala Ile Thr
65                  70                  75                  80

Trp Ala Pro Phe Pro Asn Arg Leu Trp Thr Phe Phe Tyr Asn Asn Gly
                85                  90                  95

Ala Ala Val Ile Pro Gln Leu Gly Gly Lys Ala Met Thr Leu Asp Gln
            100                 105                 110

Val Met Glu Leu Thr Asp His Gly Gln Ile Thr Leu Asp Asn Thr Leu
```

-continued

```
            115                 120                 125
Tyr Met Leu Tyr Asp Pro Asn Lys Gln Gly Thr Val Leu Gln Leu Pro
    130                 135                 140
Ala Lys Arg Cys Pro Ser Ile Asp Trp Asn Gly Lys Tyr Thr Ala Phe
145                 150                 155                 160
Ser Pro Ser Gly Pro Arg Gly Trp Leu Asp Glu Tyr Cys Glu Trp Ser
                165                 170                 175
Ile Val Arg Asp Ala Asn Gly Asn Met Arg Lys Ile Thr Phe Thr Cys
                180                 185                 190
Glu Asn Pro Ala Tyr Phe Leu Thr Met Trp Arg Ile Asp Pro Asn Ala
                195                 200                 205
Val Leu Gly Leu Tyr Arg Asp Tyr Ile Asp Pro Asn Val Gln Leu Glu
    210                 215                 220
Asp Leu Tyr Leu Arg Tyr Thr Val Asp Cys Pro Thr Gly Lys Ala Gly
225                 230                 235                 240
Asp Pro Val Ile Asp Pro Thr Thr Gly Lys Pro Ala Tyr Asp Thr Val
                245                 250                 255
Asn Lys Trp Asn Ala Gly Thr Ala Cys Val Pro Gly Gln Tyr Gly Gly
                260                 265                 270
Ala Met His Leu Thr Ser Gly Pro Asn Thr Leu Ser Ala Glu Val Tyr
                275                 280                 285
Leu Ala Ala Ala Thr Ile Leu Arg Pro Val Ser Ser Ser Gln Asn
    290                 295                 300
Ala Gln Ser Leu Ile Cys Cys Ala Gln Tyr Gly Gln Asn Tyr Arg Asn
305                 310                 315                 320
Ser Asp Pro His Ile Gly Phe Met Ala Asn Thr Thr Ala Val Asn Asn
                325                 330                 335
Arg Leu Ser Leu Thr Asn Pro Ile Gly Leu Tyr Leu Gln Gln Pro Thr
                340                 345                 350
Asp Phe Ser Ala Trp Lys Gly Pro Gln Gly Gln Asp Val Ser Gln Tyr
                355                 360                 365
Trp Arg Ile Thr Arg Gly Thr Ala Lys Ser Ala Ala Asn Gly Ser Asp
    370                 375                 380
Gln Ile Leu Gln Ala Val Phe Glu Val Pro Glu Ser Ala Gly Phe Ser
385                 390                 395                 400
Ile Asn Asp Ile Thr Ile Asn Asn Gln Lys Val Asn Tyr Val Trp Val
                405                 410                 415
Ile Ala Gln Gln Leu Leu Val Gly Leu Ser Val Thr Ala Lys Pro Leu
                420                 425                 430
Ser Ala Thr Pro Gln Ala Phe Pro Cys Val Gln Asp Arg Val Ala Gly
                435                 440                 445
Leu Gln Pro Trp Pro Val Gln Leu Leu Pro Leu Asp Leu Phe Tyr Gly
    450                 455                 460
Gln Ser Pro Thr Asp Leu Pro Ala Trp Leu Ala Pro Gly Ser Ser Asn
465                 470                 475                 480
Gln Phe Val Leu Val Gln Gly Ala Asp Pro Thr Thr Ala Gln
                485                 490                 495
Asn Ala Arg Val Gln Phe Ser Asn Pro Gly Val Thr Ala Gln Val Thr
                500                 505                 510
Gln Tyr Leu Pro Asp Ala Ser Ala Ile Pro Gly Gln Thr Asn Ser Gly
                515                 520                 525
Gly Thr Gln Ala Tyr Ile Leu Thr Ile Thr Val Ser Pro Ser Ala Ala
    530                 535                 540
```

```
Pro Gly Leu Val Ala Leu Arg Ala Leu Asn Pro Gly Glu Asp Val Asn
545                 550                 555                 560

Val Ser Ala Thr Asp His Pro Trp Glu Ser Gly Leu Ala Leu Val Pro
                565                 570                 575

Gly Ala

<210> SEQ ID NO 18
<211> LENGTH: 535
<212> TYPE: PRT
<213> ORGANISM: Pseudomonas monteilii

<400> SEQUENCE: 18

Met Met Ser Arg Ser Arg Leu Ser Leu Leu Ser Leu Leu Cys Gly Ile
1               5                   10                  15

Leu Leu Cys Leu Ser Thr Pro Gln Pro Ala Thr Ala Ala Thr Leu Ser
            20                  25                  30

Asp Ala Asp Thr Cys Val Gln Gln Leu Val Phe Asn Pro Ala Ser
                35                  40                  45

Gly Gly Phe Leu Pro Val Asn Asn Phe Asn Ala Thr Ser Gln Ala Phe
        50                  55                  60

Met Asn Cys Phe Gly Trp Gln Leu Phe Ile Ala Leu Asn Trp Pro Val
65                  70                  75                  80

Asn Pro Gly Trp Pro Ala Thr Ala Ser Leu Ala Gly Glu Pro Asp Met
                85                  90                  95

Gln Ser Thr Leu Ala Gln Phe Gly Val Pro Ser Thr Pro Gly Gln Pro
            100                 105                 110

Met Ser Val Ala Pro Val Trp Ala Ser Tyr Lys Asp Ala Asn Asp Ile
        115                 120                 125

Phe Leu Pro Gly Ala Pro Thr Pro Thr Gly Trp Gly Val Gln Thr Leu
    130                 135                 140

Val Pro Ser Asp Cys Ser Thr Gln Gly Ser Leu Lys Thr Leu Lys Val
145                 150                 155                 160

Gly Ala Arg Lys Phe Met Asn Ala Thr Ser Glu Gly Ala Ile Asn Ala
                165                 170                 175

Leu His Gly Phe His Leu Ser Thr Gly Thr Leu Ala Ser Ile Pro Asp
            180                 185                 190

Pro Val Met Glu Ala Ser Gly Gly Trp Leu Thr Asp Gln Ala Gly Lys
        195                 200                 205

Leu Val Phe Phe Glu Arg Lys Val Gly Lys Ala Glu Phe Asp Tyr Ile
    210                 215                 220

Val Asp Lys Gly Leu Tyr Asp Ala Ala Asn Gln Leu Lys Val Ala Arg
225                 230                 235                 240

Asn Leu Asp Gly Gln Thr Pro Glu Gly Leu Ser Leu Pro Ile Gly Glu
                245                 250                 255

Pro Met Arg Ser Leu Pro Thr Ser Pro Val Pro Gln Glu Gln Leu Gly
            260                 265                 270

Ala Ile Glu Leu Lys Ala Ala Trp Arg Val Leu Thr Gly Lys Pro Glu
        275                 280                 285

Leu Phe Gly Arg Tyr Leu Thr Thr Val Ala Trp Leu Lys Arg Pro Asp
    290                 295                 300

Thr Leu Glu Cys Thr Gln Glu Val Val Gly Leu Val Gly Leu His Ile
305                 310                 315                 320

Ile Asn Lys Thr Gln Ala Ser Pro Asn Phe Ile Trp Thr Thr Phe Glu
                325                 330                 335
```

```
Gln Val Asp Asn Val Pro Glu Pro Ala Gln Val Pro Pro Gln Gln Thr
            340                 345                 350

Pro Pro Asn Gly Phe Ala Phe Asn Asn Pro Asp Cys Gly Asn Gly Pro
            355                 360                 365

Glu Cys Thr Pro Asn Gln Ala Arg Ile Gln Cys Lys Gln Thr His Pro
            370                 375                 380

Asp Lys Asp Cys Thr Asp Leu Phe Pro Arg Asp Gln Pro Val Gln Thr
385                 390                 395                 400

Thr Arg Glu His Pro Val Pro Gly Asp Leu Gln Ala Leu Asn Ser Ala
                405                 410                 415

Val Gln Ala Asn Phe Ala Gln His Ser Gln Gly Lys Ser Val Phe Gln
            420                 425                 430

Tyr Tyr Lys Leu Val Asn Val Leu Trp Thr Leu Ala Pro Asn Pro Pro
            435                 440                 445

Ser Pro Glu Pro Gly Ala Asn Ala Gln Val Pro Leu Ser Tyr Gly Pro
            450                 455                 460

Phe Ile Ser Gln Gly Asn Val Pro Val Ala Asn Thr Thr Met Glu Thr
465                 470                 475                 480

Tyr Val Gln Gly Asp Asn Cys Asn Gln Cys His Gln Tyr Ala Thr Ile
                485                 490                 495

Ala Gly Ser Pro Ser Leu Ala Ser Asp Phe Ser Phe Leu Phe Asn Ser
            500                 505                 510

Ala Gly Ser Ala Ser Asn Lys Ser Leu Ile Lys Ser Val Lys Ala Phe
            515                 520                 525

Glu Thr Leu Lys Asp Arg Pro
            530                 535

<210> SEQ ID NO 19
<211> LENGTH: 578
<212> TYPE: PRT
<213> ORGANISM: Pseudomonas monteilii

<400> SEQUENCE: 19

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asn Leu Thr Gly Trp Thr Gln Ser Ser Ile Ile
            35                  40                  45

Gly Asn Pro Trp Ser Gly Leu Asn Asp Ala Pro Arg Ser Gly Tyr Tyr
        50                  55                  60

Asn Pro Leu Val Glu Gly Phe Gly Asp Val Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Ala Ala Val Ile Pro Gln Leu Gly Gly Lys Ala Met Thr Leu Asp Gln
            100                 105                 110

Val Met Glu Leu Ala Asp His Gly Gln Ile Thr Leu Asp Asn Thr Leu
            115                 120                 125

Tyr Thr Leu Tyr Asp Pro Asn Lys Lys Gly Thr Val Leu Gln Leu Pro
        130                 135                 140

Val Lys Arg Cys Pro Ser Ile Ala Trp Asn Gly Thr Tyr Lys Asp Phe
145                 150                 155                 160

Thr Pro Ser Gly Pro Arg Gly Trp Leu Asp Glu Tyr Cys Glu Trp Ser
```

```
            165                 170                 175
Ile Val Arg Asp Ala Asn Gly Asn Met Arg Lys Ile Thr Phe Thr Cys
            180                 185                 190

Glu Asn Pro Ala Tyr Phe Leu Ala Met Trp Arg Ile Asp Pro Asn Ala
            195                 200                 205

Val Leu Gly Leu Tyr Arg Glu Tyr Ile Asp Pro Ser Val Gln Leu Glu
            210                 215                 220

Asp Leu Tyr Leu Arg Tyr Ala Glu Asp Cys Pro Thr Gly Lys Ala Gly
225                 230                 235                 240

Asp Pro Val Met Asp Pro Thr Thr Gly Lys Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
            275                 280                 285

Leu Ala Ala Ala Thr Ile Leu Arg Pro Val Ser Ser Ser Gln Asn
290                 295                 300

Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Thr Ala Val Asn Asn
                325                 330                 335

Arg Leu Ser Leu Thr Asn Pro Ile Gly Leu Tyr Leu Gln Gln Pro Thr
                340                 345                 350

Asp Phe Ser Ala Trp Lys Gly Pro Gln Gly Gln Asp Val Ser Gln Tyr
                355                 360                 365

Trp Arg Ile Thr Arg Gly Thr Ala Lys Ser Ala Ala Asn Gly Ser Asp
            370                 375                 380

Gln Ile Leu Gln Ala Val Phe Glu Val Pro Ser Ala Gly Phe Ser
385                 390                 395                 400

Ile Asn Asp Ile Thr Ile Asn Asn Gln Lys Val Asn Tyr Val Trp Val
                405                 410                 415

Ile Ala Gln Gln Leu Leu Val Gly Leu Ser Val Thr Val Lys Pro Leu
            420                 425                 430

Ser Val Thr Pro Gln Ser Phe Pro Cys Val Gln Asp Arg Val Ala Gly
            435                 440                 445

Leu Gln Pro Trp Pro Val Gln Leu Leu Pro Leu Asp Leu Phe Tyr Gly
            450                 455                 460

Asn Ser Pro Thr Asp Leu Pro Ala Trp Leu Ala Pro Gly Ser Ser Asn
465                 470                 475                 480

Gln Phe Val Leu Val Gln Gly Ala Asp Lys Thr Thr Ala Gln
            485                 490                 495

Asn Ala Arg Val Gln Phe Ser Asn Pro Gly Val Thr Ala Gln Val Thr
                500                 505                 510

Gln Tyr Leu Pro Asp Ala Ser Ala Ile Pro Gly Gln Thr Asn Ala Gly
            515                 520                 525

Gly Thr Gln Ala Tyr Ile Leu Thr Ile Thr Val Ser Pro Thr Ala Ala
530                 535                 540

Pro Gly Leu Val Thr Val Arg Ala Leu Asn Pro Asp Glu Asp Val Asn
545                 550                 555                 560

Val Ser Ala Ala Asp His Pro Trp Glu Ser Gly Leu Ala Leu Val Pro
                565                 570                 575

Gly Ala
```

<210> SEQ ID NO 20
<211> LENGTH: 534
<212> TYPE: PRT
<213> ORGANISM: Pseudomonas monteilii

<400> SEQUENCE: 20

| | | | | | | | | | | | | | | | |
|---|---|---|---|---|---|---|---|---|---|---|---|---|---|---|---|
| Met | Ser | Arg | Ser | Arg | Leu | Ser | Leu | Leu | Ser | Leu | Leu | Cys | Gly | Ile | Leu |
| 1 | | | | 5 | | | | | 10 | | | | | 15 | |
| Leu | Cys | Leu | Ser | Thr | Pro | Gln | Pro | Ala | Met | Ala | Ala | Thr | Leu | Ser | Asp |
| | | | 20 | | | | | 25 | | | | | 30 | | |
| Ala | Asp | Ala | Cys | Val | Gln | Gln | Leu | Val | Phe | Asn | Pro | Ala | Ser | Gly |
| | | 35 | | | | | 40 | | | | | 45 | | | |
| Gly | Phe | Leu | Pro | Val | Asn | Asn | Phe | Asn | Ala | Thr | Ser | Gln | Ala | Phe | Met |
| | | 50 | | | | 55 | | | | | 60 | | | | |
| Asn | Cys | Phe | Gly | Trp | Gln | Leu | Phe | Ile | Ala | Leu | Asn | Trp | Pro | Val | Asn |
| 65 | | | | | 70 | | | | | 75 | | | | | 80 |
| Pro | Gly | Trp | Pro | Ala | Thr | Ala | Ser | Leu | Ala | Gly | Glu | Pro | Asp | Met | Asn |
| | | | | 85 | | | | | 90 | | | | | 95 | |
| Ser | Thr | Leu | Ala | Gln | Phe | Gly | Val | Pro | Ser | Ala | Pro | Gly | Gln | Pro | Met |
| | | | 100 | | | | | 105 | | | | | 110 | | |
| Ser | Val | Ala | Pro | Val | Trp | Ala | Ser | Tyr | Lys | Asp | Ala | Asn | Asp | Ile | Phe |
| | | | 115 | | | | | 120 | | | | | 125 | | |
| Leu | Pro | Gly | Ala | Pro | Thr | Pro | Thr | Gly | Trp | Val | Gln | Thr | Leu | Val |
| | 130 | | | | | 135 | | | | | 140 | | | | |
| Pro | Ser | Gly | Cys | Ser | Thr | Gln | Gly | Ser | Leu | Lys | Ser | Leu | Lys | Val | Gly |
| 145 | | | | | 150 | | | | | 155 | | | | | 160 |
| Ala | Arg | Lys | Phe | Met | Asn | Ala | Thr | Ser | Glu | Gly | Ala | Ile | Asn | Ala | Leu |
| | | | | 165 | | | | | 170 | | | | | 175 | |
| His | Arg | Phe | His | Leu | Ser | Thr | Gly | Thr | Leu | Ala | Ser | Ile | Pro | Asp | Pro |
| | | | 180 | | | | | 185 | | | | | 190 | | |
| Val | Met | Glu | Ala | Ser | Gly | Gly | Trp | Leu | Thr | Asp | Gln | Ser | Gly | Asn | Leu |
| | | | 195 | | | | | 200 | | | | | 205 | | |
| Val | Phe | Phe | Glu | Arg | Lys | Val | Gly | Lys | Ala | Glu | Phe | Asp | Tyr | Ile | Val |
| | 210 | | | | | 215 | | | | | 220 | | | | |
| Asp | Lys | Gly | Leu | Tyr | Asp | Ala | Ala | Asn | Gln | Leu | Lys | Val | Ala | Gln | Asn |
| 225 | | | | | 230 | | | | | 235 | | | | | 240 |
| Gln | Asp | Gly | Lys | Thr | Pro | Glu | Gly | Leu | Ser | Leu | Pro | Ile | Gly | Glu | Pro |
| | | | | 245 | | | | | 250 | | | | | 255 | |
| Met | Arg | Ser | Leu | Pro | Pro | Ser | Pro | Val | Pro | Gln | Glu | Gln | Leu | Gly | Ala |
| | | | 260 | | | | | 265 | | | | | 270 | | |
| Ile | Glu | Leu | Lys | Ala | Ala | Trp | Arg | Val | Leu | Thr | Gly | Lys | Pro | Glu | Leu |
| | | 275 | | | | | 280 | | | | | 285 | | | |
| Phe | Gly | Arg | Tyr | Leu | Thr | Thr | Val | Ala | Trp | Leu | Lys | Arg | Pro | Asp | Thr |
| | 290 | | | | | 295 | | | | | 300 | | | | |
| Leu | Asn | Cys | Thr | Gln | Glu | Val | Val | Gly | Leu | Val | Gly | Leu | His | Ile | Ile |
| 305 | | | | | 310 | | | | | 315 | | | | | 320 |
| Asn | Lys | Thr | Gln | Ala | Ser | Pro | Asn | Phe | Ile | Trp | Thr | Thr | Phe | Glu | Gln |
| | | | | 325 | | | | | 330 | | | | | 335 | |
| Val | Asp | Asn | Val | Pro | Glu | Pro | Ala | Gln | Ala | Pro | Gln | Gln | Thr | Pro |
| | | | 340 | | | | | 345 | | | | | 350 | | |
| Pro | Asn | Gly | Phe | Ala | Phe | Asn | Asn | Pro | Asp | Cys | Gly | Ser | Gly | Pro | Glu |
| | | | 355 | | | | | 360 | | | | | 365 | | |
| Cys | Thr | Pro | Asn | Gln | Ala | Arg | Ile | Gln | Cys | Lys | Gln | His | His | Pro | Asp |
| | 370 | | | | | 375 | | | | | 380 | | | | |

```
Lys Gln Cys Thr Asp Leu Phe Pro Arg Asp Gln Pro Val Gln Thr Thr
385                 390                 395                 400

Arg Glu His Pro Ile Pro Ser Asp Leu Gln Ala Leu Asn Ser Ala Val
            405                 410                 415

Gln Ala Asn Phe Ala Gln His Ser Gln Gly Gln Ser Val Phe Gln Tyr
                420                 425                 430

Tyr Lys Leu Ile Asn Val Leu Trp Thr Leu Ala Pro Asn Pro Pro Ser
            435                 440                 445

Pro Glu Pro Gly Ala Asn Ala Gln Val Pro Leu Ser Tyr Gly Pro Phe
    450                 455                 460

Ile Ser Gln Gly Asn Val Pro Val Ala Asn Thr Thr Met Glu Thr Tyr
465                 470                 475                 480

Val Gln Gly Asp Asp Cys Asn Gln Cys His Gln Tyr Ala Thr Ile Ala
                485                 490                 495

Gly Ser Pro Ser Leu Ala Ser Asp Phe Ser Phe Leu Phe Asn Ser Ala
                500                 505                 510

Gly Ser Ala Ser Thr Lys Ser Leu Ile Lys Ser Val Lys Ala Phe Gln
                515                 520                 525

Thr Leu Lys Asp Gln Pro
            530

<210> SEQ ID NO 21
<211> LENGTH: 581
<212> TYPE: PRT
<213> ORGANISM: Pseudomonas brenneri

<400> SEQUENCE: 21

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asp Ile Thr Gly Trp Thr Glu Ala Ala Ile Ile
        35                  40                  45

Gly Asn Pro Trp Ser Gly Leu Tyr Asp Ala Pro Arg Ser Ala Tyr Tyr
50                  55                  60

Asn Pro Leu Val Glu Gly Tyr Gly Asp Thr Thr Leu Pro Ala Ile Thr
65                  70                  75                  80

Trp Gln Pro Phe Pro Asn Arg Leu Trp Thr Phe Tyr Asn Asn Gly
                85                  90                  95

Thr Ala Val Ile Pro Gln Leu Gly Asn Lys Ala Met Thr Leu Gln Gln
                100                 105                 110

Val Met Glu Leu Thr Asp Asn Gly Gln Ile Thr Ile Asn Gly Thr Leu
                115                 120                 125

Tyr Thr Leu Tyr Asp Pro Asp Lys Lys Gly Thr Leu Leu Gln Leu Pro
            130                 135                 140

Val Thr Arg Cys Pro Thr Ile Asp Trp Asn Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Thr Asn Gly Asn Met Arg Lys Ile Thr Phe Thr Ser
                180                 185                 190

Glu Asn Pro Ala Tyr Phe Leu Ala Met Trp Arg Ile Asp Pro Asn Ala
                195                 200                 205

Val Leu Gly Leu Tyr Arg Asp Tyr Ile Asp Pro Asn Val Gln Leu Gln
```

```
                210                 215                 220
Asp Leu Tyr Leu Arg Tyr Thr Ala Asp Cys Lys Thr Gly Lys Ala Gly
225                 230                 235                 240

Asp Pro Val Ile Asp Pro Thr Thr Gly Leu Pro Ala Tyr Asp Thr Val
                245                 250                 255

Asn Lys Trp Asn Ser Gly Thr Ala Cys Thr Pro Gly Gln Phe Gly Gly
            260                 265                 270

Ala Met His Leu Thr Ser Gly Pro Asn Thr Leu Ser Ala Glu Val Tyr
            275                 280                 285

Leu Ala Ala Ala Ala Thr Ile Met Arg Pro Leu Lys Ser Ser Gln Ser
290                 295                 300

Ala Gln Ala Leu Ile Cys Cys Ala Gln Tyr Gly Gln Asn Tyr Arg Asn
305                 310                 315                 320

Ser Asp Pro His Ile Gly Phe Ala Ala Asn Gly Ala Thr Asn Asp Gly
                325                 330                 335

Ala Thr Pro Ser Arg Ile Ser Leu Thr Asn Pro Ile Ala Leu Tyr Leu
                340                 345                 350

Gln Gln Pro Thr Asn Phe Asn Ala Trp Lys Gly Pro Gln Gly Gln Asp
                355                 360                 365

Val Ser Gln Tyr Trp Arg Ile Thr Arg Gly Thr Ala Lys Ser Ala Ile
370                 375                 380

Asn Gly Ser Asp Gln Ile Leu Gln Ala Val Phe Glu Val Pro Glu Ser
385                 390                 395                 400

Ala Gly Phe Ser Ile Asn Asp Ile Thr Ile Asn Gly Gln Ala Val Asp
                405                 410                 415

Tyr Val Trp Val Ile Ala Gln Gln Leu Leu Val Gly Leu Ser Val Thr
                420                 425                 430

Thr Met Pro Ser Thr Ala Gln Gln Ser Pro Cys Val Gln Asp Arg
                435                 440                 445

Val Asn Gly Leu Gln Pro Trp Pro Val Gln Leu Leu Pro Leu Asp Leu
            450                 455                 460

Phe Tyr Gly Gln Ser Pro Thr Asp Leu Pro Ala Trp Leu Ala Pro Gly
465                 470                 475                 480

Thr Ser Gly Gln Phe Ala Leu Val Val Gln Gly Ala Asp Leu Lys Thr
                485                 490                 495

Thr Ala Ala Thr Ala Arg Ile Gln Phe Asn Asn Pro Gly Val Thr Ala
                500                 505                 510

Gln Val Thr Glu Phe Leu Pro Asp Ala Ser Ala Ile Pro Gly Gln Thr
            515                 520                 525

Asn Ala Gly Gly Thr Gln Gly Tyr Ile Met Thr Ile Thr Val Ala Lys
            530                 535                 540

Asp Ala Ala Pro Gly Leu Val Thr Val Arg Ala Leu Asn Pro Gly Glu
545                 550                 555                 560

Ala Asp Asn Val Ser Ala Ala Asp His Pro Trp Glu Ser Gly Leu Ala
                565                 570                 575

Leu Val Pro Ser Thr
            580

<210> SEQ ID NO 22
<211> LENGTH: 532
<212> TYPE: PRT
<213> ORGANISM: Pseudomonas brenneri

<400> SEQUENCE: 22
```

```
Met Tyr Arg Phe Arg Leu Arg Gly Leu Leu Leu Val Gly Thr Leu Leu
1               5                   10                  15

Ser Leu Phe Leu Leu Pro Thr Ala Gln Ala Ser Asp Ala Asp Thr Cys
            20                  25                  30

Val Gln Gln Gln Leu Val Phe Asp Pro Asn Ser Gly Gly Phe Leu Pro
        35                  40                  45

Val Asn Asn Phe Asn Thr Thr Gly Gln Ser Phe Met Asn Cys Phe Gly
    50                  55                  60

Trp Gln Leu Phe Ile Ala Leu Asn Trp Pro Val Asp Pro Gly Trp Pro
65                  70                  75                  80

Ala Asn Ala Ala Leu Ala Gly Glu Pro Asn Arg Lys Ile Ser Met Ala
                85                  90                  95

Gln Phe Gly Val Pro Gln Val Ala Gly Gln Pro Met Thr Thr Ala Pro
            100                 105                 110

Val Trp Ala Ser Phe Lys Asp Ala Asn Asp Ile Phe Leu Pro Gly Ala
        115                 120                 125

Arg Pro Pro Thr Gly Trp Gly Val Gln Thr Leu Val Pro Ser Asn Cys
    130                 135                 140

Ser Ser Glu Gly Ser Leu Lys Ala Leu Ser Val Gly Ala Arg Lys Phe
145                 150                 155                 160

Met Asn Ala Thr Ser Glu Ser Ala Thr Asn Ala Lys His Arg Phe His
                165                 170                 175

Leu Ser Ser Gly Thr Leu Ala Ser Ile Pro Asp Pro Ile Met Glu Ala
            180                 185                 190

Ala Gly Gly Trp Leu Thr Asp Gln Thr Gly Asn Leu Val Tyr Phe Glu
        195                 200                 205

Arg Lys Val Gly Lys Ala Glu Phe Asp Tyr Ile Val Lys Tyr Gly Leu
    210                 215                 220

Tyr Asp Ala Ala Asn Gln Met Val Val Ala Gln Asn Ser Asp Gly Asn
225                 230                 235                 240

His Pro Ala Gly Leu Ser Leu Pro Ala Gly Glu Leu Met Arg Ser Met
                245                 250                 255

Pro Ala Gln Pro Leu Pro Gln Glu Gln Leu Gly Ala Leu Glu Leu Lys
            260                 265                 270

Ala Ala Trp Arg Ile Leu Thr Gly Lys Pro Gln Leu Tyr Gly Arg Tyr
        275                 280                 285

Leu Thr Thr Val Ala Trp Leu Lys Asn Pro Ala Thr Leu Gln Cys Thr
    290                 295                 300

Gln Gln Val Val Gly Leu Val Gly Leu His Ile Ile Asn Lys Thr Gln
305                 310                 315                 320

Ser Ser Pro Asn Phe Ile Trp Thr Thr Phe Glu Gln Val Asp Asn Val
                325                 330                 335

Gln Glu Pro Gly Gln Val Pro Ala Gln Gln Thr Pro Pro Asp Gly Phe
            340                 345                 350

Thr Phe Tyr Asn Pro Asn Cys Thr Gly Gly Pro Asp Val Cys Thr Pro
        355                 360                 365

Asn Val Ala Arg Ile Gln Cys Gln Gln His His Pro Asp Arg Glu Cys
    370                 375                 380

Thr Glu Pro Tyr Pro Arg Asn Gln Pro Val Gln Thr Thr Arg Glu His
385                 390                 395                 400

Pro Leu Pro Ser Asp Met Gln Ala Leu Asn Gly Ala Val Gln Ala Asn
                405                 410                 415

Phe Ala Gln Gln Thr Asn Gly Gln Ser Val Phe Gln Tyr Tyr Lys Leu
```

```
                    420                 425                 430
Val Asn Val Leu Trp Ile Thr Ala Pro Thr Ala Pro Asp Pro Glu Pro
                435                 440                 445

Gly Ala Gly Ala Lys Val Pro Leu Ser Tyr Gly Ala Phe Ile Ser Asp
    450                 455                 460

Ser Asn Val Pro Val Ala Asn Thr Thr Met Glu Thr Tyr Val Gln Ser
465                 470                 475                 480

Met Asp Cys Asn Ala Cys His Gln Gln Ala Thr Ile Ala Gly Ser Ser
                485                 490                 495

Ser Leu Ala Ser Asp Phe Ser Phe Leu Phe Asn Asn Ala Asp Ser Ala
            500                 505                 510

Lys Gln Lys Ser Leu Ile Lys Arg Val Asn Ala Phe Glu Thr Leu Lys
        515                 520                 525

Asp Gly Pro Pro
        530

<210> SEQ ID NO 23
<211> LENGTH: 577
<212> TYPE: PRT
<213> ORGANISM: Pseudomonas gessardii

<400> SEQUENCE: 23

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asp Val Thr Gly Trp Thr Glu Ala Ala Ile Ile
        35                  40                  45

Gly Asn Pro Trp Ser Gly Leu Tyr Asp Ala Pro Arg Ser Gly Tyr Tyr
    50                  55                  60

Asn Pro Leu Val Glu Gly Tyr Gly Asp Thr Thr Pro Pro Ala Ile Thr
65                  70                  75                  80

Trp Gln Pro Phe Pro Asn Arg Leu Trp Thr Phe Phe Tyr Ser Asn Gly
                85                  90                  95

Thr Ala Val Ile Pro Gln Leu Gly Gly Lys Ala Met Thr Leu Gln Gln
            100                 105                 110

Val Met Glu Leu Thr Asp Asn Gly Gln Ile Thr Ile Asn Asp Thr Leu
        115                 120                 125

Tyr Thr Leu Tyr Asp Pro Asp Lys Lys Gly Thr Leu Leu Gln Leu Pro
    130                 135                 140

Val Thr Arg Cys Pro Ser Ile Asp Trp Asn Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asp Met Arg Lys Ile Thr Phe Thr Ser
            180                 185                 190

Glu Asn Pro Ala Tyr Phe Leu Ala Met Trp Arg Ile Asp Pro Asn Ala
        195                 200                 205

Val Leu Gly Leu Tyr Arg Asp Tyr Ile Asp Pro Asn Val Gln Leu Glu
    210                 215                 220

Asp Leu Tyr Leu Arg Tyr Ala Thr Asp Cys Pro Thr Gly Asn Ala Gly
225                 230                 235                 240

Asp Pro Val Ile Asp Pro Thr Thr Gly Leu Pro Ala Tyr Asp Thr Val
                245                 250                 255
```

Asn Lys Trp Asn Ala Gly Thr Ala Cys Thr Pro Gly Gln Phe Gly
                260                 265                 270

Ala Met His Leu Thr Ser Gly Pro Asn Thr Leu Ser Ala Glu Val Tyr
            275                 280                 285

Leu Ala Ala Ala Ala Thr Ile Met Arg Pro Leu Lys Ser Ser Gln Asn
        290                 295                 300

Pro Gln Ser Leu Ile Cys Cys Ala Gln Tyr Gly Gln Asn Tyr Arg Asn
305                 310                 315                 320

Ser Asp Pro His Ile Gly Phe Ala Ala Asn Glu Ala Ala Ile Ser Asn
                325                 330                 335

Arg Ile Ser Leu Thr Asn Pro Ile Ala Leu Tyr Leu Gln Gln Pro Thr
            340                 345                 350

Asn Phe Ser Ala Trp Lys Gly Pro Gln Gly Gln Asp Val Ser Gln Tyr
        355                 360                 365

Trp Arg Ile Thr Arg Gly Thr Ala Lys Ser Ala Ile Asn Gly Ser Asp
    370                 375                 380

Gln Ile Leu Gln Ala Val Phe Glu Val Pro Gln Ser Ala Gly Phe Ser
385                 390                 395                 400

Ile Asn Asp Ile Thr Ile Asn Gly Gln Ala Val Asp Tyr Val Trp Val
                405                 410                 415

Ile Ala Gln Gln Leu Leu Val Gly Leu Ser Val Thr Val Met Pro Ser
            420                 425                 430

Thr Thr Ala Ala Pro Ser Pro Cys Val Gln Asp Arg Val Asn Gly Leu
        435                 440                 445

Gln Pro Trp Pro Val Gln Leu Leu Pro Leu Asp Leu Phe Tyr Gly Gln
    450                 455                 460

Ser Pro Thr Asp Leu Pro Ala Trp Leu Ala Pro Gly Ser Ser Gly Gln
465                 470                 475                 480

Phe Val Leu Val Val Gln Gly Ala Asp Leu Gln Thr Ala Ala Thr
                485                 490                 495

Ala Arg Ile Gln Phe Ser Asn Pro Gly Val Thr Ala Gln Val Thr Lys
            500                 505                 510

Phe Met Pro Asp Ala Ser Ala Ile Pro Gly Gln Thr Asn Ala Gly Gly
        515                 520                 525

Thr Gln Gly Tyr Ile Met Thr Ile Ser Val Ala Ala Asn Ala Ala Pro
    530                 535                 540

Gly Leu Val Thr Val Arg Ala Leu Asn Pro Gly Glu Ala Asp Asn Val
545                 550                 555                 560

Ser Ala Ala Asp His Pro Trp Glu Ser Gly Leu Ala Leu Val Pro Ser
                565                 570                 575

Thr

<210> SEQ ID NO 24
<211> LENGTH: 532
<212> TYPE: PRT
<213> ORGANISM: Pseudomonas gessardii

<400> SEQUENCE: 24

Met Ser Arg Phe Arg Leu Ser Arg Leu Leu Leu Val Ser Thr Leu Leu
1               5                   10                  15

Ser Leu Phe Ile Leu Pro Leu Ala His Ala Ser Asp Ala Asp Asn Cys
            20                  25                  30

Val Gln Gln Gln Leu Val Phe Asn Pro Lys Ser Gly Gly Phe Met Pro
        35                  40                  45

-continued

Val Asn Asn Phe Asn Thr Thr Gly Gln Ser Phe Met Asn Cys Phe Gly
 50                  55                  60

Trp Gln Leu Phe Ile Ala Leu Asn Trp Pro Val Asp Pro Gly Trp Pro
 65                  70                  75                  80

Ala Asn Ala Ser Leu Ala Gly Glu Pro Asp Arg Thr Ile Thr Val Ala
                 85                  90                  95

Gln Phe Gly Val Pro Thr Thr Ala Gly Gln Pro Met Ser Val Ala Pro
            100                 105                 110

Val Trp Ala Ser Tyr Lys Asp Ala Asn Glu Ile Phe Leu Pro Gly Ala
            115                 120                 125

Pro Lys Pro Ser Gly Trp Gly Val Gln Thr Leu Val Pro Pro Asn Cys
130                 135                 140

Ser Ser Gln Asp Ser Leu Gln Ala Leu Ser Val Gly Ala Arg Lys Phe
145                 150                 155                 160

Met Asn Ala Thr Ser Glu Ser Ala Thr Asn Ala Lys His Arg Phe His
                165                 170                 175

Leu Ser Ser Gly Thr Leu Ala Ser Ile Pro Asp Pro Ile Met Glu Ala
            180                 185                 190

Ala Gly Gly Trp Leu Thr Asp Gln Thr Gly Asn Leu Val Tyr Phe Glu
            195                 200                 205

Arg Lys Val Gly Lys Ala Glu Phe Asp Tyr Ile Val Asp Asn Gly Leu
210                 215                 220

Tyr Asp Ala Ala Asn Gln Leu Ile Val Ala Gln Asn Ser Asp Gly Lys
225                 230                 235                 240

His Pro Ala Gly Leu Ser Leu Pro Ala Gly Glu Leu Met Arg Ser Met
                245                 250                 255

Pro Thr Thr Pro Leu Pro Gln Glu Gln Leu Gly Ala Leu Glu Leu Lys
            260                 265                 270

Ala Ala Trp Arg Ile Leu Thr Gly Gln Pro Gln Leu Tyr Gly Arg Tyr
            275                 280                 285

Leu Thr Thr Val Ala Trp Leu Lys Asn Pro Ala Thr Leu Gln Cys Thr
290                 295                 300

Gln Gln Val Val Gly Leu Val Gly Leu His Ile Ile Asn Lys Thr Gln
305                 310                 315                 320

Ser Ser Pro Asn Phe Ile Trp Thr Thr Phe Glu His Val Asp Asn Val
                325                 330                 335

Pro Glu Pro Gly Gln Val Pro Ala Gln Gln Leu Pro Pro Asp Gly Tyr
            340                 345                 350

Thr Phe Asn Asn Pro Asn Cys Thr Gly Gly Pro Asp Val Cys Thr Pro
            355                 360                 365

Asn Val Ala Arg Ile Gln Cys Lys Gln His His Pro Asp Arg Glu Cys
370                 375                 380

Thr Glu Pro Tyr Pro Arg Asp Gln Pro Val Gln Thr Thr Arg Glu His
385                 390                 395                 400

Pro Leu Ser Ser Asp Met Gln Ala Leu Asn Gly Ala Val Gln Ala Ser
                405                 410                 415

Phe Ala Gln Gln Thr Asn Gly Gln Ser Val Phe Gln Tyr Tyr Lys Leu
            420                 425                 430

Ile Asn Val Leu Trp Ile Thr Ala Pro Thr Pro Asp Pro Glu Pro
            435                 440                 445

Gly Pro Asn Ala Lys Val Pro Leu Ser Tyr Gly Ala Phe Ile Ser Asp
450                 455                 460

Ser Asn Val Pro Val Ala Asn Thr Thr Leu Glu Thr Tyr Val Gln Gly

```
                465                 470                 475                 480
Met Asn Cys Asn Asp Cys His Gln Gln Ala Thr Ile Ala Gly Ser Ala
                    485                 490                 495

Thr Leu Ala Ser Asp Phe Ser Phe Leu Phe Asn Asn Ala Asp Ser Ala
                500                 505                 510

Lys His Thr Ser Leu Ile Lys Arg Val His Ala Phe Glu Thr Leu Lys
            515                 520                 525

Asp Gly Gln Pro
        530

<210> SEQ ID NO 25
<211> LENGTH: 578
<212> TYPE: PRT
<213> ORGANISM: Pseudomonas putida

<400> SEQUENCE: 25

Met Ser Ala Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Leu Thr Gly Trp Thr Glu Ser Ser Ile Ile
        35                  40                  45

Gly Asn Pro Trp Ser Gly Leu Asn Asp Ala Pro Arg Ser Gly Tyr Tyr
50                  55                  60

Asn Pro Leu Val Glu Gly Phe Gly Asp Val Thr Ala Pro Ala Ile Thr
65                  70                  75                  80

Trp Ala Pro Phe Pro Asn Arg Leu Trp Thr Phe Phe Tyr Asn Asn Gly
                85                  90                  95

Ala Ala Val Ile Pro Gln Leu Gly Gly Lys Ala Met Thr Leu Asp Gln
            100                 105                 110

Val Met Ala Leu Thr Asp His Gly Gln Ile Thr Leu Asp Asn Thr Leu
        115                 120                 125

Tyr Met Leu Tyr Asp Pro Asn Lys Gln Gly Thr Val Leu Gln Leu Pro
130                 135                 140

Ala Lys Arg Cys Pro Ser Ile Asp Trp Asn Gly Lys Tyr Thr Ala Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asn Met Arg Lys Ile Thr Phe Thr Cys
            180                 185                 190

Glu Asn Pro Ala Tyr Phe Leu Thr Met Trp Arg Ile Asp Pro Asn Ala
        195                 200                 205

Val Leu Gly Leu Tyr Arg Asp Tyr Ile Asp Pro Asn Val Gln Leu Glu
210                 215                 220

Asp Leu Tyr Leu Arg Tyr Thr Val Asp Cys Pro Thr Gly Lys Ala Gly
225                 230                 235                 240

Asp Pro Val Ile Asp Pro Thr Thr Gly Lys Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Gly Pro Val Ser Ser Gln Asn
290                 295                 300
```

```
Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Thr Thr Ala Val Asn Asn
            325                 330                 335

Arg Leu Ser Leu Thr Asn Pro Ile Gly Leu Tyr Leu Gln Gln Pro Thr
                340                 345                 350

Asp Phe Ser Ala Trp Lys Gly Pro Gln Gly Gln Asp Val Ser Gln Tyr
            355                 360                 365

Trp Arg Ile Thr Arg Gly Thr Ala Lys Ser Ala Ala Asn Gly Ser Asp
            370                 375                 380

Gln Ile Leu Gln Ala Val Phe Glu Val Pro Glu Ser Ala Gly Phe Ser
385                 390                 395                 400

Ile Asn Asp Ile Thr Ile Asn Asn Gln Lys Val Asn Tyr Val Trp Val
                405                 410                 415

Ile Ala Gln Gln Leu Leu Val Gly Leu Ser Val Thr Val Lys Pro Leu
            420                 425                 430

Ser Thr Ala Pro Gln Ala Phe Pro Cys Val Gln Asp Arg Val Ala Gly
                435                 440                 445

Leu Gln Pro Trp Pro Val Gln Leu Leu Pro Leu Asp Leu Phe Tyr Gly
            450                 455                 460

Gln Ser Pro Thr Asp Leu Pro Ala Trp Leu Ala Pro Gly Ser Ser Asn
465                 470                 475                 480

Gln Phe Val Leu Val Val Gln Gly Ala Asp Pro Thr Thr Thr Ala Gln
                485                 490                 495

Asn Ala Arg Val Gln Phe Ser Asn Pro Gly Val Thr Ala Gln Val Thr
            500                 505                 510

Gln Tyr Leu Pro Asp Ala Ser Ala Ile Pro Ser Gln Thr Asn Ser Gly
            515                 520                 525

Gly Thr Gln Ala Tyr Ile Leu Thr Ile Thr Val Ser Pro Ser Ala Ala
530                 535                 540

Pro Gly Leu Val Ala Val Arg Ala Leu Asn Pro Gly Glu Asp Val Asn
545                 550                 555                 560

Val Ser Ala Thr Asp His Pro Trp Glu Ser Gly Leu Ala Leu Val Pro
                565                 570                 575

Gly Ala

<210> SEQ ID NO 26
<211> LENGTH: 534
<212> TYPE: PRT
<213> ORGANISM: Pseudomonas putida

<400> SEQUENCE: 26

Met Ser Arg Ser Arg Leu Ser Leu Leu Ser Leu Leu Cys Gly Ile Leu
1               5                   10                  15

Leu Cys Leu Ser Thr Pro Gln Pro Ala Thr Ala Ala Thr Leu Ser Asp
                20                  25                  30

Ala Asp Thr Cys Val Gln Lys Gln Leu Val Phe Asn Pro Ala Ser Gly
            35                  40                  45

Gly Phe Leu Pro Val Asn Asn Phe Asn Ala Thr Ser Gln Ala Phe Met
        50                  55                  60

Asn Cys Phe Gly Trp Gln Leu Phe Ile Ala Leu Asn Trp Pro Val Asn
65                  70                  75                  80

Pro Gly Trp Pro Ala Thr Ala Ser Leu Ala Gly Glu Pro Asp Met Gln
                85                  90                  95
```

```
Ser Thr Leu Ala Gln Phe Gly Val Pro Ser Ala Pro Gly Gln Pro Met
                100                 105                 110
Ser Val Ala Pro Val Trp Ala Ser Tyr Lys Asp Ala Asn Asp Ile Phe
            115                 120                 125
Leu Pro Gly Ala Pro Thr Pro Thr Gly Trp Gly Val Glu Thr Leu Val
        130                 135                 140
Pro Ser Gly Cys Ser Thr Gln Gly Ser Leu Lys Ala Leu Lys Val Gly
145                 150                 155                 160
Ala Arg Lys Phe Met Asn Ala Thr Ser Glu Gly Ala Ile Asn Ala Leu
                165                 170                 175
His Gly Phe His Leu Ser Thr Gly Thr Leu Ala Ser Ile Pro Asp Pro
            180                 185                 190
Val Met Glu Ala Ser Gly Gly Trp Leu Thr Asp Gln Ala Gly Lys Leu
        195                 200                 205
Val Phe Phe Glu Arg Lys Val Gly Lys Ala Glu Phe Asp Tyr Ile Val
210                 215                 220
Asp Lys Gly Leu Tyr Asp Ala Ala Asn Gln Leu Lys Val Ala Gln Asn
225                 230                 235                 240
Leu Asp Gly Gln Thr Pro Glu Gly Leu Ser Leu Pro Ile Gly Glu Pro
                245                 250                 255
Met Arg Ser Leu Pro Thr Ser Pro Val Pro Gln Glu Gln Leu Gly Ala
            260                 265                 270
Ile Glu Leu Lys Ala Ala Trp Arg Val Leu Thr Gly Lys Pro Glu Leu
        275                 280                 285
Phe Gly Arg Tyr Leu Thr Thr Val Ala Trp Leu Lys Arg Pro Asp Thr
    290                 295                 300
Leu Glu Cys Thr Gln Glu Val Val Gly Leu Val Gly Leu His Ile Ile
305                 310                 315                 320
Asn Lys Thr Gln Ala Ser Pro Asn Phe Ile Trp Thr Thr Phe Glu Gln
                325                 330                 335
Val Asp Asn Val Pro Glu Pro Ala Gln Val Pro Pro Gln Gln Thr Pro
            340                 345                 350
Pro Asn Gly Phe Ala Phe Asn Asn Pro Asp Cys Gly Asp Gly Pro Glu
        355                 360                 365
Cys Thr Pro Asn Gln Ala Arg Ile Gln Cys Lys Gln Thr His Pro Asp
    370                 375                 380
Lys Asp Cys Thr Asp Leu Phe Pro Arg Asp Gln Pro Val Gln Thr Thr
385                 390                 395                 400
Arg Val His Pro Val Pro Gly Asp Leu Gln Ala Leu Asn Ser Ala Val
                405                 410                 415
Gln Ala Asn Phe Ala Gln His Ser Gln Gly Lys Ser Val Phe Gln Tyr
            420                 425                 430
Tyr Lys Leu Ile Asn Val Leu Trp Thr Leu Ala Pro Asn Pro Pro Ser
        435                 440                 445
Pro Glu Pro Gly Ala Asn Ala Gln Val Pro Leu Ser Tyr Gly Pro Phe
    450                 455                 460
Ile Ser Gln Gly Asn Val Pro Val Ala Asn Thr Thr Met Glu Thr Tyr
465                 470                 475                 480
Val Gln Gly Asp Asp Cys Asn Gln Cys His Gln Tyr Ala Thr Ile Ala
                485                 490                 495
Gly Ser Pro Ser Leu Ala Ser Asp Phe Ser Phe Leu Phe Asn Ser Ala
            500                 505                 510
Gly Ser Ala Ser Asn Lys Ser Leu Ile Lys Ser Val Lys Ala Phe Glu
```

Thr Leu Lys Asp Arg Pro
    530

<210> SEQ ID NO 27
<211> LENGTH: 578
<212> TYPE: PRT
<213> ORGANISM: Pseudomonas plecoglossicida

<400> SEQUENCE: 27

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30

Thr Asp Trp Asn Asn Asn Leu Thr Gly Trp Thr Glu Ser Ser Ile Ile
        35                  40                  45

Gly Asn Pro Trp Ser Gly Leu Asn Asp Ala Pro Arg Ser Gly Tyr Tyr
    50                  55                  60

Asn Pro Leu Val Glu Gly Phe Gly Asp Val Thr Ala Pro Ala Ile Thr
65                  70                  75                  80

Trp Ala Pro Phe Pro Asn Arg Leu Trp Thr Phe Phe Tyr Asn Asn Gly
                85                  90                  95

Ala Ala Val Ile Pro Gln Leu Gly Gly Lys Ala Met Thr Leu Asp Gln
            100                 105                 110

Val Met Glu Leu Thr Asp His Gly Gln Ile Thr Leu Asp Asn Thr Leu
        115                 120                 125

Tyr Met Leu Tyr Asp Pro Asn Lys Arg Gly Thr Val Leu Gln Leu Pro
    130                 135                 140

Ala Lys Arg Cys Pro Ser Ile Asp Trp Asn Gly Lys Tyr Thr Ala Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asn Met Arg Lys Ile Thr Phe Thr Cys
            180                 185                 190

Glu Asn Pro Ala Tyr Phe Leu Thr Met Trp Arg Ile Asp Pro Asn Ala
        195                 200                 205

Val Leu Gly Leu Tyr Arg Asp Tyr Ile Asp Pro Asn Val Gln Leu Glu
    210                 215                 220

Asp Leu Tyr Leu Arg Tyr Thr Ala Asp Gly Pro Thr Gly Lys Ala Gly
225                 230                 235                 240

Asp Pro Val Ile Asp Pro Thr Thr Gly Lys Pro Ala Tyr Asp Thr Val
                245                 250                 255

Asn Lys Trp Asn Ala Gly Thr Ala Cys Val Pro Gly Gln Phe Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Arg Pro Val Ser Ser Gln Asn
    290                 295                 300

Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Thr Thr Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
            355                 360                 365

Trp Arg Ile Thr Arg Gly Thr Ala Lys Ser Ala Ala Asn Gly Ser Asp
    370                 375                 380

Gln Ile Leu Gln Ala Val Phe Glu Val Pro Glu Ser Ala Gly Phe Ser
385                 390                 395                 400

Ile Asn Asp Ile Thr Ile Asn Asn Gln Lys Val Asn Tyr Val Trp Val
                405                 410                 415

Ile Ala Gln Gln Leu Leu Val Gly Leu Ser Val Thr Val Lys Pro Leu
            420                 425                 430

Ser Thr Thr Pro Gln Ala Phe Pro Cys Val Gln Asp Arg Val Ala Gly
            435                 440                 445

Leu Gln Pro Trp Pro Val Gln Leu Leu Pro Leu Asp Leu Phe Tyr Gly
    450                 455                 460

Gln Ser Pro Thr Asp Leu Pro Ala Trp Leu Ala Pro Gly Ser Ser Asn
465                 470                 475                 480

Gln Phe Val Leu Val Val Gln Gly Ala Asp Pro Thr Thr Thr Ala Gln
                485                 490                 495

Asn Ala Arg Val Gln Phe Ser Asn Pro Gly Val Thr Ala Gln Val Thr
            500                 505                 510

Gln Tyr Leu Pro Asp Ala Ser Ala Ile Pro Gly Gln Thr Asn Ser Gly
    515                 520                 525

Gly Thr Gln Ala Tyr Ile Leu Thr Ile Thr Val Ser Pro Ser Ala Ala
530                 535                 540

Pro Gly Leu Val Thr Val Arg Ala Leu Asn Pro Gly Glu Asp Val Asn
545                 550                 555                 560

Val Ser Ala Thr Asp His Pro Trp Glu Ser Gly Leu Ala Leu Val Pro
                565                 570                 575

Gly Ala

<210> SEQ ID NO 28
<211> LENGTH: 534
<212> TYPE: PRT
<213> ORGANISM: Pseudomonas plecoglossicida

<400> SEQUENCE: 28

Met Ser Arg Ser Arg Leu Ser Leu Leu Ser Leu Leu Cys Gly Ile Leu
1               5                   10                  15

Leu Cys Leu Ser Thr Leu Gln Pro Ala Thr Ala Ala Thr Leu Ser Asp
            20                  25                  30

Ala Asp Thr Cys Val Gln Gln Leu Val Phe Asn Pro Ala Ser Gly
        35                  40                  45

Gly Phe Leu Pro Val Asn Asn Phe Asn Ala Thr Ser Gln Ala Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Ala Ser Leu Ala Gly Glu Pro Asp Met Gln
                85                  90                  95

Ser Thr Leu Ala Gln Phe Gly Val Pro Ser Ala Pro Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Thr Pro Thr Gly Trp Gly Val Gln Thr Leu Val
    130                 135                 140

```
Pro Ser Gly Cys Ser Thr Gln Gly Ser Leu Lys Ala Leu Lys Val Gly
145                 150                 155                 160

Ala Arg Lys Phe Met Asn Ala Thr Ser Glu Gly Ala Ile Asn Ala Leu
                165                 170                 175

His Gly Phe His Leu Ser Thr Gly Thr Leu Ala Ser Ile Pro Asp Pro
            180                 185                 190

Val Met Glu Ala Ser Gly Gly Trp Leu Thr Asp Gln Ala Gly Lys Leu
        195                 200                 205

Val Phe Phe Glu Arg Lys Val Gly Lys Ala Glu Phe Asp Tyr Ile Val
    210                 215                 220

Asp Lys Gly Leu Tyr Asp Ala Ala Asn Gln Leu Lys Val Ala Gln Asn
225                 230                 235                 240

Leu Asp Gly Gln Thr Pro Glu Gly Leu Ser Leu Pro Ile Gly Glu Pro
                245                 250                 255

Met Arg Ser Leu Pro Thr Ser Pro Val Pro Gln Glu Gln Leu Gly Ala
                260                 265                 270

Ile Glu Leu Lys Ala Ala Trp Arg Val Leu Thr Asp Lys Pro Glu Leu
            275                 280                 285

Phe Gly Arg Tyr Leu Thr Thr Val Ala Trp Leu Lys Arg Pro Asp Thr
        290                 295                 300

Leu Glu Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Ala Gln Val Pro Pro Gln Gln Thr Pro
                340                 345                 350

Pro Asn Gly Phe Ala Phe Asn Asn Pro Asp Cys Gly Asn Gly Pro Glu
            355                 360                 365

Cys Thr Pro Asn Gln Ala Arg Ile Gln Cys Lys Gln Thr His Pro Asp
        370                 375                 380

Lys Asp Cys Thr Asp Leu Phe Pro Arg Asp Gln Pro Val Gln Thr Thr
385                 390                 395                 400

Arg Glu His Pro Val Pro Gly Asp Leu Gln Ala Leu Asn Ser Ala Val
                405                 410                 415

Gln Ala Asn Phe Ala Gln His Ser Gln Gly Lys Ser Val Phe Gln Tyr
                420                 425                 430

Tyr Lys Leu Ile Asn Val Leu Trp Thr Leu Ala Pro Asn Pro Pro Ser
        435                 440                 445

Pro Glu Pro Gly Ala Asn Ala Gln Val Pro Leu Ser Tyr Gly Pro Phe
    450                 455                 460

Ile Ser Gln Gly Asn Val Pro Val Ala Asn Thr Thr Met Glu Thr Tyr
465                 470                 475                 480

Val Gln Gly Asp Asp Cys Asn Gln Cys His Gln Tyr Ala Thr Ile Ala
                485                 490                 495

Gly Ser Pro Ser Leu Ala Ser Asp Phe Ser Phe Leu Phe Asn Ser Ala
                500                 505                 510

Gly Ser Ala Ser Asn Lys Ser Leu Ile Lys Ser Val Lys Ala Phe Glu
            515                 520                 525

Thr Leu Lys Asp Arg Pro
    530
```

<210> SEQ ID NO 29
<211> LENGTH: 578
<212> TYPE: PRT

-continued

<213> ORGANISM: Pseudomonas putida

<400> SEQUENCE: 29

```
Met Ser Thr Pro Phe Lys Gln Phe Thr Ser Pro Ala Gly Gln Ala Pro
1               5                   10                  15
Lys Asp Tyr Asn Lys Leu Gly Leu Glu Asp Gln Leu Pro Gln Phe Glu
            20                  25                  30
Thr Asp Trp Asn Asn Asn Leu Thr Gly Trp Thr Glu Ser Ser Ile Ile
        35                  40                  45
Gly Asn Pro Trp Ser Gly Leu Asn Asp Ala Pro Arg Ser Gly Tyr Tyr
    50                  55                  60
Asn Pro Leu Val Glu Gly Phe Gly Asp Val Thr Ala Pro Ala Ile Thr
65                  70                  75                  80
Trp Ala Pro Phe Pro Asn Arg Leu Trp Thr Phe Phe Tyr Asn Asn Gly
                85                  90                  95
Ala Ala Val Ile Pro Gln Leu Gly Gly Lys Ala Met Thr Leu Asp Gln
            100                 105                 110
Val Met Ala Leu Thr Asp His Gly Gln Ile Thr Leu Asp Asn Thr Leu
        115                 120                 125
Tyr Met Leu Tyr Asp Pro Asn Lys Gln Gly Thr Val Leu Gln Leu Pro
    130                 135                 140
Ala Lys Arg Cys Pro Ser Ile Asp Trp Asn Gly Lys Tyr Thr Ala Phe
145                 150                 155                 160
Ser Pro Ser Gly Pro Arg Gly Trp Leu Asp Glu Tyr Cys Glu Trp Ser
                165                 170                 175
Ile Val Arg Asp Ala Asn Gly Asn Met Arg Lys Ile Thr Phe Thr Cys
            180                 185                 190
Glu Asn Pro Ala Tyr Phe Leu Thr Met Trp Arg Ile Asp Pro Asn Ala
        195                 200                 205
Val Leu Gly Leu Tyr Arg Asp Tyr Ile Asp Pro Asn Val Gln Leu Glu
    210                 215                 220
Asp Leu Tyr Leu Arg Tyr Thr Val Asp Cys Pro Thr Gly Lys Ala Gly
225                 230                 235                 240
Asp Pro Val Ile Asp Pro Thr Thr Gly Lys Pro Ala Tyr Asp Thr Val
                245                 250                 255
Asn Lys Trp Asn Ala Gly Thr Ala Cys Val Pro Gly Gln Tyr Gly Gly
            260                 265                 270
Ala Met His Leu Thr Ser Gly Pro Asn Thr Leu Ser Ala Glu Val Tyr
        275                 280                 285
Leu Ala Ala Ala Thr Ile Leu Arg Pro Val Ser Ser Gln Asn
    290                 295                 300
Ala Gln Ser Leu Ile Cys Cys Ala Gln Tyr Gly Gln Asn Tyr Arg Asn
305                 310                 315                 320
Ser Asp Pro His Ile Gly Phe Met Ala Asn Thr Thr Ala Val Asn Asn
                325                 330                 335
Arg Leu Ser Leu Thr Asn Pro Ile Gly Leu Tyr Leu Gln Gln Pro Thr
            340                 345                 350
Asp Phe Ser Ala Trp Lys Gly Pro Gln Gly Gln Asp Val Ser Gln Tyr
        355                 360                 365
Trp Arg Ile Thr Arg Gly Thr Ala Lys Ser Ala Ala Asn Gly Ser Asp
    370                 375                 380
Gln Ile Leu Gln Ala Val Phe Glu Val Pro Glu Ser Ala Gly Phe Ser
385                 390                 395                 400
```

-continued

```
Ile Asn Asp Ile Thr Ile Asn Asn Gln Lys Val Asn Tyr Val Trp Val
                405                 410                 415
Ile Ala Gln Gln Leu Leu Val Gly Leu Ser Val Thr Val Lys Pro Leu
            420                 425                 430
Ser Thr Ala Pro Gln Ala Phe Pro Cys Val Gln Asp Arg Val Ala Gly
        435                 440                 445
Leu Gln Pro Trp Pro Val Gln Leu Leu Pro Leu Asp Leu Phe Tyr Gly
    450                 455                 460
Gln Ser Pro Thr Asp Leu Pro Ala Trp Leu Ala Pro Gly Ser Ser Asn
465                 470                 475                 480
Gln Phe Val Leu Val Gln Gly Ala Asp Pro Thr Thr Ala Gln
            485                 490                 495
Asn Ala Arg Val Gln Phe Ser Asn Pro Gly Val Thr Ala Gln Val Thr
            500                 505                 510
Gln Tyr Leu Pro Asp Ala Ser Ala Ile Pro Gly Gln Thr Asn Ser Gly
        515                 520                 525
Gly Thr Gln Ala Tyr Ile Leu Thr Ile Thr Val Ser Pro Ser Ala Ala
    530                 535                 540
Pro Gly Leu Val Ala Val Arg Ala Leu Asn Pro Gly Glu Asp Val Asn
545                 550                 555                 560
Val Ser Ala Thr Asp His Pro Trp Glu Ser Gly Leu Ala Leu Val Pro
            565                 570                 575
Gly Ala

<210> SEQ ID NO 30
<211> LENGTH: 534
<212> TYPE: PRT
<213> ORGANISM: Pseudomonas putida

<400> SEQUENCE: 30

Met Ser Arg Ser Arg Leu Ser Leu Leu Ser Leu Leu Cys Gly Ile Leu
1               5                   10                  15
Leu Cys Leu Ser Thr Pro Gln Pro Ala Thr Ala Ala Thr Leu Ser Asp
            20                  25                  30
Ala Asp Thr Cys Val Gln Lys Gln Leu Val Phe Asn Pro Ala Ser Gly
        35                  40                  45
Gly Phe Leu Pro Val Asn Asn Phe Asn Ala Thr Ser Gln Ala Phe Met
    50                  55                  60
Asn Cys Phe Gly Trp Gln Leu Phe Ile Ala Leu Asn Trp Pro Val Asn
65                  70                  75                  80
Pro Gly Trp Pro Ala Thr Ala Ser Leu Ala Gly Glu Pro Asp Met Gln
            85                  90                  95
Ser Thr Leu Ala Gln Phe Gly Val Pro Ser Thr Pro Gly Gln Pro Met
            100                 105                 110
Ser Val Ala Pro Val Trp Ala Ser Tyr Lys Asp Ala Asn Asp Ile Phe
        115                 120                 125
Leu Pro Gly Ala Pro Thr Pro Thr Gly Trp Gly Val Gln Thr Leu Val
    130                 135                 140
Pro Ser Asp Cys Ser Thr Gln Gly Ser Leu Lys Thr Leu Lys Val Gly
145                 150                 155                 160
Ala Arg Lys Phe Met Asn Ala Thr Ser Glu Gly Ala Ile Asn Ala Leu
                165                 170                 175
His Gly Phe His Leu Ser Thr Gly Thr Leu Ala Ser Ile Pro Asp Pro
            180                 185                 190
```

```
Val Met Glu Ala Ser Gly Gly Trp Leu Thr Asp Gln Ala Gly Lys Leu
        195                 200                 205

Val Phe Phe Glu Arg Lys Val Gly Lys Ala Glu Phe Asp Tyr Ile Val
    210                 215                 220

Asp Lys Gly Leu Tyr Asp Ala Asn Gln Leu Lys Val Ala Arg Asn
225                 230                 235                 240

Leu Asp Gly Gln Thr Pro Glu Gly Leu Ser Leu Pro Ile Gly Glu Pro
                245                 250                 255

Met Arg Ser Leu Pro Thr Ser Pro Val Pro Gln Glu Gln Leu Gly Ala
                260                 265                 270

Ile Glu Leu Lys Ala Ala Trp Arg Val Leu Thr Gly Lys Pro Glu Leu
            275                 280                 285

Phe Gly Arg Tyr Leu Thr Thr Val Ala Trp Leu Lys Arg Pro Asp Thr
    290                 295                 300

Leu Glu Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Ala Gln Val Pro Pro Gln Gln Thr Pro
                340                 345                 350

Pro Asn Gly Phe Ala Phe Asn Asn Pro Asp Cys Gly Asn Gly Pro Glu
            355                 360                 365

Cys Thr Pro Asn Gln Ala Arg Ile Gln Cys Lys Gln Thr His Pro Asp
    370                 375                 380

Lys Asp Cys Thr Asp Leu Phe Pro Arg Asp Gln Pro Val Gln Thr Thr
385                 390                 395                 400

Arg Glu His Pro Val Pro Gly Asp Leu Gln Ala Leu Asn Ser Ala Val
                405                 410                 415

Gln Ala Asn Phe Ala Gln His Ser Gln Gly Lys Ser Val Phe Gln Tyr
            420                 425                 430

Tyr Lys Leu Val Asn Val Leu Trp Thr Leu Ala Pro Asn Pro Pro Ser
    435                 440                 445

Pro Glu Pro Gly Ala Asn Ala Gln Val Pro Leu Ser Tyr Gly Pro Phe
450                 455                 460

Ile Ser Gln Gly Asn Val Pro Val Ala Asn Thr Thr Met Glu Thr Tyr
465                 470                 475                 480

Val Gln Gly Asp Asn Cys Asn Gln Cys His Gln Tyr Ala Thr Ile Ala
                485                 490                 495

Gly Ser Pro Ser Leu Ala Ser Asp Phe Ser Phe Leu Phe Asn Ser Ala
            500                 505                 510

Gly Ser Ala Ser Asn Lys Ser Leu Ile Lys Ser Val Lys Ala Phe Glu
    515                 520                 525

Thr Leu Lys Asp Arg Pro
    530

<210> SEQ ID NO 31
<211> LENGTH: 578
<212> TYPE: PRT
<213> ORGANISM: Pseudomonas putida

<400> SEQUENCE: 31

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Pro Gln Phe Glu
            20                  25                  30
```

```
Thr Asp Trp Asn Asn Asn Leu Thr Gly Trp Thr Glu Ser Ser Ile Ile
        35                  40                  45

Gly Asn Pro Trp Ser Gly Leu Asn Asp Ala Pro Arg Ser Gly Tyr Tyr
 50                  55                  60

Asn Pro Leu Val Glu Gly Phe Gly Asp Val Thr Pro Pro Ala Ile Thr
 65                  70                  75                  80

Trp Ala Pro Phe Pro Asn Arg Leu Trp Thr Phe Phe Tyr Asn Asn Gly
                 85                  90                  95

Thr Ala Val Ile Pro Gln Leu Gly Gly Lys Ala Met Thr Leu Asp Gln
                100                 105                 110

Val Met Glu Leu Ala Asp His Gly Gln Ile Ser Leu Asp Asn Thr Val
            115                 120                 125

Tyr Arg Leu Tyr Asp Pro Asn Lys Gln Gly Asn Leu Leu Gln Leu Pro
    130                 135                 140

Ala Lys Arg Cys Pro Ser Ile Ala Trp Asn Gly Pro Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Gly Asn Gly Lys Met Arg Lys Ile Thr Phe Thr Cys
            180                 185                 190

Glu Asn Pro Ala Tyr Phe Leu Thr Met Trp Arg Ile Asp Pro Asn Ala
    195                 200                 205

Val Leu Gly Leu Tyr Arg Glu Tyr Ile Asp Pro Asn Val Gln Leu Glu
        210                 215                 220

Asp Leu Tyr Leu Arg Tyr Thr Glu Asp Gly Pro Thr Gly Lys Ala Gly
225                 230                 235                 240

Glu Pro Val Ile Asp Pro Thr Thr Gly Lys Pro Ala Tyr Asp Thr Val
                245                 250                 255

Asn Lys Trp Asn Ala Gly Thr Val Ser Val Pro Gly Gln Tyr Gly Gly
            260                 265                 270

Ala Met His Leu Thr Ser Gly Pro Asn Thr Leu Ser Ala Glu Val Tyr
    275                 280                 285

Leu Ala Ala Ala Thr Ile Leu Arg Pro Val Ser Ser Ser Gln Asn
        290                 295                 300

Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Ser Thr Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Thr Trp Lys Gly Pro Gln Gly Gln Asp Val Ser Gln Tyr
    355                 360                 365

Trp His Ile Thr Arg Gly Ala Ala Lys Ser Ala Ala Asn Gly Ser Asp
        370                 375                 380

Gln Ile Leu Gln Ala Val Phe Glu Ile Pro Glu Ser Ala Gly Phe Ser
385                 390                 395                 400

Ile Asn Glu Val Thr Ile Asn Lys Gln Pro Val Asn His Val Trp Val
                405                 410                 415

Ile Ala Gln Gln Leu Leu Val Gly Leu Ser Val Thr Val Lys Pro Leu
            420                 425                 430

Ala Ala Thr Pro Ala Ser Tyr Pro Cys Val Gln Asp Arg Val Ala Gly
    435                 440                 445
```

```
Leu Gln Pro Trp Pro Val Gln Leu Pro Leu Asp Leu Phe Tyr Gly
450                 455                 460

Asn Ser Pro Thr Asp Leu Pro Ala Trp Leu Ala Pro Gly Ser Ser Asn
465                 470                 475                 480

Gln Phe Val Leu Val Gln Gly Ala Asp Glu Asn Thr Thr Ala Glu
            485                 490                 495

Asn Ala Arg Val Gln Phe Ser Asn Pro Gly Val Thr Ala Gln Val Thr
                500                 505                 510

Gln Tyr Leu Pro Asp Ala Thr Ala Ile Pro Gly Gln Thr Asn Thr Gly
            515                 520                 525

Gly Thr Gln Ala Tyr Ile Leu Thr Ile Thr Val Ser Pro Thr Ala Ala
            530                 535                 540

Pro Gly Leu Val Thr Val Arg Ala Leu Asn Pro Asp Glu Asp Ala Asn
545                 550                 555                 560

Val Ser Ala Ala Asp His Pro Trp Glu Ser Gly Leu Ala Leu Val Pro
                565                 570                 575

Gly Ala

<210> SEQ ID NO 32
<211> LENGTH: 534
<212> TYPE: PRT
<213> ORGANISM: Pseudomonas putida

<400> SEQUENCE: 32

Met Ser Ser Leu Arg Leu Ser Leu Leu Ser Leu Leu Ser Gly Ile Leu
1               5                   10                  15

Leu Cys Leu Ser Ala Gln Gln Thr Ala Thr Ala Ala Thr Gln Ser Asp
                20                  25                  30

Ala Asp Ser Cys Val Gln Gln Gln Leu Val Phe Asn Pro Ala Ser Gly
            35                  40                  45

Gly Phe Leu Pro Val Asn Asn Phe Asn Ala Thr Ser Gln Ala Phe Met
        50                  55                  60

Asn Cys Phe Ala Trp Gln Leu Phe Ile Ala Leu Asn Trp Pro Val Asn
65                  70                  75                  80

Leu Gly Trp Pro Gly Thr Ala Ser Leu Ala Gly Glu Pro Asp Leu Asn
                85                  90                  95

Ser Ser Leu Ala Gln Phe Gly Val Pro Ala Thr Pro Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Thr Pro Ser Gly Trp Gly Val Gln Thr Leu Val
    130                 135                 140

Pro Ala Asn Cys Ser Thr Gln Gly Ser Leu Lys Ala Leu Lys Val Gly
145                 150                 155                 160

Ala Arg Lys Phe Met Asn Ala Thr Ser Lys Ser Ala Ile Asn Val Leu
                165                 170                 175

His Gly Phe His Leu Ser Ser Gly Thr Leu Ala Ser Ser Pro Asp Pro
            180                 185                 190

Phe Met Glu Ala Ser Gly Gly Trp Leu Thr Asp Gln Ser Gly Asn Leu
        195                 200                 205

Val Phe Phe Glu Arg Lys Val Gly Lys Ala Glu Phe Asp Tyr Ile Val
    210                 215                 220

Asp Asn Gly Leu Tyr Asp Ala Ala Asn Gln Leu Lys Val Ala Gln Asn
225                 230                 235                 240
```

Gln Asp Gly Lys Ser Pro Ala Gly Leu Ser Leu Pro Ala Gly Glu Pro
            245                 250                 255

Met Arg Ser Leu Pro Ala Ala Pro Val Pro Gln Glu Gln Leu Gly Ala
        260                 265                 270

Ile Glu Val Lys Ala Ala Trp Arg Val Leu Thr Gly Lys Pro Glu Leu
    275                 280                 285

Phe Gly Arg Tyr Leu Thr Thr Val Ala Trp Leu Lys Arg Pro Asp Thr
290                 295                 300

Leu Ala Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Ala Gln Ala Pro Pro Gln Gln Thr Pro
            340                 345                 350

Pro Asn Gly Phe Ala Phe Asn Asn Pro Asp Cys Gly Ser Gly Pro Glu
        355                 360                 365

Cys Thr Pro Asn Gln Ala Arg Ile Gln Cys Lys Gln His His Pro Asp
    370                 375                 380

Lys Asp Cys Thr Asp Arg Phe Pro Arg Asp Gln Pro Val Gln Thr Thr
385                 390                 395                 400

Arg Glu His Pro Val Pro Gly Asp Leu Gln Ala Leu Asn Ser Ala Val
                405                 410                 415

Gln Ala Asn Phe Ala Gln His Ser Gln Gly Ser Val Phe Gln Tyr
            420                 425                 430

Tyr Lys Leu Ile Asn Val Leu Trp Thr Leu Ala Pro Asn Pro Pro Ser
        435                 440                 445

Pro Glu Pro Gly Ala Asn Ala Gln Val Pro Leu Ser Tyr Gly Pro Phe
    450                 455                 460

Ile Ser Gln Gly Asn Val Pro Val Ala Asn Thr Thr Leu Glu Thr Tyr
465                 470                 475                 480

Val Gln Gly Asp Asp Cys Asn Gln Cys His Gly Tyr Ala Thr Ile Ala
                485                 490                 495

Gly Ser Pro Ser Leu Ala Ser Asp Phe Ser Phe Leu Phe Asn Ser Ala
            500                 505                 510

Asp Ser Ala Ser Asn Lys Ser Leu Ile Lys Ser Val Lys Ala Phe Glu
        515                 520                 525

Thr Leu Lys Asp Leu Pro
        530

<210> SEQ ID NO 33
<211> LENGTH: 578
<212> TYPE: PRT
<213> ORGANISM: Pseudomonas monteilii

<400> SEQUENCE: 33

Met Ser Thr Pro Phe Asn Gln Phe Thr Ser Pro Ala Glu Gln Ala Pro
1               5                   10                  15

Lys Asp Tyr Asn Lys Leu Gly Leu Glu Asn Gln Leu Pro Gln Phe Glu
            20                  25                  30

Ser Asp Trp Asn Asn Tyr Leu Thr Gly Trp Thr Glu Ser Ser Ile Ile
        35                  40                  45

Gly Asn Pro Trp Ser Ser Leu Tyr Asp Ala Pro Arg Ser Gly Tyr Tyr
    50                  55                  60

Asn Pro Leu Val Glu Gly Phe Gly Asp Val Val Val Pro Ala Ile Thr
65                  70                  75                  80

```
Trp Ala Pro Phe Pro Asn Arg Leu Trp Thr Phe Phe Tyr Asn Asn Gly
                85                  90                  95

Ala Ala Val Ile Pro Gln Leu Gly Gly Lys Ala Met Thr Leu Gln Gln
            100                 105                 110

Val Met Glu Leu Ala Asp Tyr Gly Gln Ile Thr Leu Asn Asp Thr Leu
        115                 120                 125

Tyr Thr Leu Tyr Asp Pro Asp Asn Lys Gly Thr Leu Leu Gln Leu Pro
    130                 135                 140

Ala Lys Arg Cys Pro Ser Ile Asp Trp Asn Gly Lys Tyr Thr Ala Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asn Gly Asn Met Arg Lys Ile Thr Phe Thr Cys
            180                 185                 190

Glu Asn Pro Ala Tyr Tyr Leu Ala Met Trp Arg Ile Asp Pro Asn Ala
        195                 200                 205

Val Leu Gly Leu Tyr Arg Glu Tyr Ile Asp Pro Asn Val Gln Leu Glu
    210                 215                 220

Asp Leu Tyr Leu Arg Tyr Thr Val Asp Cys Pro Thr Gly Lys Ala Gly
225                 230                 235                 240

Asp Pro Val Ile Asp Pro Thr Thr Gly Leu Pro Ala Tyr Asp Thr Val
                245                 250                 255

Asn Lys Trp Asn Ala Gly Thr Ala Cys Val Pro Gly Gln Phe Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Arg Pro Val Thr Ser Ser Gln Asn
    290                 295                 300

Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Ser Lys Ala Val Asn Asn
                325                 330                 335

Arg Leu Ser Leu Thr Asn Pro Ile Gly Leu Tyr Leu Gln Gln Pro Thr
            340                 345                 350

Asp Phe Ser Thr Trp Lys Gly Pro Gln Gly Gln Asp Val Ser Gln Tyr
        355                 360                 365

Trp Arg Val Thr Arg Gly Thr Ala Lys Ser Ala Ala Asn Gly Ser Asp
    370                 375                 380

Gln Ile Leu Gln Ala Val Phe Glu Val Pro Glu Ser Ala Gly Phe Ser
385                 390                 395                 400

Ile Asn Glu Ile Thr Ile Asn Lys Gln Pro Val Asp Tyr Val Trp Val
                405                 410                 415

Ile Ala Gln Gln Leu Leu Val Gly Leu Ser Val Ser Ala Leu Pro Pro
            420                 425                 430

Ala Thr Thr Pro Pro Ser Phe Pro Cys Val Gln Asp Arg Val Thr Gly
        435                 440                 445

Leu Gln Pro Trp Pro Val Gln Leu Leu Pro Leu Asp Leu Phe Tyr Gly
    450                 455                 460

Gln Ser Pro Thr Asp Leu Pro Ala Cys Leu Ala Pro Gly Ser Ser Asn
465                 470                 475                 480

Gln Phe Val Leu Val Val Gln Gly Ala Asp Pro Asn Thr Thr Ala Gln
                485                 490                 495
```

```
Ser Ala Arg Val Gln Phe Ser Asn Pro Gly Ile Ser Ala Gln Val Thr
            500                 505                 510

Gln Phe Leu Pro Asp Ala Ser Ala Ile Pro Gly Gln Thr Asn Ala Gly
        515                 520                 525

Gly Thr Gln Ala Tyr Ile Leu Thr Ile Thr Val Ser Pro Ser Ala Ala
    530                 535                 540

Pro Gly Leu Val Thr Val Arg Ala Leu Asn Pro Gly Glu Asp Gly Asn
545                 550                 555                 560

Val Ser Ala Ala Asp His Pro Trp Glu Ser Gly Leu Ala Leu Val Pro
                565                 570                 575

Gly Ala

<210> SEQ ID NO 34
<211> LENGTH: 534
<212> TYPE: PRT
<213> ORGANISM: Pseudomonas monteilii

<400> SEQUENCE: 34

Met Ser Arg Leu Arg Leu Ser Leu Leu Ser Leu Ser Gly Met Leu
1               5                   10                  15

Leu Cys Leu Ser Thr Leu Pro Ala Ala Thr Ala Ala Pro Met Thr Glu
            20                  25                  30

Ala Asp Ala Cys Val Gln Gln Gln Leu Val Phe Asn Pro Ala Ser Gly
        35                  40                  45

Gly Phe Leu Pro Val Asn Asn Phe Asn Ala Ser Asn Gln Ala Phe Met
    50                  55                  60

Asn Cys Phe Ala Trp Gln Leu Phe Ile Ala Leu Asn Trp Pro Val Asn
65                  70                  75                  80

Pro Gly Trp Pro Ala Thr Ala Ser Leu Ala Gly Glu Pro Asp Met Asn
                85                  90                  95

Ser Thr Leu Ala Gln Phe Gly Val Pro Ser Asp Pro Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Lys Pro Ser Gly Trp Gly Val Gln Thr Leu Val
    130                 135                 140

Pro Ser Gly Cys Gly Thr Gln Gly Ser Leu Lys Ala Leu Lys Val Gly
145                 150                 155                 160

Ala Arg Lys Phe Met Asn Ala Thr Ser Glu Ser Ala Ile Asn Ala Val
                165                 170                 175

His Gly Phe His Leu Ser Ser Gly Thr Leu Ala Ser Leu Pro Asp Ser
            180                 185                 190

Ile Met Glu Ala Ser Gly Gly Trp Leu Thr Asp Gln Ala Gly Asn Leu
        195                 200                 205

Val Phe Phe Glu Arg Lys Val Gly Lys Ala Glu Phe Asp Tyr Ile Val
    210                 215                 220

Gly Lys Gly Leu Tyr Asp Ala Ala Asn Gln Leu Lys Val Ala Gln Asn
225                 230                 235                 240

Ala Asp Gly Thr Thr Pro Glu Gly Leu Ser Leu Pro Ile Gly Glu Pro
                245                 250                 255

Met Arg Ser Leu Pro Pro Ser Pro Val Pro Gln Glu Gln Leu Gly Ala
            260                 265                 270

Ile Glu Leu Lys Ala Ala Trp Arg Ile Leu Thr Gly Lys Pro Glu Leu
        275                 280                 285
```

```
Phe Gly Arg Tyr Leu Thr Thr Val Ala Trp Leu Lys Arg Pro Asp Thr
        290                 295                 300

Leu Thr Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Gly Gln Val Pro Pro Gln Gln Thr Pro
            340                 345                 350

Pro Asn Gly Phe Ala Phe Asn Asn Pro Asp Cys Gly Ser Gly Pro Glu
        355                 360                 365

Cys Glu Pro Asn Gln Pro Arg Ile Gln Cys Lys Gln His His Pro Asp
370                 375                 380

Arg Asp Cys Thr Asp Leu Phe Pro Arg Asp Gln Pro Val Gln Thr Thr
385                 390                 395                 400

Arg Glu His Pro Val Pro Ser Asp Leu Gln Ala Leu Asn Gly Ala Val
                405                 410                 415

Gln Ala Thr Phe Ala Gln His Ser Gln Gly Lys Ser Val Phe Gln Tyr
            420                 425                 430

Tyr Lys Leu Ile Asn Val Leu Trp Thr Leu Ala Pro Asn Pro Pro Ser
        435                 440                 445

Pro Glu Pro Gly Ala Asn Ala Pro Val Pro Leu Ser Tyr Gly Ala Tyr
450                 455                 460

Ile Ser Gln Gly Asn Val Pro Val Ala Asn Thr Thr Leu Glu Thr Tyr
465                 470                 475                 480

Val Gln Gly Asp Asp Cys Asn Gln Cys His Gln Tyr Ala Thr Ile Ala
                485                 490                 495

Gly Ser Ser Ser Leu Ala Ser Asp Phe Ser Phe Leu Phe Asn Ser Ala
            500                 505                 510

Ser Ser Ala Ser Lys His Ser Leu Ile Lys Arg Val Gln Ala Phe Glu
        515                 520                 525

Thr Leu Lys Asp Arg Arg
        530

<210> SEQ ID NO 35
<211> LENGTH: 577
<212> TYPE: PRT
<213> ORGANISM: Pseudomonas poae

<400> SEQUENCE: 35

Met Ser Thr Pro Phe Thr Gln Phe Thr Ser Pro Ala Glu Gln Ala Pro
1               5                   10                  15

Lys Asp Tyr Asn Lys Leu Gly Leu Glu Asp Gln Leu Pro Ala Phe Glu
            20                  25                  30

Thr Asp Trp Asn Asn Val Thr Gly Trp Thr Gln Met Ser Ile Ile
        35                  40                  45

Gly Asn Pro Trp Ser Asn Leu Asn Asp Ala Pro Arg Ser Gly Tyr Tyr
    50                  55                  60

Asn Pro Leu Glu Ser Gly Tyr Gly Thr Leu Thr Pro Lys Thr Ile Thr
65                  70                  75                  80

Trp Gln Pro Phe Pro Asn Arg Leu Trp Thr Phe Phe Tyr Asn Glu Gly
                85                  90                  95

Ala Ala Val Val Pro Gln Leu Gly Gly Lys Ala Met Thr Leu Asp Gln
            100                 105                 110

Val Met Gln Leu Thr Asp His Gly Gln Ile Thr Leu Asn Asp Thr Leu
        115                 120                 125
```

```
Tyr Ser Leu Tyr Pro Asp Pro Lys Ala Thr Gln Leu Gln Ile Pro Ser
    130                 135                 140

Val Leu Cys Lys Ser Ile Asn Trp Asn Gly Pro Tyr Ala Asp Phe Ser
145                 150                 155                 160

Pro Ser Gly Pro Arg Gly Trp Leu Asp Glu Tyr Cys Glu Trp Ser Ile
                165                 170                 175

Thr Arg Asp Pro Asp Gly Asn Met Arg Ser Ile Met Phe Thr Ser Glu
            180                 185                 190

Asn Pro Ala Tyr Phe Leu Thr Met Trp Asn Ile Asp Pro Gly Ala Val
        195                 200                 205

Leu Gly Leu Tyr Gln Ala Tyr Val Asp Pro Gln Val Lys Leu Glu Asp
    210                 215                 220

Leu Tyr Leu Arg Tyr Thr Ala Asp Gly Pro Thr Gly Lys Ala Gly Glu
225                 230                 235                 240

Pro Val Leu Asp Pro Thr Thr Gly Gln Pro Ala Tyr Asp Thr Val Asn
                245                 250                 255

Lys Trp Asn Ser Gly Thr Val Arg Ile Pro Gly Val Ser Gly Gly Ala
            260                 265                 270

Met His Leu Thr Ser Gly Pro Asn Thr Leu Ser Ala Glu Ile Tyr Leu
        275                 280                 285

Ala Ala Ala Ala Thr Ile Leu Arg Pro Leu Thr Ser Ser Gln Asn Gln
    290                 295                 300

Gln Ser Leu Ile Cys Cys Ala Gln Tyr Gly Gln Asn Tyr Arg Asn Ser
305                 310                 315                 320

Asp Pro His Ile Gly Phe Ser Ala Asn Gln Ala Ala Val Asn Asn Leu
                325                 330                 335

Ile Ser Leu Thr Asn Pro Ile Gly Leu Tyr Leu Gln Gln Pro Lys Ser
            340                 345                 350

Phe Ser Thr Trp Lys Gly Pro Gln Gly Gln Asp Val Ser Ser Tyr Trp
        355                 360                 365

Arg Val Thr Arg Gly Thr Ala Gly Thr Gly Pro Asn Asn Ser Asp Gln
    370                 375                 380

Ile Leu Gln Ala Val Phe Glu Val Pro Ala Ser Ala Gly Phe Ser Ile
385                 390                 395                 400

Asn Glu Ile Thr Ile Asn Gly Thr Pro Ile Asp Tyr Val Trp Val Ile
                405                 410                 415

Ala Asn Glu Leu Asn Val Ala Leu Ser Val Thr Pro Ala Pro Leu Thr
            420                 425                 430

Ala Gln Pro Lys Glu Cys Ala Cys Val Ala Ala Asn Thr Thr Asp Ala
        435                 440                 445

Gln Pro Trp Pro Val Gln Leu Leu Pro Ile Asp Leu Phe Tyr Gly Gln
    450                 455                 460

Ser Pro Ser Asp Leu Pro Ala Ser Phe Ala Pro Gly Ser Ser Gly Gln
465                 470                 475                 480

Phe Val Leu Val Val Gln Gly Ala Asp Pro Asn Thr Thr Ala Ala Asp
                485                 490                 495

Ala Arg Val Gln Phe Ser Asn Pro Gly Ile Thr Ala Gln Val Thr Gln
            500                 505                 510

Phe Leu Pro Asp Ala Ser Ala Ile Pro Gly Gln Thr Asp Gly Gly Gly
        515                 520                 525

Thr Gln Gly Tyr Ile Met Thr Ile Thr Val Ser Ser Asn Ala Ala Pro
    530                 535                 540
```

```
Gly Leu Val Ser Val Arg Ala Leu Asn Pro Ser Glu Ala Ala Asn Pro
545                 550                 555                 560

Ser Ala Ser Glu His Pro Trp Glu Ser Gly Leu Ala Leu Val Pro Ser
                565                 570                 575

Ala

<210> SEQ ID NO 36
<211> LENGTH: 529
<212> TYPE: PRT
<213> ORGANISM: Pseudomonas poae

<400> SEQUENCE: 36

Met Asn Gly Trp Leu Arg Pro Leu Arg Arg Ala Arg Leu Arg Ile Ala
1               5                   10                  15

Cys Ala Ile Thr Cys Thr Leu Leu Pro Leu Leu Ala Ala Thr Pro Ala
                20                  25                  30

Asn Ala Ala Ser Asp Ala Gln Ser Cys Val Ser Gln Leu Val Phe Asp
            35                  40                  45

Pro Thr Ser Gly Gly Phe Leu Pro Val Asn Asn Phe Gly Thr Glu Gln
        50                  55                  60

Ala Phe Leu Asn Cys Phe Gly Trp Gln Leu Phe Ile Ala Met Asn Trp
65                  70                  75                  80

Pro Val Asn Pro Gly Trp Pro Ala Asn Pro Ser Leu Ala Gly Glu Pro
                85                  90                  95

Asp Thr Gln Ser Ser Ala Ala Gln Phe Gly Val Pro Pro Thr Pro Gly
            100                 105                 110

Gln Pro Met Ser Asn Ala Pro Val Trp Ala Ser Tyr Lys Asp Ala Ser
        115                 120                 125

Glu Ile Phe Leu Pro Gly Ala Ala Lys Pro Ser Gly Trp Gly Val Glu
130                 135                 140

Thr Leu Val Pro Ser Asn Cys Thr Ala Thr Gly Asn Leu Lys Ala Phe
145                 150                 155                 160

Ala Thr Gly Ala Arg Lys Phe Ile Thr Ala Thr Ser Glu Ser Ala Ile
                165                 170                 175

Asn Arg Lys His Arg Phe His Leu Ser Ser Gly Thr Gln Val Thr Leu
            180                 185                 190

Pro Asp Ser Ile Met Glu Ala Ser Gly Gly Trp Leu Thr Asp Gln Ser
        195                 200                 205

Gly Asn Leu Val Phe Phe Glu Arg Lys Val Gly Lys Ala Glu Phe Asp
210                 215                 220

Tyr Ile Val Asp Asn Gly Leu Tyr Asp Ala Ala Asn Gln Leu Ile Val
225                 230                 235                 240

Ala Gln Asn Ser Asp Asn Arg His Pro Ala Gly Leu Ser Leu Pro Ala
                245                 250                 255

Gly Lys Pro Val Arg Glu Leu Pro Ala Lys Ala Leu Pro Gln Glu Glu
            260                 265                 270

Leu Gly Ala Leu Glu Leu Lys Ala Trp Arg Val Leu Thr Asn Lys
        275                 280                 285

Pro Asp Leu Tyr Gly Arg Tyr Leu Thr Thr Val Ala Trp Leu Gln Arg
290                 295                 300

Pro Asp Thr Leu Gln Cys Thr Gln Glu Val Ile Gly Leu Val Gly Leu
305                 310                 315                 320

His Ile Ile Asn Lys Thr Gln Thr Gln Pro Asn Phe Ile Trp Thr Thr
                325                 330                 335
```

```
Phe Glu Gln Ile Asp Asn Val Pro Asp Gly Ala Ala Pro Pro Gln
                340                 345                 350

Gly Tyr Ser Phe Asn Asn Pro Glu Cys Thr Gly Asp Ala Cys Ala Pro
            355                 360                 365

Asn Val Ala Arg Val Gln Cys Asp Ala Thr His Thr Pro Pro Asp Cys
        370                 375                 380

Thr Pro Leu Asp Gln Pro Val Gln Ala Thr Arg Leu Asn Ala Thr Pro
385                 390                 395                 400

Gln Asp Met Gln Ala Leu Asn Thr Ala Val Gln Thr Phe Ala Gln
                405                 410                 415

Gln Thr Gln Gly Gln Ser Val Phe Gln Tyr Tyr Lys Leu Val Asn Val
            420                 425                 430

Leu Trp Ser Lys Thr Pro Asn Ala Pro Asn Asp Pro Gly Pro Gly Pro
        435                 440                 445

Asn Val Lys Val Pro Leu Ser Tyr Gly Pro Phe Val Ser Asp Gln Ser
        450                 455                 460

Val Val Val Ala Asn Thr Thr Met Glu Thr Tyr Val Gly Thr Asp Asn
465                 470                 475                 480

Cys Asn Asp Cys His Gln Tyr Ala Ala Ile Ala Gly Lys Ser Gly Leu
                485                 490                 495

Ala Ser Asp Phe Ser Phe Leu Phe Gly Asn Ala Asp Ser Ala Lys Asn
            500                 505                 510

Thr Arg Leu Ile Lys Arg Ile Glu Ser Phe Lys Thr Leu Lys Asp Asn
        515                 520                 525

Pro

<210> SEQ ID NO 37
<211> LENGTH: 577
<212> TYPE: PRT
<213> ORGANISM: unknown
<220> FEATURE:
<223> OTHER INFORMATION: Mountain Pine Beetle microbial communities

<400> SEQUENCE: 37

Met Ser Thr Pro Phe Thr Gln Phe Thr Ser Pro Ala Glu Gln Ala Pro
1               5                   10                  15

Lys Asp Tyr Asn Lys Leu Gly Leu Glu Asn Gln Leu Pro Thr Phe Glu
            20                  25                  30

Thr Asn Trp Asn Asn Asn Val Thr Gly Trp Thr Gln Met Ser Val Ile
        35                  40                  45

Gly Asn Pro Trp Ser Asn Leu Asn Asp Ala Pro Arg Ser Gly Tyr Tyr
    50                  55                  60

Asn Pro Leu Glu Ser Gly Tyr Gly Thr Gln Thr Pro Val Thr Ile Thr
65                  70                  75                  80

Trp Gln Pro Phe Pro Asn Arg Leu Trp Thr Phe Phe Tyr Asn Asn Gly
                85                  90                  95

Ala Ala Val Val Pro Gln Leu Gly Gly Lys Ala Met Thr Leu Asp Gln
            100                 105                 110

Val Met Gln Leu Thr Asp His Gly Gln Ile Thr Leu Asn Asn Thr Leu
        115                 120                 125

Tyr Ser Leu Tyr Pro Asp Pro Lys Ala Thr Gln Leu Gln Ile Pro Ser
    130                 135                 140

Val Leu Cys Lys Ser Ile Asn Trp Asn Gly Pro Tyr Ala Asp Phe Ser
145                 150                 155                 160

Pro Ser Gly Pro Arg Gly Trp Leu Asp Glu Tyr Cys Glu Trp Ser Ile
```

```
                165                 170                 175
Thr Arg Asp Pro Asp Gly Asn Met Arg Ser Ile Met Phe Thr Ser Glu
            180                 185                 190
Asn Pro Ala Tyr Phe Leu Thr Met Trp Asn Ile Asp Pro Gln Ala Val
            195                 200                 205
Leu Gly Leu Tyr Lys Ala Tyr Val Asp Pro Gln Val Lys Ile Glu Asp
            210                 215                 220
Leu Tyr Leu Arg Tyr Thr Ala Asn Gly Pro Thr Gly Gln Ala Gly Glu
225                 230                 235                 240
Pro Val Leu Asp Pro Thr Gly Gln Pro Ala Tyr Asp Thr Val Asn
            245                 250                 255
Lys Trp Asn Ser Gly Thr Val Arg Ile Pro Gly Val Ser Gly Gly Ala
            260                 265                 270
Met His Leu Thr Ser Gly Pro Asn Thr Leu Ser Ala Glu Ile Tyr Leu
            275                 280                 285
Ala Ala Ala Ala Thr Ile Leu Arg Pro Leu Asn Ser Ser Arg Asn Gln
            290                 295                 300
Gln Ser Leu Ile Cys Cys Ala Gln Tyr Gly Gln Asn Tyr Arg Asn Ser
305                 310                 315                 320
Asp Pro His Ile Gly Phe Ser Ala Asn Gln Ala Ala Val Asn Asn Leu
                325                 330                 335
Ile Ser Leu Thr Asn Pro Ile Gly Leu Tyr Leu Gln Gln Pro Lys Ser
            340                 345                 350
Phe Ser Thr Trp Lys Gly Pro Gln Gly Gln Asp Val Ser Ser Tyr Trp
            355                 360                 365
Arg Val Thr Arg Gly Thr Ala Gly Thr Gly Pro Asn Asn Ser Asp Gln
            370                 375                 380
Ile Leu Gln Ala Val Phe Glu Val Pro Gln Ser Ala Gly Phe Ser Ile
385                 390                 395                 400
Asn Asp Ile Thr Ile Asn Gly Thr Pro Ile Asp Tyr Val Trp Val Ile
                405                 410                 415
Ala Asn Glu Leu Asn Val Ala Leu Ser Val Thr Pro Ala Pro Leu Pro
            420                 425                 430
Ala Pro Pro Lys Glu Cys Asp Cys Val Ala Ala Asn Asn Thr Asp Ala
            435                 440                 445
Gln Pro Trp Pro Val Gln Leu Leu Pro Ile Asp Leu Phe Tyr Gly Gln
            450                 455                 460
Ser Pro Ser Asp Leu Pro Ala Ser Phe Ala Pro Gly Ser Ser Gly Gln
465                 470                 475                 480
Phe Val Leu Val Val Gln Gly Ala Asp Pro Asn Thr Ala Ala Asp
                485                 490                 495
Ala Arg Val Gln Phe Ser Asn Pro Gly Ile Thr Ala Gln Val Thr Gln
            500                 505                 510
Phe Leu Pro Asp Ala Ser Ala Ile Pro Gly Gln Thr Asp Ser Gly Gly
            515                 520                 525
Thr Gln Gly Tyr Ile Met Thr Val Thr Val Ser Ser Asn Ala Ala Pro
            530                 535                 540
Gly Leu Val Ser Val Arg Ala Leu Asn Pro Ser Glu Gly Ala Asn Pro
545                 550                 555                 560
Ser Ala Thr Gln His Pro Trp Glu Ser Gly Leu Ala Leu Val Pro Asp
                565                 570                 575
Ala
```

<210> SEQ ID NO 38
<211> LENGTH: 529
<212> TYPE: PRT
<213> ORGANISM: unknown
<220> FEATURE:
<223> OTHER INFORMATION: Mountain Pine Beetle microbial communities

<400> SEQUENCE: 38

Met Asn Gly Trp Leu Arg Pro Leu Arg Ala Arg Leu Arg Val Phe
1               5                   10                  15

Cys Trp Ile Thr Cys Ala Leu Leu Pro Leu Leu Ala Pro Ser Pro Ala
            20                  25                  30

Asn Ala Ala Thr Asp Ala Gln Ser Cys Val Ser Gln Leu Val Phe Asp
                35                  40                  45

Pro Thr Ser Gly Gly Phe Leu Pro Val Asn Asn Phe Gly Thr Glu Gln
    50                  55                  60

Asp Phe Leu Asn Cys Phe Gly Trp Gln Leu Phe Ile Ala Met Asn Trp
65                  70                  75                  80

Pro Val Asn Pro Gly Trp Pro Ala Asn Ala Ser Leu Ala Gly Glu Pro
                85                  90                  95

Asp Thr Gln Ser Ser Val Ala Gln Phe Gly Val Pro Ala Thr Pro Gly
            100                 105                 110

Gln Pro Met Ser Asn Ala Pro Val Trp Ala Ser Tyr Lys Asp Ala Ser
        115                 120                 125

Glu Ile Phe Leu Pro Gly Ala Pro Lys Pro Ser Gly Trp Gly Leu Glu
    130                 135                 140

Thr Leu Val Pro Ser Asn Cys Thr Ala Ser Gly Asn Leu Lys Ala Tyr
145                 150                 155                 160

Ala Thr Gly Ala Arg Lys Phe Ile Thr Ala Thr Ser Glu Ser Ala Ile
                165                 170                 175

Asn Arg Lys His Arg Phe His Leu Ser Ser Gly Thr Gln Val Thr Leu
            180                 185                 190

Pro Asp Ser Ile Met Glu Ala Ser Gly Gly Trp Leu Thr Asp Gln Ser
        195                 200                 205

Gly Asn Leu Val Phe Phe Glu Arg Lys Val Gly Lys Ala Glu Phe Asp
    210                 215                 220

Tyr Ile Val Asp Asn Gly Leu Tyr Asp Ala Ala Asn Gln Leu Ile Val
225                 230                 235                 240

Ala Gln Asn Ser Asp Asn Arg His Pro Ala Gly Leu Ser Leu Pro Ala
                245                 250                 255

Gly Lys Leu Val Arg Glu Leu Pro Ala Gln Ala Leu Pro Gln Glu Glu
            260                 265                 270

Leu Gly Ala Leu Glu Leu Lys Ala Ala Trp Arg Val Leu Thr Asn Lys
        275                 280                 285

Pro Glu Leu Tyr Gly Arg Tyr Leu Thr Thr Val Ala Trp Leu Gln Arg
    290                 295                 300

Pro Asp Thr Leu Gln Cys Thr Gln Glu Val Val Gly Leu Val Gly Leu
305                 310                 315                 320

His Ile Ile Asn Lys Thr Gln Thr Gln Pro Asn Phe Ile Trp Thr Thr
                325                 330                 335

Phe Glu Gln Val Asp Asn Val Pro Asp Ala Gly Pro Thr Pro Pro Gln
            340                 345                 350

Gly Tyr Ser Phe Asn Asn Pro Ala Cys Ser Gly Thr Ala Cys Thr Pro
        355                 360                 365

```
Asn Val Ala Arg Val Gln Cys Asp Ala Thr His Ala Pro Pro Asn Cys
    370                 375                 380

Thr Pro Leu Asp Gln Pro Val Gln Ala Thr Arg Val Asn Ala Thr Pro
385                 390                 395                 400

Gln Asp Leu Gln Ala Leu Asn Thr Ala Val Gln Gln Thr Phe Ala Gln
                405                 410                 415

Lys Thr Gln Gly Gln Ser Val Phe Gln Tyr Tyr Lys Leu Val Asn Val
                420                 425                 430

Leu Trp Ser Lys Thr Pro Asn Ala Pro Asn Asp Pro Gly Pro Gly Pro
                435                 440                 445

Asn Val Lys Thr Pro Leu Ser Tyr Gly Pro Phe Val Ser Asp Gln Ser
    450                 455                 460

Val Val Val Ala Asn Thr Thr Met Glu Thr Tyr Val Gln Ala Asp Asn
465                 470                 475                 480

Cys Asn Asp Cys His Gln Tyr Ala Ala Ile Ala Gly Lys Ser Gly Leu
                485                 490                 495

Ala Ser Asp Phe Ser Phe Leu Phe Gly Asn Ala Asp Ser Ala Lys Asn
                500                 505                 510

Thr Arg Leu Ile Lys Arg Ile Glu Gly Phe Lys Thr Leu Lys Asp Asp
                515                 520                 525

Gln

<210> SEQ ID NO 39
<211> LENGTH: 577
<212> TYPE: PRT
<213> ORGANISM: Pseudomonas trivialis

<400> SEQUENCE: 39

Met Ser Thr Pro Phe Thr Gln Phe Thr Ser Pro Ala Glu Gln Ala Pro
1               5                   10                  15

Lys Asp Tyr Asn Lys Leu Gly Leu Glu Asp Gln Leu Ser Thr Phe Glu
                20                  25                  30

Thr Asn Trp Asn Asn Asn Val Thr Gly Trp Thr Gln Met Ser Val Ile
            35                  40                  45

Gly Asn Pro Trp Ser Asn Leu Asn Asp Ala Pro Arg Ser Gly Tyr Tyr
    50                  55                  60

Asn Pro Leu Glu Ser Gly Tyr Gly Thr Gln Thr Pro Leu Thr Ile Thr
65                  70                  75                  80

Trp Gln Pro Phe Pro Asn Arg Leu Trp Thr Phe Phe Tyr Asn Asn Gly
                85                  90                  95

Ala Ala Val Val Pro Gln Leu Gly Gly Thr Ala Met Thr Leu Asp Gln
                100                 105                 110

Val Met Gln Leu Thr Asp His Gly Gln Ile Thr Leu Asn Asn Thr Leu
            115                 120                 125

Tyr Ser Leu Tyr Pro Asp Pro Ala Ala Thr Gln Leu Gln Ile Pro Lys
    130                 135                 140

Val Leu Cys Lys Ser Ile Asn Trp His Gly Pro Tyr Ala Asp Phe Ser
145                 150                 155                 160

Pro Ser Gly Pro Arg Gly Trp Leu Asp Glu Tyr Cys Glu Trp Ser Ile
                165                 170                 175

Thr Arg Asp Pro Asp Gly Asn Met Arg Ser Ile Met Phe Thr Ser Glu
                180                 185                 190

Asn Pro Ala Tyr Phe Leu Thr Met Trp Asn Ile Asp Pro Asn Ala Val
            195                 200                 205
```

Leu Gly Leu Tyr Gln Ala Tyr Val Asp Pro Gln Val Lys Leu Glu Asp
210                 215                 220

Leu Tyr Leu Arg Tyr Thr Ala Asn Gly Pro Thr Gly Asn Ala Gly Asp
225                 230                 235                 240

Pro Val Ile Asp Glu Thr Thr Gly Arg Pro Ala Tyr Asp Thr Val Asn
            245                 250                 255

Lys Trp Asn Ala Gly Thr Val Arg Ile Pro Gly Val Ser Gly Gly Ala
            260                 265                 270

Met His Leu Thr Ser Gly Pro Asn Thr Leu Ser Ala Glu Ile Tyr Leu
            275                 280                 285

Ala Ala Ala Ala Thr Ile Leu Arg Pro Ile Gln Ser Ser Gly Asn Gln
290                 295                 300

Gln Asn Leu Ile Cys Cys Ala Gln Tyr Gly Gln Asn Tyr Arg Asn Ser
305                 310                 315                 320

Asp Pro His Ile Gly Phe Ser Ala Asn Gln Ala Ala Val Lys Asn Leu
            325                 330                 335

Ile Ser Leu Thr Asn Pro Ile Gly Leu Tyr Leu Gln Gln Pro Lys Ser
            340                 345                 350

Phe Ser Thr Trp Lys Gly Pro Gln Gly Gln Asp Val Ser Ser Tyr Trp
            355                 360                 365

Arg Val Thr Arg Gly Thr Ala Gly Thr Gly Pro Asn Asn Ser Asp Gln
370                 375                 380

Ile Leu Gln Ala Val Phe Glu Val Pro Gln Ser Ala Gly Phe Ser Ile
385                 390                 395                 400

Asn Asp Ile Thr Ile Asn Gly Thr Pro Ile Asp Tyr Val Trp Val Ile
            405                 410                 415

Ala Asn Glu Leu Asn Val Ala Leu Ser Val Thr Pro Ala Pro Leu Thr
            420                 425                 430

Ala Thr Pro Lys Glu Cys Asp Cys Val Ala Ala Asn Asn Thr Asp Ala
            435                 440                 445

Gln Pro Trp Pro Val Gln Leu Leu Pro Leu Asp Leu Phe Tyr Gly Gln
            450                 455                 460

Ser Pro Ser Asp Leu Pro Ala Ser Phe Ala Pro Gly Ser Ser Ala Gln
465                 470                 475                 480

Phe Val Leu Val Val Gln Gly Ala Asp Pro Asn Thr Thr Val Ala Asp
            485                 490                 495

Ala Arg Val Gln Phe Ser Asn Pro Gly Ile Ser Ala Gln Val Thr Gln
            500                 505                 510

Phe Leu Pro Asp Ala Ser Ala Ile Pro Gly Gln Thr Asp Ser Gly Gly
            515                 520                 525

Thr Gln Gly Tyr Val Met Thr Val Asn Val Ser Gly Asn Ala Ala Pro
530                 535                 540

Gly Leu Val Ser Val Arg Ala Leu Asn Pro Ser Glu Ala Ala Asn Pro
545                 550                 555                 560

Ser Ala Ala Gln His Pro Trp Glu Ser Gly Leu Ala Leu Val Pro Gly
            565                 570                 575

Ala

<210> SEQ ID NO 40
<211> LENGTH: 528
<212> TYPE: PRT
<213> ORGANISM: Pseudomonas trivialis

<400> SEQUENCE: 40

```
Met Tyr Gly Trp Pro Arg Pro Leu Cys Arg Ala Arg Leu Asn Val Phe
1               5                   10                  15

Ser Leu Leu Ala Gly Ala Leu Leu Ser Leu Val Ala Pro Pro Ala
            20                  25                  30

Ser Ala Ser Asp Ala Gln Thr Cys Val Gln Gln Leu Val Phe Asp Pro
        35                  40                  45

Ala Ser Gly Gly Phe Leu Pro Val Asn Asn Phe Gly Thr Glu Gln Asp
    50                  55                  60

Phe Leu Asn Cys Phe Gly Trp Gln Leu Phe Ile Ala Met Asn Trp Pro
65                  70                  75                  80

Val Asn Pro Gly Trp Pro Ala Asp Pro Thr Leu Ala Gly Glu Pro Asp
            85                  90                  95

Thr Gln Ser Ser Ala Ala Gln Phe Gly Val Pro Gln Thr Pro Gly Lys
            100                 105                 110

Pro Met Ser Asn Ala Pro Val Trp Ala Ser Tyr Lys Asp Ala Asn Asp
            115                 120                 125

Ile Phe Leu Pro Gly Ala Pro Lys Pro Thr Gly Trp Gly Val Glu Thr
    130                 135                 140

Leu Val Pro Ser Asn Cys Thr Ala Thr Gly Asn Leu Lys Ala Leu Ser
145                 150                 155                 160

Thr Gly Ala Arg Lys Phe Ile Thr Ala Thr Ser Glu Ser Ala Ile Asn
                165                 170                 175

Arg Lys His Arg Phe His Leu Ser Ser Gly Thr Gln Val Thr Leu Pro
            180                 185                 190

Asp Ser Ile Met Glu Ala Ala Gly Gly Trp Leu Thr Asp Gln Ser Gly
            195                 200                 205

Asn Leu Val Phe Phe Glu Arg Lys Val Gly Lys Ala Glu Phe Asp Tyr
    210                 215                 220

Ile Val Asn Asn Gly Leu Tyr Asp Ala Ala Asn Gln Leu Ile Val Ala
225                 230                 235                 240

Gln Asn Ser Asp Asn Arg His Pro Ala Gly Leu Ser Leu Pro Ala Gly
                245                 250                 255

Lys Leu Val Arg Glu Leu Pro Ala Lys Ala Leu Pro Gln Glu Glu Leu
            260                 265                 270

Gly Ala Leu Glu Leu Lys Ala Ala Trp Arg Val Leu Thr His Lys Pro
    275                 280                 285

Glu Leu Tyr Ala Arg Tyr Leu Thr Thr Val Ala Trp Leu Gln Arg Pro
    290                 295                 300

Asp Thr Leu Gln Cys Thr Gln Glu Val Val Gly Leu Val Gly Leu His
305                 310                 315                 320

Ile Ile Asn Lys Thr Gln Thr Gln Pro Asn Phe Ile Trp Thr Thr Phe
                325                 330                 335

Glu Gln Val Asp Asn Val Pro Asp Gly Gly Ala Thr Pro Pro Gln Gly
            340                 345                 350

Tyr Ser Phe Asn Asn Pro Ala Cys Thr Gly Asp Ala Cys Thr Pro Asn
            355                 360                 365

Val Ala Arg Val Gln Cys Asp Ala Thr His Thr Pro Pro Asn Cys Thr
    370                 375                 380

Pro Phe Asn Gln Pro Val Gln Ala Thr Arg Ala Asn Ala Thr Pro Glu
385                 390                 395                 400

Asp Met Gln Ala Leu Asn Thr Ala Val Gln Gln Thr Phe Ala Gln Gln
            405                 410                 415

Thr Gln Gly Gln Ser Val Phe Gln Tyr Tyr Lys Leu Val Asn Val Leu
```

```
                    420              425               430
Trp Ser Lys Thr Pro Asn Ala Pro Asn Asp Pro Gly Pro Gly Pro Asn
            435             440             445
Val Lys Thr Pro Leu Ser Tyr Gly Pro Phe Val Ser Asp Gln Ser Val
        450             455             460
Ala Val Ala Asn Thr Thr Leu Glu Thr Tyr Val Gln Thr Glu Asn Cys
465             470             475             480
Asn Asp Cys His Gln Tyr Ala Ala Ile Ala Gly Gly Ser Lys Leu Ala
            485             490             495
Ser Asp Phe Ser Phe Leu Phe Gly Ser Ala Asp Ser Ala Lys Asn Thr
            500             505             510
Arg Leu Ile Lys Arg Ile Glu Ala Phe Lys Thr Leu Lys Asp Asp His
            515             520             525

<210> SEQ ID NO 41
<211> LENGTH: 577
<212> TYPE: PRT
<213> ORGANISM: Pseudomonas sp. R81

<400> SEQUENCE: 41

Met Ser Thr Pro Phe Thr Gln Phe Thr Ser Pro Ala Glu Gln Ala Pro
1               5                   10                  15
Lys Asp Tyr Asn Lys Leu Gly Leu Glu Asn Gln Leu Pro Thr Phe Glu
            20                  25                  30
Thr Asp Trp Asn Asn Asn Val Thr Gly Trp Thr Gln Met Ser Val Ile
        35                  40                  45
Gly Asn Pro Trp Ser Asn Leu Asn Asp Ala Pro Arg Ser Gly Tyr Tyr
50                  55                  60
Asn Pro Leu Asp Ser Gly Tyr Gly Thr Gln Thr Pro Val Thr Ile Thr
65                  70                  75                  80
Trp Gln Pro Phe Pro Asn Arg Leu Trp Thr Phe Phe Tyr Asn Asp Gly
                85                  90                  95
Ala Ala Val Val Pro Gln Leu Gly Gly Lys Ala Met Thr Leu Asp Gln
            100                 105                 110
Val Met Gln Leu Thr Asp His Gly Gln Ile Thr Leu Asn Asn Thr Leu
        115                 120                 125
Tyr Ser Leu Tyr Pro Asp Pro Lys Ala Thr Gln Leu Gln Ile Pro Ser
130                 135                 140
Val Leu Cys Lys Ser Ile Asn Trp Asn Gly Pro Tyr Ala Asp Phe Ser
145                 150                 155                 160
Pro Ser Gly Pro Arg Gly Trp Leu Asp Glu Tyr Cys Glu Trp Ser Ile
                165                 170                 175
Thr Arg Asp Pro Asp Gly Asn Met Arg Ser Ile Met Phe Thr Ser Glu
            180                 185                 190
Asn Pro Ala Tyr Phe Leu Thr Met Trp Asn Ile Asp Pro Gln Ala Val
        195                 200                 205
Leu Gly Leu Tyr Lys Ala Tyr Val Asp Pro Gln Val Lys Ile Glu Asp
    210                 215                 220
Leu Tyr Leu Arg Tyr Thr Ala Asn Gly Pro Thr Gly Lys Ala Gly Glu
225                 230                 235                 240
Pro Val Leu Asp Pro Thr Thr Gly Gln Pro Ala Tyr Asp Thr Val Asn
                245                 250                 255
Lys Trp Asn Ser Gly Thr Val Arg Ile Pro Gly Val Ser Gly Gly Ala
            260                 265                 270
```

```
Met His Leu Thr Ser Gly Pro Asn Thr Leu Ser Ala Glu Ile Tyr Leu
            275                 280                 285

Ala Ala Ala Thr Ile Leu Arg Pro Ile Lys Ser Ser Ala Asn Gln
290                 295                 300

Gln Ser Leu Ile Cys Cys Ala Gln Tyr Gly Gln Asn Tyr Arg Asn Ser
305                 310                 315                 320

Asp Pro His Ile Gly Phe Ser Ala Asn Gln Glu Ala Val Lys Ala Leu
                325                 330                 335

Ile Ser Leu Thr Asn Pro Ile Gly Leu Tyr Leu Gln Gln Pro Lys Ser
            340                 345                 350

Phe Ser Thr Trp Lys Gly Pro Gln Gly Gln Asp Val Ser Ser Tyr Trp
            355                 360                 365

His Val Thr Arg Gly Thr Ala Gly Thr Gly Pro Asn Lys Ser Asp Gln
            370                 375                 380

Ile Leu Gln Ala Val Phe Glu Val Pro Gln Ser Ala Gly Phe Ser Ile
385                 390                 395                 400

Asn Glu Ile Thr Ile Asn Gly Thr Pro Ile Asp Tyr Val Trp Val Ile
                405                 410                 415

Ala Asn Glu Leu Ser Val Ala Leu Ser Val Thr Pro Ala Pro Leu Thr
            420                 425                 430

Ala Thr Pro Glu Glu Cys Asp Cys Val Ala Ala Asn Thr Thr Asp Ala
            435                 440                 445

Gln Pro Trp Pro Val Gln Leu Leu Pro Ile Asp Leu Phe Tyr Gly Gln
            450                 455                 460

Ser Pro Ser Asp Leu Pro Ala Ser Phe Ala Pro Gly Ser Ser Gly Gln
465                 470                 475                 480

Phe Val Leu Val Val Gln Gly Ala Asp Pro Asn Thr Thr Ala Ala Asp
                485                 490                 495

Ala Arg Val Gln Phe Ser Asn Pro Gly Ile Thr Ala Gln Val Thr Glu
            500                 505                 510

Phe Leu Pro Asp Ala Ser Ala Ile Pro Gly Gln Thr Asp Ser Gly Gly
            515                 520                 525

Thr Gln Gly Tyr Ile Met Thr Val Thr Val Ser Ser Asn Ala Val Pro
            530                 535                 540

Gly Leu Val Ser Val Arg Ala Leu Asn Pro Ser Glu Ala Ala Asn Pro
545                 550                 555                 560

Ser Ala Thr Gln His Pro Trp Glu Ser Gly Leu Ala Leu Val Pro Gly
                565                 570                 575

Val

<210> SEQ ID NO 42
<211> LENGTH: 528
<212> TYPE: PRT
<213> ORGANISM: Pseudomonas sp. R81

<400> SEQUENCE: 42

Met Asn Lys Trp Leu Arg Pro Leu Arg Arg Ala Arg Leu Ser Val Leu
1               5                   10                  15

Cys Trp Ile Pro Cys Ala Leu Leu Pro Leu Ala Pro Ala Pro Ala Ile
                20                  25                  30

Ala Ala Ser Asp Ala Gln Ser Cys Val Ser Gln Leu Val Phe Asp Pro
            35                  40                  45

Thr Ser Gly Gly Phe Leu Pro Val Asn Asn Phe Gly Thr Glu Gln Asp
        50                  55                  60
```

```
Phe Leu Asn Cys Phe Gly Trp Gln Leu Phe Ile Ala Met Asn Trp Pro
 65                  70                  75                  80

Val Asn Pro Gly Trp Pro Ala Asp Pro Ser Leu Ala Gly Glu Pro Asp
                 85                  90                  95

Thr Gln Ser Thr Ala Ala Gln Phe Gly Val Pro Pro Thr Ser Gly Gln
            100                 105                 110

Pro Met Gly Asn Ala Pro Val Trp Ala Ser Tyr Lys Asp Ala Ser Glu
        115                 120                 125

Ile Phe Leu Pro Gly Ala Pro Lys Pro Ser Gly Trp Gly Val Glu Thr
    130                 135                 140

Leu Val Pro Ser Asn Cys Thr Ala Thr Gly Asn Leu Lys Ala Phe Ala
145                 150                 155                 160

Thr Gly Ala Arg Lys Phe Met Ala Ala Thr Ser Glu Ser Ala Ile Asn
                165                 170                 175

Arg Lys His Arg Phe His Leu Ser Ser Gly Thr Gln Val Thr Leu Pro
                180                 185                 190

Asp Ser Ile Met Glu Ala Ser Gly Gly Trp Leu Thr Asp Gln Ser Gly
            195                 200                 205

Asn Leu Val Phe Phe Glu Arg Lys Val Gly Lys Ala Glu Phe Asp Tyr
        210                 215                 220

Ile Val Asp Asn Gly Leu Tyr Asp Ala Ala Asn Gln Leu Ile Val Ala
225                 230                 235                 240

Gln Asn Ser Asp Asn Arg His Pro Ala Gly Leu Ser Leu Pro Ala Gly
                245                 250                 255

Lys Leu Val Arg Glu Leu Pro Ala Lys Ala Leu Pro Gln Glu Glu Leu
                260                 265                 270

Gly Ala Leu Glu Leu Lys Ala Ala Trp Arg Val Leu Thr Asn Lys Pro
            275                 280                 285

Gln Leu Tyr Gly Arg Tyr Leu Thr Thr Val Ala Trp Leu Gln Arg Pro
        290                 295                 300

Asp Thr Leu Gln Cys Thr Gln Glu Val Val Gly Leu Val Gly Leu His
305                 310                 315                 320

Ile Ile Asn Lys Thr Gln Thr Gln Pro Asn Phe Ile Trp Thr Thr Phe
                325                 330                 335

Glu Gln Val Asp Asn Val Pro Asp Asn Gly Thr Ala Ala Pro Glu Gly
            340                 345                 350

Tyr Ser Phe Asn Asn Pro Thr Cys Thr Gly Asp Ala Cys Thr Pro Asn
        355                 360                 365

Val Ala Arg Val Gln Cys Asp Ala Thr His Thr Pro Pro Asp Cys Thr
    370                 375                 380

Pro Leu Asp Gln Pro Val Gln Ala Thr Arg Val Asn Ala Thr Pro Gln
385                 390                 395                 400

Asp Leu Gln Met Leu Asn Thr Ala Val Gln Gln Thr Phe Ala Gln Lys
                405                 410                 415

Thr Gln Gly Gln Ser Val Phe Gln Tyr Tyr Lys Leu Val Asn Val Leu
            420                 425                 430

Trp Ser Lys Thr Pro Asn Ala Pro Asn Asp Pro Gly Pro Gly Pro Asn
        435                 440                 445

Val Lys Val Pro Leu Ser Tyr Gly Pro Phe Val Ser Asp Gln Ser Val
    450                 455                 460

Val Val Ala Asn Thr Thr Leu Glu Thr Tyr Val Gln Asn Lys Asn Cys
465                 470                 475                 480

Asn Asp Cys His Gln Tyr Ala Ala Ile Ala Gly Thr Ser Gln Leu Thr
```

```
                       485                 490                 495
Ser Asp Phe Ser Phe Leu Phe Gly Asn Ala Asp Ser Ala Lys Asn Ala
                500                 505                 510
Arg Leu Ile Lys Arg Ile Glu Ala Phe Lys Thr Leu Lys Asp Ser Pro
            515                 520                 525

<210> SEQ ID NO 43
<211> LENGTH: 577
<212> TYPE: PRT
<213> ORGANISM: Pseudomonas libanensis

<400> SEQUENCE: 43

Met Ser Thr Pro Phe Thr Gln Phe Thr Ser Pro Ala Glu Gln Ala Pro
1               5                   10                  15
Lys Asp Tyr Asn Lys Leu Gly Leu Glu Asn Gln Leu Pro Thr Phe Glu
            20                  25                  30
Thr Asp Trp Asn Asn Asn Val Thr Gly Trp Thr Gln Met Ser Val Ile
        35                  40                  45
Gly Asn Pro Trp Ser Asn Leu Asn Asp Ala Pro Arg Ser Gly Tyr Tyr
    50                  55                  60
Asn Pro Ile Glu Ser Gly Tyr Gly Thr Gln Thr Pro Val Thr Ile Thr
65                  70                  75                  80
Trp Gln Pro Phe Pro Asn Arg Leu Trp Thr Phe Phe Tyr Asn Asn Gly
                85                  90                  95
Ala Ala Val Val Pro Gln Leu Gly Gly Lys Ala Met Thr Leu Asp Gln
            100                 105                 110
Val Met Gln Leu Thr Asp His Gly Gln Ile Thr Leu Asn Asn Thr Leu
        115                 120                 125
Tyr Ser Leu Tyr Pro Asp Pro Lys Ala Thr Gln Leu Gln Ile Pro Ser
    130                 135                 140
Val Leu Cys Lys Ser Ile Asn Trp Asn Gly Pro Tyr Ala Asp Phe Ser
145                 150                 155                 160
Pro Ser Gly Pro Arg Gly Trp Leu Asp Glu Tyr Cys Glu Trp Ser Ile
                165                 170                 175
Thr Arg Asp Pro Asp Gly Asn Met Arg Ser Ile Met Phe Thr Ser Glu
            180                 185                 190
Asn Pro Ala Tyr Phe Leu Thr Met Trp Asn Ile Asp Pro Gln Ala Val
        195                 200                 205
Leu Gly Leu Tyr Lys Ala Tyr Val Asp Pro Gln Val Lys Ile Glu Asp
    210                 215                 220
Leu Tyr Leu Arg Tyr Thr Ala Asn Gly Pro Thr Gly Lys Ala Gly Asp
225                 230                 235                 240
Pro Val Leu Asp Pro Thr Thr Gly Gln Pro Ala Tyr Asp Thr Val Asn
                245                 250                 255
Lys Trp Asn Ser Gly Thr Val Arg Ile Pro Gly Val Ser Gly Gly Ala
            260                 265                 270
Met His Leu Thr Ser Gly Pro Asn Thr Leu Ser Ala Glu Ile Tyr Leu
        275                 280                 285
Ala Ala Ala Ala Thr Ile Leu Arg Pro Leu Asn Ser Ser Arg Asn Gln
    290                 295                 300
Gln Ser Leu Ile Cys Cys Ala Gln Tyr Gly Gln Asn Tyr Arg Asn Ser
305                 310                 315                 320
Asp Pro His Ile Gly Tyr Ser Ala Asn Gln Glu Ala Val Lys Ala Leu
                325                 330                 335
```

Ile Ser Leu Thr Asn Pro Ile Gly Leu Tyr Leu Gln Gln Pro Lys Ser
                340                 345                 350

Phe Ser Thr Trp Lys Gly Pro Gln Gly Gln Asp Val Ser Ser Tyr Trp
                355                 360                 365

Arg Ile Thr Arg Gly Thr Ala Gly Thr Gly Pro Asn Asn Ser Asp Gln
        370                 375                 380

Ile Leu Gln Ala Val Phe Glu Val Pro Ala Ser Ala Gly Phe Ser Ile
385                 390                 395                 400

Asn Asp Ile Thr Ile Asn Gly Thr Pro Ile Asp Tyr Val Trp Val Ile
                405                 410                 415

Ala Asn Glu Leu Asn Val Ala Leu Ser Val Thr Pro Ala Pro Leu Ser
                420                 425                 430

Gly Thr Pro Lys Glu Cys Asp Cys Val Ala Ala Asn Asn Thr Asp Ala
                435                 440                 445

Gln Pro Trp Pro Val Gln Leu Leu Pro Ile Asp Leu Phe Tyr Gly Gln
                450                 455                 460

Ser Pro Ser Asp Leu Pro Ala Ser Phe Ala Pro Gly Ser Ser Gly Gln
465                 470                 475                 480

Phe Val Leu Val Val Gln Gly Ala Asp Pro Asn Thr Thr Ala Ala Asp
                485                 490                 495

Ala Arg Val Gln Phe Ser Asn Pro Gly Ile Thr Ala Gln Val Thr Gln
                500                 505                 510

Phe Leu Pro Asp Ala Ser Ala Ile Pro Gly Gln Thr Asp Ser Gly Gly
                515                 520                 525

Thr Gln Gly Tyr Ile Met Thr Val Thr Val Ser Ser Asn Ala Ala Pro
                530                 535                 540

Gly Leu Val Ser Val Arg Ala Leu Asn Pro Ser Glu Ala Ala Asn Pro
545                 550                 555                 560

Ser Ala Thr Gln His Pro Trp Glu Ser Gly Leu Ala Leu Val Pro Val
                565                 570                 575

Ala

<210> SEQ ID NO 44
<211> LENGTH: 528
<212> TYPE: PRT
<213> ORGANISM: Pseudomonas libanensis

<400> SEQUENCE: 44

Met Asn Gly Trp Leu Arg Pro Leu Arg Arg Ala Arg Leu Asn Val Leu
1               5                   10                  15

Cys Trp Ile Thr Cys Ala Leu Leu Pro Phe Ala Pro Ala Pro Val Ser
                20                  25                  30

Ala Ala Ser Asp Ala Gln Ser Cys Val Ser Gln Leu Val Phe Asp Pro
            35                  40                  45

Thr Ser Gly Gly Phe Leu Pro Val Asn Asn Phe Gly Thr Glu Gln Asp
        50                  55                  60

Phe Leu Asn Cys Phe Gly Trp Gln Leu Phe Ile Ala Met Asn Trp Pro
65                  70                  75                  80

Val Asn Pro Gly Trp Pro Ala Asn Pro Ser Leu Ala Gly Glu Pro Asp
                85                  90                  95

Thr Gln Ser Thr Ala Ala Gln Phe Gly Val Pro Pro Thr Pro Gly Gln
            100                 105                 110

Pro Met Ser Asn Ala Pro Val Trp Ala Ser Tyr Lys Asp Ala Ser Glu
        115                 120                 125

Ile Phe Leu Pro Gly Ala Pro Lys Pro Ser Gly Trp Gly Val Glu Thr
130                 135                 140

Arg Val Pro Ser Asn Cys Thr Ala Thr Gly Asn Leu Lys Ala Phe Ser
145                 150                 155                 160

Thr Gly Ala Arg Lys Phe Ile Thr Ala Thr Ser Glu Ser Ala Ile Asn
                165                 170                 175

Arg Lys His Arg Phe His Leu Ser Ser Gly Thr Gln Val Thr Leu Pro
                180                 185                 190

Asp Ser Ile Met Glu Ala Ser Gly Gly Trp Leu Thr Asp Gln Ser Gly
            195                 200                 205

Asn Leu Val Phe Phe Glu Arg Lys Val Gly Lys Ala Glu Phe Asp Tyr
210                 215                 220

Ile Val Asp Asn Gly Leu Tyr Asp Ala Ala Asn Gln Leu Ile Val Ala
225                 230                 235                 240

Gln Asn Ser Asp Asn Arg His Pro Ala Gly Leu Ser Leu Pro Ala Gly
                245                 250                 255

Lys Leu Val Arg Glu Leu Pro Ala Gln Ala Leu Pro Gln Glu Glu Leu
                260                 265                 270

Gly Ala Leu Glu Leu Lys Ala Ala Trp Arg Val Leu Thr Asn Lys Pro
            275                 280                 285

Glu Leu Tyr Gly Arg Tyr Leu Thr Thr Val Ala Trp Leu Gln Arg Pro
290                 295                 300

Asp Thr Leu Gln Cys Thr Gln Glu Val Val Leu Val Gly Leu His
305                 310                 315                 320

Ile Ile Asn Lys Thr Gln Thr Gln Pro Asn Phe Ile Trp Thr Thr Phe
                325                 330                 335

Glu Gln Val Asp Asn Val Pro Asp Gly Gly Ala Thr Pro Pro Gly Gly
                340                 345                 350

Tyr Ser Phe Asn Asn Pro Ala Cys Thr Gly Asp Thr Cys Thr Pro Asn
                355                 360                 365

Val Ala Arg Val Gln Cys Asp Ala Thr His Thr Pro Pro Asn Cys Thr
                370                 375                 380

Pro Leu Asp Gln Pro Val Gln Ala Thr Arg Val Asn Ala Thr Pro Gln
385                 390                 395                 400

Asp Met Gln Ala Leu Asn Thr Ala Val Gln Gln Thr Phe Ala Gln Lys
                405                 410                 415

Thr Gly Gln Gly Ser Val Phe Gln Tyr Tyr Lys Leu Val Asn Val Leu
                420                 425                 430

Trp Ser Lys Thr Pro Asn Ala Pro Asn Asp Pro Gly Pro Gly Pro Asn
                435                 440                 445

Val Lys Val Pro Leu Ser Tyr Gly Pro Phe Val Ser Asp Gln Ser Val
                450                 455                 460

Val Val Ala Asn Thr Thr Met Glu Thr Tyr Val Gln Ser Asp Asn Cys
465                 470                 475                 480

Asn Asp Cys His Gln Tyr Ala Thr Ile Ala Gly Gly Ser Lys Leu Ala
                485                 490                 495

Ser Asp Phe Ser Phe Leu Phe Gly Asn Ala Asp Ser Ala Lys Asn Thr
                500                 505                 510

Arg Leu Ile Lys Arg Ile Glu Ala Phe Lys Thr Leu Lys Asp Asn Pro
                515                 520                 525

<210> SEQ ID NO 45
<211> LENGTH: 576
<212> TYPE: PRT

<213> ORGANISM: Pseudomonas asplenii

<400> SEQUENCE: 45

| | | | | | | | | | | | | | |
|---|---|---|---|---|---|---|---|---|---|---|---|---|---|

Met Ser Ile Pro Phe Thr Arg Phe Ser Pro Pro Ala Asn Gln Ala Gln
1               5                   10                  15

Lys Asp Tyr Gln Lys Leu Gly Leu Glu Gln Gln Gln Ala Gln Phe Asp
            20                  25                  30

Thr Asp Trp Ser Asn Asn Leu Ala Gly Trp Thr Glu Ala Ala Ile Ile
        35                  40                  45

Gly Asn Pro Trp Thr Gly Leu Asn Asp Ala Pro Arg Thr Gly Tyr Phe
    50                  55                  60

Asn Pro Leu Ile Ser Gly Phe Gly Asp Ala Pro Ala Val Ile Asp
65                  70                  75                  80

Trp Thr Pro Phe Pro Asn Arg Leu Ile Thr Tyr Leu Thr Gln Ala Asp
                85                  90                  95

Ser Ala Lys Asn Pro Gln Leu Gly Gly Lys Pro Leu Thr Met Asp Gln
            100                 105                 110

Val Met Gln Leu Ala Asp Thr Gly Glu Ile Asp Ile Asn Gly Thr Pro
        115                 120                 125

Leu Lys Leu Tyr Asp Pro Leu Gly Ser Asn Thr Leu Gln Leu Pro Ser
130                 135                 140

Ile Arg Cys Pro Gln Ile Asp Trp Thr Gly Pro Tyr Ala Ala Phe Thr
145                 150                 155                 160

Pro Ser Gly Pro Arg Gly Trp Leu Asp Glu Tyr Cys Glu Trp Ser Ile
                165                 170                 175

Thr Leu Asp Ala Asn Gly Asn Met Arg Ser Val Met Phe Thr Cys Glu
            180                 185                 190

Asn Pro Ala Tyr Tyr Leu Thr Met Trp Arg Ile Asp Pro Lys Ala Val
        195                 200                 205

Leu Gly Leu Tyr Arg Met Tyr Ile Asp Ser Ala Val Gln Leu Glu Asp
    210                 215                 220

Leu Tyr Leu Arg Tyr Pro Val Asp Gln Pro Thr Gly Lys Gln Gly Glu
225                 230                 235                 240

Pro Val Ile Asp Pro Thr Thr Gly Leu Pro Ala Tyr Asp Val Thr Asn
                245                 250                 255

Lys Trp Asn Ser Gly Thr Ala Arg Lys Pro Gly Leu Phe Gly Gly Ala
            260                 265                 270

Leu His Leu Thr Ser Ala Pro Asn Thr Leu Ser Ala Glu Ile Tyr Leu
        275                 280                 285

Ala Gly Ala Ser Thr Ile Gln Arg Ser Asp Lys Ser Ser Glu Thr Pro
    290                 295                 300

Gln Thr Leu Ile Cys Cys Ala Lys Tyr Gly Arg Asn Tyr Arg Asn Ser
305                 310                 315                 320

Asp Pro His Ile Gly Tyr Val Ala Asn Gly Ile Ala Tyr Gly Asn Arg
                325                 330                 335

Ile Ser Leu Thr Asp Pro Val Gly Leu Tyr Leu Gln Pro Lys Asn
            340                 345                 350

Phe Ser Lys Trp Lys Asp Pro Gln Gly Asn Ser Val Ser Gln Tyr Trp
        355                 360                 365

Gln Ile Thr Arg Gly Thr Ala Gly Thr Gly Pro Leu Gly Ser Asp Gln
    370                 375                 380

Ile Leu His Ala Val Phe Glu Val Pro Glu Gln Ala Gly Phe Ser Ile
385                 390                 395                 400

-continued

```
Asn Asp Ile Thr Ile Asp Gly Gln Lys Ile Thr His Val Gly Val Ile
                405                 410                 415

Ala Asn Gln Met Lys Val Ala Leu Ser Ala Ser Pro Leu Asp Ala Ile
            420                 425                 430

Lys Pro Val Ile Gln Pro Cys Val Thr Asp Arg Ser Thr Gly Leu Gln
        435                 440                 445

Pro Cys Pro Val Gln Leu Leu Pro Leu Ser Leu Phe Tyr Gly Leu Ser
    450                 455                 460

Pro Ser Asp Leu Pro Ala Trp Leu Ala Pro Ser Ser Asn Gln Phe
465                 470                 475                 480

Ile Leu Leu Val Gln Gly Ser Asp Ala Ala Thr Thr Ala Ala Asn Ala
                485                 490                 495

Arg Ile Gln Phe Ser Asn Pro Gly Val Lys Ala Gln Val Ile Glu Phe
            500                 505                 510

Gln Thr Asn Ala Thr Pro Ile Ala Gly Thr Thr Asp Asn Ser Gly Thr
        515                 520                 525

Gln Gly Tyr Ile Ile Thr Ile Thr Val Ala Ala Asn Ala Ala Pro Gly
    530                 535                 540

Leu Val Gln Leu Arg Val Leu Asn Pro Asp Glu Pro Val Asn Pro Ser
545                 550                 555                 560

Asp Thr Asp His Pro Trp Ala Ser Ser Leu Ala Ile Val Pro Ala Leu
                565                 570                 575

<210> SEQ ID NO 46
<211> LENGTH: 518
<212> TYPE: PRT
<213> ORGANISM: Pseudomonas asplenii

<400> SEQUENCE: 46

Met Phe Ser Leu Asp Cys Ser Arg Gly Asn Gly Arg Phe Cys Leu Pro
1               5                   10                  15

Pro Leu Leu Leu Ile Ile Trp Leu Leu Gly Ser Leu Val Ala Arg Asn
            20                  25                  30

Ala Tyr Ala Leu Ser Asp Pro Glu Thr Pro Ala Gln Cys Val Gln Gln
        35                  40                  45

Leu Val Phe Asp Pro Thr Asn Gly Ser Phe Leu Thr Ser Asp Thr Pro
    50                  55                  60

Phe Val Ala Gln Gln Ala Thr Phe Asn Cys Tyr Ala Trp Gln Met Phe
65                  70                  75                  80

Ile Ala Met Asn Trp Pro Val Asn Pro Gly Trp Pro Thr His Pro Glu
                85                  90                  95

Leu Ala Gly Glu Pro Asp Thr Lys Ser Pro Ala Ala Gln Phe Gly Val
            100                 105                 110

Pro Thr Ile Ala Asp Gln Pro Met Ser Val Ala Pro Val Trp Ala Ser
        115                 120                 125

Tyr Lys Asp Ala Asn Asp Ile Phe Leu His Gly Ala Ala Ile Pro Thr
    130                 135                 140

Ala Trp Gly Met Gln Pro Pro Glu Pro Val Gly Cys Gln Thr Lys Pro
145                 150                 155                 160

Ser Leu Leu Ser Leu Arg Val Gly Ala Arg Lys Phe Met Thr Ala Thr
                165                 170                 175

Ser Glu Ser Ala Val Asn Ala Lys His Arg Phe His Leu Ser Ser Ser
            180                 185                 190

Thr Leu Val Thr Ala Ser Asp Pro Thr Leu Glu Ala Thr Gly Gly Trp
        195                 200                 205
```

```
Leu Thr Asp Gln Ala Gly Lys Leu Val Tyr Phe Glu Arg Lys Val Gly
        210                 215                 220

Lys Ala Glu Phe Asp Tyr Ile Val Ser Asn Glu Leu Tyr Asp Ala Ala
225                 230                 235                 240

Asn Gln Leu Gln Val Ala Lys Asn Gln Gly Leu Ser Leu Pro Ala Gly
                245                 250                 255

Ala His Phe Arg Ser Pro Pro Thr Ser Pro Ile Ala Gln Glu Lys Leu
            260                 265                 270

Gly Ala Phe Glu Leu Lys Ala Ala Trp Arg Ile Leu Thr Asp Lys Pro
        275                 280                 285

Gln Leu Tyr Asp Arg Tyr Leu Thr Thr Val Thr Trp Leu Lys His Pro
    290                 295                 300

Glu Thr Gly Gln Cys Thr Gln Glu Val Val Gly Leu Val Gly Leu His
305                 310                 315                 320

Ile Ile His Lys Thr Ala Ser Gln Pro Asp Phe Ile Trp Thr Thr Phe
                325                 330                 335

Glu His Val Asp Asn Val Pro Asp Gly Gly Ser Thr Pro Thr Ala Gly
            340                 345                 350

Tyr Thr Phe Asn Asn Pro Lys Cys Thr Gly Pro Asp Cys Thr Pro Asn
        355                 360                 365

Gln Arg Arg Ile Thr Cys Thr Ala Leu Gly Cys Lys Asp Asn Tyr Pro
    370                 375                 380

Arg Asn Glu Pro Val Gln Val Thr Arg Glu Asp Ser Val Pro Ser Thr
385                 390                 395                 400

Ile Asn Asp Leu Asn Thr Val Val Gln Gln Ala Ile Ser Thr Lys Thr
                405                 410                 415

Ala Gly Lys Ser Val Phe Gln Tyr Tyr Lys Leu Val Asn Val Leu Trp
            420                 425                 430

Asp Ala Ser Pro His Ile Pro Asp Pro Glu Pro Gly Ala Asn Ala Thr
        435                 440                 445

Val Pro Leu Val Tyr Gly Ser Phe Ser Ser Asp Gly Asn Asn Thr Pro
    450                 455                 460

Val Ser Asn Thr Thr Met Glu Thr Tyr Ile Gln Asn Arg Ser Cys Asp
465                 470                 475                 480

Phe Cys His Arg Asn Ala Lys Val Ala Gly Ser Lys Ser Leu Thr Ser
                485                 490                 495

Asp Phe Ser Phe Leu Phe Glu Ser Ala Asp Ser Ser Lys Ile Pro Thr
            500                 505                 510

Leu Ile Lys Lys Met Pro
            515

<210> SEQ ID NO 47
<211> LENGTH: 580
<212> TYPE: PRT
<213> ORGANISM: Thalassospira xiamenensis

<400> SEQUENCE: 47

Met Ser Thr Pro Phe Ala Arg Phe Thr Ser Pro Ala His Gln Ala Pro
1               5                   10                  15

Lys Asp Tyr Lys Lys Leu Gly Met Glu Asn Glu Leu Ser Ala Phe Glu
            20                  25                  30

Thr Asp Trp Asn Asn Val Ala Gly Trp Thr Glu Met Ala Ile Ile
        35                  40                  45

Gly Asp Pro Trp Ser Asn Leu Asn Asp Ala Pro Arg Ala Asp Tyr Tyr
```

```
                 50                  55                  60
Asn Pro Leu Thr Glu Gly Phe Gly Glu Ala Gly Asp Ala Val Ile Ser
 65                  70                  75                  80

Trp Thr Pro Phe Pro Asn Arg Leu Ile Ala Phe Leu Thr Pro Pro Glu
                     85                  90                  95

Ala Ser Asn Asn Pro Gln Leu His Arg Pro Leu Thr Met Asp Glu Val
                100                 105                 110

Met Ser Leu Ala Asp Ser Gly Glu Ile Thr Val Asp Gly Thr Leu Tyr
                115                 120                 125

Lys Leu Tyr Asp Pro Ser Gly Ser Ala Pro Ile Leu Lys Ile Pro Ala
            130                 135                 140

Lys Arg Cys Pro Glu Ile Asp Trp Thr Gly Glu Tyr Val Asp Phe Ser
145                 150                 155                 160

Pro Ser Gly Pro Arg Gly Trp Leu Asp Glu Tyr Cys Glu Trp Ser Ile
                165                 170                 175

Thr Tyr Asp Ala Ser Gly Ser Lys Met Gln Ser Val Met Phe Thr Cys
                180                 185                 190

Glu Asn Pro Ala Tyr Tyr Leu Thr Met Trp Arg Ile Asn Pro Glu Ala
                195                 200                 205

Val Leu Gly Leu Tyr Gln Met Tyr Val Asp Pro Ala Val Lys Leu Glu
            210                 215                 220

Asp Leu Tyr Leu Arg Tyr Thr Val Asp Gln Pro Thr Gly Lys Lys Gly
225                 230                 235                 240

Asp Pro Val Met Asp Pro Thr Thr Gly Arg Pro Ala Tyr Asp Val Thr
                245                 250                 255

Asn Lys Trp Asn Arg Gly Thr Val Arg Val Pro Gly Gln Ser Gly Gly
                260                 265                 270

Ala Leu His Leu Thr Ser Gly Pro Asn Thr Leu Ser Ala Glu Ile Tyr
                275                 280                 285

Leu Ala Ala Ala Thr Ile Gln Arg Pro Asp Leu Ser Ser Arg Asp
            290                 295                 300

Pro Gln Ser Leu Ile Cys Cys Ala Gln Tyr Gly Gln Asn Tyr Arg Asn
305                 310                 315                 320

Ser Asp Pro His Ile Gly Phe Ile Ala Asn Arg Ala Ala Arg Tyr
                325                 330                 335

Arg Ile Ser Leu Thr Asp Pro Val Gly Leu Tyr Ile Gln Gln Pro Gln
                340                 345                 350

Asn Leu Ser Asn Trp Lys Gly Pro Asn Gly Glu Asp Ile Ser Gln Tyr
            355                 360                 365

Trp Lys Ile Thr Arg Gly Thr Ala Gly Thr Gly Pro Asn Asn Ser Asp
370                 375                 380

Gln Ile Leu His Ala Val Phe Asp Ile Pro Pro Ser Ala Gly Phe Thr
385                 390                 395                 400

Ile Asn Asp Cys Thr Ile Asn Gly Gln Lys Ile Ala His Ile Gly Asp
                405                 410                 415

Ile Ala Asn Gln Met Lys Ile Ala Leu Ser Ala Thr Gln Met Thr Pro
                420                 425                 430

Asn Gln Pro Leu Gln Ser Pro Met Lys Cys Val Ser Ser Arg Ser Ser
            435                 440                 445

Gly Ser Met Gln Pro Trp Pro Val Gln Phe Val Pro Ile Asp Leu Phe
            450                 455                 460

Tyr Gly Glu Ser Pro Thr Asp Leu Pro Ala Leu Met Val Pro Gly Thr
465                 470                 475                 480
```

Val Asn Ser Phe Val Leu Ile Val Gln Gly Ala Asp Lys Asn Thr Thr
                485                 490                 495

Ile Asp Asn Ala Arg Ile Glu Phe Ser Asn Pro Gly Ile Lys Ala Lys
            500                 505                 510

Val Thr Lys Phe Leu Pro Asp Ala Ser Ala Ile Pro Gly Gln Thr Asp
        515                 520                 525

Gly Gly Gly Thr Gln Gly Phe Ile Met Asp Val Ala Val Ser Ser Ser
    530                 535                 540

Ala Lys Pro Gly Ser Val Ser Leu Arg Val Leu Asn Pro Asn Glu Pro
545                 550                 555                 560

Ala Asn Pro Ser Asp Ala Asp His Pro Trp Glu Ser Gly Leu Ala Val
            565                 570                 575

Ile Pro Ser His
            580

<210> SEQ ID NO 48
<211> LENGTH: 539
<212> TYPE: PRT
<213> ORGANISM: Thalassospira xiamenensis

<400> SEQUENCE: 48

Met Asn Arg Leu His Leu Gly Ala Gly Cys Val Ile Ala Gly Phe Cys
1               5                   10                  15

Ile Leu Ala Ile Ala Gly Leu Leu Trp Val Ile Asp Val Pro Ala Gly
            20                  25                  30

Arg Ala Asp Glu Ile Asn Ile Ser Arg Val Thr Glu Ile Ala Gln Ser
        35                  40                  45

Ala Gln Gln Cys Pro Asp Gln Leu Val Phe Asp Pro Thr Ser Gly Ser
    50                  55                  60

Phe Met Thr Ser Asp Asn Leu Phe Leu Pro Thr Gln Gln Gly Asn Asn
65                  70                  75                  80

Cys Tyr Ala Trp Gln Met Phe Ile Ala Met Asn Trp Pro Val Ser Ser
                85                  90                  95

Ser Trp Pro Gly Thr Pro Ser Ala Ala Gly Glu Pro Asp Gln Asn Val
            100                 105                 110

Ser Val Glu Asn Trp Gly Val Pro Glu Asn Pro Thr Ser Pro Leu Thr
        115                 120                 125

Ser Val Pro Val Trp Gly Ser Phe Lys Asp Ala Gln Ala Ile Phe Leu
    130                 135                 140

Pro Asp Ala Ala Lys Pro Thr Asp Trp Gly Val Pro Gln Ala Val Pro
145                 150                 155                 160

Ser Gly Cys Lys Ser Asp Lys Met Leu Leu Gly Tyr Pro Ala Gly Ser
                165                 170                 175

Ala Lys Ile Leu Thr Thr Leu Ser Lys Asn Ala Val Asn Thr Ala His
            180                 185                 190

Arg Phe His Leu Ser Ser Gly Thr Arg Asp Thr Gln Ser Asp Glu Ile
        195                 200                 205

Met Glu Ala Thr Gly Gly Trp Leu Thr Asp Gln Asn Gly Asn Leu Val
    210                 215                 220

Phe Phe Glu Arg Lys Val Gly Lys Ala Glu Phe Asp Tyr Ile Met Asn
225                 230                 235                 240

Asn Ala Leu Tyr Asp Ala Ala Tyr Gln Met Arg Val Ala Thr Asn Ala
                245                 250                 255

Asp Gly Arg His Pro Ala Gly Leu Ser Leu Pro Ser Gly Lys Phe Leu

```
                  260                 265                 270
Arg Val Pro Pro Thr Glu Pro Gln Gly Gln Asp Ala Leu Gly Ala Phe
        275                 280                 285

Glu Ile Lys Ala Ala Trp Arg Val Leu Thr Gly Gln Ser Asp Ile Tyr
    290                 295                 300

Asp Arg Tyr Leu Thr Ser Val Ala Trp Leu Lys Arg Pro Asp Thr Gly
305                 310                 315                 320

Glu Cys Ser Gln Glu Val Val Gly Leu Val Gly Leu His Ile Ile His
                325                 330                 335

Lys Thr Asp Thr Phe Pro Asp Leu Ile Trp Ala Thr Phe Glu Gln Val
            340                 345                 350

Asp Asn Val Pro Asp Gly Gln Ala Thr Leu Pro Pro Gly Gly Tyr Ser
        355                 360                 365

Phe Asn Asn Pro Asn Cys Thr Gly Pro Asp Cys Lys Pro Asn Gln Pro
    370                 375                 380

Arg Ile Asp Cys Asn Asp Gln Asn Gln Cys Lys Asp Leu Tyr Pro Arg
385                 390                 395                 400

Asp Gln Pro Val Gln Val Thr Arg Glu Gln Ala Leu Thr Ser Glu Met
                405                 410                 415

Asp Thr Leu Asn Ala Gly Val Ala Gln Lys Ile Ala Ser Gln Thr Gly
            420                 425                 430

Gly Lys Ser Val Phe Gln Tyr Tyr Lys Leu Val Asn Val Leu Trp Asp
        435                 440                 445

Gly Ser Pro Ser Pro Val Met Glu Pro Gly Ala Asn Ala Ser Ile
    450                 455                 460

Pro Leu Arg Tyr Gly Thr Phe Glu Ser Glu Gly Asn Leu Lys Val Ala
465                 470                 475                 480

Asn Thr Thr Met Glu Thr Tyr Ile Gln Asp Gln Ser Cys Asp Phe Cys
                485                 490                 495

His Ala Asn Ala Thr Ile Ala Gly Ser Asp Thr Leu Ala Ser Asp Phe
            500                 505                 510

Ser Phe Ile Phe Arg Asp Ala Gly Ser Ala Lys Asn Pro Ser Leu Val
        515                 520                 525

Glu Glu Val Lys Gln Phe Met Glu Gln Ala Gln
    530                 535

<210> SEQ ID NO 49
<211> LENGTH: 577
<212> TYPE: PRT
<213> ORGANISM: Paracoccus denitrificans

<400> SEQUENCE: 49

Met Thr Ile Phe Thr Glu Phe Ser Thr Pro Ala Gln Gln Gly Pro Lys
1               5                   10                  15

Asp Tyr Gln Leu Leu Gly Leu Pro Ala Ala Asp Leu Ala Ala Phe Glu
            20                  25                  30

Ala Asp Trp Ser Ala Asn Ile Ala Gly Trp Thr Gln Met Ser Ile Ile
        35                  40                  45

Gly Asn Pro Trp Ser Asn Leu Asn Asp Thr Pro Arg Asp Asn Tyr Tyr
    50                  55                  60

Asp Pro Leu Val Glu Gly Met Gly Glu Ala Thr Ala Ala Val Ile Ser
65                  70                  75                  80

Trp Pro Pro Phe Pro Asn Arg Leu Ile Gln Phe Leu Thr Asn Pro Gly
                85                  90                  95
```

Ile Val Lys Gly Gly Gln Leu Thr Ala Pro Leu Ser Gln Asp Ala Val
            100                 105                 110

Gln Glu Leu Ala Asp Ser Gly Arg Ile Thr Gln Gly Gly Thr Ser Phe
        115                 120                 125

Val Leu Phe Asp Pro Glu Pro Gly Gln Val Leu Leu Lys Ile Pro Ala
    130                 135                 140

Asp Arg Cys Pro Ala Ile Asp Trp Asp Gly Lys Tyr Val Asp Phe Ser
145                 150                 155                 160

Pro Ser Gly Pro Arg Gly Trp Gln Asp Glu Tyr Cys Glu Trp Ser Ile
                165                 170                 175

Leu Arg Asn Ala Gln Gly Lys Met Gln Ser Ile Ala Phe Thr Cys Glu
            180                 185                 190

Asn Pro Ala Tyr Tyr Leu Thr Met Trp Arg Gln Asn Pro Lys Ala Val
        195                 200                 205

Leu Gly Ile Tyr Gln Arg Tyr Ile Asp Pro Ala Val Gln Leu Glu Asp
    210                 215                 220

Leu Phe Leu Arg Tyr Glu Tyr Asp Gln Pro Thr Gly Lys Lys Gly Asp
225                 230                 235                 240

Pro Val Leu Asp Pro Thr Thr Gly Asn Pro Ala Tyr Asp Pro Thr Asn
                245                 250                 255

Lys Trp Asn Arg Gly Pro Ala Arg Val Pro Gly Ser Phe Gly Gly Ala
            260                 265                 270

Met His Leu Thr Ser Pro Pro Asn Thr Leu Ser Ala Glu Ile Tyr Leu
        275                 280                 285

Ala Ala Ala Ala Thr Ile Gln Arg Pro Ser Ser Val Asn Gly Asn Pro
    290                 295                 300

Gln Ser Leu Ile Cys Cys Ala Gln Tyr Gly Gln Asn Phe Arg Asn Ser
305                 310                 315                 320

Asp Pro Asn Ile Gly Tyr Gly Ala Asn Val Ala Ala Arg Thr Ala Arg
                325                 330                 335

Leu Thr Leu Thr Asp Pro Val Gly Leu Tyr Ile Gln Gln Pro Gln Asn
            340                 345                 350

Phe Gln Gly Trp Ser Gly Pro Asn Gly Glu Asp Val Ser Gly Tyr Trp
        355                 360                 365

Gln Ile Leu Arg Gly Thr Ala Gly Thr Gly Pro Asn Gly Ser Asp Gln
    370                 375                 380

Ile Leu His Ala Val Phe Ala Ile Pro Glu Ser Ala Gly Tyr Ser Ile
385                 390                 395                 400

Glu Asp Cys Thr Ile Tyr Gly Leu Pro Ile Ser His Val Gly Val Ile
                405                 410                 415

Leu Asp Gln Met Lys Val Ala Leu Ala Val Thr Pro Asn Asn Ala Ala
            420                 425                 430

Pro Asp Thr Thr Ala Phe Ala Cys Val Thr Asp Arg Thr Asp Gly Thr
        435                 440                 445

Gln Pro Trp Pro Val Gln Met Val Pro Glu Ser Leu Phe Tyr Gly Glu
    450                 455                 460

Ser Pro Ser Asp Leu Pro Ala Leu Leu Arg Pro Gly Ser Lys Phe Arg
465                 470                 475                 480

Phe Val Leu Ile Val Gln Gly Ala Asp Glu Asn Thr Thr Pro Ala Thr
                485                 490                 495

Ala Arg Val Glu Phe Ser Asp Pro Asn Ile Thr Val Thr Val Glu Gln
            500                 505                 510

Phe Leu Lys Asn Ala Ser Ala Val Pro Gly Gln Thr Asn Gly Gly Gly

```
                    515                 520                 525
Thr Gln Gly Tyr Val Met Asp Ile Ala Val Gly Ala Asn Ala Gln Pro
            530                 535                 540

Gly Pro Val Ser Val Arg Ala Leu Asn Pro Ser Glu Gly Pro Ala Pro
545                 550                 555                 560

Thr Pro Glu Gln His Pro Trp Glu Ala Gly Leu Ala Val Ile Ser Ser
            565                 570                 575

Arg

<210> SEQ ID NO 50
<211> LENGTH: 502
<212> TYPE: PRT
<213> ORGANISM: Paracoccus denitrificans

<400> SEQUENCE: 50

Met Arg Thr Gly Gln Ile Leu Ile Ala Leu Val Ala Gly Val Met Leu
1               5                   10                  15

Ala Phe Ala Ala Ser Gly Gly Lys Ala Gln Thr Ala Cys Ser Ala Met
            20                  25                  30

Leu Ile Thr Asp Pro Thr Ser Ala Asp Phe Leu Thr Gly Asp Thr Pro
        35                  40                  45

Phe Gly His Thr Gln Asp Gly Met Asn Cys Tyr Gly Trp Gln Met Phe
    50                  55                  60

Leu Ser Leu Asn Trp Pro Ala Asp Pro Gly Trp Pro Gln Thr Pro Ala
65                  70                  75                  80

Met Ala Gly Glu Pro Asp Arg Ser Ala Thr Ile Ala Asp Phe Gly Leu
                85                  90                  95

Pro Gly Pro Ala Gly Gln Pro Met Gln Arg Pro Thr Val Trp Gln Ser
            100                 105                 110

Phe Met Pro Ala Pro Glu Ile Phe Lys Pro Phe Ala Ala Met Pro Thr
        115                 120                 125

Gly Trp Gly Glu Thr Ser Pro Pro Ala Ser Cys Gly Ser Ala Ser
    130                 135                 140

Leu Ala Ala Ser Ala Gly Ser Ile Arg Met Leu Asn Ala Val Ser Lys
145                 150                 155                 160

Ser Ala Val Ser Pro Arg His Gly Phe Asn Leu Asp Thr Gly Thr Met
                165                 170                 175

Ser Ser Ile Ser Asp Glu Ile Glu Glu Ala Thr Gly Gly Trp Leu Thr
            180                 185                 190

Asp Gln Lys Gly Lys Leu Val Phe Phe Glu Arg Met Ile Gly Lys Ala
        195                 200                 205

Glu Tyr Asp Tyr Ile Val Ala Lys Gly Leu Tyr Asp Ala Ala Asn Gln
    210                 215                 220

Leu Lys Val Ala Thr Asn Ala Asp Gly Ala Thr Pro Glu Gly Leu Ser
225                 230                 235                 240

Leu Pro Lys Gly Thr Pro Pro Gly Ser Ala Val Gln Asn Gln Asp Glu
                245                 250                 255

Leu Gly Ala Phe Glu Leu Lys Ala Ala Trp Arg Asn Leu Thr Gly Leu
            260                 265                 270

Asp Asp Leu Tyr Gly Arg Tyr Leu Thr Ser Thr Val Tyr Leu Leu Tyr
        275                 280                 285

Pro Asp Gly Ser Cys Glu Lys Ala Val Val Gly Leu Val Gly Leu His
    290                 295                 300

Ile Ile His Lys Thr Ala Ser Met Pro Asp Phe Val Trp Ser Thr Phe
```

```
              305                 310                 315                 320
        Glu Gln Ile Asp Asn Val Pro Gly Ala Ser Ala Pro Glu Val Asp Phe
                        325                 330                 335

Ser Phe Asn Asn Pro Ala Ser Asn Ala Lys Pro Asn Gln Met Pro His
                        340                 345                 350

Cys Val Asn Gly Val Cys Asp Tyr Ser Leu Pro Ile Gln Val Thr Arg
                        355                 360                 365

Glu Val Ala Ile Pro Ala Gly Val Ala Gln Thr Asn Arg Asp Val Gln
                370                 375                 380

Gln Leu Leu Ala Asp Arg Thr Gly Gly Lys Ser Val Phe Gln Tyr Tyr
        385                 390                 395                 400

Gln Leu Val Asn Val Leu Trp Asp Gly Ala Pro Thr Pro Ser Pro
                        405                 410                 415

Glu Pro Gly Ala Asn Ala Gln Val Pro Leu Val Tyr Gly Thr Phe Gln
                        420                 425                 430

Thr Asp Gly Ser Val Pro Val Ala Asn Thr Thr Met Glu Thr Tyr Ala
                        435                 440                 445

Gln Gln Phe Thr Pro Gly Leu Gly Pro Ser Cys Thr Ala Cys His Lys
                        450                 455                 460

Gly Ala Thr Ile Ala Asn Ser Ala Thr Leu Ala Ser Asp Phe Ser Phe
        465                 470                 475                 480

Leu Phe Ser Thr Ala Ser Ser Ala Thr Lys Leu Pro Gly Leu Phe Ile
                        485                 490                 495

Ser Arg Asp Phe Val Pro
                        500

<210> SEQ ID NO 51
<211> LENGTH: 580
<212> TYPE: PRT
<213> ORGANISM: Cellvibrio japonicus

<400> SEQUENCE: 51

Met Ser Ala Phe Thr Phe Ser Thr Pro Ala Leu Ile Gln Asp Phe Ser
1               5                   10                  15

Asp Asn Pro Ser Leu Gln Gln Leu Asn Gln Asn Trp Asp Leu Ala
                20                  25                  30

Ile Asp Ala Tyr Thr Gln Ala Ala Leu Val Ser Asn Pro Trp Thr Val
            35                  40                  45

Asp Tyr Gln Ala Pro Cys Asp Trp Tyr Val Asn Pro Lys Gln Ala Asp
    50                  55                  60

Ile Thr Ala Ala Asn Pro Val Glu Pro Ile Phe Trp Thr Ala Phe Pro
65                  70                  75                  80

Asn Arg Leu Lys Ile Tyr Phe Ser Ala Ala Glu Lys Ser Pro Tyr Gln
                85                  90                  95

Met Ala Asn Ala Gln Val Phe Ala Leu Ala Asp Phe Gly Asn Val Pro
            100                 105                 110

Gln Ser Lys Ala Phe Pro Thr Gly Leu Pro Phe Ile Ile Pro Ser Lys
        115                 120                 125

Arg Cys Pro Asn Leu Asn Trp Gln Gln Ser Ile Ala Glu Trp Val Gln
130                 135                 140

Tyr Asp Pro Lys Gly Pro Arg Gly Trp Leu Asp Glu Tyr Cys Glu Trp
145                 150                 155                 160

Ser Val Thr Arg Asn Ala Asp Gly Lys Ile Thr Lys Ile Ala Phe Thr
                165                 170                 175
```

```
Cys Glu Asn Pro Glu Tyr Trp Phe Thr Leu Trp Gln Val Ser Pro Glu
                180                 185                 190
Lys Val Leu Ala Leu Tyr Gln Gln Leu Val Ser Pro Asn Val Val Leu
            195                 200                 205
Glu Asp Leu Gln Leu Pro Ser Ala Asp Gly Lys Gly Phe Val Ile Asp
210                 215                 220
Pro Thr Thr Gly Arg Pro Ala Tyr Asn Pro Leu Asn Lys Trp Asn Ser
225                 230                 235                 240
Gly Thr Val Ala Thr Glu Thr Tyr Gly Gly Ala Val His Leu Thr Ser
                245                 250                 255
Pro Pro Asn Thr Ile Gly Ala Glu Ile Met Leu Ala Ala Gln Ala Thr
            260                 265                 270
Leu Leu Arg Asp Leu Pro Pro Asp Gln Tyr Asn Met Gln Arg Met Val
            275                 280                 285
Cys Ala Gly Ala Tyr Gly Arg Ala Tyr Arg Asn Ser Asp Pro His Ile
            290                 295                 300
Gly Leu Gln Ala Asn Gln Leu Val Lys Asn Leu Gly Val Lys Ile Thr
305                 310                 315                 320
Leu Thr Asn Pro Val Gly Leu Tyr Leu Gln Arg Pro Asp Phe Ser Ser
                325                 330                 335
Tyr Lys Thr Pro Asp Gly Lys Asp Ala Gly Gln Phe Tyr Lys Val Ile
                340                 345                 350
Arg Gly Arg Thr Ala Gln Gln Ala Gly Thr Thr Tyr Asp Gln Ile Leu
                355                 360                 365
His Ala Glu Phe Ser Val Pro Glu Glu Leu Gly Tyr Thr Val Ser Asp
            370                 375                 380
Ile Leu Ile Gly Asn Ala Val Pro Gly Ser Ser Gln Val Pro Val Pro
385                 390                 395                 400
Ile Leu Tyr Ala Gly Gln Ile Ala Glu Thr Phe His Val Cys Leu Ala
                405                 410                 415
Gly Thr Ala Ile Ala Pro Ala Thr Gly Glu Pro Ser Gln Ala Phe Leu
                420                 425                 430
Pro Pro Val Thr Asp Lys Thr Gly Asn Thr Asn Gly Gln Val Ser Met
            435                 440                 445
Leu Leu Ala Asn Pro Val Leu Leu Ala Met Gln Ala Val Asn Pro Phe
450                 455                 460
Pro Pro Phe Val Gln Leu Pro Val Gln Ile Ala Gln Gly Gln Thr Leu
465                 470                 475                 480
Thr Asn Met Ala Leu Gln Val Ser Tyr Ala Asn Asp Asn Phe Gln Glu
                485                 490                 495
Ala Gln Ile Ala Phe Trp Asp Ala Gln Gly Asn Ser Glu Pro Gly Ile
                500                 505                 510
Ser Val Thr Val Thr Ala Ile Glu Thr Ala Asp Gly Thr Pro Ala Gly
            515                 520                 525
Lys Ser Ala Gly Gly Asp Gly Leu Phe Asn Tyr Ile Ile Ser Ile Ser
            530                 535                 540
Val Ala Pro Gly Val Ser Pro Gly Phe Lys Gly Val Thr Val Arg Asn
545                 550                 555                 560
Pro Ala Cys Asp Met Pro Leu Pro Leu Pro Gly Val Leu Phe Val Thr
                565                 570                 575
Ala Lys Gly Asn
            580
```

<210> SEQ ID NO 52
<211> LENGTH: 506
<212> TYPE: PRT
<213> ORGANISM: Cellvibrio japonicus

<400> SEQUENCE: 52

Met Lys His Thr Leu Leu Ile Gly Val Thr Gly Leu Leu Val Ala
1               5                   10                  15

Ala Cys Gln Gln Pro Val Gln Glu Ser Ser Ala Ala Val Asp Ala Pro
            20                  25                  30

Ala Val Ser Thr Val Ser Ser Ser Ala Pro Ile Ser Phe Pro Cys
            35                  40                  45

Leu Asn Lys Pro Ala Val Asn Tyr Asn Thr Pro Gly Asp Thr Pro Ile
    50                  55                  60

Thr Ser Gln Asp Gly Val Asn Cys Phe Ala Trp Gln Thr Phe Ile Gly
65                  70                  75                  80

Leu Asn Trp Pro Val Asp Ala Ser His Pro Gly Glu Pro Asp Lys Thr
                85                  90                  95

Ala Ser Ala Ser Val Phe Gly Glu Pro Gly Leu His Gln Thr Ser Val
            100                 105                 110

Trp Glu Thr Tyr Ala Asn Ser Lys Ser Val Phe Arg Ala Asn Ala Gln
        115                 120                 125

Pro Pro Leu Pro Trp Gly His Thr Pro Asp Val Pro Ser Ser Cys Gln
    130                 135                 140

Lys Ile Ser Gln Thr Leu Gly Leu Arg Val Met Gln Ala Ser Arg Met
145                 150                 155                 160

Pro Gly Ser Phe Asn Met Ser Lys Glu Ala Ser Gln Ala Phe Pro Gly
                165                 170                 175

Asn Asn Pro Asn Trp Leu Ala Asp Lys Ser Gly Asn Leu Val Tyr Tyr
            180                 185                 190

Glu Ile Leu Ile Gly Lys Asp Glu Tyr Asp Tyr Ile Asn Asn Asn Gly
        195                 200                 205

Leu Tyr Asn Ala Asn Thr Gln Ala Ala His Ile Gln Gln Asn Lys Asn
    210                 215                 220

Ile Ala Met Pro Leu Gly His Asp Lys Val Leu Gly Gly Leu Glu Ile
225                 230                 235                 240

Lys Ala Ala Trp Leu Ser Val Ser Asp Pro Gln Asn Pro Lys Trp Lys
                245                 250                 255

Asn Tyr Lys Leu Ser Thr Ser Val Ile Tyr Asp Pro Val Ser Lys Asp
            260                 265                 270

Cys His Ala Ser Thr Ile Ala Leu Val Gly Met His Ile Ile Arg Lys
        275                 280                 285

Thr Ala Ser Gln Pro Gln Trp Ile Trp Ala Thr Phe Glu His Lys Asp
    290                 295                 300

Asn Ala Pro Asp Thr Ala Ser Ile Lys Ser Asp Gly Thr Val Asp Gly
305                 310                 315                 320

Asp Tyr Thr Phe Tyr Ser Asn Ser Cys Thr Val Lys Pro Val Pro Ala
                325                 330                 335

Gly Cys Lys Ala Lys Val Glu Asn Gly Thr Ser Val Thr Gln Thr Ser
            340                 345                 350

Cys His Val Asn Val Ser Pro Ala Tyr Tyr Leu Asp Thr Ser Gly Asn
        355                 360                 365

Cys Pro Ala Tyr Pro Ile Gln Val Ser Arg Asp Phe Ala Ile Lys Asp
    370                 375                 380

```
Ser Thr Asp Asn His Val Ala Ser Leu Asn Arg Ala Val Gln Gln Leu
385                 390                 395                 400

Ile Ala Ser Ser Asn Ala Asp Ser Val Tyr Thr His Tyr Gln Leu Val
            405                 410                 415

Asn Val Leu Trp Ser Ser Ala Ala Val Asn Asp Asn Ala Pro Pro Gly
        420                 425                 430

Asn Pro Pro Leu Thr Pro Leu Ser Ile Ser Gly Glu Thr Pro Ser Leu
            435                 440                 445

Asn Thr Val Pro Val Ala Asn Thr Met Leu Glu Thr Tyr Ala Gln Gly
        450                 455                 460

Phe Asn Cys Leu Ser Cys His Ala Tyr Ala Ser Val Ala Arg Asp Ala
465                 470                 475                 480

Arg Ala Gln Leu Gly Gly Lys Ala Tyr Ala Thr Asp Tyr Ser Phe Ile
            485                 490                 495

Phe Ser Phe Ala Thr Ser Pro Ala Ala Lys
            500                 505

<210> SEQ ID NO 53
<211> LENGTH: 256
<212> TYPE: PRT
<213> ORGANISM: Pseudomonas brenneri

<400> SEQUENCE: 53

Met Gly Ser Ile Thr Asp His Asn Gln Leu Leu Ala Trp Val Ala Ser
1               5                   10                  15

Leu Asp Ile Pro Glu Ala Ser Gly Val Lys Thr Arg Ser Arg Asn Val
            20                  25                  30

Val Ala Arg Ala Asn Ala Glu Asp Glu Gly Ala Ala Val Val Arg Gly
        35                  40                  45

Ser Ile Thr Ser Phe Val Thr Gly Leu Ser Gln Gln Ala Arg Asp Asp
    50                  55                  60

Val Gln Asn Ser Thr Leu Leu Met Gln Leu Ala Ala Asp Lys Lys Phe
65                  70                  75                  80

Asn Pro Glu Lys Gln Arg Glu Glu Trp Phe Lys Phe Tyr Thr Asp Gly
                85                  90                  95

Leu Ala Asn Leu Gly Trp Gly Arg Val Ser Ser Tyr Tyr Gln Ser Tyr
            100                 105                 110

Gln Pro Arg Asn Thr Asn Val Thr Met Asp Gln Val Val Leu Glu Val
        115                 120                 125

Ile Ala Ala Val Val Gly Ala Asp Ser Ala Val Tyr Lys Val Thr Glu
    130                 135                 140

Lys Thr Phe Ser Ser Leu Gln Asp Asn Pro Lys Asn Gln Ala Pro Leu
145                 150                 155                 160

Lys Leu Phe Asp Ser Ser Thr Arg Asp Ser Val Gly Thr Phe Gln
                165                 170                 175

Ile Leu Pro Val Met Gln Asp Arg Asp Gly Asn Val Val Met Val Leu
            180                 185                 190

Thr Thr Val Asn Ala Ser Thr Thr Val Gln Arg Gly Ser Phe Leu Phe
        195                 200                 205

Trp Ser Trp Ser Lys Thr Thr Ala Trp Met Tyr Arg Ala Ala Gln Gln
    210                 215                 220

Thr Val Leu Asn Glu Ser Val Tyr Ala Thr Val Arg Gln Ser Val Ile
225                 230                 235                 240

Lys Lys Leu Gly Lys Asn Ala Glu Glu Phe Ile Asp Asp Leu Glu Ile
                245                 250                 255
```

```
<210> SEQ ID NO 54
<211> LENGTH: 260
<212> TYPE: PRT
<213> ORGANISM: Pseudomonas brenneri

<400> SEQUENCE: 54

Met Lys Leu Ser Ala Asp Glu Val Tyr Val Ile Ser Gly Asn Leu Leu
1               5                   10                  15

Ser Ala Thr Pro Ser Leu Thr Asp Pro Thr Val Leu Glu Asp Ile Ala
            20                  25                  30

Asn Ser Asn Leu Leu Cys Gln Leu Ala Ala Asp Lys Asn Gln Gly Thr
        35                  40                  45

Arg Phe Ile Asp Pro Ala Ala Trp Leu Asp Phe Tyr Arg Ser Ser Leu
    50                  55                  60

Gly Arg Leu Phe Trp Arg Ile Ser Asn Ser Gly Thr Val Ser Tyr Ala
65                  70                  75                  80

Ile Pro Gln Leu Val His Lys Ile Thr Val Lys Glu Val Leu Glu Lys
                85                  90                  95

Thr Phe Tyr Lys Thr Leu Asp Arg Pro Gln Arg Ile Arg Val Glu Glu
            100                 105                 110

Ser Ile Glu Leu Leu Gly Glu Gln Ser Ala Asp Ser Pro Ser Ala Thr
        115                 120                 125

Leu Tyr Ser Leu Lys Thr Gln Val Asn Phe Asn Glu Thr Thr Ser Ser
    130                 135                 140

Pro Gly Leu Leu Pro His Ser Ile Ser Ser Val Asn Leu Gln Leu Ser
145                 150                 155                 160

Val Val His Ser Glu Thr Cys Ile Ser Val Cys Ser Val Tyr Phe Lys
                165                 170                 175

Thr Ser Thr Arg Ile Gly Asp Asp Val Phe Asn Gln Lys Phe Pro Val
            180                 185                 190

Lys Glu Leu Leu Gly Asn Val Ser Val Ser Thr Phe Glu Ala Lys Leu
        195                 200                 205

Leu Glu Ser Ser Tyr Ala Gly Ile Arg Gln Ser Ile Ile Asp Lys Leu
    210                 215                 220

Gly Glu Asp Asn Ile Arg Glu Asn Ile Leu Val Pro Ala Val Ser
225                 230                 235                 240

Pro Ser Leu Ser Asn Thr Arg His Ala Gly Ala Leu Gln Phe Val Gln
                245                 250                 255

Glu Leu Asp Ile
            260

<210> SEQ ID NO 55
<211> LENGTH: 260
<212> TYPE: PRT
<213> ORGANISM: Pseudomonas gessardii

<400> SEQUENCE: 55

Met Lys Leu Ser Thr Asp Glu Val Tyr Val Ile Ser Gly Asn Leu Leu
1               5                   10                  15

Ser Ala Thr Pro Ser Leu Thr Asp Pro Ala Val Leu Glu Asp Ile Ala
            20                  25                  30

Asn Ser Asn Leu Leu Cys Gln Leu Ala Ala Asp Lys Asn Gln Gly Thr
        35                  40                  45

Arg Phe Ile Asp Pro Ala Ala Trp Leu Asp Phe Tyr Arg Asn Ser Leu
    50                  55                  60
```

Gly Lys Leu Phe Trp Arg Ile Ser Asn Ser Gly Thr Val Ser Tyr Ala
65                  70                  75                  80

Ile Pro Gln Leu Val His Lys Ile Thr Val Lys Glu Val Leu Glu Lys
                85                  90                  95

Thr Phe Tyr Lys Asn Leu Asp Arg Pro Gln Arg Ile Arg Val Glu Asp
            100                 105                 110

Ser Ile Glu Leu Leu Gly Glu Gln Ser Val Asp Ser Pro Ser Ala Thr
        115                 120                 125

Leu Tyr Ser Leu Lys Thr Gln Val Asn Phe Asn Glu Thr Thr Ser Ser
    130                 135                 140

Pro Gly Leu Leu Pro His Ser Val Ser Ser Val Asn Leu Gln Leu Ser
145                 150                 155                 160

Val Val His Ser Glu Thr Cys Ile Ser Val Cys Ser Val Tyr Phe Lys
                165                 170                 175

Thr Ser Thr Arg Ile Gly Asp Asp Val Phe Asn Gln Lys Phe Pro Val
            180                 185                 190

Lys Glu Leu Leu Gly Asn Val Ser Val Ser Thr Phe Glu Ala Lys Leu
        195                 200                 205

Leu Glu Ser Ser Tyr Ala Ser Ile Arg Gln Ser Ile Ile Asp Lys Leu
    210                 215                 220

Gly Glu Asp Asn Ile Arg Glu Asn Ile Leu Leu Val Pro Ala Val Ser
225                 230                 235                 240

Pro Ser Leu Ser Asn Ser Arg His Ala Gly Ala Arg Gln Phe Val Gln
                245                 250                 255

Glu Leu Asp Ile
            260

<210> SEQ ID NO 56
<211> LENGTH: 260
<212> TYPE: PRT
<213> ORGANISM: Pseudomonas fluorescens

<400> SEQUENCE: 56

Met Gly Ser Ile Thr Asp His Gly Lys Leu Leu Ala Trp Val Glu Ser
1               5                   10                  15

Leu Asp Val Pro Lys Ser Thr Gly Asn Ala Asn Leu Lys Arg Ala Ser
            20                  25                  30

Ala Val Leu Arg Ser Ala Ala Gln Asn Ser Asp Glu Asp Gly Ala Ala
        35                  40                  45

Val Val Arg Gly Ser Ile Thr Ser Phe Val Thr Gly Leu Thr Pro Gln
    50                  55                  60

Ala Arg Asp Asp Val Gln Asn Ser Thr Leu Leu Met Gln Leu Ala Ala
65                  70                  75                  80

Asp Lys Lys Tyr Asn Pro Asp Thr Gln Arg Glu Glu Trp Phe Lys Phe
                85                  90                  95

Tyr Thr Asp Gly Leu Ala Asn Leu Gly Trp Gly Arg Val Ser Ser Ala
            100                 105                 110

Tyr Gln Lys Tyr Lys Pro Thr Asn Thr Asn Ala Thr Met Asp Gln Val
        115                 120                 125

Val Leu Glu Ile Ile Ser Ser Val Val Ser Pro Glu Ser Ala Leu Tyr
    130                 135                 140

Lys Val Thr Glu Lys Thr Phe Leu Ala Leu Lys Asn Asn Pro Asn Asn
145                 150                 155                 160

Lys Asp Ala Leu Lys Leu Phe Asp Val Ser Ser Thr Arg Asn Asp Leu

```
                        165                 170                 175
Gly Thr Phe Gln Ile Leu Pro Val Met Gln Asp Lys Asp Gly Asn Val
                180                 185                 190

Val Thr Val Leu Thr Cys Ile Asn Ala His Thr Glu Val Gln Lys Gly
            195                 200                 205

Ser Phe Leu Phe Trp His Trp Ser Ser Thr Ser Ala Glu Met Tyr Arg
    210                 215                 220

Ala Ala Gln Gln Val Val Leu Asn Gln Asn Val Tyr Ala Thr Val Arg
225                 230                 235                 240

Gln Ser Val Leu Lys Lys Leu Gly Lys Asn Ala Glu Asp Phe Ile Asp
                245                 250                 255

Gly Leu Asp Ile
            260

<210> SEQ ID NO 57
<211> LENGTH: 259
<212> TYPE: PRT
<213> ORGANISM: Pseudomonas fluorescens

<400> SEQUENCE: 57

Met Ser Phe Thr Ala Pro Glu Val His Val Ser Gly Asn Leu Ile
1               5                   10                  15

Ser Ala Met Pro Ser Val Asn Ser Pro Gln Val Leu Glu Asp Ile Leu
                20                  25                  30

Glu Ser Asn Leu Leu Cys Gln Met Ala Ala Asp Lys Ser Leu Gly Ser
            35                  40                  45

Arg Phe Asn Asn Pro Ala Ala Trp Leu Asp Phe Tyr Arg Asn Ser Leu
    50                  55                  60

Gly Lys Leu Phe Trp Lys Ile Thr Asn Phe Asn Thr Val Ser Tyr Pro
65                  70                  75                  80

Val Pro Ser Pro Thr Arg Ser Val Ser Val Met Gly Ile Leu Glu His
                85                  90                  95

Thr Phe Phe Lys Val Leu Ala Gln Pro Leu Arg His Gln Ile Glu Ala
                100                 105                 110

Asp Ile Glu Leu Leu Met Glu Leu Pro Leu Thr Ser Pro Ala Ser Gln
            115                 120                 125

Leu Tyr Thr Ser Lys Thr His Val Glu Met Ser Thr Arg Ala Arg Ser
    130                 135                 140

Ser Phe Asp Gly Arg Ser Glu Ser Val Ile Ser Leu Gln Ile Ser Val
145                 150                 155                 160

Val His Ser Gly Ser Leu Ile Ser Val Cys Ser Val Tyr Phe Lys Thr
                165                 170                 175

Ala Glu Pro Val Ala Ala Asp Val Phe Ser Gln Lys Phe Lys Val Arg
            180                 185                 190

Asp Leu Leu Gly Asn Ile Ser Val Asn Ser Phe Glu Ala Asp Leu Leu
        195                 200                 205

Glu Gly Ser Tyr Glu Gly Val Arg Gln Gln Ile Lys Thr Lys Leu Gly
    210                 215                 220

Glu Ala Asn Ile Arg Glu Asn Ile Leu Leu Ile Ala Asp Asn Pro Ile
225                 230                 235                 240

Pro Val Asp Glu Leu Pro His Ala Asn Ala His Gln Phe Leu Lys Gly
                245                 250                 255

Leu Asp Ile
```

```
<210> SEQ ID NO 58
<211> LENGTH: 255
<212> TYPE: PRT
<213> ORGANISM: Alcaligenes faecalis

<400> SEQUENCE: 58

Met Ser Thr Ile Thr Asp His Lys Gln Val Leu Ala Trp Ile Asn Ala
1               5                   10                  15

Leu Asp Ile Pro Asp Ala Pro Ala Gly Gly Asn Arg Val Ala Ala Arg
                20                  25                  30

Ala Thr Ser Ser Ala Asp Glu Asp Gly Ala Val Val Ala Lys Ala Ser
            35                  40                  45

Ile Pro Cys Phe Val Ser Gly Leu Thr Glu Gln Ser Arg Ala Asp Val
        50                  55                  60

Gln Asn Ser Thr Leu Leu Met Gln Leu Ala Ala Asp Lys Lys Tyr Pro
65                  70                  75                  80

Asn Glu Asn Asp Arg Glu Lys Trp Phe Lys Phe Tyr Ser Asp Gly Leu
                85                  90                  95

Thr Asn Leu Gly Trp Gly Ser Ser Ser Phe Phe Glu Arg Phe Gln
                100                 105                 110

Pro Lys Asn Thr Asp Val Thr Met Asp Gln Val Val Leu Glu Val Ile
            115                 120                 125

Leu Thr Val Val Asn Asn Val Asn Asn Pro Leu Tyr Lys Ile Ala Gln
130                 135                 140

Glu Thr Phe Gly Ala Leu Asn Lys Pro Ala Asn Gln Lys Pro Met Lys
145                 150                 155                 160

Leu Phe Asp His Ser Ser Thr Lys Glu Asp Arg Gly Lys Phe Gln Ile
                165                 170                 175

Leu Pro Ala Gly Gln Asp Gln His Gly Thr Val Ser Met Val Leu Thr
            180                 185                 190

Ala Ile Asn Ala Arg Thr Asp Ile Gln Ser Gly Ser Phe Leu Phe Trp
        195                 200                 205

Lys Trp Ser Lys Ser Thr Ala Trp Leu Tyr Arg Ala Ala Asn Leu Ile
210                 215                 220

Val Leu Asn Glu Ser Val Tyr Ser Lys Val Arg Gln Ala Val Ile Asp
225                 230                 235                 240

Lys Leu Gly Asp Asn Ala Val Asn Phe Val Leu Asp Leu Asp Ile
                245                 250                 255

<210> SEQ ID NO 59
<211> LENGTH: 268
<212> TYPE: PRT
<213> ORGANISM: Alcaligenes faecalis

<400> SEQUENCE: 59

Met Ala Phe Ser Thr Glu Gln Thr Tyr Val Val Ser Gly Asn Leu Ile
1               5                   10                  15

Ser Ala Thr Thr Glu Asp Thr Asn Thr Leu Ser Tyr Glu Asp Phe Ile
                20                  25                  30

His Ser Asn Leu Leu Ala Gln Met Gly Ala Asp Lys Lys Leu Gly Ser
            35                  40                  45

Arg Phe Val Asp Pro Ala Gly Trp Leu Ser Phe Phe Lys Asn Thr Val
        50                  55                  60

Gly Asn Leu Phe Trp Asn Leu Ser Glu Gln Gly Thr Ser Thr Leu Lys
65                  70                  75                  80

Ile Ser Ala Gly Thr Ala Ser Ile Thr Val Gln Gln Ile Leu Glu Gln
```

```
            85                  90                  95
Ser Phe Phe Lys Arg Leu Asn Gln Ala Gln Ile Asp Ser Ala Thr Ala
            100                 105                 110

Ser Val Asp Leu Phe Ser Gln Leu Ser Glu Asp Pro Ala Phe Ile
            115                 120                 125

Leu Tyr Asn Ala Lys Ser His Ala Gln Ile Ser Thr Ala Lys Val
            130                 135                 140

Ile Lys Pro Pro Gln Lys Glu Thr Tyr Ser Val Asn Leu Gln Ile Ser
145                 150                 155                 160

Ile Ala His Thr Gly Ser Glu Ile Ala Leu Cys Asn Ile Phe Phe Gln
                    165                 170                 175

Thr Ser Gln Ala Val Ser Asp Glu Leu Phe Thr Gln Lys Phe Ala Ile
                    180                 185                 190

Lys Asp Leu Ile Gly Asn Ile Asn Val Phe Tyr Leu Lys Ala Leu Leu
                    195                 200                 205

Ser Glu Thr Asn Tyr Gly His Ile Arg Gln Gln Val Ile Glu Lys Leu
                    210                 215                 220

Gly Glu Asn Ile Asn Thr Asn Ile Val Leu Val Ala Asp Asn Ser Asp
225                 230                 235                 240

Lys Pro Ser Pro Pro Phe Ser His Arg Gly Ala Gln Phe His Thr Gln
                    245                 250                 255

Pro Glu Asn Leu Ile Gln Gln Arg Thr Gly Pro Pro
                    260                 265

<210> SEQ ID NO 60
<211> LENGTH: 255
<212> TYPE: PRT
<213> ORGANISM: Alcaligenes faecalis

<400> SEQUENCE: 60

Met Ser Thr Ile Thr Asp His Lys Gln Val Leu Ala Trp Ile Asn Ala
1               5                   10                  15

Leu Asp Ile Pro Asp Ala Pro Ala Gly Gly Asn Arg Val Ala Ala Arg
                20                  25                  30

Ala Ser Ser Ser Ala Asp Glu Asp Gly Ala Val Val Ala Lys Ala Ser
            35                  40                  45

Ile Pro Cys Phe Val Ser Gly Leu Thr Glu Gln Ser Arg Ala Asp Val
        50                  55                  60

Gln Asn Ser Thr Leu Leu Met Gln Leu Ala Ala Asp Lys Lys Tyr Pro
65                  70                  75                  80

Asp Glu Asn Asp Arg Glu Lys Trp Phe Lys Phe Tyr Ser Asp Gly Leu
                85                  90                  95

Thr Asn Leu Gly Trp Gly Ser Ser Ser Phe Phe Glu Arg Phe Gln
            100                 105                 110

Pro Lys Asn Thr Asp Val Thr Met Asp Gln Val Val Leu Glu Val Ile
            115                 120                 125

Leu Thr Val Val Asn Asn Val Asn Asn Pro Leu Tyr Lys Ile Ala Gln
            130                 135                 140

Glu Thr Phe Gly Ala Leu Asn Lys Pro Ala Asn Gln Lys Pro Met Lys
145                 150                 155                 160

Leu Phe Asp His Ser Ser Thr Lys Glu Asp Arg Gly Lys Phe Gln Ile
                    165                 170                 175

Leu Pro Ala Gly Gln Asp Gln His Gly Thr Val Ser Met Val Leu Thr
                    180                 185                 190
```

```
Ala Ile Asn Ala Arg Thr Asp Ile Gln Ser Gly Ser Phe Leu Phe Trp
            195                 200                 205

Lys Trp Ser Lys Ser Thr Ala Trp Leu Tyr Arg Ala Ala Asn Leu Ile
    210                 215                 220

Val Leu Asn Glu Ser Val Tyr Ser Lys Val Arg Gln Ala Val Ile Asp
225                 230                 235                 240

Lys Leu Gly Asp Asn Ala Val Asn Phe Val Leu Asp Leu Asp Ile
                245                 250                 255

<210> SEQ ID NO 61
<211> LENGTH: 259
<212> TYPE: PRT
<213> ORGANISM: Alcaligenes faecalis

<400> SEQUENCE: 61

Met Ala Phe Ser Thr Glu Gln Thr Tyr Val Val Ser Gly Asn Leu Ile
1               5                   10                  15

Ser Ala Thr Thr Lys Asp Thr Asn Thr Leu Ser Tyr Glu Asp Phe Ile
                20                  25                  30

His Ser Asn Leu Leu Ala Gln Met Gly Ala Asp Lys Lys Leu Gly Ser
            35                  40                  45

Arg Phe Val Asp Pro Ala Gly Trp Leu Ser Phe Phe Lys Asn Thr Val
    50                  55                  60

Gly Asn Leu Phe Trp Asn Leu Ser Glu Gln Gly Thr Ser Thr Leu Lys
65                  70                  75                  80

Ile Ser Ala Gly Thr Ala Ser Ile Thr Val Leu Gln Ile Leu Glu Gln
                85                  90                  95

Ser Phe Phe Lys Arg Leu Asn Gln Ala Gln Ile Asp Ser Ala Thr Ala
            100                 105                 110

Ser Ile Asp Leu Phe Asp Gln Leu Pro Glu Asp Pro Ala Phe Ile
            115                 120                 125

Leu Tyr Asn Val Lys Ser His Ala Gln Ile Ser Ala Ala Ala Lys Ala
    130                 135                 140

Ile Lys Pro Pro Gln Lys Ala Thr Tyr Ser Val Asn Leu Gln Ile Ser
145                 150                 155                 160

Ile Ala His Thr Gly Ser Glu Ile Ala Leu Cys Asn Val Phe Phe Gln
                165                 170                 175

Thr Ser Gln Ala Val Ser Asp Glu Leu Phe Thr Gln Lys Phe Ala Ile
            180                 185                 190

Lys Asp Leu Ile Gly Asn Ile Asn Ile Phe Tyr Leu Lys Ala Gln Leu
    195                 200                 205

Ser Glu Thr Asn Tyr Gly Gln Ile Arg Gln Gln Val Ile Glu Lys Leu
    210                 215                 220

Gly Glu Asn Ile Asn Thr Asn Ile Leu Leu Val Ala Asp Asn Ser Glu
225                 230                 235                 240

Thr Pro Ser Pro Pro Ser Pro Ala Glu Ala Arg Ser Phe Ile Arg Ser
                245                 250                 255

Leu Lys Ile

<210> SEQ ID NO 62
<211> LENGTH: 255
<212> TYPE: PRT
<213> ORGANISM: Alcaligenes sp. HPC1271

<400> SEQUENCE: 62

Met Ser Thr Ile Thr Asp His Lys Gln Val Leu Ala Trp Ile Asn Ala
```

-continued

```
1               5                   10                  15
Leu Asp Ile Pro Asp Ala Pro Gly Gly Asn Arg Val Thr Ala Arg
            20                  25                  30

Ala Thr Ser Ser Ala Asp Glu Asp Gly Ala Val Val Ala Lys Ala Ser
        35                  40                  45

Ile Pro Cys Phe Val Ser Gly Leu Thr Glu Gln Ser Arg Ala Asp Val
    50                  55                  60

Gln Asn Ser Thr Leu Leu Met Gln Leu Ala Ala Asp Lys Lys Tyr Pro
65                  70                  75                  80

Asn Glu Asn Asp Arg Glu Lys Trp Phe Lys Phe Tyr Ser Asp Gly Leu
                85                  90                  95

Thr Asn Leu Gly Trp Gly Ser Ser Ser Phe Phe Glu Arg Phe Gln
            100                 105                 110

Pro Lys Asn Thr Asp Val Thr Met Asp Gln Val Val Leu Glu Val Ile
        115                 120                 125

Leu Thr Val Val Asn Asn Val Asn Asn Pro Leu Tyr Lys Ile Ala Gln
    130                 135                 140

Glu Thr Phe Gly Ala Leu Asn Lys Pro Ala Asn Gln Lys Pro Met Lys
145                 150                 155                 160

Leu Phe Asp His Ser Ser Thr Lys Glu Asp Arg Gly Lys Phe Gln Ile
                165                 170                 175

Leu Pro Ala Gly Gln Asp Gln His Gly Thr Val Ser Met Val Leu Thr
            180                 185                 190

Ala Ile Asn Ala Arg Thr Asp Ile Gln Ser Gly Ser Phe Leu Phe Trp
        195                 200                 205

Lys Trp Ser Lys Ser Thr Ala Trp Leu Tyr Arg Ala Ala Asn Leu Ile
    210                 215                 220

Val Leu Asn Glu Ser Val Tyr Ser Lys Val Arg Gln Ala Val Ile Asp
225                 230                 235                 240

Lys Leu Gly Asp Asn Ala Val Asn Phe Val Leu Asp Leu Asp Ile
                245                 250                 255
```

<210> SEQ ID NO 63
<211> LENGTH: 259
<212> TYPE: PRT
<213> ORGANISM: Alcaligenes sp. HPC1271

<400> SEQUENCE: 63

```
Met Ala Phe Ser Thr Glu Gln Thr Tyr Val Val Ser Gly Asn Leu Ile
1               5                   10                  15

Ser Ala Thr Thr Glu Asp Thr Asn Thr Leu Ser Tyr Glu Asp Phe Ile
            20                  25                  30

His Ser Asn Leu Leu Ala Gln Met Gly Ala Asp Lys Lys Leu Gly Ser
        35                  40                  45

Arg Phe Val Asp Pro Ala Gly Trp Leu Ser Phe Phe Lys Asn Thr Val
    50                  55                  60

Gly Asn Leu Phe Trp Asn Leu Ser Glu Gln Gly Thr Ser Thr Leu Lys
65                  70                  75                  80

Ile Ser Ala Gly Thr Ala Ser Ile Thr Val Leu Gln Ile Leu Glu Gln
                85                  90                  95

Ser Phe Phe Lys Arg Leu Asn Gln Ala Gln Ile Asp Ser Ala Thr Ala
            100                 105                 110

Ser Val Asp Leu Phe Ser Gln Leu Ser Glu Asp Pro Ala Phe Ile
        115                 120                 125
```

```
Leu Tyr Asn Ala Lys Ser His Ala Gln Ile Ser Ala Ala Thr Lys Val
        130                 135                 140

Ile Lys Pro Pro Gln Lys Glu Thr Tyr Ser Val Asn Leu Gln Ile Ser
145                 150                 155                 160

Ile Ala His Thr Gly Ser Glu Ile Ala Leu Cys Asn Ile Phe Phe Gln
                165                 170                 175

Thr Ser Gln Ala Val Ser Asp Glu Leu Phe Thr Gln Lys Phe Ala Ile
                180                 185                 190

Lys Asn Leu Ile Gly Asn Ile Asn Val Phe Tyr Leu Lys Ala Leu Leu
                195                 200                 205

Ser Glu Thr Asn Tyr Gly His Ile Arg Gln Gln Val Ile Glu Lys Leu
210                 215                 220

Gly Glu Asn Ile Asn Thr Asn Ile Val Leu Val Ala Asp Asn Ser Asp
225                 230                 235                 240

Lys Pro Ser Pro Pro Ser Pro Thr Glu Ala Arg Ser Phe Ile Arg Ser
                245                 250                 255

Leu Lys Ile

<210> SEQ ID NO 64
<211> LENGTH: 260
<212> TYPE: PRT
<213> ORGANISM: Enterobacter sp.

<400> SEQUENCE: 64

Met Asn Thr Asn Ala Leu Asp Phe Val Leu Lys Thr Pro Ile Glu Thr
1               5                   10                  15

Thr Ala Asp Leu Ala Pro Leu Leu Glu Arg Leu Lys Gly Val Pro Asp
                20                  25                  30

His Gly Gln Ser Lys Arg Lys Thr Met Leu Thr Asp Asn Lys Val Ser
                35                  40                  45

Ala Gln Val Asn Ala Gly Ser Leu Ile Ser Phe Thr Glu Arg Leu Asp
            50                  55                  60

Gly Gln Asn Lys Gln Asp Val Gln Asn Ser Thr Leu Phe Ala Gln Leu
65                  70                  75                  80

Ala Ala Asp Lys His Cys Asn Arg Tyr Thr Ala Pro Met Asp Trp Tyr
                85                  90                  95

Arg Phe Tyr Val Asn Val Leu Gly Gln Ile Gly Trp Asn Gln Pro Ala
                100                 105                 110

Phe Ala Phe Asp Thr Tyr Thr Ser Gly Ala Ser Thr Val Lys Leu Asp
            115                 120                 125

Glu Ala Val Leu Gly Ile Ile Ala Gln Ile Ala Thr Val Gly Glu Val
130                 135                 140

Ala Leu Val Ala Ala Met Lys Ala Leu Ser Ser Leu Ser Asp Thr
145                 150                 155                 160

Ser Lys Gln Met Leu Ile Trp Asp Ala Lys Ser Asn Ser Glu Asn Thr
                165                 170                 175

Gly Asn Phe Gln Ile Phe Pro Ala Leu Leu Pro Asn Gly Asp Val
                180                 185                 190

Val Met Met Leu Asp Gly Met Gln Phe Asp Ala Lys Arg Asn Glu Gly
            195                 200                 205

Arg Phe Leu Trp Val Thr Trp Gln Ser Thr Ser Ile Lys Ile Gln Arg
210                 215                 220

Ala Ala Asn Lys Phe Val Leu Asn Glu Gly Val Tyr Lys Gly Val Arg
225                 230                 235                 240
```

```
Gln Ala Val Ile Asp Lys Leu Gly Asp Arg Ala Ile Asp Met Ile Ala
                245                 250                 255

Asn Ile Glu Ile
            260

<210> SEQ ID NO 65
<211> LENGTH: 258
<212> TYPE: PRT
<213> ORGANISM: Pseudomonas fluorescens

<400> SEQUENCE: 65

Met Ser Phe Glu Val Cys Asp Ser Ser Val Ala Ala Cys Val Ala Arg
  1               5                  10                  15

Leu Glu Ser Tyr Asp Ile Tyr Pro Asp Ile Ser Pro Arg Ser Leu Tyr
                 20                  25                  30

Ser Gly Asp Ile Glu Pro Pro Ala Lys Gly Ser Val Val Gly Glu Gly
             35                  40                  45

Ile Leu Ala Phe Ala Gly Gly Leu Ser Ser Gln His Gln Glu Asp Ala
         50                  55                  60

Gln His Ala Phe Leu Phe Ala Ser Leu Val Ala Asn Arg Gln Tyr Pro
 65                  70                  75                  80

Leu Glu Ser Gln Gly Arg Glu Trp Tyr Tyr Lys Phe Val Glu Val Met
                 85                  90                  95

Thr Asn Ala Gly Trp Val Ala Thr Gln Arg Phe Tyr Asp Asp Leu Ser
            100                 105                 110

Ile Ala Gly Asn Thr Val Arg Met Asp Lys Leu Val Leu Asp Ile Leu
        115                 120                 125

Ala Ser Val Val Ser Gly Ile Ala Leu Gly Ser Ala Thr Ser Ala Leu
130                 135                 140

Leu Leu Arg Val Ala Asp Ser Ala Ile Thr Ala Leu Gln Lys Lys Glu
145                 150                 155                 160

Lys Thr Leu Thr Leu Phe Glu Arg Asn Leu Leu Glu His Gly Val Gly
                165                 170                 175

Gly Met Ala Ala Gly Thr Cys Val Glu Ile Asp Gly Glu Val Ser Met
            180                 185                 190

Leu Leu Gly Thr Val Arg Phe Ile Arg Arg Asn Ser Ala Thr Gln Val
        195                 200                 205

Leu Phe Ala Asp Trp Asn Ser Arg Glu Val Lys Leu Tyr Lys Gly Glu
210                 215                 220

Ser Val Phe Arg Lys Val Pro Ser Ile Val Glu Arg Thr Arg Gly Ile
225                 230                 235                 240

Ile Ile Gly Arg Leu Gly Asn His Ala Val Ser Lys Ile Glu Glu Tyr
                245                 250                 255

Glu Ile

<210> SEQ ID NO 66
<211> LENGTH: 242
<212> TYPE: PRT
<213> ORGANISM: Pseudomonas fluorescens

<400> SEQUENCE: 66

Met Asp Lys Ala Tyr Ser Ile Phe Val Asn Ala Ala Ile Ala Val Leu
  1               5                  10                  15

Val Ser Ser Thr Val Arg Gly Thr Gly Val Glu Asp Leu Met Asn Ser
                 20                  25                  30

Val Leu Leu Ala Gln Leu Val Ala Asn Lys Asn Leu Gln Arg Ile Pro
```

```
            35                  40                  45
Ser Ala Asp Trp Tyr Ala Ser Tyr Met Asp Val Leu Ser Val Ala Trp
 50                  55                  60
Val Ala Gly Ala Lys Arg Arg Lys Asp Leu Leu Pro Lys Gln Asp Ala
 65                  70                  75                  80
Ala Ser Ser Pro Val Glu Trp Val Thr Ala Ile Pro Leu Asp Asp Arg
                 85                  90                  95
Pro Asp Gln Gln Gln Ile Met Ala Val Leu Asp Arg Val Ala Ala
            100                 105                 110
Leu Pro Gly Ser Leu Pro Ala Leu Ser Ile Leu Arg Lys His Met Gln
            115                 120                 125
Lys Pro Asn Glu Pro Glu Pro Thr Gln Ser Pro Ser Ala Ser Ser Pro
            130                 135                 140
Val Arg Leu Leu Val Ile Val Ala His Ser Pro Val Ser Met Thr Gly
145                 150                 155                 160
Ile Cys Leu Gln Phe Asn Thr Gly Lys Ala Ile Asn Ala Asn Pro Trp
                165                 170                 175
Gly Gln Cys Phe Asp Gly Lys Asp Ile Asp Gly Cys Val Ser Ala Arg
            180                 185                 190
Tyr Leu Arg Met Gln Leu Ser Glu Thr Leu Phe Ala Pro Ala Arg Glu
            195                 200                 205
Val Ile Ala Arg Lys Val Gly Thr Val Val Gly Asp Asn Val Val Asp
            210                 215                 220
Ile Thr Gly Ala Ile Glu Asp Ser Val Val Arg Pro Ala Glu Glu Val
225                 230                 235                 240
Gly Arg

<210> SEQ ID NO 67
<211> LENGTH: 258
<212> TYPE: PRT
<213> ORGANISM: Pseudomonas brassicacearum

<400> SEQUENCE: 67

Met Ser Phe Glu Met Cys Asp Ser Ala Val Ala Ala Cys Val Ala Arg
 1               5                  10                  15
Leu Glu Ser Tyr Asp Ile Tyr Pro Asp Val Ser Pro Arg Ser Leu Tyr
             20                  25                  30
Val Asp Asp Val Glu Pro Pro Ala Lys Gly Ser Val Val Gly Glu Gly
             35                  40                  45
Ile Leu Ala Phe Ala Gly Gly Leu Ser Pro Gln His Gln Glu Asp Ala
 50                  55                  60
Gln His Ala Phe Leu Phe Ala Ser Leu Val Ala Asn Arg Gln Tyr Pro
 65                  70                  75                  80
Leu Glu Ser Gln Gly Arg Glu Trp Tyr Tyr Lys Phe Val Glu Val Met
             85                  90                  95
Thr Asn Ala Gly Trp Val Ala Thr Gln Arg Phe Tyr Asp Asp Leu Ser
            100                 105                 110
Val Gly Gly Asn Thr Val Arg Met Asp Lys Leu Val Leu Asp Ile Leu
            115                 120                 125
Ala Ser Val Val Ser Gly Ile Ala Leu Gly Ser Ala Thr Ser Ala Leu
            130                 135                 140
Leu Leu Arg Val Val Asp Ser Ala Ile Thr Ala Leu Gln Lys Lys Glu
145                 150                 155                 160
Glu Thr Leu Thr Leu Phe Glu Arg Asn Leu Leu Glu His Gly Val Gly
```

```
                   165                 170                 175

Gly Met Ala Ala Gly Thr Cys Val Glu Ile Asp Gly Glu Val Ser Met
                180                 185                 190

Met Leu Gly Thr Val Arg Phe Ile Arg Arg Asn Ser Ala Thr Gln Val
            195                 200                 205

Leu Phe Ala Asp Trp Asn Ser Arg Glu Val Lys Leu Tyr Lys Gly Glu
        210                 215                 220

Ser Val Phe Arg Lys Val Pro Ser Val Val Glu Arg Thr Arg Asp Ile
225                 230                 235                 240

Ile Ile Gly Arg Leu Gly Asn His Ala Val Ser Lys Ile Glu Glu Tyr
                245                 250                 255

Glu Ile

<210> SEQ ID NO 68
<211> LENGTH: 242
<212> TYPE: PRT
<213> ORGANISM: Pseudomonas brassicacearum

<400> SEQUENCE: 68

Met Asp Lys Glu Tyr Ser Val Phe Val Asn Ala Ala Ile Val Leu
1               5                   10                  15

Ala Pro Cys Ala Leu Arg Arg Thr Glu Val Asp Asp Leu Met Asn Ser
            20                  25                  30

Val Leu Leu Ala Gln Leu Val Ala Asp Lys Ser Leu Leu Arg Ala Pro
        35                  40                  45

Ala Val Asp Trp Tyr Ala Thr Tyr Leu Glu Val Leu Ser Val Ala Trp
    50                  55                  60

Ile Ser Ala Ala Lys Arg Arg Lys Asp Leu Gln Pro Gln Lys Glu Asp
65                  70                  75                  80

Thr His Ser Pro Leu Glu Trp Val Ala Ala Ile Pro Leu Asp Asp Gln
                85                  90                  95

Val Asp Gln Gln Gln Arg Ile Met Ala Val Met Glu Arg Ile Ala Ala
            100                 105                 110

Leu Pro Gly Ser Leu Pro Ala Met Gly Ile Val Arg Lys His Val Gln
        115                 120                 125

Lys Gln Tyr Glu Pro Asp Ala Ala Gln Ser Pro Ser Ser Ser Ser Pro
    130                 135                 140

Val Arg Leu Leu Val Ile Val Ala Gln Ser Pro Val Ser Met Ala Gly
145                 150                 155                 160

Val Tyr Leu Gln Phe Asn Thr Ala Lys Val Ile Glu Ala Asn Pro Trp
                165                 170                 175

Arg Gln Cys Phe Asp Gly Lys Asp Ile Asp Gly Cys Val Thr Ala Arg
            180                 185                 190

Tyr Phe Arg Thr Gln Leu Ser Glu Thr Leu Phe Ala Pro Ala Arg Glu
        195                 200                 205

Val Ile Ala Arg Lys Val Ala Ala Val Gly Asp Asn Ile Val Asp
    210                 215                 220

Ile Thr Lys Ala Ile Asp Asp Ser Gly Val Leu Pro Ala Glu Glu Val
225                 230                 235                 240

Cys Arg

<210> SEQ ID NO 69
<211> LENGTH: 263
<212> TYPE: PRT
<213> ORGANISM: unknown
```

-continued

```
<220> FEATURE:
<223> OTHER INFORMATION: Switchgrass rhizosphere microbial community
      from Michigan

<400> SEQUENCE: 69

Met Ser Val Asn Met Ile Asp Ser Ala Thr Val Ala Ala Cys Val Arg
1               5                   10                  15

Arg Leu Glu Ser Tyr Glu Ile Asp Glu Val Pro Val Val Arg Ser Arg
            20                  25                  30

Ala Phe Ala Ala Ser Gly Ile Val Glu Glu Pro Ser Lys Gly Ala
        35                  40                  45

Val Val Gly Glu Gly Ile Leu Ser Phe Val Gly Asn Leu Ser Glu Gln
50                  55                  60

Asn Gln Val Asp Ala Met His Ala Phe Leu Phe Ala Ser Leu Val Ala
65                  70                  75                  80

Asn Lys Gln Phe Pro Tyr Glu Tyr Gln Gly Lys Glu Trp Tyr Tyr Lys
                85                  90                  95

Phe Val Glu Val Met Thr Ser Ala Gly Trp Leu Thr Ser Gln Lys Tyr
            100                 105                 110

Tyr Asn Asp Ile Glu Ile Ser Gly Asn Thr Val Arg Met Asp Gln Leu
        115                 120                 125

Val Leu Glu Ile Leu Gly Ser Val Ala Gly Leu Ala Ile Pro Gly
130                 135                 140

Thr Ala Ser Ala Leu Met Leu Lys Val Ala Gly Asp Ala Ile Thr Ala
145                 150                 155                 160

Leu Lys Lys Lys Glu Thr Ala Leu Thr Leu Tyr Glu Arg Asn Leu Leu
                165                 170                 175

Glu His Gly Val Gly Gly Met Ala Ala Gly Thr Cys Thr Glu Val Asn
            180                 185                 190

Gly Glu Val Thr Leu Ala Leu Gly Thr Val Arg Phe Ile Arg Lys Asn
        195                 200                 205

Thr Ala Thr Gln Val Leu Phe Met Asp Trp Asp Ser Arg Asp Val Gln
210                 215                 220

Leu Tyr Lys Gly Glu Ser Val Phe Arg Lys Val Pro Tyr Ile Ala Asp
225                 230                 235                 240

Gln Thr Arg Asp Leu Ile Arg Thr Lys Leu Gly Thr Asn Ala Val Ser
                245                 250                 255

Lys Ile Glu Gly Tyr Glu Ile
            260

<210> SEQ ID NO 70
<211> LENGTH: 242
<212> TYPE: PRT
<213> ORGANISM: unknown
<220> FEATURE:
<223> OTHER INFORMATION: Switchgrass rhizosphere microbial community
      from Michigan

<400> SEQUENCE: 70

Met Ala Arg Glu Tyr Ser Val Phe Val Asn Ala Ala Ile Val Leu
1               5                   10                  15

Leu Pro Ser Asn Pro Val Glu Ser Ala Thr Asn Asp Leu Met Asn Ser
            20                  25                  30

Val Leu Leu Ala Gln Leu Val Ala Asn Lys Arg Ala Glu Ala Thr Ser
        35                  40                  45

Ala Val Asp Trp Tyr Glu Thr Tyr Val Gly Val Leu Gly Asp Phe Trp
50                  55                  60
```

```
Leu Thr Arg Ala Arg Ser Arg Gln Asp Ile Gln Pro Gly Lys Asp Asp
 65                  70                  75                  80

Thr Ala Ser Pro Leu Glu Trp Ile Ala Val Leu Ala Ser Ser Thr
                 85                  90                  95

Glu Asp Glu Ala Arg Leu Val Thr Ala Leu Leu Lys Gly Ile Ala Arg
                100                 105                 110

Leu Ser Asp Ser Leu Pro Ala Met Ser Leu Leu Arg Lys His Val Gln
            115                 120                 125

Lys Glu Ser Asp Asp Glu Pro Ala Glu Ile Ser Leu Gln Ser Lys Pro
130                 135                 140

Val Arg Leu Val Val Ile Val Ala Gln Asp Asn Ala Ser Met Thr Ser
145                 150                 155                 160

Val Cys Leu Gln Phe Lys Thr Arg Gln Met Leu Asp Pro Asn Pro Trp
                165                 170                 175

Gly Gln Arg Phe His Val Glu Asp Met Glu Gly Cys Val Ser Ala His
                180                 185                 190

Phe Phe His Ala His Leu Ser Glu Thr Leu Tyr Ala Pro Ala Arg Glu
            195                 200                 205

Ala Val Ala Arg Lys Val Glu Gly Val Leu Ser Asp Asn Ile Val Asp
        210                 215                 220

Ile Thr Glu Ala Ile Asp Ala Leu Ala Phe Leu Pro Thr Glu Glu Ala
225                 230                 235                 240

Gly Thr

<210> SEQ ID NO 71
<211> LENGTH: 261
<212> TYPE: PRT
<213> ORGANISM: unknown
<220> FEATURE:
<223> OTHER INFORMATION: Miscanthus rhizosphere microbial communities
      from Kellogg

<400> SEQUENCE: 71

Met Asn Val His Asp Val Glu Asp Cys Thr Val Ala Glu Cys Ile His
1               5                   10                  15

Arg Leu Glu Ser Tyr Glu Leu Asp Gly Ala Glu Val Met Arg Pro Arg
                20                  25                  30

Ser Phe Ser Val Pro Val Asn Glu Pro Gly Lys Gly Ser Ile Val
            35                  40                  45

Gly Glu Gly Ile Leu Ser Phe Thr Gly Asn Leu Ser Glu Gln Asn Arg
    50                  55                  60

Glu Asp Val Gln His Ala Phe Leu Phe Ala Ser Leu Val Ala Asn Lys
65                  70                  75                  80

Lys Tyr Pro Tyr Glu Tyr Gln Gly Lys Glu Trp Tyr Tyr Gln Phe Leu
                85                  90                  95

Glu Val Met Thr His Ala Gly Trp Leu Pro Thr Ser Lys Tyr Tyr Asn
                100                 105                 110

Asp Met Asn Ile Ser Gly Asn Thr Val Arg Met Asp Gln Leu Val Leu
            115                 120                 125

Glu Ile Leu Gly Ser Val Ala Gly Leu Ala Val Pro Gly Ser Ala
        130                 135                 140

Ser Val Leu Met Leu Lys Val Ala Gly Asp Ala Ile Thr Ala Leu Lys
145                 150                 155                 160

Lys Arg Glu Thr Ala Leu Thr Leu Tyr Glu Arg Asn Met Leu Glu His
                165                 170                 175
```

Gly Val Gly Gly Met Ala Ala Gly Thr Cys Thr Glu Val Asn Gly Glu
            180                 185                 190

Val Thr Met Ala Leu Gly Thr Val Arg Phe Ile Arg Lys Asn Thr Ala
        195                 200                 205

Lys Gln Val Leu Phe Met Asp Trp Asp Ser Arg Glu Val Lys Leu Tyr
    210                 215                 220

Arg Gly Asp Ser Val Phe Arg Lys Val Pro Tyr Ile Val Glu Gln Thr
225                 230                 235                 240

Arg Asp Thr Ile Arg Ala Lys Leu Gly Leu Asn Ala Lys Pro Lys Ile
                245                 250                 255

Glu Asp Tyr Asp Ile
            260

<210> SEQ ID NO 72
<211> LENGTH: 240
<212> TYPE: PRT
<213> ORGANISM: unknown
<220> FEATURE:
<223> OTHER INFORMATION: Miscanthus rhizosphere microbial communities
      from Kellogg

<400> SEQUENCE: 72

Met Ser Tyr Glu Tyr Ser Val Leu Ile Val Gly Ala Cys Val Val Ile
1               5                   10                  15

Ile Pro Ala Ala Asp Gly Ala Ala Gln Tyr Thr Asp Leu Val Asn Ser
            20                  25                  30

Val Leu Leu Ala Gln Leu Ile Ala Asn Lys Lys Ile Glu Lys Ala Pro
        35                  40                  45

Glu Ile Asp Trp Tyr Asn Ala Tyr Val Glu Phe Leu Asp Asp Tyr Trp
    50                  55                  60

Leu Arg Arg Thr Arg Ala Arg Gln Asp Trp Ser Ile Ala Gln Asp Arg
65                  70                  75                  80

Val Glu Ser Val Ser Asp Trp Val Ile Ala Ile Ser Gln Asp Ala
                85                  90                  95

Val Asp Lys Gly Ser Ala Thr Ala Ala Thr Leu Gln Arg Leu Ala Arg
            100                 105                 110

Leu Ser Gly Asn Glu Pro Ala Met Gly Leu Leu Arg Gly His Met Gln
        115                 120                 125

Lys Ile Ser Thr Asp Glu Ser Gly Asp Val Leu Ala Pro Ala Lys Ala
    130                 135                 140

Val Arg Leu Leu Val Val Ile Ala Gln Thr Pro Thr Ser Val Ala Ser
145                 150                 155                 160

Val Tyr Ile Glu Leu Lys Thr Arg Gln Ile Ile Ser Ala Asn Pro Leu
                165                 170                 175

Ala Gln Arg His Leu Ala Glu Asp Val Gln Gly Ser Val Cys Met Arg
            180                 185                 190

Tyr Ala Ala Ala Asn Leu Ser Glu Thr Leu Tyr Ser Pro Val Arg Asp
        195                 200                 205

Ala Ile Ala Leu Lys Val Arg Asp Lys Tyr Gln Asp Asn Val Ala Met
    210                 215                 220

Leu Thr Leu Ser Asp Asp Ala Ser Ala Met Glu Ile Cys Ala Val Asp
225                 230                 235                 240

<210> SEQ ID NO 73
<211> LENGTH: 555
<212> TYPE: PRT

<213> ORGANISM: Pseudomonas rhodesiae

<400> SEQUENCE: 73

| | | | | | | | | | | | | | | |
|---|---|---|---|---|---|---|---|---|---|---|---|---|---|---|
| Met | Ala | Lys | Leu | Thr | Gln | Phe | Ser | Thr | Pro | Ala | Asp | Ile | Gln | Asp | Phe |
| 1 | | | | 5 | | | | | 10 | | | | | 15 | |
| Ser | Asp | Ser | Pro | Ala | Gln | Gln | Glu | Arg | Met | Asn | Ala | Ala | Trp | Ser | Gly |
| | | | 20 | | | | | 25 | | | | | 30 | | |
| Asn | Ile | Asn | Arg | Trp | Val | Asn | Ala | Ala | Leu | Val | Gly | Asp | Val | Trp | Asp |
| | | 35 | | | | | 40 | | | | | 45 | | | |
| Leu | Ile | Asn | Tyr | Gly | Pro | Arg | Pro | Ala | Phe | Tyr | Asn | Pro | Leu | Asp | Thr |
| | 50 | | | | | 55 | | | | | 60 | | | | |
| Asp | Thr | Pro | Ser | Thr | Ser | Val | Asn | Ala | Pro | Ile | Thr | Trp | Asn | Ala | Phe |
| 65 | | | | | 70 | | | | | 75 | | | | | 80 |
| Pro | Gly | Arg | Ile | Pro | Ala | Leu | Phe | Pro | Asn | Gln | Ser | Ala | Asn | Trp | Leu |
| | | | | 85 | | | | | 90 | | | | | 95 | |
| Gln | Trp | Ala | Asp | Gln | Gly | Val | Pro | Ala | Asn | Val | Thr | Thr | Asn | Leu | Cys |
| | | | 100 | | | | | 105 | | | | | 110 | | |
| Thr | Gln | Gln | Ser | Val | Pro | Pro | Ala | Pro | Tyr | Ser | Pro | Thr | Gly | Pro | Arg |
| | | 115 | | | | | 120 | | | | | 125 | | | |
| Gly | Trp | Gln | Asp | Glu | Tyr | Cys | Glu | Trp | Ser | Val | Thr | Arg | Asn | Ala | Ala |
| | 130 | | | | | 135 | | | | | 140 | | | | |
| Gly | Gln | Ile | Thr | Ser | Val | Met | Phe | Thr | Cys | Glu | Asn | Pro | Glu | Tyr | Trp |
| 145 | | | | | 150 | | | | | 155 | | | | | 160 |
| Met | Thr | Leu | Trp | Gln | Val | Asp | Pro | Gly | Lys | Val | Leu | Gln | Arg | Tyr | Gln |
| | | | | 165 | | | | | 170 | | | | | 175 | |
| Gln | Leu | Ile | Asn | Pro | Ala | Val | Gln | Leu | Ala | Asp | Leu | Ser | Leu | Lys | Asp |
| | | | 180 | | | | | 185 | | | | | 190 | | |
| Ala | Gln | Gly | Gln | Thr | Val | Ile | Asp | Pro | Val | Thr | Gly | Ala | Pro | Cys | Tyr |
| | | 195 | | | | | 200 | | | | | 205 | | | |
| Asn | Pro | Leu | Asn | Lys | Trp | Asn | Ser | Gly | Thr | Gln | Thr | Leu | Pro | Gly | Ser |
| | 210 | | | | | 215 | | | | | 220 | | | | |
| Gly | Gly | Ala | Met | His | Leu | Thr | Ser | Ser | Pro | Asn | Thr | Leu | Gly | Ala | Glu |
| 225 | | | | | 230 | | | | | 235 | | | | | 240 |
| Tyr | Asp | Leu | Ala | Ala | Ala | Ala | Thr | Met | Pro | Arg | Glu | Leu | Asn | Asn | Glu |
| | | | | 245 | | | | | 250 | | | | | 255 | |
| Pro | Val | Thr | Ser | Ala | Ser | Gln | Leu | Val | Cys | Tyr | Ala | Arg | Tyr | Gly | Arg |
| | | | 260 | | | | | 265 | | | | | 270 | | |
| Ile | Gly | Arg | His | Ser | Asp | Pro | Thr | Ile | Gly | Gln | Asn | Val | Asn | Gln | Tyr |
| | | 275 | | | | | 280 | | | | | 285 | | | |
| Val | Asn | Tyr | Thr | Ser | Gly | Leu | Thr | Glu | Val | Arg | Ala | Thr | Leu | Thr | Asn |
| | 290 | | | | | 295 | | | | | 300 | | | | |
| Pro | Pro | Gly | Leu | Tyr | Ile | Gln | Thr | Pro | Asp | Phe | Ser | Gly | Tyr | Thr | Thr |
| 305 | | | | | 310 | | | | | 315 | | | | | 320 |
| Pro | Asp | Gly | Ser | Pro | Ala | Ala | Ala | Cys | Trp | Thr | Ile | Asn | Arg | Gly | His |
| | | | | 325 | | | | | 330 | | | | | 335 | |
| Leu | Ala | Gln | Thr | Ser | Asp | Asp | Ile | Asp | Arg | Ile | Leu | His | Ala | Thr | Phe |
| | | | 340 | | | | | 345 | | | | | 350 | | |
| Ser | Val | Pro | Ala | Gly | Lys | Asn | Phe | Thr | Val | Ser | Asp | Ile | Ser | Ile | Asn |
| | | 355 | | | | | 360 | | | | | 365 | | | |
| Gly | Ala | Lys | Ile | Gln | Tyr | Ala | Ser | Gln | Ile | Ala | Gly | Thr | Ile | Thr | Met |
| | 370 | | | | | 375 | | | | | 380 | | | | |
| Gly | Leu | Met | Ala | Thr | Val | Phe | Gly | Asn | Ser | Gly | Val | Thr | Gln | Gln | Pro |
| 385 | | | | | 390 | | | | | 395 | | | | | 400 |

```
Val Ala Gly Thr Leu Asp Ser Asp Asn Pro Ser Pro Ser Val Ser Ala
                405                 410                 415

Leu Gln Pro Leu Ser Val Phe Asn Ala Tyr Arg Ala Gln Glu Leu Ala
            420                 425                 430

Ser Asn Glu Gln Ala Leu Ser Ile Pro Ile Leu Ala Leu Ala Ile Arg
        435                 440                 445

Pro Gly Gln Gln Val Asp Asn Ile Ala Leu Leu Leu Asn Thr Ser Gln
    450                 455                 460

Thr Pro Asn Gly Ala Ser Phe Ser Val Val Glu Gly Gly Val Ser Ile
465                 470                 475                 480

Ser Ile Thr Gly Thr Gln Asp Leu Pro Gly Leu Asp Met Ser Leu Tyr
                485                 490                 495

Leu Val Ser Ile Ser Ala Asp Ala Asn Ala Ala Pro Gly Asp Arg Thr
            500                 505                 510

Val Leu Ala Ser Val Pro Gly Met Ala Ser Thr Gln Gln Ala Ala Ile
        515                 520                 525

Gly Leu Leu Thr Val Gly Gly Pro Thr Leu Val Thr Ser Gln Thr Gly
    530                 535                 540

Pro Ser Lys Pro Asn Phe Arg Arg Gly Arg Gly
545                 550                 555

<210> SEQ ID NO 74
<211> LENGTH: 451
<212> TYPE: PRT
<213> ORGANISM: Pseudomonas rhodesiae

<400> SEQUENCE: 74

Met Arg Arg Arg Pro Thr Val Leu Leu Gly Leu Ala Leu Leu Leu Gly
1               5                   10                  15

Leu Pro Ala Thr Gln Ala Met Gly Ala Pro Leu Cys Gly Ser Pro Phe
            20                  25                  30

Val Pro Ser Pro Thr Leu Gln Pro Thr Leu Ala Pro Pro Asn Phe Ser
        35                  40                  45

Ala Ser Asp Ser Ala Val Asp Cys Phe Met Trp Gln Thr Met Val Tyr
    50                  55                  60

Leu Asn Trp Pro Ala Thr Pro Gly Gln Arg Gly Val Pro Asn Ala Ala
65                  70                  75                  80

Ala Ser Leu Gly Ser Pro Gly Pro Ser Val Trp Gln Thr Tyr Lys Asp
                85                  90                  95

Tyr Asn Glu Leu Tyr Leu Pro Asn Gly Gln Gln Pro Ala Trp Asn
            100                 105                 110

Asp Asn Phe Leu Ser Val Gln Arg Leu Gln Thr Arg Gly Val Ala Arg
        115                 120                 125

Ala Leu Pro Ser Ile Arg Leu Leu Asn Ser Thr Ser Lys Val Phe Arg
    130                 135                 140

Ala Ala Asn Ala Asn Glu Ser Pro Ala Leu Arg Glu Ile Glu Gln Val
145                 150                 155                 160

Gly Gly Gly Val Leu Tyr Asp Gln Ala Gly Ser Pro Val Tyr Tyr Glu
                165                 170                 175

Met Leu Val Asn Glu Val Asn Phe Asp Phe Ile Tyr Asn Asn Gln Leu
            180                 185                 190

Tyr Asn Pro Ala Gln Gln Asn Leu Tyr Ala Lys Gln Lys Gly Ile Val
        195                 200                 205

Leu Pro Asn Asn Ser Ile Glu Ile Lys Ala Ala Trp Lys Val Leu Ser
    210                 215                 220
```

Asp Pro Asp Asn Pro Gln Arg Phe Leu Thr Ala Gln Ala Leu Leu Pro
225                 230                 235                 240

Gly Ser Ser Thr Pro Val Thr Val Gly Leu Val Gly Leu His Val Phe
            245                 250                 255

Gln Met Pro Ser Ser Ala Phe Asn Gln Gly Phe Trp Ala Thr Phe Gln
        260                 265                 270

Gln Leu Asp Asn Ala Pro Thr Val Ala Gly Ala Thr Pro Gly Ala His
    275                 280                 285

Tyr Ser Phe Asn Asn Pro Gln Cys Ala Pro Ala Gln Cys Pro Pro Asn
290                 295                 300

Asp Lys Thr Ser Asn Pro Thr Gln Val Val Gln Asn Phe Pro Pro Thr
305                 310                 315                 320

Pro Glu Ala Gln Asn Ile Asn His Tyr Met Gln Asn Leu Ile Ala Gln
            325                 330                 335

Gln Ala Pro Gly Ser Ala Leu Gln Tyr Tyr Gln Leu Val Asp Val Gln
        340                 345                 350

Trp Pro Thr Ser Pro Gln Ala Ile Gly Gln Pro Gly Ala Thr Ala Pro
    355                 360                 365

Ala Pro Ser Gly Thr Pro Asn His Asp Thr Leu Ile Asn Pro Val Leu
370                 375                 380

Glu Thr Phe Leu Gln Ala Asn His Lys Ser Cys Leu Gly Cys His Val
385                 390                 395                 400

Tyr Ala Ser Val Ala Ala Asp Gly Ser Asn Pro Thr His Tyr Gln
            405                 410                 415

Ala Ser Phe Ser Phe Leu Leu Gly His Ala Lys Ser Pro Ala Leu Gly
        420                 425                 430

Ser Asn Leu Lys Ser Leu Ala Gln Gln Ile Glu Asp Ala Ser Leu Ser
    435                 440                 445

Leu Gln His
    450

<210> SEQ ID NO 75
<211> LENGTH: 555
<212> TYPE: PRT
<213> ORGANISM: Pseudomonas orientalis

<400> SEQUENCE: 75

Met Ala Lys Leu Thr Gln Phe Ser Thr Pro Ala Asp Ile Gln Asp Phe
1               5                   10                  15

Ser Asp Ser Pro Ala Gln Gln Glu Arg Met Asn Ala Ala Trp Ser Gly
            20                  25                  30

Asn Ile Asn Arg Trp Val Asn Ala Ala Leu Val Gly Asp Val Trp Asp
        35                  40                  45

Leu Ile Asn Tyr Gly Pro Arg Pro Ala Phe Tyr Asn Pro Leu Asp Thr
    50                  55                  60

Asp Thr Pro Ser Thr Ser Val Asn Ala Pro Ile Thr Trp Asn Ala Phe
65                  70                  75                  80

Pro Gly Arg Ile Pro Ala Leu Phe Pro Asn Gln Ser Ala Asn Trp Leu
            85                  90                  95

Gln Trp Ala Asp Gln Gly Val Pro Ala Asn Val Thr Thr Asn Leu Cys
        100                 105                 110

Thr Gln Gln Ser Ile Pro Ala Ala Pro Tyr Ser Pro Thr Gly Pro Arg
    115                 120                 125

Gly Trp Gln Asp Glu Tyr Cys Glu Trp Ser Val Thr Arg Asn Ala Ala

```
            130                 135                 140
Gly Gln Ile Thr Ser Val Met Phe Thr Cys Glu Asn Pro Glu Tyr Trp
145                 150                 155                 160

Met Thr Leu Trp Gln Val Asp Pro Gly Lys Val Leu Gln Arg Tyr Gln
                165                 170                 175

Gln Leu Ile Asn Pro Ala Val Gln Leu Ala Asp Leu Ser Leu Lys Asp
            180                 185                 190

Ala Gln Gly Gln Thr Val Ile Asp Pro Val Thr Gly Ala Pro Cys Tyr
        195                 200                 205

Asn Pro Leu Asn Lys Trp Asn Ser Gly Thr Gln Thr Leu Pro Gly Ser
    210                 215                 220

Gly Gly Ala Met His Leu Thr Ser Ser Pro Asn Thr Leu Gly Ala Glu
225                 230                 235                 240

Tyr Asp Leu Ala Ala Ala Thr Met Pro Arg Glu Leu Asn Asn Glu
                245                 250                 255

Pro Val Thr Ser Ala Ser Gln Leu Val Cys Tyr Ala Arg Tyr Gly Arg
                260                 265                 270

Ile Gly Arg His Ser Asp Pro Thr Ile Gly Gln Asn Val Asn Gln Tyr
            275                 280                 285

Val Asn Tyr Thr Ser Gly Leu Thr Glu Val Arg Ala Thr Leu Thr Asn
        290                 295                 300

Pro Pro Gly Leu Tyr Ile Gln Thr Pro Asp Phe Ser Gly Tyr Thr Thr
305                 310                 315                 320

Pro Asp Gly Ser Pro Ala Ala Ala Cys Trp Thr Ile Asn Arg Gly His
                325                 330                 335

Leu Ala Gln Thr Ser Asp Asp Ile Asp Arg Ile Leu His Ala Thr Phe
                340                 345                 350

Ser Val Pro Ala Gly Lys Asn Phe Thr Val Ser Asp Ile Ser Ile Asn
                355                 360                 365

Gly Ala Lys Ile Gln Tyr Ala Ser Gln Ile Ala Gly Thr Ile Thr Met
        370                 375                 380

Gly Leu Met Ala Thr Val Phe Gly Asn Ser Gly Val Thr Gln Gln Pro
385                 390                 395                 400

Val Ala Gly Thr Leu Asp Ser Asp Asn Pro Ser Pro Ser Val Ser Ala
                405                 410                 415

Leu Gln Pro Leu Ser Val Phe Asn Ala Tyr Arg Ala Gln Glu Leu Ala
            420                 425                 430

Ser Asn Glu Gln Ala Leu Ser Ile Pro Ile Leu Ala Leu Ala Ile Arg
        435                 440                 445

Pro Gly Gln Gln Val Asp Asn Ile Ala Leu Leu Leu Asn Thr Ser Gln
    450                 455                 460

Thr Pro Asn Gly Ala Ser Phe Ser Val Val Glu Gly Gly Val Ser Ile
465                 470                 475                 480

Ser Ile Thr Gly Thr Gln Asp Leu Pro Gly Leu Asp Met Ser Leu Tyr
                485                 490                 495

Leu Val Ser Ile Ser Ala Asp Ala Asn Ala Ala Pro Gly Asp Arg Thr
            500                 505                 510

Val Leu Ala Ser Val Pro Gly Met Ala Ser Thr Gln Gln Ala Ala Ile
        515                 520                 525

Gly Leu Leu Thr Val Gly Gly Pro Thr Leu Val Thr Ser Gln Thr Gly
    530                 535                 540

Pro Ser Lys Pro Asn Phe Arg Arg Gly Arg Gly
545                 550                 555
```

<210> SEQ ID NO 76
<211> LENGTH: 451
<212> TYPE: PRT
<213> ORGANISM: Pseudomonas orientalis

<400> SEQUENCE: 76

| Met | Arg | Arg | Arg | Pro | Thr | Val | Leu | Leu | Gly | Leu | Ala | Leu | Leu | Leu | Gly |
| 1 | | | | 5 | | | | | 10 | | | | | 15 | |

Leu Pro Ala Thr Gln Ala Met Gly Ala Pro Leu Cys Gly Ser Pro Phe
                20                  25                  30

Val Pro Ser Pro Thr Leu Gln Pro Thr Leu Ala Asn Pro Asn Phe Ser
            35                  40                  45

Ala Ser Asp Ser Ala Val Asp Cys Phe Met Trp Gln Thr Met Val Tyr
50                  55                  60

Leu Asn Trp Pro Ala Thr Pro Gly Gln Arg Gly Val Pro Asn Ala Ala
65                  70                  75                  80

Ala Ser Leu Gly Ser Pro Gly Pro Ser Val Trp Gln Thr Tyr Lys Asp
                85                  90                  95

Tyr Asn Glu Leu Tyr Leu Pro Asn Gly Gln Pro Pro Ala Trp Asn
            100                 105                 110

Asp Asn Phe Leu Ser Val Gln Arg Leu Gln Thr Arg Gly Val Ala Arg
            115                 120                 125

Ala Leu Pro Ser Ile Arg Leu Leu Asn Ser Thr Ser Lys Val Phe Arg
            130                 135                 140

Ala Ala Asn Ala Asn Glu Ser Pro Ala Leu Arg Glu Ile Glu Gln Val
145                 150                 155                 160

Gly Gly Gly Val Leu Tyr Asp Gln Ala Gly Ser Pro Val Tyr Tyr Glu
                165                 170                 175

Met Leu Val Asn Glu Val Asn Phe Asp Phe Ile Tyr Asn Asn Gln Leu
            180                 185                 190

Tyr Asn Pro Ala Gln Gln Asn Leu Tyr Ala Lys Gln Lys Gly Ile Val
            195                 200                 205

Leu Pro Asn Asn Ser Ile Glu Ile Lys Ala Ala Trp Lys Val Leu Ser
210                 215                 220

Ala Pro Asp Asn Pro Gln Arg Phe Leu Thr Ala Gln Ala Leu Leu Pro
225                 230                 235                 240

Gly Ser Ser Thr Pro Val Thr Val Gly Leu Val Gly Leu His Val Phe
                245                 250                 255

Gln Met Pro Ser Ser Ala Phe Asn Gln Gly Phe Trp Ala Thr Phe Gln
            260                 265                 270

Gln Leu Asp Asn Ala Pro Thr Val Ala Gly Ala Ser Pro Gly Ala His
            275                 280                 285

Tyr Ser Phe Asn Asn Pro Gln Cys Ala Pro Gln Cys Pro Pro Asn
            290                 295                 300

Asp Lys Thr Ser Asn Pro Thr Gln Val Val Gln Asn Phe Pro Pro Thr
305                 310                 315                 320

Pro Glu Ala Gln Asn Ile Asn Gln Tyr Met Gln Asn Leu Ile Ala Gln
                325                 330                 335

Gln Ala Pro Gly Ser Ala Leu Gln Tyr Tyr Gln Leu Val Asp Val Gln
            340                 345                 350

Trp Pro Thr Ser Pro Gln Ala Ile Gly Gln Pro Gly Ala Thr Ala Pro
            355                 360                 365

Ala Pro Ser Gly Thr Pro Asn His Asp Thr Leu Ile Asn Pro Val Leu

```
            370                 375                 380
Glu Thr Phe Leu Gln Thr Asn His Thr Ser Cys Leu Gly Cys His Val
385                 390                 395                 400

Tyr Ala Ser Val Ala Ala Asp Gly Ser Lys Pro Ala Thr Asp Tyr Gln
                405                 410                 415

Ala Ser Phe Ser Phe Leu Leu Gly His Ala Lys Ser Pro Ala Leu Gly
                420                 425                 430

Ser Asn Leu Lys Ser Leu Ala Gln Gln Ile Glu Asp Ala Ser Leu Ser
                435                 440                 445

Leu Gln His
    450

<210> SEQ ID NO 77
<211> LENGTH: 556
<212> TYPE: PRT
<213> ORGANISM: Pseudomonas sp. PKRS11

<400> SEQUENCE: 77

Met Ala Lys Leu Ala Gln Phe Ser Pro Pro Ala Arg Ile Gln Asp Phe
1               5                   10                  15

Ser Asn Asp Pro Ala Gln Glu Cys Leu Asn Ala Ala Trp Ser Gly
                20                  25                  30

Asn Ile Asn Arg Trp Val Asn Ala Ala Leu Leu Gly Asp Val Trp Asp
            35                  40                  45

Arg Ile Asn Tyr Gly Pro Arg Pro Ala Phe Tyr Asn Pro Leu Val Thr
    50                  55                  60

Asp Thr Pro Asp Thr Ala Gly Asn Val Pro Ile Thr Trp Asn Ala Phe
65                  70                  75                  80

Pro Gly Arg Leu Gln Ala Leu Phe Pro Asn Gln Gly Ala Ser Trp Gln
                85                  90                  95

Gln Trp Ala Asp Gln Gly Val Pro Asp Lys Val Thr Thr Asp Leu Cys
                100                 105                 110

Ser Gly Lys Pro Ile Asp Pro Ala Pro Tyr Ser Pro Thr Gly Pro Arg
            115                 120                 125

Gly Trp Gln Asp Glu Tyr Cys Glu Trp Ser Val Thr Arg Asn Gly Ala
    130                 135                 140

Gly Gln Ile Thr Ser Val Met Phe Thr Cys Glu Asn Pro Glu Tyr Trp
145                 150                 155                 160

Met Thr Leu Trp Gln Val Asp Pro Gly Lys Val Leu Gln Ile Tyr Gln
                165                 170                 175

Gln Val Ile Asn Pro Ala Val Gln Leu Ser Asp Leu Cys Leu Lys Asp
                180                 185                 190

Ser His Gly Gln Thr Val Asn Asp Pro Leu Thr Gly Gln Pro Cys Tyr
            195                 200                 205

Asn Pro Leu Asn Lys Trp Asn Ser Gly Thr Arg Thr Leu Ala Asn Ser
    210                 215                 220

Gly Gly Ala Met His Leu Thr Ser Ser Pro Asn Thr Leu Gly Ala Glu
225                 230                 235                 240

Tyr Asp Leu Ala Ala Ala Ala Thr Met Pro Arg Glu Lys Asp His Asp
                245                 250                 255

Pro Val Thr Ser Ala Ala Ala Leu Val Cys Phe Ala Arg Tyr Gly Arg
                260                 265                 270

Ile Gly Arg His Ser Asp Pro Thr Ile Gly Gln Asn Val Asn Gln Tyr
            275                 280                 285
```

```
Ala Asn Tyr Thr Pro Thr Leu Pro His Pro Gln Ala Thr Leu Ala Asp
    290                 295                 300

Pro Pro Gly Leu Tyr Met Gln Thr Pro Gln Phe Ser Asp Tyr Val Thr
305                 310                 315                 320

Pro Asp Asn Thr Pro Ala Gln Thr Phe Trp Thr Val Val Arg Gly Ser
                325                 330                 335

Leu Lys Asp Pro Asn Thr Ser Glu Asp Ile Asp Arg Ile Leu His Ala
            340                 345                 350

Thr Phe Ser Val Pro Pro Glu Leu Gly Tyr Thr Val Ser Asp Ile Lys
        355                 360                 365

Ile Gly Asn Gln Pro Ile Arg Tyr Gly Ser Gln Ile Ala Ala Thr Ile
370                 375                 380

Thr Met Ala Leu Leu Ala Thr Ala Phe Pro Asn Ser Gly Val Val Gln
385                 390                 395                 400

Thr Pro Val Gly Ala Thr Leu Asp Asn Ser Asn Pro Ser Pro Ser Val
                405                 410                 415

Ser Ala Leu Gln Ala Leu Ala Val Phe Thr Ala Tyr Arg Ala Gln Glu
            420                 425                 430

Leu Ala Ser Asn Glu Gln Pro Leu Ser Ile Pro Val Leu Ala Leu Ala
        435                 440                 445

Val Ser Pro Gly Gln Gln Val Ser Asn Ile Ala Leu Leu Leu Asn Thr
450                 455                 460

Ser Asp Thr Pro Asp Gly Ala Val Phe Thr Val Pro Glu Gly Gly Val
465                 470                 475                 480

Ser Ile Arg Ile Asp Gly Thr Gln Ala Leu Pro Asn Ala Glu Leu Ser
                485                 490                 495

Leu Tyr Gln Val Thr Leu Cys Val Asp Ala Asn Ala Ala Ile Gly Asp
            500                 505                 510

Arg Ser Ile Leu Ala Ser Val Pro Ser Met Pro Ala Thr Gln Gln Ala
        515                 520                 525

Ala Ile Gly Leu Leu Thr Val Val Ala Pro Pro Gln Val Arg Leu Ala
530                 535                 540

Gly Gly Pro Arg Lys Pro His Ala Arg His Ser Arg
545                 550                 555

<210> SEQ ID NO 78
<211> LENGTH: 448
<212> TYPE: PRT
<213> ORGANISM: Pseudomonas sp. PKRS11

<400> SEQUENCE: 78

Met Arg Ala Ile Leu Ala Leu Leu Tyr Ala Gly Leu Ser Leu Ala
1               5                   10                  15

Pro Val Ala Ala Arg Ala Ala Gly Asn Pro Cys Gly Ser Pro Phe Ser
                20                  25                  30

Pro Glu Pro Val Ile Gln Pro Val Leu Ala Asn Pro Gln Ile Ser Asn
            35                  40                  45

Leu Asp Pro Ser Val Asp Cys Phe Met Trp Gln Thr Met Val Tyr Leu
        50                  55                  60

Asn Trp Pro Ala Gln Ala Gly Gln Arg Gly Leu Pro Asn Thr Asp Ala
65                  70                  75                  80

His Leu Gly Asp Pro Gly Pro Thr Val Trp Gln Thr Phe Lys Asp Phe
                85                  90                  95

Asn Glu Leu Tyr Leu Pro Gly Gly Gln Arg Pro Ala Pro Trp Asn Asp
            100                 105                 110
```

Asn Phe Leu Thr Met Gln Arg Leu Glu Leu Arg Gly Val Glu Arg Pro
            115                 120                 125

Arg Pro Ser Ile Arg Leu Leu Asn Ser Thr Ser Lys Val Phe Arg Asn
        130                 135                 140

Ala Asp Ala Ser Glu Gln Lys Ala Leu Asp Glu Phe Lys Gln Val Gly
145                 150                 155                 160

Gly Gly Val Leu Tyr Asp Gln Asn Gly Gln Pro Val Tyr Tyr Glu Met
                165                 170                 175

Leu Ile Asn Gln Ile Asn Phe Asp Tyr Ile Tyr Ser Asn Gln Leu Tyr
            180                 185                 190

Asn Ala Ala Gln Gln Asn Leu His Ala Ala Lys Gln Gly Ile Val Leu
        195                 200                 205

Pro Ser Asn Ser Ile Glu Leu Lys Ala Ala Trp Lys Val Leu Ser Pro
210                 215                 220

Gln Glu Ala Ala Pro Pro Leu Arg Phe Leu Thr Ala Gln Ala Leu Leu
225                 230                 235                 240

Pro Gly Ser Gln Val Pro Val Thr Val Gly Leu Val Gly Leu His Val
                245                 250                 255

Phe Gln Met Pro Ser Lys Asp Phe Ala Gln Gly Phe Trp Ala Thr Phe
            260                 265                 270

Ser Gln Val Asp Asn Ala Pro Thr Leu Asn Thr Pro Gly Gln Ala His
        275                 280                 285

Tyr Ser Phe Asn Asn Pro Gln Cys Ser Gln Cys Pro Val Asn Asp Leu
290                 295                 300

Gly Ser Lys Pro Thr Gln Val Val Gln Val Ala Asn Ala Val Tyr
305                 310                 315                 320

Ala Gln Ala Val Asn Gln Tyr Met Gln Ala Leu Ile Gln Gln Ala
            325                 330                 335

Pro Asn Ser Ala Leu Gln Tyr Tyr Gln Leu Ile Asn Val Gln Trp Pro
        340                 345                 350

Asn Ser Ser Val Pro Ile Gly Gln Pro Gly Gln Pro Thr Pro Ala Pro
355                 360                 365

Thr Gly Ser Pro Ser Thr Asp Thr Leu Val Asn Pro Val Leu Glu Thr
    370                 375                 380

Phe Met Gln Val Ser Asn Met Ser Cys Leu Gly Cys His Lys Ser Ala
385                 390                 395                 400

Ser Val Ala Asp Asn Gly Thr Gln Pro Pro Ser Gly Tyr Gln Ala Ser
                405                 410                 415

Tyr Ser Phe Leu Leu Gly His Ala Gln Asn Pro Pro Gln Gly Ser
            420                 425                 430

Leu Lys Ser Leu Ala Arg Gln Val Glu Glu Ala Ser Thr Ala Arg Gln
        435                 440                 445

<210> SEQ ID NO 79
<211> LENGTH: 96
<212> TYPE: PRT
<213> ORGANISM: Pseudomonas Antarctica

<400> SEQUENCE: 79

Met Lys Leu Ser Asn Val Leu Leu Ser Ile Val Phe Ala Trp Gln
1               5                   10                  15

Gly Met Ala Phe Ala Asp Thr Gln Lys Ser Asn Ala Glu Thr Leu Leu
            20                  25                  30

Ser Asn Asp Lys Pro Pro Leu Thr Gln Ala Ala Gln Glu Lys Glu Gln

-continued

```
                 35                  40                  45

Glu Asn Val Glu Ala Asp Arg Asn Glu Cys Trp Ser Ala Lys Asn Cys
             50                  55                  60

Ser Gly Lys Ile Leu Asn Asn Lys Asp Ala His Asn Cys Lys Leu Ser
 65                  70                  75                  80

Gly Gly Lys Ser Trp Arg Ser Lys Thr Thr Gly Gln Cys Thr Asn Leu
                 85                  90                  95

<210> SEQ ID NO 80
<211> LENGTH: 96
<212> TYPE: PRT
<213> ORGANISM: Pseudomonas orientalis

<400> SEQUENCE: 80

Met Lys Met Ser Ser Val Leu Leu Met Ser Ile Ala Phe Val Cys Gln
 1               5                  10                  15

Gly Met Val Phe Ala Asp Thr Gln Lys Ser Asn Thr Glu Thr Leu Phe
                 20                  25                  30

Ser Asn Asp Lys Pro Pro Leu Ile Gln Thr Ala Gln Glu Gln Glu Gln
                 35                  40                  45

Lys Glu Val Glu Val Asp Arg Asn Gln Cys Trp Ser Ala Lys Asn Cys
             50                  55                  60

Ser Gly Lys Ile Leu Asn Asn Lys Asp Ala His Asn Cys Lys Leu Ser
 65                  70                  75                  80

Gly Gly Lys Ser Trp Arg Ser Lys Thr Thr Gly Gln Cys Thr Asn Leu
                 85                  90                  95

<210> SEQ ID NO 81
<211> LENGTH: 95
<212> TYPE: PRT
<213> ORGANISM: Enterobacter asburiae

<400> SEQUENCE: 81

Met Lys Thr Leu Val Ile Ala Ile Leu Thr Ala Val Leu Cys Gln Gly
 1               5                  10                  15

Met Ala Met Ala Asp Thr Gln Lys Pro Ala Thr Gly Ala Leu Pro Ala
                 20                  25                  30

Asn Glu Lys Pro Pro Leu Val Gln Pro Ala Asp Glu His Lys Thr Ser
                 35                  40                  45

Glu Ala Asn Ala Asn Arg Asn Glu Cys Trp Ser Ala Lys Asn Cys Thr
             50                  55                  60

Gly Lys Ile Leu Asn Asn Lys Asp Ala His Asn Cys Lys Asn Ser Gly
 65                  70                  75                  80

Gly Lys Ser Trp Arg Ser Lys Thr Thr Gly Gln Cys Thr Asn Leu
                 85                  90                  95

<210> SEQ ID NO 82
<211> LENGTH: 95
<212> TYPE: PRT
<213> ORGANISM: Enterobacter sp.

<400> SEQUENCE: 82

Met Lys Thr Leu Val Ile Ala Ile Leu Thr Ala Val Leu Cys Gln Gly
 1               5                  10                  15

Met Ala Met Ala Glu Thr Gln Gln Pro Ala Ser Gly Ala Leu Pro Ala
                 20                  25                  30

Asn Glu Lys Pro Pro Leu Val Leu Thr Ala Asp Glu Lys Lys Ala Ser
                 35                  40                  45
```

```
Glu Ala Asn Ala Asp Arg Asn Glu Cys Trp Ser Ala Arg Asn Cys Ser
            50                  55                  60

Gly Lys Ile Leu Asn Asn Lys Asp Ala His Asn Cys Lys Asn Ser Gly
 65                  70                  75                  80

Gly Lys Ser Trp Arg Gly Lys Asn Ser Ser Gln Cys Thr Asn Leu
                85                  90                  95

<210> SEQ ID NO 83
<211> LENGTH: 105
<212> TYPE: PRT
<213> ORGANISM: Acidovorax avenae

<400> SEQUENCE: 83

Met Lys Lys Leu Leu Leu Ile Ala Ser Leu Val Ser Ile Ser Gly
 1               5                  10                  15

Ala Asn Val Phe Ala Gln Ala Pro Ser Ser Gly Asp Ala Pro Ala Ala
            20                  25                  30

Val Ala Gly Lys Gln Asp Gly Ala Ser His Lys Asp Thr Glu Gln Ala
            35                  40                  45

Ala Asn Val Glu Cys Asp Val Asn Ala Thr Val Gln Gln Cys Cys Ser
            50                  55                  60

Ala Ala Lys Cys Gln Gly Lys Val Leu Ser Asn Arg Asp Ala His Asn
 65                  70                  75                  80

Cys Lys Asp Lys Ser Lys Gly Lys Ser Trp His Ala Ala Ala Gln Gly
                85                  90                  95

Gly Gln Pro Ala Ala Cys Gln Arg Met
            100                 105

<210> SEQ ID NO 84
<211> LENGTH: 94
<212> TYPE: PRT
<213> ORGANISM: Serratia plymuthica

<400> SEQUENCE: 84

Met Gln Cys Asn Gly Ala Ile Leu Lys Leu Leu Cys Ala Gln Arg Lys
 1               5                  10                  15

Asp Gln Phe Met Asn Leu Arg Ile Arg Thr His Ala Met Lys Asn Leu
            20                  25                  30

Ser Ile Leu Val Val Leu Ser Ser Cys Leu Leu Leu Pro Leu Thr Ala
            35                  40                  45

Ser Ala Ala Ala Gly Thr Cys Tyr Ser Ala Lys Asn Cys Ser Gly Lys
            50                  55                  60

Val Leu Ser His Arg Asp Ala His Asn Cys Lys Val Lys Asp Lys Gly
 65                  70                  75                  80

Lys Ser Trp Arg Ser Asp Ile Thr Asn Gln Cys Thr Asn Leu
                85                  90

<210> SEQ ID NO 85
<211> LENGTH: 93
<212> TYPE: PRT
<213> ORGANISM: Serratia liquefaciens

<400> SEQUENCE: 85

Met Arg Glu Glu Ala Ile Leu Lys Leu Leu Cys Ala Gln Arg Lys Asp
 1               5                  10                  15

Gln Phe Met Asn Ser Arg Ile Arg Thr His Ala Met Lys Asn Leu Ser
            20                  25                  30
```

```
Ile Leu Val Val Leu Ser Ser Cys Leu Leu Pro Leu Thr Ala Ser
             35                  40                  45

Ala Ala Ser Gly Lys Cys Tyr Ser Ala Lys Asn Cys Ser Gly Lys Val
 50                  55                  60

Leu Ser Lys Arg Asp Ala His Asn Cys Lys Val Lys Asp Arg Gly Lys
 65                  70                  75                  80

Ser Trp Leu Ser Asp Val Thr Gly Lys Cys Thr Asn Leu
                 85                  90
```

<210> SEQ ID NO 86
<211> LENGTH: 78
<212> TYPE: PRT
<213> ORGANISM: Serratia sp.

<400> SEQUENCE: 86

```
Met Lys Leu Lys Tyr Glu Arg Ile Arg Ile Tyr Val Met Lys Ser Leu
 1               5                  10                  15

Ser Ile Val Ile Thr Leu Ala Ser Cys Leu Leu Pro Leu Thr Ala
                 20                  25                  30

Ser Ala Ala Gly Thr Cys Tyr Ser Ala Lys Asn Cys Ser Gly Lys
             35                  40                  45

Val Leu Ser His Arg Asp Ala His Asn Cys Lys Val Lys Asp Lys Gly
 50                  55                  60

Lys Ser Trp Arg Ser Asp Ile Thr Gly Gln Cys Thr Asn Leu
 65                  70                  75
```

<210> SEQ ID NO 87
<211> LENGTH: 75
<212> TYPE: PRT
<213> ORGANISM: Serratia sp.

<400> SEQUENCE: 87

```
Met Asn Ser Arg Ile Arg Thr Tyr Ala Met Lys Asn Leu Ser Ile Leu
 1               5                  10                  15

Val Val Leu Ser Ser Cys Leu Leu Pro Leu Thr Ala Ser Ala Ala
                 20                  25                  30

Ala Gly Thr Cys Tyr Ser Ala Lys Asn Cys Ser Gly Lys Val Leu Ser
             35                  40                  45

His Arg Asp Ala His Asn Cys Lys Val Lys Asp Lys Gly Lys Ser Trp
 50                  55                  60

Arg Ser Asp Ile Thr Gly Lys Cys Thr Asn Leu
 65                  70                  75
```

<210> SEQ ID NO 88
<211> LENGTH: 89
<212> TYPE: PRT
<213> ORGANISM: Pseudomonas chlororaphis

<400> SEQUENCE: 88

```
Met Ser Ala Gln Glu Asn Phe Val Gly Gly Trp Thr Pro Tyr His Lys
 1               5                  10                  15

Leu Thr Pro Lys Asp Gln Glu Val Phe Lys Glu Ala Leu Ala Gly Phe
                 20                  25                  30

Val Gly Val Gln Tyr Thr Pro Glu Leu Val Ser Thr Gln Val Val Asn
             35                  40                  45

Gly Thr Asn Tyr Arg Tyr Gln Ser Lys Ala Thr Leu Pro Gly Ser Ser
 50                  55                  60

Glu Ser Trp Gln Ala Val Val Glu Ile Tyr Ala Pro Ile Lys Gly Lys
```

```
                65                  70                  75                  80
Pro His Ile Thr Gln Ile His Arg Ile
                85

<210> SEQ ID NO 89
<211> LENGTH: 89
<212> TYPE: PRT
<213> ORGANISM: Pseudomonas chlororaphis

<400> SEQUENCE: 89

Met Ser Ala Gln Glu Asn Phe Val Gly Gly Trp Thr Pro Tyr His Lys
1               5                   10                  15

Leu Thr Pro Lys Asp Gln Glu Val Phe Lys Glu Ala Leu Ala Gly Phe
            20                  25                  30

Val Gly Val His Tyr Thr Pro Glu Gln Val Ser Thr Gln Val Val Asn
        35                  40                  45

Gly Thr Asn Tyr Arg Tyr Leu Ser Lys Ala Thr Val Pro Gly Ser Ser
    50                  55                  60

Asp Ser Trp Gln Ala Val Val Glu Ile Tyr Ala Pro Ile Lys Gly Lys
65                  70                  75                  80

Pro His Ile Thr Gln Ile His Arg Ile
                85

<210> SEQ ID NO 90
<211> LENGTH: 89
<212> TYPE: PRT
<213> ORGANISM: Pseudomonas brassicacearum

<400> SEQUENCE: 90

Met Ser Ala Gln Glu Asn Phe Val Gly Gly Trp Thr Pro Tyr His Glu
1               5                   10                  15

Leu Thr Pro Lys Asp Arg Glu Val Phe Lys Glu Ala Leu Ala Gly Phe
            20                  25                  30

Val Gly Val Gln Tyr Thr Pro Glu Lys Val Ser Thr Gln Val Val Asn
        35                  40                  45

Gly Thr Asn Tyr Arg Tyr Leu Ser Lys Ala Thr Val Pro Gly Ser Ser
    50                  55                  60

Asp Ser Trp Gln Ala Val Val Glu Ile Tyr Ala Pro Ile Lys Gly Lys
65                  70                  75                  80

Pro His Ile Thr Gln Ile His Arg Ile
                85

<210> SEQ ID NO 91
<211> LENGTH: 89
<212> TYPE: PRT
<213> ORGANISM: Pseudomonas chlororaphis

<400> SEQUENCE: 91

Met Ser Ala Gln Glu Asn Phe Val Gly Gly Trp Thr Pro Tyr His Glu
1               5                   10                  15

Leu Thr Pro Lys Asp Arg Glu Val Phe Lys Glu Ala Leu Ala Gly Phe
            20                  25                  30

Val Gly Val His Tyr Thr Pro Glu Lys Val Ser Thr Gln Val Val Asn
        35                  40                  45

Gly Thr Asn Tyr Arg Tyr Leu Ser Lys Ala Thr Val Pro Gly Ser Ser
    50                  55                  60

Asp Ser Trp Gln Ala Val Val Glu Ile Tyr Ala Pro Ile Lys Gly Lys
65                  70                  75                  80
```

```
Pro His Ile Thr Gln Ile His Arg Ile
                85

<210> SEQ ID NO 92
<211> LENGTH: 89
<212> TYPE: PRT
<213> ORGANISM: Pseudomonas chlororaphis

<400> SEQUENCE: 92

Met Ser Ala Gln Glu His Phe Val Gly Gly Trp Thr Pro Tyr His Glu
1               5                   10                  15

Leu Thr Pro Lys Asp Lys Glu Val Phe Lys Glu Ala Leu Ala Gly Phe
            20                  25                  30

Val Gly Val His Tyr Thr Pro Glu Lys Val Ser Thr Gln Val Val Asn
        35                  40                  45

Gly Thr Asn Tyr Arg Tyr Leu Ser Lys Ala Thr Leu Pro Gly Ser Ser
    50                  55                  60

Asp Ser Trp Gln Ala Val Val Glu Ile Tyr Ala Pro Ile Lys Gly Lys
65                  70                  75                  80

Pro His Ile Thr Gln Ile His Arg Ile
                85

<210> SEQ ID NO 93
<211> LENGTH: 89
<212> TYPE: PRT
<213> ORGANISM: Pseudomonas fluorescens

<400> SEQUENCE: 93

Met Ser Ala Gln Glu Asn Leu Val Gly Gly Trp Thr Pro Tyr His Glu
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Thr Lys Ala Thr Gln Pro Gly Ser Ser
    50                  55                  60

Asn Ser Trp Gln Ala Val Val Glu Ile Tyr Ala Pro Ile Asn Gly Lys
65                  70                  75                  80

Pro His Ile Thr Gln Ile Ile Arg Ile
                85

<210> SEQ ID NO 94
<211> LENGTH: 89
<212> TYPE: PRT
<213> ORGANISM: Pseudomonas fluorescens

<400> SEQUENCE: 94

Met Ser Ala Gln Glu Asn Leu Val Gly Gly Trp Thr Pro Tyr His Glu
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Ala Lys Ala Thr Gln Pro Gly Ser Pro
    50                  55                  60

Asn Ser Trp Gln Ala Val Val Glu Ile Tyr Ala Pro Ile Asn Gly Lys
65                  70                  75                  80
```

-continued

Pro His Ile Thr Gln Ile Ile Arg Ile
                85

<210> SEQ ID NO 95
<211> LENGTH: 89
<212> TYPE: PRT
<213> ORGANISM: Pseudomonas fluorescens

<400> SEQUENCE: 95

Met Ser Ala Gln Glu Asn Leu Val Gly Gly Trp Thr Pro Tyr His Glu
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Ala Gln Ala Thr Gln Pro Gly Ser Pro
    50                  55                  60

Asn Ser Trp Gln Ala Val Val Glu Ile Tyr Ala Pro Ile Asn Gly Lys
65                  70                  75                  80

Pro His Ile Thr Gln Ile Ile Arg Ile
                85

<210> SEQ ID NO 96
<211> LENGTH: 89
<212> TYPE: PRT
<213> ORGANISM: Pseudomonas fluorescens

<400> SEQUENCE: 96

Met Ser Ala Gln Glu Asn Leu Val Gly Gly Trp Thr Pro Tyr His Glu
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Ala Lys Ala Thr Gln Pro Gly Ser Pro
    50                  55                  60

Asn Ser Trp Gln Ala Val Val Glu Ile Tyr Ala Pro Ile Asn Gly Lys
65                  70                  75                  80

Pro Tyr Val Thr Gln Ile Ile Arg Ile
                85

<210> SEQ ID NO 97
<211> LENGTH: 89
<212> TYPE: PRT
<213> ORGANISM: Pseudomonas fluorescens

<400> SEQUENCE: 97

Met Ser Ala Gln Glu Asn Leu Val Gly Gly Trp Thr Gly Tyr His Glu
1               5                   10                  15

Leu Thr Pro Lys Asp Lys Glu Val Phe Lys Glu Ala Leu Glu Gly Leu
            20                  25                  30

Val Gly Val His Tyr Thr Pro Glu Leu Val Ser Ser Gln Ile Val Asn
        35                  40                  45

Gly Thr Asn Tyr Arg Tyr Gln Thr Lys Ala Thr Gln Pro Gly Ser Ser
    50                  55                  60

Thr Ser Trp Gln Ala Ile Val Glu Ile Tyr Ala Pro Ile Lys Gly Lys
65                  70                  75                  80

Pro His Ile Thr Gln Ile Ile Arg Ile

<210> SEQ ID NO 98
<211> LENGTH: 89
<212> TYPE: PRT
<213> ORGANISM: Pseudomonas rhodesiae

<400> SEQUENCE: 98

```
Met Ser Ala Gln Glu Asn Leu Val Gly Gly Trp Thr Pro Tyr His Glu
1               5                   10                  15

Leu Thr Pro Lys Asp Gln Glu Val Phe Asp Val Ala Leu Ala Gly Leu
                20                  25                  30

Val Gly Val His Tyr Thr Ala Glu Leu Val Ser Thr Gln Val Val Asn
            35                  40                  45

Gly Thr Asn Tyr Arg Tyr Gln Ala Lys Ala Thr Gln Pro Gly Ser Pro
        50                  55                  60

Asn Ser Trp Gln Ala Val Val Glu Ile Tyr Ala Pro Ile Asn Gly Lys
65                  70                  75                  80

Pro Tyr Val Thr Gln Ile Ile Arg Ile
                85
```

<210> SEQ ID NO 99
<211> LENGTH: 89
<212> TYPE: PRT
<213> ORGANISM: Pseudomonas-sp

<400> SEQUENCE: 99

```
Met Thr Ala Gln Glu His Leu Val Gly Gly Trp Thr Pro Tyr His Lys
1               5                   10                  15

Leu Thr Pro Lys Asp Gln Glu Val Phe Lys Glu Ala Leu Ala Gly Phe
                20                  25                  30

Val Gly Val Ser Tyr Thr Pro Glu Glu Val Ser Ser Gln Val Val Asn
            35                  40                  45

Gly Thr Asn Tyr Arg Tyr Lys Ser Lys Ala Thr Leu Pro Gly Ser Pro
        50                  55                  60

Asn Gly Trp Gln Ala Ile Val Glu Ile Tyr Ala Pro Thr Asn Gly Lys
65                  70                  75                  80

Pro His Ile Thr Gln Ile His Arg Ile
                85
```

<210> SEQ ID NO 100
<211> LENGTH: 91
<212> TYPE: PRT
<213> ORGANISM: Pseudomonas fluorescens

<400> SEQUENCE: 100

```
Met Ser Ala Gln Glu Asn His Val Gly Val Gly Trp Thr Ala Tyr
1               5                   10                  15

His Glu Leu Thr Pro Lys Asp His Ala Val Phe Lys Glu Ala Leu Glu
                20                  25                  30

Gly Phe Val Gly Val Gln Tyr Thr Pro Glu Thr Val Ser Thr Gln Val
            35                  40                  45

Val Ala Gly Thr Asn Tyr Arg Tyr His Ser Lys Ala Gln Gln Pro Gly
        50                  55                  60

Ser Pro Ala Ile Trp Ala Ala Ile Val Glu Ile Tyr Ala Pro Leu Lys
65                  70                  75                  80

Gly Lys Pro His Ile Thr Gln Ile Ile Arg Ile
                85                  90
```

<210> SEQ ID NO 101
<211> LENGTH: 92
<212> TYPE: PRT
<213> ORGANISM: Enterobacter-sp

<400> SEQUENCE: 101

Met Ser Glu Gln Gln Thr Leu Leu Pro Gly Gly Trp Thr Ala Tyr His
1               5                   10                  15

Pro Leu Thr Ala Gln Asp Arg Lys Val Phe Glu Glu Ala Leu Asn Gly
            20                  25                  30

His Leu Gly Val Asp Tyr Glu Pro Gln Lys Val Lys Thr Gln Val Val
        35                  40                  45

Ala Gly Thr Asn Tyr Arg Phe Leu Cys Glu Ala Ser Val Pro Pro Ser
    50                  55                  60

Thr Ala Val Trp Glu Ala Ile Val Glu Ile Tyr Ala Pro Leu Pro Gly
65                  70                  75                  80

Gln Gly Ala Pro His Ile Thr Gln Ile Ile Arg Ile
                85                  90

<210> SEQ ID NO 102
<211> LENGTH: 89
<212> TYPE: PRT
<213> ORGANISM: Shewanella denitrificans

<400> SEQUENCE: 102

Met Ser Asn Asn Glu Thr Ile Val Gly Gly Trp Thr Ala Tyr Asn Ala
1               5                   10                  15

Ile Thr Ser Ala Glu Arg Glu Ile Phe Asn Lys Ala Met Glu Gly Phe
            20                  25                  30

Val Gly Val Ser Tyr Met Pro Glu Thr Val Ser Thr Gln Val Val Ala
        35                  40                  45

Gly Met Asn Tyr Arg Phe Lys Cys Glu Ala Ser Met Pro Pro Ser Glu
    50                  55                  60

Val Leu Trp Glu Ala Ile Val Glu Ile Tyr Gln Pro Leu Lys Gly Ile
65                  70                  75                  80

Pro His Ile Thr Asn Ile Thr Lys Ile
                85

<210> SEQ ID NO 103
<211> LENGTH: 90
<212> TYPE: PRT
<213> ORGANISM: Aeromonas diversa

<400> SEQUENCE: 103

Met Ser Asp Gln Ala Val Leu Val Gly Gly Trp Thr Ala Tyr His Arg
1               5                   10                  15

Leu Thr Ala Glu Asp Gln Ala Val Phe Gln Glu Ala Leu Lys Gly Phe
            20                  25                  30

Val Gly Val Glu Tyr Lys Pro Phe Glu Val Ser Thr Gln Val Val Ala
        35                  40                  45

Gly Met Asn Tyr Arg Tyr Lys Cys Lys Thr Thr Val Pro Leu Pro Thr
    50                  55                  60

Pro Ile His Gly Glu Ala Val Val Gln Ile Phe Gln Ser Leu Asp Gly
65                  70                  75                  80

Ser Ala His Ile Thr Ser Ile Thr Pro Ile
                85                  90

<210> SEQ ID NO 104
<211> LENGTH: 90
<212> TYPE: PRT
<213> ORGANISM: Aeromonas salmonicida

<400> SEQUENCE: 104

Met Ser Glu Gln Ala Val Leu Val Gly Gly Trp Thr Ala Tyr His Lys
1               5                   10                  15

Leu Thr Ala Glu Asp Gln Ala Val Phe Asp Gln Ala Leu Lys Gly Phe
            20                  25                  30

Val Gly Val Gln Tyr Val Pro Phe Glu Val Cys Thr Gln Val Val Ala
        35                  40                  45

Gly Thr Asn Tyr Arg Phe Lys Cys Lys Ser Thr Val Pro Leu Ala Lys
    50                  55                  60

Pro Ile His Gly Glu Ala Val Val Gln Ile Phe Gln Ser Leu Asp Gly
65                  70                  75                  80

Ser Ala His Ile Thr Ser Ile Thr Pro Ile
                85                  90

<210> SEQ ID NO 105
<211> LENGTH: 90
<212> TYPE: PRT
<213> ORGANISM: Aeromonas veronii

<400> SEQUENCE: 105

Met Ser Glu Gln Ala Val Leu Val Gly Gly Trp Thr Ala Tyr His Lys
1               5                   10                  15

Leu Thr Ala Glu Asp Gln Ala Val Phe Asp Gln Ala Leu Lys Gly Phe
            20                  25                  30

Val Gly Val Gln Tyr Val Pro Phe Glu Val Ser Thr Gln Val Val Ala
        35                  40                  45

Gly Thr Asn Tyr Arg Phe Lys Cys Lys Ser Thr Val Pro Leu Ala Lys
    50                  55                  60

Pro Ile His Gly Glu Ala Val Val Gln Ile Phe Lys Ser Leu Asp Gly
65                  70                  75                  80

Asp Ala His Ile Thr Ser Ile Thr Pro Ile
                85                  90

<210> SEQ ID NO 106
<211> LENGTH: 88
<212> TYPE: PRT
<213> ORGANISM: Aeromonas molluscorum

<400> SEQUENCE: 106

Met Ser Glu Gln Ala Val Leu Leu Gly Gly Trp Thr Ala Tyr His Lys
1               5                   10                  15

Leu Ser Ala Lys Asp Gln Ala Val Phe Asn Gln Ala Leu Glu Gly Phe
            20                  25                  30

Val Gly Val Gln Tyr Thr Pro Phe Glu Val Ser Thr Gln Val Val Ala
        35                  40                  45

Gly Thr Asn Tyr Arg Phe Lys Cys Lys Ser Thr Val Pro Leu Pro Asn
    50                  55                  60

Pro Ile His Gly Glu Ala Val Gln Ile Phe Gln Ala Leu Phe Pro
65                  70                  75                  80

Lys Ser Met Gln Leu Glu Trp Asn
                85

<210> SEQ ID NO 107
<211> LENGTH: 90
<212> TYPE: PRT
<213> ORGANISM: Aeromonas aquariorum

<400> SEQUENCE: 107

Met Ser Glu Gln Ala Val Leu Leu Gly Gly Trp Thr Ala Tyr His Lys
1               5                   10                  15

Leu Ser Ala Lys Asp Gln Ala Val Phe Asn Gln Ala Leu Glu Gly Phe
            20                  25                  30

Val Gly Val Gln Tyr Thr Pro Phe Glu Val Ser Thr Gln Val Val Ala
        35                  40                  45

Gly Thr Asn Tyr Arg Phe Lys Cys Lys Thr Thr Val Pro Leu Pro Asn
    50                  55                  60

Pro Ile His Gly Glu Ala Val Val Gln Ile Phe Gln Ser Leu Asp Gly
65                  70                  75                  80

Ser Ala His Ile Thr Ser Ile Thr Pro Ile
            85                  90

<210> SEQ ID NO 108
<211> LENGTH: 1737
<212> TYPE: DNA
<213> ORGANISM: Pseudomonas brenneri

<400> SEQUENCE: 108
atgagcacac ccttcaaaca attcacctcc ccgccgggc aagcccccaa ggactacaac     60
aagctgggcc tggaaaacca gctgccgcag tttgaaaccg actggaacaa tgacctcacc    120
ggctggaccc agtccgcgat catcggcaac ccgtggtcgg cctcaatga cgcgccgcgc    180 tcgggctatt acaacccgct ggtggaaggc tacggcccca ccacgccgcc ggcgattacc    240
tgggcgccct tccccaatcg gctgtggacg ttcttctaca caacggcac ggcggtgatt    300 ccgcaattgg gcggcaaggc catgtccctg caacaggtga tggagctgac cgacaacggc    360
cagattacga tcaacaacac cctgtacatg ctctacgacc cgaacaagca aggcaccctg    420
ctgcaactgc ccgtcacccg ctgcccgacc atcgactggc aaggcaagta caaggatttc    480
tcgccctcgg ggcccgtgg ctggcttgac gaatactgcg agtggtccat cgtgcgcgat    540
gccgacggca acatgcgcaa gatcaccttc acctgcgaaa cccggcgta tttcctggcc    600 atgtggcgca ttgatccaaa tgcagtgctg ggcctgtacc gcgactacat cgacccgcag    660
gtgcagctcg aagacctcta cctgcgctac accgccgact gtccgaccgg caaagcgggc    720
gatccggtca tcgaccctac caccggccaa ccggcctacg acggtcaa caatggaac    780 gccggcaccg cctgcgtacc cggccaatac ggcggggcga tgcacctgac ctccggcccc    840
aacaccctga gcgccgaggt gtacctggcc gccgcgcga ccatcctgcg tccactggcc    900
agcagccaga attcccaggc attgatctgc tgcgcgcaat acgggcagaa ctaccgcaac    960
tccgacccgc atatcggttt ctcggccaac agcgtggcgg tgaataaccg gctgtccctg    1020
accaatccca tcggcctta cctgcaacaa cccaccgatt tctcggcgtg gaaaggccct    1080
caaggccagg acgtcagcca gtactggaaa atcacccgtg gcaccgccaa gtccgccgcc    1140
aacggctccg accagatcct gcaagcggtg tttgaagtgc cggtcagcgc cgggttttcg    1200
atcaacgaca tcaccatcag tggccagccg atcgactatg tgtgggtgat tgcccagcag    1260
ttgctggtgg gcctgagtgt gacaaccacg cccatcagcc cgacgccgga ttcctgcccc    1320
tgcgtgaagg atcgggtcaa cggcgtgcaa ccctggccgg tgcaactgct gcccctggat    1380

```
ctgttctacg ggcagtcgcc taccgacctg ccggcctggc tggcacccgg caccagcgga    1440
cagttcgccc tggtggtgca aggcgccgat ctcaagacca ccgccgagac ggcgcgggtg    1500
caattttcca atcccggcgt gacggcgcag gtcacccagt cctgccgga tgcctccgcc    1560 atccccgggc aaaccaactc cggcggcacc cagggctact tgctgaccat caccgtaagc    1620
cccactgccg ctccggggct ggtgacggtg cgcgcgctca acccgggcga agccgataac    1680
cccagcgcga cggaacaccc atgggaatcc ggattggcgc tggtgcctgg cgcctga       1737
```

<210> SEQ ID NO 109
<211> LENGTH: 1608
<212> TYPE: DNA
<213> ORGANISM: Pseudomonas brenneri

<400> SEQUENCE: 109

```
atgtccaggt tacgcttaag tgttttatcg ctgctgacca gtgtggtgct gagcctgttc     60
gccatgcagg ccgcctacgc atccccacg tccgacgccg acgcttgcgt gcagcaacag    120
ttggtgttca atccgaaaag cggcggtttc ctgccgatta caacttcaa cgccaccggc    180 cagagctttta tgaattgctt tggctggcag ttgttcattg ccctgaactg ccggtgaat    240 cccggttggc cagccacgcc cgccctcgcg ggtgagccgg acatgaacag tacattggcg    300
caattcggtg taccgactgc ctccgggcag ccgatgagcg tggcgcccgt gtgggccagc    360
tacaaggatg ccaacgatat cttcctgccc ggcgcgcccg cgccaccgg ctggggcgtg    420 caaaccctgg tgccgtccaa ttgcagcacc cagggcagcc tcagggcgat atcggtgggg    480
gcgcgcaagt tcatgaccgc cacctccgaa agcgcgatca acgcgcgtca tgggtttcac    540
ctgtccagcg gcaccctcgc ctcgattcca gacccgatca tggaagcctc cggcggctgg    600
ctgacggacc agtcgcagaa cctggtgtttt tttgaacgca aggtgggcaa ggccgagttc    660
gactacatcg tcagcaaagg gctgtacgac gcagccaacc agctgacagt cgcgcagaac    720
ctcgacaacc agaacccggg cgggctgtct ctgcccatcg tgaacccat gcgctcgctg    780 ccgcccaacc cggtgccgca ggagcaactg ggagcgctgg aggtcaaggc ggcgtggcgg    840
atccttaccg gcaaacccga gctctacggg cgttacctga ccaccgtcgc ctggctcaaa    900
aacccggcca ccttgcagtg cacccaacaa gtggtgggcc tggtgggcct gcatatcatc    960
aacaagaccc aagcctcgcc caacttcatc tggaccaccct tcgagcaggt ggacaacgtg   1020
ccggaaccca accaggtgcc gccacaacag acgccgcccg acagctttgc cttcaacaac   1080
ccgaactgcg gcaccggccc cgaatgcacg ccgaacgtgg cgcgtatcca gtgcaaacag   1140
caccatcccg accgcgactg caccgagccg tttccacggg accaacccgt gcagaccacc   1200
cgggaacatc cgctgcccac tgaactgcag gcgcttaacg gcgcggtgca ggccaacttt   1260
gcccagcaga gccagggcaa gtcggtgttc cagtactaca aactgatcaa cgtactctgg   1320
accctcaccc ccaacccgcc cacccagccg gaaccgggtg tcagtgcgca agtgccgctg   1380
tcctacgggc cgtttatcag ccagggcaac gtaccggtgg ccaacaccac cctggagacc   1440
tacgtccagg gcgataactg caatgcctgt catcagtacg cgaccatcgc cggcagctcc   1500
accctggctt cggactttc gttcctgttc aacagcgccg actcggccag caagaacagc   1560
ctggtcaagc gcgtgaaagc cttccagacc ctcaaggatc aaccgtga               1608
```

<210> SEQ ID NO 110
<211> LENGTH: 1737
<212> TYPE: DNA
<213> ORGANISM: Pseudomonas sp. Ag1

<400> SEQUENCE: 110

```
atgagcacac ccttcaaaca attcacctct cccgccgggc aagctcccaa ggactacaac    60
aagctgggcc tggaaaacca gttgccgcag tttgaaaccg actggaacaa cgacctcacc   120
ggctggaccc agtccgcgat catcggcaac cgtggtcgg gcctcaatga cgcgccgcgc    180
tcgggctatt acaacccact ggtggaaggc tacggcccca ccacgccgcc ggcgattacc   240
tgggcgccct tccccaatcg gctgtggacg tttttctaca acaacggcac ggcggtgatt   300
ccacagttgg gcggcaaggc catgtccatg caacaggtga tggagctgac cgacaacggc   360
cagattacga tcaacaacac cctgtacatg ctctacgacc cgaacaagca aggcaccctg   420
ctgcaactcc ccgtcactcg ctgcccgagc atcgactggc aaggcaagta caaggatttc   480
tcgccttcgg gccccgtgg ctggcttgac gaatattgcg agtggtccat agtgcgcgat    540
gccgacggca acatgcgcaa gatcaccttc acttgcgaaa accggcgta tttcctggcc    600
atgtggcgca tcgatccgac tgctgtactg gggctgtatc gcgactacat cgacccgcag   660
gtgcaactcg aagacctgta cctgcgctac accgccgact gcccgaccgg taaggccggc   720
gacccggtca tcgaccccac caccggtcaa ccggcctacg acaccgtcaa caatggaaac   780
gccggcaccg cctgtgtgcc aggccaatac ggcggtgcga tgcacctgac ctccggcccc   840
aacaccctga cgccgaggt gtacctggct gccgcggcga ccatcctgcg gccattgagc   900
agcagccaga attcccaggc gttgatctgc tgcgcgcaat acgggcagaa ctaccgcaac   960
tccgatccgc atatcggttt ctcggccaac agcgtggcag tgaataaccg gctgtcgctg  1020
acgaacccca tcggcctgta cctgcaacaa cccaccgact tctcggcgtg gaaaggcccc  1080
cagggccagg acgtcagcca gtactggaaa atcacccgtg gcaccgccaa gtccgccgcc  1140
aacggctccg accagattct gcaagcggtg tttgaagtgc cggtcagcgc cgggttttcg  1200
atcaacgaga tcaccatcag cggccagccg atcgactacg tgtgggtgat tgcccagcag  1260
ttgctggtgg gcctgagtgt gacaaccacg cccatcagcc cgacgccgga ttcctgcccg  1320
tgcgtgacgg accgggtcaa cggcgtgcaa ccctggccgg tacagctgct gccgctggac  1380
ctgttctacg ggcagtcacc caccgacctg ccggcctggc tggcacccgg caccagcggg  1440
cagtttgccc tggtggtgca aggcgccgac ctcaagacca ccgccgagac ggcgcgggtg  1500
caattctcca atcctggggt gacggcgcag gtcacaaagt tcctgccgga tgcctcggcc  1560
atccccgggc aaaccaactc cggtggcacc cagggctacc tgctgaccat caccgtaagc  1620
cccactgccg caccggggct ggtgacagtg cgcgccctca cccgggcga agccgataac   1680
cccagcgcgg cggaacaccc atgggaatcc ggattggcgc tggtgcctgg cgcctga     1737
```

<210> SEQ ID NO 111
<211> LENGTH: 1611
<212> TYPE: DNA
<213> ORGANISM: Pseudomonas sp. Ag1

<400> SEQUENCE: 111

```
atgtccaggt tacgcttgag tgttttatcg ctgctgacca gtgtggtgct gagcctgttc    60
gccatgcagg ccgcctacgc atcccccact tccgacgccc acgcttgcgt gcagcaacag   120
ttggtgttca acccgaaaag cggcggcttc ctgccgatca caacttcaa cgccaccggc    180
cagagcttca tgaattgctt tggctggcag ttgttcattg ccctgaactg gccggtgaat   240
cccggttggc cagccacacc tgccctcgcg ggtgagccac acatgaacag taccctggcg   300
```

| | |
|---|---:|
| caattcggcg taccgactgc ctccgggcag ccgatgagcg tggcgccggt atgggccagc | 360 |
| tacaaggacg ccaacgatat cttcctgccc ggcgcgcccg cgcccaccgg ctggggcgtg | 420 |
| caaaccctgg tgccgtccaa ttgcagcacc cagggcagcc tcagggcgat gtcggtgggg | 480 |
| gcgcgcaagt tcatgaccgc cacctccgaa agcgcgatca acgcgcggca tgggtttcac | 540 |
| ctgtccagcg gcaccctggc ctcgattccg gacccgatca tggaagcctc cggcggctgg | 600 |
| ctgacggacc agtcgcagaa cctggtgttt tttgaacgca aggtgggcaa ggccgagttc | 660 |
| gactacatcg tcagcaaagg gctgtacgac gcggccaacc agctgaaagt cgcgcagaac | 720 |
| ctcgacaacc agaaccccgg cgggctgtcc ttgcccatcg gtgaacccat gcgctcgctg | 780 |
| ccgcccaacc cggtgccgca ggagcaactg ggagctctgg aggtcaaggc agcatggcga | 840 |
| atcctcaccg gcaaacccga gctctacggg cgttacctga ccaccgtcgc ctggctcaaa | 900 |
| aacccggcca ccttgcagtg cacccagcaa gtggtgggcc tggtgggcct gcatatcatc | 960 |
| aacaagaccc aggcctcgcc caacttcatc tggaccacct cgagcaggt agacaacgtg | 1020 |
| ccggaacccg accaggtgcc gccacaacaa acgccgcccg acagctttgc cttcaataac | 1080 |
| ccgaactgcg gcaccggccc cgaatgcacg ccgaacgtgg cgcgtatcca gtgcaagcag | 1140 |
| cagcatccgg accgcgactg caccgagccg tttccacggg accaacccgt gcagaccacc | 1200 |
| cgggaacatc cgctgcccac tgaactgcag gcgcttaacg gcgcggtgca ggccaatttt | 1260 |
| gcccagcaga gccagggcaa gtcggtgttc cagtactaca aactgatcaa cgtactctgg | 1320 |
| accctcaccc caacccgcc cacccagccg gaaccgggtg tcagtgcgca agtgccgctg | 1380 |
| tcctacgggc cgtttatcag ccagggcaac gtaccggtgg ccaacaccac cctggagacc | 1440 |
| tacgtccagg gcgataactg caatgcctgt catcagtacg cgaccatcgc cggcagctcg | 1500 |
| accctggcct cggactttc gttcctgttc aacagtgccg attcggccag caagaaaagc | 1560 |
| ctggtcaagc gcgtaaaagc cttccagacc ctcaaggacg gttcaccctg a | 1611 |

<210> SEQ ID NO 112
<211> LENGTH: 1740
<212> TYPE: DNA
<213> ORGANISM: Pseudomonas sp. PAMC 25886

<400> SEQUENCE: 112

| | |
|---|---:|
| atgagcacac ccttcaatca attcacctcg cccgccgggc aagcccccaa ggactacaac | 60 |
| aagctgggcc tggaaaacca gttgccgcag tttgaaaccg actggaacaa cgacctcacc | 120 |
| ggctggaccc agtccgcgat catcggcaac cgtggtcgg gcctcaatga cgcgccgcgc | 180 |
| tcgggctatt acaacccgct ggtggaaggc tacggcccca ccacgccacc ggcgatcacc | 240 |
| tgggcgccct tccccaaccg gctgtggacg ttcttctaca caatggcac cgcggtgatt | 300 |
| ccgcaattgg gcggcaaggc catgacgttg cagcaggtga tggagctgac cgacaacggc | 360 |
| cagataaccc tcaacaacac cttgtacacg ctctacgatc cgaacaagca aggcaccctg | 420 |
| ctgcaactgc ccgtgacccg ctgcccgagc atcgactgga aggcaagta caaggatttc | 480 |
| tcgccctcgg ggcccgtgg ctggctggac gaatattgcg agtggtcgat cgtgcgcgac | 540 |
| cccggtaccc agaacatgcg caagatcacc tttacctgcg aaaacccggc gtatttcctc | 600 |
| gccatgtggc gcatcgaccc gaacgcggtg ctgggcctgt atcgcgacta catcgacccg | 660 |
| caggtgcaac tcgaggacct gtacttgcga tacaccgccg actgcccgac cggcaacaaa | 720 |
| ggcgatccgg tcatggaccc caccaccggc caaccgcct atgacacggt caacaaatgg | 780 |
| aacgccggca ccgcctgcgt gccgggccaa tatggcgggg caatgcacct gacctccggc | 840 |

```
cccaatacccc tgagcgccga ggtgtacctg gcggccgcag caaccatcct gcgtccactg      900
gccagcagcc agaattccca ggcgttgatc tgctgcgcgc aatacgggca gaactaccgc      960
aactccgacc cgcatatcgg cttttcggcc aacagcgtgg cggtgaataa ccggctgtcc     1020
ctgaccaacc ccatcggcct gtacctgcaa caacccaccg acttctcggc gtggaaaggt     1080
cctcagggcc aggacgtcag ccagtactgg aaaatcaccc ggggcaccgc aaaatctgcg     1140
gccaacggct ccgaccagat cctgcaggcg tgttcgaag tgccggtcag cgccgggttc      1200
tcgatcaacg acatcaccat cagcggccag tccatcgact acgtgtgggt gattgcccag     1260
caactgctgg tggggctgag cgtgaccacc acgcccatca gcccgacacc ggaatcctgc     1320
ccgtgcgtga ccgatcgggt caccggtgtg caaccctggc cggtacaact gctgccgctg     1380
gatctgttct acgggcagtc gcccaccgac ctgcccgcgt ggctggcacc cggtaccagc     1440
gggcagtttg ccctggtggt gcaaggcgcc gacctcaaga ccaccgccga acggcgcgg      1500 gtgcagtttt ccaatcccgg cgtcacggcg gtggtcacga gttcctgcc cgacgcctcg      1560 gccatccccg ggcaaaccaa ctccggcggc acccagggct acctgctgac catcaccgtg     1620
agccccaccg ccgcaccggg gctggtgacg gtgcgcgcgc tcaacccggg cgaagccgat     1680
aaccccagcg cggcgcagca cccatgggaa tccggttgg cgctggtgcc tggcgcctga      1740

<210> SEQ ID NO 113
<211> LENGTH: 1608
<212> TYPE: DNA
<213> ORGANISM: Pseudomonas sp. PAMC 25886

<400> SEQUENCE: 113
atgtccaggt tacgcttgag tgttttatcg ctgctgacca gtgtggtgct gagcctgttt       60
gcggtgcagt cggcctatgc gacgccacaa tccgatgccg acgcctgcgt ccagcaacag      120
ttggtgttca acccgccag cggtggattc ctgccggtca ataacttcaa cgccaccggc       180
cagagcttta tgaactgctt cggctggcag ttgttcattg ccctgaactg gccggtgaat      240
cccggttggc cagccacgcc cgccctggcg ggtgagccgg acatgcacag cagcctcgcc      300
cagttcggcg tgccgcccgc ctccgggcag ccgatgaccg tggcgccggt gtgggccagt      360
tacaaggacg ccaacgatat cttcctgccc ggcgcccccg tgcccaccgg atggggcgtg      420
caaaccctgg taccgtccaa ttgcagcacc cagggcagcc tcaaggcgat ggcggtgggg      480
gcgcgcaagt tcatgaccgc cacctcggaa agcgcgatca acgcgcggca cgggtttcac      540
ctgtccagcg gcaccctggc ctcgattccg gacccgatca tggaagcctc cggcggctgg      600
ctgacggacc agtcgaagaa cctggtgttt tttgaacgca aggtcggcaa ggccgagttt      660
gactacatcg tcagcaaagg gctgtacgac gccgccaacc agctgacagt ggcgcagaac      720
ctcgacaacc agaacccggg cgggctgtcc ctgcccatcg tgaacccat gcgctcgctg       780 ccgccagacc cggtgccgca ggagcaactc ggggccctgg aggtcaaggc cgcgtggcgg      840
atcctcaccg gtaaacccga gctctacggg cgctacctga ccaccgtcgc ctggctcaaa      900
aacccggcca cgttgcagtg cacccagcaa gtggtgggcc tggtgggcct gcacatcatc      960
aacaagaccc aggcttcgcc caacttcatc tggaccacct cgagcaggt ggacaacgtg      1020 ccggaacccg accaggtgcc gccacagcag acaccgcccg acagctttgc cttcaacaac     1080
ccgaactgtg gcaccggccc cgaatgcacg ccgaacgtgg cgcgtatcca gtgcaaacag     1140
catcatcccg accgcgactg caccgagccg tatccacgtg accaaccggt gcaaaccacc     1200
```

```
cgggaacatc cgctgcccac tgagctgcag gccctgaacg gcgcggtgca ggccaacttc    1260
gctcagcaga gccagggcaa gtcggtgttc cagtactaca aactgatcaa cgtgctctgg    1320
accctcacgc ccaacccgcc cacccagccg gagccgggcg tcagcgcgca ggtgccgctg    1380
tcctacgggc cgtttatcag ccagggcaat gtgcccgtgg ccaacaccac cctggagacc    1440
tacgtccagg gcgacaactg caacgcctgt caccagtacg cgaccatcgc cggcagctcg    1500
accctggcct cggactttc gttcctgttc aacagcgccg actcggccag caagaaaagc    1560
ctggtcaagc gggtgaaggc gttcgagacc ctcaaggacc agccctga               1608
```

<210> SEQ ID NO 114
<211> LENGTH: 1740
<212> TYPE: DNA
<213> ORGANISM: Pseudomonas sp. PAMC 25886

<400> SEQUENCE: 114

```
atgagcacac ccttcaaaca gttcacctcg cccgccgggc aagcgcccaa ggactacaac      60
aagctgggcc tggaaaacca gttgccgcag tttgaaaccg actggaacaa cgacctcacc     120
ggctggaccc agtccgcgat catcggcaac ccgtggtcgg gcctcaatga cgcgccgcgt     180
tcgggctatt acaacccgct ggtggagggc tacggcccca ccacgccacc ggcgatcacc     240
tgggcgccct tccccaaccg gctgtggacg tttttctaca caacggcac cgcggtgatt     300 ccgcagctgg gcgcaaggc catgacgttg cagcaggtga tggagctgac cgacaacggc     360
cagatcaccc tcaacaacac cctgtacacg ctctacgatc aaacaagca aggcaccctg     420 ctgcaactgc ccgtgacccg ctgcccgagc attgactggc aaggcaagta caaggatttc     480
tcgccctcgg gcccgcgcgg ctggctggac gaatactgcg agtggtcgat cgtgcgcgac     540
cccggtaccc agaacatgcg caagatcacc tttacctgcg aaaacccggc gtatttcctc     600
gccatgtggc gcatcgaccc gaacgcggta ctgggcctgt atcgcgacta catcgacccg     660
caggtgcaac tcgaggacct gtacttgcgc tacaccgccg actgcccgac cggcaacaag     720
ggcgacccgg tgatggaccc caccaccggc cagccagcct atgacacggt gaacaaatgg     780
aacgccggca ccgcctgcgt gcccggccaa tatggcggcg cgatgcacct gacctccggc     840
cccaacaccc tgagcgccga ggtgtacctg gcggccgcgg ccaccatcct gcggccgctg     900
agcagcagcg agaactccca ggcgctgatc tgctgcgcac aatacgggca gaactatcgc     960
aactccgacc cgcatatcgg tttttcggcc aacagcgtgg cggtgaataa ccggctgtcc    1020
ctgaccaacc ccatcggcct gtacctgcag caacccaccg acttctcggc gtggaaaggt    1080
ccacaaggcc aggacgtcag ccagtactgg aaaattaccc ggggcgccgc aaagtccgcc    1140
gccaacggct ccgaccagat cctgcaggcg gtgttcgagg tgccggtcag cgccgggttc    1200
tcgatcaacg acatcaccat cagcggccag tccatcgact acgtgtgggt gattgcccag    1260
caattgctgg tggggctgag cgtgaccacc acgcccatca gcccgacacc ggattcttgc    1320
ccgtgcgtga cggatcgggt caacggtgtg caaccctggc cggtacaact gctgccgctg    1380
gatctgttct acgggcagtc gcccaccgac ctgcccgcgt ggctggctcc cggtaccagc    1440
gggcagtttg ccctggtggt gcaaggcgcc gacctcaaga ccaccgccga dacgcgcggg    1500
gtgcagtttt ccaatcccgg cgtcacggcg gtggtcacga aattcctgcc cgacgcctcg    1560
gccatccccg ggcagaccaa ctccggcggc acccagggct acctgctgac catcactgtg    1620
agccccaccg ccgcacgggg gctggtgacg gtgcgcgcgc tcaacccggg cgaagccgat    1680
aaccccagcg cggcggagca cccatgggaa tccgggttgg cgctggtgcc tggcgcctga    1740
```

<210> SEQ ID NO 115
<211> LENGTH: 1608
<212> TYPE: DNA
<213> ORGANISM: Pseudomonas sp. PAMC 25886

<400> SEQUENCE: 115

```
atgtccaggt tacgcttgag tgttttatcg ctgctggcca gtgtggtgct gagcctgttt      60
gcgctgcagt cggcctatgc aacaccccaa tccgatgccg acgcctgcgt gcagcaacag     120
ctggtgttca atccgaaaag cggcggcttc ctgccggtca caacttcaa cgccaccggc      180
cagagcttca tgaactgctt tggctggcag ctgttcattg ccctgaactg gccggtgaac     240
cccggctggc cgaccaccgc cgccctggcg gcgaaccgg acatgaacag cagcctggcg      300
cagttcggcg tgccgaccac cgccgggcaa ccgatgacga tggcgccggt atgggccagc     360
tacaaggacg ccaacgatat cttcctgccg ggtgcgcctg tgcctcgggg ctggggcgtg     420
caaaccctgg tgccgtccaa ttgcagcacc cagggcagcc tcaaggcgat gtcggtgggg     480
gcgcgcaagt tcatgactgc cacctcggaa agcgcgatca acgcccgcca cggtttccac     540
ttgtccagcg gcaccctggc gacgattccc gacccgatca tggaagcctc cggcggctgg     600
ctgacggatc aggcgggcca gctggtgttt tttgaacgca agtcggcaa ggccgagttt      660
gattacatcg tcagcaaagg gctgtacgac gccgccaatc agttgaaggt ggcgcaaaac    720
ctcgacaacc agaacccggg cgggctgtcc ttgcccattg gcgaaccgat gcgctccctg    780
ccgccgaccc cggtgccaca ggaacaactc ggggcgctgg agctcaaggc gcgtggcgc      840
attctcaccg gcaagcccga actctacgga cgctacctga ccaccgtcgc ctggctgaaa    900
aacccggcca ccttgcagtg cacccagcaa gtggtgggcc tggtgggcct gcatatcatc    960
aacaagaccc aagcctcgcc gaacttcatc tggaccacct tcgaacaggt ggacaacgtc   1020
ccggaaccca accagctgcc gccacagcag acgccgcccg acagctttgc cttcaacaac   1080
cccaactgcg gcaccggccc ggaatgcacg ccgaacgtgg cacgcatcca gtgccaacag   1140
caccatcccg atcgcgattg caccgagccg tacccacggg accaaccggt gcaaaccacc   1200
cgggaacatc cgctgcccac ggagctgcag gccctgaacg gcgcggtgca ggccaacttc   1260
gcccagcaga gccagggtaa atcggtgttc cagtactaca aactgatcaa cgtactctgg   1320
accctcaccc ccaacccgcc cgtccagccg gagccggggg tcagtgcggc ggtgccgctg   1380
tcctacgggc cgtttatcag ccagggcaat gtgccggtgg ccaacacgac cctggaaacc   1440
tatgtgcagg gcgataactg caacgcctgt caccagtacg cgaccatcgc cggcagctcg   1500
accctggcct cggactttc attcctgttc aacagcgccg actcggccag caagaaaagc   1560
ctggtcaagc gggtgaaggc gtttgaaacc ctcaaggacc aaccctga               1608
```

<210> SEQ ID NO 116
<211> LENGTH: 1737
<212> TYPE: DNA
<213> ORGANISM: Pseudomonas fluorescens

<400> SEQUENCE: 116

```
atgagcacac ccttcaaaca attcacctct cccgccgggc aagctcccaa ggactacaac      60
aagctgggcc tggaaaacca gttgccgcag tttgaaaccg actggaacaa cgacctcacc     120
ggctggaccc agtctgcgat catcggcaac cgtggtcgg gcctcaatga cgcgccgcgc     180
tcgggctatt acaaccccact ggtggaaggc tacggcccca ccacgccgcc ggcgattacc    240
```

```
tgggcgccct tccccaatcg gctgtggacg tttttctaca caacggcac ggcggtgatt      300
ccgcagttgg gcggcaaggc catgtccatg caacaggtga tggagctgac cgacaacggc    360
cagattacga tcaacaacac cctgtacatg ctctacgacc cgaagaagca aggcaccctg    420
ctgcaactcc ccgtcactcg ctgcccgagc atcgactggc aaggcaagta caaggatttc    480
tcgccctctg gcccccgtgg ctggcttgac gaatattgcg agtggtccat cgtgcgcgat    540
gccgacggca acatgcgcaa gatcaccttc acttgcgaaa accggcgta tttcctggcc     600
atgtggcgca tcgatccgac tgctgtactg gggctgtatc gcgactacat cgacccacag    660
gtgcaactcg aagacctgta cctgcgctac accgccgact gcccgaccgg taaggccggc    720
gatccggtca tcgaccccac caccggtcaa ccggcctacg acaccgtcaa caaatggaac    780
gccggcaccg cctgtgtgcc tggccagtac ggcggtgcga tgcatctgac ctccggcccc    840
aacaccctga gcgccgaggt gtacctggct gccgcggcga ccatcctgcg gccattgagc    900
agcagccaga attcccaggc gttgatctgc tgtgcgcaat acgggcagaa ctaccgcaac    960
tccgatccgc atatcggttt ctcggccaac agcgtggcag tgaacaaccg gctgtcgctg    1020
accaacccca tcggcctgta cctgcaacaa cccaccgact tctcggcgtg gaaaggcccc    1080
cagggccagg acgtcagcca gtactggaaa atcaccgtg gcaccgccaa gtccgccgcc    1140
aacggctccg accagattct gcaagcggtg tttgaagtgc cggtcagcgc cgggttctcg    1200
atcaacgaca tcaccatcag cggccagccg atcgactacg tgtgggtgat gcccagcag    1260
ttgctggtgg gcctgagtgt gacaaccacg cccatcagcc cgacgccgga ttcctgcccg    1320
tgcgtgacga accgggtcaa cggtgtgcaa ccctggccgg tacagctgct gccgctggac    1380
ctgttctacg ggcagtcacc caccgacctg ccggcctggc tggcacccgg caccagcggg    1440
cagtttgccc tggtggtgca aggcgccgac ctcaagacca ccgccgagac ggcgcgggtg    1500
caattctcca atcctggggt gacggcgcag gtcacaaagt tcctgccgga tgcctcggcc    1560
atccccgggc aaaccaactc cggtggcacc cagggctacc tgctgaccat caccgtaagc    1620
cccactgccg caccggggct ggtgacagtg cgcgccctca acccgggcga agccgataac    1680
cccagcgcgg cggaacaccc atgggaatcc ggattggcgc tggtgcctgg cgcctga       1737
```

<210> SEQ ID NO 117
<211> LENGTH: 1611
<212> TYPE: DNA
<213> ORGANISM: Pseudomonas fluorescens

<400> SEQUENCE: 117

```
atgtccaggt tacgcttgag tgttttatcg ctgctgacca gtgtggtgct gagcctgttc      60
gccatgcagg ccgcctacgc atcccccact tccgacgccg acgcttgcgt gcagcaacag    120
ttggtgttca acccgaaaag cggcggcttc ctgccgatca acaacttcaa cgccaccggc    180
cagagcttca tgaattgctt tggctggcag ttgttcattg ccctgaactg gccggtgaat    240
cccggttggc cagccacgcc tgccctcgcg ggtgagccgg acatgaacag taccctggcg    300
caattcggcg taccgactgc ctccgggcag ccgatgagcg tggcgccggt atgggccagc    360
tacaaggacg ccaacgatat cttcctgccc ggcgcgcccg tgcccaccgg ctggggcgtg    420
caaaccctgg tgccgtccaa ttgcagcacc cagggcagcc tcagggcgat gtcggtgggg    480
gcgcgcaagt tcatgaccgc cacctccgaa agcgcgatca acgcgcggca tgggtttcac    540
ctgtccagcg gcaccctggc ctcgattccg gacccgatca tggaagcctc cggcggctgg    600
ctgacggacc agtcgcagaa cctggtgttt tttgaacgca aggtgggcaa ggccgagttc    660
```

```
gactacatcg tcagcaaagg gctgtacgac gcggccaacc agctgaaagt cgcgcagaac    720
ctcgacaacc agaaccccgg cgggctgtcc ttgcccatcg gtgaaccat gcgctcgctg    780
ccgcccaacc cggtgccgca ggagcaactg ggagctctgg aggtcaaggc agcatggcga    840
atcctcaccg gtaaacccga gctctacgga cgttacctga ccaccgtcgc ctggctcaaa    900
aacccggcca ccttgcagtg cacccagcag gtggtgggcc tggtgggcct gcatatcatc    960
aacaagaccc aggcctcgcc caacttcatc tggaccacct tcgagcaagt ggacaacgtg   1020
ccggaacccca accaggtgcc gccacaacaa cgccgcccg acagctttgc cttcaacaac   1080
ccgaactgcg gcaccggccc cgaatgcacg ccgaacgtgg cgcgtatcca gtgcaagcag   1140
cagcatccgg accgcgactg caccgagccg tttccacggg accaacccgt gcagaccacc   1200
cgggaacatc cgctgcccac tgaactgcag gcgcttaacg gcgcggtgca ggccaatttt   1260
gcccagcaga gccagggcaa gtcggtgttc cagtactaca aactgatcaa cgtactctgg   1320
accctcaccc ccaaccccgcc cacccagccg gaaccgggtg tcagtgcgca agtgccgctg   1380
tcctacgggc catttatcag ccagggcaac gtaccggtgg ccaacaccac cctggagacc   1440
tacgtccagg gcgacaactg caatgccgtgt catcagtacg cgaccatcgc cggcagctcg   1500
accctggcct cggactttc gttcctgttc aacagtgccg attcggccag caagaaaagc   1560
ctggtcaagc gcgtaaaagc cttccagacc ctcaaggacg gttcaccctg a            1611

<210> SEQ ID NO 118
<211> LENGTH: 1737
<212> TYPE: DNA
<213> ORGANISM: Pseudomonas sp. PAMC 26793

<400> SEQUENCE: 118
atgagcacac ccttcaaaca attcacctct cccgccgggc aagcacccaa ggactacaac    60
aagctgggcc tggaaaacca gctgccgcag tttgaaaccg actggaacaa cgacctcacc   120
ggctggaccc agtccgcaat catcggcaac ccgtggtcgg gcctcaatga cgcaccgcgc   180
tcgggctatt acaacccgct ggtggaaggc tacggcccca gcacgccgcc ggcgattacc   240
tgggcgccct tccccaatcg gctgtggacg ttcttctaca caacggcac ggcggtgatt    300
ccgcaattgg gcggcaaggc catgtccatg caacaggtga tggaactgac cgacaacggc   360
cagattacga tcaacaacac cctgtacatg ctctacgacc cgaacaagca aggcacccotg   420
ctgcaactgc ccgtcacccg ctgccgacc atcgactggc aaggcaagta caaggatttc    480
tcgcccctcgg ggcccgtgg ctggcttgac gaatactgcg agtggtccat cgtgcgtgac    540
gccaatggca acatgcgcaa gatcaccttc acctgcgaaa accggcgta tttcctggcc    600
atgtggcgca ttgatccaaa tgcagtgctg ggcctgtacc gcgactacat cgacccgcag   660
gtgcaactcg aagacctgta cttgcgctac accgccgact gcccgaccgg caaagccggc    720
gatccggtca tcgaccctac caccggccaa ccggcctacg acacggtcaa caatgtgaac    780
gccggcaccg cctgcgtacc cggccaatac ggcggggcga tgcacctgac ctccggcccc    840
aacaccttga cgccgaggt gtacctggcc gccgcagcga ccatcctgcg tccactggcc    900
agcagccaga attccaggc attgatctgc tgcgcgcaat acgggcagaa ctaccgcaac    960
tctgaccccgc atatcggttt ctcggccaac agcgtggcgg tgaataaccg gctgtccctg   1020
accaacccca tcggcccttta cctgcaacaa cccaccgatt tctcggcgtg gaaaggccct   1080
caaggccagg acgtcagcca gtactggaaa atcacccgtg gcaccgccaa gtccgccgcc   1140
```

```
aacggctccg accagattct gcaagcggtg tttgaagtgc cggtcagcgc cgggttttcg    1200
atcaacgaca tcaccatcag tggccagccg atcaactatg tgtgggtgat tgcccagcag    1260
ttgctggtgg gcctgagtgt gacaaccacg cccatcagcc cgacgccgga ttcctgcccc    1320
tgcgtgacga tcgggtcaa cggcgtgcaa ccctggccgg tgcaactgct gcccctggat     1380
ctgttctacg ggcagtcgcc taccgacctg ccggcgtggc tggcacccgg caccagcggg    1440
cagttcgctc tggtggtgca aggcgccgac ctcaagacca ccgccgagac ggcgcgggtg    1500
cagtttccca atcctagcgt gacggcgcag gtcacccagt tcctgccgga tgcctccgcc    1560
atcccagggc aaaccaactc cggtggcacc cagggctacc tgctgaccat caccgtaagc    1620
cccactgccg ctccgggact ggtgacggtg cgcgcgctca acccgggcga agccgataac    1680
cccagcgcga cggaacatcc atgggagtcc ggattggcgc tggtgcctgg cgcctga       1737
```

<210> SEQ ID NO 119
<211> LENGTH: 1608
<212> TYPE: DNA
<213> ORGANISM: Pseudomonas sp. PAMC 26793

<400> SEQUENCE: 119

```
atgtccaggt tacgcttaag tgttttatcg ctgctgacca gtgtggtgct gagcctgttc     60
gccatgcagg ccgcctacgc atcccccact tccgacgccg acgcttgcgt gcagcaacag    120
ttggtgttca acccgaaaag cggcgggttc ctgccgatca caacttcaa cgccaccggc     180 cagagcttta tgaattgctt tggctggcag ttgttcattg ccctgaactg ccggtgaat    240 cccggttggc cagccacgcc cgccctcgcg ggtgagccgg acatgaacag taccctggcg    300
caattcggtg tgccgcccgc ctccgggcag ccaatgagcg tcgcgccggt atgggccagc    360
tacaaggacg ccaacgatat cttcctgccc ggcgcccccg cgccaccgg ctggggcgtg     420 caaaccctgg tgccgtccaa ttgcagcacc cagggcagcc tcagggcgat gtcggtgggg    480
gcgcgcaagt tcatgaccgc cacctccgaa agcgcgatca cgcccgcca tggttttcac    540 ctgtccagcg gcaccttggc ctcgattcca gacccgatca tggaagcctc cggcggctgg    600
ctgacggacc agtcgcagaa cctggtgttt tttgaacgca aggtgggcaa ggccgagttc    660
gactacatcg tcagcaaagg gctgtacgac gcagccaacc agctgaaagt cgcgcagaac    720
atcgacaacc agaacccggg cgggctgtcc ttgcccatcg gtgagcccat cgcctcgctg    780
ccgcccaacc cggtgccgca ggagcaactg ggagccctgg aggtcaaggc ggcgtggcgg    840
atcctcaccg gcaaacccga gctctacggg cgttacctga ccaccgtcgc ctggctcaaa    900
aacccggcca ccttgcagtg cacccagcaa gtggtgggcc tgtgggcct gcatatcatc     960 aacaagaccc aagcctcgcc caacttcatc tggaccaccat tcgagcaggt ggacaacgtg    1020
ccggaaccca ccaggtgcc gccacaacag acgccgcccg acagctttgc cttcaacaac    1080
ccgaactgcg gcaccggccc cgaatgcacg ccgaacgtgg cgcgtatcca gtgcaaacag    1140
caccatcccg accgcgactg caccgagccg tttccacggg accaacccgt gcagaccacc    1200
cgggaacatc cgctgcccac tgaactgcag gcgcttaacg gcgcggtgca ggccaacttc    1260
gcccagcaga gccagggcaa gtcggtgttc caatactaca aattgatcaa cgtactctgg    1320
accctcaccc ccaacccgcc cacccagccg gaaccgggtg tcagtgcgca agtgccactg    1380
tcctacgggc cgtttatcag ccagggcaac gtaccggtgg ccaacaccac cctggagacc    1440
tacgtccagg gcgataactg caatgcctgt catcagtacg caaccatcgc cggcagctcc    1500
accctggctt cggactttc gttcctcttc aacagcgccg actcggccag caagaaaagc    1560
```
ctggtcaagc gcgtgaaagc cttccagacc ctcaaggatc aaccgtga         1608

<210> SEQ ID NO 120
<211> LENGTH: 1737
<212> TYPE: DNA
<213> ORGANISM: Pseudomonas putida

<400> SEQUENCE: 120
atgagcacgc ccttcaagca gttcacctct cccgccggcc agcccccaa ggactacaac      60
aagctgggcc tggaagacca gttgccgcag tttgaaaccg actggaacaa caacctcacc     120
ggctggaccg aatcgtcgat catcggcaac ccctggtcgg gcctgaacga cgcccccgc     180
tcgggttact acaacccgct ggtggaaggt tcggcgacg tgaccgcccc ggcgatcacc     240
tgggcgccct tccccaaccg gctctggacg ttcttctaca acaacggtgc ggcggtcatt     300
ccccagctgg gtgcaaggc catgaccctg gaccaggtga tggaattgac cgaccacggc     360
cagatcaccc tcgacaacac cctctacatg ctctacgacc caacaagca aggtaccgtg     420
ctgcaactgc cggccaagcg ctgcccgagc atcgactgga acggcaaata cggcgttc     480
tcgccttccg gcccgcgggg ctggctcgac gagtactgcg agtggtcgat cgtacgcgat     540
gccaacggca acatgcgcaa gatcaccttc acctgcgaaa accccgcgta cttcctgacc     600
atgtggcgca tcgacccgaa cgcagtactg gggctgtacc gcgactacat cgacccgaac     660
gtgcaactcg aagacctgta cctgcgctac accgtcgact gcccgaccgg caaggccggc     720
gacccggtca tcgaccccac caccggcaag ccggcctatg acaccgtcaa caaatggaac     780
gccggaacgg cctgtgtacc cggccagtac ggcggtgcga tgcacctgac ctccggcccc     840
aataccctca cgccgaggt gtacctggcc gccgccgcca ccattctgcg cccggtgagc     900
agcagccaga acgcccagtc gttgatctgc tgcgcgcagt acgggcaaaa ctatcgcaac     960
tctgatccgc acatcggttt catggccaat accggcag tgaacaaccg actgtcgctg    1020
accaacccca ttggcctgta cttgcagcag cccaccgatt tcagcgcctg gagggcccg    1080
caaggccagg acgtgagcca gtattggcgc atcacgcgcg gtacggccaa gtcggctgcc    1140
aatggttccg accagatcct gcaggcggtg ttcgaggtgc cggaaagcgc cggcttctcg    1200
atcaatgaca tcaccatcaa caaccagaag gtcaactatg gtgggtcat cgcccaacaa    1260
ctgctggtcg gcctgagtgt caccgtcaag ccgctcagcg ccacgcttca agcattccca    1320
tgcgtgcagg accgggtggc cggcctgcaa ccctggccag tgcaactgct gccgctggac    1380
ctgttctacg gcaatccccc aaccgacctg cccgcctggc ttgcaccggg tagcagcaac    1440
cagttcgtgc tggtggtgca agggccgac ccgactacca cggcgcagaa tgcaagggtg    1500
caattctcca accccgggt gacgcgcag gtcacccagt acctgcccga cgcgtcggcc    1560
attcccggcc agaccaactc gggcggcacc caggcctaca ttctgaccat cacggtcagc    1620
ccctccgcag cacccggcct ggtgacagtg cgtgccctca accgggtga agatgtgaac    1680
gtgagcgcga cagaccaccc ttgggaatct ggcctggcgc tggtgccggg gcctga         1737

<210> SEQ ID NO 121
<211> LENGTH: 1608
<212> TYPE: DNA
<213> ORGANISM: Pseudomonas putida

<400> SEQUENCE: 121
atgatgtcca ggtcacgctt gagtcctctg tcgctgctgt gcggcattct actgtgcctg      60

```
tcgaccctgc aacccgccac ggcggccacg ctgtcggacg ccgatacctg tgtacagcag      120
caattggtgt tcaacccggc cagcggggga ttcctgccgg tcaacaactt caatgccacc      180
agccaggcgt tcatgaactg ctttggctgg caattgttca ttgccttgaa ctggccggtg      240
aaccccggtt ggccggccac cgccagcctg gcgggtgaac ccgacatgca aagcacgctg      300
gcgcagttcg gggtcccctc cgcaccgggt cagcccatga gcgtggcccc ggtatgggcc      360
agctacaagg acgccaacga catcttcctg cccggcgcac ccacgcccac cggctggggt      420
gtgcaaaccc tggtgccgtc cggctgcagc acccagggta gcctcaaggc gctcaaggtg      480
ggcgcacgca agttcatgaa cgccacctcc gaaggcgcga tcaatgcctt gcacggtttc      540
cacctgtcga ccgggacact tgcgtccatt cccgacccgg tcatggaggc gtccggcggc      600
tggctgacgg accaggcggg caaactggta ttttttgagc gcaaggtggg caaggccgag      660
ttcgactaca tcgtcgacaa ggggctctac gacgccgcca accagttgaa ggtcgcgcaa      720
aacctcgacg gccagacacc ggagggcctg tcgttgccca tcggcgaacc gatgcgctca      780
ctgccaacct ccccagtgcc acaggaacaa ctgggcgcga tcgagctcaa ggccgcctgg      840
cgggtgctga ccggcaaacc cgagctgttc ggccgctacc tgactaccgt cgcctggctc      900
aaacgccccg acacgctgga gtgcacccag gaggtggtgg ggctggtggg cctgcatatc      960
atcaacaaga cccaggcttc gcccaacttc atctggacca ccttcgagca ggtggacaac     1020
gtgcccgaac cggcccaggt cccgccgcaa caaacccccgc cgaacgggtt cgccttcaac     1080
aaccctgact gtggcgacgg ccccgagtgc acaccgaacc aagcccgtat ccagtgcaag     1140
caaacgcatc ccgacaagga ctgcaccgat ctcttcccac gcgaccagcc ggtacagacc     1200
acccgcgaac accccgtgcc cggcgacctg caagccctca acagcgcggt acaagccaac     1260
ttcgcgcagc acagccaagg caagtcggtg ttccagtact acaagctgat caacgtactc     1320
tggaccctcg ctcccaatcc gcccagcccg gaaccgggcg ccaacgcgca agtgccgctg     1380
tcgtacgggc ccttcatcag ccagggcaac gtgccggtgg ccaacaccac catggagacc     1440
tacgtgcagg gtgatgactg caatcagtgc catcagtacg cgacgattgc cggcagcccg     1500
tcattggcct cggatttctc tttcctgttc aacagtgccg gttccgccag caacaaaagc     1560
ctgatcaaaa gcgtcaaagc cttcgaaacc ctcaaggacc gtccctga                  1608
```

<210> SEQ ID NO 122
<211> LENGTH: 1737
<212> TYPE: DNA
<213> ORGANISM: unknown
<220> FEATURE:
<223> OTHER INFORMATION: Fungus garden combined

<400> SEQUENCE: 122

```
atgagcacgc ccttcaagca gttcacctct cccgccggcc aagcccccaa ggactacaac       60
aagctgggcc tggaagacca gttgccgcag tttgaaaccg actggaacaa caacctcacc      120
ggctggaccg aatcgtcgat catcggcaac ccctggtcag gctgaacga cgccccccgc      180 tcgggttact acaacccgct ggtggaaggt ttcggcgacg tgaccgcccc ggcgatcacc      240
tgggcgccct tccccaaccg gctctggacg ttcttctaca caacggtgc ggcggtcatt      300 ccccagctag gtggcaaggc catgaccctg gaccaggtaa tggcgttgac cgaccacggc      360
cagatcaccc tcgacaacac cctctacatg ctctacgacc ccaacaagca aggtactgtg      420
ctgcaactgc cggccaagcg ctgcccgagc atcgactgga acggcaagta cacggcgttc      480
tcgccttccg ggcctcgggg ctggctcgac gagtactgcg agtggtcgat cgtacgcgat      540
```

```
gccaacggca acatgcgcaa gatcaccttc acctgcgaaa accccgcgta cttcctgacc    600
atgtggcgca tcgaccccga acgcagtactg ggcctgtacc gcgactacat cgacccgaac    660
gtgcaactcg aagacctgta cctgcgctac accgtcgact gcccgaccgg caaagccggc    720
gacccggtca tcgaccccac caccggcaag ccggcctatg acaccgtcaa caatggaaac    780
gccggaacgg cctgtgtgcc cggccagtac ggcggtgcga tgcacctgac ctccggcccc    840
aatacccctca cgcccgaggt gtacctggcc gccgccgcca ccatcctgcg cccggtgagc    900
agcagccaga acgcccagtc gttgatctgc tgcgcgcagt acgggcaaaa ctatcgcaac    960
tctgatccgc acatcggttt catggccaat accacgcag tgaacaaccg actgtcgctg    1020
accaaccccca ttggcctgta cttgcaacag cccaccgatt tcagcgcctg aagggcccg    1080
caaggccagg acgtgagcca gtactggcgc atcacgcgcg gtacggccaa gtcggctgcc    1140
aacggttccg accagatcct ccaggcggtg ttcgaggtgc cggaaagcgc tggtttctcg    1200
atcaatgaca tcaccatcaa caaccagaag gtcaactatg tgtgggtcat cgcccaacaa    1260
ctgctagtcg gcctgagcgt caccgtcaag ccgctcagca ccacgcctca agcgttccca    1320
tgcgtgcagg accgggtggc cggccggcaa ccctggccag tgcaactgct gccgctggac    1380
ctgttctacg ggcaatcccc caccgacctg cccgcctggc ttgcaccggg tagcagcaac    1440
cagttcgtgc tggtggtgca aggtgccgac ccgactacca cggcgcagaa tgcaagggtg    1500
caattctcca accctgggggt gacggcgcag gtcacccagt acctgcccga cgcatcggcc    1560
attcctggcc agaccaactc gggcggcacc caggcctaca ttctgaccat cacggtcagc    1620
ccctccgcag caccccggctt ggtggcagtg cgtgccctca atccgggtga agacgttaac    1680
gtgagcgcga cagaccaccc ttgggagtct ggcctggcgc tggtgcctgg cgcctga     1737
```

<210> SEQ ID NO 123  
<211> LENGTH: 1605  
<212> TYPE: DNA  
<213> ORGANISM: unknown  
<220> FEATURE:  
<223> OTHER INFORMATION: Fungus garden combined

<400> SEQUENCE: 123

```
atgtccaggt cacgcttgag tcttctgtcg ctgctgtgcg gcattctact gtgcctgtcg     60
accccgcaac ccgccacggc ggccacgctg tcggacgccg atacctgtgt acagcagcaa    120
ttggtgttca acccggccag cgggggattc ctgccggtca caacttcaa tgccaccagc    180
caggcgttca tgaactgctt tggctggcaa ttgttcattg ccttgaactg gccggtgaac    240
cccggttggc cagccaccgc cagcctggcg ggtgaacccg acatgcaaag cacgctggcg    300
cagttcgggg tcccctccgc accgggtcag cccatgagcg tggccccggt atgggccagc    360
tacaaggacg ccaacgacat cttcctgccc ggcgcaccca cgcctaccgg ttggggcgtg    420
caaaccctgg tgccgtccgg ctgcagcacc caggtaacc tcaaggcgct caaggtgggc    480
gcacgcaagt tcatgaacgc cacctccgaa ggcgcgatca atgccttgca cggtttccac    540
ctgtcgaccg ggacacttgc gtccattccc gacccggtca tggaggcgtc cggcggctgg    600
ctgacggacc aggcggcaa gctggtgttt ttcgaacgca aggtgggcaa ggccgagttc    660
gactacatcg tcgacaaggg gctctacgac gcagccaacc agttgaaggt cgcgcaaaac    720
ctcgacggcc agacaccgga gggcctgtcg ctgcccatcg gcgaaccgat gcgctcactg    780
ccgacctccc cagtgccaca ggagcaactt ggcgcgatcg agctcaaggc cgcctggcgg    840
```

```
gtgctgaccg gcaaacccga gctgttcggg cgctacctga ctaccgtcgc ctggctcaaa   900
cgccccgaca cgctggagtg tacccaggag gtggtgggc  tggtgggcct gcatatcatc   960
aacaagaccc aggcttcgcc caacttcatc tggaccacct tcgagcaggt ggacaacgtg  1020
cccgaaccgg cccaggtccc gccgcaacaa acccgccga acgggttcgc cttcaacaac   1080
cctgactgtg gcgacggccc cgagtgcaca ccgaaccaag cccgtatcca gtgcaagcaa  1140
acgcatcccg acaaggactg caccgatctc ttcccacgcg accagccggt acagaccacc  1200
cgcgaacacc ccgtgcccgg cgacctgcaa gccctcaaca gcgcggtaca agccaacttc  1260
gcgcagcaca gccaaggcaa gtcggtgttc cagtactaca agctgatcaa cgtactctgg  1320
accctcgccc ccaatccgcc cagcccggaa ccgggcgcca acgcgcaagt gccgttgtcg  1380
tacgggccgt tcatcagcca gggcaacgta ccggtggcca acaccaccat ggagacctac  1440
gtgcagggtg atgactgcaa tcagtgccat cagtacgcga cgattgccgg cagcccgtca  1500
ttggcctcgg atttctcttt cctgttcaac agtgccggct ccgccagcaa caaaaagcctg  1560 atcaaaagcg tcaaagcctt cgaaaccctc aaggaccgcc cctga                   1605

<210> SEQ ID NO 124
<211> LENGTH: 1734
<212> TYPE: DNA
<213> ORGANISM: Pseudomonas monteilii

<400> SEQUENCE: 124
atgagcacgc ccttcaagca gttcacatct cccgccggcc aagcccccaa ggactacaac    60
aagctgggcc tggaagacca gttgccgcag tttgaaaccg actggaacaa caacctcacc   120
ggctggaccg aatcgtcgat catcggcaac ccctggtcgg gcctgaacga cgccccccgc   180
tcgggttact acaacccgct ggtggaaggt ttcggcgacg tgaccgcccc ggcgatcacc   240
tgggcgccct tccccaaccg gctctggacg ttcttctaca caacggtgc  agcggtcatt   300 ccccagctgg gtggcaaggc catgaccctg gaccaggtga tggagttgac cgaccacggc   360
cagatcaccc tcgataacac cctctacatg ctctacgacc ccaacaagca aggtaccgtg   420
ttgcaactgc cggccaagcg ctgcccgagc atcgactgga acggcaagta cacggcgttc   480
tcgccttccg ggcctcgggg ctggctcgac gagtactgcg agtggtcgat cgtacgcgat   540
gccaacggca acatgcgcaa gatcaccttc acctgcgaaa accccgcgta cttcctgacc   600
atgtggcgca tcgacccgaa cgcagtactg gggctgtacc gcgactacat cgacccgaac   660
gtgcaactcg aagacctgta cctgcgctac accgtcgact gcccgaccgg caaagccggc   720
gacccggtca tcgaccccac caccggcaag ccggcctatg acaccgtcaa caaatggaac   780 gccgaacgg  cctgtgtgcc cggccagtat ggcggtgcga tgcacctgac ctccggcccc   840
aataccctca gcgccgaggt gtacctggcc gccgccgcca ccatcctgcg cccggtgagc   900
agcagccaga cgcccagtc  gttgatctgc tgcgcgcagt acgggcaaaa ctatcgcaac   960
tctgatccgc acatcggttt catggccaat accacggcgg tgaacaaccg actgtcgctg  1020
accaacccca ttggcctgta cttgcaacag cccaccgatt tcagcgcctg gaagggccca  1080
caaggccagg acgtgagcca gtactggcgc atcacgcgcg tacgccaa  gtcggctgcc  1140 aacggttccg accagatcct gcaggcggtg ttcgaggtgc cggaaagcgc tggtttctcg  1200
atcaatgaca tcaccatcaa caaccagaag gtcaactatg tgtgggtcat cgcccaacaa  1260
ctgttggtcg gcctgagcgt caccgccaag ccgctcagcg ccacgcccca agcattccca  1320
tgcgtgcagg accgggtggc cggcctgcaa ccctggccag tgcaactgct gccgctggac  1380
```

-continued

```
ctgttctacg ggcaatcccc caccgacctg cccgcctggc ttgcaccggg tagcagcaac    1440
cagttcgtgc tggtggtgca aggtgccgac ccgactacca cggcgcagaa tgccagggtg    1500
caattctcca accccggggt gacggcgcag gtaacccagt acctgcccga cgcgtcggcc    1560
attcccggcc agaccaactc gggcggcacc caggcctaca ttctgaccat cacggtcagc    1620
ccctccgcag cacccggcct ggtggcattg cgtgccctca acccgggtga agatgtgaac    1680
gtgagcgcga cagaccaccc ttgggaatct ggcctggcgc tggtgcctgg cgcc          1734
```

<210> SEQ ID NO 125
<211> LENGTH: 1605
<212> TYPE: DNA
<213> ORGANISM: Pseudomonas monteilii

<400> SEQUENCE: 125

```
atgatgtcca ggtcacgctt gagtcttctg tcgctgctgt gcggcattct actgtgcctg      60
tcgaccccgc aacccgccac ggcggccacg ctgtcggacg ccgataccty tgtacagcag    120
caattggtgt tcaacccggc cagcggggga ttcctgccgg tcaacaactt caatgccacc    180
agccaggcgt tcatgaactg ctttggctgg cagttgttca ttgccttgaa ctggccggtg    240
aaccccggtt ggccggccac cgccagcctg gcgggcgaac ccgacatgca aagcacgctg    300
gcgcagttcg gggtccccte cacaccgggt caacccatga gcgtggcccc ggtatgggcc    360
agctacaagg acgccaacga catcttcctg cccggcgccc ccacgccac cggctggggc     420 gtgcaaaccc tggtaccgtc cgactgcagc acccaaggta gcctcaagac actcaaggtg    480
ggcgcgcgca agttcatgaa cgccacctcc gaaggcgcga tcaatgcctt gcacggtttc    540
cacctgtcga ccgggacact tgcctccatt cccgacccgg tcatggaagc gtccggcggc    600
tggctgacgg accaggcggg caaactggtg ttttttgaac gcaaggtggg caaggccgag    660
ttcgactaca tcgtcgacaa ggggctctac gacgccgcca accaattgaa ggtcgcgcga    720
aacctcgacg gccagacacc ggagggtctg tcactgccca tcggcgaacc gatgcgctca    780
ctgcctacct ccccagtgcc acaggagcaa ctgggcgcga tcgagctcaa ggccgcctgg    840
cgggtactga ctggcaaacc cgagctgttc gggcgctacc tgactaccgt cgcctggctc    900
aaacgtcccg acacgctgga gtgcacccag gaggtggtgg ggctggtggg cctgcatatc    960
atcaacaaga cccaggcttc gcccaacttc atctggacca ccttcgagca ggtggacaac   1020
gtgcccgaac cggccaggt tccgccgcaa caaaccccgc caaacgggtt tgccttcaac    1080
aaccctgact gtggcaacgg ccccgagtgc acaccaaacc aagcccgtat ccagtgcaag    1140
caaacgcatc ccgacaagga ctgcaccgat ctcttcccgc gcgaccagcc ggtacagacc    1200
acccgcgaac acccgtgcc cggcgacctg caagccctca cagcgcggt acaagccaac    1260 ttcgcgcagc acagccaagg caagtcggtg ttccagtact acaagctggt caacgtactc    1320
tggaccctcg ctcccaaccc gcccagcccg gaaccgggcg ccaacgcgca agtgccgctg    1380
tcgtacgggc cgttcatcag ccaggggaac gtgccggtgg ccaacaccac catggagacc    1440
tacgtgcagg gtgataactg caatcagtgc catcagtacg cgacgattgc cggcagcccg    1500
tcattggcct cggatttctc tttctgttc aacagtgccg gctccgccag caacaaaagc    1560
ctgatcaaaa gcgtcaaagc cttcgaaacc ctcaaggacc gcccc                   1605
```

<210> SEQ ID NO 126
<211> LENGTH: 1738
<212> TYPE: DNA

<213> ORGANISM: Pseudomonas monteilii

<400> SEQUENCE: 126

```
atgagcacac ccttcaaaca attcacctct cccgccggac aagcccccaa ggactacaac    60
aagctgggcc tggaagacca gttgccgcag tttgaaaccg actggaacaa caacctcacc   120
ggctggaccc aatcgtccat catcggcaac ccttggtcgg gcctgaacga cgctccccgc   180
tcgggctact acaacccgct cgtagagggc ttcggcgacg tgaccccacc cgcgatcacc   240
tgggcgccct tccccaaccg cctgtggacg ttcttctaca caacggtgc ggcggtcatt    300
ccccagttgg gcggcaaggc catgaccctg gaccaggtga tggaattggc cgaccacggc   360
cagatcaccc tcgacaacac cctctacacg ctttacgacc cgaacaaaaa gggcactgtg   420
ctgcaactgc cggtcaagcg ctgccccagc atcgcctgga atggcacgta caaggatttc   480
acgccttccg gcccacgggg ctggctcgac gagtactgcg agtggtcgat cgtgcgcgat   540
gccaacggca acatgcgcaa gatcaccttc acctgtgaaa accccgcgta cttcctggcc   600
atgtggcgca tcgaccccga acgcggtcct ggcctgtacc gcgaatacat cgacccgagc   660
gtgcagctcg aagacctgta cctgcgctat gccgaagact gcccgaccgg caaggccggc   720
gatccggtca tggaccccac caccggcaag ccggcctatg acaccgtcaa caatggaac    780
gccggaaccg cctgtgtgcc cggccagtac ggcggagcga tgcacctgac atccggcccc   840
aatacccca gtgccgaggt gtacctggcc gccgccgcca ccatcctgcg cccggtgagc   900
agcagccaga tgcccagtc gctgatctgc tgcgcgcagt acgggcagaa ctatcgcaac   960
tccgacccgc acatcggctt catggccaat accacggcgg tcaacaaccg actgtcgctg  1020
accaacccta ttggcctgta cttgcaacaa cccaccgact cagcgcctg gaagggcccg   1080
caaggccagt acgtgagcca gtactggcgc atcacccgcg gtacgccaa gtcggccgcc   1140
aacggctccg accagatcct gcaggcggtg ttcgaggtgc cggaaagcgc cggcttctcg  1200
atcaatgaca tcaccatcaa caaccagaag gtcaactatg tgtgggtcat cgcccaacaa  1260
ctgttggtgg gcctgagcgt caccgtcaaa ccgctcagcg tcacacctca atccttccca  1320
tgcgtgcagg accgggtggc cggcctgcaa ccctggccgg tgcaactgct gccgctggac  1380
ctgttctacg ggaactcccc caccgacctg cccgcctggc ttgcaccggg cagcagcaat  1440
cagttcgtgc tggtggtgca aggcgccgac aagaccacca cggcgcagaa tgccagggtg  1500
caattctcca ccccggggt taccgcgcag gtcacccagt acctgcccga cgcgtcggcc  1560
attcccggcc agaccaacgc cggcggcaca caggcctaca tcctgaccat cacggtcagc  1620
cccaccgcag ccccgggcct ggtgacggtg cgtgcgctca atccggatga agacgtgaac  1680
gtgagcgcgg cagaccaccc ttgggaatcc ggcctggcgc tggtgcctgg cgcctgaa    1738
```

<210> SEQ ID NO 127
<211> LENGTH: 1605
<212> TYPE: DNA
<213> ORGANISM: Pseudomonas monteilii

<400> SEQUENCE: 127

```
atgtccaggt cacgcttgag tcttctgtcg ctgctgtgcg gcattttact gtgcctgtcg    60
accccgcaac ccgccatggc agccacgctg tcggatgccg acgcctgtgt gcagcagcag   120
ttggtgttca acccggccag cggggattc ctgccggtca caacttcaa tgccaccagc    180
caggcgttca tgaactgctt tggctggcag ctgttcattg ccttgaactg gccggtgaac   240
cccggctggc cggccaccgc cagcctggcg ggcgaacccg acatgaacag cacgctggcg   300
```

```
cagttcggtg tcccctccgc accgggccaa cccatgagcg tggccccggt atgggccagc    360
tacaaggacg ccaatgacat cttcctgccc ggcgcgccca cgcccactgg ctggggcgta    420
caaaccctgg tgccgtccgg ttgcagcact cagggtagcc tcaagtcact caaggtaggc    480
gcacgcaagt tcatgaacgc cacctccgaa ggcgcgatca atgccttgca ccgattccac    540
ctgtctaccg gaacactcgc gtccattccc gacccggtca tggaagcgtc cggcggctgg    600
ttgacggacc agtctggcaa cctggtgttt tttgagcgca aggtaggcaa ggccgagttc    660
gactacatcg tcgacaaggg gctctacgac gccgccaacc agttgaaggt ggcgcaaaac    720
caggacggca agacaccgga ggggctgtcg ctgccaatcg gcgaaccgat gcgctcgctg    780
cctccgtccc ctgtcccgca ggagcagctg ggcgcgatcg agctcaaggc cgcctggcgg    840
gtgctgaccg gcaaacccga actgttcggg cgctacctga ccaccgtcgc ctggctcaaa    900
cgccccgata ccctgaactg cacccaggaa gtggtggggc tggtgggcct gcatatcatc    960
aacaagaccc aggcttcgcc caacttcatc tggaccactt cgagcaggt cgacaacgtg   1020 cctgaaccgg cccaggcccc gccgcaacaa accccaccga acggttttgc cttcaacaac   1080
cctgactgtg gcagtggccc cgagtgcaca ccgaaccaag cccgtatcca gtgcaagcaa   1140
caccatcccg ataagcaatg caccgatctc ttcccacgcg accagccggt acagaccacc   1200
cgcgaacacc ccatacccag cgacctgcag gccctcaaca gcgcggtgca agccaacttc   1260
gcgcagcaca gtcaaggcca gtcggtgttc cagtactaca agctgatcaa cgtactctgg   1320
accctcgccc ccaatccgcc cagcccggaa ccgggcgcca acgcgcaagt gccgctgtcg   1380
tacgggccat tcatcagcca gggcaacgtg ccggtggcca acaccaccat ggagacttac   1440
gtacagggtg atgactgcaa ccagtgccat cagtacgcga cgattgccgg cagcccttcg   1500
ttggcctcgg acttctcttt cctgttcaac agtgccggtt ctgccagcac caaaagcctg   1560
atcaaaagcg tcaaagcctt ccagacccte aaggatcaac cgtga              1605
```

<210> SEQ ID NO 128
<211> LENGTH: 1746
<212> TYPE: DNA
<213> ORGANISM: Pseudomonas brenneri

<400> SEQUENCE: 128

```
atgagcacgc ccttcaagca attcacctcc cccgctgggc aagcgccaaa ggactacaac     60
aagctgggcc tggaagacca gttgccacaa ttcgaaaccg actggaacaa cgacataacc    120
ggctggaccg aagcggcgat catcggcaac ccctggtcgg gcctgtatga cgcgccccgc    180
tcggcctatt acaacccgct ggtcgaaggc tatggcgaca ccaccctgcc ggcgattacc    240
tggcaaccct ttcccaaccg gctgtggacc tttttctaca caacggcac ggcggtgatt    300 ccccaactgg gcaacaaggc catgaccctg caacaggtca tggagctgac cgacaacggc    360
cagatcacca tcaacggcac cctgtacacc ctgtacgacc cggacaagaa aggcaccctg    420
ctgcaactgc ccgtaacccg ctgcccgact atcgactgga acggcaaata caaagacttc    480
tcaccctcgg ggccacgggg ctggctggac gaatactgcg agtggtcgat cgtgcgcgat    540
accaacggca acatgcgcaa gatcacccttt accagtgaaa accggcgta cttcctggcc    600 atgtggcgca tcgatccgaa tgccgtgctg ggcttgtatc gcgactacat cgacccgaat    660
gtgcaactgc aagatctcta tctgcgctac accgccgact gcaagaccgg caaggccggt    720
gacccggtga ttgacccgac cacgggcctg ccggcctacg acacggtcaa caaatggaac    780
```

| | |
|---|---|
| tccggcactg cctgcacccc cggccagttc ggcggcgcga tgcacctgac ctctgggccc | 840 |
| aacactctca gcgccgaggt gtacctggcg gcggcggcca ctatcatgcg gccccctgaaa | 900 |
| agcagccaga gcgcccaggc gctgatctgc tgcgcgcaat atgggcagaa ctatcgcaac | 960 |
| tccgacccgc atatcggctt tgcagccaac ggggcgacaa atgatggggc cacccccagc | 1020 |
| cggatttccc tgaccaaccc catcgccctg tacctgcaac agccgaccaa cttcaatgcc | 1080 |
| tggaaaggcc cccaaggcca ggatgtgagc cagtactggc gcatcacccg cggtaccgcc | 1140 |
| aaatcggcga tcaacggctc cgaccagatc ctgcaggcgg tgttcgaggt accggaaagt | 1200 |
| gccgggttct cgatcaacga catcaccatc aatggccagg cggtggacta tgtgtggtg | 1260 |
| attgcccagc aattgctggt gggcctgagt gtcaccacca tgccgagcac cgcgcagcag | 1320 |
| caatcgcctt gcgtgcagga tcgggtcaat ggcctgcagc cctggccggt gcagttgttg | 1380 |
| ccgctggacc tgttctacgg ccagtcgccc accgacctgc cggcctggct ggccccaggt | 1440 |
| accagcgggc aattcgcgct ggtggtacaa ggcgcggacc tcaagaccac cgccgccacc | 1500 |
| gcacggatcc agttcaacaa ccccggggtc acggcgcagg tcacggagtt cctgcccgac | 1560 |
| gcctcggcca ttcccggcca gaccaatgcg ggcggcaccc agggctacat catgaccatc | 1620 |
| accgtcgcaa aagacgcggc gccgggactg gtgacagtgc gcgcgctcaa tccgggcgag | 1680 |
| gcggataacg tcagcgcggc ggaccaccct tgggagtccg ggctggcgct ggtgccatcc | 1740 |
| acttaa | 1746 |

<210> SEQ ID NO 129
<211> LENGTH: 1602
<212> TYPE: DNA
<213> ORGANISM: Pseudomonas brenneri

<400> SEQUENCE: 129

| | |
|---|---|
| atgatgtaca gatttcgctt acgtggtctg ctgctggtcg gcacgctgct gtcgctgttt | 60 |
| ctcctgccca cggcccaggc atcggatgcc gatacctgcg tccagcagca gttggtgttc | 120 |
| gaccccaaca gcggcggttt tctacccgtc aacaatttca acaccactgg ccagagcttc | 180 |
| atgaactgtt ttggctggca gctgtttatt gccctgaact ggcccgtgga tcccggatgg | 240 |
| ccagccaatg cagccctcgc gggcgagccg aacgcaagat cagcatggc gcaatttggc | 300 |
| gtgcccaggg tcgccgggca acccatgacc accgcgccgg tgtgggcaag ctttaaagac | 360 |
| gctaacgata tattcctgcc cggcgcccga ccgcccacag gctggggcgt gcagacattg | 420 |
| gtgccgtcca attgcagcag cgagggcagc ctcaaagcgt tgtcggtggg ggcgcgcaag | 480 |
| ttcatgaacg ccacctcgga aagcgcgacc aacgccaagc atcgcttcca cttgtccagc | 540 |
| ggtaccctgg cgtcgattcc cgacccgatc atggaagccg ccggtggctg gctgacggac | 600 |
| cagaccggca acctggtgta tttcgagcgc aaggtgggca aggccgagtt tgactatatc | 660 |
| gtcaagtacg ggctgtacga tgccgccaat caaatggtcg ttgcacaaaa cagcgatggc | 720 |
| aatcatccgg ccgggctgtc cctgcccgcc ggcgagctga tgcgctcgat gccggcgcaa | 780 |
| ccctgccccc aggagcaact gggcgccctg gaactcaagg ccgcctggcg tatcctcacc | 840 |
| ggcaagcccc agctctacgg gcgctacctg accaccgtgg cctggctcaa gaaccccgcc | 900 |
| accctgcagt gcacccaaca ggtggtgggc ctggtgggcc tgcatatcat caacaagacc | 960 |
| cagagttcac cgaactttat ctggaccaca ttcgagcaag tagacaacgt acaagagcca | 1020 |
| ggccaggtgc ccgcgcaaca gacaccgccc gacggtttta ccttctacaa ccccaattgc | 1080 |
| accggtggcc ctgacgtgtg cacgcccaac gtggcccgta tccagtgcca gcagcaccac | 1140 |

```
cctgatcgcg aatgcaccga gccctatcca cgcaaccaac cggtccagac cactcgcgaa    1200 cacccctgc cttcggacat gcaggccctc aacggcgccg tgcaggctaa cttcgcccag    1260
cagaccaacg gccagtcggt gttccagtac tacaaactgg tcaatgtgct gtggatcacc    1320
gccccgaccg caccggaccc ggagccgggc gcgggtgcga aggtgcccct gtcctatggc    1380
gcctttatca gcgatagcaa cgtaccggtg gccaatacca ccatggagac ctacgtccag    1440
agcatggact gcaatgcctg ccatcagcag gcgacgattg ccggcagcag cagcctggcc    1500
tcggacttct cgttcctgtt caacaacgcc gattcggcca agcaaaaaag cctgatcaaa    1560
cgcgtaaatg ccttcgaaac cctcaaggat ggcccaccat ga                      1602
```

<210> SEQ ID NO 130
<211> LENGTH: 1851
<212> TYPE: DNA
<213> ORGANISM: Pseudomonas gessardii

<400> SEQUENCE: 130

```
atgcccgctg cctggcttta tcgcccaact ggtgtgggac gacccgcgcc agaccgttgc      60
cgaccctccc tcgagtgccg gttgctgctc cgtttctacc ccccatggag atctgacatg     120
agcacgccct tcaagcaatt caccccccc gccgggcaag cgccaaagga ctacaacaag     180
ctgggcctgg aagaccagtt gccgcaattt gaaaccgact ggaacaacga cgtcaccggc     240
tggaccgaag cggcgatcat cggcaaccca tggtcgggcc tgtacgacgc gccacgctcg     300
ggctattaca acccgctggt cgagggctat ggcgacacca ccccgccggc gattacctgg     360 caacccttc caaccggct gtggacgttt ttttatagca acggcacggc ggtgattccg      420
caactgggcg gcaaggccat gaccctgcaa caggtcatgg aactgaccga caatggccag     480
atcaccatca acgacaccct gtacaccctg tacgacccgg acaagaaagg caccctgctg     540
caactgccgg tgacccgttg cccgagtatc gactggaacg gcaagtacaa ggatttctca     600
ccctcgggcc cacggggctg gctggacgag tattgcgagt ggtcgattgt ccgcgatgcc     660
aatggcgaca tgcgcaaaat caccttcacc agtgaaaacc cggcgtattt cctggccatg     720
tggcgcatcg acccgaatgc cgtgctgggg ctgtatcgcg actacatcga cccgaacgtc     780
caactcgaag acctctacct gcgctatgcc accgactgcc cgaccggcaa tgccggggat     840
ccggtgattg acccgaccac gggcctgccc gcctacgaca ctgtcaacaa atggaacgcc     900
ggcaccgcct gtacgcccgg ccagttcggc ggcgcgatgc acctgacgtc cggccccaac     960
accctcagcc ccgaggtgta cctggcggcg gcggccacga tcatgcggcc cctgaaaagc    1020
agccagaacc ctcagtcgct gatctgctgc gcgcaatatg ggcagaacta tcgcaactcc    1080
gacccgcata tcggttttgc ggccaatgag gcggccatca gcaaccgtat ctccctgacc    1140
aatcccatcg ccctgtacct gcagcaaccg accaacttca gcgcgtggaa aggcccgcag    1200
ggccaggatg tgagtcagta ctggcgcatt cccgcggca ccgccaaatc ggcgatcaac     1260
ggctccgacc agatcctcca ggcggtgttc gaggtgccgc aaagcgcggg gttctcgatc    1320
aatgacatca ccatcaacgg ccaggccgtg gactatgtgt gggtgattgc ccagcaactg    1380
ctggtgggcc tgagtgtgac cgtcatgccg agcaccacgg cggcgccgtc tccttgcgta    1440
caagaccggg tcaatggcct gcaaccctgg ccggtgcagt tattgccgct ggacctgttc    1500 tacgccagt cgcctaccga cctgccggcc tggctggccc ctggcagcag cgggcagttt    1560
gtcctggtgg tgcaaggcgc cgatctgcag accaccgccg ccacggcgag gatccagttc    1620
```

| agcaatcccg gggtgacggc acaggtcacg aagttcatgc ccgacgcctc ggccattccc | 1680 |
| ggccagacca acgcgggcgg cacccagggt tacatcatga ccatcagcgt cgcggcgaac | 1740 |
| gcggcgccgg gactggtgac ggtacgcgcg ctcaacccgg gcgaggcgga taacgtcagc | 1800 |
| gcggcggacc acccgtggga atccgggctg gcgctggtgc catccaccta a | 1851 |

<210> SEQ ID NO 131
<211> LENGTH: 1602
<212> TYPE: DNA
<213> ORGANISM: Pseudomonas gessardii

<400> SEQUENCE: 131

| atgatgtcca ggtttcgctt gagtcgtctg ctgctggtca gcaccctgct gtcactgttt | 60 |
| atcctgccct tggcccacgc gtccgatgcc gataactgcg tccagcagca actggtgttc | 120 |
| aaccccaaga gcggcgggtt tatgccggtc aacaacttca caccaccgg ccagagcttt | 180 |
| atgaattgct ttggctggca attgttcatc gccctgaact ggccggtgga ccccggctgg | 240 |
| ccggccaatg ccagcctggc gggcgagccg acagaaccca tcaccgtcgc gcaattcggc | 300 |
| gtgcccacca ccgccgggca gcccatgagc gtggcgccgg tatgggccag ctacaaagac | 360 |
| gccaatgaga ttttcctgcc cggtgcaccc aagcccagcg gttgggggt gcaaaccctg | 420 |
| gtgccgccca attgcagcag ccaggacagc ctccaggccc tgtcggtagg ggcgcgtaaa | 480 |
| ttcatgaatg ccacctcgga aagcgcgacc aacgccaagc atcgcttcca cttgtccagc | 540 |
| ggcaccctgg cgtcgattcc cgacccgatc atggaagccg ccggtggctg gctcacggac | 600 |
| cagaccggca acctggtgta tttcgaacgc aaggtgggga aggccgagtt cgactacatc | 660 |
| gtcgacaacg gtctgtacga tgccgccaat caactgatcg tcgcgcaaaa cagcgatggc | 720 |
| aaacacccgg ccggcctgtc gctgcccgcc ggtgagctga tgcgctcgat gcccaccacc | 780 |
| ccgctgcccc aggagcaact gggcgccctg gaactcaagg ccgcctggcg catcctcacc | 840 |
| ggccagcccc agctctacgg cgctacctg accactgtgg cctggctcaa gaaccccgcc | 900 |
| acctgcaat gcacccaaca ggtggtgggc ctggtgggcc tgcatatcat caacaagacc | 960 |
| cagagctcac cgaactttat ctggaccacc ttcgagcacg tggacaacgt accggaaccg | 1020 |
| ggccaggtgc ccgcgcaaca gctgcccccg gacggctaca ccttcaacaa tcccaactgc | 1080 |
| accgcgggcc ccgatgtgtg tacgccgaac gtggcgcgca tccagtgcaa acagcaccac | 1140 |
| ccggatcgcg aatgcaccga accctatcca cgggaccaac cggtgcagac cacccgcgaa | 1200 |
| cacccactgt cgtcggacat gcaggcgctc aacggcgcag tgcaggcaag cttcgcccaa | 1260 |
| cagaccaacg gccagtcggt gttccagtac tacaagctga tcaatgtgct gtggatcacc | 1320 |
| gccccgacgc cgcccgaccc cgagccgggc ccgaatgcga aggttcccct gtcctacggt | 1380 |
| gcttttatca gcgacagcaa cgtacccgtg gccaatacca ccctggagac gtacgtccag | 1440 |
| ggcatgaact gcaatgactg ccatcagcaa gcgaccattg ccggcagcgc caccctggcc | 1500 |
| tcggacttct cgttcctgtt caacaacgcc gattcggcca agcatacaag cctgatcaaa | 1560 |
| cgcgtacatg ccttcgaaac cctcaaggac ggccaaccat ga | 1602 |

<210> SEQ ID NO 132
<211> LENGTH: 1737
<212> TYPE: DNA
<213> ORGANISM: Pseudomonas putida

<400> SEQUENCE: 132

| atgagcgcgc ccttcaagca gttcacctct cccgccggcc aagcccccaa ggactacaac | 60 |

```
aagctgggcc tggaagacca gttgccgcag tttgaaaccg actggaacaa caacctcacc    120
ggctggaccg aatcgtcgat catcggcaac ccctggtcgg gcctgaacga cgcccccgc     180 tcgggttact acaacccgct ggtggaaggt ttcggcgacg tgaccgcccc ggcgatcacc    240
tgggcgccct tccccaaccg gctctggacg ttcttctaca acaacggtgc ggcggtcatt    300
ccccagctgg gtggcaaggc catgaccctg accaggtga tggcgttgac cgaccacggc     360
cagatcacgc tcgacaacac cctctacatg ctctacgacc caacaagca aggtactgtg    420 ctgcaactgc cggccaagcg ctgcccgagc atcgactgga acggcaagta cacggcgttc    480
tcgccttccg gcccgcgggg ctggctcgac gagtactgcg agtggtcgat cgtacgcgat    540
gccaacggca acatgcgcaa gatcaccttc acctgcgaaa accccgcgta cttcctgacc    600
atgtggcgca tcgacccgaa cgcagtgctg ggcctgtacc gcgactacat cgacccgaac    660
gtgcaactcg aagacctgta cctgcgctac accgtcgact gcccgaccgg caaggccggc    720
gacccggtca tcgaccccac caccggcaag ccggcctatg acaccgtcaa caaatggaac    780
gccggaacgg cctgtgtgcc cggccagtac ggcggtgcga tgcacctgac ctccggcccc    840
aataccctca cgccgaggt gtacctggcc gccgccgcca ccatcctggg cccggtgagc     900
agcagtcaga acgcccagtc gttgatctgc tgcgcgcagt acgggcaaaa ctatcgcaac    960
tctgatccgc acatcggttt catggccaat accacggcag tgaacaaccg actgtcgctg    1020
accaacccca ttggcctgta cttgcagcag cccaccgatt tcagcgcctg gaagggcccg    1080
caaggccagg acgtgagcca gtactggcgc atcacgcgcg gtacggcgaa gtcggccgcc    1140
aatggttccg accagatcct gcaggcggtg ttcgaggtgc cggaaagcgc cggcttctcg    1200
atcaacgaca tcaccatcaa caaccagaag gtcaactatg tgtgggtcat cgcccaacaa    1260
ctgctggtcg gcctgagcgt caccgtcaag ccgctcagca ctgcgcctca agcgttccca    1320
tgcgtgcagg accgggtggc cggcctgcaa ccctggccag tgcaactgct gccgctggat    1380
ctgttctacg ggcaatcccc caccgacctg cccgcctggc ttgcaccggg tagcagcaac    1440
cagttcgtgc tggtggtgca agtgccgac ccgactacca cggcgcagaa tgcaagggtg     1500
caattctcca accctggggt gacggcgcag gtcacccagt acctgcccga cgcatcggcc    1560
attcctagcc agaccaactc gggcggcacc caggcctaca ttctgaccat cacggtcagc    1620
ccctccgcag caccccggcct ggtggcagtg cgtgccctca accgggtga agatgtgaac    1680 gtgagcgcga cagaccaccc ttgggaatct ggcctggcgc tggtgcctgg cgcctga      1737
```

<210> SEQ ID NO 133
<211> LENGTH: 1605
<212> TYPE: DNA
<213> ORGANISM: Pseudomonas putida

<400> SEQUENCE: 133

```
atgtccaggt cacgcttgag tcttctgtcg ctgctgtgcg gcattctact gtgcctgtcg    60
accccgcaac ccgccacggc ggccacgctg tcggacgccg ataccgtgt acagaagcaa     120 ttggtgttca acccggccag cggggggattc ctgccggtca caacttcaa tgccaccagc    180 caggcgttca tgaactgctt tggctggcag ttgttcattg ccttgaactg gccggtgaac    240 ccggttggc cagccaccgc cagcctggcg ggtgaacccg acatgcaaag cacgctggcg    300
cagttcgggg tccctctgc accgggtcag cccatgagcg tggccccggt atgggccagc     360
tacaaggacg ccaacgacat cttcctgccc ggcgcaccca cgcctaccgg ctggggcgtg    420
```

```
gaaaccctgg tgccgtccgg ctgcagcacc cagggtagcc tcaaggcgct caaggtgggc      480
gcacgcaagt tcatgaacgc cacctccgaa ggcgcgatca atgccttgca cggtttccac      540
ctgtcgaccg ggacacttgc gtccattccc gacccggtca tggaggcgtc cggcggctgg      600
ctgacggacc aggcgggcaa actggtattt tttgagcgca aggtgggcaa ggccgagttc      660
gactacatcg tcgacaaggg gctctacgac gctgccaacc agttgaaggt cgcgcaaaac      720
ctcgacggcc agacaccgga gggcctgtcg ctgcccatcg gcgaaccgat gcgctcactg      780
ccgacctccc cagtgccaca ggagcaactg ggcgcgatcg agctcaaggc cgcctggcgg      840
gtgctgaccg gcaaacccga gctgttcggg cgctacctga ctaccgtcgc ctggctcaaa      900
cgccccgaca cgctggagtg cacccaggag gtggtgggcc tggtgggcct gcatatcatc      960
aacaagaccc aggcttcgcc caacttcatc tggaccacct cgagcaggt  ggacaacgtg     1020 cccgaaccgg cccaggtccc gccgcaacaa accccgccaa acgggtttgc cttcaacaac     1080
cctgactgtg cgacggccc cgagtgcaca ccgaaccaag cccgtatcca gtgcaagcaa     1140
acgcatcccg acaaggactg caccgatctc ttcccacgcg accagccggt acagaccacc     1200
cgcgtacacc ccgtgcccgg cgacctgcaa gccctcaaca gcgcggtaca agccaacttc     1260
gcgcagcaca gccaaggcaa gtcggtgttt cagtactaca agctgatcaa cgtactctgg     1320
accctcgccc ccaatccgcc cagcccggaa ccgggcgcca acgcgcaagt gccgctgtcg     1380
tacgggccgt tcatcagcca gggcaacgtg ccggtggcca acaccaccat ggagacctac     1440
gtgcagggtg atgactgcaa tcagtgccat cagtacgcga cgattgccgg cagcccgtca     1500
ttggcctcgg atttctcttt cctgttcaac agtgccggct ccgccagcaa caaaagcctg     1560
atcaaaagcg tcaaagcctt cgaaaccctc aaggaccgcc cctga                    1605
```

<210> SEQ ID NO 134
<211> LENGTH: 1737
<212> TYPE: DNA
<213> ORGANISM: Pseudomonas plecoglossicida

<400> SEQUENCE: 134

```
atgagcacgc ccttcaagca gttcacctct cccgccggcc aagcccccaa ggactacaac       60
aagctgggcc tggaagacca gttgccgcag tttgaaaccg actggaacaa caacctcacc      120
ggctggaccg aatcgtccat catcggcaac ccttggtcgg gcctgaacga cgccccccgc      180
tcgggttact acaacccgct ggtggaaggc ttcggcgacg tgaccgcccc ggcgatcacc      240
tgggcgccct tccccaaccg gctctggacc ttcttctaca caacggtgc ggcggtcatt      300 ccccagttgg gtggcaaggc catgaccctg gaccaggtga tggagttgac cgaccacggc      360
cagatcaccc tcgacaacac cctctacatg ctctacgacc caacaaacg aggtaccgtg      420 ctgcaactgc cggccaagcg ctgcccgagc atcgactgga acggcaagta cacggcgttc      480
tcgccttccg gccacggggc tggctcgac gagtactgcg agtggtcgat cgtgcgcgat      540
gccaacggca acatgcgcaa gatcaccttc acctgcgaaa accccgcgta cttcctgacc      600
atgtggcgta tcgacccgaa cgcagtattg ggcctgtacc gcgactacat cgacccgaac      660
gtgcaactcg aagacctgta cctgcgctac accgccgacg gccgaccgg caaggccggt      720 gacccggtca tcgaccccac caccggcaag ccggcctatg acaccgtcaa caatggaac      780 gccggaacgg cctgtgtgcc cggccagttc ggcggtgcga tgcacctgac ctccggcccc      840
aatcccctca cgccgaggt gtacctgccc gccgccgcca ccatcctgcg cccggtgagc      900
agcagccaga acgcccagtc gttgatctgc tgcgcgcagt acgggcagaa ctatcgcaac      960
```

```
tctgatccgc acatcggttt catggccaat accacggcgg tgaacaaccg actgtcgctg      1020
accaacccca ttggcctgta cttgcaacag cccaccgact tcagcgcctg aagggcccg       1080 caaggccagg acgtgagcca gtactggcgc atcacgcgtg gtacggccaa gtcggctgcc     1140
aacggttccg accagatcct gcaggcggtg ttcgaggtgc cggaaagcgc cggcttctcg     1200
atcaatgaca tcaccatcaa caaccagaag gtcaactatg tgtgggtcat cgcccaacaa    1260
ctgctggtcg gcctgagcgt caccgtcaag ccgctcagca ccacgcctca agcgttccca     1320
tgcgtgcagg accgggtggc cggcctgcaa ccctggccag tgcagctgct gccgctggac     1380
ctgttctacg gcaatcccc aaccgacctg cccgcctggc ttgcaccggg cagcagcaac      1440
cagttcgtgc tggtggtgca aggcgccgac ccgactacca cggcgcagaa tgccagggtg     1500
caattctcca accctggggt gacggcgcag gtcacccagt acctgcccga cgcgtcggcc     1560
attcccggcc agaccaactc gggcggcacc caggcctaca ttctgaccat cacggtcagc     1620
ccctccgcag cacccggcct ggtgacagtg cgtgccctca acccgggtga agatgtgaac     1680
gtgagcgcga cagaccatcc ttgggaatct ggcctggcgc tggtgccggg ggcctga       1737

<210> SEQ ID NO 135
<211> LENGTH: 1605
<212> TYPE: DNA
<213> ORGANISM: Pseudomonas plecoglossicida

<400> SEQUENCE: 135
atgtccaggt cacgcttgag tcttctgtcg ctgctgtgcg gcattctgct gtgcctgtcg       60
accctgcaac ccgccacggc ggccacgctg tcggacgccg atacctgtgt gcagcagcaa     120
ttggtgttca acccggccag cgggggattc ctgccggtca caacttcaa tgccaccagc      180 caggcgttca tgaactgctt tggctggcag ctgttcattg ccttgaactg gccggtgaac     240
cccggttggc cggccaccgc cagcctggcg ggcgaacccg acatgcaaag cacgctggcg     300
cagttcgggg tcccctccgc accgggtcaa cccatgagcg tggccccggt atgggccagc    360
tacaaggacg ccaacgacat cttcctgccc ggcgcaccca cgcccaccgg ctggggcgtg     420
caaaccctgg tgccatccgg ctgcagcacc cagggtagcc tcaaggcact caaggtcggc    480
gcacgcaagt tcatgaacgc cacctccgaa ggcgcgatca atgccttgca cggtttccac     540
ctgtcgaccg gacacttgc gtccattccc gacccggtca tggaggcgtc cggcggctgg      600
ctgacggacc aggcgggcaa actggtgttt tcgaacgca aggtgggcaa ggccgagttc      660
gactacatcg tcgacaaggg gctctacgac gccgccaacc agttgaaggt cgcgcaaaac    720
ctcgacggcc agacaccgga gggcctgtcg ctgcccatcg gcgaaccgat gcgctcactg    780
ccgacctccc cagtgccaca ggagcaactg ggcgcgatcg agctcaaggc tgcctggcgg    840
gtactgaccg acaaacccga gctgttcggg cgctacctga ctaccgtcgc ctggctcaaa    900
cgccccgaca cgctggagtg tacccaggag gtggtgggc tggtgggcct gcatatcatc    960
aacaagaccc aggcttcgcc caacttcatc tggaccacct tcgagcaggt ggacaacgtg   1020
cccgaaccgg cccaggtccc gccgcaacaa acccgccga acgggtttgc cttcaacaac     1080
cctgactgtg caacggcccc cgagtgcaca ccaaaccaag cccgtatcca gtgcaagcaa    1140
acgcatcccg acaaggactg caccgatctc ttcccacgcg accagccggt acagaccacc    1200
cgcgaacacc ccgtgcccgg cgacctgcaa gccctcaaca gcgcggtaca agccaacttc    1260
gcgcagcaca gccaaggcaa gtcggtgttc cagtactaca agctgatcaa cgtactctgg    1320
```

```
acccctcgccc ccaatccgcc cagcccggaa ccgggcgcca acgcgcaagt gccgttgtcg    1380
tacgggccgt tcatcagcca gggcaatgtg ccggtggcca acaccaccat ggagacctac    1440
gtgcagggtg acgactgcaa ccagtgccat cagtacgcga cgattgccgg cagcccctcg    1500
ttggcctcgg acttctcctt cctgttcaac agtgccggct ccgccagcaa caaaagcctg    1560
atcaaaagcg tcaaagcctt cgaaaccctc aaggaccgcc cctga                    1605
```

<210> SEQ ID NO 136
<211> LENGTH: 1737
<212> TYPE: DNA
<213> ORGANISM: Pseudomonas putida

<400> SEQUENCE: 136

```
atgagcacgc ccttcaagca gttcacctct cccgccggcc aagcccccaa ggactacaac      60
aagctgggcc tggaagacca gttgccgcag tttgaaaccg actggaacaa caacctcacc     120
ggctggaccg aatcgtcgat catcggcaac ccctggtcgg gcctgaacga cgccccccgc     180
tcgggttact acaacccgct ggtggaaggt ttcggcgacg tgaccgcccc ggcgatcacc     240
tgggcgccct tccccaaccg gctctggacg ttcttctaca caacggtgc ggcggtcatt     300 ccccagctgg gtggcaaggc catgaccctg gaccaggtga tggcgttgac cgaccacggc     360
cagatcacgc tcgacaacac cctctacatg ctctacgacc ccaacaagca aggtactgtg     420
ctgcaactgc cggccaagcg ctgcccgagc atcgactgga acggcaagta cacggcgttc     480
tcgccttccg gcccgcgggg ctggctcgac gagtactgcg agtggtcgat cgtacgcgat     540
gccaacggca acatgcgcaa gatccacttc acctgcgaaa accccgcgta cttcctgacc     600
atgtggcgca tcgacccgaa cgcagtgctg ggcctgtacc gcgactacat cgacccgaac     660
gtgcaactcg aagacctgta cctgcgctac accgtcgact gcccgaccgg caaggccggc     720
gacccggtca tcgaccccac caccggcaag ccggcctatg acaccgtcaa caatggaac     780 gccggaacgg cctgtgtgcc cggccagtac ggcggtgcga tgcacctgac ctccggcccc     840 aatacccta cgccgaggt gtacctggcc gccgccgcca ccatcctgcg cccggtgagc     900
agcagtcaga acgcccagtc gttgatctgc tgcgcgcagt acgggcaaaa ctatcgcaac     960
tctgatccgc acatcggttt catggccaat accacggcag tgaacaaccg actgtcgctg    1020 accaaccca ttggcctgta cttgcagcag cccaccgatt tcagcgcctg gaagggcccg    1080
caaggccagg acgtgagcca gtactggcgc atcacgcgcg gtacggcgaa gtcggccgcc    1140
aatggttccg accagatcct gcaggcggtg ttcgaggtgc cggaaagcgc cggcttctcg    1200
atcaacgaca tcaccatcaa caaccagaag gtcaactatg tgtgggtcat cgcccaacaa    1260
ctgctggtcg gcctgagcgt caccgtcaag ccgctcagca ctgcgcctca gcgttccca    1320 tgcgtgcagg accgggtggc cggcctgcaa ccctggccag tgcaactgct gccgctggat    1380
ctgttctacg gcaatccccc caccgacctg cccgcctggc ttgcaccggg tagcagcaac    1440
cagttcgtgc tggtggtgca aggtgccgac ccgactacca cggcgcagaa tgcaagggtg    1500
caattctcca accctggggt gacggcgcag gtcacccagt acctgcccga cgcatcggcc    1560
attcctggcc agaccaactc gggcggcacc caggcctaca ttctgaccat cacggtcagc    1620
ccctccgcag caccggcct ggtggcagtg cgtgccctca cccgggtga agatgtgaac    1680 gtgagcgcga cagaccaccc ttgggaatct ggcctggcgc tggtgcctgg cgcctga      1737
```

<210> SEQ ID NO 137
<211> LENGTH: 1605

```
<212> TYPE: DNA
<213> ORGANISM: Pseudomonas putida

<400> SEQUENCE: 137
atgtccaggt cacgcttgag tcttctgtcg ctgctgtgcg gcattctact gtgcctgtcg      60
accccgcaac ccgccacggc ggccacgctg tcggacgccg atacctgtgt acagaagcaa     120
ttggtgttca acccggccag cggggggattc ctgccggtca caacttcaa tgccaccagc     180 caggcgttca tgaactgctt tggctggcag ttgttcattg ccttgaactg gccggtgaac     240
cccggttggc cggccaccgc cagcctggcg ggcgaacccg acatgcaaag cacgctggcg     300
cagttcgggg tccccctccac accgggtcaa cccatgagcg tggccccggt atgggccagc     360
tacaaggacg ccaacgacat cttcctgccc ggcgccccca cgccaccgg ctggggcgtg      420 caaaccctgg taccgtccga ctgcagcacc caaggtagcc tcaagacact caaggtgggc     480
gcgcgcaagt tcatgaacgc cacctccgaa ggcgcgatca atgccttgca cggtttccac     540
ctgtcgaccg ggacacttgc ctccattccc gacccggtca tggaagcgtc cggcggctgg     600
ctgacggacc aggcgggcaa actggtgttt tttgaacgca aggtgggcaa ggccgagttc     660
gactacatcg tcgacaaggg gctctacgac gccgccaacc aattgaaggt cgcgcgaaac     720
ctcgacggcc agacaccgga gggtctgtca ctgcccatcg gcgaaccgat gcgctcactg     780
cctacctccc cagtgccaca ggagcaactg ggcgcgatcg agctcaaggc cgcctggcgg     840
gtactgactg gcaaacccga gctgttcggg cgctacctga ctaccgtcgc ctggctcaaa     900
cgtcccgaca cgctggagtg cacccaggag gtggtgggc tggtgggcct gcatatcatc      960
aacaagaccc aggcttcgcc caacttcatc tggaccacct tcgagcaggt ggacaacgtg    1020
cccgaaccgg cccaggttcc gccgcaacaa acccgccaa cgggtttgc cttcaacaac     1080 cctgactgtg gcaacggccc cgagtgcaca ccaaaccaag cccgtatcca gtgcaagcaa    1140
acgcatcccg acaaggactg caccgatctc ttcccgcgcg accagccggt acagaccacc    1200
cgcgaacacc ccgtgcccgg cgacctgcaa gccctcaaca gcgcggtaca agccaacttc    1260
gcgcagcaca gccaaggcaa gtcggtgttc cagtactaca agctggtcaa cgtactctgg    1320
accctcgctc ccaacccgcc cagcccggaa ccggcgccaa acgcgcaagt gccgctgtcg    1380
tacgggccgt tcatcagcca gggggaacgtg ccggtggcca acaccaccat ggagacctac    1440
gtgcagggtg ataactgcaa tcagtgccat cagtacgcga cgattgccgg cagcccgtca    1500
ttggcctcgg atttctcttt tctgttcaac agtgccggct ccgccagcaa caaaagtctg    1560
atcaaaagcg tcaaagcctt cgaaaccctc aaggaccgcc cctga                    1605

<210> SEQ ID NO 138
<211> LENGTH: 1737
<212> TYPE: DNA
<213> ORGANISM: Pseudomonas putida

<400> SEQUENCE: 138
atgagcacgc ccttcaagca gttcacctcg cccgccggcc aagcccccaa ggactacaac      60
aagctgggcc tagaagacca gctgccgcag ttcgaaaccg actggaacaa caacctcacc     120
ggctggaccg agtcgtcgat catcggcaac ccctggtcgg gcctgaacga tgcgccccgc     180
tcgggttact acaacccgct ggtggaaggc ttcgcgacg tgaccccgcc ggcaatcacc      240 tgggcgccctt tccccaaccg actgtggacg ttcttctaca caatggcac ggcggtcatt     300 ccgcagctgg gtggcaaggc catgaccctg gaccaggtga tggagttggc cgaccatggc     360
```

```
cagatcagcc tcgacaacac cgtctacagg ctctatgacc cgaacaagca aggcaacctg    420
ctgcaactgc cggccaagcg ctgcccgagc atcgcctgga acggcccgta caaggatttc    480
tcgccttccg gcccacgggg ctggctcgac gaatactgcg agtggtccat cgtgcgcgat    540
ggcaacggca aaatgcgcaa gatcaccttc acctgtgaaa accggcgta tttcctgacc     600
atgtggcgca tcgacccgaa tgcggtgctg ggcctgtacc gcgaatacat cgacccgaac    660
gtgcagctcg aagacctgta cctgcgctat accgaagacg gcccgaccgg caaggccggt    720
gagccggtca tcgatcccac caccggcaag ccggcgtacg acaccgtcaa caaatggaat    780
gccggcacgg tcagtgtgcc cggccagtat ggcggggcaa tgcacctgac ctccggcccc    840
aatacccctca gtgccgaggt gtacctcgcc gccgccgcca ccatcctgcg accggtcagc    900
agcagccaga cgcccagtc gctgatctgc tgcgcgcagt acgggcagaa ctaccgcaac    960
tccgacccgc acatcggttt catggccaac agcacggcgg tgaacaaccg cctgtcgctg    1020
accaacccga ttggcctgta cttgcaacaa cccaccgact tcagtacctg gaagggcccg    1080
caaggccagg atgtgagcca gtactggcat atcacgcgcg gcgcggccaa gtccgcggcc    1140
aacggttccg accagatcct tcaggcggtg ttcgaaatac cggaaagcgc cggtttctcg    1200
atcaacgagg tcaccatcaa caaacaaccg gtcaaccatg tgtgggtcat cgcccaacag    1260
ttgctggtgg gcctgagcgt caccgtcaag ccactcgccg ccacgcctgc ttcctacccc    1320
tgcgtgcagg accgggtggc aggcctgcaa ccctggccgg tgcagctgct gccgttggac    1380
ctgttctacg gcaactcacc caccgacctg cccgcctggc ttgccccggg cagcagcaac    1440
caattcgtgc tggtggtgca aggcgccgac gagaacacca ccgcagagaa cgcccgggtg    1500
caattctcca accccggggt taccgcgcag gtcacccagt acctgcccga cgcaacggcc    1560
atacccggcc agaccaatac cggcggcacc caggcttaca tcctgacgat cacggtcagc    1620
cccactgccg caccggcct ggtgacggta cgtgcgctca cccggacga agacgccaac    1680
gtgagcgcgg cagaccaccc ttgggaatcc ggcctggcgc tggtgcctgg cgcctga       1737

<210> SEQ ID NO 139
<211> LENGTH: 1605
<212> TYPE: DNA
<213> ORGANISM: Pseudomonas putida

<400> SEQUENCE: 139
atgtccagcc tacgcttgag tcttctgtcg ctgctaagcg gcattctcct gtgcctgtcc     60
gcccagcaaa cagccacggc ggccacgcag tccgacgccg atagcgtgt gcagcagcaa    120
ctggtgttca acccggccag tggcgggttc ctgccggtca acaacttcaa tgccaccagc    180
caggcgttca tgaactgctt tgcctggcag ttgttcattg ccctgaactg gccggtgaac    240
ctcggttggc caggcactgc cagcctggcc ggggaacccg acctgaacag cagcctggcg    300
cagttcgggg tacctgccac accgggtcaa cccatgagcg tggcgccggt gtgggccagc    360
tacaaggacg ccaacgacat cttcctgccc ggcgcaccca cgcccagcgg ctggggcgtg    420
caaaccctgg taccggccaa ttgcagcacc cagggcagcc tcaaggcact caaggtcggc    480
gcgcgcaagt tcatgaacgc aacctccaag agcgcgatca cgtcttgca cggtttccac    540
ctgtccagcg ggacgctggc atccagcccc gacccgttca tggaggcgtc tggcggctgg    600
ctgacagacc agtcgggcaa cctggtgttt ttcgaacgca aggtgggcaa ggccgaattc    660
gactacatcg tcgacaacgg cctctacgac gcggccaacc agctgaaggt cgcgcaaaac    720
caggacggca agtccccggc ggggctgtcg ctgcccgccg gcgaaccgat gcgctccctg    780
```

```
cctgccgccc cggtcccgca ggagcaactg ggggcgatcg aagtcaaagc cgcctggcgg    840
gtgctgaccg gcaaacccga gctgttcggg cgctacctga ccaccgtcgc ctggctcaaa    900
cgccccgaca cgctggcctg cacccaggaa gtggttggcc tggtgggcct gcatatcatc    960
aacaagaccc aggcttcgcc caacttcatc tggaccacct cgagcaggt ggacaacgtg    1020 cccgaaccgg cccaggcccc gccgcaacaa accccgccga acgggtttgc cttcaacaac    1080
cccgactgtg gcagcggccc cgagtgcaca ccgaaccagg cccgtatcca gtgcaagcaa    1140
caccaccccg acaaggactg caccgatcgc ttcccacgcg accagccggt acagaccacc    1200
cgcgaacacc ccgtgcccgg cgacctgcaa gcgctcaaca gcgcggtaca agccaacttc    1260
gcgcagcaca gccaaggcca gtcggtgttc cagtactaca agctgatcaa cgtactctgg    1320
accctcgccc ccaatccgcc cagccccgaa ccgggcgcca acgcgcaagt gccgctgtca    1380
tacgggccgt tcataagcca gggcaacgtg ccggtggcca ataccaccct ggagacctat    1440
gtacagggtg atgactgcaa ccagtgccac cagtacgcga cgattgccgg cagcccgtcg    1500
ttggcctcgg acttctcttt cctgttcaac agtgccgatt ccgccagcaa caaaagcctg    1560
atcaaaagcg tcaaagcctt cgaaaccctc aaggacctcc cctga                   1605
```

<210> SEQ ID NO 140
<211> LENGTH: 1737
<212> TYPE: DNA
<213> ORGANISM: Pseudomonas monteilii

<400> SEQUENCE: 140

```
atgagcacgc ccttcaacca gttcacttct cccgccgaac aagcacccaa ggactacaac     60
aagctgggcc tggaaaacca gctgccgcag ttcgagagcg actggaacaa ctacctcacc    120
ggctggaccg aatcgtccat catcggcaac ccgtggtcga gcctgtacga cgcgccgcgc    180
tcgggctact acaacccgct ggtggaaggt ttcggtgatg tggttgtgcc ggcgatcacc    240
tgggcgccct tccccaaccg gctatggacg ttctttaca caacggtgc cgcagtcatt     300 ccccagctgg gtggcaaagc catgaccctg caacaggtga tggagctggc cgactacggc    360
cagatcaccc tcaacgacac cctctacacg ctgtacgacc cggacaacaa aggcaccctg    420
ctgcaactgc cggccaaacg ctgccccagc atcgactgga acggcaagta caccgcgttc    480
tcgcccctcc gcgccacgcg gctggcttga gaatactgcg agtggtcgat cgtgcgcgac    540
gccaacggca acatgcgcaa gattaccttc acctgcgaaa accggcgta ctacctggcc     600 atgtggcgca tcgaccccga acgccgtgctg ggcctgtacc gtgaatacat cgaccccaac    660
gtgcagctcg aagacctgta cctgcgctac accgtcgatt gcccgaccgg caaggctggc    720
gacccggtca tcgaccccac caccggcctg ccggcctatg acacggtgaa caagtggaat    780
gccggcacgg cctgtgtgcc cggccaattt ggcggggcca tgcacctgac ctcaggcccc    840
aacaccctca gcgccgaggt gtacctggcc gccgccgcta ccatcctgcg cccggtgacc    900
agcagccaga acgcccagtc gctgatctgc tgcgcccagt atgggcagaa ctatcgcaac    960
tccgaccccg cacatcggttt catggccaat tccaaggcag tgaacaaccg cttgtcactg   1020
accaatccga ttggcctgta cctgcagcag cccaccgact tcagcacctg gaaaggcccg   1080
caaggccagg atgtgagcca gtattggcgg ttacgcgcg gcactgccaa gtcggccgcc   1140
aacggctccg accaaatcct ccaggccgtg ttcgaagtgc cggaaagcgc aggcttctcg   1200
atcaacgaga tcacgatcaa caagcaaccg gttgactatg tgtgggtcat cgcccaacaa   1260
```

| | |
|---|---|
| ctgctggtgg gcctgagcgt cagtgctcta ccgcccgcca ccaccccctcc atccttcccc | 1320 |
| tgcgtgcagg accgggtgac gggcctgcag ccctggccgg tgcagttgct gccgctggac | 1380 |
| ctgttctacg gccagtcacc caccgacctg ccggcctgtc ttgcgccggg cagcagcaac | 1440 |
| cagttcgtgc tggtggtaca aggcgccgac ccgaacacca cggcgcagag tgccagggtg | 1500 |
| cagttctcca accctggcat cagcgcgcag gtcacccagt cctgcctga cgcctcagcc | 1560 |
| attcccgggc agaccaatgc gggcggcacc caggcctaca tcctgaccat cacggtcagc | 1620 |
| cccagcgccg ccccggcct ggtgacggtg cgtgccctca tccgggcga agacgggaac | 1680 |
| gtgagcgcag cagaccaccc gtgggaatcc ggcctggcgc tggtacctgg cgcctga | 1737 |

<210> SEQ ID NO 141
<211> LENGTH: 1605
<212> TYPE: DNA
<213> ORGANISM: Pseudomonas monteilii

<400> SEQUENCE: 141

| | |
|---|---|
| atgtccaggt tacgcttgag tcttctgtcg ctactaagcg gcatgctgct gtgcctgtcg | 60 |
| accctgccag ccgccacggc ggcgccaatg acggaggccg acgcctgtgt acagcaacag | 120 |
| ttggtgttca accggccag cggcgggttc ctgccggtca caacttcaa tgccagcaac | 180 |
| caggcgttca tgaactgttt tgcctggcag ctgttcattg ccctgaactg gccggtgaat | 240 |
| cccggctggc cagccaccgc cagcctggcc ggcgaacccg acatgaacag caccctggcg | 300 |
| cagttcggtg tgccctccga cccggggcaa ccgatgagcg tggcgccggt gtgggccagc | 360 |
| tacaaggacg ccaacgacat cttcctgccc ggcgcccca agcccagcgg ctggggcgtg | 420 |
| caaaccctgg tgccatccgg ttgcggcacc cagggcagcc tcaaggcgct caaggtgggg | 480 |
| gcacgcaagt tcatgaacgc cacctccgaa agcgcgatca acgccgtgca cggtttccac | 540 |
| ctgtccagcg ggacgctcgc atcccttccc gactcgatca tggaagcatc cggtggctgg | 600 |
| ctgaccgacc aggcgggcaa cctggtgttc ttcgagcgca aggtgggcaa ggccgagttc | 660 |
| gactacatcg tcggcaaggg gctgtacgac gccgccaacc agttgaaggt cgcgcaaaac | 720 |
| gccgacggca ctacaccgga ggggttgtcg ttgcccattg gcgagccgat cgctcgctg | 780 |
| ccgccatccc cggtgccgca ggaacaactc ggcgcgatcg aactcaaggc cgcctggcgc | 840 |
| atactgaccg gcaaacccga actgttcggg cgctacctga ccaccgtcgc ctggctcaag | 900 |
| cgccccgaca cgctgacgtg tacccaggaa gtggtggggc tggtgggcct gcatatcatc | 960 |
| aacaagaccc aggcctcgcc gaacttcatc tggaccactt tcgagcaggt cgacaacgtg | 1020 |
| cccgagccgg gtcaggtacc gccgcaacaa accccgccga acggcttcgc cttcaacaac | 1080 |
| ccggactgcg gcagcggccc tgagtgtgaa ccgaaccagc cccgtatcca atgcaagcaa | 1140 |
| caccaccccg accgggactg caccgatctg ttcccacgcg accagccagt gcagaccacg | 1200 |
| cgcgagcatc ctgtgccgag cgacctgcaa gcgctgaacg gcgcagtgca agccaccttc | 1260 |
| gcgcagcaca gccagggcaa gtcggtgttc cagtactaca aactgatcaa cgtactctgg | 1320 |
| accctcgcgc ccaacccgcc cagcccggaa ccaggagcca acgcgccggt gccgttgtcg | 1380 |
| tacggggcgt acatcagcca gggcaatgtg ccggtgccca acaccaccct ggaaacctat | 1440 |
| gtgcagggtg atgactgcaa ccagtgccat cagtacgcga cgattgccgg cagcagttcg | 1500 |
| ctggcctcgg acttctcgtt cctgttcaac agtgccagct cagccagcaa gcacagcctg | 1560 |
| atcaagcgtg tccaagcctt cgaaacgctg aaggaccgtc gctga | 1605 |

<210> SEQ ID NO 142
<211> LENGTH: 1734
<212> TYPE: DNA
<213> ORGANISM: Pseudomonas poae

<400> SEQUENCE: 142

```
atgagcacac ccttcaccca attcacctcc cctgccgaac aagcgcccaa ggactacaac      60
aagttgggcc tggaggacca gttgccggcg ttcgaaaccg actggaacaa caacgtcacc     120
ggctggaccc agatgtcgat catcggcaac ccctggtcca acctcaacga tgcaccgcgc     180
tcgggctatt acaacccgct ggagagcggc tacggcacgc tgacgccaaa gaccatcacc     240
tggcagccct tccccaatcg gctgtggacg tttttctata acgagggcgc tgccgtggtc     300
ccgcaactgg gcggcaaggc catgaccctg accaggtga tgcaactgac cgaccacggc      360
cagatcaccc tcaacgacac cctctattcg ctgtacccgg accccaaggc cacccaactg     420
cagatcccca gcgtgctgtg caaatccatc aactggaacg ccccctacgc cgacttttcg     480
ccctcgggtc cacggggctg gctggacgaa tactgcgagt ggtcgatcac ccgcgacccc     540
gacggcaaca tgcgcagcat catgttcacc agcgagaacc cggcgtattt cctgaccatg     600
tggaacatcg acccgggtgc cgtgctgggc ctgtaccagg cgtatgtcga cccgcaggtg     660
aaactcgaag acctgtacct cgctacacc gccgacggcc cgaccggcaa ggccggcgaa      720
ccggtactcg accccaccac cggccagccc gcctacgaca ccgtgaacaa atggaacagc     780
ggcaccgtgc gcataccggg cgtatcgggc ggcgcgatgc acctgacttc cggccccaat     840
accctgagtg ccgagatcta cctggcggcg cggccacca tcctgcggcc actcaccagc      900
agccagaacc agcagagcct gatctgctgc gcgcaatacg gcagaacta ccgcaactcc      960
gacccgcata tcgggttctc cgcgaaccag gcggcggtca caacctgat ctcgttgacc     1020
aaccctatcg gcctgtacct gcagcaaccc aagtccttca gcacctggaa gggcccgcaa     1080
ggccaggatg tcagcagcta ctggcgcgtt accgtggca ccgccggcac cggcccgaac     1140
aactccgacc agattctcca ggcggtcttc gaggtgccgg ccagcgcggg gttctcgatc     1200
aatgagatca ccatcaacgg cacgccgatc gactacgtgt gggtgatcgc caacgaactg     1260
aacgtggccc tcagcgtgac ccctgcgccg ctcacgcccc agcccaagga gtgtgcctgc     1320
gtggcggcca acaccaccga tgcgcaaccc tggcccgtgc agttgctgcc gattgacctg     1380
ttctacggcc aatcccccag cgacttgccg gccagttttg cccccggcag ctcaggccag     1440
ttcgtattgg tggtacaagg cgccgacccg aacaccacgg cggcggatgc acgggtgcag     1500
ttctccaacc cggcatcac ggcccaggtc acgcagttcc tgccggatgc ctcggcgatt      1560
cccggccaga ccgacggcgg cggcacccag ggctacatca tgaccatcac cgtcagcagc     1620
aacgcggcgc cggggctggt cagtgtgcgt gcgctgaacc ccagcgaagc ggccaacccg     1680
agtgcctccg agcacccctg ggaaagcggc ctggccctgg tgcccagcgc ctga           1734
```

<210> SEQ ID NO 143
<211> LENGTH: 1587
<212> TYPE: DNA
<213> ORGANISM: Pseudomonas poae

<400> SEQUENCE: 143

```
atgaacggat ggcttcgccc gctgcgccgg gcacgcttgc gtattgcctg cgcaatcacc      60
tgcacccttc tcccactgct ggccgccaca ccggccaatg ccgcctcgga cgcccagagc     120
tgcgtcagcc agctggtgtt cgatcccacc agcggcggct tcctgccggt gaacaatttc     180
```

| | |
|---|---|
| ggcaccgagc aggcttttct caattgtttc ggctggcagt tgttcatcgc catgaactgg | 240 |
| ccggtcaatc ccggctggcc ggccaaccca agcctggccg gtgagccgga cacccaaagc | 300 |
| agcgcggccc agttcggcgt gccgccaacc cccggccaac cgatgagcaa tgccccggtg | 360 |
| tgggccagct acaaggatgc cagcgaaatc ttcctgcccg cgcgccaa gccgtccggc | 420 |
| tggggcgtgg aaaccctggt gccgtccaat tgcaccgcca ccggcaacct caaggcgttt | 480 |
| gccacggggg cgcgtaaatt catcaccgcc acctcggaaa gcgcgatcaa ccgcaagcac | 540 |
| cgcttccacc tgtccagcgg cacccaggtg accctgccgg attcgatcat ggaagcgtcc | 600 |
| ggcggctggc tcacggacca gtcgggcaac ctggtgtttt cgagcgcaa ggtgggcaag | 660 |
| gccgagttcg actacatcgt cgacaacggt ttgtacgacg ccgccaacca actgatcgtg | 720 |
| gcgcaaaaca gcgacaaccg cacccccgcc ggcctgtcac tgccggccgg caagccggtg | 780 |
| cgcgagctgc cagccaaggc gctaccccag gaggagctgg gtgccctgga actcaaggcg | 840 |
| gcctggcgcg tgctcaccaa caagcccgac ttgtacgggc gctacctgac caccgtggcc | 900 |
| tggctgcaac gcccggacac gctgcaatgc acccaggaag tgataggcct ggtagggctg | 960 |
| catatcatca acaagaccca gacccagccg aacttcatct ggaccaccctt cgagcagatc | 1020 |
| gacaacgtgc ccgatggcgg cgccgccca ccccagggct acagcttcaa caaccccgag | 1080 |
| tgcaccggcg atgcctgcgc gccaaacgtc gcccgcgtgc agtgcgacgc cacccacacg | 1140 |
| ccgcccgact gcacgcccct ggaccagccg gtgcaggcca ccggctcaa cgccacgccc | 1200 |
| caggacatgc aggcgctgaa cacggcggtg cagcagacct cgcccagca gacccagggc | 1260 |
| cagtcggtgt tccagtacta caaactggtg aacgtgctgt ggtccaagac gcccaacgcc | 1320 |
| cccaacgatc caggccctgg gccgaacgtg aaggtgccgc tgtcctatgg gccgtttgtc | 1380 |
| agcgaccaga gtgtcgtggt cgccaacacc acgatggaaa cctacgtgca gacagacaac | 1440 |
| tgcaatgact gccaccagta cgcggcgatt gccggcaaat ccgggctggc gtcggacttc | 1500 |
| tcgttcctgt tcggcaatgc cgactcggcg aaaaatacgc ggctgatcaa acgcatcgag | 1560 |
| tcgttcaaga ccctcaagga caacccg | 1587 |

<210> SEQ ID NO 144
<211> LENGTH: 1734
<212> TYPE: DNA
<213> ORGANISM: unknown
<220> FEATURE:
<223> OTHER INFORMATION: Mountain Pine Beetle microbial communities

<400> SEQUENCE: 144

| | |
|---|---|
| atgagcacgc ccttcaccca attcacctcc cctgccgaac aagcccccaa ggactacaac | 60 |
| aagctgggcc tggagaacca actgcccacc ttcgaaacca actggaacaa caacgtcacc | 120 |
| ggctggaccc agatgtcggt gatcggcaac ccgtggtcca acctcaacga cgcaccgcgc | 180 |
| tcgggctact acaacccgct ggagagcggc tacggcacgc agacgccagt gaccatcacc | 240 |
| tggcagcccct tccccaatcg gctgtggacg ttcttctaca caacggcgc cgccgtggtc | 300 |
| ccgcaactgg gcggcaaggc catgaccctg gaccaggtga tgcagttgac tgaccatggc | 360 |
| cagatcaccc tgaacaacac cctctattcg ctgtaccccgg accccaaggc aacccaactg | 420 |
| cagatcccca gcgtgctgtg caagtccatc aactggaacg tccttacgc cgactttcca | 480 |
| ccctcgggcc cacggggctg gctggatgaa tactgcgagt ggtcgatcac ccgcgatccc | 540 |
| gacggcaaca tgcgcagcat catgttcacc agcgagaacc cggcgtactt cctgaccatg | 600 |
| tggaacatcg atccgcaggc cgtgctgggg ttgtacaagg cgtatgtcga cccgcaagtg | 660 |

```
aagatcgaag acctgtacct gcgctacacc gccaacggcc cgaccggcca ggccggcgaa    720
ccggtgctcg accccaccac cggccagccc gcctatgaca cggtgaacaa atggaacagc    780
ggcaccgtgc gtatcccagg ggtgtcgggc ggcgccatgc acctgacctc cgggcccaat    840
accctgagtg ctgagatcta cctggcggcg gccgccacta cctgcggcc gctcaacagc    900 agccgtaacc agcagagcct gatctgctgc gcgcagtacg ggcagaacta tcgcaactcc    960
gacccgcata tcggcttttc cgccaaccag gcggcggtca acaacctgat ctcattgacc   1020
aaccccatcg gcctgtacct gcaacagccg aaatccttca gcacctggaa aggcccgcaa   1080
ggccaggatg tcagcagcta ctggcgcgtc acccgtggca cggccggcac cggtccaaac   1140
aactccgacc agatcctgca ggcggtgttc gaggtgccac aaagcgcggg gttctcgatc   1200
aatgacatta ccatcaacgg cacgccgatc gactacgtgt gggtgatcgc caatgaattg   1260
aatgtggccc tgagcgtcac cccggcgccg ctccccgcac cgcccaagga atgcgattgc   1320
gtggcggcca acaaccacga tgcgcaaccc tggccggtgc agttgctgcc gatcgacctg   1380
ttctacggcc agtctcccag cgacttgccg gccagctttg cccccggcag ttccggccag   1440
ttcgtgctgg tggtgcaagg cgccgacccg aacaccacgg cggcggatgc gcgggtgcag   1500
ttttccaacc cagggattac cgcccaggtc acccagttct tgccggatgc gtcggccatt   1560
ccagggcaga ccgacagcgg cggcacccag ggctacatca tgacggtcac cgtcagcagc   1620
aacgcggcac cggggctggt cagcgtgcgt gcgctgaacc ccagcgaagg cgccaacccg   1680
agtgccaccc agcacccatg ggaaagcggc ctggccctgg tgcccgacgc ctga          1734

<210> SEQ ID NO 145
<211> LENGTH: 1590
<212> TYPE: DNA
<213> ORGANISM: unknown
<220> FEATURE:
<223> OTHER INFORMATION: Mountain Pine Beetle microbial communities

<400> SEQUENCE: 145
atgaacggat ggcttcgccc gctgcgtcgg gcacgcttgc gtgtgttctg ctggatcacc     60 tgcgccctte tcccactgct ggccccgtca ccggccaatg cggctaccga tgcccagagc    120
tgcgtcagcc agctggtgtt cgaccccacc agcggcggct tcctgccggt gaataacttc    180
ggcaccgagc aggactttct caattgtttc ggctggcagc tgttcatcgc catgaactgg    240
cccgtcaacc ctggctggcc ggccaacgcg agcctggccg gcgagccgga cacccaaagc    300
agcgtggccc aattcggcgt gccggcaaca cccggccagc caatgagcaa cgccccggtg    360
tgggccagct ataaggatgc cagcgagatc ttcctgcctg gtgcgcccaa ccctctggc    420 tggggcttgg aaaccctggt gccgtccaat tgcaccgcca gcggcaacct caaggcctat    480
gccaccggcg cacgtaagtt catcaccgcc acctcggaaa gcgcgatcaa ccgcaagcac    540
cgtttccacc tgtccagcgg cacccaggtg accctgccgg actcgatcat ggaagcctcc    600
ggcggctggc tgacggacca gtcgggcaac ctggtgtttt tcgagcgcaa ggtcggcaaa    660
gccgagttcg actacatcgt cgataacggg ctgtacgacg ctgccaacca attgatcgtg    720
gcgcagaaca gcgacaaccg gcaccccgcc gggctgtcct tgcccgccgg caaactggtg    780
cgtgaactgc agcccaggc actgccccaa gaggaattgg gcgccctgga gctgaaggcg    840
gcctggcgcg tactcaccaa caagcccgaa ttgtacgggc gctacctgac caccgtcgcg    900
tggctgcaac gcccggacac gctgcagtgc acccaggaag tggtgggcct ggtgggcctg    960
```

```
catatcatca acaagaccca gacccagccg aacttcatct ggaccacctt cgagcaggtc   1020
gacaacgtgc ccgacgccgg cccgacaccg ccccaaggct acagcttcaa caacccggca   1080
tgcagcggca ctgcctgcac gcccaacgtc gcccgcgtgc agtgcgacgc cacccacgcc   1140
ccgcccaact gcacgcccct ggatcagccg gtgcaggcca cgcgggtcaa tgccacgccc   1200
caggacctgc aggccttgaa tacggctgta cagcaaacct tcgcccagaa acccagggc   1260 cagtcggtgt tccagtacta caaactggtg aatgtgctgt ggtccaagac gcccaatgcg   1320
cccaacgatc caggccctgg gcccaacgtg aaaacgccgc tgtcctacgg gccgtttgtc   1380
agcgaccaga gcgtcgtcgt cgccaatacc acgatggaaa cctacgtgca ggcagacaac   1440
tgcaacgact gtcaccagta cgcggcgatt gccggcaagt cgggcctggc atcagacttt   1500
tcgttcctgt tcggcaatgc cgattcggcg aagaacaccc gcctgatcaa acgcatcgag   1560
gggttcaaga ccctcaagga tgatcaatag                                   1590
```

<210> SEQ ID NO 146
<211> LENGTH: 1734
<212> TYPE: DNA
<213> ORGANISM: Pseudomonas trivialis

<400> SEQUENCE: 146

```
atgagcacgc ccttcaccca attcacctcc cctgccgaac aagcgcccaa ggactacaac     60
aagctgggcc tggaggacca gctatcgacc ttcgaaacca attggaacaa caacgtcacc    120
ggctggaccc aaatgtcggt catcggcaac ccctggtcga acctcaatga cgcaccgcgt    180
tcgggctact acaacccgct ggaaagcggc tacggcacgc agacaccgct gaccattacc    240
tggcagccct tccccaatcg actgtggacg ttttctaca acaatggcgc cgccgtggtt     300
ccgcaactgg gcggcacggc catgaccctg gaccaggtga tgcagttgac cgatcacggc    360
cagatcaccc ttaacaacac gctttattcg ctgtacccgg accggcggc aacccaactg     420 cagatcccca aagtgttgtg caagtccatc aactggcacg cccctatgc cgatttttcg     480 ccctcgggtc cacggggctg gctggatgag tattgcgagt ggtccatcac ccgcgacccc    540
gacggcaaca tgcgcagcat catgttcacc agcgagaacc cggcctactt cctgaccatg    600
tggaacatcg acccaaatgc cgtgctgggg ctgtaccagg cgtacgtcga cccgcaggtg    660
aaactcgaag acctgtacct gcgctacacc gccaacggcc cgaccggcaa tgccggtgac    720
ccggtgatcg atgaaaccac cgggcggccc gcctatgaca ccgtcaacaa atggaacgcc    780
ggcaccgtgc gtataccggg cgtctcaggc ggcgcgatgc acctgacctc cgggcccaac    840 acctgagtg ccgagatcta cctggcggcc gcggctacca tccttcggcc gatccaaagc     900
agcggcaacc aacagaacct gatctgttgc gctcaatacg gcagaactna tcgcaactcc    960
gacccgcata tcggcttttc cgccaaccag gctgcggtta aaaacctgat ctcgttgacc   1020
aatcccatcg gcctgtacct gcaacagccg aaatccttca gcacctggaa aggccctcaa   1080
ggccaggatg tgagcagcta ctggcgcgtc acccgtggca ctgccggcac cggcccgaac   1140
aactccgacc agatcttgca ggcggtgttc gaggtgccgc aaagcgcggg gttctcgatc   1200
aatgacatca ccatcaacgg cacaccgatc gactacgtgt gggtgattgc caacgaattg   1260
aatgtcgcct tgagcgtgac gccagcaccg ttgaccgcca cgcccaagga atgcgattgc   1320
gtggccgcca ataaccccga tgcccaaccc tggcccgtgc aactgctgcc attggacctg   1380
ttctacggca gtcacccagt tgacttgccg gccagttttg cacccggcag ctcagctcag   1440
ttcgtgctgg tggtgcaagg ggcagacccg aacaccaccg tggcggatgc gcgggtgcag   1500
```

```
tttccaacc cggggatcag cgcccaggtc acgcagttct tgccggatgc ctcggcgatt    1560
cccgggcaga ccgacagtgg cggcacgcaa ggctacgtca tgaccgtcaa cgtcagcggc    1620
aacgctgcgc cggggctggt cagcgtgcgg gcgctgaacc ccagcgaagc cgccaacccc    1680
agcgcggccc aacacccatg ggaaagcggc cttgcgctgg tgccaggcgc ctga          1734
```

<210> SEQ ID NO 147
<211> LENGTH: 1587
<212> TYPE: DNA
<213> ORGANISM: Pseudomonas trivialis

<400> SEQUENCE: 147

```
atgtacggat ggcctcgccc gctgtgtcgg gctcgcttga atgttttctc gttactggcc    60
ggcgccctgc tgtcactggt ggcgccgcca ccggccagcg cttcggacgc gcagacctgc    120
gtccagcaac tggtgttcga ccccgcaagt gggggcttcc tgccggtgaa caatttcggc    180
accgagcagg actttctcaa ttgtttcggc tggcaactgt tcatcgccat gaactggccg    240
gtcaatcccg gctggccggc cgacccgacc ctggcgggcg agccagacac gcaaagcagc    300
gctgcacagt tcggcgtgcc gcaaacgccc ggcaagccga tgagcaacgc gccggtgtgg    360
gccagctaca aggacgccaa cgacattttc ctgcccggtg cacccaaacc gaccggctgg    420
ggcgtggaaa ccctggtgcc gtccaattgc accgccaccg gcaacctgaa agcgctctcc    480
accggcgcgc gcaaattcat taccgccacg tcggaaagcg cgatcaaccg caagcaccgc    540
ttccacctgt ccagcggcac ccaggtgacc ctgcccgatt cgatcatgga agccgccggc    600
ggctggctga cggaccagtc gggcaacctg gtgttttttcg agcgcaaggt cggcaaggcc    660
gagttcgact acatcgtcaa taacggcttg tacgacgccg ccaatcaatt gatcgtggcg    720
cagaacagcg acaaccgaca ccccgccggc ctgtcgttgc ctgcgggcaa gctggtgcgt    780
gagctgccgg ccaaggcgct gccccaggaa gagttgggcg ccctggaact caaggcggcc    840
tggcgcgtcc tcacccacaa acccgagctg tacgcacgct acctgaccac cgtcgcctgg    900
ctgcaacgcc ctgacacgct gcaatgcacc caggaagtcg tgggtctggt gggcctgcat    960
atcatcaaca agacccagac ccagccgaac ttcatctgga ccacgttcga gcaggtcgac    1020
aacgtgcctg acggcggcgc tacaccgccg cagggctaca gcttcaacaa cccggcctgc    1080
accggtgatg cctgcacacc caacgtcgcc cgcgtgcaat gtgacgccac ccacacgccg    1140
cccaactgca cgccatttaa ccaaccggta caggccacac gggccaatgc cacgcctgag    1200
gacatgcaag cgttaaacac ggcggtgcag cagaccttcg cccagcagac ccagggccaa    1260
tcagtgttcc agtactacaa actggtgaac gtgctgtggt ctaaaacgcc caacgcacct    1320
aacgatccag gcctgggcc gaacgtgaag acgccgctgt cctatgggcc gtttgtcagc    1380
gatcaaagtg ttgccgtcgc caataccacc ctggaaacct atgtgcagac agagaactgc    1440
aacgactgcc accagtacgc ggccattgcc ggtggttcca aattggcgtc ggacttctcc    1500
ttcctgttcg gcagcgccga ctccgcgaag aacactcgcc tgatcaaacg catcgaggcg    1560
ttcaagaccc tcaaggatga tcattag                                       1587
```

<210> SEQ ID NO 148
<211> LENGTH: 1734
<212> TYPE: DNA
<213> ORGANISM: Pseudomonas sp. R81

<400> SEQUENCE: 148

```
atgagcacgc ccttcaccca attcacctcg cctgccgagc aagcccccaa ggactacaac    60
aagctgggcc tggaaaacca gctgccgacc ttcgaaaccg actggaacaa caacgtcacc   120
ggctggaccc agatgtcggt gatcggcaac ccctggtcca acctcaatga cgcaccgcgt   180
tcgggctatt acaacccgct ggacagcgga tacggcacgc agacgccagt gaccatcacc   240
tggcagccct tccccaaccg gctgtggacg ttttttctaca cgacggcgc cgccgtggtc    300 ccacaattgg gcggcaaggc catgacccct gaccaggtga tgcagttgac cgaccacggt   360
cagatcacgc tcaacaacac cctgtattcg ctgtacccgg acccgaaagc gacccagctg   420
cagatcccca gcgtgctgtg caagtccatc aactggaacg gccccctacgc tgactttttca  480 ccctcgggcc cacggggctg gctggatgaa tattgcgagt ggtcgatcac ccgcgacccc   540
gacggcaaca tgcgcagcat catgttcacc agcgagaacc cggcctattt cctgaccatg   600
tggaacatcg acccgcaggc cgtgctcggg ctgtacaaag cgtacgtcga cccgcaagtg   660
aagatcgaag acctgtacct gcgctacacc gccaacggcc cgaccggcaa ggccggcgag   720
ccggtgcttg acccgaccac cggccagccc gcctacgaca ccgtgaacaa atggaacagc   780
ggcactgtgc gtataccggg cgtgtcgggc ggcgcgatgc acctgacctc cggccccaat   840
accttgagtg ccgagatcta cctcgcggcc gcggccacca tcctgcggcc gatcaagagc   900
agcgccaacc aacagagcct gatctgctgc gcccaatacg ggcagaacta ccgcaactcc   960
gatccgcata tcggtttctc cgctaaccag gaagccgtca agcccctgat ttcactgacc  1020
aaccccatcg gcctgtacct gcaacaaccg aaatccttca gcacctggaa aggccctcaa  1080
ggccaggatg tcagcagcta ctggcatgtc acccgaggca ctgctggcac cgggccgaac  1140
aagtccgacc agatcctgca agccgtcttc gaggtgcccc aaagcgcggg gttctcgatc  1200
aacgaaatca ccatcaacgg cacgccgatt gattacgtgt gggtgatcgc caacgagctg  1260
agtgtggccc tcagcgtcac cccggcaccg ctcaccgcca cgcccgagga atgcgattgc  1320
gtagcggcga acaccaccga tgcgcaaccc tggccggtgc agttgctgcc gattgacctg  1380
ttctacggac agtcccccag cgacttgccg gccagctttg cccccggcag ctcaggccag  1440
ttcgtgctgg tggtgcaagg ggccgatccg aataccactg cggcggatgc gcgggtgcag  1500
ttttccaatc cagggatcac tgcccaggtc acggaattcc tgccggatgc ctcggcgatt  1560
ccagggcaga ccgacagcgg cggcacccag ggctacatca tgaccgtcac cgtcagcagc  1620
aacgcggtgc cggggctggt cagcgtgcgc gcgcttaacc ccagcgaagc cgccaacccc  1680
agcgccaccc agcacccgtg ggaaagcggc ctggcgctgg tgcctggcgt ctga         1734
```

<210> SEQ ID NO 149
<211> LENGTH: 1587
<212> TYPE: DNA
<213> ORGANISM: Pseudomonas sp. R81

<400> SEQUENCE: 149

```
atgaacaaat ggcttcgccc gctgcgtcgg gcacgcttga gtgtgttgtg ctggataccc    60
tgcgcccttc tccccctcgc ccccgcaccg gccattgcgg cctcggacgc ccagagctgc   120
gtcagtcaac tggtgttcga tcccaccagc ggcggcttcc tgccggtcaa caactttggc   180
accgagcagg actttctcaa ttgtttcggc tggcagttgt tcatcgccat gaactggccg   240
gtcaatcccg gctggccagc cgacccgagc ctggccggtg agccggacac gcaaagcacc   300
gcggcccagt tcggcgtacc gccaacgtcc ggccagccca tggcaatgc cccggtgtgg    360 gccagctaca aggatgccag cgagatcttc ctgcccggcg cccccaaacc ctcgggttgg   420
```

```
ggcgtggaaa ccctggtgcc gtccaattgc accgccaccg gcaacctcaa ggcgtttgcc      480
acgggcgcgc gtaaattcat ggcggccacg tctgaaagcg cgatcaaccg caagcaccgt      540
ttccatttgt ccagcggcac ccaggtgacc ttgccggact cgatcatgga ggcttccggt      600
ggctggctta cggaccagtc gggcaacctg gtgttttcg agcgcaaggt cggcaaggcc       660
gagttcgatt acatcgtcga taacgggctg tacgacgccg ccaaccaact gatcgtggcg      720
cagaacagcg acaaccggca ccccgccggc ctgtcattgc ccgccggcaa actggtgcgc      780
gagctgccgg ccaaagctct gccccaggaa gaactcggcg ccctggaact caaggcggcc      840
tggcgcgtac tcaccaacaa accccagctg tacgggcgtt atctgaccac cgtcgcctgg      900
ctgcagcgcc ccgacacgct gcagtgcacc caggaagtgg tggggctggt gggcttgcac      960
atcatcaaca agacccagac tcagccgaac ttcatctgga ccaccttcga gcaggtcgac     1020
aacgtgccgg acaacggcac ggctgcgccc gagggctaca gtttcaacaa cccgacctgc     1080
accggtgatg cctgcacgcc caacgtcgca cgggtgcaat gcgatgccac ccacacgccg     1140
cccgactgca cgccccttga tcagccggtg caggccacgc gggtcaatgc cacgccccag     1200
gacctgcaga tgctgaacac cgctgtgcag cagaccttcg cccaaaagac ccagggccaa     1260
tcggtgttcc agtactacaa actggtgaat gtgctgtggt ccaaaacgcc taacgcgccc     1320
aacgatccgg ccctgggcc caacgtgaag gtgccgctgt cctatggacc gtttgtcagc     1380
gaccagagtg tcgtcgtcgc caacaccacc ctcgaaacct acgtgcaaaa caagaactgc     1440
aacgactgcc accagtacgc ggcgattgcc ggcacctccc aactgacatc ggacttctcc     1500
ttcctgtttg gtaatgccga ttcggcgaag aacgcgcgcc tgatcaaacg catcgaggcg     1560
ttcaagaccc tcaaggacag cccgtaa                                         1587
```

<210> SEQ ID NO 150
<211> LENGTH: 1734
<212> TYPE: DNA
<213> ORGANISM: Pseudomonas libanensis

<400> SEQUENCE: 150

```
atgagcacgc ccttcaccca attcacctcc ccggccgaac aagcccccaa ggactacaac       60
aagctaggcc tggaaaacca gttgccgacc ttcgaaaccg actggaacaa caacgtcacc      120
ggctggaccc agatgtcggt gatcggcaac ccctggtcca acctcaacga cgcaccacgc      180
tcgggctact acaacccgat cgaaagcggc tacggcacac agacgccagt gaccatcacc      240
tggcagcccc tcccaaccg gctgtggacg tttttctata caatggcgc cgccgtggtc       300 ccgcaactgg gtgcaaggc catgaccctg gaccaggtga tgcagttgac cgatcacggc      360
cagatcaccc tcaacaacac cctgtattcg ctctacccgg accgaaggc gacccaactg      420 cagatcccca gcgtgctgtg caagtccatc aactggaacg gccctacgc cgactttca       480 ccttcggcc caaggggctg gctggatgaa tactgcgagt ggtcgatcac ccgcgacccc      540
gacggcaaca tgcgcagcat catgttcacc agcgagaacc cggcgtattt cctgaccatg      600
tggaacatcg accgcaggc cgtgctgggg ctgtacaaag cctatgtcga cccacaagtg       660
aagatcgaag acctgtacct cgcctacacc gccaacggcc cgaccggcaa ggccggtgac      720
ccggtgcttg accccaccac cggccagccc gcctacgaca ccgtgaacaa atggaattcc      780
ggcaccgtgc gtattccgg cgtatcgggc ggcgcgatgc acctgacctc cggccccaat      840
accttgagtg ccgaaatcta cctggcagcg gcggcgacta tcttgcgccc gctcaacagc      900
```

| | |
|---|---|
| agccgtaacc agcaaagcct gatctgctgc gcccagtacg gcagaaacta ccgcaactcc | 960 |
| gatccgcata tcggttattc cgccaaccag gaagccgtga aagccctgat ttccttgacc | 1020 |
| aaccccatcg gcctgtacct gcaacaaccc aagtccttca gcacctggaa aggcccgcaa | 1080 |
| ggccaggacg tgagcagcta ctggcgcatc acccgtggca ccgccggcac cgggccgaac | 1140 |
| aactccgacc agattctgca ggcggtgttc gaggtgccgg ccagcgcggg gttctcgatc | 1200 |
| aatgacatca ccatcaacgg cacgccgatt gactacgtgt gggtgatcgc caacgagctg | 1260 |
| aatgtggcct tgagcgtcac cccggcaccg ctcagcggca cgcccaagga gtgcgattgc | 1320 |
| gtggcggcca acaatccgga tgcgcaaccc tggcccgtgc agttgctgcc gattgacctg | 1380 |
| ttctacggcc aatcccccag cgacttgccg gccagctttg cgcccggcag ctcaggccag | 1440 |
| ttcgtgctgg tggtgcaagg cgccgacccg aacaccacgg cggcggatgc acgggtgcag | 1500 |
| ttctccaacc caggcatcac ggcccaggtc acgcagtttc tgccggatgc ttcggcgatt | 1560 |
| cctgggcaga ccgacagcgg cggcacccag ggctacatca tgaccgtcac cgtcagcagc | 1620 |
| aacgcggcgc cggggctggt cagcgtgcgc gcgctgaacc ccagcgaagc cgccaacccc | 1680 |
| agcgccaccc agcacccatg ggaaagtggc ctggcgctgg tgcccgtcgc ctga | 1734 |

<210> SEQ ID NO 151
<211> LENGTH: 1587
<212> TYPE: DNA
<213> ORGANISM: Pseudomonas libanensis

<400> SEQUENCE: 151

| | |
|---|---|
| atgaacggat ggcttcgccc gctgcgccgg gcacgcttga atgtgttgtg ctggatcacc | 60 |
| tgcgcccttc tccccttcgc acccgcaccg gtcagcgcgg cgtcagatgc ccagagctgc | 120 |
| gtcagtcagt tggtgttcga ccccaccagc ggcggcttcc tgccggtgaa caacttcggc | 180 |
| accgagcagg actttctcaa ctgtttcggc tggcagttgt tcatcgccat gaactggccg | 240 |
| gtcaaccccg gctggccagc caaccccgagc ctggccgggg agccggacac gcaaaagcacc | 300 |
| gcggcccagt tcggcgtgcc gccaacgccc ggccagccca tgagcaatgc cccggtgtgg | 360 |
| gccagctaca aggatgccag cgagatcttc ctgcccgggg cgcccaagcc ctccggctgg | 420 |
| ggcgtggaaa cccgggtgcc gtccaattgc accgccaccg gcaacctcaa ggcgttttcc | 480 |
| acgggcgcgc gtaaattcat cacggccact tccgaaagcg cgatcaaccg caaacaccgc | 540 |
| ttccacttgt ccagcggcac ccaggtgacc ttgccggatt cgatcatgga ggcttccggc | 600 |
| ggctggctca cggaccagtc gggcaacctg gtgttttttcg agcgcaaggt cggcaaggcc | 660 |
| gagttcgact acatcgtcga caacgggctg tacgacgccg ccaaccaact gatcgtggcg | 720 |
| cagaacagcg acaaccggca cccggccggc ctgtcactgc cggccggcaa actggtgcgc | 780 |
| gagctgccgg cccaggcgct gccccaggaa gaactcggcg ccctggaact caaggcggcc | 840 |
| tggcgcgtac tcaccaacaa acccgagctg tacgggcgtt acctgaccac cgtcgcctgg | 900 |
| ctgcaacgcc cggatacgct gcaatgcacc caggaagtgg tgggcctggt gggcctgcac | 960 |
| atcatcaaca gacccagac ccagccgaac ttcatctgga ccaccttcga gcaggtcgac | 1020 |
| aacgtgcccg acgcggcgc cacccccgccc ggcggctaca gcttcaacaa cccggcctgc | 1080 |
| accggtgaca cgtgcacgcc caacgtcgca cgggtgcagt gcgatgccac ccacacaccg | 1140 |
| cccaactgca cgcccttga tcagccggtg caggccacgc gggtcaatgc cacgcctcag | 1200 |
| gacatgcaag cgctgaacac ggcggtgcag cagactttcg cgcagaagac ccagggccag | 1260 |
| tcggtgttcc agtactacaa actggtgaat gtgctgtggt ccaagacgcc caacgcgccc | 1320 |

```
aacgatccag gccctgggcc aacgtgaag gtgccgctgt cctatgggcc gtttgtcagc    1380
gaccagagtg tcgtcgtcgc caacaccacg atggaaacct atgtgcagag cgacaactgc    1440
aacgactgcc atcagtacgc gacgattgcc ggcgggtcca aactggcgtc ggatttctcg    1500
ttcctgttcg gcaatgccga ctccgcgaaa aatacgcgcc tgatcaaacg catcgaggcg    1560
ttcaagaccc tcaaggacaa tccgtag                                        1587
```

<210> SEQ ID NO 152
<211> LENGTH: 1731
<212> TYPE: DNA
<213> ORGANISM: Pseudomonas asplenii

<400> SEQUENCE: 152

```
atgagcatcc cgttcacacg attcagccca cccgccaatc aggctcagaa ggactaccag      60
aaactgggcc tggaacagca acaagcgcaa ttcgataccg actggagcaa caatctagca     120
ggctggaccg aagcagcaat cattggcaac ccatggaccg gcctgaacga cgcaccgcgc     180
acgggatact tcaacccgct gatttcgggc tttggtgatg cccctccagc ggtcatcgac     240
tggacgccgt tccccaatcg actgattacc tacctcacgc aagccgactc ggcaaaaaac     300
ccacaactgg gtgcaagcc actgaccatg gaccaggtca tgcaactggc cgataccggc     360
gaaatcgata tcaatggtac cccgctcaaa ctctacgacc cgctaggcag caacaccctg     420
cagttgcctt ccattcgctg cccccagatc gactggaccg gccctacgc ggccttcacc     480 ccgtccggcc cacgcggatg gctggacgaa tactgcgagt ggtcgatcac cctcgacgcc     540
aacggcaaca tgcgcagtgt gatgttcacc tgcgagaacc cggcctacta cctgaccatg     600
tggcgcatcg accccaaggc ggtgttaggc ctgtaccgaa tgtacatcga ctcggccgtg     660
cagttggaag acctgtacct gcgctacccg gtcgaccagc cgaccggcaa gcagggcgaa     720
ccggtgatcg accctaccac tgggctgccc gcatacgacg tgaccaacaa gtggaactcg     780
ggtaccgcgc gcaagcccgg cctgtttgga ggtgccctgc accttacttc cgcccccaac     840
accctcagcg ccgagatcta cctggcgggt gcttcgacca tccagcgctc ggataagagt     900
agtgaaaccc cacagacgct gatctgctgc gctaagtacg gcggaacta ccgtaactcc     960 gacccgcaca tcggctacgt cgccaacggg atagcctacg caaccgcat ttccctgacc    1020 gacccagtcg gtctgtacct gcaacagccc aagaacttca gcaaatggaa agacccgcag    1080
ggcaatagcg tcagccagta ctggcagatc acccgtggca ccgccggaac cgggccactg    1140
ggctccgacc agatcctgca tgccgtattc gaagtgcctg agcaggcagg tttctcgatc    1200
aacgacatta ccattgacgg tcagaagatc acccatgtcg gggtgatcgc caaccagatg    1260
aaggtcgccc tatcggcctc gcctctggac gccatcaagc ccgtcatcca gccttgcgtg    1320
acagaccgca gcacggggct gcagccatgt ccggttcaac tactgccgct ctcgctgttc    1380
tacggtctct cgcccagcga tctacccgcc tggctagcgc cgagcagcag caaccagttc    1440
atcctccttg tacagggttc ggatgctgcc accaccgctg ccaatgcgcg tatccagttc    1500
tccaacccgg gcgtgaaagc acaggtcatt gagttccaga ccaacgccac gccaattgcg    1560
ggcacgaccg acaacagcgg tacccagggc tacatcatca ccatcactgt ggcggccaat    1620
gctgcaccgg gcctggtgca gctgcgggtg ctcaacccg acgagccggt caatccaagc    1680
gataccgatc acccatgggc cagttcactg gcgatcgtgc cagcgctta g              1731
```

<210> SEQ ID NO 153

<211> LENGTH: 1557
<212> TYPE: DNA
<213> ORGANISM: Pseudomonas asplenii

<400> SEQUENCE: 153

```
atgttctcac tcgattgttc ccggggggaat ggccggttct gcctgcctcc cttgttactg      60
atcatttggc tgctcggcag cctggtcgcc cgaaacgcct atgcgctatc cgaccccgaa     120
acaccggccc aatgcgtgca gcagttggtg ttcgacccaa ccaacggcag cttcctgacc     180
agcgacaccc cctttgtagc tcaacaggcc accttcaact gctatgcctg cagatgttc      240
atcgccatga actggccggt gaacccgggc tggcccaccc acccagagct ggcgggcgaa     300
cccgatacca aaagcccggc cgcccagttc ggtgtgccga cgatagcgga ccagcccatg     360
agcgttgcac cggtctgggc cagctacaag gacgccaacg acatcttcct gcacggcgcg     420
gccattccta ccgcctgggg catgcagccc cctgagccgg tcggctgcca gacaaaaccc     480
tcgcttctgt ccctgcgggt cggggcacgc aagttcatga ccgccacctc agagagcgcg     540
gtgaacgcca acatcgtttt ccacctgtcc agcagtaccc tggtgaccgc ctccgacccg     600
accctggaag ccaccggcgg ctggctaacc gatcaggccg gtaagctggt ctatttcgag     660
cgcaaggtgg gaaaggccga gttcgactat atcgtaagca atgaactgta tgacgcggct     720
aaccagttgc aggtggcgaa gaaccagggg ctgtccctac ccgccggggc gcattttcgc     780
agcccgccga cgtcacccat tgcgcaggaa aaactcggcg catttgaact taaggcagcg     840
tggcgcatcc tcaccgacaa accccagctg tacgaccgtt acctgaccac cgtcacctgg     900
ctgaaacacc cggaaaccgg ccagtgcaca caggaagtgg taggcctagt ggggctgcat     960
atcattcaca agaccgccag ccaaccggac ttcatatgga ccacgtttga acacgtggac    1020
aacgtgccag atggcggttc tacacccacc gctggctata cgttcaacaa ccccaagtgc    1080
accggccctg attgcacgcc aaatcaacgg cgcatcactt gcacggcctt gggctgcaaa    1140
gacaactatc cccgcaacga gccggtgcag gttaccccgtg aagattcagt acccagcact    1200
atcaacgacc tcaacactgt cgtgcagcaa gccatctcca ccaagaccgc cggtaagtcg    1260
gtgttccagt actacaaact ggtcaatgtg ctgtgggacg cctcaccaca cataccggac    1320
ccagaacccg cgccaatgc aacagtgccg ctggtctacg gcagcttcag cagcgacggc    1380
aacaacacac ccgtgtccaa taccaccatg gagacctaca tccagaacag gtcgtgcgac    1440
ttctgccaca ggaatgccaa ggtagcgggg agcaagagcc tgacctcgga cttttcgttc    1500
ctgttcgaga gtgccgactc gtccaagata ccgacactga tcaagaagat gccctag       1557
```

<210> SEQ ID NO 154
<211> LENGTH: 1743
<212> TYPE: DNA
<213> ORGANISM: Thalassospira xiamenensis

<400> SEQUENCE: 154

```
atgagcacac cctttgccag atttacgtcg cccgcccatc aggcacccaa ggattacaaa      60
aagcttggta tggaaaacga actgtcggct tttgaaaccg attggaacaa taatgttgcc     120
ggttggaccg agatggcgat cattggtgat ccgtggtcga acctgaatga tgcaccacgg     180
gcggattact ataacccgct gaccgaggga tttggtgaag ccggtgacgc agtcatcagt     240
tggaccccgt tcccgaaccg cttgatcgcc tttctgaccc cacccgaggc atccaacaac     300
ccgcaactgc atcgaccatt gaccatggat gaggttatga gccttgccga tagtggcgag     360
atcaccgtcg atggcacgct ttacaagctc tatgatccga gcggttcggc tccgatcctg     420
```

```
aaaatcccgg ccaaacggtg tccggagatc gactggaccg gggaatacgt tgatttctcg      480
ccatccggcc cacgtggctg gcttgatgaa tattgtgaat ggtcgattac ctatgatgcg      540
tcgggcagca agatgcaaag cgtcatgttt acctgcgaaa acccggccta ttacctgacg      600
atgtggcgga tcaatcccga ggcggtcctt ggcctttatc agatgtatgt tgatccggcg      660
gtcaagcttg aagaccttta tttgcgttac acggttgatc agccgaccgg taaaaaaggc      720
gatcctgtca tggatccgac caccggacgt ccggcctatg acgtgaccaa caagtggaac      780
cgcggcacgg tgcgggttcc cggccagtcg ggcggggcgc tgcatctgac gtcaggcccc      840
aatacgctga gtgctgaaat ttaccttgcc gcggcggcaa ccattcagcg tccggattta      900
agcagccgcg atccgcaaag cctgatttgt tgtgcgcaat acggtcagaa ctatcgtaat      960
tccgatccgc atatcggttt catcgccaac cgggctgcgg cacgttaccg tatttcactg     1020
accgatccgg tcgggcttta tatccagcag ccccagaacc tttcgaactg gaaggggccg     1080
aatggcgagg atatcagcca gtattggaaa atcacccgtg gcacggcggg aaccggtccg     1140
aacaattcgg accagatact gcatgcggtg tttgatattc cgccaagtgc cggtttcacg     1200
atcaatgact gcacgatcaa tggtcagaag attgctcata ttggcgatat cgccaaccag     1260
atgaaaattg cccttcggc aacgcagatg actccgaacc aaccgttgca gtcaccgatg     1320
aaatgcgttt caagccgcag cagcggcagt atgcagccct ggccggttca gtttgtgccg     1380
attgatctgt tttatgggga atctccgacc gatcttccgg cattgatggt accgggaacg     1440
gtgaatagct tgttctgat cgtgcaggga gcggataaaa acaccacgat cgacaacgcg     1500
cggattgagt tttccaaccc cgggatcaag gccaaagtga ccaagttcct gccagatgca     1560
tcggcgattc cgggccagac cgacggcggc ggtacgcagg gcttcattat ggatgttgct     1620
gtatcgtcat cggcaaagcc gggatccgtc agtctccggg ttctgaaccc gaatgaaccg     1680
gccaatccat cggatgctga tcatccgtgg gaaagtggtt tggcggttat tcccagtcat     1740
taa                                                                  1743
```

<210> SEQ ID NO 155
<211> LENGTH: 1620
<212> TYPE: DNA
<213> ORGANISM: Thalassospira xiamenensis

<400> SEQUENCE: 155

```
atgaaccgat tacatttggg ggcaggctgt gtgattgcgg ggttttgtat cctggcgatt       60
gcgggacttc tttgggtgat tgatgttccg gctggcaggg cggatgaaat caatatcagc      120
cgggtgacgg aaatagccca atcggcacag caatgcccgg atcaactggt tttcgatccg      180
acaagcgggt cgttcatgac cagtgacaat ctgttcctgc caacccagca gggtaacaat      240
tgttatgcgt ggcaaatgtt catcgcgatg aactggccgg tcagcagttc atggccggga      300
acaccatcgg ccgcaggtga gccagatcaa acgtttcgg tggaaaattg gggggtaccg      360
gaaaatccga cctcaccctt aaccagcgta ccggtctggg gcagtttcaa ggatgcgcag      420
gcgatcttcc tgcctgatgc ggccaagccg accgattggg gcgtgccgca agccgtgccg      480
tcgggatgta aaagtgacaa gatgttgctg ggttatccgc tggttcggc aaagatttta      540 acaacgcttt caaaaaatgc ggtcaatact gcccatcggt tccatctttc aagtggtacg      600
cgtgataccc agtccgacga gatcatgaa gccaccggcg gatggttgac agatcagaac      660
ggcaatctgg tgttttcga acgaaaggtc ggcaaggccg agttcgatta catcatgaac      720
```

```
aatgcgcttt atgacgctgc ctatcagatg cgggtcgcaa ccaatgctga tggtcgacat      780
ccggcgggat tgtccctgcc aagtggcaag ttcctgcgtg ttccaccgac ggaaccgcaa      840
ggtcaggatg cgcttggagc gttcgagatc aaggcagcgt ggcgggtcct gacagggcaa      900
agcgacattt atgaccggta tctgacatcg gttgcatggc tgaaacgtcc tgataccggt      960
gaatgcagcc aagaagttgt cggtttggtc gggcttcata tcattcacaa gaccgataca     1020
ttccccgatc tgatctgggc aaccttcgag caggtcgaca atgtgcccga cgggcaggca     1080
actttaccgc ctggcggata ttcctttaac aacccgaatt gtaccggacc ggattgcaaa     1140
cccaatcagc cgcgcattga ctgtaacgat cagaaccagt gcaaggatct ttatccccgc     1200
gatcagcccg tacaggttac gcgcgaacag gccctaacca gtgaaatgga tacgctaaat     1260
gccggtgttg cccaaaagat cgcatcgcaa accggcggga atcggtgtt tcagtattac      1320 aagctggtca atgtgttgtg ggatggcagc ccaagccccc cagtcatgga gcccggtgcg     1380
aatgcatcga taccgctgcg ctatggcacc tttgagtccg agggtaatct gaaagtcgcc     1440
aatacaacca tggaaaccta catccaggat caatcctgcg atttttgtca tgccaatgcg     1500
acgattgctg gcagcgatac gctagcatcg gatttctcat tcattttccg cgatgccgga     1560
tcggcgaaaa acccgtcact ggtggaagag gtaaaacaat tcatggagca ggcacaatga     1620

<210> SEQ ID NO 156
<211> LENGTH: 1734
<212> TYPE: DNA
<213> ORGANISM: Paracoccus denitrificans

<400> SEQUENCE: 156
atgaccatat tcacggaatt ttcgaccccc gcacagcagg gcccgaagga ttaccagctt       60
ctcggcctgc cagccgccga tctggccgcg ttcgaggcgg actggagcgc gaatatcgcc      120
ggctggaccc agatgtcgat catcggcaat ccctggtcca acctgaacga cacaccgcgc      180
gacaactact atgatccgct ggtcgagggg atgggcgagg ccacggcggc cgtcatcagc      240
tggccgccct ttccgaaccg gctgatccag ttcctaacca atcccggcat cgtcaagggc      300
gggcagttga cggcaccgct tagccaggat gcggtgcagg aactggccga tagcggccgg      360
atcacccagg gcgggacgag tttcgtgctg ttcgatccag aaccgggtca ggtattgctg      420
aagatccccg ccgaccgctg cccggccatc gattgggacg gcaagtatgt cgacttctcg      480
ccctcggggc gcgcgggctg gcaggacgaa tattgcgaat ggtcgatcct gcgcaatgcc      540
cagggaaaaa tgcagtccat cgccttcacc tgcgagaatc cggcctatta cctgaccatg      600
tggcggcaga accgaaggc ggtgctgggc atctatcagc gctatatcga cccggcggtg       660
cagctggagg atctgttcct gcgctatgaa tacgatcagc cgacgggcaa gaagggcgat      720
ccggtccttg atccgacaac gggcaatccg gcctatgacc cgacgaacaa atggaacagg      780
ggccccgcac gggtgcccgg ttcgttcggg ggagcgatgc atctgacgtc gccgcccaat      840
acgctgtcgg cagagatcta tcttgccgcc gccgcgacga tccagcgccc ctcctcggtc      900
aatggcaatc cgcaatcgct gatctgctgc gcgcaatacg ccagaacctt ccgcaactcg      960
gatcccaata tcggctatgg cgcgaatgtc ccgcgcgga ccgccaggct gacgctgacc      1020
gatccggtcg gcctctacat ccagcagccg cagaactttc agggttggag cggtccgaat      1080
ggcgaagatg tctcaggcta ttggcaaatc ctgcgcggga cggcgggcac cgggccgaac      1140
gggtccgacc agatcctgca cgcggtcttt gccatcccg aaagcgccgg ctattcgatc       1200
gaggattgca ccatctacgg cctgccgatt tcgcatgtcg gcgtcattct ggaccagatg      1260
```

```
aaggtcgcgc tggcggtcac gccgaacaat gccgccccgg acacgaccgc attcgcctgc    1320
gtgaccgacc gaaccgacgg cacacaaccc tggccggtgc agatggtgcc ggagagcctg    1380
ttctatggtg aatcaccctc ggatctgccg gcgcttctgc ggcccggaag caagttccgc    1440
tttgtcctga tcgtgcaggg ggcggatgag aacaccacgc ccgcaaccgc aagggtcgaa    1500
ttctccgatc cgaatatcac cgtcacggtc gagcagttcc tgaaaaacgc ctcggcagtg    1560
ccggggcaga ccaatggcgg cggcacgcag ggttatgtca tggacatcgc cgttggcgcg    1620
aacgcgcaac ccggtccggt ctcggttcgg gcgttgaacc cgtccgaagg gccggcgccg    1680
acgcccgagc agcaccccctg ggaagcgggc cttgcggtca tctcgtctcg gtaa         1734
```

```
<210> SEQ ID NO 157
<211> LENGTH: 1509
<212> TYPE: DNA
<213> ORGANISM: Paracoccus denitrificans

<400> SEQUENCE: 157
```

```
atgcgcacag gtcagatcct catcgcactg gtcgcaggcg tcatgcttgc ctttgccgca      60
tccggcggca aggcccagac cgcctgcagc gccatgctca tcaccgatcc gacctcggcc     120
gatttcctga ccggagacac gcccttcggc catacccagg acggaatgaa ctgctatgga     180
tggcagatgt tcctgtcgct gaactggccg gccgatcccg gatggccgca aacgcccgcc     240
atggccggcg agccggatcg cagcgcgaca atcgccgatt tcggcctgcc cggcccggcg     300
ggacagccga tgcagcgacc cacggtctgg caaagcttca tgccggcgcc cgagatattc     360
aagccctttg cggccatgcc gaccggctgg ggagaaacct cgccgccgcc cgccagttgc     420
ggctccgcct cgctggcagc ctcggccggg tcgatccgca tgctgaacgc ggtctccaaa     480
tccgccgtga gcccgcgtca cggcttcaac ctcgacaccg gaacgatgtc atccatatcg     540
gacgaaatcg aagaggctac gggtggctgg ctgaccgatc agaagggcaa gctggtgttt     600
ttcgaacgga tgatcggcaa ggccgaatac gactatatcg tcgcgaaggg cctgtatgac     660
gcggccaacc agttgaaagt ggcgaccaat gccgacggag ccaccccccga aggcctgtcc     720 ctgcccaaag gcacgccacc gggatcggcc gttcagaacc aggatgagct tggcgccttc     780
gagctgaagg ccgcctggcg gaacctgacc gggctggatg acctttatgg ccgctatctg     840
acctccacgg tctatctgct gtatcccgac ggctcttgcg aaaaggctgt cgtcgggctg     900
gtcggtctcc atatcattca caagaccgcc tccatgccag atttcgtctg gtccaccttc     960
gagcagatcg acaatgttcc gggcgcgtcc cgcccggaag tggatttcag tttcaacaac    1020
ccggcctcga atgcgaagcc gaaccagatg ccgcactgtg tgaatggtgt ctgcgactat    1080
tccctcccca tccaggtcac gcgcgaagtc gcgatcccgg ccggtgtggc gcagaccaac    1140
cgcgacgtgc agcagttgct tgcggaccgg acgggggggca agtcggtgtt ccagtactac    1200
cagctcgtga acgtgctgtg ggacggcgca ccgaccccgc cgtcaccgga cccggcgcg     1260 aatgcccagg ttccgctggt ctatggcacc ttccagacgg atggcagcgt gccggtcgcc    1320
aatacgacga tggagaccta tgcgcagcaa ttcaccccgc gtctgggggcc gtcctgcacc    1380 gcctgccaca agggcgccac catcgccaac agcgcaacgc tggcgtcgga tttttccttc    1440
ctgttctcga ccgcgtccag cgccacgaaa ctgccgggcc tgttcatatc ccgcgacttt    1500
gttccatga                                                            1509
```

```
<210> SEQ ID NO 158
```

<211> LENGTH: 1743
<212> TYPE: DNA
<213> ORGANISM: Cellvibrio japonicus

<400> SEQUENCE: 158

```
atgtcagcgt ttacattttc cactcctgca ttaattcagg atttcagcga caaccctcc      60
ctgcagcagc aactcaacca aaattgggat ttggcaattg atgcgtatac ccaggctgcc    120
ctggttagca atccctggac tgtggattac caggctccct gcgattggta tgtgaatccc    180
aaacaggcgg atattaccgc agctaatccg gttgaaccta ttttttggac ggcttttccc    240
aaccgcttga aaatttattt ttcggcggct gaaaaaagtc cttatcaaat ggcgaatgcg    300
caggttttg cgctggcgga ttttggcaat gttccgcaat cgaaggcgtt tcccacaggt     360
ttgccgttta ttattcccag caagcgctgc cctaatttga attggcagca gtcgattgct    420
gagtgggtac agtacgatcc taaagggccg cgcggttggt tggatgaata ttgtgagtgg    480
tccgtgacgc gcaatgccga tggaaaaatt accaagattg cgtttacctg cgagaatccg    540
gagtactggt ttaccctgtg gcaggtttca ccggaaaaag tattggcgct ttaccagcaa    600
ttggtgagcc cgaatgtggt gctggaggat ttgcaattgc catcagccga tggcaaggga    660
tttgttatcg atccgacaac agggcgccct gcctataacc ccttgaataa atggaattcc    720
ggtacggtgg cgacagaaac ctatggcggt gctgtgcatc tcaccagccc accgaacacc    780
atcggtgcgg aaattatgtt ggcggcacag gcaaccctgt tgcgcgattt gccgccggac    840
cagtacaaca tgcagcgtat ggtatgcgcc ggtgcctatg acgcgctta tcgcaacagt     900
gatccgcata tcggtttgca ggcaaaccag ttggtgaaaa acctgggtgt gaaaatcacc    960
ttaaccaacc cggtgggttt gtatttgcag cgcccggatt tcagcagcta aagacaccc   1020
gatggtaagg atgccggcca attctataag gtcattcgcg gtcgcaccgc ccaacaggca   1080
ggtacgactt acgaccagat attgcatgcg gaattttcag taccggaaga actgggttat   1140
accgtcagtg atattttgat tggcaacgcc gtgcccggca gttcccaggt gcctgtgccg   1200
attctctatg cgggtcaaat tgcagaaaca ttccatgtat gcctggcggg aacagcgatt   1260
gcccccgcta caggtgaacc ttcgcaagca ttttttaccac cggtgactga taaaaccggt   1320
aataccaacg gccaggtgag catgctgttg caacccgg tattgctggc catgcaggca     1380
gtgaaccct ttccccgtt tgtgcaattg ccggtacaaa ttgcccaggg tcaaacactc     1440
accaatatgg ctttgcaggt cagttacgcc aatgacaatt ccaggaggc gcaaattgca    1500
ttctgggatg cacagggcaa tagcgagccg gcatcagtg tgacagtaac ggccatagag    1560
actgctgatg ggacaccggc gggaaaaagc gccggtggtg atggactgtt taattacatt   1620
atcagcatca gtgtcgcgcc gggggtaagt cccggcttta aggtgtgac ggtgcgcaac    1680
cccgcatgtg atatgcccttt gccgttgccg ggtgtgttgt ttgtgactgc aaaaggaaac   1740
taa                                                                 1743
```

<210> SEQ ID NO 159
<211> LENGTH: 1521
<212> TYPE: DNA
<213> ORGANISM: Cellvibrio japonicus

<400> SEQUENCE: 159

```
atgaagcata cattactgat aggggttacc accggtttgc tggtggctgc ctgccagcaa     60
ccggtacagg agtcatccgc agcggttgac gctcccgccg tgagcacggt gtccagcagc    120
agtgcgccaa tcagctttcc ctgcctgaat aaaccggcgg ttaattacaa cacaccgggg    180
```

-continued

```
gatacaccca tcacttcgca agatggtgtg aattgttttg cctggcaaac gtttattggc      240
ctgaactggc cggtcgatgc cagccatccg ggtgagccgg ataagacggc gtctgcgtct      300
gtgtttggtg agccgggttt gcaccaaacc tcggtgtggg aaacctatgc caatagcaag      360
agtgtatttc gtgcaaacgc ccaaccaccc ctgccctggg gacatacgcc cgatgtgcca      420
tccagctgtc aaaaaatatc ccagacactg gcttgcgcg ttatgcaggc gagccgcatg       480
ccgggcagtt ttaatatgag taaggaggcc tcgcaggcat ttcccggcaa caatcccaat      540
tggctggcgg ataagagtgg caacctggtg tattacgaaa tcctgattgg caaggacgag      600
tacgattaca tcaataataa tggtttgtat aacgccaata cccaggctgc ccatatccag      660
cagaacaaga atattgccat gcccctgggc cacgacaagg tgctgggtgg gttggagatt      720
aaagcggcct ggctgagcgt gagcgatcca caaaatccca gtggaaaaa ttacaagctc       780 agtaccagtg tgatttacga tccggtttcc aaggattgcc acgcgagcac gattgcgtta      840
gtgggcatgc acattatccg caagaccgca tcgcaaccgc agtggatctg gccacgttt      900 gagcacaagg acaatgcgcc ggatactgcc agtattaaaa gtgatggcac ggtggatggc      960
gattacacct tctatagcaa cagctgcacg gtcaaaccgg tgccggcggg ttgcaaggcc      1020
aaggttgaaa atggcacatc ggttacccaa acctcctgcc acgtgaatgt atcgcccgcg      1080
tattatctgg atactagcgg caactgtccg gcctatccca tccaggtgag ccgcgatttt      1140
gcgatcaagg attccaccga taaccacgtg gcctcgctca accgcgcagt acaacaactg      1200
attgccagca gcaatgccga ttcggtgtat acccattacc agctggtgaa tgtgctctgg      1260
tcatcggcgg cggtgaatga caatgcacca ccgggcaatc cgccgctgac gcccttatcg      1320
atcagcggtg aaacgccatc gctcaatacc gtgccggttg ccaataccat gctggaaacc      1380
tacgcacagg gttttaactg tttgtcctgc catgcctatg ccagtgtcgc gcgcgatgcc      1440
agggcacagc tgggcggtaa ggcttacgca acggattaca gttttatttt tagttttgcg      1500
acgtcacccg ctgccaaata g                                                1521
```

<210> SEQ ID NO 160
<211> LENGTH: 771
<212> TYPE: DNA
<213> ORGANISM: Pseudomonas brenneri

<400> SEQUENCE: 160

```
atgggttcca ttactgatca taatcaactg ctggcctggg tagcatcctt ggatattccc      60
gaagcttccg gagtaaaaac ccgttcgcgt aatgtggttc cgcgtgctaa tgccgaggac     120
gaaggcgcgg cagtagtacg cggtagtatt acttcgtttg tgaccggcct gagtcaacaa     180
gcgcgtgatg acgtgcaaaa cagcacgttg ttgatgcagt tggctgcgga taaaaaattc     240
aatccggaaa acaacgggga agagtggttc aagttctata ccgatggcct tgctaacctg     300
ggctgggggc gtgttagctc gtattatcag agctatcagc cgcgtaatac caatgtcacc     360
atggaccagg tcgtacttga ggtgattgct gcagtcgtgg gcgctgacag cgctgtgtac     420
aaggtgactg aaaaaacctt ctcgtcactc caagacaatc cgaagaacca ggccccgctg     480
aaactgttcg acagtagcag cactcgggac agcgtgggca cgttccagat actcccagtg     540
atgcaggata gggacggaaa cgtggtaatg gtactgacta ccgtcaacgc cagtaccacg     600
gtacagcgag gcagcttcct gttctggagt tggagcaaga ccaccgcgtg gatgtatcgg     660
gctgcacagc agactgtgct caatgagtcg gtatatgcga ctgttcgcca atctgtcatc     720
```

```
aagaagctgg gcaaaaacgc cgaagaattc atcgatgatc tggaaattta a                771
```

<210> SEQ ID NO 161
<211> LENGTH: 783
<212> TYPE: DNA
<213> ORGANISM: Pseudomonas brenneri

<400> SEQUENCE: 161

```
atgaaattgt ctgccgacga agtttatgtg atttcgggta acttgctatc cgcgacgcct    60
tcgctcaccg atcctacggt acttgaagat atcgccaatt caaaccttt gtgccagttg    120
gcagccgata agaatcaagg cacgcggttt atcgatccag ctgcgtggct ggacttctat   180
cgaagctcac taggtaggtt gttctggcgc atcagtaatt caggcacggt tagttatgct    240
ataccgcaac tcgtgcataa aattaccgtg aaagaagttt tggaaaaaac gttctacaag    300
actctggatc gcccccagcg catccgggtt gaagaaagta ttgaattgtt gggtgagcaa    360
tcagccgata gcccgtcggc gacattgtac agcctcaaga cccaggtcaa tttcaatgag    420
acgacatcat ctccaggtct cttgccccac tctatatcgt ccgttaactt gcaactcagt    480
gtggtgcaca gtgagacgtg catttcggtg tgcagtgttt acttcaaaac gtcgacccgg    540
atcggtgatg atgtattcaa tcagaagttc ccggtaaaag aactgctggg caatgttagt    600
gtgagtacgt tcgaagccaa gctgctggaa tcgagttatg ccggcataag gcagagcatc    660
atcgataagt tgggtgagga caatattcgc gagaacattc tgcttgtccc cgccgtttca    720
ccgtcgttgt ccaacacgcg ccacgcgggg gcgctgcagt tcgtgcagga actggatatt   780
tag                                                                    783
```

<210> SEQ ID NO 162
<211> LENGTH: 783
<212> TYPE: DNA
<213> ORGANISM: Pseudomonas gessardii

<400> SEQUENCE: 162

```
atgaaattgt ctaccgacga agtttatgtg atttcgggta acttgctttc cgcgacgcct    60
tcgctcaccg atcctgcggt acttgaagat atcgccaatt caaaccttt gtgccagttg    120
gcagccgata agaatcaagg cacgcggttt atcgacccag ctgcgtggct ggacttctat   180
agaaactcac taggtaagtt gttctggcga atcagtaatt caggcacggt tagttatgct    240
ataccgcaac tcgtgcataa aattaccgtg aaagaagttc tggaaaaaac gttctacaag    300
aatctggacc gcccccagcg catccgggtt gaagatagta ttgaattatt gggtgagcaa    360
tcagtcgaca gtccgtcggc gacattgtac agcctcaaga cccaggtcaa tttcaatgag    420
acgacatcat ctccaggtct cttgccccac tctgtatcgt ccgttaactt gcaactcagt    480
gtggtgcaca gtgagacgtg catttcggtg tgcagtgttt acttcaaaac gtcgacccgg    540
atcggtgatg atgtattcaa tcagaagttc ccggtaaaag aactgctggg caatgttagt    600
gtgagtacgt tcgaagccaa gctgctggaa tcgagttatg ccagcataag gcagagcatc    660
atcgataagt tgggtgagga caatattcgc gagaacattc tgcttgtccc cgccgtttca    720
ccgtcgttgt ccaactcgcg ccacgcgggg gcgcggcagt tcgtgcagga actggatatt   780
tag                                                                    783
```

<210> SEQ ID NO 163
<211> LENGTH: 783
<212> TYPE: DNA
<213> ORGANISM: Pseudomonas fluorescens

<400> SEQUENCE: 163

```
atgggtcaa ttactgatca tggaaaactg ttggcttggg tcgagtcgct ggatgtaccc    60
aagtcgaccg gcaatgccaa cctcaagcgc gcttcggctg tgctgcgcag tgccgcgcag   120
aacagtgatg aagatggcgc cgcagtcgtg cgcggcagta tcacttcgtt tgtgaccggc   180
ctgacgcccc aggcacggga tgacgtgcaa aacagcacgt tgttgatgca attggcggcg   240
gacaagaaat acaacccgga tacacaacgg aagagtggt caagttcta caccgatggt    300
ttggccaacc tgggttgggg acgtgtgtct cggcgtacc agaaatacaa gccgaccaac    360
accaatgcca ccatggacca ggttgtgctt gaaatcatca gctccgtggt cagcccggaa   420
agcgcgctgt acaaggtgac tgaaaaaacc ttcctggcac tcaagaacaa cccgaacaac   480
aaagatgcgc tgaagctgtt cgatgtcagc agcacccgca acgacctggg caccttccag   540
atcttgccgg tgatgcagga caaggacggc aacgtggtca cggtgctgac ctgcatcaac   600
gcccataccg aggtacaaaa gggtagcttc ctgttctggc actggagctc gaccagtgcg   660
gaaatgtacc gcgccgcgca acaagttgta ctcaatcaga atgtgtacgc caccgtgcgc   720
cagtcggtat tgaagaagct tgggaaaaat gccgaagact tcattgatgg tctggacatc   780
taa                                                                 783
```

<210> SEQ ID NO 164
<211> LENGTH: 780
<212> TYPE: DNA
<213> ORGANISM: Pseudomonas fluorescens

<400> SEQUENCE: 164

```
atgagttta ctgcccctga agttcatgtg gtttcaggca acctgatatc ggcgatgccg    60
tcggtcaaca gccctcaggt acttgaagat attcttgaat cgaatttgtt gtgccagatg   120
gcggcggata aaagtttggg ttcgcgattc aataatccgg ctgcctggct ggatttttat   180
cgcaactcgc tgggcaagct gttctggaaa atcaccaact tcaacacggt cagttatccc   240
gtgccgtcac ctacgcgttc cgtgagcgtc atgggcatac tggagcacac tttcttcaag   300
gtgttggcgc agccacttcg tcatcagata gaagcggata tcgagttgct gatggagctg   360
ccgctgacga gccagcatc gcagctatac acctcaaaga cccatgtgga aatgagcacg   420
cgtgcgcgct caagttttga tgggcgctct gagtcggtga tcagcctgca aatcagcgtt   480
gtccacagcg ggtcgctgat ttcggtgtgc agtgtctact tcaagaccgc agagccggtg   540
gcagctgatg tgttcagtca gaagttcaag gtgagggatt gctgggcaa catcagcgtc   600
aactcgttcg aggctgattt gttggagggt agttacgaag gcgttcgaca gcaaatcaag   660
acgaagctgg gtgaagccaa tatccgcgag aatatcctgt tgatcgctga caccccatc   720
ccggtggacg aattgcccca cgcaaatgcc catcagtttc tcaaagggtt ggatatctga   780
```

<210> SEQ ID NO 165
<211> LENGTH: 768
<212> TYPE: DNA
<213> ORGANISM: Alcaligenes faecalis

<400> SEQUENCE: 165

```
atgagcacga ttactgacca caagcaggta ttggcatgga ttaacgccct ggacattccc    60
gacgcccgg ccggcggcaa ccgtgtagcc gcacgagcga ccagcagtgc cgacgaagat   120
ggtgccgtcg ttgccaaagc cagcatccct tgctttgtca gcggactgac cgaacaatcc   180
```

| | |
|---|---|
| cgcgccgacg tgcaaaacag caccttgttg atgcaactgg ccgctgacaa gaaatacccc | 240 |
| aacgaaaatg atcgcgaaaa atggttcaag ttttactccg atgggctgac caacctgggc | 300 |
| tggggtagca gcagcagctt ctttgaacgc ttccaaccca agaatacgga cgtcaccatg | 360 |
| gaccaggtcg tactggaggt gatactgaca gtggttaaca acgtcaataa tccgctatac | 420 |
| aaaatcgccc aggaaacatt cggcgccttg aacaagcctg ccaatcaaaa gcccatgaag | 480 |
| ctgtttgacc acagcagcac caaagaagac cgcggcaaat tccagattct gcctgctggc | 540 |
| caggaccagc acggcaccgt cagcatggtg ctgaccgcca tcaatgcacg gaccgacatc | 600 |
| caatccggca gcttcctgtt ctggaaatgg agcaaatcca ccgcttggct ctaccgcgca | 660 |
| gccaacctga ttgtgctcaa tgaatcggtg tactcgaagg tacgccaggc agtcatcgac | 720 |
| aagctcggcg ataacgctgt gaactttgtg ctggatctgg atatttaa | 768 |

<210> SEQ ID NO 166
<211> LENGTH: 807
<212> TYPE: DNA
<213> ORGANISM: Alcaligenes faecalis

<400> SEQUENCE: 166

| | |
|---|---|
| atggcttttt ctactgagca aacctatgtg gtgtcaggca atctgatttc tgccaccaca | 60 |
| gaagacacca atacgctgag ctatgaagac tttatccatt ccaacctttt ggcccagatg | 120 |
| ggcgccgaca aaaaactggg ctcccgcttt gttgaccccg caggctggct gagttttttc | 180 |
| aagaatacag taggcaatct gttctggaac ctgagcgagc agggaaccag cacgttgaaa | 240 |
| atctcagccg gtaccgcaag catcaccgtg cagcaaatac tggagcagag tttttttcaaa | 300 |
| cggctcaacc aagcgcaaat cgatagcgcc acggcaagtg ttgatctgtt tagtcaactc | 360 |
| tctgaagatg atcctgcctt catcctctat aacgcgaaat cacatgccca gatctctacg | 420 |
| gctaccaagg tgatcaagcc accccaaaaa gagacttata gcgtcaactt gcaaatcagc | 480 |
| attgcccata caggtcgga aatcgcactg tgcaatattt tcttccaaac cagccaggca | 540 |
| gtcagcgacg aattattcac acagaaattc gcaatcaaag atctgattgg aaacattaat | 600 |
| gtgttttatt taaaggctct actctccgag accaattacg ccacatcag gcaacaggtt | 660 |
| atcgaaaagc tgggtgagaa catcaacacc aatattgtgc tggtagccga taacagcgat | 720 |
| aagccctccc ccccttctc ccacagaggc gcgcagttc atacgcagcc tgaaaatcta | 780 |
| atccagcaac gcacaggccc accatga | 807 |

<210> SEQ ID NO 167
<211> LENGTH: 768
<212> TYPE: DNA
<213> ORGANISM: Alcaligenes faecalis

<400> SEQUENCE: 167

| | |
|---|---|
| atgagcacga ttactgatca caagcaggta ttggcatgga ttaacgccct ggacattccc | 60 |
| gacgctccgg ccgcggcaa ccgcgtcgcc gcacgagcaa gcagcagtgc cgacgaagat | 120 |
| ggtgccgtcg tcgccaaggc cagcatcccg tgctttgtca gcggactgac cgaacaatcc | 180 |
| cgcgccgacg tgcaaaacag caccttgttg atgcaactgg ccgctgacaa gaaatacccc | 240 |
| gacgaaaatg atcgggaaaa atggttcaag ttttactccg atgggctgac caacctgggc | 300 |
| tggggtagca gcagcagctt ctttgagcgc ttccaaccca agaacacgga cgtcaccatg | 360 |
| gaccaggtcg tactggaggt gatattgacg gtcgttaaca acgtcaataa tccgctgtac | 420 |
| aaaatcgccc aggaaacatt tggcgccctg aacaagcctg ccaatcaaaa gcccatgaag | 480 |

```
ctgtttgacc acagcagcac caaagaagac cgcggcaaat tccagattct gcctgcaggc    540
caggaccagc acggcaccgt cagcatggtg ctgaccgcca tcaatgcacg gaccgacatc    600
caatccggca gcttcctgtt ctggaaatgg agcaaatcca ccgcttggct ctatcgcgcc    660
gccaacctga ttgtgctcaa tgaatcggtg tactcgaagg tacgtcaggc agtcatcgac    720
aagctcggcg ataacgccgt gaactttgtg ctggatctgg atatttaa                768
```

<210> SEQ ID NO 168
<211> LENGTH: 780
<212> TYPE: DNA
<213> ORGANISM: Alcaligenes faecalis

<400> SEQUENCE: 168

```
atggctttt ctactgagca aacctatgtg gtgtcaggca acctgatttc tgccaccacg     60
aaagatacca atacgctgag ctatgaagac tttattcatt ccaatctttt ggctcagatg    120
ggcgccgata aaaaactggg ttcccgcttt gttgaccccg caggctggct gagttttttc    180
aagaatacag taggcaatct gttctggaac ctgagcgagc aaggaaccag cacgctgaaa    240
atctcagccg gtaccgcaag catcaccgtg ctgcaaatac tggagcagag ttttttcaaa    300
cgactaaacc aagcacaaat cgatagcgcc acggcaagta ttgatctgtt tgatcaactc    360
cctgaagatt atcctgcctt catcctctat aacgtgaaat cacatgccca gatctctgcg    420
gctgccaagg caatcaagcc gccccaaaaa gcgacatata gcgtcaactt gcaaatcagc    480
attgcccata ccgggtctga aattgcactg tgcaacgttt tcttccaaac cagccaagcc    540
gtcagcgatg aactgttcac tcagaaattc gcaatcaaag atctgattgg caacatcaat    600 atctttatt taaaggctca gctctccgag accaactacg gccaaatcag gcagcaggtt    660
atcgagaagc tgggtgagaa catcaacacc aatattttgc tggtagccga taacagcgaa    720
acgccctccc ctccttctcc tgcagaagcg cgcagtttca tacgcagcct gaaaatctaa    780
```

<210> SEQ ID NO 169
<211> LENGTH: 768
<212> TYPE: DNA
<213> ORGANISM: Alcaligenes sp. HPC1271

<400> SEQUENCE: 169

```
atgagcacga ttactgacca caagcaggta ttggcatgga ttaacgccct ggacattccc     60
gacgccccgg ccggcggcaa ccgtgtaacc gcacgagcga ccagcagtgc cgacgaagat    120
ggtgccgtcg ttgccaaagc cagcatccct tgctttgtca gcggactgac cgaacaatcc    180
cgcgccgacg tgcaaaacag caccttgttg atgcaactgg ccgctgacaa gaaataccc    240 aacgaaaatg atcgcgaaaa atggttcaag ttttactcgg atgggctgac caacctgggc    300
tggggtagca gcagtagctt cttttgaacgc ttccaaccca agaatacgga cgtcaccatg    360
gaccaggtcg tactggaggt gatactgaca gtggttaaca acgtcaataa tccggctatac   420 aaaatcgccc aggaaacatt cggcgccttg aacaagcctg ccaatcaaaa acccatgaag    480
ctgtttgacc acagcagcac caaagaagac cgcggcaaat tccagattct gcctgctggc    540
caggaccagc acggcaccgt cagcatggtg ctgaccgcca tcaatgcacg gaccgacatc    600
caatccggca gcttcctgtt ctggaaatgg agcaaatcca ccgcttggct ctaccgcgca    660
gccaacctga ttgtgctcaa tgaatcggtg tactcgaaag tacgccaggc agtcatcgac    720
aagctcggcg ataacgccgt gaactttgtg ctggatctgg atatttaa                 768
```

<210> SEQ ID NO 170
<211> LENGTH: 780
<212> TYPE: DNA
<213> ORGANISM: Alcaligenes sp. HPC1271

<400> SEQUENCE: 170

| | | |
|---|---|---|
| atggctttt ctactgagca aacctatgtg gtgtcaggca atctgatttc tgccaccacg | 60 |
| gaagacacca atacgctgag ctatgaagac tttatccatt ccaacctttt ggcccagatg | 120 |
| ggcgccgata aaaaactggg ctcccgcttt gttgaccccg caggctggct gagtttttc | 180 |
| aaaaatacag taggcaatct gttctggaac ctgagcgagc agggaaccag cacgctgaaa | 240 |
| atctcagccg gtaccgcaag catcaccgtg ctgcaaatac tggagcagag ttttttcaaa | 300 |
| cggctcaacc aagcgcaaat cgatagcgcc acggcaagtg ttgatctgtt tagtcaactc | 360 |
| tctgaagatg atcctgcctt catcctctat aacgcgaaat cacatgccca gatctctgcg | 420 |
| gctaccaagg tgatcaaacc gccccaaaaa gagacttata gcgtcaactt gcaaatcagt | 480 |
| attgcccata cagggtcgga aatcgcactg tgcaatattt tcttccaaac cagccaggca | 540 |
| gtcagcgacg aattattcac acagaaattc gcaatcaaaa atctgattgg aaacattaat | 600 |
| gtgttttatt taaaggctct actctccgag accaattacg gccacatcag caacaagtt | 660 |
| atcgaaaagc tgggtgagaa catcaacacc aatattgtgc tggtagccga taacagcgat | 720 |
| aagccctccc cccccttccccc cacagaggcg cgcagtttca tacgcagcct gaaaatttaa | 780 |

<210> SEQ ID NO 171
<211> LENGTH: 783
<212> TYPE: DNA
<213> ORGANISM: Enterobacter sp.

<400> SEQUENCE: 171

| | | |
|---|---|---|
| atgaatacta acgctttgga ttttgtgctt aaaacaccga ttgaaaccac tgccgatctg | 60 |
| gcaccgttac tggaacgtct aaaggggggta ccggatcatg gtcagtcaaa aagaaaaacc | 120 |
| atgctgactg ataataaagt atctgcacaa gtcaatgccg gcagcctcat ctcatttacc | 180 |
| gaacgtttgg atgggcagaa taaacaagat gtgcagaact caacactgtt cgctcaactg | 240 |
| gcggcggata acactgcaa ccgttatact gcgcccatgg attggtatcg tttttatgtc | 300 |
| aatgtactgg gccaaattgg ctggaaccaa cctgctttcg cgtttgatac ctatacgtca | 360 |
| ggtgccagta ccgtaaaact ggatgaggct gtgttgggga tcattgcgca aatcgctact | 420 |
| gtcggtgagg ttgcattagt ggcagcggca atgaaggcgt tatccagcct gagcgatacc | 480 |
| tcaaagcaaa tgcttatctg ggacgcgaaa tcaaattcgg aaaacaccgg taattttcaa | 540 |
| attttcccgg cagatctgtt accaaatggc gatgtggtaa tgatgcttga tggtatgcaa | 600 |
| tttgatgcaa agcgcaatga ggggcgtttt ctgtgggtaa cctggcaatc cacctcgatc | 660 |
| aaaattcaac gcgcggcaaa taattcgtc ttaaacgaag tgtttataa gggggtgcgc | 720 |
| caggccgtta ttgataaact gggtgatcgg gcaatcgata tgattgcaaa tattgaaatc | 780 |
| tga | 783 |

<210> SEQ ID NO 172
<211> LENGTH: 777
<212> TYPE: DNA
<213> ORGANISM: Pseudomonas fluorescens

<400> SEQUENCE: 172

| | | |
|---|---|---|
| atgagttttg aagtgtgtga cagcagcgtg gccgcctgtg tggcgcgtct ggaaagttat | 60 |

```
gatatctatc cagatatcag tccccgctcg ttgtattcgg gtgatatcga gcctccggcg      120
aaggggtcgg ttgtcggtga aggtatcctg gccttcgccg gtggtctttc ttcgcaacac      180
caggaagatg cgcagcatgc ctttctcttt gcgtccctgg tcgccaacag gcagtaccct      240
ctcgaatccc aggggcgaga gtggtactac aagtttgttg aagtcatgac gaacgccggt      300
tgggtcgcca cgcagcgctt ctacgatgat ctgagcatcg ccggcaacac cgtgcgaatg      360
gacaagctgg tgtttggacat cctgcttcc gtagtgtcgg ggattgccct cggaagcgcg      420
acttcggcgt tgctattgag ggtcgccgac agtgcaatca cggccctgca gaagaaggaa      480
aagaccctga cccttttcga gcgaaacctg ctggaacatg tgtgggcgg aatggcggcc      540 gggacctgtg ttgaaatcga cggtgaggtc agcatgctgc ttggcactgt gcgctttatc      600
cggcgcaaca gcgcgaccca gtcttgtttt gcagattgga acagtcgcga agtgaagttg      660
tataaaggtg agtcggtttt caggaaagtg ccgagtattg tcgagcgaac ccgaggcatc      720
attattggtc ggctgggtaa tcatgccgtc agcaagatcg aagagtacga aatctaa        777

<210> SEQ ID NO 173
<211> LENGTH: 729
<212> TYPE: DNA
<213> ORGANISM: Pseudomonas fluorescens

<400> SEQUENCE: 173
atggacaagg catattcgat ttttgttaac gcggcggcga ttgttttagt ttcctccact       60
gtgcggggaa caggggttga agacctgatg aattcggtct tgctcgcgca attggtggct      120
aacaagaatc tgcagcgcat accaagcgct gattggtacg ctagttatat ggacgtcctg      180
agtgtcgcct gggtagcggg tgccaaacgc cgaaaggacc tgctaccgaa acaagacgct      240
gccagctcgc cagtggagtg ggttacagca ataccttgg acgatcggcc ggaccagcaa      300
cagcagatca tggcggtgtt ggaccgtgtc gccgcgttac ccggctcgct gccggcgctg      360
agtatcctgc gcaagcatat gcaaaaacca acgaacctg agccgacgca gagcccttca      420
gcgtccagcc ccgtgcgctt gttggtgatc gtagcgcaca gccccgtttc gatgaccggt      480
atctgtttgc aattcaacac agggaaagcg atcaatgcca acccttgggg gcaatgcttt      540
gatggaaagg acatcgacgg ttgtgtgtcg gcgcgttatt tgcgcatgca actgagcgaa      600
acattgttcg cgccggcccg tgaggttatc gcccgtaagg tagggactgt cgtgggcgac      660
aacgtggtgg atatcaccgg ggctatcgag gattcggttg ttcgtcctgc cgaggaggtc      720
gggcgatga                                                              729

<210> SEQ ID NO 174
<211> LENGTH: 777
<212> TYPE: DNA
<213> ORGANISM: Pseudomonas brassicacearum

<400> SEQUENCE: 174
atgagttttg aaatgtgtga tagcgctgta gccgcctgtg tggcgcggtt ggaaagttat       60
gatatttacc ctgatgtcag tcctcgttcg ttgtatgtgg acgatgttga gccaccggcg      120
aagggatcgg ttgtcggtga aggcatcctg gcgttcgccg gtggtctttc tccccagcat      180
caagaggatg cgcagcatgc ttttctcttt gcttccctgg tcgccaacag gcaataccct      240
ctcgaatccc aaggacgaga gtggtactac aagtttgttg aagtcatgac gaacgccggt      300
tgggtcgcta cgcagcgctt ctatgatgac ctgagcgtcg cggtaacac cgtgcggatg      360
```

```
gacaagctgg tgttggacat cctcgcctcc gtagtgtcgg gtattgccct cggaagcgcg    420
acttcggcgt tgctgttgag ggtcgtcgac agtgcaatca ctgccttgca gaagaaggaa    480
gagaccctga ccctttttga gcgaaacctg ctggagcatg gggtaggcgg aatggcagcg    540
ggtacctgtg tcgaaattga cggtgaagtc agcatgatgc ttggcaccgt gcgctttatc    600
cggcgcaaca gcgcaaccca ggtcttgttt gcggattgga atagccgcga agtgaagtta    660
tataaaggcg agtcggtttt tcgaaaagtt ccaagtgttg tcgagcgaac tcgagatatc    720
attattgggc ggctgggtaa tcatgccgta agcaagatcg aagagtacga aatctaa      777
```

<210> SEQ ID NO 175
<211> LENGTH: 729
<212> TYPE: DNA
<213> ORGANISM: Pseudomonas brassicacearum

<400> SEQUENCE: 175

```
atggataagg aatattcggt ttttgttaac gctgcggcga ttgttttagc gccctgcgca     60
ctacggcgca cggaagttga cgacctgatg aattcggtct tgctcgcaca actggttgct    120
gataagagtc tgctgcgtgc accagcggtt gattggtacg ccacttattt ggaggtcttg    180
agtgtcgcct ggatatcagc tgccaaaagg cgaaaggatc tgcagccgca aaagaagat     240 acccattcgc cattggagtg ggtggcggcc atcccttgg atgatcaggt ggatcagcaa     300
cagcggatca tggcggtgat ggagcgtatc gcagcgttac ccggctcgct gcctgcgatg    360
gggattgtgc gcaagcatgt gcaaaaacaa tacgagcctg acgcggcaca gagcccgtca    420
tcttccagcc ccgtgcgctt gctggtgatc gtggcgcaaa gccctgtttc gatggctggt    480
gtctatttgc aattcaacac agcgaaagtg atcgaggcca atccttggag gcagtgcttt    540
gatggcaaag acatcgacgg ttgtgtgacg gcacgttatt tccgcacgca actgagcgaa    600
acattgttcg cgcctgcccg tgaggttatc gcccgtaagg tcgcggctgc cgtgggtgac    660
aacattgtcg atatcaccaa ggctatcgat gattcaggtg ttcttcctgc cgaagaggtc    720
tgcagatga                                                           729
```

<210> SEQ ID NO 176
<211> LENGTH: 792
<212> TYPE: DNA
<213> ORGANISM: unknown
<220> FEATURE:
<223> OTHER INFORMATION: Switchgrass rhizosphere microbial community
      from Michigan

<400> SEQUENCE: 176

```
atgagtgtaa atatgatcga tagtgctact gttgctgcct gtgtaaggcg tctggaaagt     60
tacgaaattg atgaagtgcc agttgtacgt tctcgtgcat ttgctgcaag tgggattgtt    120
gttgaggagc cttcgaaggg ggctgtcgtt ggcgaaggca ttttgtcctt cgtaggcaac    180
ctgtccgagc aaaatcaagt agatgcgatg cacgcctttc ttttttgccag ccttgttgcg    240 aataagcaat ttccttacga gtatcagggc aaggaatggt actacaagtt tgtcgaagtt    300
atgacctccg ccggttggct gacgagccaa aaatattaca cgacattga aattagcgga     360 aataccgttc ggatggacca gttggtactg gaaatccttg gctcggtggt cgctggcctc    420
gctataccag gcactgcttc tgcactgatg ctgaaggttg ccggtgatgc cattaccgcc    480
ttgaaaaaga aagaaacggc tttaacgctg tatgaacgga atttgttgga acatggcgta    540
ggcggtatgg ctgcaggaac ctgtaccgaa gtcaatggtg aggtaaccct ggcactaggg    600
```

```
actgtacgtt ttattcgcaa aaatacagca acccaagtcc tgttcatgga ttgggatagt    660
cgtgatgtgc agctgtataa aggtgaatct gttttcagaa aggttcctta tatcgctgac    720
caaacccgag acctgattcg gacaaaactt gggacgaatg cagtcagtaa aatcgaaggc    780
tacgagatct ga                                                        792
```

<210> SEQ ID NO 177
<211> LENGTH: 729
<212> TYPE: DNA
<213> ORGANISM: unknown
<220> FEATURE:
<223> OTHER INFORMATION: Switchgrass rhizosphere microbial community
      from Michigan

<400> SEQUENCE: 177

```
atggcaaggg aatattcggt atttgttaat gccgctgcta tcgttttatt gccgagcaat     60
cccgtggagt cagcaactaa cgacctgatg aattcagtcc tgcttgcaca actggtcgcc    120
aataagcgtg ccgaagccac gagcgcggtc gattggtatg agacctatgt gggggtgctg    180
ggtgatttct ggttaacgag ggccagaagc aggcaagata tccagccggg aaaagacgat    240
accgcttcac cgcttgaatg gatcgctgcg gtgctggcaa gtagcactga ggatgaggcg    300
cggctggtga cggcgttgtt gaagggtatc gcacgactat ccgattcttt gcccgcgatg    360
agtttgctgc gcaagcatgt gcaaaaagag tccgatgatg aaccggcaga aatctccttg    420
cagtccaagc ctgttcgctt ggtcgtgatc gtggcccaag acaacgcttc gatgaccagc    480
gtctgcctcc aattcaaaac acggcaaatg cttgacccca atccctgggg gcagcgcttc    540
catgtcgagg atatggaggg ctgcgtttcg gcccattttt tccatgcgca cctgtccgag    600
acattgtacg cgcccgcccg tgaagcggtc gcccgcaagg ttgagggcgt tttgagcgac    660
aacatcgtgg atatcacgga ggccatcgat gctttggcct ttctgcccac tgaggaggct    720
ggcacatga                                                            729
```

<210> SEQ ID NO 178
<211> LENGTH: 786
<212> TYPE: DNA
<213> ORGANISM: unknown
<220> FEATURE:
<223> OTHER INFORMATION: Miscanthus rhizosphere microbial communities
      from Kellogg

<400> SEQUENCE: 178

```
atgaatgttc atgatgtcga agattgcact gtagccgaat gtattcatcg tttggaaagt     60
tatgagctgg acggcgctga agttatgcgc cctcgcagtt tctcggtacc ggttgtcaat    120
gaacccggca aggttccat cgtgggtgag ggcatcttgt cctttaccgg caacctgagt     180
gagcaaaatc gggaagatgt tcaacacgct tttctattcg cgagtctggt cgcaaacaaa    240
aagtacccgt atgagtatca gggtaaggaa tggtattacc agttcctgga agtcatgacc    300
catgcaggct ggctgccgac cagtaagtac tacaacgaca tgaacatcag cggtaacacc    360
gtacggatgg atcaattggt gctggagatc ctcggcagtg tggttgccgg gcttgccgtg    420
cctggctccg cctccgtcct gatgctgaag gtggcaggcg atgcaatcac cgcattgaaa    480
aaacgtgaaa ccgcgttgac cctgtatgag cgcaacatgc tggagcacgg tgtgggtggt    540
atggcggccg gcacctgcac cgaagtcaac ggtgaagtca ccatggcatt gggtactgtt    600
cgtttcatcc gcaagaacac cgcaaagcaa gtgctgttca tggattggga ctcccgcgag    660
gtgaaactgt atcgcggtga ctctgtcttc aggaaagtgc cttatatcgt cgagcaaacc    720
```

```
cgcgacacga ttcgtgcaaa acttggtttg aatgcgaaac caaagatcga agattacgac    780
atctga                                                               786

<210> SEQ ID NO 179
<211> LENGTH: 723
<212> TYPE: DNA
<213> ORGANISM: unknown
<220> FEATURE:
<223> OTHER INFORMATION: Miscanthus rhizosphere microbial communities
      from Kellogg

<400> SEQUENCE: 179
atgagttacg aatattctgt attgatcgtt ggggcttgtg tcgtgattat tccggccgcg     60 gatgggcgg cccaatatac ggatctggtc aattccgtgt tgctggcgca actgattgcc    120
aataagaaga tcgaaaaagc tccggaaatt gactggtaca acgcttatgt agaatttctg    180
gatgattact ggctgcgacg tacaagagcg cgacaggatt ggtctatcgc caagacaga    240 gtcgagtctg tcagcgactg ggtcattgca gcgatttcac aagatgctgt ggataaagga    300
agcgctactg cggcaacatt gcagcggctg gcaaggttgt ccggcaacga gcctgcaatg    360
ggtttgctgc gcggtcacat gcagaaaata tccactgacg agtcgggtga tgtacttgcg    420
cccgcaaagg ctgtgcgttt gctggtggtt atcgcgcaga cgccgacatc ggtcgcaagc    480
gtctacatcg agcttaagac ccgccagatc atcagtgcca atccgctggc ccagcgacat    540
ctggctgagg atgtacaagg cagcgtttgc atgcgctacg ccgctgctaa cttgtccgaa    600
actctctaca gccctgtgcg cgacgccatt gccttgaagg tcaggacaa gtatcaggac    660 aacgtagcga tgttgacatt gagcgatgat gcttcggcca tggagatctg tgcggtagat    720
tga                                                                  723

<210> SEQ ID NO 180
<211> LENGTH: 1668
<212> TYPE: DNA
<213> ORGANISM: Pseudomonas rhodesiae

<400> SEQUENCE: 180
atggccaaac tcacgcaatt ttccaccccc gccgacatcc aggacttcag tgacagcccc     60
gcccagcaag agcggatgaa cgccgcctgg agcggcaaca tcaatcgctg ggtcaacgca    120
gcactggtgg gcgacgtctg ggacctgatc aactacggcc cgcgcccggc cttctacaac    180
cctctggaca ccgacacccc gagcacctcg gtgaatgccc ccatcacctg gaacgccttc    240
cccgggcgca tccccgcgtt gttccccaac cagtcggcga actggctgca atgggccgac    300
cagggcgtgc cggccaacgt caccaccaac ctctgcaccc aacagagcgt ccccccggcg    360
ccctactcgc ccaccggccc ccggggctgg caggacgaat actgtgaatg gagcgtgacc    420
cgcaacgccg ccgggcagat caccagcgtg atgttcacct gtgagaaccc ggaatactgg    480
atgaccctgt ggcaagtgga cccgggcaaa gtgctgcagc gctaccagca gttgatcaac    540
ccggcggtgc aactggccga cctgagcctc aaggacgccc agggccaaac ggtgatcgac    600
ccggtgaccg gagcgccgtg ctacaacccg ctgaacaagt ggaacagcgg cacccagacc    660
ctgcccggca gcggcggcgc catgcacctg accagctcgc ccaacaccct gggtgccgag    720
tacgacctgg cagcggccgc gaccatgccc cgggagctga caacgaaccc ggtgacctcg    780
gcctcgcaac tggtgtgcta cgcccgttac gggcgcatcg gccgcacag cgacccgacc    840 atcggccaga acgtcaacca gtacgtcaac tacacctccg ggctgaccga ggtccgggcg    900
```

```
accctgacca acccgccggg tctgtacatc cagaccccgg acttcagcgg ctacaccacc      960
cccgacggca gcccggcggc ggcctgctgg accatcaacc gaggccacct ggcgcagacc     1020
tcggacgaca tcgaccgcat cctccacgcg accttcagcg tgcccgcggg caaaaacttc     1080
accgtcagcg acatcagcat caacggtgca aaaatccagt acgcctcgca gatcgccggc     1140
accatcacca tgggcttgat ggccacggtg tttggcaaca gcggcgtgac ccagcaaccg     1200
gtggccggca ccctggacag cgacaacccc agcccgtcgg tatcggcgct gcaaccgctg     1260
tcggtgttca acgcctaccg ggcccaggaa ctggccagca cgagcaggc gctgtcgatt      1320
ccaatcctgg ccctggccat ccgccccgga cagcaagtgg acaacatcgc cttgctgctc     1380
aacaccagcc agaccccgaa cggcgccagc ttcagcgtgg tcgaaggcgg cgtcagcatc     1440
agcatcaccg gcacccagga cctgccgggg ttggacatga gcctgtacct ggtgagcatc     1500
agcgccgacg ccaacgccgc cccgggggat cgcacggtcc tcgccagcgt gcctggcatg     1560
gccagcaccc aacaggcggc gatcggcctg ctgaccgtcg gcggcccaac cctggtcacc     1620
tcccagaccg gcccgagcaa gccgaacttc cgtcgcggtc gcggctga               1668

<210> SEQ ID NO 181
<211> LENGTH: 1356
<212> TYPE: DNA
<213> ORGANISM: Pseudomonas rhodesiae

<400> SEQUENCE: 181
atgcgccgtc gtcccacggt gttactcggc ctggccctgc tactcggttt accggccacc       60
caggccatgg gcgcgccgct gtgcggcagc ccgttcgtcc cctcgccgac cctgcaaccg      120
acactcgccc ccccaatttt cagcgccagc gacagcgcgg tggactgctt catgtggcaa      180
accatggtct acctcaactg gccggccacc ccaggccaac ggggcgtacc gaatgccgcc      240
gccagcctgg gcagcccggg ccccagcgtc tggcagacct acaaggatta caacgagctg      300
tacctgccca atgccagcaa ccgccagccc tggaacgaca acttcctgtc ggtgcagcgc      360
ttgcagaccc gaggcgtggc acgggcgttg ccgtcgatcc gcctgcttaa cagcaccagc      420
aaggtctttc gcgccgccaa tgccaacgaa tccccgcgc tacgggaaat cgagcaggtc       480
ggcggcggcg tgctctacga ccaggccggc agcccggtgt actacgaaat gctggtgaat      540
gaggtcaact tcgacttcat ctacaacaac cagctgtaca ccccgcccca gcagaacctc      600
tatgccaagc aaaaaggcat cgtgctgccg aacaactcca tcgagatcaa ggccgcctgg      660
aaggtgctga gcgacccgga taaccccag cgctttctca ccgcccaagc gttgctgccc       720
ggcagcagca cgccggtgac cgtgggcctg tcgggctgc atgtgttcca gatgccttcc       780
agcgcgttca accaggggtt ctgggcgacc ttccagcagc tcgacaacgc cccacggtg       840
gccggcgcca ccccaggggc gcactactcg ttcaacaacc gcagtgcgc gccggcccag      900
tgcccgccca atgacaaaac cagcaatccg acccaggtgg tgcagaactt cccgccgacg      960
ccagaggcgc agaacatcaa ccactacatg cagaacctga tcgcccagca ggccccgggc     1020
tccgcgttgc agtactacca gttggtggac gtgcaatggc cgacttcgcc acaagccatc     1080
ggtcagcccg gggccacggc gccggcgccc agtggcacgc cgaaccacga cacctgatc      1140
aacccggtgc tggaaaccctt tctccaggcc aatcacaaga gctgcctggg ttgccatgtg     1200
tacgccagcg tggcggcgga cggcagcaac ccgcccaccc actaccaggc cagcttcagc     1260
ttcctgctgg gccacgccaa aagcccggcc ctgggaagca acctgaaaag cctggcgcaa     1320
```

| | |
|---|---|
| cagatcgagg acgcgtccct gagcctgcaa cactga | 1356 |

<210> SEQ ID NO 182
<211> LENGTH: 1668
<212> TYPE: DNA
<213> ORGANISM: Pseudomonas orientalis

<400> SEQUENCE: 182

| | |
|---|---|
| atggccaaac tcacgcaatt ttccaccccc gccgacatcc aggacttcag tgacagcccc | 60 |
| gcccagcaag agcggatgaa cgccgcctgg agcggcaaca tcaatcgctg ggtcaacgcg | 120 |
| gcactggtgg cgacgtctg ggacttgatc aactacggcc cgcgcccggc cttctacaac | 180 |
| cctctggaca ccgacacccc gagcacttcg gtgaatgccc ccatcacctg gaacgccttc | 240 |
| cccgggcgca tccccgcgct gttccccaac cagtcggcga actggctgca atgggccgac | 300 |
| cagggcgtgc cggccaacgt caccaccaac ctctgcaccc agcagagcat ccccgcggcg | 360 |
| ccctactcgc ccaccggccc ccggggctgg caggacgaat actgtgaatg gagcgtgacc | 420 |
| cgcaacgccg ccgggcagat caccagcgtg atgttcacct gtgagaaccc ggaatactgg | 480 |
| atgaccctgt ggcaagtgga cccgggcaaa gtgctgcagc gctaccagca gttgatcaac | 540 |
| ccggcggtgc agttggccga cctgagcctc aaggatgccc agggacaaac ggtgatcgac | 600 |
| ccggtgaccg gagcgccgtg ctacaacccg ctgaacaagt ggaacagcgg cacccagacc | 660 |
| ctgcccggca gcggcggcgc catgcacctg accagctcgc ccaacaccct gggtgccgag | 720 |
| tacgacctgg cagcggccgc gaccatgccc cgggagctga caacgaacc ggtgacctcg | 780 |
| gcctcgcaac tggtgtgcta cgcccgttac gggcgcatcg gccgcacag cgacccgacc | 840 |
| atcggccaga acgtcaacca gtacgtcaac tacacctccg ggctgaccga ggtccgggcg | 900 |
| accctgacca cccgccgggg gctgtacatc cagacccccgg acttcagcgg ctacaccacc | 960 |
| cctgacggca gcccggcggc ggcctgctgg accatcaacc gaggccacct ggcgcagacc | 1020 |
| tcggacgaca tcgaccgcat cctccacgcg accttcagcg tgcccgcggg caaaaacttc | 1080 |
| accgtcagcg acatcagcat caacggtgca aaaatccagt acgcctcgca gatcgccggc | 1140 |
| accatcacca tgggcttgat ggccacggtg tttggcaaca gcggcgtgac ccagcaaccg | 1200 |
| gtggccggca ccctggacag cgacaacccc agcccgtcgg tatcggcact gcaaccgctg | 1260 |
| tcggtgttca cgcctaccg ggcccaggaa ctggccagca cgagcaggc actgtcgatt | 1320 |
| ccgatcctgg ccctggccat ccgccccggg cagcaagtgg acaacatcgc cttgctgctc | 1380 |
| aacaccagcc agaccccgaa cggcgccagc ttcagcgtgg tcgaaggcgg cgtcagcatc | 1440 |
| agcatcaccg gcacccagga cctgccgggg ctggacatga gcctgtacct ggtgagcatc | 1500 |
| agcgccgacg ccaacgccgc cccggggat cgcacggttc tcgccagcgt gcctggcatg | 1560 |
| gccagcaccc aacaggcggc gatcggcctg ctgaccgtcg gcggcccaac cctggtcacc | 1620 |
| tcccagaccg gcccgagcaa gccgaacttc cgtcgcggtc gcggctga | 1668 |

<210> SEQ ID NO 183
<211> LENGTH: 1356
<212> TYPE: DNA
<213> ORGANISM: Pseudomonas orientalis

<400> SEQUENCE: 183

| | |
|---|---|
| atgcgccgtc gtcctacggt gttactcggc ctggccctgc tactcggctt accggccacc | 60 |
| caggccatgg gcgcgccgct atgcggcagc ccgttcgtcc cctcgccaac cctgcaaccg | 120 |
| acactcgcca accccaattt cagcgccagc gacagcgcgg tggactgctt catgtggcaa | 180 |

| | |
|---|---|
| accatggtct acctcaactg gccggccacc ccaggccaac ggggcgtacc gaatgccgcc | 240 |
| gccagcctgg gcagcccggg ccccagcgtc tggcagacct acaaggatta caacgagctg | 300 |
| tacctgccca atggccagca accgccagcc tggaacgaca acttcctgtc ggtgcagcgc | 360 |
| ttgcagaccc gaggcgtggc acgggcgttg ccgtcgatcc gcctgcttaa cagcaccagc | 420 |
| aaggtctttc gcgccgccaa tgccaacgaa tccccggcgc tacgggaaat cgagcaggtc | 480 |
| ggcggcggcg tgctctacga ccaggccggc agcccggtgt actacgaaat gctggtgaat | 540 |
| gaggtcaact tcgacttcat ctacaacaac cagctgtaca ccccgccca gcagaacctc | 600 |
| tatgccaagc aaaaaggcat cgtgctgccg aacaactcca tcgagatcaa ggccgcctgg | 660 |
| aaggtgctga gcgccccgga taaccccag cgctttctca ccgcccaagc gttgctgccc | 720 |
| ggcagcagca cgccggtgac cgtgggcctg gtcgggctgc atgtgttcca gatgccttcc | 780 |
| agcgccttca accagggatt ctgggcgacc ttccagcagc tcgacaacgc ccccacggtg | 840 |
| gccggcgcca gccagggggc acactactcg ttcaacaacc gcagtgcgc gccggcccag | 900 |
| tgcccgccca atgacaaaac cagcaatccg acccaggtgg tgcagaactt cccgccgacg | 960 |
| ccagaggcgc agaacatcaa ccaatacatg cagaacctga tcgcccaaca ggccccgggc | 1020 |
| tccgccttgc agtactacca gttggtggac gtgcaatggc cgacttcgcc acaagccatc | 1080 |
| ggtcagcccg ggccacggc accggcgccc agtggcacgc cgaaccacga caccctgatc | 1140 |
| aacccggtgc tggaaacctt cctccagacc aatcacacga gctgcctggg ttgccatgtg | 1200 |
| tacgccagcg tggcggcgga cggcagcaag ccggccaccg actaccaggc cagcttcagc | 1260 |
| ttcctgctgg gccacgccaa aagcccggcc ctgggcagca acctgaaaag cctggcgcaa | 1320 |
| cagatcgagg acgcgtccct gagcctgcaa cactga | 1356 |

<210> SEQ ID NO 184
<211> LENGTH: 1671
<212> TYPE: DNA
<213> ORGANISM: Pseudomonas sp. PKRS11

<400> SEQUENCE: 184

| | |
|---|---|
| atggccaaac tcgcgcaatt ctcgcctccc gcccgtatcc aggacttcag caacgacccc | 60 |
| gcccagcagg agtgtttgaa cgctgcctgg agcggcaaca tcaatcgctg ggtcaacgcc | 120 |
| gccctgctgg gggacgtctg ggatcgaatc aattacggac cgcgcccggc gttctacaat | 180 |
| ccgttggtga ccgataccc cgacaccgcg ggcaatgtgc cgatcacctg gaacgccttc | 240 |
| cccggccgcc tgcaagcgct gtttccgaac cagggcgcgt cgtggcaaca gtgggccgac | 300 |
| cagggcgtgc cggataaagt caccaccgac ctctgcagcg gcaagcccat tgacccggcc | 360 |
| ccctactcgc ccaccggtcc acggggctgg caggacgaat actgcgaatg gagcgtgacc | 420 |
| cgcaacggtg ccggacagat caccagcgtg atgttcacct gcgaaaaccc cgagtactgg | 480 |
| atgaccctgt ggcaggtcga tccgggcaag gtgctgcaga tctaccagca ggtgatcaac | 540 |
| ccggcggtgc aactgtcgga cctgtgcctg aaagacagcc atggccagac ggtcaacgat | 600 |
| ccgctcaccg gccagccgtg ctacaacccg ctgaacaaat ggaacagcgg caccgcacc | 660 |
| ctggcgaaca gcggtggcgc catgcacctg accagctccc ccaataccct cggcgcggaa | 720 |
| tacgacctgg ccgccgcggc caccatgccg cgcgaaaagg accacgaccc ggtgacctcg | 780 |
| gccgcagccc tggtgtgctt tgcccgctat ggccggatcg gccgcacag cgatccgacc | 840 |
| attggccaga acgtcaacca gtacgccaac tacaccccga ccctaccgca tccccaggcc | 900 |

| | |
|---|---|
| accctcgccg acccctccggg gctgtacatg cagaccccgc agttcagcga ctacgtcacc | 960 |
| cccgacaaca ccccggcgca gactttctgg accgtggtgc gtggcagcct gaaagacccg | 1020 |
| aatacgtccg aggacatcga tcgcatcctg cacgccacct tcagtgtccc tccggaactg | 1080 |
| ggctacaccg tcagcgacat caagatcggc aaccagccga tccggtacgg ctcgcagatc | 1140 |
| gccgccacca tcaccatggc cctgctggcc acggccttc ccaacagtgg agtggtgcag | 1200 |
| accccggtcg gcgcgacgct cgacaactcg aaccccagcc cctcggtcag cgccctgcag | 1260 |
| gcacttgcgg tgttcaccgc gtaccgggcc caggagctgg ccagcaatga caaccgctg | 1320 |
| tcgataccgg tactggctct ggccgtcagt ccggggcagc aggtgagcaa tatcgccctg | 1380 |
| ctgctcaaca ccagcgacac cccggatggc gcggtgttca cggtgcccga aggcggggta | 1440 |
| agcatccgta tcgacggcac ccaagcgcta cccaatgcgg agctgagcct gtatcaggtg | 1500 |
| acgctgtgcg tcgacgccaa tgccgccatc ggcgaccgca gcatcctggc cagcgtgccg | 1560 |
| agcatgccag ccacccaaca ggcggccatc ggcctgctga cggtcgtcgc cccgccccag | 1620 |
| gtccggcttg ccggcggacc gcgcaaacct cacgcccgtc acagtcgcta a | 1671 |

<210> SEQ ID NO 185
<211> LENGTH: 1350
<212> TYPE: DNA
<213> ORGANISM: Pseudomonas sp. PKRS11

<400> SEQUENCE: 185

| | |
|---|---|
| atgcgtgcca ttctcgccct cttgctgtac gccggattgt cgctggcgcc ggtcgcggcc | 60 |
| cgggccgccg gcaatccctg tggcagcccc ttcagcccgg aaccggtcat ccagccggtc | 120 |
| ctggccaacc cgcagataag caacctggac ccgtcggtgg actgcttcat gtggcaaacc | 180 |
| atggtctacc tcaactggcc ggccaggcc ggccagcgtg gtctcccaa taccgacgcg | 240 |
| cacctgggcg accccggccc cacggtctgg caaaccttca aggacttcaa cgaactctac | 300 |
| ctgcccggtg gccagcgccc ggccccctgg aacgacaact tcctcaccat gcaacgcctg | 360 |
| gaattgcgcg gcgtggagcg gccaaggcca tcgatccgcc tgctcaacag caccagcaag | 420 |
| gtgtttcgca atgccgatgc cagcgaacaa aaggccctgg acgaattcaa gcaagtgggc | 480 |
| ggcggcgtgc tctacgacca gaacggccag ccggtgtact acgagatgct gatcaaccag | 540 |
| atcaacttcg attacatcta cagcaatcag ctgtacaacg ctgcccagca gaatctccac | 600 |
| gccgccaagc agggcatcgt cctgcccagc aactccatcg aactcaaggc ggcctggaaa | 660 |
| gtcctcagcc ccaggaagc cgcgccgccc ttgcgctttc tcactgccca ggccctgctc | 720 |
| ccgggcagcc aggtgccggt taccgtcggc ctggtgggcc tgcacgtgtt ccagatgccc | 780 |
| tccaaggact cgcccaggg cttctgggcg acctttcc aggtggacaa cgcccccacc | 840 |
| ctgaatacac ctggccaggc ccattactcg ttcaataacc cgcagtgcag ccagtgtccg | 900 |
| gtcaacgacc ttggcagcaa gccgacgcag gtggtgcagg tccaggccaa cgccgtctac | 960 |
| gcccaggccg tcaaccagta catgcaggcg ctgatccagc agcaggcgcc gaactcggcc | 1020 |
| ttgcagtatt accaactgat caacgtgcag tggcccaact catcggtacc catcggccag | 1080 |
| cccggccagc cgacacctgc gccaaccggc agccccgagca ccgacaccct ggtcaatccg | 1140 |
| gtgctggaaa cctttatgca ggtcagcaac atgagctgcc tgggttgcca caagtccgcc | 1200 |
| agcgttgccg acaatggcac gcagccgccc agcggctatc aggcaagcta cagtttcctc | 1260 |
| ctgggccacg cccagaaccc gccgccgcaa ggcagcctca agagccttgc gcgacaggtg | 1320 |
| gaagaagcct cgacagcccg tcaacggtag | 1350 |

<210> SEQ ID NO 186
<211> LENGTH: 291
<212> TYPE: DNA
<213> ORGANISM: Pseudomonas Antarctica

<400> SEQUENCE: 186

```
atgaaattat caaatgtctt actattgagt atcgtatttg cttggcaagg catggccttc      60
gccgatacac agaagtctaa tgccgaaacc ttgttatcta acgacaaacc accgctaaca     120
caggcggcgc aggagaagga acaagaaaat gttgaggctg accggaatga atgttggtcc     180
gctaagaatt gttctggaaa gatcctaaac aataaagatg cgcacaactg taaattatcc     240
ggcggtaagt catggcggag caagactaca gggcaatgca ctaatctttt a              291
```

<210> SEQ ID NO 187
<211> LENGTH: 291
<212> TYPE: DNA
<213> ORGANISM: Pseudomonas orientalis

<400> SEQUENCE: 187

```
atgaaaatgt ccagcgtctt actgatgagt attgcgtttg tatgtcaagg catggtcttc      60
gctgatacac agaagtccaa tactgaaacc ttgttttcca acgacaagcc accgctgata     120
cagacggccc aagagcagga acaaaaagag gttgaggttg accgcaatca atgttggtcc     180
gccaagaatt gctctggaaa gatcctgaac aataaagatg cacataactg taagttgtcc     240
ggcggtaagt cttggcggag caagactaca gggcagtgca ccaatctgta g              291
```

<210> SEQ ID NO 188
<211> LENGTH: 288
<212> TYPE: DNA
<213> ORGANISM: Enterobacter asburiae

<400> SEQUENCE: 188

```
atgaaaacac tcgttatcgc aattctcacc gctgttcttt gccagggcat ggcgatggct      60
gatacacaga aaccagcaac cggggctttg ccagcaaatg aaaaaccccc tctcgttcag     120
ccagctgacg aacataaaac gagcgaggca atgccaatc gtaatgaatg ctggtcagca     180
aaaaattgta ccggaaaaat ccttaataat aaggatgcgc ataattgcaa aaactccggg     240
ggtaaatcat ggcggagtaa aaccaccgga cagtgtacca atctttga                  288
```

<210> SEQ ID NO 189
<211> LENGTH: 288
<212> TYPE: DNA
<213> ORGANISM: Enterobacter sp.

<400> SEQUENCE: 189

```
atgaaaacac tcgttatcgc aattcttacc gctgttctgt gccagggcat ggcgatggcc      60
gaaacgcagc aaccggcatc cggggctttg cctgccaatg aaaagccgcc cctggtgctg     120
acggccgacg aaaaaaaagc gagtgaggct aatgccgaca ggaatgaatg ctggtcggcc     180
agaaattgta gcgggaaaat ccttaataat aaggatgcgc ataactgcaa aaactccggg     240
ggtaaatcct ggcggggtaa aaactccagc cagtgcacca atctttaa                  288
```

<210> SEQ ID NO 190
<211> LENGTH: 318
<212> TYPE: DNA
<213> ORGANISM: Acidovorax avenae

<400> SEQUENCE: 190

```
atgaaaaagc tgttgctcat cgcttcgtta ctcgtttcca tttccggtgc gaatgtgttc    60
gcccaggcac cgtcatccgg cgatgctccc gcagccgtcg cgggcaagca ggatggggcc   120
tcgcacaaag acacggaaca ggcggccaat gtggaatgcg acgtcaatgc gaccgtccag   180
cagtgctgct ctgccgccaa atgccagggg aaagtgctca gcaatcgcga tgcccacaac   240
tgcaaggaca gtccaagggg caagagctgg catgcggcgg cgcaagggga cagcccgct   300
gcgtgccagc ggatgtaa                                                  318
```

<210> SEQ ID NO 191
<211> LENGTH: 285
<212> TYPE: DNA
<213> ORGANISM: Serratia plymuthica

<400> SEQUENCE: 191

```
atgcagtgta atggggctat tttaaagttg ttgtgcgcgc aacgaaaaga ccaatttatg    60
aacttacgca taaggacaca tgctatgaaa aatttgtcga ttttagttgt tctatcttcc   120
tgcctcttac ttcctttaac cgcgtctgcg gctgctggta cgtgctatag tgcgaagaac   180
tgctccggta aagtgttaag ccatcgagat gcacataact gcaaggtcaa ggataagggt   240
aagtcttggc gcagtgatat cacaaatcaa tgtaccaacc tgtga                  285
```

<210> SEQ ID NO 192
<211> LENGTH: 282
<212> TYPE: DNA
<213> ORGANISM: Serratia liquefaciens

<400> SEQUENCE: 192

```
atgcgtgagg aggctatttt aaagttgttg tgcgcgcaac gaaaagacca atttatgaat    60
tcacgcataa ggacacatgc tatgaaaaat ttgtcgattt tagttgttct atcttcatgc   120
ctcttacttc ctctaactgc gtcggcggcg tccggtaagt gctacagtgc taagaactgt   180
tctggaaaag ttttaagcaa aagagacgcg cataactgca aggtcaagga tcggggcaaa   240
tcttggctta gtgatgtcac aggcaaatgt accaacctgt ga                     282
```

<210> SEQ ID NO 193
<211> LENGTH: 237
<212> TYPE: DNA
<213> ORGANISM: Serratia sp.

<400> SEQUENCE: 193

```
atgaaactta aatatgaacg aataaggata tatgttatga aaagtctatc gattgttatt    60
actctcgctt catgcttact gctacctctg actgcgtctg cggccgcagg cacatgttat   120
agcgcaaaga actgttccgg gaaggtgctt agccaccggg atgcccataa ctgcaaggtt   180
aaggacaaag gtaaatcctg gcgcagtgat attacaggcc aatgcacgaa tctttga     237
```

<210> SEQ ID NO 194
<211> LENGTH: 228
<212> TYPE: DNA
<213> ORGANISM: Serratia sp.

<400> SEQUENCE: 194

```
atgaattcac gcataaggac atatgctatg aaaaatttgt cgattttagt tgtactatct    60
tcatgcctct tactccctct aaccgcttct gcagctgctg gcacatgcta tagcgcaaag   120
aactgctctg gaaaagtttt aagccatcga gacgcgcata actgcaaggt caaggacaag   180
```

```
ggtaaatctt ggcgcagtga tatcactggc aagtgtacca atctgtaa        228
```

<210> SEQ ID NO 195
<211> LENGTH: 270
<212> TYPE: DNA
<213> ORGANISM: Pseudomonas chlororaphis

<400> SEQUENCE: 195

```
atgtcggctc aagagaactt tgttggcgga tggactcctt atcacaaact gaccccaaag    60
gatcaggaag tattcaaaga agccctggcc gggttcgtgg gtgtgcagta cacacctgaa   120
ctggtttcga cccaggtcgt caacggcacg aactatcgct atcaatcgaa agcgacgctg   180
cctggctcgt cggaaagttg gcaagcggta gtggaaatct acgcgcctat caaaggcaag   240
ccgcacatca cccagatcca ccggatctaa                                    270
```

<210> SEQ ID NO 196
<211> LENGTH: 270
<212> TYPE: DNA
<213> ORGANISM: Pseudomonas chlororaphis

<400> SEQUENCE: 196

```
atgtcggctc aagagaactt tgttggcgga tggactcctt accacaaact gactccaaag    60
gatcaggaag tattcaaaga agccctggcc ggattcgtgg gtgtgcacta cacgcctgaa   120
caggtttcaa cccaggtcgt caacggtacg aactaccgtt atctgtcgaa agcaacggtg   180
cctggctcgt cggacagctg gcaagcggtc gtagaaatct acgcgcctat caagggcaag   240
ccgcacatca cccagatcca ccggatctaa                                    270
```

<210> SEQ ID NO 197
<211> LENGTH: 270
<212> TYPE: DNA
<213> ORGANISM: Pseudomonas brassicacearum

<400> SEQUENCE: 197

```
atgtcggctc aagagaactt tgttggcgga tggactcctt accacgaact gactccaaag    60
gatcgggaag tattcaaaga ggccctggcc gggttcgtgg gtgtgcaata cacccctgaa   120
aaagtttcga cccaagtcgt caacggcacg aactatcgtt atctgtcgaa agcaacggtg   180
cctggctcgt cggacagctg gcaagccgta gtggaaatct acgcgcctat taaaggcaag   240
ccgcacatca cccagatcca ccggatctaa                                    270
```

<210> SEQ ID NO 198
<211> LENGTH: 270
<212> TYPE: DNA
<213> ORGANISM: Pseudomonas chlororaphis

<400> SEQUENCE: 198

```
atgtcggctc aagagaactt tgttggcgga tggactcctt accacgaact gactccaaag    60
gatcgggaag tattcaaaga ggccctggcc gggttcgtgg gtgtgcacta cacccctgaa   120
aaagtttcga cccaagtcgt caacggcacg aactatcgct atctgtcgaa agcaacggtg   180
cctggctcgt cggacagctg gcaggccgta gtggaaatct acgcgcctat taaaggcaag   240
ccgcacatca cccagatcca ccggatctaa                                    270
```

<210> SEQ ID NO 199
<211> LENGTH: 270
<212> TYPE: DNA

<213> ORGANISM: Pseudomonas chlororaphis

<400> SEQUENCE: 199

```
atgtcggctc aagaacattt tgttggcgga tggactcctt accacgaact gacgccaaag      60
gataaagaag tattcaagga agccctggcc gggttcgtgg gtgtgcacta caccccctgaa    120
aaggtttcga cccaggtcgt caacggcact aactaccgtt atctgtccaa agccacgctg    180
cctggctcct ctgacagctg gcaggcggta gtggaaatct acgcgccgat caaaggcaag    240
ccgcacatca cccagatcca tcggatctaa                                      270
```

<210> SEQ ID NO 200
<211> LENGTH: 270
<212> TYPE: DNA
<213> ORGANISM: Pseudomonas fluorescens

<400> SEQUENCE: 200

```
atgtcggctc aagaaaatct tgttggcgga tggactcctt accacgaact gactccaaag      60
gatcaggaag tattcgatga agccctggcc gggctcgtgg gtgtgcacta caccgccgag    120
ctggtttcga cccaggtcgt taacggcacc aactatcgtt atcagacgaa agcaacgcag    180
ccgggttcat caaacagctg gcaagcggtc gtggaaattt acgcgcctat taacggcaag    240
ccgcatatca cccagatcat tcggatctaa                                      270
```

<210> SEQ ID NO 201
<211> LENGTH: 270
<212> TYPE: DNA
<213> ORGANISM: Pseudomonas fluorescens

<400> SEQUENCE: 201

```
atgtcggctc aagaaaatct tgttggcgga tggactcctt accacgaact gactccaaag      60
gatcaggaag tattcgatga agccctggcc gggctcgtgg gtgtgcacta caccgctgag    120
ctggtttcga cccaggtcgt taacggtacc aactatcgtt atcaggctaa agcaacgcaa    180
cctggttcgc caaacagctg gcaagcggtc gtggaaattt acgcgcctat taacggcaag    240
ccgcatatca cccagatcat ccggatctaa                                      270
```

<210> SEQ ID NO 202
<211> LENGTH: 270
<212> TYPE: DNA
<213> ORGANISM: Pseudomonas fluorescens

<400> SEQUENCE: 202

```
atgtcggctc aagagaatct cgttggcgga tggactcctt atcacgaact gactccaaag      60
gatcaggaag tattcgatga agccctggcc gggctcgtgg gtgtgcacta caccgctgaa    120
ctggtttcca cccaggtcgt caacggcacc aactatcgtt atcaggcgca agcaacgcag    180
cctggttcgc caaacagctg gcaagcggtc gtggaaattt acgcgcctat taacggcaaa    240
ccgcacatca cccagatcat ccggatctaa                                      270
```

<210> SEQ ID NO 203
<211> LENGTH: 270
<212> TYPE: DNA
<213> ORGANISM: Pseudomonas fluorescens

<400> SEQUENCE: 203

```
atgtcggctc aagaaaatct cgttggcgga tggactcctt atcacgaact gactccaaag      60
gatcaggaag tattcgatga agccctggcc gggctcgtgg gtgtgcacta caccgctgag    120
```

```
ctggtttcga cccaggtcgt taacggtacc aactatcgtt atcaggcgaa agcaacgcag    180
cctggttcac caaacagctg gcaagcggtc gtggaaattt acgcgccgat taacggcaag    240
ccgtatgtca cccagatcat ccggatctaa                                      270
```

<210> SEQ ID NO 204
<211> LENGTH: 270
<212> TYPE: DNA
<213> ORGANISM: Pseudomonas fluorescens

<400> SEQUENCE: 204

```
atgtcggctc aagaaaacct cgttggcgga tggactggct accacgaact gactccaaaa    60
gataaggaag tattcaaaga agctctggag ggactcgtcg gtgtgcatta cacacctgaa   120
ctggtttcga gccagatcgt taatggcact aattatcgct atcaaactaa agcgacccag   180
ccaggctcgt caacgagctg gcaagccatc gtggaaattt acgcgcctat caagggcaag   240
ccgcatatca ctcagatcat ccggatctaa                                      270
```

<210> SEQ ID NO 205
<211> LENGTH: 270
<212> TYPE: DNA
<213> ORGANISM: Pseudomonas rhodesiae

<400> SEQUENCE: 205

```
atgtcggctc aagaaaatct cgttggcgga tggactcctt atcacgaact gactccaaag    60
gatcaggaag tattcgatgt agctctggcc gggctcgtgg gtgtgcacta caccgctgag   120
ctggtttcga cccaggtcgt taacggtacc aactatcgtt atcaggcgaa agcaacgcag   180
cctggttcac caaacagctg gcaagcggtc gtggaaattt acgcgcctat caacggcaag   240
ccgtatgtca cccagatcat ccggatctaa                                      270
```

<210> SEQ ID NO 206
<211> LENGTH: 270
<212> TYPE: DNA
<213> ORGANISM: Pseudomonas sp.

<400> SEQUENCE: 206

```
atgacagctc aagaacatct tgttggtgga tggaccccct accacaaact gactcccaag    60
gatcaggaag tcttcaaaga agcactggcc ggcttcgttg gcgtgagcta cacgcccgaa   120
gaggtttcca gccaagtcgt taatggcacc aactatcgct acaagtcgaa agccacgctt   180 ccggggttcgc caaacggctg gcaagcgatc gtagaaatct acgcgccaac taatggcaag   240
ccgcacatca ctcagatcca tcggatctaa                                      270
```

<210> SEQ ID NO 207
<211> LENGTH: 276
<212> TYPE: DNA
<213> ORGANISM: Pseudomonas fluorescens

<400> SEQUENCE: 207

```
atgtcagctc aagaaaacca cgttggcgtt ggcggatgga ctgcttacca cgaactgacc    60
ccaaaggacc atgctgtatt caagaggcc ttggaaggct ttgtgggggt gcaatacacc   120
cctgagacgg tttcgactca ggtcgtcgcc ggcacaaact atcgctatca ctcgaaagca   180
cagcagcctg gttcgccagc aatctgggca gcaatcgtgg aaatctacgc cccccctcaaa   240 ggtaaaccgc acatcaccca gatcatccgc atctaa                             276
```

<210> SEQ ID NO 208
<211> LENGTH: 279
<212> TYPE: DNA
<213> ORGANISM: Enterobacter-sp

<400> SEQUENCE: 208

```
atgtcggaac aacaaacgct gctgcctggc ggctggacgg cttatcatcc gctgactgct    60
caggaccgaa aagtgttcga agaggcgctc aacgggcatc tgggcgtgga ttacgagcca   120
caaaaggtaa aaacccaggt cgtggccgga acaaactacc gcttcctttg tgaggcttcg   180
gtcccgccgt ctacggccgt ctgggaagcg atagtggaaa tttatgcgcc attaccggga   240
cagggcgccc cgcatattac tcaaattatc agaatttag                          279
```

<210> SEQ ID NO 209
<211> LENGTH: 270
<212> TYPE: DNA
<213> ORGANISM: Shewanella denitrificans

<400> SEQUENCE: 209

```
atgtcaaata atgaaactat cgttggtggt tggacagctt acaacgcaat cacatctgct    60
gaaagagaaa ttttcaataa agccatggag ggttttgttg gtgtaagtta catgccagag   120
acggtttcaa cccaggttgt tgcgggaatg aattatcgtt ttaaatgcga agcgtctatg   180
ccaccatcag aagtgttatg ggaagcaatt gttgaaatat atcagccatt aaagggcatc   240
ccgcacatca caaacatcac aaaaatataa                                    270
```

<210> SEQ ID NO 210
<211> LENGTH: 273
<212> TYPE: DNA
<213> ORGANISM: Aeromonas diversa

<400> SEQUENCE: 210

```
atgtcggatc aagctgtgct ggttggcgga tggactgcat atcacaggct gactgcggaa    60
gaccaagcgg tgtttcagga agcgctgaaa ggatttgttg gggtggagta taagcccttt   120
gaagtttcca cccaggtggt agcgggtatg aactaccgct acaagtgcaa gaccacggta   180
cccttgccga ctccgatcca tggcgaagcc gtggtacaga tcttccagtc gctggacggc   240
tctgcccata tcacctccat cactcccatc taa                                273
```

<210> SEQ ID NO 211
<211> LENGTH: 273
<212> TYPE: DNA
<213> ORGANISM: Aeromonas salmonicida

<400> SEQUENCE: 211

```
atgtcagaac aagcagtgtt ggtgggtgga tggaccgcat atcacaagct gaccgccgag    60
gatcaggcgg tatttgacca ggcgctgaaa ggatttgtcg gggtgcagta cgtacccttt   120
gaagtctgca cccaggtggt ggccggcacc aactaccgct caagtgcaa gagcacagtg    180 ccgcttgcca aaccgatcca tggcgaagcc gtggtgcaga tcttccagtc tctggatggc   240
tcggcccata tcacctccat taccccgatc tga                                273
```

<210> SEQ ID NO 212
<211> LENGTH: 273
<212> TYPE: DNA
<213> ORGANISM: Aeromonas veronii

<400> SEQUENCE: 212

-continued

```
atgtcagaac aagcagtgtt ggtgggtgga tggaccgcat atcacaagct gaccgccgag    60
gatcaggcgg tatttgatca ggcgctgaaa ggatttgtcg gggtgcagta cgtacccttt   120
gaagtctcca ctcaagtggt ggctggcacc aactaccgct tcaagtgcaa gagcactgtg   180
ccgcttgcca aaccgatcca tggcgaagcc gtggtacaga tcttcaaatc actggacggg   240
gatgcccata tcacctccat taccccgatc tga                                273
```

<210> SEQ ID NO 213
<211> LENGTH: 267
<212> TYPE: DNA
<213> ORGANISM: Aeromonas molluscorum

<400> SEQUENCE: 213

```
atgtcagaac aagcagtgct gttgggcgga tggactgcct accacaagct gagcgccaag    60
gatcaggcgg tattcaacca ggcgctggaa ggatttgtcg gggtgcagta cacacccttt   120
gaagtctcca cccaggtcgt cgccggtacc aactaccgct tcaaatgcaa gagcactgtg   180
ccgctgccca accccatcca cggggaagcc gtggtgcaga tcttccaggc gttgtttccc   240
aaatcgatgc agcttgaatg gaactaa                                        267
```

<210> SEQ ID NO 214
<211> LENGTH: 273
<212> TYPE: DNA
<213> ORGANISM: Aeromonas aquariorum

<400> SEQUENCE: 214

```
atgtcagaac aagcagtgtt gttgggcgga tggactgcct accacaagct gagcgccaaa    60
gatcaggccg tattcaacca ggcgctggaa ggatttgtcg gggtgcagta cacccccttt   120
gaagtctcca cccaggtcgt cgccggcacc aactaccgtt tcaaatgcaa aactactgtg   180
ccgctgccta acccgatcca cggagaagcc gtagtgcaga tcttccagtc gctggatggc   240
tcggcccata tcacctccat taccccgatc tga                                273
```

<210> SEQ ID NO 215
<211> LENGTH: 5
<212> TYPE: PRT
<213> ORGANISM: Artificial Sequence
<220> FEATURE:
<223> OTHER INFORMATION: Cleavage linker

<400> SEQUENCE: 215

Glu Glu Lys Lys Asn
1               5

<210> SEQ ID NO 216
<211> LENGTH: 16
<212> TYPE: DNA
<213> ORGANISM: Artificial Sequence
<220> FEATURE:
<223> OTHER INFORMATION: 16S riibosomal primer

<400> SEQUENCE: 216
taccttgtta cgactt                                                    16

<210> SEQ ID NO 217
<211> LENGTH: 20
<212> TYPE: DNA
<213> ORGANISM: Artificial Sequence
<220> FEATURE:
<223> OTHER INFORMATION: 16S ribosomal primer

<400> SEQUENCE: 217
agagtttgat cmtggctcag                                                      20

<210> SEQ ID NO 218
<211> LENGTH: 1737
<212> TYPE: DNA
<213> ORGANISM: Pseudomonas sp. VLB120

<400> SEQUENCE: 218
atgagcacgt ccttcacaca gttcacctcg cccgccggcc aagcccccaa ggactacaac    60
aagctgggcc tggaagacca gttgccgcag tttgaaaccg actggaacaa caacctcacc   120
ggctggaccc aatcgtccat catcggcaac ccctggtcca acctgaacga cgccccccgc   180
tcgggttact acaatccgct cgtcgaaggc ttcggtgacg tgactgtccc cgcgatcacc   240
tgggcgccct ccccaaccg gctctggacg ttttttctaca caacggtgc ggcgatcgtt   300 ccccaactgg gcggcaacgc catgactctg gagcaggtga tggaattggc cgatcacggc   360
cagatcaccc tcaacaacac cctctacaaa ctctacgatc ccgacaacca agggaccttg   420
ctgcaactgc cggccaagcg ctgccccagc atcgactgga aaggccagta cacggcgttc   480
tcgccctccg gcccacgggg ctggctcgac gagtactgcg agtggtccat cgtgcgcgat   540
accgacggca acatgcgcaa gatcacattc acctgcgaaa accccgccta tttcctggcc   600
atgtggcgca tcgatccgaa cgcggtactg gcctgtaccc gggactacat cgacccgaac   660
gtacaactcg aagacctgta cctgcgctat gccgtcgatt gcccgaccgg caaggccgga   720
gatccagtga tcgaccccac caccggccag ccggcctatg acacggtcaa caaatggaac   780
gccggtacgg cctgtgtacc cggccagtac ggcggcgcga tgcacctgac gtccggcccc   840
aacaccctca gtgccgaggt gtacctggct gccgccgcca ccctcctgcg accggtgagc   900
agcagccaga cgcccagtc gctgatctgc tgcgcgcagt acggacagaa ctatcgcaac   960
tccgacccgc acatcggctt catggccaat accaaggcgg tgaacaatcg gctgtcgctg  1020 accaaccca ttggcctgta cctgcaacag cccaccgatt tcagcgcctg gaaaggcccg  1080
cagggccagg acgtgagcca gtattggcgc atcacgcgcg gcaggccaa gtcggcggcc  1140 aacggctccg accagatcct gcaggcggtg ttcgaggttc cgcaaagcgc aggcttctcg  1200
atcaatgaca tcaccatcaa tggccaacgg gtcgactatg tgtgggtcat cgcccaacaa  1260
ctgctggtgg gcctgagcgt caccgccaag ccgatcaccg tcacacccc gtcgttccct  1320 tgcgtacagg cgcggggtga ggggctgcaa ccctggccgg ttcaactgct gccagtagac  1380
ctgttctacg acaatcacc caccgacctg cccgcctggc ttgcaccggg aagcagcaac  1440
tcgttcgtac tggtggtgca gggcgccgac ccgagcacca cgacgcagaa tgcacgggtg  1500
caattctcca accccggcat cacggcgcag gtcacccact acctgccaga cgcatccgcc  1560
attcccggac agaccaactc cggcggtacc caggcctaca tcctcaccat cacggtgagc  1620
ccgacggcag caccccggtct ggtcatggtg cgcgcgctca atccgggcga agacgcgaac  1680
gtgagcgcgg ccgatcaccc ttgggaggcc ggcctggcgc tggtgcccgg cgcctga     1737

<210> SEQ ID NO 219
<211> LENGTH: 1605
<212> TYPE: DNA
<213> ORGANISM: Pseudomonas sp. VLB120

<400> SEQUENCE: 219

```
atgtccaggt cacgcttgag tctcatctcg ctgttgagcg gcatgttgct gtatctgtcg    60
gccctgcctc ccgctgcggc agccacgatg tcggatgccg acagctgtgt gcagcagcaa   120
ttggtgttca atccggccag tggagggttc ctgccggtca caacttcaa tgccaccaac    180 caggcattca tgaactgttt tgcctggcag ttgttcatcg ccctgaattg gccggtcaat   240
cccggctggc ctgccaccgc cagcctggcg ggtgaacccg acatgaacag caccctggcg   300
caattcggag tgccctcttc cccggggcaa cccatgagcg tggcgcccgt gtgggccagc   360
tacaaagatg ccaacgacat cttcctgccc ggcgcgccca cgcccaccgg ttggggcgtg   420
caaaccatgg taccgtccgg ttgcagcacc cagggcagtc tgaaggccct gaaggtaggt   480
gcacgcaagt tcatgaatgc cacctcagaa ggcgcgatca acgccttgca tggtttccac   540
ctctcgaccg ggacggtcgc ttctattccc gaccccgtca tggaagcgtc cggcggctgg   600
ctgacggacc agtctggcaa cttggtgttc tttgaacgca aagtgggcaa ggccgagttc   660
gactacatcg tcgagaaggg gctctatgat gccgccaatc agttgaaggt cgcgcaaaac   720
ctcgatggca atacaccgga aggcctgtcg ctgcccctcg gcgagccaat gcgttcgctg   780
ccgccgaccc ctgtgccaca ggagcagctg ggcgcgcttg agctcaaggc gcgtggcgt    840 gtgctgaccg gcaaacccga gctgttcggg cgctacctga ccaccgtcgc ctggctcaaa   900
cgccccgaca cactggagtg cacccaggaa gtggtgggc tggtgggcct gcatatcatc    960
aacaagaccc aggcgtcgcc caatttcatc tggaccacct cgagcaggt ggacaacgtg   1020 cccgaaccgg accaggcccc gccgcaagga accccgccga acggtttctc tttcaacaac   1080
cccgactgtg ggagcggccc tgcgtgtgaa cccaatgtgg ctcgtatcca gtgcaagcaa   1140
taccaccccg acaaggactg caccgatctc tttccacgcg accagccggt acagaccacc   1200
cgtgagcacc ccgtccccag cgacctgcaa gccctgaaca gcgcggtgca atccaacttt   1260
gcacagcaga cccacggcca gtcggtgttc cagtactaca agctgatcaa cgtactgtgg   1320
accctcgcgc ccaatcctcc cagcccggag ccgggcgcca tgcccaggt gccgctgtca    1380 tacgggccgt tcatcagtca gggcaacgtg ccggtggcca acaccaccat ggagacttac   1440
gtacagggcg atgactgcaa caaatgccat cagtacgcga cgattgccgg cagcccctcc   1500
ttggcctcgg acttctcctt cctgttcaac agcgcgagtt ccgccggcca taaaagcctg   1560
atcaagcgcg tcaagccctt cgaaacgctc aaggaccgcc cctga                  1605
```

<210> SEQ ID NO 220
<211> LENGTH: 1734
<212> TYPE: DNA
<213> ORGANISM: Pseudomonas putida

<400> SEQUENCE: 220

```
atgagcacgc ccttcaagca gttcacctct cccgctggcc aagcccccaa ggactacaac    60
aagctaggcc tggaggacca gttgcagcag tttgaaaccg actggaacaa cgacctcacc   120
ggctggaccg agtcgtcgat catcggcaac ccttggtcgg ccagaacga cgcgcctcgc    180 tctggctatt acaacccgct ggtggagggt ttcggtgaag tgaccccgcc cgcgatcacc   240
tgggcgccct tccccaaccg gctgtggacg ttcttctaca caacggtgc agcggtcgtt    300 ccgcaacttg gcagagccat gaccctgaac caggtgatgg agctggccga ccgcggccag   360 atcacccctcg acaacaccct ctacacgcta tacgacccgg acaaacaggg caccctgctg   420
caactaccgg ccaagcgctg cccaagtatc gactggaacg gcaggtacac ggcgttctca   480
ccttccggcc cgcggggctg gctcgacgag tattgcgagt ggtcgatcgt acgcgatgcc   540
```

```
aacggcaaca tgcgcaagat caccttcacc tgcgaaaacc ccgcctactt cctggccatg    600
tggcgcatcg acccgcaggc agtattgggc ctgtaccgcg actacataga ccccagcgtg    660
caactcgagg acctgtacct gcgctacacc gtcgactgcc cgaccggcaa agccggcgat    720
ccggtcatcg acccgaccac tggccagccg gcctatgaca ccgtcaacaa atggaacgcc    780
ggcaccgcct gcgttcccgg gcaatacggt ggtgcgatgc acctgacctc cggccccaac    840
accctcagtg ccgaggtgta cctggccgcc gccgccacca cctgcgccc ggtcagcagc     900 agccagaatg cccagtcgct gatctgctgc gcgcagtatg gcagaacta ccgcaactcc     960 gacccgcaca tcggcttcat ggccaattcg acggcagtga aaaatcgcct gtcgctgacc   1020
aacccgattg cctctacct gcagcaacct accgatttca gtggctggaa aggcccgcaa    1080
ggccaggacg taagccagta ctggcgcatc cccgcggca ccgccaagtc ggccgccaac    1140
gggtccgacc aaatcctgca ggcggtgttc gaagtcccag aaagcgccgg tttctcgatc   1200
aacgacatca ccatcaacaa ccagccggtc aactatgtgt gggtcatcgc ccagcaactg   1260
ttggtgggcc tgagcgtcac cgtcaagccg cttgctacca caccgccctc cttcccgtgc   1320
gtgcaggacc ggcagaccgg ccggcaaccc tggccggtgc agctgctgcc actggacttg   1380
ttctacgggc agtcccccac cgacctgccc gcctggctgg caccgggtag cagcaactcg   1440
ttcgtgcttg tggtgcaagg cgcagacgcc aacaccacgg cgcagaacgc cagggtgcaa   1500
ttctccaacc ctggggtgac ggcacaggtc acccagtacc tgcccgacgc gtcggcgatt   1560
cctggccaga ccaactctgg tggcactcaa gcctacatgc tgaccatcac ggtcagcccc   1620
aacgcagcac ccggcctggt gacggtgcgt gcactgaacc cgggcgaaga cgtgaacgta   1680
agcgcggcag accacccgtg ggaatccggc ctggcgctgg tgcctggcgc ctga          1734

<210> SEQ ID NO 221
<211> LENGTH: 1590
<212> TYPE: DNA
<213> ORGANISM: Pseudomonas putida

<400> SEQUENCE: 221
atgatgtcca gcttacgcct gagccttctg tcgctgctca gcggcatcct gctttgcctg     60
cagaccctgc aacccgctgc tgcggccacg ctgtcggacg ccgatgcctg tgtgcagcaa    120
cagttggtgt tcaaccctgc gagcgggggg tttctgccgg tcaataactt caatgccacc    180
agccaggcgt tcatgaactg cttcggctgg caactgttca ttgccttgaa ctggccagta    240
aaccccggct ggccggccac ccccagcctg gcgggcgaac ccgacaggca aagcacccctg   300 gcgcagttcg gtgtgccgac cacggcgggt gaaccgatga gcgtggcccc ggtgtgggcc    360
agctacaagg acgccaacga tatctttctg ccaggcgcgc ccgcgcccac cggttggggg   420
gtacaaaccc tggtaccaag cagctgcaat agccagggta gcctgaaggc gctcaaggtg   480
ggtgcgcgca aattcatgaa cgctacctca gaaggcgcga tcaacgccct gcacgggttc    540
cacctgtcta ccgggacact ggcatccatt cccgaccgg tcatggaagc gtccggcggc    600
tggctgacgg atcagtcggg caacctggta ttttctcgaac gcaaggtagg caaggccgaa   660
ttcgactaca tcgtcgagca tgggctatat gacgcggcca accagttgaa gctcgcccaa    720
accgaggggc tgtcgctgcc catcggtgaa gcgatgcgcg aactgccgcc gtcgcctgtg    780
ccgcaggagc aactgggcgc aatcgagctc aaggccgcct gccgggtgct gactggcaaa    840
cccgaactgt tcggtcgcta cctcaccacc gtcgcctggc tcaagcgccc cgacaccctg    900
```

```
gcatgcaccc aggaagtggt gggcctggtg ggcctgcaca tcatcaacaa gacccaggct    960
tcgcccaact tcatctggac cacgttcgag caggtggaca cgtgcccga acctgcccag   1020
gtgccgccgc agcaaacccc gccgggcggt tttgcgttca acaaccccga atgtggcacc   1080
ggccccgagt gtaaaccgaa cgtggcccgt atccagtgca agcaacacca ccccgaccgc   1140
gactgcagcg acctcttccc gcgcgaccag ccggtacaga ccacccgtga ataccccgtg   1200
cccagtgccc tgcaggccct gaacagcgca gtgcaagcca acttcgcgca gcaaagccag   1260
ggccagtcgg tgttccagta ctacaagctg atcaatgtgc tgtggaccct tgcccccaac   1320
ccacccagcc cagaaccggg tgccaacgca caggtgccgt tgtcctacgg gccgttcatc   1380
agcgagggcc ccgtgccagt ggccaacacc accatggaaa cctacgtgca gggtgatgac   1440
tgcaaccagt gccatcagta cgcgaccatt gccggcagtc cctcgctggc ttcggacttc   1500
tcgttcctgt tcaacactgc cagctcggcc agccagaaaa gcctgatcaa gcgcgtcaaa   1560
gccttcgaga ccctcaagga ccggccctga                                    1590

<210> SEQ ID NO 222
<211> LENGTH: 1734
<212> TYPE: DNA
<213> ORGANISM: Pseudomonas poae

<400> SEQUENCE: 222
atgagcacac ccttcacccca attcacctcc cctgccgaac aagcgcccaa ggactacaac     60
aagctcggcc tggaggacca attgccgacc ttcgagaccg actggaacaa caacgtcacc    120
ggctggaccc agatgtcgat catcggcaac ccctggtcca acctcaacga tgcaccgcgc    180
tcgggctatt acaacccgct ggagagcggc tacggcacgc tgacgccgaa gaccatcacc    240
tggcagcccc ttcccaatcg cctctggacg ttcttctaca acaacggcgc cgccgtggtc    300
ccgcaactgg cggcaaggc catgaccctg gaccaggtga tgcaactgac cgaccacggc    360
cagatcaccc tcaataacac cctgtattcg ctgtacccgg accgcaggc gacccaactg    420
cagatcccca gcgtgctgtg caaatccatc aactggaacg gccctacgc cgactttcg     480
ccctctggcc cacggggctg gctggatgaa tactgcgagt ggtcgatcac ccgcgacccc    540
gacggcaaca tgcgcagcat catgttcacc agcgagaacc cggcgtactt cctgaccatg    600
tggaacatcg accgggtgc cgtgctgggc ctgtaccagg cgtatgtcga cccgcaggtg    660
aaactcgaag acctgtacct cgcctacacc gccgacggcc cgaccggcaa ggccggcgaa    720
ccggtgctcg accccaccac cggccagccc gcctacgaca ccgtgaacaa atggaacagc    780
ggcaccgtgc gcataccggg cgtgtcgggc ggcgcgatgc acctgacctc cggccccaat    840
accctgagtg ccgagatcta cctggcgcg ccgccacca tcctgcggcc gctcagcagc    900
agccagaacc agcagagcct gatctgctgc gcgcagtacg ggcagaacta ccgcaactcc    960
gacccgcata tcgggttctc cgccaaccag gcggcggtca caacctgat ctcgttgacc    1020
aaccccatcg gcctgtacct gcagcaaccc aagtccttca gcacctggaa aggcccgcaa    1080
ggcgaggatg tcagcagcta ctggcgcgtc acccgtggca ccgccggcac cggcccgaac    1140
aactccgacc agatcctcca ggcggtcttc gaagtgccgg ccagtgcagg gttctcgatc    1200
aatgacatca ccatcagcgg cacgccgatc gactacgtgt gggtgatcgc caacgaactg    1260
aatgtggccc tcagcgtgac cccggcaccg ctcaccgccc agcccaagga gtgcgcctgc    1320
gtggcggcca acaccaccga tgcgcagccc tggccggtgc agttgctgcc gattgacctg    1380
ttctacggcc aatcccccag cgacttgccg gccagctttg cgcccggcag ctcaagccag    1440
```

-continued

| | |
|---|---|
| ttcgtgctgg tggtgcaagg cgccgacccg aacaccacgg cggcggatgc acgggtgcag | 1500 |
| ttctccaacc cgggcatcac ggcccaggtc acgcagttcc tgccggatgc ctcggcgatt | 1560 |
| cccgggcaga ccgacggcgg cggcacccag ggctacatca tgaccattac cgtcagcagc | 1620 |
| aacgcggcgc cggggctggt cagcgtgcgt gcgctcaacc ccaacgaagc ggccaacccg | 1680 |
| agtgccaccg agcacccatg ggaaagcggc ctggccctgg tgcccagcgc ctga | 1734 |

<210> SEQ ID NO 223
<211> LENGTH: 1590
<212> TYPE: DNA
<213> ORGANISM: Pseudomonas poae

<400> SEQUENCE: 223

| | |
|---|---|
| atgaacggat ggcttcgccc gctgcgccgg gcacgcttgc gtattgtctg cacaatcacc | 60 |
| tgcgcccttc tcccgtggct ggccccgca ccggcaagtg ccgcctcgga tgcccagagc | 120 |
| tgcgtcagcc agttggtgtt cgaccccacc agcggcggct tcctgccggt gaacaatttc | 180 |
| ggcaccgagc aggcttttct caattgtttc ggctggcagt tgttcatcgc catgaactgg | 240 |
| ccggtcaacc ccggctggcc cgccaacccg agcctggccg gtgagccgga tacgcaaagc | 300 |
| agcgcggccc agttcggcgt gccgccaacc ccaggccaac cgatgagcaa tgccccggtg | 360 |
| tgggccagct acaaggatgc cagcgagatc ttcctgcccg gcgcggccaa gcgtccggc | 420 |
| tggggcgtgg aaaccctggt gccgtccaat tgcaccgcca ccggcaatct caaggcgttt | 480 |
| gccacgggcg cgcgtaaatt catcaccgcc acctcggaaa gcgcgatcaa ccgcaagcac | 540 |
| cgcttccacc tgtccagcgg cacccaggtg accctgcccg attcgatcat ggaagcctcc | 600 |
| ggcggttggc taacggacca gtccggcaac ctggtgtttt cgagcgcaa ggtgggcaag | 660 |
| gccgagttcg actacatcgt cgacaacggc ttgtacgacg ccgccaacca gctgatcgtg | 720 |
| gcgcagaaca cgcgacaaccg gcaccccgcc ggcctgtcac tgccggccgg caagctggtg | 780 |
| cgtgaactgc cggccaaggc gctaccccag gaggaactcg gcgccctgga actcaaggcc | 840 |
| gcctggcgcg tgctcaccaa caagcccgcc ctatacgggc gctacctgac caccgtggcc | 900 |
| tggctgcaac gcccggacac gctgcaatgc acccaggaag tgattggcct ggtgggcctg | 960 |
| catatcatca acaagaccca gacccagccg aatttcatct ggaccacctt cgagcaggtc | 1020 |
| gacaacgtgc ctgacggtgg tgccgcgccg cccgagggct acagcttcaa caaccccggca | 1080 |
| tgcaccggtg atgcctgcac gccgaatgtg cccgcgtgc agtgcgacgc cacgcacacg | 1140 |
| ccgcccaact gcacgcccct cgaccagccg gtgcaggcca cccgcgccaa cgccacgccc | 1200 |
| caggacatgc aggcgctgaa caccgcggtg cagcagacct cgcccagca gacccagggc | 1260 |
| cagtcggtat tccagtacta caaactggtg aatgtgctgt ggtccaagac gcccaatgcg | 1320 |
| cccaacgacc caggcccagg gccgaacgtg caggtaccgc tgtcctatgg gccgtttgtc | 1380 |
| agcgaccaga gtgtcgtcgt cgccaacacc accatggaaa cctacgtgca gaccgacaac | 1440 |
| tgcaacgact gccaccagta cgcggcgatt gccggaaaat ccgggctggc gtcggacttc | 1500 |
| tccttcctgt tcagcaatgc cgactcggcg aagaacacgc ggctgatcaa acgcatcgag | 1560 |
| tcgttcaaga ccctcaagga caacccgtaa | 1590 |

<210> SEQ ID NO 224
<211> LENGTH: 771
<212> TYPE: DNA
<213> ORGANISM: Pseudomonas entomophila

<400> SEQUENCE: 224

```
atgggttcta ttactgatca tgatcaactg atcgcttggg ttcaatcgct ggatattcct      60
gagcccacga aaagtattgc gcggtcacgc aatgcggtgg ttcgcgccag cagcgaagaa     120
gaaggagctg cggtggtgcg cggtagcgtg acatcgttcg ttactggatt gaaacagcaa     180
gcgcgcgatg atgtgcagaa cagtacgctg ctgatgcaac tggcggccga caagaaatat     240
aatcccgaca cgcaacggga ggagtggttc aagttctaca ccgatggctt agccaacctg     300
ggctgggggc gcgtcagttc gatttaccag aaatataacc cgcgtaatac caatgtcacc     360
atggatgaag tggtgctgga ggtgatcgct gcggttgtcg gtgctgacag tgccgtgtac     420
aaggtcaccg agaagacctt cgcggcgctg aaagcaacc cgaagaatca ggggcgctg      480
aagctgttcg acagtaccac cactcgcgac gacatcggca cgttccagat ccttccggtc     540
atgcaggacc gggatggcaa cgtggtcatg gtactgacca cagtcaacgc cagcaccact     600
gtgcaaaagg gtagcttcct gttctggagc tggagcaaga ccacggcctg gatgtatcgg     660
gctgcgcagc agacggtgct caacgaatcg gtgtactcac gcgtgcgtga gtcggtgatc     720
cagaaattgg gcaagaatgc cgaagatttt attgatggtc tcgatatcta a             771
```

<210> SEQ ID NO 225
<211> LENGTH: 783
<212> TYPE: DNA
<213> ORGANISM: Pseudomonas entomophila

<400> SEQUENCE: 225

```
atggcattat cagccgatga agtttatgtg gtttcgggca acctgctgtc tgcaatgccc      60
aagcttgttg atcctgtgat gttcgaagat tttgccaatt ccaatttgct ctgccaattg     120
gcggcggaca agaaccaagg cacgcggttt gttgatccgc ccgcctggct agacttctac     180
aggaatgcat tgggcaaggt gttctggagg atcagtaatt ccgggacggt cagttttaac     240
ataccgcctc tggttcgcag cataacgata aaggaagtgc tggagaagac gttctataaa     300
acactggatc atgaagtctc gctgcaatta gatagcagta tcgagcgttt ggaagagcag     360
ccagaagaga gtgctgctgc acgcttgtat cgtgcgaaga cccaggtcac ttacaagtcc     420
gccgtctcgg acctggccgt ccggccgcac cccatctcga ccattaatct gcagataagc     480
gcggtgcaga gtgaggtaa atatcggtc tgtagtgtct atttttacaac gtcggctgat     540
attgaaagtg atgtgttcaa ccagaagttt ctggtcagtc agctccgggg caatgtcagc     600
gtgagtacgt ttgatgcaaa attgctggag tcgagttacg cgggtatccg acagagcgtt     660
atcgaaaagt tggggcctga aaatatccgc gagaacatca tccaggtgtc agctgaggtg     720
ttctcccctcg cgggcccgcg ccatgccggt gccaagcagt tcattcagga actggaaatc     780
tag                                                                    783
```

<210> SEQ ID NO 226
<211> LENGTH: 270
<212> TYPE: DNA
<213> ORGANISM: Pseudomonas chlororaphis

<400> SEQUENCE: 226

```
atgtcggctc aagaaaactt tgttggcgga tggactcctt atcacgaact gactccaaag      60
gatcgggaag tattcaaaga ggccctggcc gggttcgtgg gtgtgaacta caccctgaa      120
aaagtttcga cccaggtcgt caacggcacg aactatcgtt atctgtcgaa agcaacggtg     180
cctggctcct cggacagctg gcaagcggta gtggaaatct acgcgcctat caaaggcaag     240
```

```
ccgcacatca cccagatcca ccggatctaa                                    270
```

<210> SEQ ID NO 227
<211> LENGTH: 270
<212> TYPE: DNA
<213> ORGANISM: Pseudomonas rhodesiae

<400> SEQUENCE: 227

```
atgtcggctc aagagaatct cgttggcgga tggactcctt atcacgaact gactccaaag    60
gatcaggaag tattcgatga agccctggcc gggctcgtgg gtgtgcacta caccgccgag   120
ttggtttcga cccaggtcgt taacggcacc aactatcgtt atcagacgaa agcaacgcag   180
ccgggttcat caaacagctg gcaagcgatc gtggaaattt acgcgccgat taatggcaag   240
ccacatatca cccagatcat ccggatctaa                                    270
```

<210> SEQ ID NO 228
<211> LENGTH: 270
<212> TYPE: DNA
<213> ORGANISM: Pseudomonas rhodesiae

<400> SEQUENCE: 228

```
atgtcggctc aagaaaatct cgttggcgga tggactcctt atcacgtact gactccaaag    60
gatcaggaag tattcgatga agccctggcc gggctcgtgg gtgtgcacta caccgccgag   120
ctggtttcga cccaggtcgt taacggcacc aactatcgtt atcaggcgaa agccacgcag   180
cctggttcgc caaacagctg gcaagcggtc gtggaaattt acgcgccgat taacggcaag   240
ccgtatgtca cccagatcat ccggatctaa                                    270
```

<210> SEQ ID NO 229
<211> LENGTH: 273
<212> TYPE: DNA
<213> ORGANISM: Aeromonas hydrophila

<400> SEQUENCE: 229

```
atgtcagaac aagcagtgtt gttgggtgga tggactgcct accacaagct gagcgccaag    60
gatcaggccg tattcaacca ggcgctggaa ggatttgtcg gggtgcagta cacacccttt   120
gaagtctcca cccaggtcgt cgccggcacc aactaccgtt tcaaatgcaa aagcactgtg   180
ccgctgccca acccgatcca cggggaagcc gtggtgcaga tcttccaatc cctggatggg   240
tcggcccata tcacctccat caccccgatt tga                                273
```

<210> SEQ ID NO 230
<211> LENGTH: 273
<212> TYPE: DNA
<213> ORGANISM: Aeromonas veronii

<400> SEQUENCE: 230

```
atgtcagaac aagcagtgtt ggtgggtgga tggaccgcat atcacaagct gaccgccgag    60
gatcaggcag tgttcaacca ggcgatgaaa ggatttgtcg gggtgcagta cgtacccttt   120
gaagtctcca ctcaagtggt ggctggcacc aactaccgct tcaagtgcaa gagcactgtg   180
ccgcttgcca aaccgatcca tggcgaagcc gtggtacaga tcttcaaatc actggacggg   240
gatgcccata tcacctccat taccccaatc tga                                273
```

<210> SEQ ID NO 231
<211> LENGTH: 273
<212> TYPE: DNA
```

-continued

<213> ORGANISM: Haemophilus piscium

<400> SEQUENCE: 231

```
atgtcagaac aagcagtgtt gttgggtgga tggaccgcat accacaagct gagcgcaaaa    60
gatcaggcgg tatttgacct ggcactgaaa ggatttgtcg gggtgcagta ccagccgttt   120
gaagtctcca cccaggtggt ggctggcacc aactaccgtt tcaaatgcaa aaccacggtg   180
ccgctgccca acccgatcca cggggaagcc gtggtgcaga tcttccagtc tctggatggc   240
tctgctcata tcacctccat cacccccgatc tga                              273
```

<210> SEQ ID NO 232
<211> LENGTH: 578
<212> TYPE: PRT
<213> ORGANISM: Pseudomonas sp. VLB120

<400> SEQUENCE: 232

```
Met Ser Thr Ser Phe Thr Gln Phe Thr Ser Pro Ala Gly Gln Ala Pro
 1               5                  10                  15

Lys Asp Tyr Asn Lys Leu Gly Leu Glu Asp Gln Leu Pro Gln Phe Glu
            20                  25                  30

Thr Asp Trp Asn Asn Leu Thr Gly Trp Thr Gln Ser Ser Ile Ile
        35                  40                  45

Gly Asn Pro Trp Ser Asn Leu Asn Asp Ala Pro Arg Ser Gly Tyr Tyr
 50                  55                  60

Asn Pro Leu Val Glu Gly Phe Gly Asp Val Thr Val Pro Ala Ile Thr
 65                  70                  75                  80

Trp Ala Pro Phe Pro Asn Arg Leu Trp Thr Phe Tyr Asn Asn Gly
                85                  90                  95

Ala Ala Ile Val Pro Gln Leu Gly Gly Asn Ala Met Thr Leu Glu Gln
            100                 105                 110

Val Met Glu Leu Ala Asp His Gly Gln Ile Thr Leu Asn Asn Thr Leu
        115                 120                 125

Tyr Lys Leu Tyr Asp Pro Asp Asn Gln Gly Thr Leu Leu Gln Leu Pro
130                 135                 140

Ala Lys Arg Cys Pro Ser Ile Asp Trp Lys Gly Gln Tyr Thr Ala Phe
145                 150                 155                 160

Ser Pro Ser Gly Pro Arg Gly Trp Leu Asp Glu Tyr Cys Glu Trp Ser
                165                 170                 175

Ile Val Arg Asp Thr Asp Gly Asn Met Arg Lys Ile Thr Phe Thr Cys
            180                 185                 190

Glu Asn Pro Ala Tyr Phe Leu Ala Met Trp Arg Ile Asp Pro Asn Ala
        195                 200                 205

Val Leu Gly Leu Tyr Arg Asp Tyr Ile Asp Pro Asn Val Gln Leu Glu
    210                 215                 220

Asp Leu Tyr Leu Arg Tyr Ala Val Asp Cys Pro Thr Gly Lys Ala Gly
225                 230                 235                 240

Asp Pro Val Ile Asp Pro Thr Thr Gly Gln Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Ala Thr Leu Leu Arg Pro Val Ser Ser Gln Asn
    290                 295                 300
```

```
Ala Gln Ser Leu Ile Cys Cys Ala Gln Tyr Gly Gln Asn Tyr Arg Asn
305                 310                 315                 320

Ser Asp Pro His Ile Gly Phe Met Ala Asn Thr Lys Ala Val Asn Asn
            325                 330                 335

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
            355                 360                 365

Trp Arg Ile Thr Arg Gly Thr Ala Lys Ser Ala Ala Asn Gly Ser Asp
            370                 375                 380

Gln Ile Leu Gln Ala Val Phe Glu Val Pro Gln Ser Ala Gly Phe Ser
385                 390                 395                 400

Ile Asn Asp Ile Thr Ile Asn Gly Gln Arg Val Asp Tyr Val Trp Val
            405                 410                 415

Ile Ala Gln Gln Leu Leu Val Gly Leu Ser Val Thr Ala Lys Pro Ile
            420                 425                 430

Thr Val Thr Pro Pro Ser Phe Pro Cys Val Gln Ala Arg Val Glu Gly
            435                 440                 445

Leu Gln Pro Trp Pro Val Gln Leu Leu Pro Val Asp Leu Phe Tyr Gly
450                 455                 460

Gln Ser Pro Thr Asp Leu Pro Ala Trp Leu Ala Pro Gly Ser Ser Asn
465                 470                 475                 480

Ser Phe Val Leu Val Val Gln Gly Ala Asp Pro Ser Thr Thr Thr Gln
            485                 490                 495

Asn Ala Arg Val Gln Phe Ser Asn Pro Gly Ile Thr Ala Gln Val Thr
            500                 505                 510

His Tyr Leu Pro Asp Ala Ser Ala Ile Pro Gly Gln Thr Asn Ser Gly
            515                 520                 525

Gly Thr Gln Ala Tyr Ile Leu Thr Ile Thr Val Ser Pro Thr Ala Ala
            530                 535                 540

Pro Gly Leu Val Met Val Arg Ala Leu Asn Pro Gly Glu Asp Ala Asn
545                 550                 555                 560

Val Ser Ala Ala Asp His Pro Trp Glu Ala Gly Leu Ala Leu Val Pro
            565                 570                 575

Gly Ala

<210> SEQ ID NO 233
<211> LENGTH: 534
<212> TYPE: PRT
<213> ORGANISM: Pseudomonas sp. VLB120

<400> SEQUENCE: 233

Met Ser Arg Ser Arg Leu Ser Leu Ile Ser Leu Leu Ser Gly Met Leu
1               5                   10                  15

Leu Tyr Leu Ser Ala Leu Pro Pro Ala Ala Ala Thr Met Ser Asp
            20                  25                  30

Ala Asp Ser Cys Val Gln Gln Gln Leu Val Phe Asn Pro Ala Ser Gly
            35                  40                  45

Gly Phe Leu Pro Val Asn Asn Phe Asn Ala Thr Asn Gln Ala Phe Met
50                  55                  60

Asn Cys Phe Ala Trp Gln Leu Phe Ile Ala Leu Asn Trp Pro Val Asn
65                  70                  75                  80

Pro Gly Trp Pro Ala Thr Ala Ser Leu Ala Gly Glu Pro Asp Met Asn
            85                  90                  95
```

-continued

Ser Thr Leu Ala Gln Phe Gly Val Pro Ser Ser Pro Gly Gln Pro Met
              100                 105                 110

Ser Val Ala Pro Val Trp Ala Ser Tyr Lys Asp Ala Asn Asp Ile Phe
        115                 120                 125

Leu Pro Gly Ala Pro Thr Pro Thr Gly Trp Gly Val Gln Thr Met Val
    130                 135                 140

Pro Ser Gly Cys Ser Thr Gln Gly Ser Leu Lys Ala Leu Lys Val Gly
145                 150                 155                 160

Ala Arg Lys Phe Met Asn Ala Thr Ser Glu Gly Ala Ile Asn Ala Leu
                165                 170                 175

His Gly Phe His Leu Ser Thr Gly Thr Val Ala Ser Ile Pro Asp Pro
            180                 185                 190

Val Met Glu Ala Ser Gly Gly Trp Leu Thr Asp Gln Ser Gly Asn Leu
        195                 200                 205

Val Phe Phe Glu Arg Lys Val Gly Lys Ala Glu Phe Asp Tyr Ile Val
    210                 215                 220

Glu Lys Gly Leu Tyr Asp Ala Ala Asn Gln Leu Lys Val Ala Gln Asn
225                 230                 235                 240

Leu Asp Gly Asn Thr Pro Glu Gly Leu Ser Leu Pro Leu Gly Glu Pro
                245                 250                 255

Met Arg Ser Leu Pro Pro Thr Pro Val Pro Gln Glu Gln Leu Gly Ala
            260                 265                 270

Leu Glu Leu Lys Ala Ala Trp Arg Val Leu Thr Gly Lys Pro Glu Leu
        275                 280                 285

Phe Gly Arg Tyr Leu Thr Thr Val Ala Trp Leu Lys Arg Pro Asp Thr
    290                 295                 300

Leu Glu Cys Thr Gln Glu Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asp Gln Ala Pro Pro Gln Gly Thr Pro
            340                 345                 350

Pro Asn Gly Phe Ser Phe Asn Asn Pro Asp Cys Gly Ser Gly Pro Ala
        355                 360                 365

Cys Glu Pro Asn Val Ala Arg Ile Gln Cys Lys Gln Tyr His Pro Asp
    370                 375                 380

Lys Asp Cys Thr Asp Leu Phe Pro Arg Asp Gln Pro Val Gln Thr Thr
385                 390                 395                 400

Arg Glu His Pro Val Pro Ser Asp Leu Gln Ala Leu Asn Ser Ala Val
                405                 410                 415

Gln Ser Asn Phe Ala Gln Gln Thr His Gly Gln Ser Val Phe Gln Tyr
            420                 425                 430

Tyr Lys Leu Ile Asn Val Leu Trp Thr Leu Ala Pro Asn Pro Pro Ser
        435                 440                 445

Pro Glu Pro Gly Ala Asn Ala Gln Val Pro Leu Ser Tyr Gly Pro Phe
    450                 455                 460

Ile Ser Gln Gly Asn Val Pro Val Ala Asn Thr Thr Met Glu Thr Tyr
465                 470                 475                 480

Val Gln Gly Asp Asp Cys Asn Lys Cys His Gln Tyr Ala Thr Ile Ala
                485                 490                 495

Gly Ser Pro Ser Leu Ala Ser Asp Phe Ser Phe Leu Phe Asn Ser Ala
            500                 505                 510

Ser Ser Ala Gly His Lys Ser Leu Ile Lys Arg Val Lys Ala Phe Glu

```
                515                 520                 525
Thr Leu Lys Asp Arg Pro
    530

<210> SEQ ID NO 234
<211> LENGTH: 577
<212> TYPE: PRT
<213> ORGANISM: Pseudomonas putida

<400> SEQUENCE: 234

Met Ser Thr Pro Phe Lys Gln Phe Thr Ser Pro Ala Gly Gln Ala Pro
1               5                   10                  15

Lys Asp Tyr Asn Lys Leu Gly Leu Glu Asp Gln Leu Gln Gln Phe Glu
            20                  25                  30

Thr Asp Trp Asn Asn Asp Leu Thr Gly Trp Thr Glu Ser Ser Ile Ile
        35                  40                  45

Gly Asn Pro Trp Ser Gly Gln Asn Asp Ala Pro Arg Ser Gly Tyr Tyr
    50                  55                  60

Asn Pro Leu Val Glu Gly Phe Gly Glu Val Thr Pro Ala Ile Thr
65              70                  75                  80

Trp Ala Pro Phe Pro Asn Arg Leu Trp Thr Phe Phe Tyr Asn Asn Gly
            85                  90                  95

Ala Ala Val Val Pro Gln Leu Gly Arg Ala Met Thr Leu Asn Gln Val
            100                 105                 110

Met Glu Leu Ala Asp Arg Gly Gln Ile Thr Leu Asp Asn Thr Leu Tyr
        115                 120                 125

Thr Leu Tyr Asp Pro Asp Lys Gln Gly Thr Leu Leu Gln Leu Pro Ala
    130                 135                 140

Lys Arg Cys Pro Ser Ile Asp Trp Asn Gly Arg Tyr Thr Ala Phe Ser
145                 150                 155                 160

Pro Ser Gly Pro Arg Gly Trp Leu Asp Glu Tyr Cys Glu Trp Ser Ile
            165                 170                 175

Val Arg Asp Ala Asn Gly Asn Met Arg Lys Ile Thr Phe Thr Cys Glu
        180                 185                 190

Asn Pro Ala Tyr Phe Leu Ala Met Trp Arg Ile Asp Pro Gln Ala Val
    195                 200                 205

Leu Gly Leu Tyr Arg Asp Tyr Ile Asp Pro Ser Val Gln Leu Glu Asp
210                 215                 220

Leu Tyr Leu Arg Tyr Thr Val Asp Cys Pro Thr Gly Lys Ala Gly Asp
225                 230                 235                 240

Pro Val Ile Asp Pro Thr Thr Gly Gln Pro Ala Tyr Asp Thr Val Asn
            245                 250                 255

Lys Trp Asn Ala Gly Thr Ala Cys Val Pro Gly Gln Tyr Gly Gly Ala
        260                 265                 270

Met His Leu Thr Ser Gly Pro Asn Thr Leu Ser Ala Glu Val Tyr Leu
    275                 280                 285

Ala Ala Ala Thr Ile Leu Arg Pro Val Ser Ser Gln Asn Ala
    290                 295                 300

Gln Ser Leu Ile Cys Cys Ala Gln Tyr Gly Gln Asn Tyr Arg Asn Ser
305                 310                 315                 320

Asp Pro His Ile Gly Phe Met Ala Asn Ser Thr Ala Val Lys Asn Arg
            325                 330                 335

Leu Ser Leu Thr Asn Pro Ile Gly Leu Tyr Leu Gln Gln Pro Thr Asp
        340                 345                 350
```

```
Phe Ser Gly Trp Lys Gly Pro Gln Gly Gln Asp Val Ser Gln Tyr Trp
            355                 360                 365

Arg Ile Thr Arg Gly Thr Ala Lys Ser Ala Ala Asn Gly Ser Asp Gln
    370                 375                 380

Ile Leu Gln Ala Val Phe Glu Val Pro Glu Ser Ala Gly Phe Ser Ile
385                 390                 395                 400

Asn Asp Ile Thr Ile Asn Asn Gln Pro Val Asn Tyr Val Trp Val Ile
                405                 410                 415

Ala Gln Gln Leu Leu Val Gly Leu Ser Val Thr Val Lys Pro Leu Ala
            420                 425                 430

Thr Thr Pro Pro Ser Phe Pro Cys Val Gln Asp Arg Gln Thr Gly Arg
            435                 440                 445

Gln Pro Trp Pro Val Gln Leu Leu Pro Leu Asp Leu Phe Tyr Gly Gln
        450                 455                 460

Ser Pro Thr Asp Leu Pro Ala Trp Leu Ala Pro Gly Ser Ser Asn Ser
465                 470                 475                 480

Phe Val Leu Val Val Gln Gly Ala Asp Ala Asn Thr Thr Ala Gln Asn
                485                 490                 495

Ala Arg Val Gln Phe Ser Asn Pro Gly Val Thr Ala Gln Val Thr Gln
            500                 505                 510

Tyr Leu Pro Asp Ala Ser Ala Ile Pro Gly Gln Thr Asn Ser Gly Gly
        515                 520                 525

Thr Gln Ala Tyr Met Leu Thr Ile Thr Val Ser Pro Asn Ala Ala Pro
            530                 535                 540

Gly Leu Val Thr Val Arg Ala Leu Asn Pro Gly Glu Asp Val Asn Val
545                 550                 555                 560

Ser Ala Ala Asp His Pro Trp Glu Ser Gly Leu Ala Leu Val Pro Gly
                565                 570                 575

Ala

<210> SEQ ID NO 235
<211> LENGTH: 528
<212> TYPE: PRT
<213> ORGANISM: Pseudomonas putida

<400> SEQUENCE: 235

Met Ser Ser Leu Arg Leu Ser Leu Leu Ser Leu Ser Gly Ile Leu
1               5                   10                  15

Leu Cys Leu Gln Thr Leu Gln Pro Ala Ala Ala Thr Leu Ser Asp
            20                  25                  30

Ala Asp Ala Cys Val Gln Gln Leu Val Phe Asn Pro Ala Ser Gly
        35                  40                  45

Gly Phe Leu Pro Val Asn Asn Phe Asn Ala Thr Ser Gln Ala Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Pro Ser Leu Ala Gly Glu Pro Asp Arg Gln
                85                  90                  95

Ser Thr Leu Ala Gln Phe Gly Val Pro Thr Thr Ala Gly Glu Pro Met
            100                 105                 110

Ser Val Ala Pro Val Trp Ala Ser Tyr Lys Asp Ala Asn Asp Ile Phe
        115                 120                 125

Leu Pro Gly Ala Pro Ala Pro Thr Gly Trp Gly Val Gln Thr Leu Val
    130                 135                 140
```

-continued

```
Pro Ser Ser Cys Asn Ser Gln Gly Ser Leu Lys Ala Leu Lys Val Gly
145                 150                 155                 160

Ala Arg Lys Phe Met Asn Ala Thr Ser Glu Gly Ala Ile Asn Ala Leu
            165                 170                 175

His Gly Phe His Leu Ser Thr Gly Thr Leu Ala Ser Ile Pro Asp Pro
        180                 185                 190

Val Met Glu Ala Ser Gly Gly Trp Leu Thr Asp Gln Ser Gly Asn Leu
    195                 200                 205

Val Phe Phe Glu Arg Lys Val Gly Lys Ala Glu Phe Asp Tyr Ile Val
210                 215                 220

Glu His Gly Leu Tyr Asp Ala Ala Asn Gln Leu Lys Leu Ala Gln Thr
225                 230                 235                 240

Glu Gly Leu Ser Leu Pro Ile Gly Glu Ala Met Arg Glu Leu Pro Pro
            245                 250                 255

Ser Pro Val Pro Gln Glu Gln Leu Gly Ala Ile Glu Leu Lys Ala Ala
        260                 265                 270

Trp Arg Val Leu Thr Gly Lys Pro Glu Leu Phe Gly Arg Tyr Leu Thr
    275                 280                 285

Thr Val Ala Trp Leu Lys Arg Pro Asp Thr Leu Ala Cys Thr Gln Glu
290                 295                 300

Val Val Gly Leu Val Gly Leu His Ile Ile Asn Lys Thr Gln Ala Ser
305                 310                 315                 320

Pro Asn Phe Ile Trp Thr Thr Phe Glu Gln Val Asp Asn Val Pro Glu
            325                 330                 335

Pro Ala Gln Val Pro Pro Gln Thr Pro Pro Gly Gly Phe Ala Phe
        340                 345                 350

Asn Asn Pro Glu Cys Gly Thr Gly Pro Glu Cys Lys Pro Asn Val Ala
    355                 360                 365

Arg Ile Gln Cys Lys Gln His His Pro Asp Arg Asp Cys Ser Asp Leu
370                 375                 380

Phe Pro Arg Asp Gln Pro Val Gln Thr Thr Arg Glu Tyr Pro Val Pro
385                 390                 395                 400

Ser Ala Leu Gln Ala Leu Asn Ser Ala Val Gln Ala Asn Phe Ala Gln
            405                 410                 415

Gln Ser Gln Gly Gln Ser Val Phe Gln Tyr Tyr Lys Leu Ile Asn Val
        420                 425                 430

Leu Trp Thr Leu Ala Pro Asn Pro Pro Ser Pro Glu Pro Gly Ala Asn
    435                 440                 445

Ala Gln Val Pro Leu Ser Tyr Gly Pro Phe Ile Ser Glu Gly Pro Val
450                 455                 460

Pro Val Ala Asn Thr Thr Met Glu Thr Tyr Val Gln Gly Asp Cys
465                 470                 475                 480

Asn Gln Cys His Gln Tyr Ala Thr Ile Ala Gly Ser Pro Ser Leu Ala
            485                 490                 495

Ser Asp Phe Ser Phe Leu Phe Asn Thr Ala Ser Ser Ala Ser Gln Lys
        500                 505                 510

Ser Leu Ile Lys Arg Val Lys Ala Phe Glu Thr Leu Lys Asp Arg Pro
    515                 520                 525
```

<210> SEQ ID NO 236
<211> LENGTH: 577
<212> TYPE: PRT
<213> ORGANISM: Pseudomonas poae

<400> SEQUENCE: 236

-continued

```
Met Ser Thr Pro Phe Thr Gln Phe Thr Ser Pro Ala Glu Gln Ala Pro
1               5                   10                  15

Lys Asp Tyr Asn Lys Leu Gly Leu Glu Asp Gln Leu Pro Thr Phe Glu
            20                  25                  30

Thr Asp Trp Asn Asn Val Thr Gly Trp Thr Gln Met Ser Ile Ile
        35                  40                  45

Gly Asn Pro Trp Ser Asn Leu Asn Asp Ala Pro Arg Ser Gly Tyr Tyr
    50                  55                  60

Asn Pro Leu Glu Ser Gly Tyr Gly Thr Leu Thr Pro Lys Thr Ile Thr
65                  70                  75                  80

Trp Gln Pro Phe Pro Asn Arg Leu Trp Thr Phe Phe Tyr Asn Asn Gly
                85                  90                  95

Ala Ala Val Val Pro Gln Leu Gly Gly Lys Ala Met Thr Leu Asp Gln
                100                 105                 110

Val Met Gln Leu Thr Asp His Gly Gln Ile Thr Leu Asn Asn Thr Leu
        115                 120                 125

Tyr Ser Leu Tyr Pro Asp Pro Gln Ala Thr Gln Leu Gln Ile Pro Ser
    130                 135                 140

Val Leu Cys Lys Ser Ile Asn Trp Asn Gly Pro Tyr Ala Asp Phe Ser
145                 150                 155                 160

Pro Ser Gly Pro Arg Gly Trp Leu Asp Glu Tyr Cys Glu Trp Ser Ile
                165                 170                 175

Thr Arg Asp Pro Asp Gly Asn Met Arg Ser Ile Met Phe Thr Ser Glu
                180                 185                 190

Asn Pro Ala Tyr Phe Leu Thr Met Trp Asn Ile Asp Pro Gly Ala Val
            195                 200                 205

Leu Gly Leu Tyr Gln Ala Tyr Val Asp Pro Gln Val Lys Leu Glu Asp
    210                 215                 220

Leu Tyr Leu Arg Tyr Thr Ala Asp Gly Pro Thr Gly Lys Ala Gly Glu
225                 230                 235                 240

Pro Val Leu Asp Pro Thr Thr Gly Gln Pro Ala Tyr Asp Thr Val Asn
                245                 250                 255

Lys Trp Asn Ser Gly Thr Val Arg Ile Pro Gly Val Ser Gly Gly Ala
            260                 265                 270

Met His Leu Thr Ser Gly Pro Asn Thr Leu Ser Ala Glu Ile Tyr Leu
    275                 280                 285

Ala Ala Ala Ala Thr Ile Leu Arg Pro Leu Ser Ser Ser Gln Asn Gln
    290                 295                 300

Gln Ser Leu Ile Cys Cys Ala Gln Tyr Gly Gln Asn Tyr Arg Asn Ser
305                 310                 315                 320

Asp Pro His Ile Gly Phe Ser Ala Asn Gln Ala Ala Val Asn Asn Leu
                325                 330                 335

Ile Ser Leu Thr Asn Pro Ile Gly Leu Tyr Leu Gln Gln Pro Lys Ser
            340                 345                 350

Phe Ser Thr Trp Lys Gly Pro Gln Gly Glu Asp Val Ser Ser Tyr Trp
        355                 360                 365

Arg Val Thr Arg Gly Thr Ala Gly Thr Gly Pro Asn Asn Ser Asp Gln
    370                 375                 380

Ile Leu Gln Ala Val Phe Glu Val Pro Ala Ser Ala Gly Phe Ser Ile
385                 390                 395                 400

Asn Asp Ile Thr Ile Ser Gly Thr Pro Ile Asp Tyr Val Trp Val Ile
                405                 410                 415
```

```
Ala Asn Glu Leu Asn Val Ala Leu Ser Val Thr Pro Ala Pro Leu Thr
            420                 425                 430

Ala Gln Pro Lys Glu Cys Ala Cys Val Ala Ala Asn Thr Thr Asp Ala
            435                 440                 445

Gln Pro Trp Pro Val Gln Leu Leu Pro Ile Asp Leu Phe Tyr Gly Gln
            450                 455                 460

Ser Pro Ser Asp Leu Pro Ala Ser Phe Ala Pro Gly Ser Ser Gln
465                 470                 475                 480

Phe Val Leu Val Val Gln Gly Ala Asp Pro Asn Thr Thr Ala Ala Asp
                485                 490                 495

Ala Arg Val Gln Phe Ser Asn Pro Gly Ile Thr Ala Gln Val Thr Gln
            500                 505                 510

Phe Leu Pro Asp Ala Ser Ala Ile Pro Gly Gln Thr Asp Gly Gly Gly
            515                 520                 525

Thr Gln Gly Tyr Ile Met Thr Ile Thr Val Ser Ser Asn Ala Ala Pro
            530                 535                 540

Gly Leu Val Ser Val Arg Ala Leu Asn Pro Asn Glu Ala Ala Asn Pro
545                 550                 555                 560

Ser Ala Thr Glu His Pro Trp Glu Ser Gly Leu Ala Leu Val Pro Ser
            565                 570                 575

Ala

<210> SEQ ID NO 237
<211> LENGTH: 529
<212> TYPE: PRT
<213> ORGANISM: Pseudomonas poae

<400> SEQUENCE: 237

Met Asn Gly Trp Leu Arg Pro Leu Arg Arg Ala Arg Leu Arg Ile Val
1               5                   10                  15

Cys Thr Ile Thr Cys Ala Leu Leu Pro Trp Leu Ala Pro Ala Pro Ala
                20                  25                  30

Ser Ala Ala Ser Asp Ala Gln Ser Cys Val Ser Gln Leu Val Phe Asp
            35                  40                  45

Pro Thr Ser Gly Gly Phe Leu Pro Val Asn Asn Phe Gly Thr Glu Gln
        50                  55                  60

Ala Phe Leu Asn Cys Phe Gly Trp Gln Leu Phe Ile Ala Met Asn Trp
65                  70                  75                  80

Pro Val Asn Pro Gly Trp Pro Ala Asn Pro Ser Leu Ala Gly Glu Pro
                85                  90                  95

Asp Thr Gln Ser Ser Ala Ala Gln Phe Gly Val Pro Pro Thr Pro Gly
            100                 105                 110

Gln Pro Met Ser Asn Ala Pro Val Trp Ala Ser Tyr Lys Asp Ala Ser
            115                 120                 125

Glu Ile Phe Leu Pro Gly Ala Ala Lys Pro Ser Gly Trp Gly Val Glu
        130                 135                 140

Thr Leu Val Pro Ser Asn Cys Thr Ala Thr Gly Asn Leu Lys Ala Phe
145                 150                 155                 160

Ala Thr Gly Ala Arg Lys Phe Ile Thr Ala Thr Ser Glu Ser Ala Ile
                165                 170                 175

Asn Arg Lys His Arg Phe His Leu Ser Ser Gly Thr Gln Val Thr Leu
            180                 185                 190

Pro Asp Ser Ile Met Glu Ala Ser Gly Gly Trp Leu Thr Asp Gln Ser
        195                 200                 205
```

-continued

```
Gly Asn Leu Val Phe Phe Glu Arg Lys Val Gly Lys Ala Glu Phe Asp
    210                 215                 220

Tyr Ile Val Asp Asn Gly Leu Tyr Asp Ala Ala Asn Gln Leu Ile Val
225                 230                 235                 240

Ala Gln Asn Ser Asp Asn Arg His Pro Ala Gly Leu Ser Leu Pro Ala
                245                 250                 255

Gly Lys Leu Val Arg Glu Leu Pro Ala Lys Ala Leu Pro Gln Glu Glu
            260                 265                 270

Leu Gly Ala Leu Glu Leu Lys Ala Ala Trp Arg Val Leu Thr Asn Lys
        275                 280                 285

Pro Ala Leu Tyr Gly Arg Tyr Leu Thr Thr Val Ala Trp Leu Gln Arg
290                 295                 300

Pro Asp Thr Leu Gln Cys Thr Gln Glu Val Ile Gly Leu Val Gly Leu
305                 310                 315                 320

His Ile Ile Asn Lys Thr Gln Thr Gln Pro Asn Phe Ile Trp Thr Thr
                325                 330                 335

Phe Glu Gln Val Asp Asn Val Pro Asp Gly Gly Ala Ala Pro Pro Glu
            340                 345                 350

Gly Tyr Ser Phe Asn Asn Pro Ala Cys Thr Gly Asp Ala Cys Thr Pro
        355                 360                 365

Asn Val Pro Arg Val Gln Cys Asp Ala Thr His Thr Pro Asn Cys
370                 375                 380

Thr Pro Leu Asp Gln Pro Val Gln Ala Thr Arg Ala Asn Ala Thr Pro
385                 390                 395                 400

Gln Asp Met Gln Ala Leu Asn Thr Ala Val Gln Gln Thr Phe Ala Gln
                405                 410                 415

Gln Thr Gln Gly Gln Ser Val Phe Gln Tyr Tyr Lys Leu Val Asn Val
            420                 425                 430

Leu Trp Ser Lys Thr Pro Asn Ala Pro Asn Asp Pro Gly Pro Gly Pro
        435                 440                 445

Asn Val Gln Val Pro Leu Ser Tyr Gly Pro Phe Val Ser Asp Gln Ser
    450                 455                 460

Val Val Val Ala Asn Thr Thr Met Glu Thr Tyr Val Gln Thr Asp Asn
465                 470                 475                 480

Cys Asn Asp Cys His Gln Tyr Ala Ala Ile Ala Gly Lys Ser Gly Leu
                485                 490                 495

Ala Ser Asp Phe Ser Phe Leu Phe Ser Asn Ala Asp Ser Ala Lys Asn
            500                 505                 510

Thr Arg Leu Ile Lys Arg Ile Glu Ser Phe Lys Thr Leu Lys Asp Asn
        515                 520                 525

Pro

<210> SEQ ID NO 238
<211> LENGTH: 256
<212> TYPE: PRT
<213> ORGANISM: Pseudomonas entomophila

<400> SEQUENCE: 238

Met Gly Ser Ile Thr Asp His Asp Gln Leu Ile Ala Trp Val Gln Ser
1               5                   10                  15

Leu Asp Ile Pro Glu Pro Thr Lys Ser Ile Ala Arg Ser Arg Asn Ala
                20                  25                  30

Val Val Arg Ala Ser Ser Glu Glu Glu Gly Ala Ala Val Val Arg Gly
            35                  40                  45
```

```
Ser Val Thr Ser Phe Val Thr Gly Leu Lys Gln Gln Ala Arg Asp Asp
 50                  55                  60

Val Gln Asn Ser Thr Leu Leu Met Gln Leu Ala Ala Asp Lys Lys Tyr
 65                  70                  75                  80

Asn Pro Asp Thr Gln Arg Glu Glu Trp Phe Lys Phe Tyr Thr Asp Gly
                 85                  90                  95

Leu Ala Asn Leu Gly Trp Gly Arg Val Ser Ser Ile Tyr Gln Lys Tyr
            100                 105                 110

Asn Pro Arg Asn Thr Asn Val Thr Met Asp Glu Val Val Leu Glu Val
            115                 120                 125

Ile Ala Ala Val Val Gly Ala Asp Ser Ala Val Tyr Lys Val Thr Glu
130                 135                 140

Lys Thr Phe Ala Ala Leu Glu Ser Asn Pro Lys Asn Gln Gly Ala Leu
145                 150                 155                 160

Lys Leu Phe Asp Ser Thr Thr Arg Asp Asp Ile Gly Thr Phe Gln
                165                 170                 175

Ile Leu Pro Val Met Gln Asp Arg Asp Gly Asn Val Val Met Val Leu
            180                 185                 190

Thr Thr Val Asn Ala Ser Thr Thr Val Gln Lys Gly Ser Phe Leu Phe
            195                 200                 205

Trp Ser Trp Ser Lys Thr Thr Ala Trp Met Tyr Arg Ala Ala Gln Gln
210                 215                 220

Thr Val Leu Asn Glu Ser Val Tyr Ser Arg Val Arg Glu Ser Val Ile
225                 230                 235                 240

Gln Lys Leu Gly Lys Asn Ala Glu Asp Phe Ile Asp Gly Leu Asp Ile
                245                 250                 255

<210> SEQ ID NO 239
<211> LENGTH: 260
<212> TYPE: PRT
<213> ORGANISM: Pseudomonas entomophila

<400> SEQUENCE: 239

Met Ala Leu Ser Ala Asp Glu Val Tyr Val Val Ser Gly Asn Leu Leu
1               5                   10                  15

Ser Ala Met Pro Lys Leu Val Asp Pro Val Met Phe Glu Asp Phe Ala
                20                  25                  30

Asn Ser Asn Leu Leu Cys Gln Leu Ala Ala Asp Lys Asn Gln Gly Thr
            35                  40                  45

Arg Phe Val Asp Pro Pro Ala Trp Leu Asp Phe Tyr Arg Asn Ala Leu
 50                  55                  60

Gly Lys Val Phe Trp Arg Ile Ser Asn Ser Gly Thr Val Ser Phe Asn
 65                  70                  75                  80

Ile Pro Pro Leu Val Arg Ser Ile Thr Ile Lys Glu Val Leu Glu Lys
                85                  90                  95

Thr Phe Tyr Lys Thr Leu Asp His Glu Val Ser Leu Gln Leu Asp Ser
            100                 105                 110

Ser Ile Glu Arg Leu Glu Glu Gln Pro Glu Glu Ser Ala Ala Ala Arg
            115                 120                 125

Leu Tyr Arg Ala Lys Thr Gln Val Thr Tyr Lys Ser Ala Val Ser Asp
130                 135                 140

Leu Ala Val Arg Pro His Pro Ile Ser Thr Ile Asn Leu Gln Ile Ser
145                 150                 155                 160

Ala Val Gln Ser Gly Gly Lys Ile Ser Val Cys Ser Val Tyr Phe Thr
                165                 170                 175
```

```
Thr Ser Ala Asp Ile Glu Ser Asp Val Phe Asn Gln Lys Phe Leu Val
            180                 185                 190

Ser Gln Leu Arg Gly Asn Val Ser Val Ser Thr Phe Asp Ala Lys Leu
        195                 200                 205

Leu Glu Ser Ser Tyr Ala Gly Ile Arg Gln Ser Val Ile Glu Lys Leu
    210                 215                 220

Gly Pro Glu Asn Ile Arg Glu Asn Ile Gln Val Ser Ala Glu Val
225                 230                 235                 240

Phe Ser Leu Ala Gly Pro Arg His Ala Gly Ala Lys Gln Phe Ile Gln
                245                 250                 255

Glu Leu Glu Ile
        260

<210> SEQ ID NO 240
<211> LENGTH: 89
<212> TYPE: PRT
<213> ORGANISM: Pseudomonas chlororaphis

<400> SEQUENCE: 240

Met Ser Ala Gln Glu Asn Phe Val Gly Gly Trp Thr Pro Tyr His Glu
1               5                   10                  15

Leu Thr Pro Lys Asp Arg Glu Val Phe Lys Glu Ala Leu Ala Gly Phe
            20                  25                  30

Val Gly Val Asn Tyr Thr Pro Glu Lys Val Ser Thr Gln Val Val Asn
        35                  40                  45

Gly Thr Asn Tyr Arg Tyr Leu Ser Lys Ala Thr Val Pro Gly Ser Ser
    50                  55                  60

Asp Ser Trp Gln Ala Val Val Glu Ile Tyr Ala Pro Ile Lys Gly Lys
65                  70                  75                  80

Pro His Ile Thr Gln Ile His Arg Ile
                85

<210> SEQ ID NO 241
<211> LENGTH: 89
<212> TYPE: PRT
<213> ORGANISM: Pseudomonas rhodesiae

<400> SEQUENCE: 241

Met Ser Ala Gln Glu Asn Leu Val Gly Gly Trp Thr Pro Tyr His Glu
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Thr Lys Ala Thr Gln Pro Gly Ser Ser
    50                  55                  60

Asn Ser Trp Gln Ala Ile Val Glu Ile Tyr Ala Pro Ile Asn Gly Lys
65                  70                  75                  80

Pro His Ile Thr Gln Ile Ile Arg Ile
                85

<210> SEQ ID NO 242
<211> LENGTH: 89
<212> TYPE: PRT
<213> ORGANISM: Pseudomonas rhodesiae

<400> SEQUENCE: 242
```

```
Met Ser Ala Gln Glu Asn Leu Val Gly Gly Trp Thr Pro Tyr His Val
1               5                   10                  15

Leu Thr Pro Lys Asp Gln Glu Val Phe Asp Glu Ala Leu Ala Gly Leu
            20                  25                  30

Val Gly Val His Tyr Thr Ala Glu Leu Val Ser Thr Gln Val Val Asn
        35                  40                  45

Gly Thr Asn Tyr Arg Tyr Gln Ala Lys Ala Thr Gln Pro Gly Ser Pro
    50                  55                  60

Asn Ser Trp Gln Ala Val Val Glu Ile Tyr Ala Pro Ile Asn Gly Lys
65                  70                  75                  80

Pro Tyr Val Thr Gln Ile Ile Arg Ile
                85
```

<210> SEQ ID NO 243
<211> LENGTH: 90
<212> TYPE: PRT
<213> ORGANISM: Aeromonas hydrophila

<400> SEQUENCE: 243

```
Met Ser Glu Gln Ala Val Leu Leu Gly Gly Trp Thr Ala Tyr His Lys
1               5                   10                  15

Leu Ser Ala Lys Asp Gln Ala Val Phe Asn Gln Ala Leu Glu Gly Phe
            20                  25                  30

Val Gly Val Gln Tyr Thr Pro Phe Glu Val Ser Thr Gln Val Val Ala
        35                  40                  45

Gly Thr Asn Tyr Arg Phe Lys Cys Lys Ser Thr Val Pro Leu Pro Asn
    50                  55                  60

Pro Ile His Gly Glu Ala Val Val Gln Ile Phe Gln Ser Leu Asp Gly
65                  70                  75                  80

Ser Ala His Ile Thr Ser Ile Thr Pro Ile
                85                  90
```

<210> SEQ ID NO 244
<211> LENGTH: 90
<212> TYPE: PRT
<213> ORGANISM: Aeromonas veronii

<400> SEQUENCE: 244

```
Met Ser Glu Gln Ala Val Leu Val Gly Gly Trp Thr Ala Tyr His Lys
1               5                   10                  15

Leu Thr Ala Glu Asp Gln Ala Val Phe Asn Gln Ala Met Lys Gly Phe
            20                  25                  30

Val Gly Val Gln Tyr Val Pro Phe Glu Val Ser Thr Gln Val Val Ala
        35                  40                  45

Gly Thr Asn Tyr Arg Phe Lys Cys Lys Ser Thr Val Pro Leu Ala Lys
    50                  55                  60

Pro Ile His Gly Glu Ala Val Val Gln Ile Phe Lys Ser Leu Asp Gly
65                  70                  75                  80

Asp Ala His Ile Thr Ser Ile Thr Pro Ile
                85                  90
```

<210> SEQ ID NO 245
<211> LENGTH: 90
<212> TYPE: PRT
<213> ORGANISM: Haemophilus piscium

<400> SEQUENCE: 245

```
Met Ser Glu Gln Ala Val Leu Leu Gly Gly Trp Thr Ala Tyr His Lys
```

-continued

```
1               5                   10                  15
Leu Ser Ala Lys Asp Gln Ala Val Phe Asp Leu Ala Leu Lys Gly Phe
            20                  25                  30

Val Gly Val Gln Tyr Gln Pro Phe Glu Val Ser Thr Gln Val Val Ala
            35              40                  45

Gly Thr Asn Tyr Arg Phe Lys Cys Lys Thr Thr Val Pro Leu Pro Asn
        50              55                  60

Pro Ile His Gly Glu Ala Val Val Gln Ile Phe Gln Ser Leu Asp Gly
65                  70                  75                  80

Ser Ala His Ile Thr Ser Ile Thr Pro Ile
                85              90
```